(12) United States Patent
Goddard et al.

(10) Patent No.: US 7,196,174 B2
(45) Date of Patent: Mar. 27, 2007

(54) PRO1557 POLYPEPTIDE ENCODED BY A NUCLEIC ACID HIGHLY EXPRESSED IN ESOPHAGEAL AND KIDNEY TUMORS

(75) Inventors: Audrey Goddard, San Francisco, CA (US); Paul J. Godowski, Hillsborough, CA (US); J. Christopher Grimaldi, San Francisco, CA (US); Austin L. Gurney, Belmont, CA (US); William I. Wood, Hillsborough, CA (US); Colin K. Watanabe, Moraga, CA (US)

(73) Assignee: Genentech, Inc., South San Francisco, CA (US)

( * ) Notice: Subject to any disclaimer, the term of this patent is extended or adjusted under 35 U.S.C. 154(b) by 335 days.

(21) Appl. No.: 10/063,591

(22) Filed: May 3, 2002

(65) Prior Publication Data

US 2003/0180906 A1 Sep. 25, 2003

Related U.S. Application Data

(63) Continuation of application No. 10/006,867, filed on Dec. 6, 2001, which is a continuation of application No. PCT/US00/23328, filed on Aug. 24, 2000, which is a continuation-in-part of application No. 09/403,297, filed as application No. PCT/US99/20111 on Sep. 1, 1999, now abandoned.

(60) Provisional application No. 60/105,881, filed on Oct. 27, 1998.

(51) Int. Cl.
*C07K 14/435* (2006.01)
*C07K 16/46* (2006.01)
*C07K 19/00* (2006.01)

(52) U.S. Cl. .................. 530/387.1; 530/350; 530/402; 536/23.5

(58) Field of Classification Search ............... 536/23.1, 536/23.5; 530/350, 300, 402; 435/69.1, 435/69.7
See application file for complete search history.

(56) References Cited

U.S. PATENT DOCUMENTS 5,536,637 A 7/1996 Jacobs (Continued)

FOREIGN PATENT DOCUMENTS

WO WO 97/38085 10/1997

(Continued)

OTHER PUBLICATIONS

Hu et al., Analysis of genomic and proteomic data using advanced literature mining, J. Proteome Res. 2:405-412, 2003.*

(Continued)

*Primary Examiner*—Lorraine Spector
*Assistant Examiner*—Claire M. Kaufman
(74) *Attorney, Agent, or Firm*—Elizabeth M. Barnes; Mark T. Kresnak; Knobbe, Martens, Olson & Bear LLP

(57) ABSTRACT

The present invention is directed to novel polypeptides and to nucleic acid molecules encoding those polypeptides. Also provided herein are vectors and host cells comprising those nucleic acid sequences, chimeric polypeptide molecules comprising the polypeptides of the present invention fused to heterologous polypeptide sequences, antibodies which bind to the polypeptides of the present invention and to methods for producing the polypeptides of the present invention.

6 Claims, 168 Drawing Sheets

```
GGGGCTTCGGCGCCAGCGGCCAGCGCTAGTCGGTCTGGTAAGGATTTACAAAAGGTGCAGGTATG
AGCAGGTCTGAAGACTAACATTTTGTGAAGTTGTAAAACAGAAAACCTGTTAGAAATGTGGTGGT
TTCAGCAAGGCCTCAGTTTCCTTCCTTCAGCCCTTGTAATTTGGACATCTGCTGCTTTCATATTT
TCATACATTACTGCAGTAACACTCCACCATATAGACCCGGCTTTACCTTATATCAGTGACACTGG
TACAGTAGCTCCAGAAAAATGCTTATTTGGGGCAATGCTAAATATTGCGGCAGTTTTATGCATTG
CTACCATTTATGTTCGTTATAAGCAAGTTCATGCTCTGAGTCCTGAAGAGAACGTTATCATCAAA
TTAAACAAGGCTGGCCTTGTACTTGGAATACTGAGTTGTTTAGGACTTTCTATTGTGGCAAACTT
CCAGAAAACAACCCTTTTTGCTGCACATGTAAGTGGAGCTGTGCTTACCTTTGGTATGGGCTCAT
TATATATGTTTGTTCAGACCATCCTTTCCTACCAAATGCAGCCCAAAATCCATGGCAAACAAGTC
TTCTGGATCAGACTGTTGTTGGTTATCTGGTGTGGAGTAAGTGCACTTAGCATGCTGACTTGCTC
ATCAGTTTTGCACAGTGGCAATTTTGGGACTGATTTAGAACAGAAACTCCATTGGAACCCCGAGG
ACAAAGGTTATGTGCTTCACATGATCACTACTGCAGCAGAATGGTCTATGTCATTTTCCTTCTTT
GGTTTTTTCCTGACTTACATTCGTGATTTTCAGAAAATTCTTTACGGGTGGAAGCCAATTTACA
TGGATTAACCCTCTATGACACTGCACCTTGCCCTATTAACAATGAACGAACACGGCTACTTTCCA
GAGATATTTGATGAAAGGATAAAATATTTCTGTAATGATTATGATTCTCAGGGATTGGGGAAAGG
TTCACAGAAGTTGCTTATTCTTCTCTGAAATTTTCAACCACTTAATCAAGGCTGACAGTAACACT
GATGAATGCTGATAATCAGGAAACATGAAAGAAGCCATTTGATAGATTATTCTAAAGGATATCAT
CAAGAAGACTATTAAAAACACCTATGCCTATACTTTTTTATCTCAGAAAATAAAGTCAAAAGACT
ATG
```

U.S. PATENT DOCUMENTS

| | | | |
|---|---|---|---|
| 6,025,156 | A | 2/2000 | Gwynn et al. |
| 6,124,433 | A | 9/2000 | Falb et al. |
| 6,156,500 | A | 12/2000 | Falb |
| 6,162,604 | A | 12/2000 | Jacob |
| 6,228,582 | B1 | 5/2001 | Rodier et al. |
| 6,395,306 | B1 | 5/2002 | Cui et al. |
| 6,414,117 | B1 | 7/2002 | Levinson |
| 6,465,185 | B1 | 10/2002 | Goldfine et al. |
| 6,498,235 | B2 | 12/2002 | Sheppard et al. |
| 6,562,343 | B1 | 5/2003 | Levinson |
| 6,645,499 | B1 | 11/2003 | Lal et al. |
| 6,730,502 | B2 | 5/2004 | Van Hijum et al. |
| 6,737,522 | B2 | 5/2004 | Sundick et al. |

FOREIGN PATENT DOCUMENTS

| | | |
|---|---|---|
| WO | WO 200070049 A2 * | 11/2000 |

OTHER PUBLICATIONS

Wu et al., BNF-1, a novel gene encoding a putative extracellular matrix protein is overexpressed in tumor tissues, Gene 311:105-110, 2003.*

Fessler et al., A genomic and proteomic analysis of activation of the human neutrophil by lipoplysaccharide and its mediateion by p38 mitogen-activated protein kinase, J. Biol. Chem. 277(35): 31291-302, Aug. 2002.*

Toler et al., Loss of communication in ovarian cancer, Am. J. Obstet. Gynocol., 194:e27-e-31, 2006.*

Berner et al., Clinicopathological associations of CD44 mRNA and protein expression in primary breast carcinomas, Histopathol. 42:546-554, 2003.*

Oda et al., Expression of MDR1/p-glycoprotein and multidrug resistance-associated protein in childhood solid tumours, Virchows Arch. 430:99-105, 1997.*

Papotti et al., Expression of somataostatin receptor types 1-5 in 81 cases of gastrointestinal and pancreatice endocrine tumors, Virshows Arch. 440:461-475, 2002.*

Klein et al., Selection for Genes Encoding Secreted Proteins and Receptors. *Proc. Natl. Acad. Sci.*, 93:7108-7113 (1996).

Database Search, DNA Sequence Alignments [BLASTN 2.2.1[Jul. 12, 2001], NCBI].

Database Search, Protein Sequence Alignments [BLASTN 2.2.1 [ Jul. 12, 2001], NCBI].

Allman, et al. 1996. BCL-6 expression during B-cell activation. *Blood*, 87(12):5257-5268.

Chen, et al. 2002. Discordant Protein and mRNA Expression in Lung Adenocarcinomas. *Molecular & Cellular Proteomics 1.4*, 304-313.

Fu, et al. 1996. Translational regulation of human p53 gene expression. *The EMBO Journal*, vol. 15, No. 16, pp. 4392-4401.

Gökmen-Polar, et al., Feb. 2001, Elevated Protein Kinase C βII Is an Early Promotive Event in Colon Carcinogenesis, *Cancer Research, vol. 61*, pp. 1375-1381.

Hanash, S. 2003. Making sense of microarray data to classify cancer. *The Pharmacogenomics Jorunal*, 3:308-311.

Hanash, S. Mar. 2005. Integrated global profiling of cancer. *Nature Reviews, Applied Proteomics Collection*, pp. 9-14.

Hancock, W. S. 2004. Do We Have Enouigh Biomarkers? *Journal of Proteome Research*, 3(4):685.

Haynes, et al., 1998. Proteome analysis: Biological assay or data archive? *Electrophoresis*, vol. 19, pp. 1862-1871.

Jang A. Hill RP, Sep. 1997. An examination of the affects of hypoxia, acidosis, and glucose starvation on the expression of metastasis-associated genes in murine tumor cells. *Clin. Exp. Metastasis 15(5)*: pp. 469-483.

Konopka, et al. Jun. 1986. Variable Expression of the Translocated c-abl Oncogene in Philadelphia-Chromosome-Positive B-Lymphoid Cell Lines from Chronic Myelogenous Leukemia Patients, *National Academy of Sciences of the United States of America*, vol. 83, No. 11, pp. 4049-4052.

Ohara, et al. 2001. Directional cDNA library construction assisted by the in vitro recombination reaction. *Nucleic Acids Research*, vol. 29, No. e22, pp. 1-8.

Powell, et al. Oct. 1998. Expression of cytochrome P4502E1 in human liver: assessment by mRNA, genotype and phenotype. *Pharmacogenetics*, vol. 5: pp. 411-421.

Vallejo, et al. Dec. 2000. Evidence of tissue-specific, post-transcriptional regulation of NRF-2 expression. *Biochimie* 82(12): 1129-33.

Wang, et al. 1996. mRNA Differential display: Application in the discovery of novel pharmacological targets. *Trends Pharmacol. Sci.*, 17(8):276-279.

Alberts, et al. 1994. *Molecular Biology of the Cell, 3rd Edition*, pp. 403-404, 453. New York: Garland Publishing.

Alberts, et al. 2002. *Molecular Biology of the Cell 4th Edition*, pp. 302, 363-364, 379, 435. New York: Garland Publishing.

GENBANK Accession No. AA040433.

Grimaldi, et al. 1989. The t(5;14) chromosomal translocation in a case of acute lymphocytic leukemia joins the interleukin-3 gene to the immunoglobulin heavy chain gene. *Blood*, 73(8):2081-2085.

Gygi, et al. Mar. 1999. Correlation between Protein and mRNA Abundance in Yeast: *Molecular and Cellular Biology*, 1720-1730.

Hanna, et al. Aug. 1999. HER-2/neu breast cancer predictive testing. *Pathology Associates Medical Laboratories*.

Hyman et al. Nov. 2002. Impact of DNA Amplication of Gene Expression Patterns. *Cancer Research*, 62:6240-6245.

Lewin, B. 1994. Oncogenes: Gene Expression and Cancer, Chap. 39, pp. 1196-1201. *Genes V*. New York: Oxford University Press.

Lewin, B. 1997. Regulation of Transcription, Chap. 29, pp. 847-848. *Genes VI*. New York: Oxford University Press.

Meeker, et al. 1990. Activation of the interleukin-3 gene by chromosome translocation in acute lymphocytic leukemia with eosinophilia. *Blood*, 76(2):285-289.

Meric, et al. 2002. Translation Initiation in cancer: A novel target for therapy. *Molecular Cancer Therapeutics*, 1:971-979.

Ørntoft, et al. 2002. Genome-wide study of gene copy numbers, transcripts, and protein levels in pairs of non-invasive and invasive human transitional cell carcinomas. *Molecular & Cellular Proteomics*, 1:37-45.

Pollack, et al. 2002. Microarray analysis reveals a major direct role of DNA copy number alteration in the transcriptional program of human breast tumors. *PNAS*, 99(20):12963-12968.

Singleton, et al. 1992. Clinical and pathologic significance of the c-erbB-2 (*HER-2/neu*)oncogene. *Pathol. Annu*, 1(27):165-190.

Wi et al., BNF-1, A Novel Gene Encoding a Putative Extracellular Matrix Protein is Overexpressed in Tumor Tissues, Genes 311:105-110, 2003.

Zhigang, et al. 2004. Prostate stem cell antigen (PSCA) expression in human prostate cancer tissues and its potential role in prostate carcinogenesis and progression of prostate cancer. *World Journal of Surgical Oncology*, 2:13.

Alberts, et al. 1994. *Molecular Biology of the Cell, 3rd Edition*, pp. 1216-1217. New York: Garland Publishing.

Anderson, et al. 1997. A comparison of selected mRNA and protein abundances in human liver. *Electrophoresis*, 18:533-537.

Tokunaga, et al. 2000. Application of quantitative RT-PCR using "TaqMan" technology to evaluate the expression of CK 18 mRNA in various cell lines. *J. Exp. Clin. Cancer Res.*, 19(3):375-381.

Labaer, Joshua. 2003. Letter to the editor: Mining the literature and large datasets. *Nature Biotechnology*, 21(9):976-977.

Lian, et al. 2001. Genomic and proteomic analysis of the myeloid differentiation program. *Blood*, 98(3):513-524.

Lichtinghagen, et al. 2002. Different mRNA and protein expression of matrix metalloproteinases 2 and 9 abd tissue inhibitor of metalloproteanases 1 in benign and malignant prostate tissue. *European Urology*, 42:398-406.

Yousef, et al. 2003. Parallel overexpression of seven kallikrein genes in ovarian cancer. *Cancer Research*, 63:2223-2227.

Abe, et al., "An increased high-mobility group A2 expression level is associated with malignant phenotype in pancreatic exocrine tissue." *Br J Cancer*. Dec. 1, 2003;89(11):2104-9. (Abstract Only).

Ando, et al. "Selective apoptosis of natural killer-cell tumours by l-asparaginase." *Br. J. Haematol*. Sep. 2005;130(6):860-8. (Abstract Only).

Aust, et al. "Human thyroid carcinoma cell lines and normal thyrocytes: expression and regulation of matrix metalloproteinase-1 and tissue matrix metalloproteinase inhibitor-1 messenger-RNA and protein." *Thyroid*. Oct. 1997;7(5):713-24. (Abstract Only).

Barnes, et al. "Expression of embryonic fibronectin isoform EIIIA parallels alpha-smooth muscle actin in maturing and diseased kidney." *J Histochem Cytochem*. Jun. 1999;47(6):787-98. (Abstract Only).

Bea, et al. "BMI-1 gene amplication and overexpression in hematological malignancies occur mainly in mantle cell lymphomas." *Cancer Res*. Mar. 15, 2001;61(6):2409-12. (Abstract Only).

Blaschke, et al. "Rapid quantitation of proinflammatory and chemoattractant cytokine expression in small tissue samples and monocyte-derived dendritic cells: validation of a new real-time RT-PCR technology." *J Immunol Methods*. Dec. 1, 2000;246(1-2):79-90. (Abstract Only).

Buckley, et al. "Butyrate-induced reversal of dexamethasone resistance in autonomous rat Nb2 lymphoma cells." *Apoptosis*. 1997;2(6):518-28. (Abstract Only).

Caberlotto, et al. "Alterations in neuropeptide Y levels and Y1 binding sites in the Flinders Sensitive Line rats, a genetic animal model of depression."*Neurosci Lett*. Apr. 23, 1999;265(3):191-4. (Abstract Only).

Caberlotto, et al. "Neurokinin 1 receptor and relative abundance of the short and long isoforms in the human brain." *Eur J Neurosci*. May 2003;17(9):1736-46. (Abstract Only).

Celis, et al. 2000. Gene expression profiling: monitoring transcription and translation products using DNA microarrays and proteomics. *FEBS Letters*, 480:2-16.

Choi, et al. "Characterization of cyclin D2 expression in human endometrium." 166: *J Soc Gynecol Investig*. Jan.-Feb. 2002;9(1):41-6. (Abstract Only).

Couvelard, et al. "Human chorionic gonadotrophin beta expression in malignant Barrett's oesophagus." *Virchows Arch*. Sep. 2004;445(3):279-84. Epub Aug. 10, 2004. (Abstract Only).

Crick, F. 1970. Central dogma of molecular biology. *Nature*, 227:561-563.

Dagenais, et al. "Downregulation of ENaC activity and expression by TNF-alpha in alveolar epithelial cells." *Am J Physiol Lung Cell Mol Physiol*. Feb. 2004;286(2):L301-11. Epub Sep. 26, 2003. (Abstract Only).

de Boer, et al. "Involvement of the CCND1 gene in hairy cell leukemia." *Ann Oncol*. Mar. 1996;7(3):251-6. (Abstract Only).

Debieve, et al. "Inhibin and activin production and subunit expression in human placental cells cultured in vitro." *Mol Hum Reprod*. Aug. 2000;6(8):743-9. (Abstract Only).

Dong, et al. "Expression of membrane-type matrix metalloproteinases 4, 5, and 6 in mouse corneas infected with *P. aeruginosa*." *Invest Ophthalmol Vis Sci*. Dec. 2001;42(13):3223-7.

Duchrow, et al. "Assessment of proliferative activity in colorectal carcinomas by quantitative reverse transcriptase-polymerase chain reaction (RT-PCR)." *Cancer Invest*. 2001;19(6):588-96. (Abstract Only).

Dyer, et al. "Molecular characterisation of carbohydrate digestion and absorption in equine small intestine." *Equine Vet J*. Jul. 2002;34(4):349-58. (Abstract Only).

Egwuagu, et al. "Suppressors of cytokine signaling proteins are differentially expressed in Th1 and Th2 cells: implications for Th cell lineage commitment and maintenance." *J Immunol*. Apr. 1, 2001;168(7):3181-7. (ABstract Only).

Eleore, et al. "Modulation of the glutamatergic receptors (AMPA and NMDA) and of glutamate vesicular transporter 2 in the rat facial nucleus after axotomy." *Neuroscience*. 2005;136(1):147-60. Epub Sep. 21, 2005. (Abstract Only).

El-Ghrably, et al. "Intravitreal invading cells contribute to vitreal cytokine milieu in proliferative vitreoretinopathy." *Br J Ophthalmol*. Apr. 2001;85(4):461-70. (Abstract Only).

Feroze-Merzoug, et al. 2001. Molecular profiling in prostate cancer. *Cancer and Metastasis Reviews*, 20:165-171.

Forsberg, et al. "Altered levels of scavenging enzymes in embryos subjected to a diabetic environment." *Free Radic Res*. Jun. 1996;24(6):451-9. (Abstract Only).

Frevschuss, et al. "Induction of the estrogen receptor by growth hormone and glucocorticoid substitution in primary cultures of rat hepatocytes."*Endocrinology*. Oct. 1993;133(4):1548-54. (Abstract Only).

Fu, et al. "Cyclin D1-negative mantle cell lymphoma: a clinicopathologic study based on gene expression profiling." *Blood*. Dec. 15, 2005; 106(13):4315-21. Epub Aug. 25, 2005 (Abstract Only).

Fuchs, et al. "Oxytocin receptors in bovine cervix: distribution and gene expression during the estrous cycle." *Biol Reprod*. Mar. 1996;54(3):700-8. (Abstract Only).

Furuta, et al. "Silencing of the thrombomodulin gene in human malignant melanoma" *Melanoma Res*. Feb. 2005;15(1):15-20. (Abstract Only).

Futcher, et al. "A sampling of the yeast proteome." *Mol Cell Biol*. Nov. 1999;19(11):7357-7368.

George, et al. "Pre-translational regulation of cytochrome P450 genes is responsible for disease-specific changes of individual P450 enzymes among patients with cirrhosis." *Biochem Pharmacol*. Mar. 30, 1995;49(7):873-81. (Abstract Only).

Giroux, et al. "Cyclooxygenase-2 expression in macrophages: modulation by protein kinase C-alpha." *J Immunol*. Oct. 1, 2000;165(7):3985-91. (Abstract Only).

Gnatenko, et al. "Transcript profiling of human platelets using microarray and serial analysis of gene expression." *Blood*. Mar. 15, 2003;101(6):2285-93. Epub Nov. 14, 2002. (Abstract Only).

Godbout, et al. "Overexpression of a DEAD box protein (DDX1) in neuroblastoma and retinoblastoma cell lines."*J Biol Chem*. Aug. 14, 1998;273(33):21161-8. (Abstract Only).

Goldenberg, et al. "Modulation of gap junction mediated intercellular communication in TM3 Leydig cells." *J Endocrinol*. May 2003;177(2):327-35. (Abstract Only).

Golebiowski, et al. "Expression level of Ubc9 protein in rat tissues." *Acta Biochim Pol*. 2003;50(4):1065-73. (Abstract Only).

Greenbaum, et al. 2003. Comparing protein abundance and mRNA expression levels on a genomic scale. *Genome Biology*, 4(9):117. 1-117.8.

Grem, et al. "Thymidine kinase, thymidylate synthase, and dihydropyrimidine dehydrogenase profiles of cell lines of the National Cancer Institute's Anticancer Drug Screen." *Clin Cancer Res*. Apr. 2001;7(4):999-1009. (Abstract Only).

Grenback, et al. "Galanin in pituitary adenomas." *Regul Pept*. Feb. 15, 2004;117(2):127-39. (Abstract Only).

Gromova, et al."Protein abundancy and mRNA levels of the adipocyte-type fatty acid binding protein correlate in non-invasive and invasive bladder transitional cell carcinomas." *Int J Oncol*. Aug. 1998;13(2):379-83 (Abstract Only).

Guo, et al. "The pathogenic role of macrophage migration inhibitory factor in acute respiratory distress syndrome" *Zhonghua Jie He He Hu Xi Za Zhi*. Jun. 2002;25(6):337-40. (Abstract Only).

Habu, et al. "Restored expression and activity of organic ion transporters rOAT1, rOAT3 and rOCT2 after hyperuricemia in the rat kidney." *Biochem Pharmacol*. Mar. 15, 2005;69(6):993-9. (Abstract Only).

Hahn, et al. "Regulation of cytochrome P4501A1 in teleosts: sustained induction of CYP1A1 mRNA, protein, and catalytic activity by 2,3,7,8-tetrachlorodibenzofuran in the marine fish *Stenotomus chrysops*." *Toxicol Appl Pharmacol*. Aug. 1994;127(2):187-98. (Abstract Only).

Hahnel, et al. "Expression of the pS2 gene in breast tissues assessed by pS2-mRNA analysis and pS2-protein radioimmunoassay." *Breast Cancer Res Treat*. 1992;24(1):71-4. (Abstract Only).

Hamilton, et al. "The role of the epidermal growth factor receptor in sustaining neutrophil inflammation in severe asthma." *Clin Exp Allergy*. Feb. 2003;33(2):233-40. (Abstract Only).

Hassett, et al. "Human hepatic microsomal epoxide hydrolase: comparative analysis of polymorphic expression." *Arch Biochem Biophys*. Jan. 15, 1997;337(2):275-83. (Abstract Only).

Holten-Andersen, et al. "Localization of tissue inhibitor of metalloproteinase 1 (TMP-1) in human colorectal adenoma and adenocarcinoma." *Int J Cancer*. Jan. 10, 2005;113(2):198-206. (Abstract Only).

Houghten, et al. 1986. Relative Importance of Position and Individual Amino Acid Residues in Peptide Antigen-Antibody Interactions: Implications in the Mechanism of Antigenic Drift and Antigenic Shift. New Approaches to Immunization, *Vaccines86*, Cold Spring Harbor Laboratory, p. 21-25.

Huang, et al. "Tissue plasminogen activator induced by dengue virus infection of human endothelial cells." *J Med Virol.* Aug. 2003;70(4):610-6. (Abstract Only).

Huettner, et al. "Neu oncogene expression in ovarian tumors: a quantitative study." *Mod Patjol.* May 1992;5(3):250-6. (Abstract Only).

Hui, et al. "Real-time quantitative RT-PCR of cyclin D1 mRNA in mantle cell lymphoma: comparison with FISH and immunohistochemistry." *Leuk Lymphoma.* Aug. 2003;44(8):1385-94. (Abstract Only).

Husain, et al. "Elevation of topoisomerase I messenger RNA, protein, and catalytic activity in human tumors: demonstration of tumor-type specificity and implications for cancer chemotherapy." *Cancer Res.* Jan. 15, 1994;54(2):539-46. (Abstract Only).

Ihmann, et al. "High-level mRNA quantification of proliferation marker pKi-67 is correlated with favorable prognosis in colorectal carcinoma" *J Cancer Res Clin Oncol.* Dec. 2004;130(12):749-56. Epub Sep. 21, 2004. (Abstract Only).

Ikegami, et al. "Modulation of glucagon receptor expression and response in transfected human embryonic kidney cells." *Am J Physiol Cell Physiol.* Oct. 2001;281(4):C1396-402. (Abstract Only).

Irving, et al. 2000. Proteins emerge from disarray *Nature Biotechnology* 18:932-933.

Jacquemin, et al. "Developmental regulation of acidic fibroblast growth factor (aFGF) expression in bovine retina." *Int J Dev Biol.* Sep. 1993;37(3):417-23. (Abstract Only).

Jaime, et al. "The p21(Cip1) protein, a cyclin inhibitor, regulates the levels and the intracellular localization of CDC25A in mice regenerating livers." *Hepatology.* May 2002;35(5):1063-71. (Abstract Only).

Janssens, et al. "Alteration of frizzled expression in renal cell carcinoma." *Tumour Biol.* Jul.-Aug., 2004;25(4):161-71. (Abstract Only).

Jungbluth, et al. "Immunohistochemical analysis of NY-ESO-1 antigen expression in normal and malignant human tissues." *Int J Cancer.* Jun. 15, 2001;92(6):856-60. (Abstract Only).

Kalabis, et al. "Multidrug resistance phosphoglycoprotein (ABCB1) in the mouse placenta: fetal protection" *Biol Reprod.* Oct. 2005;73(4):591-7. Epub May 25, 2005. (Abstract Only).

Kammori, et al. "Expression of human telomerase reverse transcriptase gene and protein, and of estrogen and progesterone receptors, in breast tumors: Preliminary data from neo-adjuvant chemotherapy." *Int J. Oncol.* Nov. 2005;27(5):1257-63. (Abstract Only).

Khal, et al. "Expression of the ubiquitin-proteasome pathway and muscle loss in experimental cancer cachexia." *Br J Cancer.* Oct. 3, 2005; 93(7):774-80. (Abstract Only).

Khal, et al. "Increased expression of proteasome subunits in skeletal muscle of cancer patients with weight loss." *Int J Biochem Cell Biol.* Oct. 2005;37(10):2196-206. Epub Dec. 2004. (Abstract Only).

Kogo, et al. "Cell type-specific occurence of caveolin-1alpha and -1beta in the lung caused by expression of distinct mRNAs." *J Biol Chem.* Jun. 11, 2004;279(24):25574-81. Epub Apr. 2, 2004. (Abstract Only).

Kommoss, et al. "Oncogene and growth factor expression in ovarian cancer." *Acta Obstet Gynecol Scand Suppl.* 1992;155:19-24. (Abstract Only).

Kumar, et al. "Somatostatin receptors in primary human breast cancer: quantitative analysis of mRNA for subtypes 1-5 and correlation with receptor protein expression and tumor pathology." *Breast Cancer Res Treat.* Jul. 2005;92(2):175-86. (Abstract Only).

Kuo, et al. "Atranscriptomic and proteomic analysis of the effect of CpG-ODN on human THP-1 monocytic leukemia cells." *Proteomics.* Mar. 2005;5(4):894-906. (Abstract Only).

Landmark, et al. "Cellular location and age-dependent changes of the regulatory subunits of cAMP-dependent protein kinase in rat testis." *J Reprod Fertil.* Nov. 1993;99(2):323-34. (Abstract Only).

Lassmann, et al. "Quantification of CK20 gene and protein expression in colorectal cancer by RT-PCR and immunohistochemistry reveals inter- and intratumour heterogeneity." *J Pathol.* Oct. 2002;198(2):198-206. (Abstract Only).

Legrand, et al. "Expression of the multidrug resistance-associated protein (MRP) mRNA and protein in normal peripheral blood and bone marrow haemopoietic cells." *Br J Haematol.* Jul. 1996;94(1):23-33. (Abstract Only).

Lemstrom, et al. "Vascular endothelial growth factor enhances cardiac allograft arteriosclerosis." *Circulation.* May 28, 2002;105(21):2524-30. (Abstract Only).

Li, et al. "Enhanced expressions of arachidonic acid-sensitive tandem-pore domain potassium channels in rat experimental acute cerebral ischemia." *Biochem Biophys Res Commun.* Feb. 25, 2005;327(4):1163-9. (Abstract Only).

Li, et al. "Retinal preconditioning and the induction of heat-shock protein 27." *Invest Ophthamol Vis Sci.* Mar. 2003;44(3):1299-304. (Abstract Only).

Lichtinghagen, et al. 2002. Different mRNA and protein expression of matrix metalloproteinases 2 and 9 and tissue inhibitor of metalloproteinases 1 in benign and malignant prostate tissue. *European Urology*, 42:398-406.

Lindberg, et al. "Increasing expression of tissue plasminogen activator and plasminogen activator inhibitor type 2 in dog gingival tissues with progressive inflammation." *Arch Oral Biol.* Jan. 2001;46(1):23-31. (Abstract Only).

Macabeo-Ong, et al."Effect of duration of fixation on quantitative reverse transcription polymerase chain reaction analyses." *Mod Pathol.* Sep. 2002;15(9):979-87. (Abstract Only).

Madoz-Gurpide, et al. 2003. Molecular analysis of cancer using DNA and protein microarrays. *Adv. Exp. Med. Biol.*, 532:51-58.

Maruyama, et al. "Id-1 and Id-2 are overexpressed in pancreatic cancer and in dysplastic lesions in chronic pancreatitis." *Am J Pathol.* Sep. 1999;155(3):815-22. (Abstract Only).

McGuiness, et al. Mar. 1991, Point mutation in meningococcal *por* A gene associated with increased endemic disease. *The Lancet*, 337:514-517.

McGuiness. et al., Feb. 1993, Class 1 outer membrane protein of *Neisseria meningitides*: epitope analysis of the antigenic diversity between strains, implications for subtype definition and molecular epidemiology. *Mol. Microbiology*, 7:505-514.

Meehan, et al. "Tightly regulated and inducible expression of a yoked hormone-receptor complex in HEK 293 cells." *J Mol Endocrinol.* Feb. 2004;32(1):247-55. (Abstract Only).

Mendoza-Rodriguez, et al. "c-fos and estrogen receptor gene expression pattern in the rat uterine epithelium during the estrous cycle." *Mol Reprod Dev.* Apr. 2003;64(4):379-88. (Abstract Only).

Meoni, et al. "[3H]MK-801 binding and the mRNA for the NMDAR1 subunit of the NMDA receptor are differentially distributed in human and rat forebrain." *Brain Res Mol Brain Res.* Feb. 1998;54(1):13-23. (Abstract Only).

Mezzano, et al. "Overexpression of chemokines, fibrogenic cytokines, and myofibroblasts in human membranous nephropathy." *Kidney Int.* Jan. 2000;57(1):147-58. (Abstract Only).

Mingrone, et al. "Decreased uncoupling protein expression and intramyocytic triglyceride depletion in formerly obese subjects." *Obes Res.* May 2003;11(5):632-40. (Abstract Only).

Miralles, et al. "Differential expression of the short and long forms of the gamma 2 subunit of the GABAA/benzodiazepine receptors." *Brain Res Mol Brain Res.*Jul. 1994;24(1-4):129-39. (Abstract Only).

Mizrachi, et al. "Follicle-stimulating hormone receptor and its messenger ribonucleic acid are present in the bovine cervix and can regulate cervical prostanoid synthesis." *Biol Reprod.* Sep. 1999;61(3):776-84. (Abstract Only).

Monaghan, et al. "The alpha(v)beta6 integrin receptor for Foot-and-mouth disease virus is expressed constitutively on the epithelial cells targeted in cattle." *J Gen Virol.* Oct. 2005;86(Pt 10):2769-80. (Abstract Only).

Montuori, et al. "Urokinase-mediated posttranscriptional regulation of urokinase-receptor expression in non small cell lung carcinoma." *Int J Cancer.* Jun. 20, 2003;105(3):353-60. (Abstract Only).

Munaut, et al. "Vascular endothelial growth factor expression correlates with matrix metalloproteinases MT1-MMP, MMP-2 and MMP-9 in human glioblastomas." *Int J Cancer.* Oct. 10, 2003;106(6):848-55. (Abstract Only).

Nagaraja, et al. "Gene expression signatures and biomarkers of noninvasive and invasive breast cancer cells: comprehensive profiles by representational difference analysis, microarrays and proteomics." *Oncogene.* (2006) 25:2328-2388.

Nie, et al. "DNA hypermethylation is a mechanism for loss of expression of the HLA class I genes i human esophageal squamous cell carcinomas." *Carcingenesis.* Oct. 2001;22(10):1615-23. (Abstract Only).

Nuciforo, et al. "Molecular and immunohistochemical analysis of HER2/neu oncogene in synovial sarcoma." *Hum Pathol.* Jul. 2003;34(7):639-45. (Abstract Only).

Oberringer, et al. "Differential expression of heat shock protein 70 in well healing and chronic human wound tissue." *Biochem Biophys Res Commun.* Sep. 25, 1995;214(3):1009-14. (Abstract Only).

Pachmann, et al. "Expression of bcr-abl mRNA in individual chronic myelogenous leukaemia cells as determined by in situ amplification." *Br J Haematol.* Mar. 2001;112(3):749-59. (Abstract Only).

Pairon, et al. "Cell localization and regulation of expression of cytochrome P450 1A1 and 2B1 in rat lung after induction with 3-methylcholanthrene using mRNA hybridization and immunohistochemostry." *Am J Respir Cell Mol Biol.* Oct. 1994;11(4):386-96. (Abstract Only).

Papotti, et al. "Correlative immunohistochemical and reverse transcriptase polymerase chain reaction analysis of somatostatin receptor type 2 in neuroendocrine tumors of the lung." *Diagn Mol Pathol.* Mar. 2000;9(1):47-57. (Abstract Only).

Papotti, et al. "Expression of somatostatin receptor types 1-5 in 81 cases of gastrointestinal and pancreatic endocrine tumors. A correlative immunohistochemical and reverse-transcriptase polymerase chain reaction analysis." *Virchows Arch.* May 2002;440(5):461-75. Epub Mar. 23, 2002. (Abstract Only).

Paredes, et al. "P-cadherin overexpression is an indicator of clinical outcome in invasive breast carcinomas and is associated with CDH3 promoter hypomethylation." *Clin Cancer Res* Aug. 15, 2005;11(16):5869-77. (Abstract Only).

Politis, et al. "Mammary-derived growth inhibitor protein and messenger ribonucleic acid concentrations in different physiological states of the gland." *J Dairy Sci.* Jun. 1992;75(6):1423-9. (Abstract Only).

Preesman, et al. "T-cell receptor V beta-family usage in primary cutaneous and primary nodal T-cell non-Hodgkin's lymphomas." *J Invest Dermatol.* Nov. 1992;99(5):587-93. (Abstract Only).

Pullig, et al. "Matrilin-3 in human articular cartilage: increased expression in osteoarthritis." *Osteoarthritis Cartilage.* Apr. 2002;10(4):253-63. (Abstract Only).

Rey, et al. "Up-regulation of mitochondrial peripheral benzodiazepine receptor expression by tumor necrosis factor alpha in testicular leydig cells. Possible involvement in cell survival." *Biochem Pharmacol.* Dec. 1, 2000;60(11):1639-46. (Abstract Only).

Rudlowski, et al. "GLUT1 messenger RNA and protein induction relates to the malignant transformation of cervical cancer." *Am J Clin Pathol.* Nov. 2003;120(5):691-8. (Abstract Only).

Sagynaliev, et al. "Web-based data warehouse on gene expression in human colorectal cancer." *Proteomics* 2005, 5:3066-3078.

Sasaki, et al. "Expression and distribution of laminin alpha1 and alpha2 chains in embryonic and adult mouse tissues: an immunochemical approach." *Exp Cell Res.* May 1, 2002;275(2):185-99. (Abstract Only).

Sedelies, et al. "Discordant regulation of granzyme H and granzyme B expression in human lymphocytes." *J Biol Chem.* Jun. 18, 2004;279(25):26581-7. Epub Apr. 6, 2004. (Abstract Only).

Shen, et al. "BCL2 protein expression parallels its mRNA level in normal and malignant B cells.": *Blood.* Nov. 1, 2004;104(9):2936-9. Epub Jul. 8, 2004. (Abstract Only).

Shinohara, et al. "Quantitative determinations of the steady state transcript levels of hexokinase isozymes and glucose transporter isoforms in normal rat tissues and the malignant tumor cell line AH130." *Biochim Biophys Acta.* Jan. 5, 1998;1368(1):129-36. (Abstract Only).

Silvers, et al. "UVA irradiation-induced activation of activator protein-1 is correlated with induced expression of AP-1 family members in the human keratinocyte cell line HaCaT." *Photochem Photobiol.* Mar. 2002;75(3):302-10. (Abstract Only).

Song, et al. "Rat kidney glutamyl aminopeptidase (aminopeptides A): molecular identity and cellular localization." *Am J Physiol.* Oct. 1994;267(4 Pt 2):F546-57. (Abstract Only).

Spaziani, et al. "Tumor necrosis factor-alpha upregulates the prostaglandin E2 EP1 receptor subtype and the cyclooxygenase-2 isoform in cultured amnion WISH cells." *J Interferon Cytokine Res.* Dec. 1998;18(12):1039-44. (Abstract Only).

Spika, et al. "Transcriptional activity of potent glucocorticoids: relevance of glucocorticoid receptor isoforms and drug metabolites." *Skin Pharmacol Appl Skin Physiol.* May-Jun. 2003;16(3):143-50. (Abstract Only).

Splinter, et al. "Specific inhibition of AQP1 water channels in isolated rat intrahepatic bile duct units by small interfering RNAs." *J Biol Chem.* Feb. 21, 2003;278(8):6268-74. Epub Dec. 4, 2002. (Abstract Only).

Stearns, et al. "Type IV collagenase (M(r) 72,000) expression in human prostate:benign and malignant tissue." *Cancer Res.* Feb. 15, 1993;53(4):878-83. (Abstract Only).

Stein, et al. "The decompensated detrusor III: impact of bladder outlet obstruction on sarcoplasmic endoplasmic reticulum protein and gene expression." *J Urol.* Sep. 2000;164(3 Pt 2):1026-30. (Abstract Only).

Strickland, et al. "TNF-alpha and IL-8 are upregulated in the epidermis of normal human skin after UVB exposure: correlation with neutrophil accumulation and E-selectin expression." *J Invest Dermatol.* May 1997;108(5):763-8. (Abstract Only).

Strutz, et al. "Basic fibroblast growth factor expression is increased in human renal fibrogenesis and may mediate autocrine fibroblast proliferation." *Kidney Int.* Apr. 2000;57(4):1521-38. (Abstract Only).

Takahashi, et al. "Adiposity elevates plasma MCP-1 levels leading to the increased CD11b-positive monocytes in mice.": *J Biol Chem.* Nov. 21, 2003;278(47):46654-60. Epub Sep. 16, 2003. (Abstract Only).

Takimoto, et al. "Augmented expression of neuronal nitric oxide synthase in the atria parasympathetically decreases heart rate during acute myocardial infarction in rats." *Circulation.* Jan. 29, 2002;105(4):490-6. (Abstract Only).

Telek, et al. "Differential upregulation of cellular adhesion molecules at the sites of oxidative stress in experimental acute pancreatitis." *J Surg Res.* Mar. 2001;96(1):56-67. (Abstract Only).

Timchenko, et al. "Myotonic dystrophy: an unstable CTG repeat in a protein kinase gene." *Semin Cell Biol.* Feb. 1995;6(1):13-9. (Abstract Only).

Torronen, et al. "Induction of class 3 aldehyde dehydrogenase in the mouse hepatoma cell line Hepa-1 by various chemicals." *Chem Biol Interact.* Aug. 14, 1992;83(2):107-19. (Abstract Only).

Ullmannova, et al. "Relationship between cyclin D1 and p21 (Waf1/Cip1) during differentiation of human myeloid leukemia cell lines." *Leuk Res.* Dec. 2003;27(12):1115-23. (Abstract Only).

Valle, et al. 2003. New approaches for biomarker discovery in lung cancer. *Expert Rev. Mol. Diagn.*, 3(1):55-67.

Van Beers, et al. "Intestinal carbamoyl phosphate synthase I in human and rat. Expression during developlment shows species differences and mosaic expression in duodenum of both species." *J Histochem Cytochem.* Feb. 1998;46(2):231-40. (Abstract Only).

van der Wilt, et al. "Expression of deoxycytidine kinase in leukaemic cells compared with solid tumour cell lines, liver metastases and normal liver." *Eur J Cancer.* Mar. 2003;39(5):691-7. (Abstract Only).

Waldherr, et al. "Expression of cytokines and growth factors in human glomerulonephritides." *Pediatr Nephrol.* Aug. 1993;7(4):471-8. (Abstract Only).

Waghray, et al. "Identification of androgen-refulated genes in the prostate cancer cell line LNCaP by serial analysis of gene expression and proteomic analysis." *Proteomics* 2001, 1:1327-1338.

Walmer, et al. "Malignant transformation of the human endometrium is associated with overexpression of lactoferrin messenger RNA and protein." *Cancer Res.* Mar. 1, 1995;55(5):1168-75. (Abstract Only).

Wang, et al. "Cell proliferation in human soft tissue tumors correlates with platelet-derived growth factor B chain expression: an immunohistochemical and in situ hybridization study." *Cancer Res.* Jan. 15, 1994;54(2):560-4. (Abstract Only).

Wang, et al. " Down-regulation of prostate-specific antigen expression by finasteride through inhibition of complex formation between androgen receptor and steroid receptor-binding consensus in the promoter of the PSA gene in LNCaP cells." *Cancer Res.* Feb. 15, 1997;57(4):714-9. (Abstract Only).

Wang, et al. "Expression of cadherins and catenins in paired tumour and non-neoplastic primary prostate cultures and corresponding prostatectomy specimens." *Urol Res.* Oct. 2000;28(5):308-15. (Abstract Only).

Wang, et al. 2002. Novel candidate tumor marker genes for lung adenocarcinoma. *Oncogene*, 21:7598-7604.

Weterman, et al. "Expression of calcyclin in human melanocytic lesion." *Cancer Res.* Dec. 15, 1993;53(24):6061-6. (Abstract Only).

Williams, et al. "Estrogen regulation of the cytochrome P450 3A subfamily in humans." *J Pharmacol Exp Ther*. Nov. 2004;311(2):728-35. Epub Jul. 2004. (Abstract Only).

Winstead E.R., 2000. The Evolving Art of Arrays, www.genomenewsnetwork.org, pp. 1-4.

Wojtaszek, et al. "Severely decreased MARCKS expression correlates with ras reversion but not with mitogenic responsiveness." *Oncogene.* Mar. 1993;8(3):755-60. (Abstract Only).

Xi, et al. "Expression of human telomerase reverse transcriptase in cervix cancer and its significance" *Zhonghua Fu Chan Ke Za Zhi.* Jun. 2005;40(6):407-10. (Abstract Only).

Yousef, et al. 2003. Parallel overexpression of seven kallikrein genes in ovarian cancer. *Cancer Research*, 63:2223-2227.

Zhong, et al. "Expression of superoxide dismutases, catalase, and glutathione peroxidase in glioma cells." *Free Radic Biol Med*. Dec. 1999;27(11-12):1334-45. (Abstract Only).

\* cited by examiner

FIGURE 1

GGGGCTTCGGCGCCAGCGGCCAGCGCTAGTCGGTCTGGTAAGGATTTACAAAAGGTGCAGGTATG
AGCAGGTCTGAAGACTAACATTTTGTGAAGTTGTAAAACAGAAAACCTGTTAGAAATGTGGTGGT
TTCAGCAAGGCCTCAGTTTCCTTCCTTCAGCCCTTGTAATTTGGACATCTGCTGCTTTCATATTT
TCATACATTACTGCAGTAACACTCCACCATATAGACCCGGCTTTACCTTATATCAGTGACACTGG
TACAGTAGCTCCAGAAAAATGCTTATTTGGGGCAATGCTAAATATTGCGGCAGTTTTATGCATTG
CTACCATTTATGTTCGTTATAAGCAAGTTCATGCTCTGAGTCCTGAAGAGAACGTATCATCAAA
TTAAACAAGGCTGGCCTTGTACTTGGAATACTGAGTTGTTTAGGACTTTCTATTGTGGCAAACTT
CCAGAAAACAACCCTTTTGCTGCACATGTAAGTGGAGCTGTGCTTACCTTTGGTATGGGCTCAT
TATATATGTTTGTTCAGACCATCCTTTCCTACCAAATGCAGCCCAAAATCCATGGCAAACAAGTC
TTCTGGATCAGACTGTTGTTGGTTATCTGGTGTGGAGTAAGTGCACTTAGCATGCTGACTTGCTC
ATCAGTTTTGCACAGTGGCAATTTGGGACTGATTTAGAACAGAAACTCCATTGGAACCCCGAGG
ACAAAGGTTATGTGCTTCACATGATCACTACTGCAGCAGAATGGTCTATGTCATTTTCCTTCTTT
GGTTTTTTCCTGACTTACATTCGTGATTTTCAGAAAATTTCTTTACGGGTGGAAGCCAATTTACA
TGGATTAACCCTCTATGACACTGCACCTTGCCCTATTAACAATGAACGAACACGGCTACTTTCCA
GAGATATTTGATGAAAGGATAAAATATTTCTGTAATGATTATGATTCTCAGGGATTGGGGAAAGG
TTCACAGAAGTTGCTTATTCTTCTCTGAAATTTTCAACCACTTAATCAAGGCTGACAGTAACACT
GATGAATGCTGATAATCAGGAAACATGAAGAAGCCATTTGATAGATTATTCTAAAGGATATCAT
CAAGAAGACTATTAAAAACACCTATGCCTATACTTTTTATCTCAGAAAATAAAGTCAAAAGACT
ATG

FIGURE 2

<subunit 1 of 1, 266 aa, 1 stop
<MW: 29766, pI: 8.39, NX(S/T): 0

MWWFQQGLSFLPSALVIWTSAAFIFSYITAVTLHHIDPALPYISDTGTVAPEKCLFGAMLNIAAV
LCIATIYVRYKQVHALSPEENVIIKLNKAGLVLGILSCLGLSIVANFQKTTLFAAHVSGAVLTFG
MGSLYMFVQTILSYQMQPKIHGKQVFWIRLLLVIWCGVSALSMLTCSSVLHSGNFGTDLEQKLHW
NPEDKGYVLHMITTAAEWSMSFSFFGFFLTYIRDFQKISLRVEANLHGLTLYDTAPCPINNERTR
LLSRDI

Important features:

Type II transmembrane domain:

amino acids 13-33

Other Transmembrane domains:

amino acids 54-73, 94-113, 160-180, 122-141

N-myristoylation sites.

amino acids 57-63, 95-101, 99-105, 124-130, 183-189

FIGURE 3

```
CGGACGCGTGGGCGGACGCGTGGGGGAGAGCCGCAGTCCCGGCTGCAGCACCTGGGAGAAGGCAGACC
GTGTGAGGGGGCCTGTGGCCCCAGCGTGCTGTGGCCTCGGGGAGTGGGAAGTGGAGGCAGGAGCCTTC
CTTACACTTCGCCATGAGTTTCCTCATCGACTCCAGCATCATGATTACCTCCCAGATACTATTTTTG
GATTTGGGTGGCTTTTCTTCATGCGCCAATTGTTTAAAGACTATGAGATACGTCAGTATGTTGTACAG
GTGATCTTCTCCGTGACGTTTGCATTTCTTGCACCATGTTTGAGCTCATCATCTTTGAAATCTTAGG
AGTATTGAATAGCAGCTCCGTTATTTTCACTGGAAAATGAACCTGTGTGTAATTCTGCTGATCCTGG
TTTTCATGGTGCCTTTTTACATTGGCTATTTTATTGTGAGCAATATCCGACTACTGCATAAACAACGA
CTGCTTTTTTCCTGTCTCTTATGGCTGACCTTTATGTATTTCTTCTGGAAACTAGGAGATCCCTTTCC
CATTCTCAGCCCAAAACATGGGATCTTATCCATAGAACAGCTCATCAGCCGGGTTGGTGTGATTGGAG
TGACTCTCATGGCTCTTCTTTCTGGATTTGGTGCTGTCAACTGCCCATACACTTACATGTCTTACTTC
CTCAGGAATGTGACTGACACGGATATTCTAGCCCTGGAACGGCGACTGCTGCAAACCATGGATATGAT
CATAAGCAAAAGAAAAGGATGGCAATGGCACGGAGAACAATGTTCCAGAAGGGGGAAGTGCATAACA
AACCATCAGGTTTCTGGGGAATGATAAAAAGTGTTACCACTTCAGCATCAGGAAGTGAAAATCTTACT
CTTATTCAACAGGAAGTGGATGCTTTGGAAGAATTAAGCAGGCAGCTTTTTCTGGAAACAGCTGATCT
ATATGCTACCAAGGAGAGAATAGAATACTCCAAAACCTTCAAGGGGAAATATTTTAATTTTCTTGGTT
ACTTTTTCTCTATTTACTGTGTTTGGAAAATTTTCATGGCTACCATCAATATTGTTTTTGATCGAGTT
GGGAAAACGGATCCTGTCACAAGAGGCATTGAGATCACTGTGAATTATCTGGGAATCCAATTTGATGT
GAAGTTTTGGTCCCAACACATTTCCTTCATTCTTGTTGGAATAATCATCGTCACATCCATCAGAGGAT
TGCTGATCACTCTTACCAAGTTCTTTTATGCCATCTCTAGCAGTAAGTCCTCCAATGTCATTGTCCTG
CTATTAGCACAGATAATGGGCATGTACTTTGTCTCCTCTGTGCTGCTGATCCGAATGAGTATGCCTTT
AGAATACCGCACCATAATCACTGAAGTCCTTGGAGAACTGCAGTTCAACTTCTATCACCGTTGGTTTG
ATGTGATCTTCCTGGTCAGCGCTCTCTCTAGCATACTCTTCCTCTATTTGGCTCACAAACAGGCACCA
GAGAAGCAAATGGCACCTTGAACTTAAGCCTACTACAGACTGTTAGAGGCCAGTGGTTTCAAAATTTA
GATATAAGAGGGGGGAAAAATGGAACCAGGGCCTGACATTTTATAAACAAACAAAATGCTATGGTAGC
ATTTTTCACCTTCATAGCATACTCCTTCCCCGTCAGGTGATACTATGACCATGAGTAGCATCAGCCAG
AACATGAGAGGGAGAACTAACTCAAGACAATACTCAGCAGAGAGCATCCCGTGTGGATATGAGGCTGG
TGTAGAGGCGGAGAGGAGCCAAGAAACTAAAGGTGAAAAATACACTGGAACTCTGGGCAAGACATGT
CTATGGTAGCTGAGCCAAACACGTAGGATTTCCGTTTTAAGGTTCACATGGAAAAGGTTATAGCTTTG
CCTTGAGATTGACTCATTAAAATCAGAGACTGTAACAAAAAAAAAAAAAAAAAAAAAAGGGCGGCCGCG
ACTCTAGAGTCGACCTGCAGAAGCTTGGCCGCCATGGCCCAACTTGTTTATTGCAGCTTATAATG
```

FIGURE 4

MSFLIDSSIMITSQILFFGFGWLFFMRQLFKDYEIRQYVVQVIFSVTFAFSCTMFELIIFEILGV
LNSSSRYFHWKMNLCVILLILVFMVPFYIGYFIVSNIRLLHKQRLLFSCLLWLTFMYFFWKLGDP
FPILSPKHGILSIEQLISRVGVIGVTLMALLSGFGAVNCPYTYMSYFLRNVTDTDILALERRLLQ
TMDMIISKKKRMAMARRTMFQKGEVHNKPSGFWGMIKSVTTSASGSENLTLIQQEVDALEELSRQ
LFLETADLYATKERIEYSKTFKGKYFNFLGYFFSIYCVWKIFMATINIVFDRVGKTDPVTRGIEI
TVNYLGIQFDVKFWSQHISFILVGIIIVTSIRGLLITLTKFFYAISSSKSSNVIVLLLAQIMGMY
FVSSVLLIRMSMPLEYRTIITEVLGELQFNFYHRWFDVIFLVSALSSILFLYLAHKQAPEKQMAP

Important features:
Signal peptide:
amino acids 1-23

Potential transmembrane domains:
amino acids 37-55, 81-102, 150-168, 288-311, 338-356, 375-398, 425-444

N-glycosylation sites.
amino acids 67-70, 180-183 and 243-246

Eukaryotic cobalamin-binding proteins
amino acids 151-160

FIGURE 5

AGCAGGGAAATCCGGATGTCTCGGTTATGAAGTGGAGCAGTGAGTGTGAGCCTCAACATAGTTCC
AGAACTCTCCATCCGGACTAGTTATTGAGCATCTGCCTCTCATATCACCAGTGGCCATCTGAGGT
GTTTCCCTGGCTCTGAAGGGGTAGGCACG<u>ATG</u>GCCAGGTGCTTCAGCCTGGTGTTGCTTCTCACT
TCCATCTGGACCACGAGGCTCCTGGTCCAAGGCTCTTTGCGTGCAGAAGAGCTTTCCATCCAGGT
GTCATGCAGAATTATGGGGATCACCCTTGTGAGCAAAAAGGCGAACCAGCAGCTGAATTTCACAG
AAGCTAAGGAGGCCTGTAGGCTGCTGGGACTAAGTTTGGCCGGCAAGGACCAAGTTGAAACAGCC
TTGAAAGCTAGCTTTGAAACTTGCAGCTATGGCTGGGTTGGAGATGGATTCGTGGTCATCTCTAG
GATTAGCCCAAACCCCAAGTGTGGGAAAAATGGGGTGGGTGTCCTGATTTGGAAGGTTCCAGTGA
GCCGACAGTTTGCAGCCTATTGTTACAACTCATCTGATACTTGGACTAACTCGTGCATTCCAGAA
ATTATCACCACCAAAGATCCCATATTCAACACTCAAACTGCAACACAAACAACAGAATTTATTGT
CAGTGACAGTACCTACTCGGTGGCATCCCCTTACTCTACAATACCTGCCCCTACTACTACTCCTC
CTGCTCCAGCTTCCACTTCTATTCCACGGAGAAAAAATTGATTTGTGTCACAGAAGTTTTTATG
GAAACTAGCACCATGTCTACAGAAACTGAACCATTTGTTGAAAATAAAGCAGCATTCAAGAATGA
AGCTGCTGGGTTTGGAGGTGTCCCCACGGCTCTGCTAGTGCTTGCTCTCCTCTTCTTTGGTGCTG
CAGCTGGTCTTGGATTTTGCTATGTCAAAAGGTATGTGAAGGCCTTCCCTTTTACAAACAAGAAT
CAGCAGAAGGAAATGATCGAAACCAAAGTAGTAAAGGAGGAGAAGGCCAATGATAGCAACCCTAA
TGAGGAATCAAAGAAAACTGATAAAAACCCAGAAGAGTCCAAGAGTCCAAGCAAAACTACCGTGC
GATGCCTGGAAGCTGAAGTT<u>TAG</u>ATGAGACAGAAATGAGGAGACACACCTGAGGCTGGTTTCTTT
CATGCTCCTTACCCTGCCCCAGCTGGGGAAATCAAAAGGGCCAAAGAACCAAAGAAGAAAGTCCA
CCCTTGGTTCCTAACTGGAATCAGCTCAGGACTGCCATTGGACTATGGAGTGCACCAAAGAGAAT
GCCCTTCTCCTTATTGTAACCCTGTCTGGATCCTATCCTCCTACCTCCAAAGCTTCCCACGGCCT
TTCTAGCCTGGCTATGTCCTAATAATATCCCACTGGGAGAAAGGAGTTTTGCAAAGTGCAAGGAC
CTAAAACATCTCATCAGTATCCAGTGGTAAAAAGGCCTCCTGGCTGTCTGAGGCTAGGTGGGTTG
AAAGCCAAGGAGTCACTGAGACCAAGGCTTTCTCTACTGATTCCGCAGCTCAGACCCTTTCTTCA
GCTCTGAAAGAGAAACACGTATCCCACCTGACATGTCCTTCTGAGCCCGGTAAGAGCAAAAGAAT
GGCAGAAAAGTTTAGCCCCTGAAAGCCATGGAGATTCTCATAACTTGAGACCTAATCTCTGTAAA
GCTAAAATAAAGAAATAGAACAAGGCTGAGGATACGACAGTACACTGTCAGCAGGGACTGTAAAC
ACAGACAGGGTCAAAGTGTTTTCTCTGAACACATTGAGTTGGAATCACTGTTTAGAACACACACA
CTTACTTTTTCTGGTCTCTACCACTGCTGATATTTTCTCTAGGAAATATACTTTTACAAGTAACA
AAAATAAAAACTCTTATAAATTTCTATTTTTATCTGAGTTACAGAAATGATTACTAAGGAAGATT
ACTCAGTAATTTGTTTAAAAAGTAATAAAATTCAACAAACATTTGCTGAATAGCTACTATATGTC
AAGTGCTGTGCAAGGTATTACACTCTGTAATTGAATATTATTCCTCAAAAAATTGCACATAGTAG
AACGCTATCTGGGAAGCTATTTTTTCAGTTTTGATATTTCTAGCTTATCTACTTCCAAACTAAT
TTTTATTTTTGCTGAGACTAATCTTATTCATTTTCTCTAATATGGCAACCATTATAACCTTAATT
TATTATTAACATACCTAAGAAGTACATTGTTACCTCTATATACCAAAGCACATTTTAAAAGTGCC
ATTAACAAATGTATCACTAGCCCTCCTTTTTCCAACAAGAAGGGACTGAGAGATGCAGAAATATT
TGTGACAAAAAATTAAAGCATTTAGAAAACTT

FIGURE 6

MARCFSLVLLLTSIWTTRLLVQGSLRAEELSIQVSCRIMGITLVSKKANQQLNFTEAKEACRLLG
LSLAGKDQVETALKASFETCSYGWVGDGFVVISRISPNPKCGKNGVGVLIWKVPVSRQFAAYCYN
SSDTWTNSCIPEIITTKDPIFNTQTATQTTEFIVSDSTYSVASPYSTIPAPTTTPPAPASTSIPR
RKKLICVTEVFMETSTMSTETEPFVENKAAFKNEAAGFGGVPTALLVLALLFFGAAAGLGFCYVK
RYVKAFPFTNKNQQKEMIETKVVKEEKANDSNPNEESKKTDKNPEESKSPSKTTVRCLEAEV

Signal sequence:

amino acids 1-16

Transmembrane domain:

amino acids 235-254

N-glycosylation site.

amino acids 53-57, 130-134, 289-293

Casein kinase II phosphorylation site.

amino acids 145-149, 214-218

Tyrosine kinase phosphorylation site.

amino acids 79-88

N-myristoylation site.

amino acids 23-29, 65-71, 234-240, 235-239, 249-255, 253-259

FIGURE 7

```
CGCCGCGCTCCCGCACCCGCGGCCCGCCCACCGCGCCGCTCCCGCATCTGCACCCGCAGCCCGGC
GGCCTCCCGGCGGGAGCGAGCAGATCCAGTCCGGCCCGCAGCGCAACTCGGTCCAGTCGGGGCGG
CGGCTGCGGGCGCAGAGCGGAGATGCAGCGGCTTGGGGCCACCCTGCTGTGCCTGCTGCTGGCGG
CGGCGGTCCCCACGGCCCCCGCGCCCGCTCCGACGGCGACCTCGGCTCCAGTCAAGCCCGGCCCG
GCTCTCAGCTACCCGCAGGAGGAGGCCACCCTCAATGAGATGTTCCGCGAGGTTGAGGAACTGAT
GGAGGACACGCAGCACAAATTGCGCAGCGCGGTGGAAGAGATGGAGGCAGAAGAAGCTGCTGCTA
AAGCATCATCAGAAGTGAACCTGGCAAACTTACCTCCCAGCTATCACAATGAGACCAACACAGAC
ACGAAGGTTGGAAATAATACCATCCATGTGCACCGAGAAATTCACAAGATAACCAACAACCAGAC
TGGACAAATGGTCTTTTCAGAGACAGTTATCACATCTGTGGGAGACGAAGAAGGCAGAAGGAGCC
ACGAGTGCATCATCGACGAGGACTGTGGGCCCAGCATGTACTGCCAGTTTGCCAGCTTCCAGTAC
ACCTGCCAGCCATGCCGGGGCCAGAGGATGCTCTGCACCCGGGACAGTGAGTGCTGTGGAGACCA
GCTGTGTGTCTGGGGTCACTGCACCAAAATGGCCACCAGGGGCAGCAATGGACCATCTGTGACA
ACCAGAGGGACTGCCAGCCGGGCTGTGCTGTGCCTTCCAGAGAGGCCTGCTGTTCCCTGTGTGC
ACACCCCTGCCCGTGGAGGGCGAGCTTTGCCATGACCCCGCCAGCCGGCTTCTGGACCTCATCAC
CTGGGAGCTAGAGCCTGATGGAGCCTTGGACCGATGCCCTTGTGCCAGTGGCCTCCTCTGCCAGC
CCCACAGCCACAGCCTGGTGTATGTGTGCAAGCCGACCTTCGTGGGCAGCCGTGACCAAGATGGG
GAGATCCTGCTGCCCAGAGAGGTCCCCGATGAGTATGAAGTTGGCAGCTTCATGGAGGAGGTGCG
CCAGGAGCTGGAGGACCTGGAGAGGAGCCTGACTGAAGAGATGGCGCTGGGGGAGCCTGCGGCTG
CCGCCGCTGCACTGCTGGGAGGGGAAGAGATTTAGATCTGGACCAGGCTGTGGGTAGATGTGCAA
TAGAAATAGCTAATTTATTTCCCCAGGTGTGTGCTTTAGGCGTGGGCTGACCAGGCTTCTTCCTA
CATCTTCTTCCCAGTAAGTTTCCCCTCTGGCTTGACAGCATGAGGTGTTGTGCATTTGTTCAGCT
CCCCCAGGCTGTTCTCCAGGCTTCACAGTCTGGTGCTTGGGAGAGTCAGGCAGGGTTAAACTGCA
GGAGCAGTTTGCCACCCCTGTCCAGATTATTGGCTGCTTTGCCTCTACCAGTTGGCAGACAGCCG
TTTGTTCTACATGGCTTTGATAATTGTTTGAGGGGAGGAGATGGAAACAATGTGGAGTCTCCCTC
TGATTGGTTTTGGGGAAATGTGGAGAAGAGTGCCCTGCTTTGCAAACATCAACCTGGCAAAAATG
CAACAAATGAATTTTCCACGCAGTTCTTTCCATGGGCATAGGTAAGCTGTGCCTTCAGCTGTTGC
AGATGAAATGTTCTGTTCACCCTGCATTACATGTGTTTATTCATCCAGCAGTGTTGCTCAGCTCC
TACCTCTGTGCCAGGGCAGCATTTTCATATCCAAGATCAATTCCCTCTCTCAGCACAGCCTGGGG
AGGGGGTCATTGTTCTCCTCGTCCATCAGGGATCTCAGAGGCTCAGAGACTGCAAGCTGCTTGCC
CAAGTCACACAGCTAGTGAAGACCAGAGCAGTTTCATCTGGTTGTGACTCTAAGCTCAGTGCTCT
CTCCACTACCCCACACCAGCCTTGGTGCCACCAAAAGTGCTCCCCAAAAGGAAGGAGAATGGGAT
TTTTCTTGAGGCATGCACATCTGGAATTAAGGTCAAACTAATTCTCACATCCCTCTAAAAGTAAA
CTACTGTTAGGAACAGCAGTGTTCTCACAGTGTGGGGCAGCCGTCCTTCTAATGAAGACAATGAT
ATTGACACTGTCCCTCTTTGGCAGTTGCATTAGTAACTTTGAAAGGTATATGACTGAGCGTAGCA
TACAGGTTAACCTGCAGAAACAGTACTTAGGTAATTGTAGGGCGAGGATTATAAATGAAATTTGC
AAAATCACTTAGCAGCAACTGAAGACAATTATCAACCACGTGGAGAAAATCAAACCGAGCAGGGC
TGTGTGAAACATGGTTGTAATATGCGACTGCGAACACTGAACTCTACGCCACTCCACAAATGATG
TTTTCAGGTGTCATGGACTGTTGCCACCATGTATTCATCCAGAGTTCTTAAAGTTTAAAGTTGCA
CATGATTGTATAAGCATGCTTTCTTTGAGTTTTAAATTATGTATAAACATAAGTTGCATTTAGAA
ATCAAGCATAAATCACTTCAACTGCAAAAAAAAAAAAAAAAAAAAAAAAAAA
```

FIGURE 8

MQRLGATLLCLLLAAAVPTAPAPAPTATSAPVKPGPALSYPQEEATLNEMFREVEELMEDTQHKL
RSAVEEMEAEEAAAKASSEVNLANLPPSYHNETNTDTKVGNNTIHVHREIHKITNNQTGQMVFSE
TVITSVGDEEGRRSHECIIDEDCGPSMYCQFASFQYTCQPCRGQRMLCTRDSECCGDQLCVWGHC
TKMATRGSNGTICDNQRDCQPGLCCAFQRGLLFPVCTPLPVEGELCHDPASRLLDLITWELEPDG
ALDRCPCASGLLCQPHSHSLVYVCKPTFVGSRDQDGEILLPREVPDEYEVGSFMEEVRQELEDLE
RSLTEEMALGEPAAAAAALLGGEEI

Signal sequence:

amino acids 1-19

N-glycosylation site.

amino acids 96-100, 106-110, 121-125, 204-208

Casein kinase II phosphorylation site.

amino acids 46-50, 67-71, 98-102, 135-139, 206-210, 312-316, 327-331

N-myristoylation site.

amino acids 202-208, 217-223

Amidation site.

amino acids 140-144

FIGURE 9

```
CGGACGCGTGGGCGGACGCGTGGGGGCTGTGAGAAAGTGCCAATAAATACATCATGCAACCCCAC
GGCCCACCTTGTGAACTCCTCGTGCCCAGGGCTGATGTGCGTCTTCCAGGGCTACTCATCCAAAG
GCCTAATCCAACGTTCTGTCTTCAATCTGCAAATCTATGGGGTCCTGGGGCTCTTCTGGACCCTT
AACTGGGTACTGGCCCTGGGCCAATGCGTCCTCGCTGGAGCCTTTGCCTCCTTCTACTGGGCCTT
CCACAAGCCCCAGGACATCCCTACCTTCCCCTTAATCTCTGCCTTCATCCGCACACTCCGTTACC
ACACTGGGTCATTGGCATTTGGAGCCCTCATCCTGACCCTTGTGCAGATAGCCCGGGTCATCTTG
GAGTATATTGACCACAAGCTCAGAGGAGTGCAGAACCCTGTAGCCCGCTGCATCATGTGCTGTTT
CAAGTGCTGCCTCTGGTGTCTGGAAAAATTTATCAAGTTCCTAAACCGCAATGCATACATCATGA
TCGCCATCTACGGGAAGAATTTCTGTGTCTCAGCCAAAAATGCGTTCATGCTACTCATGCGAAAC
ATTGTCAGGGTGGTCGTCCTGGACAAAGTCACAGACCTGCTGCTGTTCTTTGGGAAGCTGCTGGT
GGTCGGAGGCGTGGGGGTCCTGTCCTTCTTTTTTTCTCCGGTCGCATCCCGGGGCTGGGTAAAG
ACTTTAAGAGCCCCCACCTCAACTATTACTGGCTGCCCATCATGACCTCCATCCTGGGGGCCTAT
GTCATCGCCAGCGGCTTCTTCAGCGTTTTCGGCATGTGTGTGGACACGCTCTTCCTCTGCTTCCT
GGAAGACCTGGAGCGGAACAACGGCTCCCTGGACCGGCCCTACTACATGTCCAAGAGCCTTCTAA
AGATTCTGGGCAAGAAGAACGAGGCGCCCCGGACAACAAGAAGAGGAAGAAGTGACAGCTCCGG
CCCTGATCCAGGACTGCACCCCACCCCCACCGTCCAGCCATCCAACCTCACTTCGCCTTACAGGT
CTCCATTTTGTGGTAAAAAAGGTTTTAGGCCAGGCGCCGTGGCTCACGCCTGTAATCCAACACT
TTGAGAGGCTGAGGCGGGCGGATCACCTGAGTCAGGAGTTCGAGACCAGCCTGGCCAACATGGTG
AAACCTCCGTCTCTATTAAAAATACAAAAATTAGCCGAGAGTGGTGGCATGCACCTGTCATCCCA
GCTACTCGGGAGGCTGAGGCAGGAGAATCGCTTGAACCCGGGAGGCAGAGGTTGCAGTGAGCCGA
GATCGCGCCACTGCACTCCAACCTGGGTGACAGACTCTGTCTCCAAAACAAAACAAACAAACAAA
AAGATTTTATTAAAGATATTTTGTTAACTC
```

FIGURE 10

RTRGRTRGGCEKVPINTSCNPTAHLVNSSCPGLMCVFQGYSSKGLIQRSVFNLQIYGVLGLFWTL
NWVLALGQCVLAGAFASFYWAFHKPQDIPTFPLISAFIRTLRYHTGSLAFGALILTLVQIARVIL
EYIDHKLRGVQNPVARCIMCCFKCCLWCLEKFIKFLNRNAYIMIAIYGKNFCVSAKNAFMLLMRN
IVRVVVLDKVTDLLLFFGKLLVVGGVGVLSFFFFSGRIPGLGKDFKSPHLNYYWLPIMTSILGAY
VIASGFFSVFGMCVDTLFLCFLEDLERNNGSLDRPYYMSKSLLKILGKKNEAPPDNKKRKK

Important features:

Transmembrane domains:

amino acids 57-80 (type II), 110-126, 215-231, 254-274

N-glycosylation sites.

amino acids 16-20, 27-31, 289-293

Hypothetical YBR002c family proteins.

amino acids 276-288

Ammonium transporters proteins.

amino acids 204-231

N-myristoylation sites.

amino acids 60-65, 78-84

Amidation site.

amino acids 306-310

FIGURE 11

```
GCCCCGCGCCCGGCGCCGGGCGCCCGAAGCCGGGAGCCACCGCCATGGGGGCCTGCCTGGGAGCCTGC
TCCCTGCTCAGCTGCGCGTCCTGCCTCTGCGGCTCTGCCCCCTGCATCCTGTGCAGCTGCTGCCCCGC
CAGCCGCAACTCCACCGTGAGCCGCCTCATCTTCACGTTCTTCCTCTTCCTGGGGGTGCTGGTGTCCA
TCATTATGCTGAGCCCGGGCGTGGAGAGTCAGCTCTACAAGCTGCCCTGGGTGTGTGAGGAGGGGCC
GGGATCCCCACCGTCCTGCAGGGCACATCGACTGTGGCTCCCTGCTTGGCTACCGCGCTGTCTACCG
CATGTGCTTCGCCACGGCGGCCTTCTTCTTCTTCTTTTTCACCCTGCTCATGCTCGCGTGAGCAGCA
GCCGGGACCCCGGGCTGCCATCCAGAATGGGTTTTGGTTCTTTAAGTTCCTGATCCTGGTGGGCCTC
ACCGTGGGTGCCTTCTACATCCCTGACGGCTCCTTCACCAACATCTGGTTCTACTTCGGCGTCGTGGG
CTCCTTCCTCTTCATCCTCATCCAGCTGGTGCTGCTCATCGACTTTGCGCACTCCTGGAACCAGCGGT
GGCTGGGCAAGGCCGAGGAGTGCGATTCCCGTGCCTGGTACGCAGGCCTCTTCTTCTTCACTCTCCTC
TTCTACTTGCTGTCGATCGCGGCCGTGGCGCTGATGTTCATGTACTACACTGAGCCCAGCGGCTGCCA
CGAGGGCAAGGTCTTCATCAGCCTCAACCTCACCTTCTGTGTCTGCGTGTCCATCGCTGCTGTCCTGC
CCAAGGTCCAGGACGCCCAGCCCAACTCGGGTCTGCTGCAGGCCTCGGTCATCACCCTCTACACCATG
TTTGTCACCTGGTCAGCCCTATCCAGTATCCCTGAACAGAAATGCAACCCCATTTGCCAACCCAGCT
GGGCAACGAGACAGTTGTGGCAGGCCCCGAGGGCTATGAGACCCAGTGGTGGGATGCCCCGAGCATTG
TGGGCCTCATCATCTTCCTCCTGTGCACCCTCTTCATCAGTCTGCGCTCCTCAGACCACCGGCAGGTG
AACAGCCTGATGCAGACCGAGGAGTGCCCACCTATGCTAGACGCCACACAGCAGCAGCAGCAGCAGGT
GGCAGCCTGTGAGGGCCGGGCCTTTGACAACGAGCAGGACGGCGTCACCTACAGCTACTCCTTCTTCC
ACTTCTGCCTGGTGCTGGCCTCACTGCACGTCATGATGACGCTCACCAACTGGTACAAGCCCGGTGAG
ACCCGGAAGATGATCAGCACGTGGACCGCCGTGTGGGTGAAGATCTGTGCCAGCTGGGCAGGGCTGCT
CCTCTACCTGTGGACCCTGGTAGCCCACTCCTCCTGCGCAACCGCGACTTCAGCTGAGGCAGCCTCA
CAGCCTGCCATCTGGTGCCTCCTGCCACCTGGTGCCTCTCGGCTCGGTGACAGCCAACCTGCCCCCTC
CCCACACCAATCAGCCAGGCTGAGCCCCACCCCTGCCCCAGCTCCAGGACCTGCCCCTGAGCCGGGC
CTTCTAGTCGTAGTGCCTTCAGGGTCCGAGGAGCATCAGGCTCCTGCAGAGCCCCATCCCCCCGCCAC
ACCCACACGGTGGAGCTGCCTCTTCCTTCCCCTCCTCCCTGTTGCCCATACTCAGCATCTCGGATGAA
AGGGCTCCCTTGTCCTCAGGCTCCACGGGAGCGGGGCTGCTGGAGAGAGCGGGGAACTCCCACCACAG
TGGGGCATCCGGCACTGAAGCCCTGGTGTTCCTGGTCACGTCCCCAGGGGACCCTGCCCCCTTCCTG
GACTTCGTGCCTTACTGAGTCTCTAAGACTTTTTCTAATAAACAAGCCAGTGCGTGTAAAAAAAA
```

FIGURE 12

MGACLGACSLLSCASCLCGSAPCILCSCCPASRNSTVSRLIFTFFLFLGVLVSIIMLSPGVESQL
YKLPWVCEEGAGIPTVLQGHIDCGSLLGYRAVYRMCFATAAFFFFFFTLLMLCVSSSRDPRAAIQ
NGFWFFKFLILVGLTVGAFYIPDGSFTNIWFYFGVVGSFLFILIQLVLLIDFAHSWNQRWLGKAE
ECDSRAWYAGLFFFTLLFYLLSIAAVALMFMYYTEPSGCHEGKVFISLNLTFCVCVSIAAVLPKV
QDAQPNSGLLQASVITLYTMFVTWSALSSIPEQKCNPHLPTQLGNETVVAGPEGYETQWWDAPSI
VGLIIFLLCTLFISLRSSDHRQVNSLMQTEECPPMLDATQQQQQQVAACEGRAFDNEQDGVTYSY
SFFHFCLVLASLHVMMTLTNWYKPGETRKMISTWTAVWVKICASWAGLLLYLWTLVAPLLLRNRD
FS

Signal sequence:

amino acids 1-20

Transmembrane domains:

amino acids 40-58, 101-116, 134-150, 162-178, 206-223, 240-257, 272-283, 324-340, 391-406, 428-444

FIGURE 13

```
CGGGCCAGCCTGGGGCGGCCGGCCAGGAACCACCCGTTAAGGTGTCTTCTCTTTAGGGATGGTGA
GGTTGGAAAAAGACTCCTGTAACCCTCCTCCAGGATGAACCACCTGCCAGAAGACATGGAGAACG
CTCTCACCGGGAGCCAGAGCTCCCATGCTTCTCTGCGCAATATCCATTCCATCAACCCCACACAA
CTCATGGCCAGGATTGAGTCCTATGAAGGAAGGGAAAAGAAAGGCATATCTGATGTCAGGAGGAC
TTTCTGTTTGTTTGTCACCTTTGACCTCTTATTCGTAACATTACTGTGGATAATAGAGTTAAATG
TGAATGGAGGCATTGAGAACACATTAGAGAAGGAGGTGATGCAGTATGACTACTATTCTTCATAT
TTTGATATATTTCTTCTGGCAGTTTTTCGATTTAAAGTGTTAATACTTGCATATGCTGTGTGCAG
ACTGCGCCATTGGTGGGCAATAGCGTTGACAACGGCAGTGACCAGTGCCTTTTTACTAGCAAAAG
TGATCCTTTCGAAGCTTTTCTCTCAAGGGGCTTTTGGCTATGTGCTGCCCATCATTTCATTCATC
CTTGCCTGGATTGAGACGTGGTTCCTGGATTTCAAAGTGTTACCTCAAGAAGCAGAAGAAGAAA
CAGACTCCTGATAGTTCAGGATGCTTCAGAGAGGGCAGCACTTATACCTGGTGGTCTTTCTGATG
GTCAGTTTTATTCCCCTCCTGAATCCGAAGCAGGATCTGAAGAAGCTGAAGAAAAACAGGACAGT
GAGAAACCACTTTTAGAACTATGAGTACTACTTTTGTTAAATGTGAAAAACCCTCACAGAAAGTC
ATCGAGGCAAAAGAGGCAGGCAGTGGAGTCTCCCTGTCGACAGTAAAGTTGAAATGGTGACGTC
CACTGCTGGCTTTATTGAACAGCTAATAAAGATTTATTTATTGTAATACCTCACAAACGTTGTAC
CATATCCATGCACATTTAGTTGCCTGCCTGTGGCTGGTAAGGTAATGTCATGATTCATCCTCTCT
TCAGTGAGACTGAGCCTGATGTGTTAACAAATAGGTGAAGAAAGTCTTGTGCTGTATTCCTAATC
AAAAGACTTAATATATTGAAGTAACACTTTTTTAGTAAGCAAGATACCTTTTTATTTCAATTCAC
AGAATGGAATTTTTTTGTTTCATGTCTCAGATTTATTTTGTATTTCTTTTTTAACACTCTACATT
TCCCTTGTTTTTTAACTCATGCACATGTGCTCTTTGTACAGTTTTAAAAAGTGTAATAAAATCTG
ACATGTCAATGTGGCTAGTTTTATTTTTCTTGTTTTGCATTATGTGTATGGCCTGAAGTGTTGGA
CTTGCAAAAGGGGAAGAAAGGAATTGCGAATACATGTAAAATGTCACCAGACATTTGTATTATTT
TTATCATGAAATCATGTTTTTCTCTGATTGTTCTGAAATGTTCTAAATACTCTTATTTTGAATGC
ACAAAATGACTTAAACCATTCATATCATGTTTCCTTTGCGTTCAGCCAATTTCAATTAAAATGAA
CTAAATTAAAAA
```

FIGURE 14

MNHLPEDMENALTGSQSSHASLRNIHSINPTQLMARIESYEGREKKGISDVRRTFCLFVTFDLLF
VTLLWIIELNVNGGIENTLEKEVMQYDYYSSYFDIFLLAVFRFKVLILAYAVCRLRHWWAIALTT
AVTSAFLLAKVILSKLFSQGAFGYVLPIISFILAWIETWFLDFKVLPQEAEEENRLLIVQDASER
AALIPGGLSDGQFYSPPESEAGSEEAEEKQDSEKPLLEL

Important features of the protein:
Signal peptide:
amino acids 1-20

Transmembrane domains:
amino acids 54-72, 100-118, 130-144, 146-166

N-myristoylation sites.
amino acids 14-20, 78-84, 79-85, 202-208, 217-223

FIGURE 15

```
ACTCGAACGCAGTTGCTTCGGGACCCAGGACCCCCTCGGGCCCGACCCGCCAGGAAAGACTGAGG
CCGCGGCCTGCCCCGCCCGGCTCCCTGCGCCGCCGCCGCCTCCCGGGACAGAAGATGTGCTCCAG
GGTCCCTCTGCTGCTGCCGCTGCTCCTGCTACTGGCCCTGGGGCCTGGGGTGCAGGGCTGCCCAT
CCGGCTGCCAGTGCAGCCAGCCACAGACAGTCTTCTGCACTGCCCGCCAGGGGACCACGGTGCCC
CGAGACGTGCCACCCGACACGGTGGGGCTGTACGTCTTTGAGAACGGCATCACCATGCTCGACGC
AGGCAGCTTTGCCGGCCTGCCGGGCCTGCAGCTCCTGGACCTGTCACAGAACCAGATCGCCAGCC
TGCCCAGCGGGGTCTTCCAGCCACTCGCCAACCTCAGCAACCTGGACCTGACGGCCAACAGGCTG
CATGAAATCACCAATGAGACCTTCCGTGGCCTGCGGCGCCTCGAGCGCCTCTACCTGGGCAAGAA
CCGCATCCGCCACATCCAGCCTGGTGCCTTCGACACGCTCGACCGCCTCCTGGAGCTCAAGCTGC
AGGACAACGAGCTGCGGGCACTGCCCCGCTGCGCCTGCCCCGCCTGCTGCTGCTGGACCTCAGC
CACAACAGCCTCCTGGCCCTGGAGCCCGGCATCCTGGACACTGCCAACGTGGAGGCGCTGCGGCT
GGCTGGTCTGGGGCTGCAGCAGCTGGACGAGGGGCTCTTCAGCCGCTTGCGCAACCTCCACGACC
TGGATGTGTCCGACAACCAGCTGGAGCGAGTGCCACCTGTGATCCGAGGCCTCCGGGGCCTGACG
CGCCTGCGGCTGGCCGGCAACACCCGCATTGCCCAGCTGCGGCCCGAGGACCTGGCCGGCCTGGC
TGCCCTGCAGGAGCTGGATGTGAGCAACCTAAGCCTGCAGGCCCTGCCTGGCGACCTCTCGGGCC
TCTTCCCCGCCTGCGGCTGCTGGCAGCTGCCCGCAACCCCTTCAACTGCGTGTGCCCCTGAGC
TGGTTTGGCCCCTGGGTGCGCGAGAGCCACGTCACACTGGCCAGCCCTGAGGAGACGCGCTGCCA
CTTCCCGCCCAAGAACGCTGGCCGGCTGCTCCTGGAGCTTGACTACGCCGACTTTGGCTGCCCAG
CCACCACCACCACAGCCACAGTGCCCACCACGAGGCCCGTGGTGCGGGAGCCCACAGCCTTGTCT
TCTAGCTTGGCTCCTACCTGGCTTAGCCCCACAGCGCCGGCCACTGAGGCCCCCAGCCCGCCCTC
CACTGCCCCACCGACTGTAGGGCCTGTCCCCCAGCCCCAGGACTGCCCACCGTCCACCTGCCTCA
ATGGGGCACATGCCACCTGGGGACACGGCACCACCTGGCGTGCTTGTGCCCCGAAGGCTTCACG
GGCCTGTACTGTGAGAGCCAGATGGGGCAGGGGACACGGCCCAGCCCTACACCAGTCACGCCGAG
GCCACCACGGTCCCTGACCCTGGGCATCGAGCCGGTGAGCCCCACCTCCCTGCGCGTGGGCCTGC
AGCGCTACCTCCAGGGGAGCTCCGTGCAGCTCAGGAGCCTCCGTCTCACCTATCGCAACCTATCG
GGCCCTGATAAGCGGCTGGTGACGCTGCGACTGCCTGCCTCGCTCGCTGAGTACACGGTCACCCA
GCTGCGGCCCAACGCCACTTACTCCGTCTGTGTCATGCCTTTGGGGCCCGGCCGGGTGCCGGAGG
GCGAGGAGGCCTGCGGGGAGGCCCATACACCCCAGCCGTCCACTCCAACCACGCCCCAGTCACC
CAGGCCCGCGAGGGCAACCTGCCGCTCCTCATTGCGCCCGCCCTGGCCGCGGTGCTCCTGGCCGC
GCTGGCTGCGGTGGGGGCAGCCTACTGTGTGCGGCGGGGCGGGCCATGGCAGCAGCGGCTCAGG
ACAAAGGGCAGGTGGGGCCAGGGGCTGGGCCCCTGGAACTGGAGGGAGTGAAGGTCCCCTTGGAG
CCAGGCCCGAAGGCAACAGAGGGCGGTGGAGAGGCCCTGCCCAGCGGGTCTGAGTGTGAGGTGCC
ACTCATGGGCTTCCCAGGGCCTGGCCTCCAGTCACCCCTCCACGCAAAGCCCTACATCTAAGCCA
GAGAGAGACAGGGCAGCTGGGCCGGGCTCTCAGCCAGTGAGATGGCCAGCCCCCTCCTGCTGCC
ACACCACGTAAGTTCTCAGTCCCAACCTCGGGGATGTGTGCAGACAGGGCTGTGTGACCACAGCT
GGGCCCTGTTCCCTCTGGACCTCGGTCTCCTCATCTGTGAGATGCTGTGGCCCAGCTGACGAGCC
CTAACGTCCCCAGAACCGAGTGCCTATGAGGACAGTGTCCGCCCTGCCCTCCGCAACGTGCAGTC
CCTGGGCACGGCGGGCCCTGCCATGTGCTGGTAACGCATGCCTGGCTCCTGCTGGGCTCTCCCAC
TCCAGGCGGACCCTGGGGGCCAGTGAAGGAAGCTCCCGGAAAGAGCAGAGGGAGAGCGGGTAGGC
GGCTGTGTGACTCTAGTCTTGGCCCCAGGAAGCGAAGGAACAAAAGAAACTGGAAAGGAAGATGC
TTTAGGAACATGTTTTGCTTTTTTAAAATATATATATTTATAAGAGATCCTTTCCCATTTATTCT
GGGAAGATGTTTTCAAACTCAGAGACAAGGACTTTGGTTTTTGTAAGACAAACGATGATATGAA
GGCCTTTTGTAAGAAAAAATAAAGATGAAGTGTGAAA
```

FIGURE 16

MCSRVPLLLPLLLLLALGPGVQGCPSGCQCSQPQTVFCTARQGTTVPRDVPPDTVGLYVFENGIT
MLDAGSFAGLPGLQLLDLSQNQIASLPSGVFQPLANLSNLDLTANRLHEITNETFRGLRRLERLY
LGKNRIRHIQPGAFDTLDRLLELKLQDNELRALPPLRLPRLLLLDLSHNSLLALEPGILDTANVE
ALRLAGLGLQQLDEGLFSRLRNLHDLDVSDNQLERVPPVIRGLRGLTRLRLAGNTRIAQLRPEDL
AGLAALQELDVSNLSLQALPGDLSGLFPRLRLLAAARNPFNCVCPLSWFGPWVRESHVTLASPEE
TRCHFPPKNAGRLLLELDYADFGCPATTTTATVPTTRPVVREPTALSSSLAPTWLSPTAPATEAP
SPPSTAPPTVGPVPQPQDCPPSTCLNGGTCHLGTRHHLACLCPEGFTGLYCESQMGQGTRPSPTP
VTPRPPRSLTLGIEPVSPTSLRVGLQRYLQGSSVQLRSLRLTYRNLSGPDKRLVTLRLPASLAEY
TVTQLRPNATYSVCVMPLGPGRVPEGEEACGEAHTPPAVHSNHAPVTQAREGNLPLLIAPALAAV
LLAALAAVGAAYCVRRGRAMAAAAQDKGQVGPGAGPLELEGVKVPLEPGPKATEGGGEALPSGSE
CEVPLMGFPGPGLQSPLHAKPYI

Important features:

Signal peptide:

amino acids 1-23

Transmembrane domain:

amino acids 579-599

EGF-like domain cysteine pattern signature.

amino acids 430-442

Leucine zipper pattern.

amino acids 197-219, 269-291

N-glycosylation sites.

amino acids 101-105, 117-121, 273-277, 500-504, 528-532

Tyrosine kinase phosphorylation sites.

amino acids 124-131, 337-345

N-myristoylation sites.

amino acids 23-29, 27-33, 70-76, 142-148, 187-193, 348-354, 594-600, 640-646

FIGURE 17

```
GCAGCGGCGAGGCGGCGGTGGTGGCTGAGTCCGTGGTGGCAGAGGCGAAGGCGACAGCTCATGCG
GGTCCGGATAGGGCTGACGCTGCTGCTGTGTGCGGTGCTGCTGAGCTTGGCCTCGGCGTCCTCGG
ATGAAGAAGGCAGCCAGGATGAATCCTTAGATTCCAAGACTACTTTGACATCAGATGAGTCAGTA
AAGGACCATACTACTGCAGGCAGAGTAGTTGCTGGTCAAATATTTCTTGATTCAGAAGAATCTGA
ATTAGAATCCTCTATTCAAGAAGAGGAAGACAGCCTCAAGAGCCAAGAGGGGAAAGTGTCACAG
AAGATATCAGCTTTCTAGAGTCTCCAAATCCAGAAAACAAGGACTATGAAGAGCCAAAGAAAGTA
CGGAAACCAGCTTTGACCGCCATTGAAGGCACAGCACATGGGGAGCCCTGCCACTTCCCTTTTCT
TTTCCTAGATAAGGAGTATGATGAATGTACATCAGATGGGAGGGAAGATGGCAGACTGTGGTGTG
CTACAACCTATGACTACAAAGCAGATGAAAAGTGGGCTTTTGTGAAACTGAAGAAGAGGCTGCT
AAGAGACGGCAGATGCAGGAAGCAGAAATGATGTATCAAACTGGAATGAAAATCCTTAATGGAAG
CAATAAGAAAAGCCAAAAAGAGAAGCATATCGGTATCTCCAAAAGGCAGCAAGCATGAACCATA
CCAAAGCCCTGGAGAGAGTGTCATATGCTCTTTTATTTGGTGATTACTTGCCACAGAATATCCAG
GCAGCGAGAGAGATGTTTGAGAAGCTGACTGAGGAAGGCTCTCCCAAGGGACAGACTGCTCTTGG
CTTTCTGTATGCCTCTGGACTTGGTGTTAATTCAAGTCAGGCAAAGGCTCTTGTATATTATACAT
TTGGAGCTCTTGGGGGCAATCTAATAGCCCACATGGTTTTGGTAAGTAGACTTTAGTGGAAGGCT
AATAATATTAACATCAGAAGAATTTGTGGTTTATAGCGGCCACAACTTTTTCAGCTTTCATGATC
CAGATTTGCTTGTATTAAGACCAAATATTCAGTTGAACTTCCTTCAAATTCTTGTTAATGGATAT
AACACATGGAATCTACATGTAAATGAAAGTTGGTGGAGTCCACAATTTTTCTTTAAAATGATTAG
TTTGGCTGATTGCCCCTAAAAAGAGAGATCTGATAAATGGCTCTTTTTAAATTTTCTCTGAGTTG
GAATTGTCAGAATCATTTTTTACATTAGATTATCATAATTTTAAAAATTTTCTTTAGTTTTTCA
AAATTTTGTAAATGGTGGCTATAGAAAAACAACATGAAATATTATACAATATTTTGCAACAATGC
CCTAAGAATTGTTAAAATTCATGGAGTTATTTGTGCAGAATGACTCCAGAGAGCTCTACTTTCTG
TTTTTTACTTTTCATGATTGGCTGTCTTCCCATTTATTCTGGTCATTTATTGCTAGTGACACTGT
GCCTGCTTCCAGTAGTCTCATTTTCCCTATTTTGCTAATTTGTTACTTTTTCTTTGCTAATTTGG
AAGATTAACTCATTTTTAATAAAATTATGTCTAAGATTAAAAAAAAAAAAAAAAAAAAAAAAAAA
AAAAAAAAAAAAAAAAAAAAAAAAAAAAAAAAAAAAAAAAAAAAAA
```

FIGURE 18

MRVRIGLTLLLCAVLLSLASASSDEEGSQDESLDSKTTLTSDESVKDHTTAGRVVAGQIFLDSEESEL
ESSIQEEEDSLKSQEGESVTEDISFLESPNPENKDYEEPKKVRKPALTAIEGTAHGEPCHFPFLFLDK
EYDECTSDGREDGRLWCATTYDYKADEKWGFCETEEEAAKRRQMQEAEMMYQTGMKILNGSNKKSQKR
EAYRYLQKAASMNHTKALERVSYALLFGDYLPQNIQAAREMFEKLTEEGSPKGQTALGFLYASGLGVN
SSQAKALVYYTFGALGGNLIAHMVLVSRL

Important features:
Signal peptide:
amino acids 1-21

N-glycosylation sites.
amino acids 195-199, 217-221, 272-276

Tyrosine kinase phosphorylation site.
amino acids 220-228

N-myristoylation sites.
amino acids 120-126, 253-259, 268-274, 270-274, 285-291, 289-295

Glycosaminoglycan attachment site.
amino acids 267-271

Microbodies C-terminal targeting signal.
amino acids 299-303

Type II fibronectin collagen-binding domain protein.
amino acids 127-169

Fructose-bisphosphate aldolase class-II protein.
amino acids 101-119

FIGURE 19

AATTCAGATTTTAAGCCCATTCTGCAGTGGAATTTCATGAACTAGCAAGAGGACACCATCTTCTT
GTATTATACAAGAAAGGAGTGTACCTATCACACACAGGGGGAAAAATGCTCTTTTGGGTGCTAGG
CCTCCTAATCCTCTGTGGTTTTCTGTGGACTCGTAAAGGAAAACTAAAGATTGAAGACATCACTG
ATAAGTACATTTTTATCACTGGATGTGACTCGGGCTTTGGAAACTTGGCAGCCAGAACTTTTGAT
AAAAAGGGATTTCATGTAATCGCTGCCTGTCTGACTGAATCAGGATCAACAGCTTTAAAGGCAGA
AACCTCAGAGAGACTTCGTACTGTGCTTCTGGATGTGACCGACCCAGAGAATGTCAAGAGGACTG
CCCAGTGGGTGAAGAACCAAGTTGGGGAGAAAGGTCTCTGGGGTCTGATCAATAATGCTGGTGTT
CCCGGCGTGCTGGCTCCCACTGACTGGCTGACACTAGAGGACTACAGAGAACCTATTGAAGTGAA
CCTGTTTGGACTCATCAGTGTGACACTAAATATGCTTCCTTTGGTCAAGAAAGCTCAAGGGAGAG
TTATTAATGTCTCCAGTGTTGGAGGTCGCCTTGCAATCGTTGGAGGGGGCTATACTCCATCCAAA
TATGCAGTGGAAGGTTTCAATGACAGCTTAAGACGGGACATGAAAGCTTTTGGTGTGCACGTCTC
ATGCATTGAACCAGGATTGTTCAAAACAAACTTGGCAGATCCAGTAAAGGTAATTGAAAAAAAAC
TCGCCATTTGGGAGCAGCTGTCTCCAGACATCAAACAACAATATGGAGAAGGTTACATTGAAAAA
AGTCTAGACAAACTGAAAGGCAATAAATCCTATGTGAACATGGACCTCTCTCCGGTGGTAGAGTG
CATGGACCACGCTCTAACAAGTCTCTTCCCTAAGACTCATTATGCCGCTGGAAAAGATGCCAAAA
TTTTCTGGATACCTCTGTCTCACATGCCAGCAGCTTTGCAAGACTTTTTATTGTTGAAACAGAAA
GCAGAGCTGGCTAATCCCAAGGCAGTGTGACTCAGCTAACCACAAATGTCTCCTCCAGGCTATGA
AATTGGCCGATTTCAAGAACACATCTCCTTTTCAACCCCATTCCTTATCTGCTCCAACCTGGACT
CATTTAGATCGTGCTTATTTGGATTGCAAAAGGGAGTCCCACCATCGCTGGTGGTATCCCAGGGT
CCCTGCTCAAGTTTTCTTTGAAAAGGAGGGCTGGAATGGTACATCACATAGGCAAGTCCTGCCCT
GTATTTAGGCTTTGCCTGCTTGGTGTGATGTAAGGGAAATTGAAAGACTTGCCCATTCAAAATGA
TCTTTACCGTGGCCTGCCCCATGCTTATGGTCCCCAGCATTTACAGTAACTTGTGAATGTTAAGT
ATCATCTCTTATCTAAATATTAAAGATAAGTCAACCCAAAAAAAAAAAAAAAAAAAAAAAAAAAA
AAAAAAAAAAAA

FIGURE 20

MLFWVLGLLILCGFLWTRKGKLKIEDITDKYIFITGCDSGFGNLAARTFDKKGFHVIAACLTESG
STALKAETSERLRTVLLDVTDPENVKRTAQWVKNQVGEKGLWGLINNAGVPGVLAPTDWLTLEDY
REPIEVNLFGLISVTLNMLPLVKKAQGRVINVSSVGGRLAIVGGGYTPSKYAVEGFNDSLRRDMK
AFGVHVSCIEPGLFKTNLADPVKVIEKKLAIWEQLSPDIKQQYGEGYIEKSLDKLKGNKSYVNMD
LSPVVECMDHALTSLFPKTHYAAGKDAKIFWIPLSHMPAALQDFLLLKQKAELANPKAV

Important features of the protein:
Signal peptide:
amino acids 1-17

Transmembrane domain:
amino acids 136-152

N-glycosylation sites.
amino acids 161-163, 187-190 and 253-256

Glycosaminoglycan attachment site.
amino acids 39-42

N-myristoylation sites.
amino acids 36-41, 42-47, 108-113, 166-171, 198-203 and 207-212

FIGURE 21

CTGAGGCGGCGGTAGC<u>ATG</u>GAGGGGGAGAGTACGTCGGCGGTGCTCTCGGGCTTTGTGCTCGGCG
CACTCGCTTTCCAGCACCTCAACACGGACTCGGACACGGAAGGTTTTCTTCTTGGGGAAGTAAAA
GGTGAAGCCAAGAACAGCATTACTGATTCCCAAATGGATGATGTTGAAGTTGTTTATACAATTGA
CATTCAGAAATATATTCCATGCTATCAGCTTTTTAGCTTTTATAATTCTTCAGGCGAAGTAAATG
AGCAAGCACTGAAGAAAATATTATCAAATGTCAAAAAGAATGTGGTAGGTTGGTACAAATTCCGT
CGTCATTCAGATCAGATCATGACGTTTAGAGAGAGGCTGCTTCACAAAAACTTGCAGGAGCATTT
TTCAAACCAAGACCTTGTTTTTCTGCTATTAACACCAAGTATAATAACAGAAAGCTGCTCTACTC
ATCGACTGGAACATTCCTTATATAAACCTCAAAAAGGACTTTTTCACAGGGTACCTTTAGTGGTT
GCCAATCTGGGCATGTCTGAACAACTGGGTTATAAAACTGTATCAGGTTCCTGTATGTCCACTGG
TTTTAGCCGAGCAGTACAAACACACAGCTCTAAATTTTTTGAAGAAGATGGATCCTTAAAGGAGG
TACATAAGATAAATGAAATGTATGCTTCATTACAAGAGGAATTAAAGAGTATATGCAAAAAGTG
GAAGACAGTGAACAAGCAGTAGATAAACTAGTAAAGGATGTAAACAGATTAAAACGAGAAATTGA
GAAAAGGAGAGGAGCACAGATTCAGGCAGCAAGAGAGAAGAACATCCAAAAAGACCCTCAGGAGA
ACATTTTCTTTGTCAGGCATTACGGACCTTTTTCCAAATTCTGAATTTCTTCATTCATGTGTT
ATGTCTTTAAAAAATAGACATGTTTCTAAAAGTAGCTGTAACTACAACCACCATCTCGATGTAGT
AGACAATCTGACCTTAATGGTAGAACACACTGACATTCCTGAAGCTAGTCCAGCTAGTACACCAC
AAATCATTAAGCATAAAGCCTTAGACTTAGATGACAGATGGCAATTCAAGAGATCTCGGTTGTTA
GATACACAAGACAAACGATCTAAAGCAAATACTGGTAGTAGTAACCAAGATAAAGCATCCAAAAT
GAGCAGCCCAGAAACAGATGAAGAAATTGAAAGATGAAGGGTTTTGGTGAATATTCACGGTCTC
CTACATTT<u>TGA</u>TCCTTTTAACCTTACAAGGAGATTTTTTATTTGGCTGATGGGTAAAGCCAAAC
ATTTCTATTGTTTTACTATGTTGAGCTACTTGCAGTAAGTTCATTTGTTTTTACTATGTTCACC
TGTTTGCAGTAATACACAGATAACTCTTAGTGCATTTACTTCACAAAGTACTTTTTCAAACATCA
GATGCTTTTATTTCCAAACCTTTTTTTCACCTTTCACTAAGTTGTTGAGGGGAAGGCTTACACAG
ACACATTCTTTAGAATTGGAAAAGTGAGACCAGGCACAGTGGCTCACACCTGTAATCCCAGCACT
TAGGGAAGACAAGTCAGGAGGATTGATTGAAGCTAGGAGTTAGAGACCAGCCTGGGCAACGTATT
GAGACCATGTCTATTAAAAAATAAAATGGAAAAGCAAGAATAGCCTTATTTTCAAAATATGGAAA
GAAATTTATATGAAAATTTATCTGAGTCATTAAAATTCTCCTTAAGTGATACTTTTTTAGAAGTA
CATTATGGCTAGAGTTGCCAGATAAAATGCTGGATATCATGCAATAAATTTGCAAAACATCATCT
AAAATTTAAAAAAAAAAAAAAAAAAAAAA

FIGURE 22

MEGESTSAVLSGFVLGALAFQHLNTDSDTEGFLLGEVKGEAKNSITDSQMDDVEVVYTIDIQKYI
PCYQLFSFYNSSGEVNEQALKKILSNVKKNVVGWYKFRRHSDQIMTFRERLLHKNLQEHFSNQDL
VFLLLTPSIITESCSTHRLEHSLYKPQKGLFHRVPLVVANLGMSEQLGYKTVSGSCMSTGFSRAV
QTHSSKFFEEDGSLKEVHKINEMYASLQEELKSICKKVEDSEQAVDKLVKDVNRLKREIEKRRGA
QIQAAREKNIQKDPQENIFLCQALRTFFPNSEFLHSCVMSLKNRHVSKSSCNYNHHLDVVDNLTL
MVEHTDIPEASPASTPQIIKHKALDLDDRWQFKRSRLLDTQDKRSKANTGSSNQDKASKMSSPET
DEEIEKMKGFGEYSRSPTF

Important features:
Signal peptide:
amino acids 1-19

N-glycosylation sites.
amino acids 75-79, 322-326

N-myristoylation site.
amino acids 184-154

Growth factor and cytokines receptors family.
amino acids 134-150

FIGURE 23

```
GGCACAGCCGCGCGGCGGAGGGCAGAGTCAGCCGAGCCGAGTCCAGCCGGACGAGCGGACCAGCGCAGGGCAGCCCAA
GCAGCGCGCAGCGAACGCCCGCCGCCGCCCACACCCTCTGCGGTCCCCGCGGCGCCTGCCACCCTTCCCTCCTTCCCC
GCGTCCCCGCCTCGCCGGCCAGTCAGCTTGCCGGGTTCGCTGCCCCGCGAAACCCCGAGGTCACCAGCCCGCGCCTCT
GCTTCCCTGGGCCGCGCGCCGCCTCCACGCCCTCCTTCTCCCCTGGCCCGGCGCCTGGCACCGGGGACCGTTGCCTGA
CGCGAGGCCCAGCTCTACTTTTCGCCCCGCGTCTCCTCCGCCTGCTCGCCTCTTCCACCAACTCCAACTCCTTCTCCC
TCCAGCTCCACTCGCTAGTCCCCGACTCCGCCAGCCCTCGGCCCGCTGCCGTAGCGCCGCTTCCCGTCCGGTCCCAAA
GGTGGGAACGCGTCCGCCCCGGCCCGCACCATGGCACGGTTCGGCTTGCCCGCGCTTCTCTGCACCCTGGCAGTGCTC
AGCGCCGCGCTGCTGGCTGCCGAGCTCAAGTCGAAAAGTTGCTCGGAAGTGCGACGTCTTTACGTGTCCAAAGGCTTC
AACAAGAACGATGCCCCCTCCACGAGATCAACGGTGATCATTTGAAGATCTGTCCCCAGGGTTCTACCTGCTGCTCT
CAAGAGATGGAGGAGAAGTACAGCCTGCAAAGTAAAGATGATTTCAAAAGTGTGGTCAGCGAACAGTGCAATCATTTG
CAAGCTGTCTTTGCTTCACGTTACAAGAAGTTTGATGAATTCTTCAAAGAACTACTTGAAAATGCAGAGAAATCCCTG
AATGATATGTTTGTGAAGACATATGGCCATTTATACATGCAAAATTCTGAGCTATTTAAAGATCTCTTCGTAGAGTTG
AAACGTTACTACGTGGTGGGAAATGTGAACCTGGAAGAAATGCTAAATGACTTCTGGGCTCGCCTCCTGGAGCGGATG
TTCCGCCTGGTGAACTCCCAGTACCACTTTACAGATGAGTATCTGGAATGTGTGAGCAAGTATACGGAGCAGCTGAAG
CCCTTCGGAGATGTCCCTCGCAAATTGAAGCTCCAGGTTACTCGTGCTTTTGTAGCAGCCCGTACTTTCGCTCAAGGC
TTAGCGGTTGCGGGAGATGTCGTGAGCAAGGTCTCCGTGGTAAACCCCACAGCCCAGTGTACCCATGCCCTGTTGAAG
ATGATCTACTGCTCCCACTGCCGGGGTCTCGTGACTGTGAAGCCATGTTACAACTACTGCTCAAACATCATGAGAGGC
TGTTTGGCCAACCAAGGGGATCTCGATTTTGAATGGAACAATTTCATAGATGCTATGCTGATGGTGGCAGAGAGGCTA
GAGGGTCCTTTCAACATTGAATCGGTCATGGATCCCATCGATGTGAAGATTTCTGATGCTATTATGAACATGCAGGAT
AATAGTGTTCAAGTGTCTCAGAAGGTTTTCCAGGGATGTGGACCCCCCAAGCCCCTCCCAGCTGGACGAATTTCTCGT
TCCATCTCTGAAAGTGCCTTCAGTGCTCGCTTCAGACCACATCACCCCGAGGAACGCCCAACCACAGCAGCTGGCACT
AGTTTGGACCGACTGGTTACTGATGTCAAGGAGAAACTGAAACAGGCCAAGAAATTCTGGTCCTCCCTTCCGAGCAAC
GTTTGCAACGATGAGAGGATGGCTGCAGGAAACGGCAATGAGGATGACTGTTGGAATGGGAAAGGCAAAAGCAGGTAC
CTGTTTGCAGTGACAGGAAATGGATTAGCCAACCAGGGCAACAACCCAGAGGTCCAGGTTGACACCAGCAAACCAGAC
ATACTGATCCTTCGTCAAATCATGGCTCTTCGAGTGATGACCAGCAAGATGAAGAATGCATACAATGGGAACGACGTG
GACTTCTTTGATATCAGTGATGAAAGTAGTGGAGAAGGAAGTGGAAGTGGCTGTGAGTATCAGCAGTGCCCTTCAGAG
TTTGACTACAATGCCACTGACCATGCTGGGAAGAGTGCCAATGAGAAAGCCGACAGTGCTGGTGTCCGTCCTGGGGCA
CAGGCCTACCTCCTCACTGTCTTCTGCATCTTGTTCCTGGTTATGCAGAGAGAGTGGAGATAATTCTCAAACTCTGAG
AAAAAGTGTTCATCAAAAAGTTAAAAGGCACCAGTTATCACTTTTCTACCATCCTAGTGACTTTGCTTTTTAAATGAA
TGGACAACAATGTACAGTTTTTACTATGTGGCCACTGGTTTAAGAAGTGCTGACTTTGTTTTCTCATTCAGTTTTGGG
AGGAAAAGGGACTGTGCATTGAGTTGGTTCCTGCTCCCCCAAACCATGTTAAACGTGGCTAACAGTGTAGGTACAGAA
CTATAGTTAGTTGTGCATTTGTGATTTATCACTCTATTATTTGTTTGTATGTTTTTTTCTCATTTCGTTTGTGGGTT
TTTTTTTCCAACTGTGATCTCGCCTTGTTTCTTACAAGCAAACCAGGGTCCCTTCTTGGCACGTAACATGTACGTATT
TCTGAAATATTAAATAGCTGTACAGAAGCAGGTTTTATTTATCATGTTATCTTATTAAAAGAAAAAGCCCAAAAAGC
```

FIGURE 24

MARFGLPALLCTLAVLSAALLAAELKSKSCSEVRRLYVSKGFNKNDAPLHEINGDHLKICPQGST
CCSQEMEEKYSLQSKDDFKSVVSEQCNHLQAVFASRYKKFDEFFKELLENAEKSLNDMFVKTYGH
LYMQNSELFKDLFVELKRYYVVGNVNLEEMLNDFWARLLERMFRLVNSQYHFTDEYLECVSKYTE
QLKPFGDVPRKLKLQVTRAFVAARTFAQGLAVAGDVVSKVSVVNPTAQCTHALLKMIYCSHCRGL
VTVKPCYNYCSNIMRGCLANQGDLDFEWNNFIDAMLMVAERLEGPFNIESVMDPIDVKISDAIMN
MQDNSVQVSQKVFQGCGPPKPLPAGRISRSISESAFSARFRPHHPEERPTTAAGTSLDRLVTDVK
EKLKQAKKFWSSLPSNVCNDERMAAGNGNEDDCWNGKGKSRYLFAVTGNGLANQGNNPEVQVDTS
KPDILILRQIMALRVMTSKMKNAYNGNDVDFFDISDESSGEGSGSGCEYQQCPSEFDYNATDHAG
KSANEKADSAGVRPGAQAYLLTVFCILFLVMQREWR

Important features:
Signal peptide:
amino acids 1-22

ATP/GTP-binding site motif A (P-loop).
amino acids 515-524

N-glycosylation site.
amino acids 514-518

Glycosaminoglycan attachment sites.
amino acids 494-498, 498-502

N-myristoylation sites.
amino acids 63-69, 224-230, 276-282, 438-444, 497-503, 531-537

Glypicans proteins.
amino acids 54-75, 105-157, 238-280, 309-346, 423-460, 468-506

FIGURE 25

CTCGCCCTCAAATGGGAACGCTGGCCTGGGACTAAAGCATAGACCACCAGGCTGAGTATCCTGAC
CTGAGTCATCCCCAGGGATCAGGAGCCTCCAGCAGGGAACCTTCCATTATATTCTTCAAGCAACT
TACAGCTGCACCGACAGTTGCG<u>ATG</u>AAAGTTCTAATCTCTTCCCTCCTCCTGTTGCTGCCACTAA
TGCTGATGTCCATGGTCTCTAGCAGCCTGAATCCAGGGGTCGCCAGAGGCCACAGGGACCGAGGC
CAGGCTTCTAGGAGATGGCTCCAGGAAGGCGGCCAAGAATGTGAGTGCAAAGATTGGTTCCTGAG
AGCCCCGAGAAGAAAATTCATGACAGTGTCTGGGCTGCCAAAGAAGCAGTGCCCCTGTGATCATT
TCAAGGGCAATGTGAAGAAAACAAGACACCAAAGGCACCACAGAAAGCCAAACAAGCATTCCAGA
GCCTGCCAGCAATTTCTCAAACAATGTCAGCTAAGAAGCTTTGCTCTGCCTTTG<u>TAG</u>GAGCTCTG
AGCGCCCACTCTTCCAATTAAACATTCTCAGCCAAGAAGACAGTGAGCACACCTACCAGACACTC
TTCTTCTCCCACCTCACTCTCCCACTGTACCCACCCCTAAATCATTCCAGTGCTCTCAAAAAGCA
TGTTTTTCAAGATCATTTTGTTTGTTGCTCTCTCTAGTGTCTTCTTCTCGTCAGTCTTAGCCT
GTGCCCTCCCCTTACCCAGGCTTAGGCTTAATTACCTGAAAGATTCCAGGAAACTGTAGCTTCCT
AGCTAGTGTCATTTAACCTTAAATGCAATCAGGAAGTAGCAAACAGAAGTCAATAAATATTTTT
AAATGTCAAAAAAAAAAAAAAAAA

FIGURE 26

MKVLISSLLLLLPLMLMSMVSSSLNPGVARGHRDRGQASRRWLQEGGQECECKDWFLRAPRRKFM
TVSGLPKKQCPCDHFKGNVKKTRHQRHHRKPNKHSRACQQFLKQCQLRSFALPL

Important features:

Signal peptide:

amino acids 1-22

N-myristoylation sites.

amino acids 27-33, 46-52

FIGURE 27

GGACGCCAGCGCCTGCAGAGGCTGAGCAGGGAAAAAGCCAGTGCCCCAGCGGAAGCACAGCTCAG
AGCTGGTCTGCC<u>ATG</u>GACATCCTGGTCCCACTCCTGCAGCTGCTGGTGCTGCTTCTTACCCTGCC
CCTGCACCTCATGGCTCTGCTGGGCTGCTGGCAGCCCCTGTGCAAAAGCTACTTCCCCTACCTGA
TGGCCGTGCTGACTCCCAAGAGCAACCGCAAGATGGAGAGCAAGAAACGGGAGCTCTTCAGCCAG
ATAAAGGGGCTTACAGGAGCCTCCGGGAAAGTGGCCCTACTGGAGCTGGGCTGCGGAACCGGAGC
CAACTTTCAGTTCTACCCACCGGGCTGCAGGGTCACCTGCCTAGACCCAAATCCCCACTTTGAGA
AGTTCCTGACAAAGAGCATGGCTGAGAACAGGCACCTCCAATATGAGCGGTTTGTGGTGGCTCCT
GGAGAGGACATGAGACAGCTGGCTGATGGCTCCATGGATGTGGTGGTCTGCACTCTGGTGCTGTG
CTCTGTGCAGAGCCCAAGGAAGGTCCTGCAGGAGGTCCGGAGAGTACTGAGACCGGGAGGTGTGC
TCTTTTTCTGGGAGCATGTGGCAGAACCATATGGAAGCTGGGCCTTCATGTGGCAGCAAGTTTTC
GAGCCCACCTGGAAACACATTGGGGATGGCTGCTGCCTCACCAGAGAGACCTGGAAGGATCTTGA
GAACGCCCAGTTCTCCGAAATCCAAATGGAACGACAGCCCCCTCCCTTGAAGTGGCTACCTGTTG
GGCCCCACATCATGGGAAAGGCTGTCAAACAATCTTTCCCAAGCTCCAAGGCACTCATTTGCTCC
TTCCCCAGCCTCCAATTAGAACAAGCCACCCACCAGCCTATCTATCTTCCACTGAGAGGGACC<u>TA</u>
<u>G</u>CAGAATGAGAGAAGACATTCATGTACCACCTACTAGTCCCTCTCTCCCCAACCTCTGCCAGGGC
AATCTCTAACTTCAATCCCGCCTTCGACAGTGAAAAAGCTCTACTTCTACGCTGACCCAGGGAGG
AAACACTAGGACCCTGTTGTATCCTCAACTGCAAGTTTCTGGACTAGTCTCCAACGTTTGCCTC
CCAATGTTGTCCCTTTCCTTCGTTCCCATGGTAAAGCTCCTCTCGCTTTCCTCCTGAGGCTACAC
CCATGCGTCTCTAGGAACTGGTCACAAAAGTCATGGTGCCTGCATCCCTGCCAAGCCCCCCTGAC
CCTCTCTCCCCACTACCACCTTCTTCCTGAGCTGGGGGCACCAGGGAGAATCAGAGATGCTGGGG
ATGCCAGAGCAAGACTCAAAGAGGCAGAGGTTTTGTTCTCAAATATTTTTAATAAATAGACGAA
ACCACG

FIGURE 28

MDILVPLLQLLVLLLTLPLHLMALLGCWQPLCKSYFPYLMAVLTPKSNRKMESKKRELFSQIKGL
TGASGKVALLELGCGTGANFQFYPPGCRVTCLDPNPHFEKFLTKSMAENRHLQYERFVVAPGEDM
RQLADGSMDVVVCTLVLCSVQSPRKVLQEVRRVLRPGGVLFFWEHVAEPYGSWAFMWQQVFEPTW
KHIGDGCCLTRETWKDLENAQFSEIQMERQPPPLKWLPVGPHIMGKAVKQSFPSSKALICSFPSL
QLEQATHQPIYLPLRGT

Important features:

Signal peptide:

amino acids 1-23

Leucine zipper pattern.

amino acids 10-32

N-myristoylation sites.

amino acids 64-70, 78-84, 80-86, 91-97, 201-207

FIGURE 29

CAATGTTTGCCTATCCACCTCCCCCAAGCCCCTTTACCT<u>ATG</u>CTGCTGCTAACGCTGCTGCTGCT
GCTGCTGCTGCTTAAAGGCTCATGCTTGGAGTGGGGACTGGTCGGTGCCCAGAAAGTCTCTTCTG
CCACTGACGCCCCCATCAGGGATTGGGCCTTCTTTCCCCCTTCCTTTCTGTGTCTCCTGCCTCAT
CGGCCTGCCATGACCTGCAGCCAAGCCCAGCCCCGTGGGGAAGGGGAGAAAGTGGGGGATGGC<u>TA</u>
<u>A</u>GAAAGCTGGGAGATAGGGAACAGAAGAGGGTAGTGGGTGGGCTAGGGGGCTGCCTTATTTAAA
GTGGTTGTTTATGATTCTTATACTAATTTATACAAAGATATTAAGGCCCTGTTCATTAAGAAATT
GTTCCCTTCCCCTGTGTTCAATGTTTGTAAAGATTGTTCTGTGTAAATATGTCTTTATAATAAAC
AGTTAAAAGCTGAAAAAAAAAAAAAAAAAAAAAAAAAAA

FIGURE 30

MLLLTLLLLLLLLKGSCLEWGLVGAQKVSSATDAPIRDWAFFPPSFLCLLPHRPAMTCSQAQPRG
EGEKVGDG

Important features:

Signal peptide:

amino acids 1-15

Growth factor and cytokines receptors family:

amino acids 3-18

FIGURE 31

```
GTTTGAATTCCTTCAACTATACCCACAGTCCAAAAGCAGACTCACTGTGTCCCAGGCTACCAGTT
CCTCCAAGCAAGTCATTTCCCTTATTTAACCGATGTGTCCCTCAAACACCTGAGTGCTACTCCCT
ATTTGCATCTGTTTTGATAAATGATGTTGACACCCTCCACCGAATTCTAAGTGGAATCATGTCGG
GAAGAGATACAATCCTTGGCCTGTGTATCCTCGCATTAGCCTTGTCTTTGGCCATGATGTTTACC
TTCAGATTCATCACCACCCTTCTGGTTCACATTTTCATTTCATTGGTTATTTTGGGATTGTTGTT
TGTCTGCGGTGTTTTATGGTGGCTGTATTATGACTATACCAACGACCTCAGCATAGAATTGGACA
CAGAAAGGGAAAATATGAAGTGCGTGCTGGGGTTTGCTATCGTATCCACAGGCATCACGGCAGTG
CTGCTCGTCTTGATTTTTGTTCTCAGAAAGAGAATAAAATTGACAGTTGAGCTTTTCCAAATCAC
AAATAAAGCCATCAGCAGTGCTCCCTTCCTGCTGTTCCAGCCACTGTGGACATTTGCCATCCTCA
TTTTCTTCTGGGTCCTCTGGGTGGCTGTGCTGCTGAGCCTGGGAACTGCAGGAGCTGCCCAGGTT
ATGGAAGGCGGCCAAGTGGAATATAAGCCCCTTTCGGGCATTCGGTACATGTGGTCGTACCATTT
AATTGGCCTCATCTGGACTAGTGAATTCATCCTTGCGTGCCAGCAAATGACTATAGCTGGGGCAG
TGGTTACTTGTTATTTCAACAGAAGTAAAAATGATCCTCCTGATCATCCCATCCTTTCGTCTCTC
TCCATTCTCTTCTTCTACCATCAAGGAACCGTTGTGAAAGGGTCATTTTTAATCTCTGTGGTGAG
GATTCCGAGAATCATTGTCATGTACATGCAAAACGCACTGAAAGAACAGCAGCATGGTGCATTGT
CCAGGTACCTGTTCCGATGCTGCTACTGCTGTTTCTGGTGTCTTGACAAATACCTGCTCCATCTC
AACCAGAATGCATATACTACAACTGCTATTAATGGGACAGATTTCTGTACATCAGCAAAAGATGC
ATTCAAAATCTTGTCCAAGAACTCAAGTCACTTTACATCTATTAACTGCTTTGGAGACTTCATAA
TTTTTCTAGGAAAGGTGTTAGTGGTGTGTTTCACTGTTTTTGGAGGACTCATGGCTTTTAACTAC
AATCGGGCATTCCAGGTGTGGGCAGTCCCTCTGTTATTGGTAGCTTTTTTTGCCTACTTAGTAGC
CCATAGTTTTTTATCTGTGTTTGAAACTGTGCTGGATGCACTTTTCCTGTGTTTTGCTGTTGATC
TGGAAACAAATGATGGATCGTCAGAAAAGCCCTACTTTATGGATCAAGAATTTCTGAGTTTCGTA
AAAAGGAGCAACAAATTAAACAATGCAAGGGCACAGCAGGACAAGCACTCATTAAGGAATGAGGA
GGGAACAGAACTCCAGGCCATTGTGAGATAGATACCCATTTAGGTATCTGTACCTGGAAAACATT
TCCTTCTAAGAGCCATTTACAGAATAGAAGATGAGACCACTAGAGAAAGTTAGTGAATTTTTTT
TTAAAAGACCTAATAAACCCTATTCTTCCTCAAAA
```

FIGURE 32

```
MSGRDTILGLCILALALSLAMMFTFRFITTLLVHIFISLVILGLLFVCGVLWWLYYDYTNDLSIE
LDTERENMKCVLGFAIVSTGITAVLLVLIFVLRKRIKLTVELFQITNKAISSAPFLLFQPLWTFA
ILIFFWVLWVAVLLSLGTAGAAQVMEGGQVEYKPLSGIRYMWSYHLIGLIWTSEFILACQQMTIA
GAVVTCYFNRSKNDPPDHPILSSLSILFFYHQGTVVKGSFLISVVRIPRIIVMYMQNALKEQQHG
ALSRYLFRCCYCCFWCLDKYLLHLNQNAYTTTAINGTDFCTSAKDAFKILSKNSSHFTSINCFGD
FIIFLGKVLVVCFTVFGGLMAFNYNRAFQVWAVPLLLVAFFAYLVAHSFLSVFETVLDALFLCFA
VDLETNDGSSEKPYFMDQEFLSFVKRSNKLNNARAQQDKHSLRNEEGTELQAIVR
```

Important features:

Signal peptide:

amino acids 1-20

Putative transmembrane domains:

amino acids 35-54, 75-97, 126-146, 185-204, 333-350, 352-371

N-glycosylation sites.

amino acids 204-208, 295-299, 313-317

N-myristoylation sites.

amino acids 147-153, 178-184, 196-202, 296-275, 342-348

FIGURE 33

```
GTTCGATTAGCTCCTCTGAGAAGAAGAGAAAAGGTTCTTGGACCTCTCCCTGTTTCTTCCTTAGA
ATAATTTGTATGGGATTTGTGATGCAGGAAAGCCTAAGGGAAAAAGAATATTCATTCTGTGTGGT
GAAAATTTTTTGAAAAAAAAATTGCCTTCTTCAAACAAGGGTGTCATTCTGATATTATGAGGAC
TGTTGTTCTCACTATGAAGGCATCTGTTATTGAAATGTTCCTTGTTTTGCTGGTGACTGGAGTAC
ATTCAAACAAAGAAACGGCAAAGAAGATTAAAAGGCCCAAGTTCACTGTGCCTCAGATCAACTGC
GATGTCAAAGCCGGAAAGATCATCGATCCTGAGTTCATTGTGAAATGTCCAGCAGGATGCCAAGA
CCCCAAATACCATGTTTATGGCACTGACGTGTATGCATCCTACTCCAGTGTGTGTGGCGCTGCCG
TACACAGTGGTGTGCTTGATAATTCAGGAGGGAAAATACTTGTTCGGAAGGTTGCTGGACAGTCT
GGTTACAAAGGGAGTTATTCCAACGGTGTCCAATCGTTATCCCTACCACGATGGAGAGAATCCTT
TATCGTCTTAGAAAGTAAACCCAAAAAGGGTGTAACCTACCCATCAGCTCTTACATACTCATCAT
CGAAAAGTCCAGCTGCCCAAGCAGGTGAGACCACAAAAGCCTATCAGAGGCCACCTATTCCAGGG
ACAACTGCACAGCCGGTCACTCTGATGCAGCTTCTGGCTGTCACTGTAGCTGTGGCCACCCCCAC
CACCTTGCCAAGGCCATCCCCTTCTGCTGCTTCTACCACCAGCATCCCCAGACCACAATCAGTGG
GCCACAGGAGCCAGGAGATGGATCTCTGGTCCACTGCCACCTACACAAGCAGCCAAAACAGGCCC
AGAGCTGATCCAGGTATCCAAAGGCAAGATCCTTCAGGAGCTGCCTTCCAGAAACCTGTTGGAGC
GGATGTCAGCCTGGGACTTGTTCCAAAAGAAGAATTGACCACACAGTCTTTGGAGCCAGTATCCC
TGGGAGATCCAAACTGCAAAATTGACTTGTCGTTTTAATTGATGGGAGCACCAGCATTGGCAAA
CGGCGATTCCGAATCCAGAAGCAGCTCCTGGCTGATGTTGCCCAAGCTCTTGACATTGGCCCTGC
CGGTCCACTGATGGGTGTTGTCCAGTATGGAGACAACCCTGCTACTCACTTTAACCTCAAGACAC
ACACGAATTCTCGAGATCTGAAGACAGCCATAGAGAAAATTACTCAGAGAGGAGGACTTTCTAAT
GTAGGTCGGGCCATCTCCTTTGTGACCAAGAACTTCTTTTCCAAAGCCAATGGAAACAGAAGCGG
GGCTCCCAATGTGGTGGTGGTGATGGTGGATGGCTGGCCCACGGACAAAGTGGAGGAGGCTTCAA
GACTTGCGAGAGAGTCAGGAATCAACATTTTCTTCATCACCATTGAAGGTGCTGCTGAAAATGAG
AAGCAGTATGTGGTGGAGCCCAACTTTGCAAACAAGGCCGTGTGCAGAACAAACGGCTTCTACTC
GCTCCACGTGCAGAGCTGGTTTGGCCTCCACAAGACCCTGCAGCCTCTGGTGAAGCGGGTCTGCG
ACACTGACCGCCTGGCCTGCAGCAAGACCTGCTTGAACTCGGCTGACATTGGCTTCGTCATCGAC
GGCTCCAGCAGTGTGGGGACGGCAACTTCCGCACCGTCCTCCAGTTTGTGACCAACCTCACCAA
AGAGTTTGAGATTTCCGACACGGACACGCGCATCGGGGCCGTGCAGTACACCTACGAACAGCGGC
TGGAGTTTGGGTTCGACAAGTACAGCAGCAAGCCTGACATCCTCAACGCCATCAAGAGGGTGGGC
TACTGGAGTGGTGGCACCAGCACGGGGCTGCCATCAACTTCGCCCTGGAGCAGCTCTTCAAGAA
GTCCAAGCCCAACAAGAGGAAGTTAATGATCCTCATCACCGACGGGAGGTCCTACGACGACGTCC
GGATCCCAGCCATGGCTGCCCATCTGAAGGGAGTGATCACCTATGCGATAGGCGTTGCCTGGGCT
GCCCAAGAGGAGCTAGAAGTCATTGCCACTCACCCCGCCAGAGACCACTCCTTCTTTGTGGACGA
GTTTGACAACCTCCATCAGTATGTCCCCAGGATCATCCAGAACATTTGTACAGAGTTCAACTCAC
AGCCTCGGAACTGAATTCAGAGCAGGCAGAGCACCAGCAAGTGCTGCTTTACTAACTGACGTGTT
GGACCACCCCACCGCTTAATGGGGCACGCACGGTGCATCAAGTCTTGGGCAGGGCATGGAGAAAC
AAATGTCTTGTTATTATTCTTTGCCATCATGCTTTTTCATATTCCAAAACTTGGAGTTACAAAGA
TGATCACAAACGTATAGAATGAGCCAAAAGGCTACATCATGTTGAGGGTGCTGGAGATTTTACAT
TTTGACAATTGTTTTCAAAATAAATGTTCGGAATACAGTGCAGCCCTTACGACAGGCTTACGTAG
AGCTTTTGTGAGATTTTTAAGTTGTTATTTCTGATTTGAACTCTGTAACCCTCAGCAAGTTTCAT
TTTTGTCATGACAATGTAGGAATTGCTGAATTAAATGTTTAGAAGGATGAAAAATAAAAAAAAAA
AAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAG
```

FIGURE 34

MRTVVLTMKASVIEMFLVLLVTGVHSNKETAKKIKRPKFTVPQINCDVKAGKIIDPEFIVKCPAG
CQDPKYHVYGTDVYASYSSVCGAAVHSGVLDNSGGKILVRKVAGQSGYKGSYSNGVQSLSLPRWR
ESFIVLESKPKKGVTYPSALTYSSSKSPAAQAGETTKAYQRPPIPGTTAQPVTLMQLLAVTVAVA
TPTTLPRPSPSAASTTSIPRPQSVGHRSQEMDLWSTATYTSSQNRPRADPGIQRQDPSGAAFQKP
VGADVSLGLVPKEELSTQSLEPVSLGDPNCKIDLSFLIDGSTSIGKRRFRIQKQLLADVAQALDI
GPAGPLMGVVQYGDNPATHFNLKTHTNSRDLKTAIEKITQRGGLSNVGRAISFVTKNFFSKANGN
RSGAPNVVVVMVDGWPTDKVEEASRLARESGINIFFITIEGAAENEKQYVVEPNFANKAVCRTNG
FYSLHVQSWFGLHKTLQPLVKRVCDTDRLACSKTCLNSADIGFVIDGSSSVGTGNFRTVLQFVTN
LTKEFEISDTDTRIGAVQYTYEQRLEFGFDKYSSKPDILNAIKRVGYWSGGTSTGAAINFALEQL
FKKSKPNKRKLMILITDGRSYDDVRIPAMAAHLKGVITYAIGVAWAAQEELEVIATHPARDHSFF
VDEFDNLHQYVPRIIQNICTEFNSQPRN

Important features:
Signal peptide:
amino acids 1-26

Transmembrane domain:
amino acids 181-200

N-glycosylation sites.
amino acids 390-394, 520-524

N-myristoylation sites.
amino acids 23-29, 93-99, 115-121, 262-268, 367-373, 389-395,
431-437, 466-472, 509-515, 570-576, 571-577, 575-581, 627-633

Amidation site.
amino acids 304-308

FIGURE 35

CCGAGCACAGGAGATTGCCTGCGTTTAGGAGGTGGCTGCGTTGTGGGAAAAGCTATCAAGGAAGAAATTGC
CAAACCATGTCTTTTTTTCTGTTTTCAGAGTAGTTCACAACAGATCTGAGTGTTTTAATTAAGCATGGAAT
ACAGAAAACAACAAAAAACTTAAGCTTTAATTTCATCTGGAATTCCACAGTTTTCTTAGCTCCCTGGACCC
GGTTGACCTGTTGGCTCTTCCCGCTGGCTGCTCTATCACGTGGTGCTCTCCGACTACTCACCCCGAGTGTA
AAGAACCTTCGGCTCGCGTGCTTCTGAGCTGCTGTGGATGGCCTCGGCTCTCTGGACTGTCCTTCCGAGTA
GGATGTCACTGAGATCCCTCAAATGGAGCCTCCTGCTGCTGTCACTCCTGAGTTTCTTTGTGATGTGGTAC
CTCAGCCTTCCCCACTACAATGTGATAGAACGCGTGAACTGGATGTACTTCTATGAGTATGAGCCGATTTA
CAGACAAGACTTTCACTTCACACTTCGAGAGCATTCAAACTGCTCTCATCAAAATCCATTTCTGGTCATTC
TGGTGACCTCCCACCCTTCAGATGTGAAAGCCAGGCAGGCCATTAGAGTTACTTGGGGTGAAAAAAAGTCT
TGGTGGGGATATGAGGTTCTTACATTTTTCTTATTAGGCCAAGAGGCTGAAAAGGAAGACAAAATGTTGGC
ATTGTCCTTAGAGGATGAACACCTTCTTTATGGTGACATAATCCGACAAGATTTTTTAGACACATATAATA
ACCTGACCTTGAAAACCATTATGGCATTCAGGTGGGTAACTGAGTTTTGCCCCAATGCCAAGTACGTAATG
AAGACAGACACTGATGTTTTCATCAATACTGGCAATTTAGTGAAGTATCTTTTAAACCTAAACCACTCAGA
GAAGTTTTTCACAGGTTATCCTCTAATTGATAATTATTCCTATAGAGGATTTTACCAAAAAACCCATATTT
CTTACCAGGAGTATCCTTTCAAGGTGTTCCCTCCATACTGCAGTGGGTTGGGTTATATAATGTCCAGAGAT
TTGGTGCCAAGGATCTATGAAATGATGGGTCACGTAAAACCCATCAAGTTTGAAGATGTTTATGTCGGGAT
CTGTTTGAATTTATTAAAAGTGAACATTCATATTCCAGAAGACACAAATCTTTTCTTTCTATATAGAATCC
ATTTGGATGTCTGTCAACTGAGACGTGTGATTGCAGCCCATGGCTTTTCTTCCAAGGAGATCATCACTTTT
TGGCAGGTCATGCTAAGGAACACCACATGCCATTATTAACTTCACATTCTACAAAAAGCCTAGAAGGACAG
GATACCTTGTGGAAAGTGTTAAATAAAGTAGGTACTGTGGAAAATCATGGGGAGGTCAGTGTGCTGGCTT
ACACTGAACTGAAACTCATGAAAAACCCAGACTGGAGACTGGAGGGTTACACTTGTGATTTATTAGTCAGG
CCCTTCAAAGATGATATGTGGAGGAATTAAATATAAAGGAATTGGAGGTTTTTGCTAAAGAAATTAATAGG
ACCAAACAATTTGGACATGTCATTCTGTAGACTAGAATTTCTTAAAAGGGTGTTACTGAGTTATAAGCTCA
CTAGGCTGTAAAAACAAAACAATGTAGAGTTTTATTTATTGAACAATGTAGTCACTTGAAGGTTTTGTGTA
TATCTTATGTGGATTACCAATTTAAAAATATATGTAGTTCTGTGTCAAAAAACTTCTTCACTGAAGTTATA
CTGAACAAAATTTTACCTGTTTTTGGTCATTTATAAAGTACTTCAAGATGTTGCAGTATTTCACAGTTATT
ATTATTTAAAATTACTTCAACTTTGTGTTTTTAAATGTTTTGACGATTTCAATACAAGATAAAAAGGATAG
TGAATCATTCTTTACATGCAAACATTTTCCAGTTACTTAACTGATCAGTTTATTATTGATACATCACTCCA
TTAATGTAAAGTCATAGGTCATTATTGCATATCAGTAATCTCTTGGACTTTGTTAAATATTTTACTGTGGT
AATATAGAGAAGAATTAAAGCAAGAAAATCTGAAAA

FIGURE 36

MASALWTVLPSRMSLRSLKWSLLLLSLLSFFVMWYLSLPHYNVIERVNWMYFYEYEPIYRQDFHF
TLREHSNCSHQNPFLVILVTSHPSDVKARQAIRVTWGEKKSWWGYEVLTFFLLGQEAEKEDKMLA
LSLEDEHLLYGDIIRQDFLDTYNNLTLKTIMAFRWVTEFCPNAKYVMKTDTDVFINTGNLVKYLL
NLNHSEKFFTGYPLIDNYSYRGFYQKTHISYQEYPFKVFPPYCSGLGYIMSRDLVPRIYEMMGHV
KPIKFEDVYVGICLNLLKVNIHIPEDTNLFFLYRIHLDVCQLRRVIAAHGFSSKEIITFWQVMLR
NTTCHY

Important features:

Type II transmembrane domain:
amino acids 20-39

N-glycosylation sites.
amino acids 72-76, 154-158, 198-202, 212-216, 326-330

Glycosaminoglycan attachment site.
amino acids 239-243

Ly-6 / u-PAR domain proteins.
amino acids 23-37

N-myristoylation site.
amino acids 271-277

FIGURE 37

```
CGCTCGGGCACCAGCCGCGGCAAGGATGGAGCTGGGTTGCTGGACGCAGTTGGGGCTCACTTTTCTTCAGCTCCTTCTCATC
TCGTCCTTGCCAAGAGAGTACACAGTCATTAATGAAGCCTGCCCTGGAGCAGAGTGGAATATCATGTGTCGGGAGTGCTGTG
AATATGATCAGATTGAGTGCGTCTGCCCCGGAAAGAGGGAAGTCGTGGGTTATACCATCCCTTGCTGCAGGAATGAGGAGAA
TGAGTGTGACTCCTGCCTGATCCACCCAGGTTGTACCATCTTTGAAAACTGCAAGAGCTGCCGAAATGGCTCATGGGGGGGT
ACCTTGGATGACTTCTATGTGAAGGGGTTCTACTGTGCAGAGTGCCGAGCAGGCTGGTACGGAGGAGACTGCATGCGATGTG
GCCAGGTTCTGCGAGCCCCAAAGGGTCAGATTTTGTTGGAAAGCTATCCCCTAAATGCTCACTGTGAATGGACCATTCATGC
TAAACCTGGGTTTGTCATCCAACTAAGATTTGTCATGTTGAGTCTGGAGTTTGACTACATGTGCCAGTATGACTATGTTGAG
GTTCGTGATGGAGACAACCGCGATGGCCAGATCATCAAGCGTGTCTGTGGCAACGAGCGGCCAGCTCCTATCCAGAGCATAG
GATCCTCACTCCACGTCCTCTTCCACTCCGATGGCTCCAAGAATTTTGACGGTTTCCATGCCATTTATGAGGAGATCACAGC
ATGCTCCTCATCCCCTTGTTTCCATGACGGCACGTGCGTCCTTGACAAGGCTGGATCTTACAAGTGTGCCTGCTTGGCAGGC
TATACTGGGCAGCGCTGTGAAAATCTCCTTGAAGAAAGAAACTGCTCAGACCCTGGGGGCCCAGTCAATGGGTACCAGAAAA
TAACAGGGGGCCCTGGGCTTATCAACGGACGCCATGCTAAAATTGGCACCGTGGTGTCTTTCTTTTGTAACAACTCCTATGT
TCTTAGTGGCAATGAGAAAAGAACTTGCCAGCAGAATGGAGAGTGGTCAGGGAAACAGCCCATCTGCATAAAAGCCTGCCGA
GAACCAAAGATTTCAGACCTGGTGAGAAGGAGAGTTCTTCCGATGCAGGTTCAGTCAAGGGAGACACCATTACACCAGCTAT
ACTCAGCGGCCTTCAGCAAGCAGAAACTGCAGAGTGCCCCTACCAAGAAGCCAGCCCTTCCCTTTGGAGATCTGCCCATGGG
ATACCAACATCTGCATACCCAGCTCCAGTATGAGTGCATCTCACCCTTCTACCGCCGCCTGGGCAGCAGCAGGAGGACATGT
CTGAGGACTGGGAAGTGGAGTGGGCGGGCACCATCCTGCATCCCTATCTGCGGGAAAATTGAGAACATCACTGCTCCAAAGA
CCCAAGGGTTGCGCTGGCCGTGGCAGGCAGCCATCTACAGGAGGACCAGCGGGGTGCATGACGGCAGCCTACACAAGGGAGC
GTGGTTCCTAGTCTGCAGCGGTGCCCTGGTGAATGAGCGCACTGTGGTGGTGGCTGCCCACTGTGTTACTGACCTGGGGAAG
GTCACCATGATCAAGACAGCAGACCTGAAAGTTGTTTTGGGGAAATTCTACCGGGATGATGACCGGGATGAGAAGACCATCC
AGAGCCTACAGATTTCTGCTATCATTCTGCATCCCAACTATGACCCCATCCTGCTTGATGCTGACATCGCCATCCTGAAGCT
CCTAGACAAGGCCCGTATCAGCACCCGAGTCCAGCCCATCTGCCTCGCTGCCAGTCGGGATCTCAGCACTTCCTTCCAGGAG
TCCCACATCACTGTGGCTGGCTGGAATGTCCTGGCAGACGTGAGGAGCCCTGGCTTCAAGAACGACACACTGCGCTCTGGGG
TGGTCAGTGTGGTGGACTCGCTGCTGTGTGAGGAGCAGCATGAGGACCATGGCATCCCAGTGAGTGTCACTGATAACATGTT
CTGTGCCAGCTGGGAACCCACTGCCCCTTCTGATATCTGCACTGCAGAGACAGGAGGCATCGCGGCTGTGTCCTTCCCGGGA
CGAGCATCTCCTGAGCCACGCTGGCATCTGATGGGACTGGTCAGCTGGAGCTATGATAAACATGCAGCCACAGGCTCTCCA
CTGCCTTCACCAAGGTGCTGCCTTTTAAAGACTGGATTGAAAGAAATATGAAATGAACCATGCTCATGCACTCCTTGAGAAG
TGTTTCTGTATATCCGTCTGTACGTGTGTCATTGCGTGAAGCAGTGTGGGCCTGAAGTGTGATTTGGCCTGTGAACTTGGCT
GTGCCAGGGCTTCTGACTTCAGGGACAAAACTCAGTGAAGGGTGAGTAGACCTCCATTGCTGGTAGGCTGATGCCGCGTCCA
CTACTAGGACAGCCAATTGGAAGATGCCAGGGCTTGCAAGAAGTAAGTTTCTTCAAAGAAGACCATATACAAAACCTCTCCA
CTCCACTGACCTGGTGGTCTTCCCCAACTTTCAGTTATACGAATGCCATCAGCTTGACCAGGGAAGATCTGGGCTTCATGAG
GCCCCTTTTGAGGCTCTCAAGTTCTAGAGAGCTGCCTGTGGGACAGCCCAGGGCAGCAGAGCTGGGATGTGGTGCATGCCTT
TGTGTACATGGCCACAGTACAGTCTGGTCCTTTTCCTTCCCCATCTCTTGTACACATTTTAATAAAATAAGGGTTGGCTTCT
GAACTACAAAAAAAAAAAAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
```

FIGURE 38

MELGCWTQLGLTFLQLLLISSLPREYTVINEACPGAEWNIMCRECCEYDQIECVCPGKREVVGYT
IPCCRNEENECDSCLIHPGCTIFENCKSCRNGSWGGTLDDFYVKGFYCAECRAGWYGGDCMRCGQ
VLRAPKGQILLESYPLNAHCEWTIHAKPGFVIQLRFVMLSLEFDYMCQYDYVEVRDGDNRDGQII
KRVCGNERPAPIQSIGSSLHVLFHSDGSKNFDGFHAIYEEITACSSSPCFHDGTCVLDKAGSYKC
ACLAGYTGQRCENLLEERNCSDPGGPVNGYQKITGGPGLINGRHAKIGTVVSFFCNNSYVLSGNE
KRTCQQNGEWSGKQPICIKACREPKISDLVRRRVLPMQVQSRETPLHQLYSAAFSKQKLQSAPTK
KPALPFGDLPMGYQHLHTQLQYECISPFYRRLGSSRRTCLRTGKWSGRAPSCIPICGKIENITAP
KTQGLRWPWQAAIYRRTSGVHDGSLHKGAWFLVCSGALVNERTVVVAAHCVTDLGKVTMIKTADL
KVVLGKFYRDDDRDEKTIQSLQISAIILHPNYDPILLDADIAILKLLDKARISTRVQPICLAASR
DLSTSFQESHITVAGWNVLADVRSPGFKNDTLRSGVVSVVDSLLCEEQHEDHGIPVSVTDNMFCA
SWEPTAPSDICTAETGGIAAVSFPGRASPEPRWHLMGLVSWSYDKTCSHRLSTAFTKVLPFKDWI
ERNMK

Important features of the protein:

Signal peptide:

amino acids 1-23

EGF-like domain cysteine pattern signature.

amino acids 260-272

N-glycosylation sites.

amino acids 96-100, 279-283, 316-320, 451-455, 614-618

N-myristoylation sites.

amino acids 35-41, 97-103, 256-262, 284-290, 298-304, 308-314, 474-480, 491-497, 638-644, 666-672

Amidation site.

amino acids 56-60

Serine proteases, trypsin family.

amino acids 489-506

CUB domain proteins profile.

amino acids 150-167

FIGURE 39

```
GGTTCCTACATCCTCTCATCTGAGAATCAGAGAGCATAATCTTCTTACGGGCCCGTGATTTATTAACGTGGCTTAATC
TGAAGGTTCTCAGTCAAATTCTTTGTGATCTACTGATTGTGGGGCATGGCAAGGTTTGCTTAAAGGAGCTTGGCTGG
TTTGGGCCCTTGTAGCTGACAGAAGGTGGCCAGGGAGAATGCAGCACACTGCTCGGAGAATGAAGGCGCTTCTGTTGC
TGGTCTTGCCTTGGCTCAGTCCTGCTAACTACATTGACAATGTGGGCAACCTGCACTTCCTGTATTCAGAACTCTGTA
AAGGTGCCTCCCACTACGGCCTGACCAAAGATAGGAAGAGGCGCTCACAAGATGGCTGTCCAGACGGCTGTGCGAGCC
TCACAGCCACGGCTCCCTCCCCAGAGGTTTCTGCAGCTGCCACCATCTCCTTAATGACAGACGAGCCTGGCCTAGACA
ACCCTGCCTACGTGTCCTCGGCAGAGGACGGGCAGCCAGCAATCAGCCCAGTGGACTCTGGCCGGAGCAACCGAACTA
GGGCACGGCCCTTTGAGAGATCCACTATTAGAAGCAGATCATTTAAAAAAAATAAATCGAGCTTTGAGTGTTCTTCGAA
GGACAAAGAGCGGGAGTGCAGTTGCCAACCATGCCGACCAGGGCAGGGAAAATTCTGAAAACACCACTGCCCCTGAAG
TCTTTCCAAGGTTGTACCACCTGATTCCAGATGGTGAAATTACCAGCATCAAGATCAATCGAGTAGATCCCAGTGAAA
GCCTCTCTATTAGGCTGGTGGGAGGTAGCGAAACCCCACTGGTCCATATCATTATCCAACACATTTATCGTGATGGGG
TGATCGCCAGAGACGGCCGGCTACTGCCAGGAGACATCATTCTAAAGGTCAACGGGATGGACATCAGCAATGTCCCTC
ACAACTACGCTGTGCGTCTCCTGCGGCAGCCCTGCCAGGTGCTGTGGCTGACTGTGATGCGTGAACAGAAGTTCCGCA
GCAGGAACAATGGACAGGCCCCGGATGCCTACAGACCCCGAGATGACAGCTTTCATGTGATTCTCAACAAAAGTAGCC
CCGAGGAGCAGCTTGGAATAAAACTGGTGCGCAAGGTGGATGAGCCTGGGGTTTTCATCTTCAATGTGCTGGATGGCG
GTGTGGCATATCGACATGGTCAGCTTGAGGAGAATGACCGTGTGTTAGCCATCAATGGACATGATCTTCGATATGGCA
GCCCAGAAAGTGCGGCTCATCTGATTCAGGCCAGTGAAAGACGTGTTCACCTCGTCGTGTCCCGCCAGGTTCGGCAGC
GGAGCCCTGACATCTTTCAGGAAGCCGGCTGGAACAGCAATGGCAGCTGGTCCCCAGGGCCAGGGGAGAGGAGCAACA
CTCCCAAGCCCCTCCATCCTACAATTACTTGTCATGAGAAGGTGGTAAATATCCAAAAAGACCCCGGTGAATCTCTCG
GCATGACCGTCGCAGGGGGAGCATACATAGAGAATGGGATTTGCCTATCTATGTCATCAGTGTTGAGCCCGGAGGAG
TCATAAGCAGAGATGGAAGAATAAAAACAGGTGACATTTTGTTGAATGTGGATGGGGTCGAACTGACAGAGGTCAGCC
GGAGTGAGGCAGTGGCATTATTGAAAAGAACATCATCCTCGATAGTACTCAAAGCTTTGGAAGTCAAAGAGTATGAGC
CCCAGGAAGACTGCAGCAGCCCAGCAGCCCTGGACTCCAACCACAACATGGCCCCACCCAGTGACTGGTCCCCATCCT
GGGTCATGTGGCTGGAATTACCACGGTGCTTGTATAACTGTAAAGATATTGTATTACGAAGAAACACAGCTGGAAGTC
TGGGCTTCTGCATTGTAGGAGGTTATGAAGAATACAATGGAAACAAACCTTTTTTCATCAAATCCATTGTTGAAGGAA
CACCAGCATACAATGATGGAAGAATTAGATGTGGTGATATTCTTCTTGCTGTCAATGGTAGAAGTACATCAGGAATGA
TACATGCTTGCTTGGCAAGACTGCTGAAAGAACTTAAAGGAAGAATTACTCTAACTATTGTTTCTTGGCCTGGCACTT
TTTTATAGAATCAATGATGGGTCAGAGGAAAACAGAAAAATCACAAATAGGCTAAGAAGTTGAAACACTATATTTATC
TTGTCAGTTTTTATATTTAAAGAAAGAATACATTGTAAAAATGTCAGGAAAAGTATGATCATCTAATGAAAGCCAGTT
ACACCTCAGAAAATATGATTCCAAAAAAATTAAAACTACTAGTTTTTTTTCAGTGTGGAGGATTTCTCATTACTCTAC
AACATTGTTTATATTTTTCTATTCAATAAAAAGCCCTAAAACAACTAAAATGATTGATTTGTATACCCCACTGAATT
CAAGCTGATTTAAATTTAAAATTTGGTATATGCTGAAGTCTGCCAAGGGTACATTATGGCCATTTTAATTTACAGCT
AAAATATTTTTTAAAATGCATTGCTGAGAAACGTTGCTTTCATCAAACAAGAATAAATATTTTTCAGAAGTTAAA
```

FIGURE 40

MKALLLLVLPWLSPANYIDNVGNLHFLYSELCKGASHYGLTKDRKRRSQDGCPDGCASLTATAPS
PEVSAAATISLMTDEPGLDNPAYVSSAEDGQPAISPVDSGRSNRTRARPFERSTIRSRSFKKINR
ALSVLRRTKSGSAVANHADQGRENSENTTAPEVFPRLYHLIPDGEITSIKINRVDPSESLSIRLV
GGSETPLVHIIIQHIYRDGVIARDGRLLPGDIILKVNGMDISNVPHNYAVRLLRQPCQVLWLTVM
REQKFRSRNNGQAPDAYRPRDDSFHVILNKSSPEEQLGIKLVRKVDEPGVFIFNVLDGGVAYRHG
QLEENDRVLAINGHDLRYGSPESAAHLIQASERRVHLVVSRQVRQRSPDIFQEAGWNSNGSWSPG
PGERSNTPKPLHPTITCHEKVVNIQKDPGESLGMTVAGGASHREWDLPIYVISVEPGGVISRDGR
IKTGDILLNVDGVELTEVSRSEAVALLKRTSSSIVLKALEVKEYEPQEDCSSPAALDSNHNMAPP
SDWSPSWVMWLELPRCLYNCKDIVLRRNTAGSLGFCIVGGYEEYNGNKPFFIKSIVEGTPAYNDG
RIRCGDILLAVNGRSTSGMIHACLARLLKELKGRITLTIVSWPGTFL

Important features:

Signal peptide:

amino acids 1-15

N-glycosylation sites.

amino acids 108-112, 157-161, 289-293, 384-388

Tyrosine kinase phosphorylation sites.

amino acids 433-441, 492-500

N-myristoylation sites.

amino acids 51-57, 141-147, 233-239, 344-350, 423-429, 447-453, 467-473, 603-609

FIGURE 41

ACCAGGCATTGTATCTTCAGTTGTCATCAAGTTCGCAATCAGATTGGAAAAGCTCAACTTGAAGCTTT
CTTGCCTGCAGTGAAGCAGAGAGATAGATATTATTCACGTAATAAAAAACATGGGCTTCAACCTGACT
TTCCACCTTTCCTACAAATTCCGATTACTGTTGCTGTTGACTTTGTGCCTGACAGTGGTTGGGTGGGC
CACCAGTAACTACTTCGTGGGTGCCATTCAAGAGATTCCTAAAGCAAAGGAGTTCATGGCTAATTTCC
ATAAGACCCTCATTTTGGGGAAGGGAAAAACTCTGACTAATGAAGCATCCACGAAGAAGGTAGAACTT
GACAACTGTCCTTCTGTGTCTCCTTACCTCAGAGGCCAGAGCAAGCTCATTTTCAAACCAGATCTCAC
TTTGGAAGAGGTACAGGCAGAAAATCCCAAAGTGTCCAGAGGCCGGTATCGCCCTCAGGAATGTAAAG
CTTTACAGAGGGTCGCCATCCTCGTTCCCCACCGGAACAGAGAGAAACACCTGATGTACCTGCTGGAA
CATCTGCATCCCTTCCTGCAGAGGCAGCAGCTGGATTATGGCATCTACGTCATCCACCAGGCTGAAGG
TAAAAAGTTTAATCGAGCCAAACTCTTGAATGTGGGCTATCTAGAAGCCCTCAAGGAAGAAAATTGGG
ACTGCTTTATATTCCACGATGTGGACCTGGTACCCGAGAATGACTTTAACCTTTACAAGTGTGAGGAG
CATCCCAAGCATCTGGTGGTTGGCAGGAACAGCACTGGGTACAGGTTACGTTACAGTGGATATTTTGG
GGGTGTTACTGCCCTAAGCAGAGAGCAGTTTTTCAAGGTGAATGGATTCTCTAACAACTACTGGGGAT
GGGGAGGCGAAGACGATGACCTCAGACTCAGGGTTGAGCTCCAAAGAATGAAAATTTCCCGGCCCCTG
CCTGAAGTGGGTAAATATACAATGGTCTTCCACACTAGAGACAAAGGCAATGAGGTGAACGCAGAACG
GATGAAGCTCTTACACCAAGTGTCACGAGTCTGGAGAACAGATGGGTTGAGTAGTTGTTCTTATAAAT
TAGTATCTGTGGAACACAATCCTTTATATATCAACATCACAGTGGATTTCTGGTTTGGTGCATGACCC
TGGATCTTTTGGTGATGTTTGGAAGAACTGATTCTTTGTTTGCAATAATTTTGGCCTAGAGACTTCAA
ATAGTAGCACACATTAAGAACCTGTTACAGCTCATTGTTGAGCTGAATTTTTCCTTTTTGTATTTTCT
TAGCAGAGCTCCTGGTGATGTAGAGTATAAAACAGTTGTAACAAGACAGCTTTCTTAGTCATTTTGAT
CATGAGGGTTAAATATTGTAATATGGATACTTGAAGGACTTTATATAAAAGGATGACTCAAAGGATAA
AATGAACGCTATTTGAGGACTCTGGTTGAAGGAGATTTATTTAAATTTGAAGTAATATATTATGGGAT
AAAAGGCCACAGGAAATAAGACTGCTGAATGTCTGAGAGAACCAGAGTTGTTCTCGTCCAAGGTAGAA
AGGTACGAAGATACAATACTGTTATTCATTTATCCTGTACAATCATCTGTGAAGTGGTGGTGTCAGGT
GAGAAGGCGTCCACAAAAGAGGGGAGAAAAGGCGACGAATCAGGACACAGTGAACTTGGGAATGAAGA
GGTAGCAGGAGGGTGGAGTGTCGGCTGCAAAGGCAGCAGTAGCTGAGCTGGTTGCAGGTGCTGATAGC
CTTCAGGGGAGGACCTGCCCAGGTATGCCTTCCAGTGATGCCCACCAGAGAATACATTCTCTATTAGT
TTTTAAAGAGTTTTTGTAAAATGATTTTGTACAAGTAGGATATGAATTAGCAGTTTACAAGTTTACAT
ATTAACTAATAATAAATATGTCTATCAAATACCTCTGTAGTAAAATGTGAAAAGCAAAA

FIGURE 42

MGFNLTFHLSYKFRLLLLLTLCLTVVGWATSNYFVGAIQEIPKAKEFMANFHKTLILGKGKTLTN
EASTKKVELDNCPSVSPYLRGQSKLIFKPDLTLEEVQAENPKVSRGRYRPQECKALQRVAILVPH
RNREKHLMYLLEHLHPFLQRQQLDYGIYVIHQAEGKKFNRAKLLNVGYLEALKEENWDCFIFHDV
DLVPENDFNLYKCEEHPKHLVVGRNSTGYRLRYSGYFGGVTALSREQFFKVNGFSNNYWGWGGED
DDLRLRVELQRMKISRPLPEVGKYTMVFHTRDKGNEVNAERMKLLHQVSRVWRTDGLSSCSYKLV
SVEHNPLYINITVDFWFGA

Important features:
Signal peptide:
amino acids 1-27

N-glycosylation sites.
amino acids 4-8, 220-224, 335-339

Xylose isomerase proteins.
amino acids 191-202

FIGURE 43

GCTCAAGACCCAGCAGTGGGACAGCCAGACAGACGGCACGATGGCACTGAGCTCCCAGATCTGGG
CCGCTTGCCTCCTGCTCCTCCTCCTCCTCGCCAGCCTGACCAGTGGCTCTGTTTTCCCACAACAG
ACGGGACAACTTGCAGAGCTGCAACCCCAGGACAGAGCTGGAGCCAGGGCCAGCTGGATGCCCAT
GTTCCAGAGGCGAAGGAGGCGAGACACCCACTTCCCCATCTGCATTTTCTGCTGCGGCTGCTGTC
ATCGATCAAAGTGTGGGATGTGCTGCAAGACGTAGAACCTACCTGCCCTGCCCCCGTCCCCTCCC
TTCCTTATTTATTCCTGCTGCCCCAGAACATAGGTCTTGGAATAAAATGGCTGGTTCTTTTGTTT
TCCAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAA

FIGURE 44

MALSSQIWAACLLLLLLLLASLTSGSVFPQQTGQLAELQPQDRAGARASWMPMFQRRRRRDTHFPI
CIFCCGCCHRSKCGMCCKT

Important features:

Signal peptide:

amino acids 1-24 cAMP- and cGMP-dependent protein kinase phosphorylation site.

amino acids 58-59

N-myristoylation site.

amino acids 44-50

Prokaryotic membrane lipoprotein lipid attachment site.

amino acids 1-12

FIGURE 45

GTGGCTTCATTTCAGTGGCTGACTTCCAGAGAGCAATATGGCTGGTTCCCCAACATGCCTCACCC
TCATCTATATCCTTTGGCAGCTCACAGGGTCAGCAGCCTCTGGACCCGTGAAAGAGCTGGTCGGT
TCCGTTGGTGGGGCCGTGACTTTCCCCCTGAAGTCCAAAGTAAAGCAAGTTGACTCTATTGTCTG
GACCTTCAACACAACCCCTCTTGTCACCATACAGCCAGAAGGGGGCACTATCATAGTGACCCAAA
ATCGTAATAGGGAGAGAGTAGACTTCCCAGATGGAGGCTACTCCTGAAGCTCAGCAAACTGAAG
AAGAATGACTCAGGGATCTACTATGTGGGGATATACAGCTCATCACTCCAGCAGCCCTCCACCCA
GGAGTACGTGCTGCATGTCTACGAGCACCTGTCAAAGCCTAAAGTCACCATGGGTCTGCAGAGCA
ATAAGAATGGCACCTGTGTGACCAATCTGACATGCTGCATGGAACATGGGGAAGAGGATGTGATT
TATACCTGGAAGGCCCTGGGGCAAGCAGCCAATGAGTCCCATAATGGGTCCATCCTCCCCATCTC
CTGGAGATGGGGAGAAAGTGATATGACCTTCATCTGCGTTGCCAGGAACCCTGTCAGCAGAAACT
TCTCAAGCCCCATCCTTGCCAGGAAGCTCTGTGAAGGTGCTGCTGATGACCCAGATTCCTCCATG
GTCCTCCTGTGTCTCCTGTTGGTGCCCCTCCTGCTCAGTCTCTTTGTACTGGGGCTATTTCTTTG
GTTTCTGAAGAGAGAGAGACAAGAAGAGTACATTGAAGAGAAGAAGAGAGTGGACATTTGTCGGG
AAACTCCTAACATATGCCCCCATTCTGGAGAGAACACAGAGTACGACACAATCCCTCACACTAAT
AGAACAATCCTAAAGGAAGATCCAGCAAATACGGTTTACTCCACTGTGGAAATACCGAAAAAGAT
GGAAAATCCCCACTCACTGCTCACGATGCCAGACACACCAAGGCTATTTGCCTATGAGAATGTTA
TCTAGACAGCAGTGCACTCCCCTAAGTCTCTGCTCA

FIGURE 46

MAGSPTCLTLIYILWQLTGSAASGPVKELVGSVGGAVTFPLKSKVKQVDSIVWTFNTTPLVTIQP
EGGTIIVTQNRNRERVDFPDGGYSLKLSKLKKNDSGIYYVGIYSSSLQQPSTQEYVLHVYEHLSK
PKVTMGLQSNKNGTCVTNLTCCMEHGEEDVIYTWKALGQAANESHNGSILPISWRWGESDMTFIC
VARNPVSRNFSSPILARKLCEGAADDPDSSMVLLCLLLVPLLLSLFVLGLFLWFLKRERQEEYIE
EKKRVDICRETPNICPHSGENTEYDTIPHTNRTILKEDPANTVYSTVEIPKKMENPHSLLTMPDT
PRLFAYENVI

Important features:

Signal peptide:

amino acids 1-22

Transmembrane domain:

amino acids 224-250

Leucine zipper pattern.

amino acids 229-251

N-glycosylation sites.

amino acids 98-102, 142-146, 148-152, 172-176, 176-180, 204-208, 291-295

FIGURE 47

GGCTCGAGCGTTTCTGAGCCAGGGGTGACCATGACCTGCTGCGAAGGATGGACATCCTGCAATGG
ATTCAGCCTGCTGGTTCTACTGCTGTTAGGAGTAGTTCTCAATGCGATACCTCTAATTGTCAGCT
TAGTTGAGGAAGACCAATTTTCTCAAAACCCCATCTCTTGCTTTGAGTGGTGGTTCCCAGGAATT
ATAGGAGCAGGTCTGATGGCCATTCCAGCAACAACAATGTCCTTGACAGCAAGAAAAGAGCGTG
CTGCAACAACAGAACTGGAATGTTTCTTTCATCATTTTTCAGTGTGATCACAGTCATTGGTGCTC
TGTATTGCATGCTGATATCCATCCAGGCTCTCTTAAAAGGTCCTCTCATGTGTAATTCTCCAAGC
AACAGTAATGCCAATTGTGAATTTTCATTGAAAAACATCAGTGACATTCATCCAGAATCCTTCAA
CTTGCAGTGGTTTTTCAATGACTCTTGTGCACCTCCTACTGGTTTCAATAAACCCACCAGTAACG
ACACCATGGCGAGTGGCTGGAGAGCATCTAGTTTCCACTTCGATTCTGAAGAAAACAAACATAGG
CTTATCCACTTCTCAGTATTTTTAGGTCTATTGCTTGTTGGAATTCTGGAGGTCCTGTTTGGGCT
CAGTCAGATAGTCATCGGTTTCCTTGGCTGTCTGTGTGGAGTCTCTAAGCGAAGAAGTCAAATTG
TGTAGTTTAATGGGAATAAAATGTAAGTATCAGTAGTTTGAAAAAAAAAA

FIGURE 48

MTCCEGWTSCNGFSLLVLLLLGVVLNAIPLIVSLVEEDQFSQNPISCFEWWFPGIIGAGLMAIPA
TTMSLTARKRACCNNRTGMFLSSFFSVITVIGALYCMLISIQALLKGPLMCNSPSNSNANCEFSL
KNISDIHPESFNLQWFFNDSCAPPTGFNKPTSNDTMASGWRASSFHFDSEENKHRLIHFSVFLGL
LLVGILEVLFGLSQIVIGFLGCLCGVSKRRSQIV

Important features:

Transmembrane domains:

amino acids 10-31 (type II), 50-72, 87-110, 191-213

N-glycosylation sites.

amino acids 80-84, 132-136, 148-152, 163-167 cAMP- and cGMP-dependent protein kinase phosphorylation site.

amino acids 223-227

N-myristoylation sites.

amino acids 22-28, 54-60, 83-89, 97-103, 216-222

Prokaryotic membrane lipoprotein lipid attachment site.

amino acids 207-218

TNFR/NGFR family cysteine-rich region protein.

amino acids 4-12

FIGURE 49

ATCCGTTCTCTGCGCTGCCAGCTCAGGTGAGCCCTCGCCAAGGTGACCTCGCAGGACACTGGTGA
AGGAGCAGTGAGGAACCTGCAGAGTCACACAGTTGCTGACCAATTGAGCTGTGAGCCTGGAGCAG
ATCCGTGGGCTGCAGACCCCCGCCCCAGTGCCTCTCCCCCTGCAGCCCTGCCCCTCGAACTGTGA
C<u>ATG</u>GAGAGAGTGACCCTGGCCCTTCTCCTACTGGCAGGCCTGACTGCCTTGGAAGCCAATGACC
CATTTGCCAATAAAGACGATCCCTTCTACTATGACTGGAAAAACCTGCAGCTGAGCGGACTGATC
TGCGGAGGGCTCCTGGCCATTGCTGGGATCGCGGCAGTTCTGAGTGGCAAATGCAAATACAAGAG
CAGCCAGAAGCAGCACAGTCCTGTACCTGAGAAGGCCATCCCACTCATCACTCCAGGCTCTGCCA
CTACTTGC<u>TGA</u>GCACAGGACTGGCCTCCAGGGATGGCCTGAAGCCTAACACTGGCCCCAGCACC
TCCTCCCTGGGAGGCCTTATCCTCAAGGAAGGACTTCTCTCCAAGGGCAGGCTGTTAGGCCCCT
TTCTGATCAGGAGGCTTCTTTATGAATTAAACTCGCCCCACCACCCCCTCA

FIGURE 50

MERVTLALLLLAGLTALEANDPFANKDDPFYYDWKNLQLSGLICGGLLAIAGIAAVLSGKCKYKS
SQKQHSPVPEKAIPLITPGSATTC

Important features:
Signal peptide:
amino acids 1-16

Transmembrane domain:
amino acids 36-59

N-myristoylation sites.
amino acids 41-47, 45-51, 84-90

Extracellular proteins SCP/Tpx-1/Ag5/PR-1/Sc7.
amino acids 54-67

FIGURE 51

```
GTGGACTCTGAGAAGCCCAGGCAGTTGAGGACAGGAGAGAGAAGGCTGCAGACCCAGAGGGAGGG
AGGACAGGGAGTCGGAAGGAGGAGGACAGAGGAGGGCACAGAGACGCAGAGCAAGGGCGGCAAGG
AGGAGACCCTGGTGGGAGGAAGACACTCTGGAGAGAGAGGGGGCTGGGCAGAGATGAAGTTCCAG
GGGCCCCTGGCCTGCCTCCTGCTGGCCCTCTGCCTGGGCAGTGGGGAGGCTGGCCCCCTGCAGAG
CGGAGAGGAAAGCACTGGGACAAATATTGGGGAGGCCCTTGGACATGGCCTGGGAGACGCCCTGA
GCGAAGGGGTGGGAAAGGCCATTGGCAAAGAGGCCGGAGGGGCAGCTGGCTCTAAAGTCAGTGAG
GCCCTTGGCCAAGGGACCAGAGAAGCAGTTGGCACTGGAGTCAGGCAGGTTCCAGGCTTTGGCGC
AGCAGATGCTTTGGGCAACAGGGTCGGGGAAGCAGCCCATGCTCTGGGAAACACTGGGCACGAGA
TTGGCAGACAGGCAGAAGATGTCATTCGACACGGAGCAGATGCTGTCCGCGGCTCCTGGCAGGGG
GTGCCTGGCCACAGTGGTGCTTGGGAAACTTCTGGAGGCCATGGCATCTTTGGCTCTCAAGGTGG
CCTTGGAGGCCAGGGCCAGGGCAATCCTGGAGGTCTGGGGACTCCGTGGGTCCACGGATACCCCG
GAAACTCAGCAGGCAGCTTTGGAATGAATCCTCAGGGAGCTCCCTGGGGTCAAGGAGGCAATGGA
GGGCCACCAAACTTTGGGACCAACACTCAGGGAGCTGTGGCCCAGCCTGGCTATGGTTCAGTGAG
AGCCAGCAACCAGAATGAAGGGTGCACGAATCCCCCACCATCTGGCTCAGGTGGAGGCTCCAGCA
ACTCTGGGGGAGGCAGCGGCTCACAGTCGGGCAGCAGTGGCAGTGGCAGCAATGGTGACAACAAC
AATGGCAGCAGCAGTGGTGGCAGCAGCAGTGGCAGCAGCAGTGGCAGCAGCAGTGGCGGCAGCAG
TGGCGGCAGCAGTGGTGGCAGCAGTGGCAACAGTGGTGGCAGCAGAGGTGACAGCGGCAGTGAGT
CCTCCTGGGGATCCAGCACCGGCTCCTCCTCCGGCAACCACGGTGGGAGCGGCGGAGGAAATGGA
CATAAACCCGGTGTGAAAAGCCAGGGAATGAAGCCCGCGGGAGCGGGGAATCTGGGATTCAGCG
CTTCAGAGGACAGGGAGTTTCCAGCAACATGAGGGAAATAAGCAAAGAGGGCAATCGCCTCCTTG
GAGGCTCTGGAGACAATTATCGGGGCAAGGGTCGAGCTGGGGCAGTGGAGGAGGTGACGCTGTT
GGTGGAGTCAATACTGTGAACTCTGAGACGTCTCCTGGGATGTTTAACTTTGACACTTTCTGGAA
GAATTTTAAATCCAAGCTGGGTTTCATCAACTGGGATGCCATAAACAAGGACCAGAGAAGCTCTC
GCATCCCGTGACCTCCAGACAAGGAGCCACCAGATTGGATGGGAGCCCCCACACTCCCTCCTTAA
AACACCACCCTCTCATCACTAATCTCAGCCCTTGCCCTTGAAATAAACCTTAGCTGCCCCACAAA
AAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAA
```

FIGURE 52

MKFQGPLACLLLALCLGSGEAGPLQSGEESTGTNIGEALGHGLGDALSEGVGKAIGKEAGGAAGSKVS
EALGQGTREAVGTGVRQVPGFGAADALGNRVGEAAHALGNTGHEIGRQAEDVIRHGADAVRGSWQGVP
GHSGAWETSGGHGIFGSQGGLGGQGQGNPGGLGTPWVHGYPGNSAGSFGMNPQGAPWGQGGNGGPPNF
GTNTQGAVAQPGYGSVRASNQNEGCTNPPPSGSGGGSSNSGGGSGSQSGSSGSGSGSNGDNNNGSSSGGS
SSGSSSGSSSGGSSGGSSGGSSGNSGGSRGDSGSESSWGSSTGSSSGNHGGSGGGNGHXPGCEKPGNE
ARGSGESGIQGFRGQGVSSNMREISKEGNRLLGGSGDNYRGQGSSWGSGGGDAVGGVNTVNSETSPGM
FNFDTFWKNFKSKLGFINWDAINKDQRSSRIP

Signal peptide:

amino acids 1-21

N-glycosylation site.

amino acids 265-269

Glycosaminoglycan attachment site.

amino acids 235-239, 237-241, 244-248, 255-259, 324-328, 388-392

Casein kinase II phosphorylation site.

amino acids 26-30, 109-113, 259-263, 300-304, 304-308

N-myristoylation site.

amino acids 17-23, 32-38, 42-48, 50-56, 60-66, 61-67, 64-70, 74-80,
90-96, 96-102, 130-136, 140-146, 149-155, 152-158, 155-161,
159-165, 163-169, 178-184, 190-196, 194-200, 199-205, 218-224,
236-242, 238-244, 239-245, 240-246, 245-251, 246-252, 249-252,
253-259, 256-262, 266-272, 270-276, 271-277, 275-281, 279-285,
283-289, 284-290, 287-293, 288-294, 291-297, 292-298, 295-301,
298-304, 305-311, 311-317, 315-321, 319-325, 322-328, 323-329,
325-331, 343-349, 354-360, 356-362, 374-380, 381-387, 383-389,
387-393, 389-395, 395-401

Cell attachment sequence.

amino acids 301-304

FIGURE 53

```
GGAGAAGAGGTTGTGTGGGACAAGCTGCTCCCGACAGAAGGATGTCGCTGCTGAGCCTGCCCTGG
CTGGGCCTCAGACCGGTGGCAATGTCCCCATGGCTACTCCTGCTGCTGGTTGTGGGCTCCTGGCT
ACTCGCCCGCATCCTGGCTTGGACCTATGCCTTCTATAACAACTGCCGCCGGCTCCAGTGTTTCC
CACAGCCCCCAAAACGGAACTGGTTTTGGGGTCACCTGGGCCTGATCACTCCTACAGAGGAGGGC
TTGAAGGACTCGACCCAGATGTCGGCCACCTATTCCCAGGGCTTTACGGTATGGCTGGGTCCCAT
CATCCCCTTCATCGTTTTATGCCACCCTGACACCATCCGGTCTATCACCAATGCCTCAGCTGCCA
TTGCACCCAAGGATAATCTCTTCATCAGGTTCCTGAAGCCCTGGCTGGGAGAAGGGATACTGCTG
AGTGGCGGTGACAAGTGGAGCCGCCACCGTCGGATGCTGACGCCCGCCTTCCATTTCAACATCCT
GAAGTCCTATATAACGATCTTCAACAAGAGTGCAAACATCATGCTTGACAAGTGGCAGCACCTGG
CCTCAGAGGGCAGCAGTCGTCTGGACATGTTTGAGCACATCAGCCTCATGACCTTGGACAGTCTA
CAGAAATGCATCTTCAGCTTTGACAGCCATTGTCAGGAGAGGCCCAGTGAATATATTGCCACCAT
CTTGGAGCTCAGTGCCCTTGTAGAGAAAAGAAGCCAGCATATCCTCCAGCACATGGACTTTCTGT
ATTACCTCTCCCATGACGGGCGGCGCTTCCACAGGGCCTGCCGCCTGGTGCATGACTTCACAGAC
GCTGTCATCCGGGAGCGGCGTCGCACCCTCCCCACTCAGGGTATTGATGATTTTTTCAAAGACAA
AGCCAAGTCCAAGACTTTGGATTTCATTGATGTGCTTCTGCTGAGCAAGGATGAAGATGGGAAGG
CATTGTCAGATGAGGATATAAGAGCAGAGGCTGACACCTTCATGTTTGGAGGCCATGACACCACG
GCCAGTGGCCTCTCCTGGGTCCTGTACAACCTTGCGAGGCACCCAGAATACCAGGAGCGCTGCCG
ACAGGAGGTGCAAGAGCTTCTGAAGGACCGCGATCCTAAAGAGATTGAATGGGACGACCTGGCCC
AGCTGCCCTTCCTGACCATGTGCGTGAAGGAGAGCCTGAGGTTACATCCCCCAGCTCCCTTCATC
TCCCGATGCTGCACCCAGGACATTGTTCTCCCAGATGGCCGAGTCATCCCCAAAGGCATTACCTG
CCTCATCGATATTATAGGGGTCCATCACAACCCAACTGTGTGGCCGGATCCTGAGGTCTACGACC
CCTTCCGCTTTGACCCAGAGAACAGCAAGGGGAGGTCACCTCTGGCTTTTATTCCTTTCTCCGCA
GGGCCCAGGAACTGCATCGGGCAGGCGTTCGCCATGGCGGAGATGAAAGTGGTCCTGGCGTTGAT
GCTGCTGCACTTCCGGTTCCTGCCAGACCACACTGAGCCCCGCAGGAAGCTGGAATTGATCATGC
GCGCCGAGGGCGGGCTTTGGCTGCGGGTGGAGCCCCTGAATGTAGGCTTGCAGTGACTTTCTGAC
CCATCCACCTGTTTTTTTGCAGATTGTCATGAATAAAACGGTGCTGTCAAA
```

FIGURE 54

MSLLSLPWLGLRPVAMSPWLLLLLVVGSWLLARILAWTYAFYNNCRRLQCFPQPPKRNWFWGHLG
LITPTEEGLKDSTQMSATYSQGFTVWLGPIIPFIVLCHPDTIRSITNASAAIAPKDNLFIRFLKP
WLGEGILLSGGDKWSRHRRMLTPAFHFNILKSYITIFNKSANIMLDKWQHLASEGSSRLDMFEHI
SLMTLDSLQKCIFSFDSHCQERPSEYIATILELSALVEKRSQHILQHMDFLYYLSHDGRRFHRAC
RLVHDFTDAVIRERRRTLPTQGIDDFFKDKAKSKTLDFIDVLLLSKDEDGKALSDEDIRAEADTF
MFGGHDTTASGLSWVLYNLARHPEYQERCRQEVQELLKDRDPKEIEWDDLAQLPFLTMCVKESLR
LHPPAPFISRCCTQDIVLPDGRVIPKGITCLIDIIGVHHNPTVWPDPEVYDPFRFDPENSKGRSP
LAFIPFSAGPRNCIGQAFAMAEMKVVLALMLLHFRFLPDHTEPRRKLELIMRAEGGLWLRVEPLN
VGLQ

Important features:

Transmembrane domains:

amino acids 13-32 (type II), 77-102

Cytochrome P450 cysteine heme-iron ligand signature.

amino acids 461-471

N-glycosylation sites.

amino acids 112-116, 168-172

FIGURE 55

ATCGCATCAATTGGGAGTACCATCTTCCTC<u>ATG</u>GGACCAGTGAAACAGCTGAAGCGAATGTTTGA
GCCTACTCGTTTGATTGCAACTATCATGGTGCTGTTGTGTTTTGCACTTACCCTGTGTTCTGCCT
TTTGGTGGCATAACAAGGGACTTGCACTTATCTTCTGCATTTTGCAGTCTTTGGCATTGACGTGG
TACAGCCTTTCCTTCATACCATTTGCAAGGGATGCTGTGAAGAAGTGTTTTGCCGTGTGTCTTGC
A<u>TAA</u>TTCATGGCCAGTTTTATGAAGCTTTGGAAGGCACTATGGACAGAAGCTGGTGGACAGTTTT
GTAACTATCTTCGAAACCTCTGTCTTACAGACATGTGCCTTTTATCTTGCAGCAATGTGTTGCTT
GTGATTCGAACATTTGAGGGTTACTTTTGGAAGCAACAATACATTCTCGAACCTGAATGTCAGTA
GCACAGGATGAGAAGTGGGTTCTGTATCTTGTGGAGTGGAATCTTCCTCATGTACCTGTTTCCTC
TCTGGATGTTGTCCCACTGAATTCCCATGAATACAAACCTATTCAGCAACAGCAAAAAAAAAAAA
AAAAAAAAAAAAAAAAAAAAAAAAAAAAAAAAAAAAAAAAAAAAAAAAAAAAAA

FIGURE 56

MGPVKQLKRMFEPTRLIATIMVLLCFALTLCSAFWWHNKGLALIFCILQSLALTWYSLSFIPFAR
DAVKKCFAVCLA

Important features:

Signal peptide:

amino acids 1-33

Type II fibronectin collagen-binding domain protein.

amino acids 30-72

FIGURE 57

```
CGGCTCGAGCTCGAGCCGAATCGGCTCGAGGGGCAGTGGAGCACCCAGCAGGCCGCCAACATGCTCTGTCTGTGCCTG
TACGTGCCGGTCATCGGGGAAGCCCAGACCGAGTTCCAGTACTTTGAGTCGAAGGGGCTCCCTGCCGAGCTGAAGTCC
ATTTTCAAGCTCAGTGTCTTCATCCCCTCCCAGGAATTCTCCACCTACCGCCAGTGGAAGCAGAAAATTGTACAAGCT
GGAGATAAGGACCTTGATGGGCAGCTAGACTTTGAAGAATTTGTCCATTATCTCCAAGATCATGAGAAGAAGCTGAGG
CTGGTGTTTAAGATTTTGGACAAAAAGAATGATGGACGCATTGACGCGCAGGAGATCATGCAGTCCCTGCGGGACTTG
GGAGTCAAGATATCTGAACAGCAGGCAGAAAAAATTCTCAAGAGCATGGATAAAAACGGCACGATGACCATCGACTGG
AACGAGTGGAGAGACTACCACCTCCTCCACCCCGTGGAAAACATCCCCGAGATCATCCTCTACTGGAAGCATTCCACG
ATCTTTGATGTGGGTGAGAATCTAACGGTCCCGGATGAGTTCACAGTGGAGGAGAGGCAGACGGGGATGTGGTGGAGA
CACCTGGTGGCAGGAGGTGGGGCAGGGGCCGTATCCAGAACCTGCACGGCCCCCCTGGACAGGCTCAAGGTGCTCATG
CAGGTCCATGCCTCCCGCAGCAACAACATGGGCATCGTTGGTGGCTTCACTCAGATGATTCGAGAAGGAGGGGCCAGG
TCACTCTGGCGGGGCAATGGCATCAACGTCCTCAAAATTGCCCCCGAATCAGCCATCAAATTCATGGCCTATGAGCAG
ATCAAGCGCCTTGTTGGTAGTGACCAGGAGACTCTGAGGATTCACGAGAGGCTTGTGGCAGGGTCCTTGGCAGGGGCC
ATCGCCCAGAGCAGCATCTACCCAATGGAGGTCCTGAAGACCCGGATGGCGCTGCGGAAGACAGGCCAGTACTCAGGA
ATGCTGGACTGCGCCAGGAGGATCCTGGCCAGAGAGGGGGTGGCCGCCTTCTACAAAGGCTATGTCCCCAACATGCTG
GGCATCATCCCCTATGCCGGCATCGACCTTGCAGTCTACGAGACGCTCAAGAATGCCTGGCTGCAGCACTATGCAGTG
AACAGCGCGGACCCCGGCGTGTTTGTGCTCCTGGCCTGTGGCACCATGTCCAGTACCTGTGGCCAGCTGGCCAGCTAC
CCCCTGGCCCTAGTCAGGACCCGGATGCAGGCGCAAGCCTCTATTGAGGGCGCTCCGGAGGTGACCATGAGCAGCCTC
TTCAAACATATCCTGCGGACCGAGGGGGCCTTCGGGCTGTACAGGGGCTGGCCCCCAACTTCATGAAGGTCATCCCA
GCTGTGAGCATCAGCTACGTGGTCTACGAGAACCTGAAGATCACCCTGGGCGTGCAGTCGCGGTGACGGGGGGAGGGC
CGCCCGGCAGTGGACTCGCTGATCCTGGGCCGCAGCCTGGGGTGTGCAGCCATCTCATTCTGTGAATGTGCCAACACT
AAGCTGTCTCGAGCCAAGCTGTGAAAACCCTAGACGCACCCGCAGGGAGGGTGGGGAGAGCTGGCAGGCCCAGGGCTT
GTCCTGCTGACCCCAGCAGACCCTCCTGTTGGTTCCAGCGAAGACCACAGGCATTCCTTAGGGTCCAGGGTCAGCAGG
CTCCGGGCTCACATGTGTAAGGACAGGACATTTTCTGCAGTGCCTGCCAATAGTGAGCTTGGAGCCTGGAGGCCGGCT
TAGTTCTTCCATTTCACCCTTGCAGCCAGCTGTTGGCCACGGCCCTGCCCTCTGGTCTGCCGTGCATCTCCCTGTGC
CCTCTTGCTGCCTGCCTGTCTGCTGAGGTAAGGTGGGAGGAGGGCTACAGCCCACATCCCACCCCCTCGTCCAATCCC
ATAATCCATGATGAAAGGTGAGGTCACGTGGCCTCCCAGGCCTGACTTCCCAACCTACAGCATTGACGCCAACTTGGC
TGTGAAGGAAGAGGAAAGGATCTGGCCTTGTGGTCACTGGCATCTGAGCCCTGCTGATGGCTGGGGCTCTCGGGCATG
CTTGGGAGTGCAGGGGGCTCGGGCTGCCTGGCCTGGCTGCACAGAAGGCAAGTGCTGGGGCTCATGGTGCTCTGAGCT
GGCCTGGACCCTGTCAGGATGGGCCCCACCTCAGAACCAAACTCACTGTCCCCACTGTGGCATGAGGGCAGTGGAGCA
CCATGTTTGAGGGCGAAGGGCAGAGCGTTTGTGTGTTCTGGGGAGGGAAGGAAAAGGTGTTGGAGGCCTTAATTATGG
ACTGTTGGGAAAAGGGTTTTGTCCAGAAGGACAAGCCGGACAAATGAGCGACTTCTGTGCTTCCAGAGGAAGACGAGG
GAGCAGGAGCTTGGCTGACTGCTCAGAGTCTGTTCTGACGCCCTGGGGGTTCCTGTCCAACCCCAGCAGGGGCGCAGC
GGGACCAGCCCCACATTCCACTTGTGTCACTGCTTGGAACCTATTTATTTTGTATTTATTTGAACAGAGTTATGTCCT
AACTATTTTTATAGATTTGTTTAATTAATAGCTTGTCATTTTCAAGTTCATTTTTTATTCATATTTATGTTCATGGTT
GATTGTACCTTCCCAAGCCCGCCCAGTGGGATGGGAGGAGGAGGAGAAGGGGGCCTTGGGCCGCTGCAGTCACATCT
GTCCAGAGAAATTCCTTTTGGGACTGGAGGCAGAAAAGCGGCCAGAAGGCAGCAGCCCTGGCTCCTTTCCTTTGGCAG
GTTGGGGAAGGGCTTGCCCCCAGCCTTAGGATTTCAGGGTTTGACTGGGGGCGTGGAGAGAGGGGAGGAACCTCAAT
AACCTTGAAGGTGGAATCCAGTTATTTCCTGCGCTGCGAGGGTTTCTTTATTTCACTCTTTTCTGAATGTCAAGGCAG
TGAGGTGCCTCTCACTGTGAATTTGTGGTGGGCGGGGCTGGAGGAGAGGGTGGGGGCTGGCTCCGTCCCTCCCAGC
CTTCTGCTGCCCTTGCTTAACAATGCCGGCCAACTGGCGACCTCACGGTTGCACTTCCATTCCACCAGAATGACCTGA
TGAGGAAATCTTCAATAGGATGCAAAGATCAATGCAAAAATTGTTATATATGAACATATAACTGGAGTCGTCAAAAAG
CAAATTAAGAAAGAATTGGACGTTAGAAGTTGTCATTTAAAGCAGCCTTCTAATAAAGTTGTTTCAAAGCTGAAAAAA
AAAAAAAAAAAAAAAAAAAAAAAAAAAAAAAAAAAAAAAAAAAAAAAAAAAA
```

FIGURE 58

MLCLCLYVPVIGEAQTEFQYFESKGLPAELKSIFKLSVFIPSQEFSTYRQWKQKIVQAGDKDLDG
QLDFEEFVHYLQDHEKKLRLVFKILDKKNDGRIDAQEIMQSLRDLGVKISEQQAEKILKSMDKNG
TMTIDWNEWRDYHLLHPVENIPEIILYWKHSTIFDVGENLTVPDEFTVEERQTGMWWRHLVAGGG
AGAVSRTCTAPLDRLKVLMQVHASRSNNMGIVGGFTQMIREGGARSLWRGNGINVLKIAPESAIK
FMAYEQIKRLVGSDQETLRIHERLVAGSLAGAIAQSSIYPMEVLKTRMALRKTGQYSGMLDCARR
ILAREGVAAFYKGYVPNMLGIIPYAGIDLAVYETLKNAWLQHYAVNSADPGVFVLLACGTMSSTC
GQLASYPLALVRTRMQAQASIEGAPEVTMSSLFKHILRTEGAFGLYRGLAPNFMKVIPAVSISYV
VYENLKITLGVQSR

Important features:

Signal peptide:

amino acids 1-16

Putative transmembrane domains:

amino acids 284-304, 339-360, 376-394

Mitochondrial energy transfer proteins signature.

amino acids 206-215, 300-309

N-glycosylation sites.

amino acids 129-133, 169-173

Elongation Factor-hand calcium-binding protein.

amino acids 54-73, 85-104, 121-140

FIGURE 59

```
GGAAGGCAGCGGCAGCTCCACTCAGCCAGTACCCAGATACGCTGGGAACCTTCCCCAGCCATGGC
TTCCCTGGGGCAGATCCTCTTCTGGAGCATAATTAGCATCATCATTATTCTGGCTGGAGCAATTG
CACTCATCATTGGCTTTGGTATTTCAGGGAGACACTCCATCACAGTCACTACTGTCGCCTCAGCT
GGGAACATTGGGGAGGATGGAATCCTGAGCTGCACTTTTGAACCTGACATCAAACTTTCTGATAT
CGTGATACAATGGCTGAAGGAAGGTGTTTTAGGCTTGGTCCATGAGTTCAAAGAAGGCAAAGATG
AGCTGTCGGAGCAGGATGAAATGTTCAGAGGCCGGACAGCAGTGTTTGCTGATCAAGTGATAGTT
GGCAATGCCTCTTTGCGGCTGAAAAACGTGCAACTCACAGATGCTGGCACCTACAAATGTTATAT
CATCACTTCTAAAGGCAAGGGGAATGCTAACCTTGAGTATAAAACTGGAGCCTTCAGCATGCCGG
AAGTGAATGTGGACTATAATGCCAGCTCAGAGACCTTGCGGTGTGAGGCTCCCCGATGGTTCCCC
CAGCCCACAGTGGTCTGGGCATCCCAAGTTGACCAGGGAGCCAACTTCTCGGAAGTCTCCAATAC
CAGCTTTGAGCTGAACTCTGAGAATGTGACCATGAAGGTTGTGTCTGTGCTCTACAATGTTACGA
TCAACAACACATACTCCTGTATGATTGAAAATGACATTGCCAAAGCAACAGGGGATATCAAAGTG
ACAGAATCGGAGATCAAAAGGCGGAGTCACCTACAGCTGCTAAACTCAAAGGCTTCTCTGTGTGT
CTCTTCTTTCTTTGCCATCAGCTGGGCACTTCTGCCTCTCAGCCCTTACCTGATGCTAAAATAAT
GTGCCTTGGCCACAAAAAAGCATGCAAAGTCATTGTTACAACAGGGATCTACAGAACTATTTCAC
CACCAGATATGACCTAGTTTTATATTTCTGGGAGGAAATGAATTCATATCTAGAAGTCTGGAGTG
AGCAAACAAGAGCAAGAAACAAAAAGAAGCCAAAAGCAGAAGGCTCCAATATGAACAAGATAAAT
CTATCTTCAAAGACATATTAGAAGTTGGGAAAATAATTCATGTGAACTAGACAAGTGTGTTAAGA
GTGATAAGTAAAATGCACGTGGAGACAAGTGCATCCCCAGATCTCAGGGACCTCCCCCTGCCTGT
CACCTGGGGAGTGAGAGGACAGGATAGTGCATGTTCTTTGTCTCTGAATTTTTAGTTATATGTGC
TGTAATGTTGCTCTGAGGAAGCCCCTGGAAAGTCTATCCCAACATATCCACATCTTATATTCCAC
AAATTAAGCTGTAGTATGTACCCTAAGACGCTGCTAATTGACTGCCACTTCGCAACTCAGGGGCG
GCTGCATTTTAGTAATGGGTCAAATGATTCACTTTTTATGATGCTTCCAAAGGTGCCTTGGCTTC
TCTTCCCAACTGACAAATGCCAAAGTTGAGAAAAATGATCATAATTTTAGCATAAACAGAGCAGT
CGGGGACACCGATTTTATAAATAAACTGAGCACCTTCTTTTTAAACAAAAAAAAAAAAAAAAAAA
AAAAAAAAAAAAAAAAAAAAAAAAAAAAAA
```

FIGURE 60

MASLGQILFWSIISIIIILAGAIALIIGFGISGRHSITVTTVASAGNIGEDGILSCTFEPDIKLS
DIVIQWLKEGVLGLVHEFKEGKDELSEQDEMFRGRTAVFADQVIVGNASLRLKNVQLTDAGTYKC
YIITSKGKGNANLEYKTGAFSMPEVNVDYNASSETLRCEAPRWFPQPTVVWASQVDQGANFSEVS
NTSFELNSENVTMKVVSVLYNVTINNTYSCMIENDIAKATGDIKVTESEIKRRSHLQLLNSKASL
CVSSFFAISWALLPLSPYLMLK

Important features:
Signal peptide:
amino acids 1-28

Transmembrane domain:
amino acids 258-281

N-glycosylation sites.
amino acids 112-116, 160-164, 190-194, 196-200, 205-209, 216-220, 220-224

N-myristoylation sites.
amino acids 52-58, 126-132, 188-194

FIGURE 61

TGACGTCAGAATCACCATGGCCAGCTATCCTTACCGGCAGGGCTGCCCAGGAGCTGCAGGACAAG
CACCAGGAGCCCCTCCGGGTAGCTACTACCCTGGACCCCCAATAGTGGAGGGCAGTATGGTAGT
GGGCTACCCCCTGGTGGTGGTTATGGGGGTCCTGCCCCTGGAGGGCCTTATGGACCACCAGCTGG
TGGAGGGCCCTATGGACACCCCAATCCTGGGATGTTCCCCTCTGGAACTCCAGGAGGACCATATG
GCGGTGCAGCTCCCGGGGGCCCCTATGGTCAGCCACCTCCAAGTTCCTACGGTGCCCAGCAGCCT
GGGCTTTATGGACAGGGTGGCGCCCCTCCCAATGTGGATCCTGAGGCCTACTCCTGGTTCCAGTC
GGTGGACTCAGATCACAGTGGCTATATCTCCATGAAGGAGCTAAAGCAGGCCCTGGTCAACTGCA
ATTGGTCTTCATTCAATGATGAGACCTGCCTCATGATGATAAACATGTTTGACAAGACCAAGTCA
GGCCGCATCGATGTCTACGGCTTCTCAGCCCTGTGGAAATTCATCCAGCAGTGGAAGAACCTCTT
CCAGCAGTATGACCGGGACCGCTCGGGCTCCATTAGCTACACAGAGCTGCAGCAAGCTCTGTCCC
AAATGGGCTACAACCTGAGCCCCCAGTTCACCCAGCTTCTGGTCTCCCGCTACTGCCCACGCTCT
GCCAATCCTGCCATGCAGCTTGACCGCTTCATCCAGGTGTGCACCCAGCTGCAGGTGCTGACAGA
GGCCTTCCGGGAGAAGGACACAGCTGTACAAGGCAACATCCGGCTCAGCTTCGAGGACTTCGTCA
CCATGACAGCTTCTCGGATGCTATGACCCAACCATCTGTGGAGAGTGGAGTGCACCAGGGACCTT
TCCTGGCTTCTTAGAGTGAGAGAAGTATGTGGACATCTCTTCTTTTCCTGTCCCTCTAGAAGAAC
ATTCTCCCTTGCTTGATGCAACACTGTTCCAAAAGAGGGTGGAGAGTCCTGCATCATAGCCACCA
AATAGTGAGGACCGGGGCTGAGGCCACACAGATAGGGGCCTGATGGAGGAGAGGATAGAAGTTGA
ATGTCCTGATGGCCATGAGCAGTTGAGTGGCACAGCCTGGCACCAGGAGCAGGTCCTTGTAATGG
AGTTAGTGTCCAGTCAGCTGAGCTCCACCCTGATGCCAGTGGTGAGTGTTCATCGGCCTGTTACC
GTTAGTACCTGTGTTCCCTCACCAGGCCATCCTGTCAAACGAGCCCATTTTCTCCAAAGTGGAAT
CTGACCAAGCATGAGAGAGATCTGTCTATGGGACCAGTGGCTTGGATTCTGCCACACCCATAAAT
CCTTGTGTGTTAACTTCTAGCTGCCTGGGGCTGGCCCTGCTCAGACAAATCTGCTCCCTGGGCAT
CTTTGGCCAGGCTTCTGCCCCCTGCAGCTGGGACCCCTCACTTGCCTGCCATGCTCTGCTCGGCT
TCAGTCTCCAGGAGACAGTGGTCACCTCTCCCTGCCAATACTTTTTTAATTTGCATTTTTTTC
ATTTGGGGCCAAAAGTCCAGTGAAATTGTAAGCTTCAATAAAAGGATGAAACTCTGA

FIGURE 62

MASYPYRQGCPGAAGQAPGAPPGSYYPGPPNSGGQYGSGLPPGGGYGGPAPGGPYGPPAGGGPYG
HPNPGMFPSGTPGGPYGGAAPGGPYGQPPPSSYGAQQPGLYGQGGAPPNVDPEAYSWFQSVDSDH
SGYISMKELKQALVNCNWSSFNDETCLMMINMFDKTKSGRIDVYGFSALWKFIQQWKNLFQQYDR
DRSGSISYTELQQALSQMGYNLSPQFTQLLVSRYCPRSANPAMQLDRFIQVCTQLQVLTEAFREK
DTAVQGNIRLSFEDFVTMTASRML

Important features of the protein:

Signal peptide:

amino acids 1-19

N-glycosylation site.

amino acids 147-150

Casein kinase II phosphorylation sites.

amino acids 135-138, 150-153, 202-205, 271-274

N-myristoylation sites.

amino acids 9-14, 15-20, 19-24, 33-38, 34-39, 39-44, 43-48, 61-66, 70-75, 78-83, 83-88, 87-92, 110-115

FIGURE 63

CAGGATGCAGGGCCGCGTGGCAGGGAGCTGCGCTCCTCTGGGCCTGCTCCTGGTCTGTCTTCATC
TCCCAGGCCTCTTTGCCCGGAGCATCGGTGTTGTGGAGGAGAAAGTTTCCCAAAACTTCGGGACC
AACTTGCCTCAGCTCGGACAACCTTCCTCCACTGGCCCCTCTAACTCTGAACATCCGCAGCCCGC
TCTGGACCCTAGGTCTAATGACTTGGCAAGGGTTCCTCTGAAGCTCAGCGTGCCTCCATCAGATG
GCTTCCCACCTGCAGGAGGTTCTGCAGTGCAGAGGTGGCCTCCATCGTGGGGGCTGCCTGCCATG
GATTCCTGGCCCCTGAGGATCCTTGGCAGATGATGGCTGCTGCGGCTGAGGACCGCCTGGGGGA
AGCGCTGCCTGAAGAACTCTCTTACCTCTCCAGTGCTGCGGCCCTCGCTCCGGGCAGTGGCCCTT
TGCCTGGGGAGTCTTCTCCCGATGCCACAGGCCTCTCACCTGAGGCTTCACTCCTCCACCAGGAC
TCGGAGTCCAGACGACTGCCCCGTTCTAATTCACTGGGAGCCGGGGAAAAATCCTTTCCCAACG
CCCTCCCTGGTCTCTCATCCACAGGGTTCTGCCTGATCACCCCTGGGGTACCCTGAATCCCAGTG
TGTCCTGGGGAGGTGGAGGCCCTGGGACTGGTTGGGGAACGAGGCCCATGCCACACCCTGAGGGA
ATCTGGGGTATCAATAATCAACCCCCAGGTACCAGCTGGGGAAATATTAATCGGTATCCAGGAGG
CAGCTGGGGAAATATTAATCGGTATCCAGGAGGCAGCTGGGGGAATATTAATCGGTATCCAGGAG
GCAGCTGGGGGAATATTCATCTATACCCAGGTATCAATAACCCATTTCCTCCTGGAGTTCTCCGC
CCTCCTGGCTCTTCTTGGAACATCCCAGCTGGCTTCCCTAATCCTCCAAGCCCTAGGTTGCAGTG
GGGCTAGAGCACGATAGAGGGAAACCCAACATTGGGAGTTAGAGTCCTGCTCCCGCCCCTTGCTG
TGTGGGCTCAATCCAGGCCCTGTTAACATGTTTCCAGCACTATCCCCACTTTTCAGTGCCTCCCC
TGCTCATCTCCAATAAAATAAAAGCACTTATGAAAAAAAAAAAAAAAAAAAAAAAAAAAAAAAAA
AAAAAAAAAAAAAAAAAAAAAAAAAAAAAAAAAAAAAAAAAAAAAAAAAAAAAAAAAAAAAAAA

FIGURE 64

MQGRVAGSCAPLGLLLVCLHLPGLFARSIGVVEEKVSQNFGTNLPQLGQPSSTGPSNSEHPQPAL
DPRSNDLARVPLKLSVPPSDGFPPAGGSAVQRWPPSWGLPAMDSWPPEDPWQMMAAAAEDRLGEA
LPEELSYLSSAAALAPGSGPLPGESSPDATGLSPEASLLHQDSESRRLPRSNSLGAGGKILSQRP
PWSLIHRVLPDHPWGTLNPSVSWGGGGPGTGWGTRPMPHPEGIWGINNQPPGTSWGNINRYPGGS
WGNINRYPGGSWGNINRYPGGSWGNIHLYPGINNPFPPGVLRPPGSSWNIPAGFPNPPSPRLQWG

Important features of the protein:

Signal peptide:

amino acids 1-26

Casein kinase II phosphorylation sites.

amino acids 56-59, 155-158

N-myristoylation sites.

amino acids 48-53, 220-225, 221-226, 224-229, 247-252, 258-263, 259-264, 269-274, 270-275, 280-285, 281-286, 305-310

FIGURE 65

AAGGAGAGGCCACCGGGACTTCAGTGTCTCCTCCATCCCAGGAGCGCAGTGGCCACTATGGGGTC
TGGGCTGCCCCTTGTCCTCCTCTTGACCCTCCTTGGCAGCTCACATGGAACAGGGCCGGGTATGA
CTTTGCAACTGAAGCTGAAGGAGTCTTTTCTGACAAATTCCTCCTATGAGTCCAGCTTCCTGGAA
TTGCTTGAAAAGCTCTGCCTCCTCCTCCATCTCCCTTCAGGGACCAGCGTCACCCTCCACCATGC
AAGATCTCAACACCATGTTGTCTGCAACACATGACAGCCATTGAAGCCTGTGTCCTTCTTGGCCC
GGGCTTTTGGGCCGGGGATGCAGGAGGCAGGCCCCGACCCTGTCTTTCAGCAGGCCCCCACCCTC
CTGAGTGGCAATAAATAAAATTCGGTATGCTG

FIGURE 66

MGSGLPLVLLLTLLGSSHGTGPGMTLQLKLKESFLTNSSYESSFLELLEKLCLLLHLPSGTSVTL
HHARSQHHVVCNT

Important features:
Signal peptide:
amino acids 1-19

N-glycosylation site.
amino acids 37-41

N-myristoylation sites.
amino acids 15-21, 19-25, 60-66

FIGURE 67

ACGGACCGAGGGTTCGAGGGAGGGACACGGACCAGGAACCTGAGCTAGGTCAAAGACGCCCGGGC
CAGGTGCCCCGTCGCAGGTGCCCCTGGCCGGAGATGCGGTAGGAGGGGCGAGCGCGAGAAGCCCC
TTCCTCGGCGCTGCCAACCCGCCACCCAGCCCATGGCGAACCCCGGGCTGGGGCTGCTTCTGGCG
CTGGGCCTGCCGTTCCTGCTGGCCCGCTGGGGCCGAGCCTGGGGGCAAATACAGACCACTTCTGC
AAATGAGAATAGCACTGTTTTGCCTTCATCCACCAGCTCCAGCTCCGATGGCAACCTGCGTCCGG
AAGCCATCACTGCTATCATCGTGGTCTTCTCCCTCTTGGCTGCCTTGCTCCTGGCTGTGGGGCTG
GCACTGTTGGTGCGGAAGCTTCGGGAGAAGCGGCAGACGGAGGGCACCTACCGGCCCAGTAGCGA
GGAGCAGTTCTCCCATGCAGCCGAGGCCCGGGCCCCTCAGGACTCCAAGGAGACGGTGCAGGGCT
GCCTGCCCATCTAGGTCCCCTCTCCTGCATCTGTCTCCCTTCATTGCTGTGTGACCTTGGGGAAA
GGCAGTGCCCTCTCTGGGCAGTCAGATCCACCCAGTGCTTAATAGCAGGGAAGAAGGTACTTCAA
AGACTCTGCCCCTGAGGTCAAGAGAGGATGGGCTATTCACTTTTATATATTTATATAAAATTAG
TAGTGAGATGTAAAAAAAAAAAAAAAAAAA

FIGURE 68

MANPGLGLLLALGLPFLLARWGRAWGQIQTTSANENSTVLPSSTSSSSDGNLRPEAITAIIVVFS
LLAALLLAVGLALLVRKLREKRQTEGTYRPSSEEQFSHAAEARAPQDSKETVQGCLPI

Important features:

Signal peptide:

amino acids 1-19

Transmembrane domain:

amino acids 56-80

N-glycosylation site.

amino acids 36-40 cAMP- and cGMP-dependent protein kinase phosphorylation site.

amino acids 86-90

Tyrosine kinase phosphorylation site.

amino acids 86-94

N-myristoylation sites.

amino acids 7-13, 26-32

FIGURE 69

```
GCCAGGAATAACTAGAGAGGAACAATGGGGTTATTCAGAGGTTTTGTTTTCCTCTTAGTTCTGTGCCTGCTGCACCAG
TCAAATACTTCCTTCATTAAGCTGAATAATAATGGCTTTGAAGATATTGTCATTGTTATAGATCCTAGTGTGCCAGAA
GATGAAAAAATAATTGAACAAATAGAGGATATGGTGACTACAGCTTCTACGTACCTGTTTGAAGCCACAGAAAAAGA
TTTTTTTTCAAAAATGTATCTATATTAATTCCTGAGAATTGGAAGGAAAATCCTCAGTACAAAAGGCCAAAACATGAA
AACCATAAACATGCTGATGTTATAGTTGCACCACCTACACTCCCAGGTAGAGATGAACCATACACCAAGCAGTTCACA
GAATGTGGAGAGAAAGGCGAATACATTCACTTCACCCCTGACCTTCTACTTGGAAAAAAACAAAATGAATATGGACCA
CCAGGCAAACTGTTTGTCCATGAGTGGGCTCACCTCCGGTGGGAGTGTTTGATGAGTACAATGAAGATCAGCCTTTC
TACCGTGCTAAGTCAAAAAAAATCGAAGCAACAAGGTGTTCCGCAGGTATCTCTGGTAGAAATAGAGTTTATAAGTGT
CAAGGAGGCAGCTGTCTTAGTAGAGCATGCAGAATTGATTCTACAACAAAACTGTATGGAAAAGATTGTCAATTCTTT
CCTGATAAAGTACAAACAGAAAAAGCATCCATAATGTTTATGCAAAGTATTGATTCTGTTGTTGAATTTTGTAACGAA
AAAACCCATAATCAAGAAGCTCCAAGCCTACAAAACATAAAGTGCAATTTTAGAAGTACATGGGAGGTGATTAGCAAT
TCTGAGGATTTTAAAAACACCATACCCATGGTGACACCACCTCCTCCACCTGTCTTCTCATTGCTGAAGATCAGTCAA
AGAATTGTGTGCTTAGTTCTTGATAAGTCTGGAAGCATGGGGGGTAAGGACCGCCTAAATCGAATGAATCAAGCAGCA
AAACATTTCCTGCTGCAGACTGTTGAAAATGGATCCTGGGTGGGGATGGTTCACTTTGATAGTACTGCCACTATTGTA
AATAAGCTAATCCAAATAAAAAGCAGTGATGAAAGAAACACACTCATGGCAGGATTACCTACATATCCTCTGGGAGGA
ACTTCCATCTGCTCTGGAATTAAATATGCATTTCAGGTGATTGGAGAGCTACATTCCCAACTCGATGGATCCGAAGTA
CTGCTGCTGACTGATGGGGAGGATAACACTGCAAGTTCTTGTATTGATGAAGTGAAACAAAGTGGGGCCATTGTTCAT
TTTATTGCTTTGGGAAGAGCTGCTGATGAAGCAGTAATAGAGATGAGCAAGATAACAGGAGGAAGTCATTTTTATGTT
TCAGATGAAGCTCAGAACAATGGCCTCATTGATGCTTTTGGGGCTCTTACATCAGGAAATACTGATCTCTCCCAGAAG
TCCCTTCAGCTCGAAAGTAAGGGATTAACACTGAATAGTAATGCCTGGATGAACGACACTGTCATAATTGATAGTACA
GTGGGAAAGGACACGTTCTTTCTCATCACATGGAACAGTCTGCCTCCCAGTATTTCTCTGGGATCCCAGTGGAACA
ATAATGGAAAATTTCACAGTGGATGCAACTTCCAAAATGGCCTATCTCAGTATTCCAGGAACTGCAAAGGTGGGCACT
TGGGCATACAATCTTCAAGCCAAAGCGAACCCAGAAACATTAACTATTACAGTAACTTCTCGAGCAGCAAATTCTTCT
GTGCCTCCAATCACAGTGAATGCTAAAATGAATAAGGACGTAAACAGTTTCCCCAGCCCAATGATTGTTTACGCAGAA
ATTCTACAAGGATATGTACCTGTTCTTGGAGCCAATGTGACTGCTTTCATTGAATCACAGAATGGACATACAGAAGTT
TTGGAACTTTTGGATAATGGTGCAGGCGCTGATTCTTTCAAGAATGATGGAGTCTACTCCAGGTATTTTACAGCATAT
ACAGAAAATGGCAGATATAGCTTAAAAGTTCGGGCTCATGGAGGAGCAAACACTGCCAGGCTAAAATTACGGCCTCCA
CTGAATAGAGCCGCGTACATACCAGGCTGGGTAGTGAACGGGGAAATTGAAGCAAACCCGCCAAGACCTGAAATTGAT
GAGGATACTCAGACCACCTTGGAGGATTTCAGCCGAACAGCATCCGGAGGTGCATTTGTGGTATCACAAGTCCCAAGC
CTTCCCTTGCCTGACCAATACCCACCAAGTCAAATCACAGACCTTGATGCCACAGTTCATGAGGATAAGATTATTCTT
ACATGGACAGCACCAGGAGATAATTTTGATGTTGGAAAAGTTCAACGTTATATCATAAGAATAAGTGCAAGTATTCTT
GATCTAAGAGACAGTTTTGATGATGCTCTTCAAGTAAATACTACTGATCTGTCACCAAAGGAGGCCAACTCCAAGGAA
AGCTTTGCATTTAAACCAGAAAATATCTCAGAAGAAAATGCAACCCACATATTTATTGCCATTAAAAGTATAGATAAA
AGCAATTTGACATCAAAAGTATCCAACATTGCACAAGTAACTTTGTTTATCCCTCAAGCAAATCCTGATGACATTGAT
CCTACACCTACTCCTACTCCTACTCCTGATAAAGTCATAATTCTGGAGTTAATATTTCTACGCTGGTATTG
TCTGTGATTGGGTCTGTTGTAATTGTTAACTTTATTTTAAGTACCACCATTTGAACCTTAACGAAGAAAAAAATCTTC
AAGTAGACCTAGAAGAGAGTTTTAAAAAACAAAACAATGTAAGTAAAGGATATTTCTGAATCTTAAAATTCATCCCAT
GTGTGATCATAAACTCATAAAAATAATTTTAAGATGTCGGAAAAGGATACTTTGATTAAATAAAAACACTCATGGATA
TGTAAAAACTGTCAAGATTAAAATTTAATAGTTTCATTTATTTGTTATTTTATTTGTAAGAAATAGTGATGAACAAAG
ATCCTTTTTCATACTGATACCTGGTTGTATATTATTTGATGCAACAGTTTTCTGAAATGATATTTCAAATTGCATCAA
GAAATTAAAATCATCTATCTGAGTAGTCAAAATACAAGTAAAGGAGAGCAAATAAACAACATTTGGAAAAAAAAAAA
AAAAAAAAAAAAAAAAAAAAAAAAAAAAAAAAAAAAAAAAAAAAAAAAAAAAAAAAAAAA
```

FIGURE 70

```
MGLFRGFVFLLVLCLLHQSNTSFIKLNNNGFEDIVIVIDPSVPEDEKIIEQIEDMVTTASTYLFE
ATEKRFFFKNVSILIPENWKENPQYKRPKHENHKHADVIVAPPTLPGRDEPYTKQFTECGEKGEY
IHFTPDLLLGKKQNEYGPPGKLFVHEWAHLRWGVFDEYNEDQPFYRAKSKKIEATRCSAGISGRN
RVYKCQGGSCLSRACRIDSTTKLYGKDCQFFPDKVQTEKASIMFMQSIDSVVEFCNEKTHNQEAP
SLQNIKCNFRSTWEVISNSEDFKNTIPMVTPPPPPVFSLLKISQRIVCLVLDKSGSMGGKDRLNR
MNQAAKHFLLQTVENGSWVGMVHFDSTATIVNKLIQIKSSDERNTLMAGLPTYPLGGTSICSGIK
YAFQVIGELHSQLDGSEVLLLTDGEDNTASSCIDEVKQSGAIVHFIALGRAADEAVIEMSKITGG
SHFYVSDEAQNNGLIDAFGALTSGNTDLSQKSLQLESKGLTLNSNAWMNDTVIIDSTVGKDTFFL
ITWNSLPPSISLWDPSGTIMENFTVDATSKMAYLSIPGTAKVGTWAYNLQAKANPETLTITVTSR
AANSSVPPITVNAKMNKDVNSFPSPMIVYAEILQGYVPVLGANVTAFIESQNGHTEVLELLDNGA
GADSFKNDGVYSRYFTAYTENGRYSLKVRAHGGANTARLKLRPPLNRAAYIPGWVVNGEIEANPP
RPEIDEDTQTTLEDFSRTASGGAFVVSQVPSLPLPDQYPPSQITDLDATVHEDKIILTWTAPGDN
FDVGKVQRYIIRISASILDLRDSFDDALQVNTTDLSPKEANSKESFAFKPENISEENATHIFIAI
KSIDKSNLTSKVSNIAQVTLFIPQANPDDIDPTPTPTPTPTPDKSHNSGVNISTLVLSVIGSVVI
VNFILSTTI
```

Signal peptide:
amino acids 1-21

Putative transmembrane domains:
amino acids 284-300, 617-633

Leucine zipper pattern.
amino acids 469-491, 476-498

N-glycosylation site.
amino acids 20-24, 75-79, 340-344, 504-508, 542-546, 588-592, 628-632, 811-815, 832-836, 837-841, 852-856, 896-900

FIGURE 71

```
CTCCTTAGGTGGAAACCCTGGGAGTAGAGTACTGACAGCAAAGACCGGGAAAGACCATACGTCCCCGGGCAGGGGTGA
CAACAGGTGTCATCTTTTTGATCTCGTGTGTGGCTGCCTTCCTATTTCAAGGAAAGACGCCAAGGTAATTTTGACCCA
GAGGAGCAATGATGTAGCCACCTCCTAACCTTCCCTTCTTGAACCCCCAGTTATGCCAGGATTTACTAGAGAGTGTCA
ACTCAACCAGCAAGCGGCTCCTTCGGCTTAACTTGTGGTTGGAGGAGAGAACCTTTGTGGGGCTGCGTTCTCTTAGCA
GTGCTCAGAAGTGACTTGCCTGAGGGTGGACCAGAAGAAAGGAAAGGTCCCCTCTTGCTGTTGGCTGCACATCAGGAA
GGCTGTGATGGGAATGAAGGTGAAAACTTGGAGATTTCACTTCAGTCATTGCTTCTGCCTGCAAGATCATCCTTTAAA
AGTAGAGAAGCTGCTCTGTGTGGTGGTTAACTCCAAGAGGCAGAACTCGTTCTAGAAGGAAATGGATGCAAGCAGCTC
CGGGGGCCCCAAACGCATGCTTCCTGTGGTCTAGCCCAGGGAAGCCCTTCCGTGGGGCCCCGGCTTTGAGGGATGCC
ACCGGTTCTGGACGCATGGCTGATTCCTGAATGATGATGGTTCGCCGGGGGCTGCTTGCGTGGATTTCCCGGGTGGTG
GTTTTGCTGGTGCTCCTCTGCTGTGCTATCTCTGTCCTGTACATGTTGGCCTGCACCCCAAAAGGTGACGAGGAGCAG
CTGGCACTGCCCAGGGCCAACAGCCCCACGGGGAAGGAGGGGTACCAGGCCGTCCTTCAGGAGTGGGAGGAGCAGCAC
CGCAACTACGTGAGCAGCCTGAAGCGGCAGATCGCACAGCTCAAGGAGGAGCTGCAGGAGGAGGAGTGAGCAGCTCAGG
AATGGGCAGTACCAAGCCAGCGATGCTGCTGGCCTGGGTCTGGACAGGAGCCCCCAGAGAAAACCCAGGCCGACCTC
CTGGCCTTCCTGCACTCGCAGGTGGACAAGGCAGAGGTGAATGCTGGCGTCAAGCTGGCCACAGAGTATGCAGCAGTG
CCTTTCGATAGCTTTACTCTACAGAAGGTGTACCAGCTGGAGACTGGCCTTACCCGCCACCCCGAGGAGAAGCCTGTG
AGGAAGGACAAGCGGGATGAGTTGGTGGAAGCCATTGAATCAGCCTTGGAGACCCTGAACAATCCTGCAGAGAACAGC
CCCAATCACCGTCCTTACACGGCCTCTGATTTCATAGAAGGGATCTACCGAACAGAAAGGGACAAAGGGACATTGTAT
GAGCTCACCTTCAAAGGGGACCACAAACACGAATTCAAACGGCTCATCTTATTTCGACCATTCGACCCCATCATGAAA
GTGAAAAATGAAAAGCTCAACATGGCCAACACGCTTATCAATGTTATCGTGCCTCTAGCAAAAAGGGTGGACAAGTTC
CGGCAGTTCATGCAGAATTTCAGGGAGATGTGCATTGAGCAGGATGGGAGAGTTCCATCTCACTGTTGTTTACTTTGGG
AAAGAAGAAATAAATGAAGTCAAAGGAATACTTGAAAACACTTCCAAAGCTGCCAACTTCAGGAACTTTACCTTCATC
CAGCTGAATGGAGAATTTTCTCGGGGAAAGGGACTTGATGTTGGAGCCCGCTTCTGGAAGGGAAGCAACGTCCTTCTC
TTTTTCTGTGATGTGGACATCTACTTCACATCTGAATTCCTCAATACGTGTAGGCTGAATACACAGCCAGGGAAGAAG
GTATTTTATCCAGTTCTTTTCAGTCAGTACAATCCTGGCATAATATACGGCCACCATGATGCAGTCCCTCCCTTGGAA
CAGCAGCTGGTCATAAAGAAGGAAACTGGATTTTGGAGAGACTTTGGATTTGGGATGACGTGTCAGTATCGGTCAGAC
TTCATCAATATAGGTGGGTTTGATCTGGACATCAAAGGCTGGGGCGGAGAGGATGTGCACCTTTATCGCAAGTATCTC
CACAGCAACCTCATAGTGGTACGGACGCCTGTGCGAGGACTCTTCCACCTCTGGCATGAGAAGCGCTGCATGGACGAG
CTGACCCCCGAGCAGTACAAGATGTGCATGCAGTCCAAGGCCATGAACGAGGCATCCCACGGCCAGCTGGGCATGCTG
GTGTTCAGGCACGAGATAGAGGCTCACCTTCGCAAACAGAAACAGAAGACAAGTAGCAAAAAAACATGAACTCCCAGA
GAAGGATTGTGGGAGACACTTTTTCTTTCCTTTTGCAATTACTGAAAGTGGCTGCAACAGAGAAAAGACTTCCATAAA
GGACGACAAAAGAATTGGACTGATGGGTCAGAGATGAGAAAGCCTCCGATTTCTCTCTGTTGGGCTTTTTACAACAGA
AATCAAAATCTCCGCTTTGCCTGCAAAAGTAACCCAGTTGCACCCTGTGAAGTGTCTGACAAAGGCAGAATGCTTGTG
AGATTATAAGCCTAATGGTGTGGAGGTTTTGATGGTGTTTACAATACACTGAGACCTGTTGTTTTGTGTGCTCATTGA
AATATTCATGATTTAAGAGCAGTTTTGTAAAAAATTCATTAGCATGAAAGGCAAGCATATTTCTCCTCATATGAATGA
GCCTATCAGCAGGGCTCTAGTTTCTAGGAATGCTAAAATATCAGAAGGCAGGAGAGGAGATAGGCTTATTATGATACT
AGTGAGTACATTAAGTAAAATAAAATGGACCAGAAAAGAAAAGAAACCATAAATATCGTGTCATATTTTCCCCAAGAT
TAACCAAAAATAATCTGCTTATCTTTTTGGTTGTCCTTTTAACTGTCTCCGTTTTTTTCTTTTATTTAAAAATGCACT
TTTTTTCCCTTGTGAGTTATAGTCTGCTTATTTAATTACCACTTTGCAAGCCTTACAAGAGAGCACAAGTTGGCCTAC
ATTTTTATATTTTTAAGAAGATACTTTGAGATGCATTATGAGAACTTTCAGTTCAAAGCATCAAATTGATGCCATAT
CCAAGGACATGCCAAATGCTGATTCTGTCAGGCACTGAATGTCAGGCATTGAGACATAGGGAGGGAATGGTTTGTACT
AATACAGACGTACAGATACTTTCTCTGAAGAGTATTTTCGAAGAGGAGCAACTGAACACTGGAGGAAAAGAAAATGAC
ACTTTCTGCTTTACAGAAAAGGAAACTCATTCAGACTGGTGATATCGTGATGTACCTAAAAGTCAGAAACCACATTTT
CTCCTCAGAAGTAGGGACCGCTTTCTTACCTGTTTAAATAAACCAAAGTATACCGTGTGAACCAAACAATCTCTTTTC
AAAACAGGGTGCTCCTCCTGGCTTCTGGCTTCCATAAGAAGAAATGGAGAAAAATATATATATATATATATATATTGT
GAAAGATCAATCCATCTGCCAGAATCTAGTGGGATGGAAGTTTTGCTACATGTTATCCACCCCAGGCCAGGTGGAAG
TAACTGAATTATTTTTTAAATTAAGCAGTTCTACTCAATCACCAAGATGCTTCTGAAAATTGCATTTTATTACCATTT
CAAACTATTTTTAAAAATAAATACAGTTAACATAGAGTGGTTTCTTCATTCATGTGAAAATTATTAGCCAGCACCAG
ATGCATGAGCTAATTATCTCTTTGAGTCCTTGCTTCTGTTTGCTCACAGTAAACTCATTGTTTAAAAGCTTCAAGAAC
ATTCAAGCTGTTGGTGTGTTAAAAAATGCATTGTATTGATTTGTACTGGTAGTTTATGAAATTTAATTAAAACACAGG
CCATGAATGGAAGGTGGTATTGCACAGCTAATAAAATATGATTTGTGGATATGAA
```

FIGURE 72

MMMVRRGLLAWISRVVVLLVLLCCAISVLYMLACTPKGDEEQLALPRANSPTGKEGYQAVLQEWE
EQHRNYVSSLKRQIAQLKEELQERSEQLRNGQYQASDAAGLGLDRSPPEKTQADLLAFLHSQVDK
AEVNAGVKLATEYAAVPFDSFTLQKVYQLETGLTRHPEEKPVRKDKRDELVEAIESALETLNNPA
ENSPNHRPYTASDFIEGIYRTERDKGTLYELTFKGDHKHEFKRLILFRPFSPIMKVKNEKLNMAN
TLINVIVPLAKRVDKFRQFMQNFREMCIEQDGRVHLTVVYFGKEEINEVKGILENTSKAANFRNF
TFIQLNGEFSRGKGLDVGARFWKGSNVLLFFCDVDIYFTSEFLNTCRLNTQPGKKVFYPVLFSQY
NPGIIYGHHDAVPPLEQQLVIKKETGFWRDFGFGMTCQYRSDFINIGGFDLDIKGWGGEDVHLYR
KYLHSNLIVVRTPVRGLFHLWHEKRCMDELTPEQYKMCMQSKAMNEASHGQLGMLVFRHEIEAHL
RKQKQKTSSKKT

Important features:

Signal peptide:

amino acids 1-27

N-glycosylation sites.

amino acids 315-319, 324-328

N-myristoylation sites.

amino acids 96-102, 136-142, 212-218, 311-317, 339-345, 393-399

Amidation site.

amino acids 377-381

FIGURE 73

```
GAGACTGCAGAGGGAGATAAAGAGAGAGGGCAAAGAGGCAGCAAGAGATTTGTCCTGGGGATCCA
GAAACCCATGATACCCTACTGAACACCGAATCCCCTGGAAGCCCACAGAGACAGAGACAGCAAGA
GAAGCAGAGATAAATACACTCACGCCAGGAGCTCGCTCGCTCTCTCTCTCTCTCTCACTCCTC
CCTCCCTCTCTCTGCCTGTCCTAGTCCTCTAGTCCTCAAATTCCCAGTCCCCTGCACCCCTTC
CTGGGACACTATGTTGTTCTCCGCCCTCCTGCTGGAGGTGATTTGGATCCTGGCTGCAGATGGGG
GTCAACACTGGACGTATGAGGGCCCACATGGTCAGGACCATTGGCCAGCCTCTTACCCTGAGTGT
GGAAACAATGCCCAGTCGCCCATCGATATTCAGACAGACAGTGTGACATTTGACCCTGATTTGCC
TGCTCTGCAGCCCCACGGATATGACCAGCCTGGCACCGAGCCTTTGGACCTGCACAACAATGGCC
ACACAGTGCAACTCTCTCTGCCCTCTACCCTGTATCTGGGTGGACTTCCCCGAAAATATGTAGCT
GCCCAGCTCCACCTGCACTGGGGTCAGAAAGGATCCCCAGGGGGGTCAGAACACCAGATCAACAG
TGAAGCCACATTTGCAGAGCTCCACATTGTACATTATGACTCTGATTCCTATGACAGCTTGAGTG
AGGCTGCTGAGAGGCCTCAGGGCCTGGCTGTCCTGGGCATCCTAATTGAGGTGGGTGAGACTAAG
AATATAGCTTATGAACACATTCTGAGTCACTTGCATGAAGTCAGGCATAAAGATCAGAAGACCTC
AGTGCCTCCCTTCAACCTAAGAGAGCTGCTCCCCAAACAGCTGGGGCAGTACTTCCGCTACAATG
GCTCGCTCACAACTCCCCCTTGCTACCAGAGTGTGCTCTGGACAGTTTTTTATAGAAGGTCCCAG
ATTTCAATGGAACAGCTGGAAAAGCTTCAGGGGACATTGTTCTCCACAGAAGAGGAGCCCTCTAA
GCTTCTGGTACAGAACTACCGAGCCCTTCAGCCTCTCAATCAGCGCATGGTCTTTGCTTCTTTCA
TCCAAGCAGGATCCTCGTATACCACAGGTGAAATGCTGAGTCTAGGTGTAGGAATCTTGGTTGGC
TGTCTCTGCCTTCTCCTGGCTGTTTATTTCATTGCTAGAAAGATTCGGAAGAAGAGGCTGGAAAA
CCGAAAGAGTGTGGTCTTCACCTCAGCACAAGCCACGACTGAGGCATAAATTCCTTCTCAGATAC
CATGGATGTGGATGACTTCCCTTCATGCCTATCAGGAAGCCTCTAAAATGGGGTGTAGGATCTGG
CCAGAAACACTGTAGGAGTAGTAAGCAGATGTCCTCCTTCCCCTGGACATCTCTTAGAGAGGAAT
GGACCCAGGCTGTCATTCCAGGAAGAACTGCAGAGCCTTCAGCCTCTCCAAACATGTAGGAGGAA
ATGAGGAAATCGCTGTGTTGTTAATGCAGAGANCAAACTCTGTTTAGTTGCAGGGGAAGTTTGGG
ATATACCCCAAAGTCCTCTACCCCCTCACTTTTATGGCCCTTTCCCTAGATATACTGCGGGATCT
CTCCTTAGGATAAAGAGTTGCTGTTGAAGTTGTATATTTTGATCAATATATTTGGAAATTAAAG
TTTCTGACTTT
```

FIGURE 74

MLFSALLLEVIWILAADGGQHWTYEGPHGQDHWPASYPECGNNAQSPIDIQTDSVTFDPDLPALQ
PHGYDQPGTEPLDLHNNGHTVQLSLPSTLYLGGLPRKYVAAQLHLHWGQKGSPGGSEHQINSEAT
FAELHIVHYDSDSYDSLSEAAERPQGLAVLGILIEVGETKNIAYEHILSHLHEVRHKDQKTSVPP
FNLRELLPKQLGQYFRYNGSLTTPPCYQSVLWTVFYRRSQISMEQLEKLQGTLFSTEEEPSKLLV
QNYRALQPLNQRMVFASFIQAGSSYTTGEMLSLGVGILVGCLCLLLAVYFIARKIRKKRLENRKS
VVFTSAQATTEA

Important features of the protein:
Signal peptide:
amino acids 1-15

Transmembrane domain:
amino acids 291-310

N-glycosylation site.
amino acids 213-216

Eukaryotic-type carbonic anhydrases proteins
amino acids 197-245, 104-140, 22-69

FIGURE 75

```
TGCCGCTGCCGCCGCTGCTGCTGTTGCTCCTGGCGGCGCCTTGGGGACGGGCAGTTCCCTGTGTC
TCTGGTGGTTTGCCTAAACCTGCAAACATCACCTTCTTATCCATCAACATGAAGAATGTCCTACA
ATGGACTCCACCAGAGGGTCTTCAAGGAGTTAAAGTTACTTACACTGTGCAGTATTTCATCACAA
ATTGGCCCACCAGAGGTGGCACTGACTACAGATGAGAAGTCCATTTCTGTTGTCCTGACAGCTCC
AGAGAAGTGGAAGAGAAATCCAGAAGACCTTCCTGTTTCCATGCAACAAATATACTCCAATCTGA
AGTATAACGTGTCTGTGTTGAATACTAAATCAAACAGAACGTGGTCCCAGTGTGTGACCAACCAC
ACGCTGGTGCTCACCTGGCTGGAGCCGAACACTCTTTACTGCGTACACGTGGAGTCCTTCGTCCC
AGGGCCCCCTCGCCGTGCTCAGCCTTCTGAGAAGCAGTGTGCCAGGACTTTGAAAGATCAATCAT
CAGAGTTCAAGGCTAAAATCATCTTCTGGTATGTTTTGCCCATATCTATTACCGTGTTTCTTTTT
TCTGTGATGGGCTATTCCATCTACCGATATATCCACGTTGGCAAAGAGAAACACCCAGCAAATTT
GATTTTGATTTATGGAAATGAATTTGACAAAAGATTCTTTGTGCCTGCTGAAAAAATCGTGATTA
ACTTTATCACCCTCAATATCTCGGATGATTCTAAAATTTCTCATCAGGATATGAGTTTACTGGGA
AAAAGCAGTGATGTATCCAGCCTTAATGATCCTCAGCCCAGCGGGAACCTGAGGCCCCCTCAGGA
GGAAGAGGAGGTGAAACATTTAGGGTATGCTTCGCATTTGATGGAAATTTTTTGTGACTCTGAAG
AAAACACGGAAGGTACTTCTCTCACCCAGCAAGAGTCCCTCAGCAGAACAATACCCCGGATAAA
ACAGTCATTGAATATGAATATGATGTCAGAACCACTGACATTTGTGCGGGGCCTGAAGAGCAGGA
GCTCAGTTTGCAGGAGGAGGTGTCCACACAAGGAACATTATTGGAGTCGCAGGCAGCGTTGGCAG
TCTTGGGCCCGCAAACGTTACAGTACTCATACACCCCTCAGCTCCAAGACTTAGACCCCCTGGCG
CAGGAGCACACAGACTCGGAGGAGGGGCCGGAGGAAGAGCCATCGACGACCCTGGTCGACTGGGA
TCCCCAAACTGGCAGGCTGTGTATTCCTTCGCTGTCCAGCTTCGACCAGGATTCAGAGGGCTGCG
AGCCTTCTGAGGGGATGGGCTCGGAGAGGAGGGTCTTCTATCTAGACTCTATGAGGAGCCGGCT
CCAGACAGGCCACCAGGAGAAAATGAAACCTATCTCATGCAATTCATGGAGGAATGGGGGTTATA
TGTGCAGATGGAAAACTGATGCCAACACTTCCTTTTGCCTTTTGTTTCCTGTGCAAACAAGTGAG
TCACCCCTTTGATCCCAGCCATAAAGTACCTGGGATGAAAGAAGTTTTTTCCAGTTTGTCAGTGT
CTGTGAGAATTACTTATTTCTTTTCTCTATTCTCATAGCACGTGTGTGATTGGTTCATGCATGTA
GGTCTCTTAACAATGATGGTGGGCCTCTGGAGTCCAGGGGCTGGCCGGTTGTTCTATGCAGAGAA
AGCAGTCAATAAATGTTTGCCAGACTGGGTGCAGAATTTATTCAGGTGGGTGT
```

FIGURE 76

MSYNGLHQRVFKELKLLTLCSISSQIGPPEVALTTDEKSISVVLTAPEKWKRNPEDLPVSMQQIY
SNLKYNVSVLNTKSNRTWSQCVTNHTLVLTWLEPNTLYCVHVESFVPGPPRRAQPSEKQCARTLK
DQSSEFKAKIIFWYVLPISITVFLFSVMGYSIYRYIHVGKEKHPANLILIYGNEFDKRFFVPAEK
IVINFITLNISDDSKISHQDMSLLGKSSDVSSLNDPQPSGNLRPPQEEEEVKHLGYASHLMEIFC
DSEENTEGTSLTQQESLSRTIPPDKTVIEYEYDVRTTDICAGPEEQELSLQEEVSTQGTLLESQA
ALAVLGPQTLQYSYTPQLQDLDPLAQEHTDSEEGPEEEPSTTLVDWDPQTGRLCIPSLSSFDQDS
EGCEPSEGDGLGEEGLLSRLYEEPAPDRPPGENETYLMQFMEEWGLYVQMEN

Important features:
Signal peptide:
amino acids 1-28

Transmembrane domain:
amino acids 140-163

N-glycosylation sites.
amino acids 71-74, 80-83, 89-92, 204-207, 423-426

FIGURE 77

```
GAGGAGCGGGCCGAGGACTCCAGCGTGCCCAGGTCTGGCATCCTGCACTTGCTGCCCTCTGACAC
CTGGGAAGATGGCCGGCCCGTGGACCTTCACCCTTCTCTGTGGTTTGCTGGCAGCCACCTTGATC
CAAGCCACCCTCAGTCCCACTGCAGTTCTCATCCTCGGCCCAAAAGTCATCAAAGAAAAGCTGAC
ACAGGAGCTGAAGGACCACAACGCCACCAGCATCCTGCAGCAGCTGCCGCTGCTCAGTGCCATGC
GGGAAAAGCCAGCCGGAGGCATCCCTGTGCTGGGCAGCCTGGTGAACACCGTCCTGAAGCACATC
ATCTGGCTGAAGGTCATCACAGCTAACATCCTCCAGCTGCAGGTGAAGCCCTCGGCCAATGACCA
GGAGCTGCTAGTCAAGATCCCCCTGGACATGGTGGCTGGATTCAACACGCCCCTGGTCAAGACCA
TCGTGGAGTTCCACATGACGACTGAGGCCCAAGCCACCATCCGCATGGACACCAGTGCAAGTGGC
CCCACCCGCCTGGTCCTCAGTGACTGTGCCACCAGCCATGGGAGCCTGCGCATCCAACTGCTGTA
TAAGCTCTCCTTCCTGGTGAACGCCTTAGCTAAGCAGGTCATGAACCTCCTAGTGCCATCCCTGC
CCAATCTAGTGAAAACCAGCTGTGTCCCGTGATCGAGGCTTCCTTCAATGGCATGTATGCAGAC
CTCCTGCAGCTGGTGAAGGTGCCCATTTCCCTCAGCATTGACCGTCTGGAGTTTGACCTTCTGTA
TCCTGCCATCAAGGGTGACACCATTCAGCTCTACCTGGGGGCCAAGTTGTTGGACTCACAGGGAA
AGGTGACCAAGTGGTTCAATAACTCTGCAGCTTCCCTGACAATGCCCACCCTGGACAACATCCCG
TTCAGCCTCATCGTGAGTCAGGACGTGGTGAAAGCTGCAGTGGCTGCTGTGCTCTCTCCAGAAGA
ATTCATGGTCCTGTTGGACTCTGTGCTTCCTGAGAGTGCCCATCGGCTGAAGTCAAGCATCGGGC
TGATCAATGAAAAGGCTGCAGATAAGCTGGGATCTACCCAGATCGTGAAGATCCTAACTCAGGAC
ACTCCCGAGTTTTTTATAGACCAAGGCCATGCCAAGGTGGCCCAACTGATCGTGCTGGAAGTGTT
TCCCTCCAGTGAAGCCCTCCGCCCTTTGTTCACCCTGGGCATCGAAGCCAGCTCGGAAGCTCAGT
TTTACACCAAAGGTGACCAACTTATACTCAACTTGAATAACATCAGCTCTGATCGGATCCAGCTG
ATGAACTCTGGGATTGGCTGGTTCCAACCTGATGTTCTGAAAAACATCATCACTGAGATCATCCA
CTCCATCCTGCTGCCGAACCAGAATGGCAAATTAAGATCTGGGGTCCCAGTGTCATTGGTGAAGG
CCTTGGGATTCGAGGCAGCTGAGTCCTCACTGACCAAGGATGCCCTTGTGCTTACTCCAGCCTCC
TTGTGGAAACCCAGCTCTCCTGTCTCCCAGTGAAGACTTGGATGGCAGCCATCAGGGAAGGCTGG
GTCCCAGCTGGGAGTATGGGTGTGAGCTCTATAGACCATCCCTCTCTGCAATCAATAAACACTTG
CCTGTGAAAAA
```

FIGURE 78

```
MAGPWTFTLLCGLLAATLIQATLSPTAVLILGPKVIKEKLTQELKDHNATSILQQLPLLSAMREK
PAGGIPVLGSLVNTVLKHIIWLKVITANILQLQVKPSANDQELLVKIPLDMVAGFNTPLVKTIVE
FHMTTEAQATIRMDTSASGPTRLVLSDCATSHGSLRIQLLYKLSFLVNALAKQVMNLLVPSLPNL
VKNQLCPVIEASFNGMYADLLQLVKVPISLSIDRLEFDLLYPAIKGDTIQLYLGAKLLDSQGKVT
KWFNNSAASLTMPTLDNIPFSLIVSQDVVKAAVAAVLSPEEFMVLLDSVLPESAHRLKSSIGLIN
EKAADKLGSTQIVKILTQDTPEFFIDQGHAKVAQLIVLEVFPSSEALRPLFTLGIEASSEAQFYT
KGDQLILNLNNISSDRIQLMNSGIGWFQPDVLKNIITEIIHSILLPNQNGKLRSGVPVSLVKALG
FEAAESSLTKDALVLTPASLWKPSSPVSQ
```

Important features of the protein:

Signal peptide:

amino acids 1-21

N-glycosylation sites.

amino acids 48-51, 264-267, 401-404

Glycosaminoglycan attachment site.

amino acids 412-415

LBP / BPI / CETP family proteins.

amino acids 407-457

FIGURE 79

```
GAGAGAAGTCAGCCTGGCAGAGAGACTCTGAAATGAGGGATTAGAGGTGTTCAAGGAGCAAGAGC
TTCAGCCTGAAGACAAGGGAGCAGTCCCTGAAGACGCTTCTACTGAGAGGTCTGCCATGGCCTCT
CTTGGCCTCCAACTTGTGGGCTACATCCTAGGCCTTCTGGGGCTTTTGGGCACACTGGTTGCCAT
GCTGCTCCCCAGCTGGAAAACAAGTTCTTATGTCGGTGCCAGCATTGTGACAGCAGTTGGCTTCT
CCAAGGGCCTCTGGATGGAATGTGCCACACACAGCACAGGCATCACCCAGTGTGACATCTATAGC
ACCCTTCTGGGCCTGCCCGCTGACATCCAGGCTGCCCAGGCCATGATGGTGACATCCAGTGCAAT
CTCCTCCCTGGCCTGCATTATCTCTGTGGTGGGCATGAGATGCACAGTCTTCTGCCAGGAATCCC
GAGCCAAAGACAGAGTGGCGGTAGCAGGTGGAGTCTTTTTCATCCTTGGAGGCCTCCTGGGATTC
ATTCCTGTTGCCTGGAATCTTCATGGGATCCTACGGGACTTCTACTCACCACTGGTGCCTGACAG
CATGAAATTTGAGATTGGAGAGGCTCTTTACTTGGGCATTATTTCTTCCCTGTTCTCCCTGATAG
CTGGAATCATCCTCTGCTTTTCCTGCTCATCCCAGAGAAATCGCTCCAACTACTACGATGCCTAC
CAAGCCCAACCTCTTGCCACAAGGAGCTCTCCAAGGCCTGGTCAACCTCCCAAAGTCAAGAGTGA
GTTCAATTCCTACAGCCTGACAGGGTATGTGTGAAGAACCAGGGGCCAGAGCTGGGGGGTGGCTG
GGTCTGTGAAAAACAGTGGACAGCACCCCGAGGGCCACAGGTGAGGGACACTACCACTGGATCGT
GTCAGAAGGTGCTGCTGAGGATAGACTGACTTTGGCCATTGGATTGAGCAAAGGCAGAAATGGGG
GCTAGTGTAACAGCATGCAGGTTGAATTGCCAAGGATGCTCGCCATGCCAGCCTTTCTGTTTTCC
TCACCTTGCTGCTCCCCTGCCCTAAGTCCCCAACCCTCAACTTGAAACCCCATTCCCTTAAGCCA
GGACTCAGAGGATCCCTTTGCCCTCTGGTTTACCTGGGACTCCATCCCCAAACCCACTAATCACA
TCCCACTGACTGACCCTCTGTGATCAAAGACCCTCTCTCTGGCTGAGGTTGGCTCTTAGCTCATT
GCTGGGGATGGGAAGGAGAAGCAGTGGCTTTTGTGGGCATTGCTCTAACCTACTTCTCAAGCTTC
CCTCCAAAGAAACTGATTGGCCCTGGAACCTCCATCCCACTCTTGTTATGACTCCACAGTGTCCA
GACTAATTTGTGCATGAACTGAAATAAAACCATCCTACGGTATCCAGGGAACAGAAAGCAGGATG
CAGGATGGGAGGACAGGAAGGCAGCCTGGGACATTTAAAAAAATA
```

FIGURE 8o

MASLGLQLVGYILGLLGLLGTLVAMLLPSWKTSSYVGASIVTAVGFSKGLWMECATHSTGITQCD
IYSTLLGLPADIQAAQAMMVTSSAISSLACIISVVGMRCTVFCQESRAKDRVAVAGGVFFILGGL
LGFIPVAWNLHGILRDFYSPLVPDSMKFEIGEALYLGIISSLFSLIAGIILCFSCSSQRNRSNYY
DAYQAQPLATRSSPRPGQPPKVKSEFNSYSLTGYV

Important features of the protein:

Signal peptide:

amino acids 1-24

Transmembrane domains:

amino acids 82-102, 117-140, 163-182

N-glycosylation site.

amino acids 190-193

PMP-22 / EMP / MP20 family proteins.

amino acids 46-59

FIGURE 81

CCCACGCGTCCGCGCCTCTCCCTTCTGCTGGACCTTCCTTCGTCTCTCCATCTCTCCCTCCTTTC
CCCGCGTTCTCTTTCCACCTTTCTCTTCTTCCCACCTTAGACCTCCCTTCCTGCCCTCCTTTCCT
GCCCACCGCTGCTTCCTGGCCCTTCTCCGACCCCGCTCTAGCAGCAGACCTCCTGGGGTCTGTGG
GTTGATCTGTGGCCCCTGTGCCTCCGTGTCCTTTTCGTCTCCCTTCCTCCCGACTCCGCTCCCGG
ACCAGCGGCCTGACCCTGGGGAAAGG<u>ATG</u>GTTCCCGAGGTGAGGGTCCTCTCCTCCTTGCTGGGA
CTCGCGCTGCTCTGGTTCCCCCTGGACTCCCACGCTCGAGCCCGCCCAGACATGTTCTGCCTTTT
CCATGGGAAGAGATACTCCCCCGGCGAGAGCTGGCACCCCTACTTGGAGCCACAAGGCCTGATGT
ACTGCCTGCGCTGTACCTGCTCAGAGGGCGCCCATGTGAGTTGTTACCGCCTCCACTGTCCGCCT
GTCCACTGCCCCCAGCCTGTGACGGAGCCACAGCAATGCTGTCCCAAGTGTGTGGAACCTCACAC
TCCCTCTGGACTCCGGGCCCCACCAAAGTCCTGCCAGCACAACGGGACCATGTACCAACACGGAG
AGATCTTCAGTGCCCATGAGCTGTTCCCCTCCCGCCTGCCCAACCAGTGTGTCCTCTGCAGCTGC
ACAGAGGGCCAGATCTACTGCGGCCTCACAACCTGCCCCGAACCAGGCTGCCCAGCACCCCTCCC
ACTGCCAGACTCCTGCTGCCAAGCCTGCAAAGATGAGGCAAGTGAGCAATCGGATGAAGAGGACA
GTGTGCAGTCGCTCCATGGGGTGAGACATCCTCAGGATCCATGTTCCAGTGATGCTGGGAGAAAG
AGAGGCCCGGGCACCCCAGCCCCCACTGGCCTCAGCGCCCCTCTGAGCTTCATCCCTCGCCACTT
CAGACCCAAGGGAGCAGGCAGCACAACTGTCAAGATCGTCCTGAAGGAGAAACATAAGAAAGCCT
GTGTGCATGGCGGGAAGACGTACTCCCACGGGGAGGTGTGGCACCCGGCCTTCCGTGCCTTCGGC
CCCTTGCCCTGCATCCTATGCACCTGTGAGGATGGCCGCCAGGACTGCCAGCGTGTGACCTGTCC
CACCGAGTACCCCTGCCGTCACCCCGAGAAAGTGGCTGGGAAGTGCTGCAAGATTTGCCCAGAGG
ACAAAGCAGACCCTGGCCACAGTGAGATCAGTTCTACCAGGTGTCCCAAGGCACCGGGCCGGGTC
CTCGTCCACACATCGGTATCCCCAAGCCCAGACAACCTGCGTCGCTTTGCCCTGGAACACGAGGC
CTCGGACTTGGTGGAGATCTACCTCTGGAAGCTGGTAAAAGATGAGGAAACTGAGGCTCAGAGAG
GTGAAGTACCTGGCCCAAGGCCACACAGCCAGAATCTTCCACTTGACTCAGATCAAGAAAGTCAG
GAAGCAAGACTTCCAGAAAGAGGCACAGCACTTCCGACTGCTCGCTGGCCCCACGAAGGTCACT
GGAACGTCTTCCTAGCCCAGACCCTGGAGCTGAAGGTCACGGCCAGTCCAGACAAAGTGACCAAG
ACATAACAAAGACC<u>TAA</u>CAGTTGCAGATATGAGCTGTATAATTGTTGTTATTATATATTAATAAA
TAAGAAGTTGCATTACCCTCAAAAAAAAAAAAAAAAAAAAAAA

FIGURE 82

MVPEVRVLSSLLGLALLWFPLDSHARARPDMFCLFHGKRYSPGESWHPYLEPQGLMYCLRCTCSE
GAHVSCYRLHCPPVHCPQPVTEPQQCCPKCVEPHTPSGLRAPPKSCQHNGTMYQHGEIFSAHELF
PSRLPNQCVLCSCTEGQIYCGLTTCPEPGCPAPLPLPDSCCQACKDEASEQSDEEDSVQSLHGVR
HPQDPCSSDAGRKRGPGTPAPTGLSAPLSFIPRHFRPKGAGSTTVKIVLKEKHKKACVHGGKTYS
HGEVWHPAFRAFGPLPCILCTCEDGRQDCQRVTCPTEYPCRHPEKVAGKCCKICPEDKADPGHSE
ISSTRCPKAPGRVLVHTSVSPSPDNLRRFALEHEASDLVEIYLWKLVKDEETEAQRGEVPGPRPH
SQNLPLDSDQESQEARLPERGTALPTARWPPRRSLERLPSPDPGAEGHGQSRQSDQDITKT

Signal peptide:
amino acids 1-25

FIGURE 83

```
GACAGCTGTGTCTCGATGGAGTAGACTCTCAGAACAGCGCAGTTTGCCCTCCGCTCACGCAGAGCCTCTCC
GTGGCTTCCGCACCTTGAGCATTAGGCCAGTTCTCCTCTTCTCTCTAATCCATCCGTCACCTCTCCTGTCA
TCCGTTTCCATGCCGTGAGGTCCATTCACAGAACACATCCATGGCTCTCATGCTCAGTTTGGTTCTGAGTC
TCCTCAAGCTGGGATCAGGGCAGTGGCAGGTGTTTGGGCCAGACAAGCCTGTCCAGGCCTTGGTGGGGGAG
GACGCAGCATTCTCCTGTTTCCTGTCTCCTAAGACCAATGCAGAGGCCATGGAAGTGCGGTTCTTCAGGGG
CCAGTTCTCTAGCGTGGTCCACCTCTACAGGGACGGGAAGGACCAGCCATTTATGCAGATGCCACAGTATC
AAGGCAGGACAAAACTGGTGAAGGATTCTATTGCGGAGGGGCGCATCTCTCTGAGGCTGGAAAACATTACT
GTGTTGGATGCTGGCCTCTATGGGTGCAGGATTAGTTCCCAGTCTTACTACCAGAAGGCCATCTGGGAGCT
ACAGGTGTCAGCACTGGGCTCAGTTCCTCTCATTTCCATCACGGGATATGTTGATAGAGACATCCAGCTAC
TCTGTCAGTCCTCGGGCTGGTTCCCCGGCCCACAGCGAAGTGGAAAGGTCCACAAGGACAGGATTTGTCC
ACAGACTCCAGGACAAACAGAGACATGCATGGCCTGTTTGATGTGGAGATCTCTCTGACCGTCCAAGAGAA
CGCCGGGAGCATATCCTGTTCCATGCGGCATGCTCATCTGAGCCGAGAGGTGGAATCCAGGGTACAGATAG
GAGATACCTTTTTCGAGCCTATATCGTGGCACCTGGCTACCAAAGTACTGGGAATACTCTGCTGTGGCCTA
TTTTTTGGCATTGTTGGACTGAAGATTTTCTTCTCCAAATTCCAGTGGAAAATCCAGGCGGAACTGGACTG
GAGAAGAAAGCACGGACAGGCAGAATTGAGAGACGCCCGGAAACACGCAGTGGAGGTGACTCTGGATCCAG
AGACGGCTCACCCGAAGCTCTGCGTTTCTGATCTGAAAACTGTAACCCATAGAAAAGCTCCCCAGGAGGTG
CCTCACTCTGAGAAGAGATTTACAAGGAAGAGTGTGGTGGCTTCTCAGAGTTTCCAAGCAGGGAAACATTA
CTGGGAGGTGGACGGAGGACACAATAAAAGGTGGCGCGTGGGAGTGTGCCGGGATGATGTGGACAGGAGGA
AGGAGTACGTGACTTTGTCTCCCGATCATGGGTACTGGGTCCTCAGACTGAATGGAGAACATTTGTATTTC
ACATTAAATCCCCGTTTTATCAGCGTCTTCCCCAGGACCCCACCTACAAAAATAGGGGTCTTCCTGGACTA
TGAGTGTGGGACCATCTCCTTCTTCAACATAAATGACCAGTCCCTTATTTATACCCTGACATGTCGGTTTG
AAGGCTTATTGAGGCCCTACATTGAGTATCCGTCCTATAATGAGCAAAATGGAACTCCCATAGTCATCTGC
CCAGTCACCCAGGAATCAGAGAAAGAGGCCTCTTGGCAAAGGGCCTCTGCAATCCCAGAGACAAGCAACAG
TGAGTCCTCCTCACAGGCAACCACGCCCTTCCTCCCCAGGGGTGAAATGTAGGATGAATCACATCCCACAT
TCTTCTTTAGGGATATTAAGGTCTCTCTCCCAGATCCAAAGTCCCGCAGCAGCCGGCCAAGGTGGCTTCCA
GATGAAGGGGACTGGCCTGTCCACATGGGAGTCAGGTGTCATGGCTGCCCTGAGCTGGAGGGAAGAAGG
CTGACATTACATTTAGTTTGCTCTCACTCCATCTGGCTAAGTGATCTTGAAATACCACCTCTCAGGTGAAG
AACCGTCAGGAATTCCCATCTCACAGGCTGTGGTGTAGATTAAGTAGACAAGGAATGTGAATAATGCTTAG
ATCTTATTGATGACAGAGTGTATCCTAATGGTTTGTTCATTATATTACACTTTCAGTAAAAAAA
```

FIGURE 84

MALMLSLVLSLLKLGSGQWQVFGPDKPVQALVGEDAAFSCFLSPKTNAEAMEVRFFRGQFSSVVH
LYRDGKDQPFMQMPQYQGRTKLVKDSIAEGRISLRLENITVLDAGLYGCRISSQSYYQKAIWELQ
VSALGSVPLISITGYVDRDIQLLCQSSGWFPRPTAKWKGPQGQDLSTDSRTNRDMHGLFDVEISL
TVQENAGSISCSMRHAHLSREVESRVQIGDTFFEPISWHLATKVLGILCCGLFFGIVGLKIFFSK
FQWKIQAELDWRRKHGQAELRDARKHAVEVTLDPETAHPKLCVSDLKTVTHRKAPQEVPHSEKRF
TRKSVVASQSFQAGKHYWEVDGGHNKRWRVGVCRDDVDRRKEYVTLSPDHGYWVLRLNGEHLYFT
LNPRFISVFPRTPPTKIGVFLDYECGTISFFNINDQSLIYTLTCRFEGLLRPYIEYPSYNEQNGT
PIVICPVTQESEKEASWQRASAIPETSNSESSSQATTPFLPRGEM

Signal peptide:

amino acids 1-17

Transmembrane domain:

amino acids 239-255

FIGURE 85

AACAGACGTTCCCTCGCGGCCCTGGCACCTCTAACCCCAGAC<u>ATG</u>CTGCTGCTGCTGCTGCCCCT
GCTCTGGGGGAGGGAGAGGGCGGAAGGACAGACAAGTAAACTGCTGACGATGCAGAGTTCCGTGA
CGGTGCAGGAAGGCCTGTGTGTCCATGTGCCCTGCTCCTTCTCCTACCCCTCGCATGGCTGGATT
TACCCTGGCCCAGTAGTTCATGGCTACTGGTTCCGGGAAGGGGCCAATACAGACCAGGATGCTCC
AGTGGCCACAAACAACCCAGCTCGGGCAGTGTGGGAGGAGACTCGGGACCGATTCCACCTCCTTG
GGGACCCACATACCAAGAATTGCACCCTGAGCATCAGAGATGCCAGAAGAAGTGATGCGGGGAGA
TACTTCTTTCGTATGGAGAAAGGAAGTATAAAATGGAATTATAAACATCACCGGCTCTCTGTGAA
TGTGACAGCCTTGACCCACAGGCCCAACATCCTCATCCCAGGCACCCTGGAGTCCGGCTGCCCCC
AGAATCTGACCTGCTCTGTGCCCTGGGCCTGTGAGCAGGGGACACCCCTATGATCTCCTGGATA
GGGACCTCCGTGTCCCCCCTGGACCCCTCCACCACCCGCTCCTCGGTGCTCACCCTCATCCCACA
GCCCCAGGACCATGGCACCAGCCTCACCTGTCAGGTGACCTTCCCTGGGGCCAGCGTGACCACGA
ACAAGACCGTCCATCTCAACGTGTCCTACCCGCCTCAGAACTTGACCATGACTGTCTTCCAAGGA
GACGGCACAGTATCCACAGTCTTGGGAAATGGCTCATCTCTGTCACTCCCAGAGGGCCAGTCTCT
GCGCCTGGTCTGTGCAGTTGATGCAGTTGACAGCAATCCCCCTGCCAGGCTGAGCCTGAGCTGGA
GAGGCCTGACCCTGTGCCCCTCACAGCCCTCAAACCCGGGGGTGCTGGAGCTGCCTTGGGTGCAC
CTGAGGGATGCAGCTGAATTCACCTGCAGAGCTCAGAACCCTCTCGGCTCTCAGCAGGTCTACCT
GAACGTCTCCCTGCAGAGCAAAGCCACATCAGGAGTGACTCAGGGGGTGGTCGGGGAGCTGGAG
CCACAGCCCTGGTCTTCCTGTCCTTCTGCGTCATCTTCGTTGTAGTGAGGTCCTGCAGGAAGAAA
TCGGCAAGGCCAGCAGCGGGCGTGGGAGATACGGGCATAGAGGATGCAAACGCTGTCAGGGGTTC
AGCCTCTCAGGGGCCCCTGACTGAACCTTGGGCAGAAGACAGTCCCCCAGACCAGCCTCCCCCAG
CTTCTGCCCGCTCCTCAGTGGGGGAAGGAGAGCTCCAGTATGCATCCCTCAGCTTCCAGATGGTG
AAGCCTTGGGACTCGCGGGGACAGGAGGCCACTGACACCGAGTACTCGGAGATCAAGATCCACAG
A<u>TGA</u>GAAACTGCAGAGACTCACCCTGATTGAGGGATCACAGCCCCTCCAGGCAAGGGAGAAGTCA
GAGGCTGATTCTTGTAGAATTAACAGCCCTCAACGTGATGAGCTATGATAACACTATGAATTATG
TGCAGAGTGAAAAGCACACAGGCTTTAGAGTCAAAGTATCTCAAACCTGAATCCACACTGTGCCC
TCCCTTTTATTTTTTTAACTAAAAGACAGACAAATTCCTA

FIGURE 86

MLLLLLPLLWGRERAEGQTSKLLTMQSSVTVQEGLCVHVPCSFSYPSHGWIYPGPVVHGYWFREG
ANTDQDAPVATNNPARAVWEETRDRFHLLGDPHTKNCTLSIRDARRSDAGRYFFRMEKGSIKWNY
KHHRLSVNVTALTHRPNILIPGTLESGCPQNLTCSVPWACEQGTPPMISWIGTSVSPLDPSTTRS
SVLTLIPQPQDHGTSLTCQVTFPGASVTTNKTVHLNVSYPPQNLTMTVFQGDGTVSTVLGNGSSL
SLPEGQSLRLVCAVDAVDSNPPARLSLSWRGLTLCPSQPSNPGVLELPWVHLRDAAEFTCRAQNP
LGSQQVYLNVSLQSKATSGVTQGVVGGAGATALVFLSFCVIFVVVRSCRKKSARPAAGVGDTGIE
DANAVRGSASQGPLTEPWAEDSPPDQPPPASARSSVGEGELQYASLSFQMVKPWDSRGQEATDTE
YSEIKIHR

Signal peptide:
amino acids 1-15

Transmembrane domain:
amino acids 351-370

FIGURE 87

```
AGAAAGCTGCACTCTGTTGAGCTCCAGGGCGCAGTGGAGGGAGGGAGTGAAGGAGCTCTCTGTAC
CCAAGGAAAGTGCAGCTGAGACTCAGACAAGATTACAATGAACCAACTCAGCTTCCTGCTGTTTC
TCATAGCGACCACCAGAGGATGGAGTACAGATGAGGCTAATACTTACTTCAAGGAATGGACCTGT
TCTTCGTCTCCATCTCTGCCCAGAAGCTGCAAGGAAATCAAAGACGAATGTCCTAGTGCATTTGA
TGGCCTGTATTTTCTCCGCACTGAGAATGGTGTTATCTACCAGACCTTCTGTGACATGACCTCTG
GGGGTGGCGGCTGGACCCTGGTGGCCAGCGTGCATGAGAATGACATGCGTGGGAAGTGCACGGTG
GGCGATCGCTGGTCCAGTCAGCAGGGCAGCAAAGCAGACTACCCAGAGGGGGACGGCAACTGGGC
CAACTACAACACCTTTGGATCTGCAGAGGCGGCCACGAGCGATGACTACAAGAACCCTGGCTACT
ACGACATCCAGGCCAAGGACCTGGGCATCTGGCACGTGCCCAATAAGTCCCCCATGCAGCACTGG
AGAAACAGCTCCCTGCTGAGGTACCGCACGGACACTGGCTTCCTCCAGACACTGGGACATAATCT
GTTTGGCATCTACCAGAAATATCCAGTGAAATATGGAGAAGGAAAGTGTTGGACTGACAACGGCC
CGGTGATCCCTGTGGTCTATGATTTTGGCGACGCCCAGAAAACAGCATCTTATTACTCACCCTAT
GGCCAGCGGGAATTCACTGCGGGATTTGTTCAGTTCAGGGTATTTAATAACGAGAGAGCAGCCAA
CGCCTTGTGTGCTGGAATGAGGGTCACCGGATGTAACACTGAGCATCACTGCATTGGTGGAGGAG
GATACTTTCCAGAGGCCAGTCCCCAGCAGTGTGGAGATTTTTCTGGTTTTGATTGGAGTGGATAT
GGAACTCATGTTGGTTACAGCAGCAGCCGTGAGATAACTGAGGCAGCTGTGCTTCTATTCTATCG
TTGAGAGTTTTGTGGGAGGGAACCCAGACCTCTCCTCCCAACCATGAGATCCCAAGGATGGAGAA
CAACTTACCCAGTAGCTAGAATGTTAATGGCAGAAGAGAAAACAATAAATCATATTGACTCAAGA
AAAAAA
```

FIGURE 88

MNQLSFLLFLIATTRGWSTDEANTYFKEWTCSSSPSLPRSCKEIKDECPSAFDGLYFLRTENGVI
YQTFCDMTSGGGGWTLVASVHENDMRGKCTVGDRWSSQQGSKADYPEGDGNWANYNTFGSAEAAT
SDDYKNPGYYDIQAKDLGIWHVPNKSPMQHWRNSSLLRYRTDTGFLQTLGHNLFGIYQKYPVKYG
EGKCWTDNGPVIPVVYDFGDAQKTASYYSPYGQREFTAGFVQFRVFNNERAANALCAGMRVTGCN
TEHHCIGGGGYFPEASPQQCGDFSGFDWSGYGTHVGYSSSREITEAAVLLFYR

Important features:
Signal peptide:
amino acids 1-16

N-glycosylation site.
amino acids 163-167

Glycosaminoglycan attachment sites.
amino acids 74-78, 289-293

N-myristoylation sites.
amino acids 76-82, 115-121, 124-130, 253-259, 292-298

FIGURE 89

CTAGATTTGTCGGCTTGCGGGGAGACTTCAGGAGTCGCTGTCTCTGAACTTCCAGCCTCAGAGAC
CGCCGCCCTTGTCCCCGAGGGCATGGGCCGGGTCTCAGGGCTTGTGCCCTCTCGCTTCCTGACG
CTCCTGGCGCATCTGGTGGTCGTCATCACCTTATTCTGGTCCCGGGACAGCAACATACAGGCCTG
CCTGCCTCTCACGTTCACCCCGAGGAGTATGACAAGCAGGACATTCAGCTGGTGGCCGCGCTCT
CTGTCACCCTGGGCCTCTTTGCAGTGGAGCTGGCCGGTTTCCTCTCAGGAGTCTCCATGTTCAAC
AGCACCCAGAGCCTCATCTCCATTGGGGCTCACTGTAGTGCATCCGTGGCCCTGTCCTTCTTCAT
ATTCGAGCGTTGGGAGTGCACTACGTATTGGTACATTTTTGTCTTCTGCAGTGCCCTTCCAGCTG
TCACTGAAATGGCTTTATTCGTCACCGTCTTTGGGCTGAAAAAGAAACCCTTCTGATTACCTTCA
TGACGGGAACCTAAGGACGAAGCCTACAGGGGCAAGGGCCGCTTCGTATTCCTGGAAGAAGGAAG
GCATAGGCTTCGGTTTTCCCCTCGGAAACTGCTTCTGCTGGAGGATATGTGTTGGAATAATTACG
TCTTGAGTCTGGGATTATCCGCATTGTATTTAGTGCTTTGTAATAAAATATGTTTTGTAGTAACA
TTAAGACTTATATACAGTTTTAGGGGACAATTAAAAAAAAAAAA

FIGURE 90

MGRVSGLVPSRFLTLLAHLVVVITLFWSRDSNIQACLPLTFTPEEYDKQDIQLVAALSVTLGLFA
VELAGFLSGVSMFNSTQSLISIGAHCSASVALSFFIFERWECTTYWYIFVFCSALPAVTEMALFV
TVFGLKKKPF

Transmembrane domain:

amino acids 12-28 (type II), 51-66, 107-124

FIGURE 91

```
CTGGGACCCCGAAAAGAGAAGGGGAGAGCGAGGGGACGAGAGCGGAGGAGGAAGATGCAACTGAC
TCGCTGCTGCTTCGTGTTCCTGGTGCAGGGTAGCCTCTATCTGGTCATCTGTGGCCAGGATGATG
GTCCTCCCGGCTCAGAGGACCCTGAGCGTGATGACCACGAGGGCCAGCCCCGGCCCCGGGTGCCT
CGGAAGCGGGGCCACATCTCACCTAAGTCCCGCCCCATGGCCAATTCCACTCTCCTAGGGCTGCT
GGCCCCGCCTGGGGAGGCTTGGGGCATTCTTGGGCAGCCCCCAACCGCCCGAACCACAGCCCCC
CACCCTCAGCCAAGGTGAAGAAAATCTTTGGCTGGGGCGACTTCTACTCCAACATCAAGACGGTG
GCCCTGAACCTGCTCGTCACAGGGAAGATTGTGGACCATGGCAATGGGACCTTCAGCGTCCACTT
CCAACACAATGCCACAGGCCAGGGAAACATCTCCATCAGCCTCGTGCCCCCAGTAAAGCTGTAG
AGTTCCACCAGGAACAGCAGATCTTCATCGAAGCCAAGGCCTCCAAAATCTTCAACTGCCGGATG
GAGTGGGAGAAGGTAGAACGGGGCCGCCGGACCTCGCTTTGCACCCACGACCCAGCCAAGATCTG
CTCCCGAGACCACGCTCAGAGCTCAGCCACCTGGAGCTGCTCCCAGCCCTTCAAAGTCGTCTGTG
TCTACATCGCCTTCTACAGCACGGACTATCGGCTGGTCCAGAAGGTGTGCCCAGATTACAACTAC
CATAGTGATACCCCCTACTACCCATCTGGGTGACCCGGGGCAGGCCACAGAGGCCAGGCCAGGGC
TGGAAGGACAGGCCTGCCCATGCAGGAGACCATCTGGACACCGGGCAGGGAAGGGGTTGGGCCTC
AGGCAGGGAGGGGGTGGAGACGAGGAGATGCCAAGTGGGGCCAGGGCCAAGTCTCAAGTGGCAG
AGAAAGGGTCCCAAGTGCTGGTCCCAACCTGAAGCTGTGGAGTGACTAGATCACAGGAGCACTGG
AGGAGGAGTGGGCTCTCTGTGCAGCCTCACAGGGCTTTGCCACGGAGCCACAGAGAGATGCTGGG
TCCCCGAGGCCTGTGGGCAGGCCGATCAGTGTGGCCCCAGATCAAGTCATGGGAGGAAGCTAAGC
CCTTGGTTCTTGCCATCCTGAGGAAAGATAGCAACAGGGAGGGGGAGATTTCATCAGTGTGGACA
GCCTGTCAACTTAGGATGGATGGCTGAGAGGGCTTCCTAGGAGCCAGTCAGCAGGGTGGGGTGGG
GCCAGAGGAGCTCTCCAGCCCTGCCTAGTGGGCGCCCTGAGCCCCTTGTCGTGTGCTGAGCATGG
CATGAGGCTGAAGTGGCAACCCTGGGGTCTTTGATGTCTTGACAGATTGACCATCTGTCTCCAGC
CAGGCCACCCCTTTCCAAAATTCCCTCTTCTGCCAGTACTCCCCCTGTACCACCCATTGCTGATG
GCACACCCATCCTTAAGCTAAGACAGGACGATTGTGGTCCTCCCACACTAAGGCCACAGCCCATC
CGCGTGCTGTGTGTCCCTCTTCCACCCCAACCCCTGCTGGCTCCTCTGGGAGCATCCATGTCCCG
GAGAGGGGTCCCTCAACAGTCAGCCTCACCTGTCAGACCGGGGTTCTCCCGGATCTGGATGGCGC
CGCCCTCTCAGCAGCGGGCACGGGTGGGCGGGGCCGGCCGCAGAGCATGTGCTGGATCTGTTC
TGTGTGTCTGTCTGTGGGTGGGGGAGGGGAGGGAAGTCTTGTGAAACCGCTGATTGCTGACTTT
TGTGTGAAGAATCGTGTTCTTGGAGCAGGAAATAAAGCTTGCCCCGGGGCA
```

FIGURE 92

MQLTRCCFVFLVQGSLYLVICGQDDGPPGSEDPERDDHEGQPRPRVPRKRGHISPKSRPMANSTL
LGLLAPPGEAWGILGQPPNRPNHSPPPSAKVKKIFGWGDFYSNIKTVALNLLVTGKIVDHGNGTF
SVHFQHNATGQGNISISLVPPSKAVEFHQEQQIFIEAKASKIFNCRMEWEKVERGRRTSLCTHDP
AKICSRDHAQSSATWSCSQPFKVVCVYIAFYSTDYRLVQKVCPDYNYHSDTPYYPSG

Important features of the protein:

Signal peptide:

amino acids 1-14

N-glycosylation sites.

amino acids 62-65, 127-130, 137-140, 143-146

2-oxo acid dehydrogenases acyltransferase amino acids 61-71

FIGURE 93

CGGTGGCCATGACTGCGGCCGTGTTCTTCGGCTGCGCCTTCATTGCCTTCGGGCCTGCGCTCGCC
CTTTATGTCTTCACCATCGCCATCGAGCCGTTGCGTATCATCTTCCTCATCGCCGGAGCTTTCTT
CTGGTTGGTGTCTCTACTGATTTCGTCCCTTGTTTGGTTCATGGCAAGAGTCATTATTGACAACA
AAGATGGACCAACACAGAAATATCTGCTGATCTTTGGAGCGTTTGTCTCTGTCTATATCCAAGAA
ATGTTCCGATTTGCATATTATAAACTCTTAAAAAAAGCCAGTGAAGGTTTGAAGAGTATAAACCC
AGGTGAGACAGCACCCTCTATGCGACTGCTGGCCTATGTTTCTGGCTTGGGCTTTGGAATCATGA
GTGGAGTATTTTCCTTTGTGAATACCCTATCTGACTCCTTGGGGCCAGGCACAGTGGGCATTCAT
GGAGATTCTCCTCAATTCTTCCTTTATTCAGCTTTCATGACGCTGGTCATTATCTTGCTGCATGT
ATTCTGGGGCATTGTATTTTTTGATGGCTGTGAGAAGAAAAAGTGGGGCATCCTCCTTATCGTTC
TCCTGACCCACCTGCTGGTGTCAGCCCAGACCTTCATAAGTTCTTATTATGGAATAAACCTGGCG
TCAGCATTTATAATCCTGGTGCTCATGGGCACCTGGGCATTCTTAGCTGCGGGAGGCAGCTGCCG
AAGCCTGAAACTCTGCCTGCTCTGCCAAGACAAGAACTTTCTTCTTTACAACCAGCGCTCCAGAT
AACCTCAGGGAACCAGCACTTCCCAAACCGCAGACTACATCTTTAGAGGAAGCACAACTGTGCCT
TTTTCTGAAAATCCCTTTTTCTGGTGGAATTGAGAAAGAAATAAAACTATGCAGATA

FIGURE 94

MTAAVFFGCAFIAFGPALALYVFTIAIEPLRIIFLIAGAFFWLVSLLISSLVWFMARVIIDNKDG
PTQKYLLIFGAFVSVYIQEMFRFAYYKLLKKASEGLKSINPGETAPSMRLLAYVSGLGFGIMSGV
FSFVNTLSDSLGPGTVGIHGDSPQFFLYSAFMTLVIILLHVFWGIVFFDGCEKKKWGILLIVLLT
HLLVSAQTFISSYYGINLASAFIILVLMGTWAFLAAGGSCRSLKLCLLCQDKNFLLYNQRSR

Important features of the protein:

Signal peptide:

amino acids 1-19

Transmembrane domains:

amino acids 32-51, 119-138, 152-169, 216-235

Glycosaminoglycan attachment site.

amino acids 120-123

Sodium:neurotransmitter symporter family protein amino acids 31-65

FIGURE 95

AATTTTTCACCAGAGTAAACTTGAGAAACCAACTGGACCTTGAGTATTGTACATTTTGCCTCGTG
GACCCAAAGGTAGCAATCTGAAACATGAGGAGTACGATTCTACTGTTTTGTCTTCTAGGATCAAC
TCGGTCATTACCACAGCTCAAACCTGCTTTGGGACTCCCTCCCACAAAACTGGCTCCGGATCAGG
GAACACTACCAAACCAACAGCAGTCAAATCAGGTCTTTCCTTCTTTAAGTCTGATACCATTAACA
CAGATGCTCACACTGGGGCCAGATCTGCATCTGTTAAATCCTGCTGCAGGAATGACACCTGGTAC
CCAGACCCACCCATTGACCCTGGGAGGGTTGAATGTACAACAGCAACTGCACCCACATGTGTTAC
CAATTTTTGTCACACAACTTGGAGCCCAGGGCACTATCCTAAGCTCAGAGGAATTGCCACAAATC
TTCACGAGCCTCATCATCCATTCCTTGTTCCCGGGAGGCATCCTGCCCACCAGTCAGGCAGGGGC
TAATCCAGATGTCCAGGATGGAAGCCTTCCAGCAGGAGGAGCAGGTGTAAATCCTGCCACCCAGG
GAACCCCAGCAGGCCGCCTCCCAACTCCCAGTGGCACAGATGACGACTTTGCAGTGACCACCCCT
GCAGGCATCCAAAGGAGCACACATGCCATCGAGGAAGCCACCACAGAATCAGCAAATGGAATTCA
GTAAGCTGTTTCAAATTTTTTCAACTAAGCTGCCTCGAATTTGGTGATACATGTGAATCTTTATC
ATTGATTATATTATGGAATAGATTGAGACACATTGGATAGTCTTAGAAGAAATTAATTCTTAATT
TACCTGAAAATATTCTTGAAATTTCAGAAAATATGTTCTATGTAGAGAATCCCAACTTTTAAAAA
CAATAATTCAATGGATAAATCTGTCTTTGAAATATAACATTATGCTGCCTGGATGATATGCATAT
TAAAACATATTTGGAAAACTGGAAAAAAAAAAAAAAAAAAAAAAAAAAAAAAAAAAAAAAAAAAA
AAAAAAAAAAAAAAAAAAAAAAAAAAAAAA

FIGURE 96

MRSTILLFCLLGSTRSLPQLKPALGLPPTKLAPDQGTLPNQQQSNQVFPSLSLIPLTQM
LTLGPDLHLLNPAAGMTPGTQTHPLTLGGLNVQQQLHPHVLPIFVTQLGAQGTILSSEE
LPQIFTSLIIHSLFPGGILPTSQAGANPDVQDGSLPAGGAGVNPATQGTPAGRLPTPSG
TDDDFAVTTPAGIQRSTHAIEEATTESANGIQ

Signal peptide:
amino acids 1-16

FIGURE 97

```
GCTCAAGTGCCCTGCCTTGCCCCACCCAGCCCAGCCTGGCCAGAGCCCCCTGGAGAAGGAGCTCT
CTTCTTGCTTGGCAGCTGGACCAAGGGAGCCAGTCTTGGGCGCTGGAGGGCCTGTCCTGACCATG
GTCCCTGCCTGGCTGTGGCTGCTTTGTGTCTCCGTCCCCCAGGCTCTCCCCAAGGCCCAGCCTGC
AGAGCTGTCTGTGGAAGTTCCAGAAAACTATGGTGGAAATTTCCCTTTATACCTGACCAAGTTGC
CGCTGCCCCGTGAGGGGGCTGAAGGCCAGATCGTGCTGTCAGGGGACTCAGGCAAGGCAACTGAG
GGCCCATTTGCTATGGATCCAGATTCTGGCTTCCTGCTGGTGACCAGGGCCCTGGACCGAGAGGA
GCAGGCAGAGTACCAGCTACAGGTCACCCTGGAGATGCAGGATGGACATGTCTTGTGGGGTCCAC
AGCCTGTGCTTGTGCACGTGAAGGATGAGAATGACCAGGTGCCCCATTTCTCTCAAGCCATCTAC
AGAGCTCGGCTGAGCCGGGGTACCAGGCCTGGCATCCCCTTCCTCTTCCTTGAGGCTTCAGACCG
GGATGAGCCAGGCACAGCCAACTCGGATCTTCGATTCCACATCCTGAGCCAGGCTCCAGCCCAGC
CTTCCCCAGACATGTTCCAGCTGGAGCCTCGGCTGGGGCTCTGGCCCTCAGCCCCAAGGGGAGC
ACCAGCCTTGACCACGCCCTGGAGAGGACCTACCAGCTGTTGGTACAGGTCAAGGACATGGGTGA
CCAGGCCTCAGGCCACCAGGCCACTGCCACCGTGGAAGTCTCCATCATAGAGAGCACCTGGGTGT
CCCTAGAGCCTATCCACCTGGCAGAGAATCTCAAAGTCCTATACCCGCACCACATGGCCCAGGTA
CACTGGAGTGGGGGTGATGTGCACTATCACCTGGAGAGCCATCCCCCGGGACCCTTTGAAGTGAA
TGCAGAGGGAAACCTCTACGTGACCAGAGAGCTGGACAGAGAAGCCCAGGCTGAGTACCTGCTCC
AGGTGCGGGCTCAGAATTCCCATGGCGAGGACTATGCGGCCCCTCTGGAGCTGCACGTGCTGGTG
ATGGATGAGAATGACAACGTGCCTATCTGCCCTCCCCGTGACCCCACAGTCAGCATCCCTGAGCT
CAGTCCACCAGGTACTGAAGTGACTAGACTGTCAGCAGAGGATGCAGATGCCCCCGGCTCCCCCA
ATTCCCACGTTGTGTATCAGCTCCTGAGCCCTGAGCCTGAGGATGGGGTAGAGGGGAGAGCCTTC
CAGGTGGACCCCACTTCAGGCAGTGTGACGCTGGGGGTGCTCCCACTCCGAGCAGGCCAGAACAT
CCTGCTTCTGGTGCTGGCCATGGACCTGGCAGGCGCAGAGGGTGGCTTCAGCAGCACGTGTGAAG
TCGAAGTCGCAGTCACAGATATCAATGATCACGCCCTGAGTTCATCACTTCCCAGATTGGGCCT
ATAAGCCTCCCTGAGGATGTGGAGCCCGGGACTCTGGTGGCCATGCTAACAGCCATTGATGCTGA
CCTCGAGCCCGCCTTCCGCCTCATGGATTTTGCCATTGAGAGGGGAGACACAGAAGGGACTTTTG
GCCTGGATTGGGAGCCAGACTCTGGGCATGTTAGACTCAGACTCTGCAAGAACCTCAGTTATGAG
GCAGCTCCAAGTCATGAGGTGGTGGTGGTGGTGCAGAGTGTGGCGAAGCTGGTGGGGCCAGGCCC
AGGCCCTGGAGCCACCGCCACGGTGACTGTGCTAGTGGAGAGAGTGATGCCACCCCCAAGTTGG
ACCAGGAGAGCTACGAGGCCAGTGTCCCCATCAGTGCCCCAGCCGGCTCTTTCCTGCTGACCATC
CAGCCCTCCGACCCCATCAGCCGAACCCTCAGGTTCTCCCTAGTCAATGACTCAGAGGGCTGGCT
CTGCATTGAGAAATTCTCCGGGGAGGTGCACACCGCCCAGTCCCTGCAGGGCGCCCAGCCTGGGG
ACACCTACACGGTGCTTGTGGAGGCCCAGGATACAGCCCTGACTCTTGCCCCTGTGCCCTCCCAA
TACCTCTGCACACCCCGCCAAGACCATGGCTTGATCGTGAGTGGACCCAGCAAGGACCCCGATCT
GGCCAGTGGGCACGGTCCCTACAGCTTCACCCTTGGTCCCAACCCCACGGTGCAACGGGATTGGC
GCCTCCAGACTCTCAATGGTTCCCATGCCTACCTCACCTTGGCCCTGCATTGGGTGGAGCCACGT
GAACACATAATCCCCGTGGTGGTCAGCCACAATGCCCAGATGTGGCAGCTCCTGGTTCGAGTGAT
CGTGTGTCGCTGCAACGTGGAGGGGCAGTGCATGCGCAAGGTGGGCCGCATGAAGGGCATGCCCA
CGAAGCTGTCGGCAGTGGGCATCCTTGTAGGCACCCTGGTAGCAATAGGAATCTTCCTCATCCTC
ATTTTCACCCACTGGACCATGTCAAGGAAGAAGGACCCGGATCAACCAGCAGACAGCGTGCCCCT
GAAGGCGACTGTCTGAATGGCCCAGGCAGCTCTAGCTGGGAGCTTGGCCTCTGGCTCCATCTGAG
TCCCCTGGGAGAGAGCCCAGCACCCAAGATCCAGCAGGGGACAGGACAGAGTAGAAGCCCCTCCA
TCTGCCCTGGGGTGGAGGCACCATCACCATCACCAGGCATGTCTGCAGAGCCTGGACACCAACTT
TATGGACTGCCCATGGGAGTGCTCCAAATGTCAGGGTGTTTGCCCAATAATAAAGCCCCAGAGAA
CTGGGCTGGGCCCTATGGGAAAAAAAAAAAAAAAAAAAAAAAAAAAAAAAAAAAAG
```

FIGURE 98

MVPAWLWLLCVSVPQALPKAQPAELSVEVPENYGGNFPLYLTKLPLPREGAEGQIVLSGDSGKAT
EGPFAMDPDSGFLLVTRALDREEQAEYQLQVTLEMQDGHVLWGPQPVLVHVKDENDQVPHFSQAI
YRARLSRGTRPGIPFLFLEASDRDEPGTANSDLRFHILSQAPAQPSPDMFQLEPRLGALALSPKG
STSLDHALERTYQLLVQVKDMGDQASGHQATATVEVSIIESTWVSLEPIHLAENLKVLYPHHMAQ
VHWSGGDVHYHLESHPPGPFEVNAEGNLYVTRELDREAQAEYLLQVRAQNSHGEDYAAPLELHVL
VMDENDNVPICPPRDPTVSIPELSPPGTEVTRLSAEDADAPGSPNSHVVYQLLSPEPEDGVEGRA
FQVDPTSGSVTLGVLPLRAGQNILLLVLAMDLAGAEGGFSSTCEVEVAVTDINDHAPEFITSQIG
PISLPEDVEPGTLVAMLTAIDADLEPAFRLMDFAIERGDTEGTFGLDWEPDSGHVRLRLCKNLSY
EAAPSHEVVVVVQSVAKLVGPGPGPGATATVTVLVERVMPPPKLDQESYEASVPISAPAGSFLLT
IQPSDPISRTLRFSLVNDSEGWLCIEKFSGEVHTAQSLQGAQPGDTYTVLVEAQDTALTLAPVPS
QYLCTPRQDHGLIVSGPSKDPDLASGHGPYSFTLGPNPTVQRDWRLQTLNGSHAYLTLALHWVEP
REHIIPVVVSHNAQMWQLLVRVIVCRCNVEGQCMRKVGRMKGMPTKLSAVGILVGTLVAIGIFLI
LIFTHWTMSRKKDPDQPADSVPLKATV

Signal peptide:
amino acids 1-18

Transmembrane domain:
amino acids 762-784

FIGURE 99

```
GGCTGACCGTGCTACATTGCCTGGAGGAAGCCTAAGGAACCCAGGCATCCAGCTGCCCACGCCTG
AGTCCAAGATTCTTCCCAGGAACACAAACGTAGGAGACCCACGCTCCTGGAAGCACCAGCCTTTA
TCTCTTCACCTTCAAGTCCCCTTTCTCAAGAATCCTCTGTTCTTTGCCCTCTAAAGTCTTGGTAC
ATCTAGGACCCAGGCATCTTGCTTTCCAGCCACAAAGAGACAGATGAAGATGCAGAAAGGAAATG
TTCTCCTTATGTTTGGTCTACTATTGCATTTAGAAGCTGCAACAAATTCCAATGAGACTAGCACC
TCTGCCAACACTGGATCCAGTGTGATCTCCAGTGGAGCCAGCACAGCCACCAACTCTGGGTCCAG
TGTGACCTCCAGTGGGGTCAGCACAGCCACCATCTCAGGGTCCAGCGTGACCTCCAATGGGGTCA
GCATAGTCACCAACTCTGAGTTCCATACAACCTCCAGTGGGATCAGCACAGCCACCAACTCTGAG
TTCAGCACAGCGTCCAGTGGGATCAGCATAGCCACCAACTCTGAGTCCAGCACAACCTCCAGTGG
GGCCAGCACAGCCACCAACTCTGAGTCCAGCACACCTCCAGTGGGGCCAGCACAGTCACCAACT
CTGGGTCCAGTGTGACCTCCAGTGGAGCCAGCACTGCCACCAACTCTGAGTCCAGCACAGTGTCC
AGTAGGGCCAGCACTGCCACCAACTCTGAGTCTAGCACACTCTCCAGTGGGGCCAGCACAGCCAC
CAACTCTGACTCCAGCACAACCTCCAGTGGGGCTAGCACAGCCACCAACTCTGAGTCCAGCACAA
CCTCCAGTGGGGCCAGCACAGCCACCAACTCTGAGTCCAGCACAGTGTCCAGTAGGGCCAGCACT
GCCACCAACTCTGAGTCCAGCACAACCTCCAGTGGGCCAGCACAGCCACCAACTCTGAGTCCAG
AACGACCTCCAATGGGGCTGGCACAGCCACCAACTCTGAGTCCAGCACGACCTCCAGTGGGGCCA
GCACAGCCACCAACTCTGACTCCAGCACAGTGTCCAGTGGGGCCAGCACTGCCACCAACTCTGAG
TCCAGCACGACCTCCAGTGGGGCCAGCACAGCCACCAACTCTGAGTCCAGCACGACCTCCAGTGG
GGCTAGCACAGCCACCAACTCTGACTCCAGCACAACCTCCAGTGGGGCCGGCACAGCCACCAACT
CTGAGTCCAGCACAGTGTCCAGTGGGATCAGCACAGTCACCAATTCTGAGTCCAGCACACCCTCC
AGTGGGGCCAACACAGCCACCAACTCTGAGTCCAGTACGACCTCCAGTGGGGCCAACACAGCCAC
CAACTCTGAGTCCAGCACAGTGTCCAGTGGGGCCAGCACTGCCACCAACTCTGAGTCCAGCACAA
CCTCCAGTGGGGTCAGCACAGCCACCAACTCTGAGTCCAGCACAACCTCCAGTGGGGCTAGCACA
GCCACCAACTCTGACTCCAGCACAACCTCCAGTGAGGCCAGCACAGCCACCAACTCTGAGTCTAG
CACAGTGTCCAGTGGGATCAGCACAGTCACCAATTCTGAGTCCAGCACAACCTCCAGTGGGGCCA
ACACAGCCACCAACTCTGGGTCCAGTGTGACCTCTGCAGGCTCTGGAACAGCAGCTCTGACTGGA
ATGCACACAACTTCCCATAGTGCATCTACTGCAGTGAGTGAGGCAAAGCCTGGTGGGTCCCTGGT
GCCGTGGGAAATCTTCCTCATCACCCTGGTCTCGGTTGTGGCGGCCGTGGGGCTCTTTGCTGGGC
TCTTCTTCTGTGTGAGAAACAGCCTGTCCCTGAGAAACACCTTTAACACAGCTGTCTACCACCCT
CATGGCCTCAACCATGGCCTTGGTCCAGGCCCTGGAGGGAATCATGGAGCCCCCACAGGCCCAG
GTGGAGTCCTAACTGGTTCTGGAGGAGACCAGTATCATCGATAGCCATGGAGATGAGCGGGAGGA
ACAGCGGGCCCTGAGCAGCCCCGGAAGCAAGTGCCGCATTCTTCAGGAAGGAAGAGACCTGGGCA
CCCAAGACCTGGTTTCCTTTCATTCATCCCAGGAGACCCCTCCCAGCTTTGTTTGAGATCCTGAA
AATCTTGAAGAAGGTATTCCTCACCTTTCTTGCCTTTACCAGACACTGGAAAGAGAATACTATAT
TGCTCATTTAGCTAAGAAATAAATACATCTCATCTAACACACACGACAAAGAGAAGCTGTGCTTG
CCCCGGGGTGGGTATCTAGCTCTGAGATGAACTCAGTTATAGGAGAAAACCTCCATGCTGGACTC
CATCTGGCATTCAAAATCTCCACAGTAAAATCCAAAGACCTCAAAAAAAAAAAAAAAAAAAAAA
AAAAAAAAAAAAAAAAAAAAAAAAAAAAAA
```

FIGURE 100

MKMQKGNVLLMFGLLLHLEAATNSNETSTSANTGSSVISSGASTATNSGSSVTSSGVSTATISGS
SVTSNGVSIVTNSEFHTTSSGISTATNSEFSTASSGISIATNSESSTTSSGASTATNSESSTPSS
GASTVTNSGSSVTSSGASTATNSESSTVSSRASTATNSESSTLSSGASTATNSDSSTTSSGASTA
TNSESSTTSSGASTATNSESSTVSSRASTATNSESSTTSSGASTATNSESRTTSNGAGTATNSES
STTSSGASTATNSDSSTVSSGASTATNSESSTTSSGASTATNSESSTTSSGASTATNSDSSTTSS
GAGTATNSESSTVSSGISTVTNSESSTPSSGANTATNSESSTTSSGANTATNSESSTVSSGASTA
TNSESSTTSSGVSTATNSESSTTSSGASTATNSDSSTTSSEASTATNSESSTVSSGISTVTNSES
STTSSGANTATNSGSSVTSAGSGTAALTGMHTTSHSASTAVSEAKPGGSLVPWEIFLITLVSVVA
AVGLFAGLFFCVRNSLSLRNTFNTAVYHPHGLNHGLGPGPGGNHGAPHRPRWSPNWFWRRPVSSI
AMEMSGRNSGP

Signal peptide:
amino acids 1-20

Transmembrane domain:
amino acids 510-532

FIGURE 101

GGCCGGACGCCTCCGCGTTACGGGATGAATTAACGGCGGGTTCCGCACGGAGGTTGTGACCCCTA
CGGAGCCCCAGCTTGCCCACGCACCCCACTCGGCGTCGCGCGGCGTGCCCTGCTTGTCACAGGTG
GGAGGCTGGAACTATCAGGCTGAAAAACAGAGTGGGTACTCTCTTCTGGGAAGCTGGCAACAAAT
GGATGATGTGATATATGCATTCCAGGGGAAGGGAAATTGTGGTGCTTCTGAACCCATGGTCAATT
AACGAGGCAGTTTCTAGCTACTGCACGTACTTCATAAAGCAGGACTCTAAAAGCTTTGGAATCAT
GGTGTCATGGAAAGGGATTTACTTTATACTGACTCTGTTTTGGGGAAGCTTTTTGGAAGCATTT
TCATGCTGAGTCCCTTTTTACCTTTGATGTTTGTAAACCCATCTTGGTATCGCTGGATCAACAAC
CGCCTTGTGGCAACATGGCTCACCCTACCTGTGGCATTATTGGAGACCATGTTTGGTGTAAAAGT
GATTATAACTGGGGATGCATTTGTTCCTGGAGAAAGAAGTGTCATTATCATGAACCATCGGACAA
GAATGGACTGGATGTTCCTGTGGAATTGCCTGATGCGATATAGCTACCTCAGATTGGAGAAAATT
TGCCTCAAAGCGAGTCTCAAAGGTGTTCCTGGATTTGGTTGGGCCATGCAGGCTGCTGCCTATAT
CTTCATTCATAGGAAATGGAAGGATGACAAGAGCCATTTCGAAGACATGATTGATTACTTTTGTG
ATATTCACGAACCACTTCAACTCCTCATATTCCCAGAAGGGACTGATCTCACAGAAACAGCAAG
TCTCGAAGTAATGCATTTGCTGAAAAAAATGGACTTCAGAAATATGAATATGTTTTACATCCAAG
AACTACAGGCTTTACTTTTGTGGTAGACCGTCTAAGAGAAGGTAAGAACCTTGATGCTGTCCATG
ATATCACTGTGGCGTATCCTCACAACATTCCTCAATCAGAGAAGCACCTCCTCCAAGGAGACTTT
CCCAGGGAAATCCACTTTCACGTCCACCGGTATCCAATAGACACCCTCCCCACATCCAAGGAGGA
CCTTCAACTCTGGTGCCACAAACGGTGGGAAGAGAAAGAAGAGAGGCTGCGTTCCTTCTATCAAG
GGGAGAAGAATTTTTATTTTACCGGACAGAGTGTCATTCCACCTTGCAAGTCTGAACTCAGGGTC
CTTGTGGTCAAATTGCTCTCTATACTGTATTGGACCCTGTTCAGCCCTGCAATGTGCCTACTCAT
ATATTTGTACAGTCTTGTTAAGTGGTATTTTATAATCACCATTGTAATCTTTGTGCTGCAAGAGA
GAATATTTGGTGGACTGGAGATCATAGAACTTGCATGTTACCGACTTTTACACAAACAGCCACAT
TTAAATTCAAAGAAAAATGAGTAAGATTATAAGGTTTGCCATGTGAAAACCTAGAGCATATTTTG
GAAATGTTCTAAACCTTTCTAAGCTCAGATGCATTTTTGCATGACTATGTCGAATATTTCTTACT
GCCATCATTATTTGTTAAAGATATTTTGCACTTAATTTTGTGGGAAAAATATTGCTACAATTTTT
TTTAATCTCTGAATGTAATTTCGATACTGTGTACATAGCAGGGAGTGATCGGGGTGAAATAACTT
GGGCCAGAATATTATTAAACAATCATCAGGCTTTTAAA

FIGURE 102

MHSRGREIVVLLNPWSINEAVSSYCTYFIKQDSKSFGIMVSWKGIYFILTLFWGSFFGSIFMLSP
FLPLMFVNPSWYRWINNRLVATWLTLPVALLETMFGVKVIITGDAFVPGERSVIIMNHRTRMDWM
FLWNCLMRYSYLRLEKICLKASLKGVPGFGWAMQAAAYIFIHRKWKDDKSHFEDMIDYFCDIHEP
LQLLIFPEGTDLTENSKSRSNAFAEKNGLQKYEYVLHPRTTGFTFVVDRLREGKNLDAVHDITVA
YPHNIPQSEKHLLQGDFPREIHFHVHRYPIDTLPTSKEDLQLWCHKRWEEKEERLRSFYQGEKNF
YFTGQSVIPPCKSELRVLVVKLLSILYWTLFSPAMCLLIYLYSLVKWYFIITIVIFVLQERIFGG
LEIIELACYRLLHKQPHLNSKKNE

Important features of the protein:

Signal peptide:

amino acids 1-22

Transmembrane domains:

amino acids 44-63, 90-108, 354-377

FIGURE 103

```
CGGCTCGAGCGGCTCGAGTGAAGAGCCTCTCCACGGCTCCTGCGCCTGAGACAGCTGGCCTGACC
TCCAAATCATCCATCCACCCCTGCTGTCATCTGTTTTCATAGTGTGAGATCAACCCACAGGAATA
TCCATGGCTTTTGTGCTCATTTTGGTTCTCAGTTTCTACGAGCTGGTGTCAGGACAGTGGCAAGT
CACTGGACCGGGCAAGTTTGTCCAGGCCTTGGTGGGGGAGGACGCCGTGTTCTCCTGCTCCCTCT
TTCCTGAGACCAGTGCAGAGGCTATGGAAGTGCGGTTCTTCAGGAATCAGTTCCATGCTGTGGTC
CACCTCTACAGAGATGGGGAAGACTGGGAATCTAAGCAGATGCCACAGTATCGAGGGAGAACTGA
GTTTGTGAAGGACTCCATTGCAGGGGGCGTGTCTCTCTAAGGCTAAAAAACATCACTCCCTCGG
ACATCGGCCTGTATGGGTGCTGGTTCAGTTCCCAGATTTACGATGAGGAGGCCACCTGGGAGCTG
CGGGTGGCAGCACTGGGCTCACTTCCTCTCATTTCCATCGTGGGATATGTTGACGGAGGTATCCA
GTTACTCTGCCTGTCCTCAGGCTGGTTCCCCCAGCCCACAGCCAAGTGGAAAGGTCCACAAGGAC
AGGATTTGTCTTCAGACTCCAGAGCAAATGCAGATGGGTACAGCCTGTATGATGTGGAGATCTCC
ATTATAGTCCAGGAAAATGCTGGGAGCATATTGTGTTCCATCCACCTTGCTGAGCAGAGTCATGA
GGTGGAATCCAAGGTATTGATAGGAGAGACGTTTTCCAGCCCTCACCTTGGCGCCTGGCTTCTA
TTTTACTCGGGTTACTCTGTGGTGCCCTGTGTGGTGTTGTCATGGGGATGATAATTGTTTTCTTC
AAATCCAAAGGGAAAATCCAGGCGGAACTGGACTGGAGAAGAAAGCACGGACAGGCAGAATTGAG
AGACGCCCGGAAACACGCAGTGGAGGTGACTCTGGATCCAGAGACGGCTCACCCGAAGCTCTGCG
TTTCTGATCTGAAAACTGTAACCCATAGAAAAGCTCCCCAGGAGGTGCCTCACTCTGAGAAGAGA
TTTACAAGGAAGAGTGTGGTGGCTTCTCAGGGTTTCCAAGCAGGGAGACATTACTGGGAGGTGGA
CGTGGGACAAAATGTAGGGTGGTATGTGGGAGTGTGTCGGGATGACGTAGACAGGGGGAAGAACA
ATGTGACTTTGTCTCCCAACAATGGGTATTGGGTCCTCAGACTGACAACAGAACATTTGTATTTC
ACATTCAATCCCCATTTTATCAGCCTCCCCCCAGCACCCCTCCTACACGAGTAGGGGTCTTCCT
GGACTATGAGGGTGGGACCATCTCCTTCTTCAATACAAATGACCAGTCCCTTATTTATACCCTGC
TGACATGTCAGTTTGAAGGCTTGTTGAGACCCTATATCCAGCATGCGATGTATGACGAGGAAAAG
GGGACTCCCATATTCATATGTCCAGTGTCCTGGGGATGAGACAGAGAAGACCCTGCTTAAAGGGC
CCCACACCACAGACCCAGACACAGCCAAGGGAGAGTGCTCCCGACAGGTGGCCCCAGCTTCCTCT
CCGGAGCCTGCGCACAGAGAGTCACGCCCCCACTCTCCTTTAGGGAGCTGAGGTTCTTCTGCCC
TGAGCCCTGCAGCAGCGGCAGTCACAGCTTCCAGATGAGGGGGGATTGGCCTGACCCTGTGGGAG
TCAGAAGCCATGGCTGCCCTGAAGTGGGGACGGAATAGACTCACATTAGGTTTAGTTTGTGAAAA
CTCCATCCAGCTAAGCGATCTTGAACAAGTCACAACCTCCCAGGCTCCTCATTTGCTAGTCACGG
ACAGTGATTCCTGCCTCACAGGTGAAGATTAAAGAGACAACGAATGTGAATCATGCTTGCAGGTT
TGAGGGCACAGTGTTTGCTAATGATGTGTTTTATATTATACATTTTCCCACCATAAACTCTGTT
TGCTTATTCCACATTAATTTACTTTTCTCTATACCAAATCACCCATGGAATAGTTATTGAACACC
TGCTTTGTGAGGCTCAAAGAATAAAGAGGAGGTAGGATTTTTCACTGATTCTATAAGCCCAGCAT
TACCTGATACCAAAACCAGGCAAAGAAAACAGAAGAAGAGGAAGGAAAACTACAGGTCCATATCC
CTCATTAACACAGACACAAAAATTCTAAATAAAATTTAACAAATTAAACTAAACAATATATTTA
AAGATGATATATAACTACTCAGTGTGGTTTGTCCCACAAATGCAGAGTTGGTTTAATATTTAAAT
ATCAACCAGTGTAATTCAGCACATTAATAAAGTAAAAAGAAAACCATAAAAAAAAAAAAAA
```

FIGURE 104

MAFVLILVLSFYELVSGQWQVTGPGKFVQALVGEDAVFSCSLFPETSAEAMEVRFFRNQFHAVVH
LYRDGEDWESKQMPQYRGRTEFVKDSIAGGRVSLRLKNITPSDIGLYGCWFSSQIYDEEATWELR
VAALGSLPLISIVGYVDGGIQLLCLSSGWFPQPTAKWKGPQGQDLSSDSRANADGYSLYDVEISI
IVQENAGSILCSIHLAEQSHEVESKVLIGETFFQPSPWRLASILLGLLCGALCGVVMGMIIVFFK
SKGKIQAELDWRRKHGQAELRDARKHAVEVTLDPETAHPKLCVSDLKTVTHRKAPQEVPHSEKRF
TRKSVVASQGFQAGRHYWEVDVGQNVGWYVGVCRDDVDRGKNNVTLSPNNGYWVLRLTTEHLYFT
FNPHFISLPPSTPPTRVGVFLDYEGGTISFFNTNDQSLIYTLLTCQFEGLLRPYIQHAMYDEEKG
TPIFICPVSWG

Signal peptide:
amino acids 1-17

Transmembrane domains:
amino acids 131-150, 235-259

FIGURE 105

```
CCTTCACAGGACTCTTCATTGCTGGTTGGCAATGATGTATCGGCCAGATGTGGTGAGGGCTAGGAAAAGAG
TTTGTTGGGAACCCTGGGTTATCGGCCTCGTCATCTTCATATCCCTGATTGTCCTGGCAGTGTGCATTGGA
CTCACTGTTCATTATGTGAGATATAATCAAAAGAAGACCTACAATTACTATAGCACATTGTCATTTACAAC
TGACAAACTATATGCTGAGTTTGGCAGAGAGGCTTCTAACAATTTTACAGAAATGAGCCAGAGACTTGAAT
CAATGGTGAAAAATGCATTTTATAAATCTCCATTAAGGGAAGAATTTGTCAAGTCTCAGGTTATCAAGTTC
AGTCAACAGAAGCATGGAGTGTTGGCTCATATGCTGTTGATTTGTAGATTTCACTCTACTGAGGATCCTGA
AACTGTAGATAAAATTGTTCAACTTGTTTTACATGAAAAGCTGCAAGATGCTGTAGGACCCCCTAAAGTAG
ATCCTCACTCAGTTAAAATTAAAAAAATCAACAAGACAGAAACAGACAGCTATCTAAACCATTGCTGCGGA
ACACGAAGAAGTAAAACTCTAGGTCAGAGTCTCAGGATCGTTGGTGGGACAGAAGTAGAAGAGGGTGAATG
GCCCTGGCAGGCTAGCCTGCAGTGGGATGGGAGTCATCGCTGTGGAGCAACCTTAATTAATGCCACATGGC
TTGTGAGTGCTGCTCACTGTTTTACAACATATAAGAACCCTGCCAGATGGACTGCTTCCTTTGGAGTAACA
ATAAAACCTTCGAAAATGAAACGGGGTCTCCGGAGAATAATTGTCCATGAAAAATACAAACACCCATCACA
TGACTATGATATTTCTCTTGCAGAGCTTTCTAGCCCTGTTCCCTACACAAATGCAGTACATAGAGTTTGTC
TCCCTGATGCATCCTATGAGTTTCAACCAGGTGATGTGATGTTTGTGACAGGATTTGGAGCACTGAAAAAT
GATGGTTACAGTCAAAATCATCTTCGACAAGCACAGGTGACTCTCATAGACGCTACAACTTGCAATGAACC
TCAAGCTTACAATGACGCCATAACTCCTAGAATGTTATGTGCTGGCTCCTTAGAAGGAAAAACAGATGCAT
GCCAGGGTGACTCTGGAGGACCACTGGTTAGTTCAGATGCTAGAGATATCTGGTACCTTGCTGGAATAGTG
AGCTGGGAGATGAATGTGCGAAACCCAACAAGCCTGGTGTTTATACTAGAGTTACGGCCTTGCGGGACTG
GATTACTTCAAAAACTGGTATCTAAGAGACAAAAGCCTCATGGAACAGATAACATTTTTTTTGTTTTTG
GGTGTGGAGGCCATTTTTAGAGATACAGAATTGGAGAAGACTTGCAAAACAGCTAGATTTGACTGATCTCA
ATAAACTGTTTGCTTGATGCATGTATTTTCTTCCCAGCTCTGTTCCGCACGTAAGCATCCTGCTTCTGCCA
GATCAACTCTGTCATCTGTGAGCAATAGTTGAAACTTTATGTACATAGAGAAATAGATAATACAATATTAC
ATTACAGCCTGTATTCATTTGTTCTCTAGAAGTTTTGTCAGAATTTTGACTTGTTGACATAAATTTGTAAT
GCATATATACAATTTGAAGCACTCCTTTTCTTCAGTTCCTCAGCTCCTCTCATTTCAGCAAATATCCATTT
TCAAGGTGCAGAACAAGGAGTGAAAGAAAATATAAGAAGAAAAAAATCCCCTACATTTTATTGGCACAGAA
AAGTATTAGGTGTTTTTCTTAGTGGAATATTAGAAATGATCATATTCATTATGAAAGGTCAAGCAAAGACA
GCAGAATACCAATCACTTCATCATTTAGGAAGTATGGGAACTAAGTTAAGGAAGTCCAGAAAGAAGCCAAG
ATATATCCTTATTTTCATTTCCAAACAACTACTATGATAAATGTGAAGAAGATTCTGTTTTTTTGTGACCT
ATAATAATTATACAAACTTCATGCAATGTACTTGTTCTAAGCAAATTAAAGCAAATATTTATTTAACATTG
TTACTGAGGATGTCAACATATAACAATAAAATATAAATCACCCA
```

FIGURE 106

MMYRPDVVRARKRVCWEPWVIGLVIFISLIVLAVCIGLTVHYVRYNQKKTYNYYSTLSFTTDKLY
AEFGREASNNFTEMSQRLESMVKNAFYKSPLREEFVKSQVIKFSQQKHGVLAHMLLICRFHSTED
PETVDKIVQLVLHEKLQDAVGPPKVDPHSVKIKKINKTETDSYLNHCCGTRRSKTLGQSLRIVGG
TEVEEGEWPWQASLQWDGSHRCGATLINATWLVSAAHCFTTYKNPARWTASFGVTIKPSKMKRGL
RRIIVHEKYKHPSHDYDISLAELSSPVPYTNAVHRVCLPDASYEFQPGDVMFVTGFGALKNDGYS
QNHLRQAQVTLIDATTCNEPQAYNDAITPRMLCAGSLEGKTDACQGDSGGPLVSSDARDIWYLAG
IVSWGDECAKPNKPGVYTRVTALRDWITSKTGI

Transmembrane domain:
amino acids 21-40 (type II)

FIGURE 107

```
AGAGAAAGAAGCGTCTCCAGCTGAAGCCAATGCAGCCCTCCGGCTCTCCGCGAAGAAGTTCCCTG
CCCCGATGAGCCCCGCCGTGCGTCCCGACTATCCCCAGGCGGGCGTGGGGCACCGGGCCCAGC
GCCGACGATCGCTGCCGTTTTGCCCTTGGGAGTAGGATGTGGTGAAAGGATGGGGCTTCTCCCTT
ACGGGGCTCACAATGGCCAGAGAAGATTCCGTGAAGTGTCTGCGCTGCCTGCTCTACGCCCTCAA
TCTGCTCTTTTGGTTAATGTCCATCAGTGTGTTGGCAGTTTCTGCTTGGATGAGGGACTACCTAA
ATAATGTTCTCACTTTAACTGCAGAAACGAGGGTAGAGGAAGCAGTCATTTTGACTTACTTTCCT
GTGGTTCATCCGGTCATGATTGCTGTTTGCTGTTTCCTTATCATTGTGGGATGTTAGGATATTG
TGGAACGGTGAAAGAAATCTGTTGCTTCTTGCATGGTACTTTGGAAGTTTGCTTGTCATTTTCT
GTGTAGAACTGGCTTGTGGCGTTTGGACATATGAACAGGAACTTATGGTTCCAGTACAATGGTCA
GATATGGTCACTTTGAAAGCCAGGATGACAAATTATGGATTACCTAGATATCGGTGGCTTACTCA
TGCTTGGAATTTTTTTCAGAGAGAGTTTAAGTGCTGTGGAGTAGTATATTTCACTGACTGGTTGG
AAATGACAGAGATGGACTGGCCCCCAGATTCCTGCTGTGTTAGAGAATTCCCAGGATGTTCCAAA
CAGGCCCACCAGGAAGATCTCAGTGACCTTTATCAAGAGGGTTGTGGGAAGAAAATGTATTCCTT
TTTGAGAGGAACCAAACAACTGCAGGTGCTGAGGTTTCTGGGAATCTCCATTGGGGTGACACAAA
TCCTGGCCATGATTCTCACCATTACTCTGCTCTGGGCTCTGTATTATGATAGAAGGGAGCCTGGG
ACAGACCAAATGATGTCCTTGAAGAATGACAACTCTCAGCACCTGTCATGTCCCTCAGTAGAACT
GTTGAAACCAAGCCTGTCAAGAATCTTTGAACACACATCCATGGCAAACAGCTTTAATACACACT
TTGAGATGGAGGAGTTATAAAAAGAAATGTCACAGAAGAAAACCACAAACTTGTTTATTGGACT
TGTGAATTTTTGAGTACATACTATGTGTTTCAGAAATATGTAGAAATAAAATGTTGCCATAAAA
TAACACCTAAGCATATACTATTCTATGCTTTAAAATGAGGATGGAAAAGTTTCATGTCATAAGTC
ACCACCTGGACAATAATTGATGCCCTTAAAATGCTGAAGACAGATGTCATACCCACTGTGTAGCC
TGTGTATGACTTTTACTGAACACAGTTATGTTTTGAGGCAGCATGGTTTGATTAGCATTTCCGCA
TCCATGCAAACGAGTCACATATGGTGGGACTGGAGCCATAGTAAAGGTTGATTTACTTCTACCAA
CTAGTATATAAAGTACTAATTAAATGCTAACATAGGAAGTTAGAAAATACTAATAACTTTTATTA
CTCAGCGATCTATTCTTCTGATGCTAAATAAATTATATATCAGAAAACTTTCAATATTGGTGACT
ACCTAAATGTGATTTTTGCTGGTTACTAAAATATTCTTACCACTTAAAAGAGCAAGCTAACACAT
TGTCTTAAGCTGATCAGGGATTTTTTGTATATAAGTCTGTGTTAAATCTGTATAATTCAGTCGAT
TTCAGTTCTGATAATGTTAAGAATAACCATTATGAAAAGGAAAATTTGTCCTGTATAGCATCATT
ATTTTTAGCCTTTCCTGTTAATAAAGCTTTACTATTCTGTCCTGGCTTATATTACACATATAAC
TGTTATTTAAATACTTAACCACTAATTTTGAAAATTACCAGTGTGATACATAGGAATCATTATTC
AGAATGTAGTCTGGTCTTTAGGAAGTATTAATAAGAAAATTTGCACATAACTTAGTTGATTCAGA
AAGGACTTGTATGCTGTTTTTCTCCCAAATGAAGACTCTTTTTGACACTAAACACTTTTAAAAA
GCTTATCTTTGCCTTCTCCAAACAAGAAGCAATAGTCTCCAAGTCAATATAAATTCTACAGAAAA
TAGTGTTCTTTTTCTCCAGAAAAATGCTTGTGAGAATCATTAAAACATGTGACAATTTAGAGATT
CTTTGTTTTATTTCACTGATTAATATACTGTGGCAAATTACACAGATTATTAAATTTTTTACAA
GAGTATAGTATATTTATTTGAAATGGGAAAAGTGCATTTTACTGTATTTTGTGTATTTGTTTAT
TTCTCAGAATATGGAAAGAAAATTAAAATGTGTCAATAAATATTTTCTAGAGAGTAA
```

FIGURE 108

MAREDSVKCLRCLLYALNLLFWLMSISVLAVSAWMRDYLNNVLTLTAETRVEEAVILTYFPVVHP
VMIAVCCFLIIVGMLGYCGTVKRNLLLLAWYFGSLLVIFCVELACGVWTYEQELMVPVQWSDMVT
LKARMTNYGLPRYRWLTHAWNFFQREFKCCGVVYFTDWLEMTEMDWPPDSCCVREFPGCSKQAHQ
EDLSDLYQEGCGKKMYSFLRGTKQLQVLRFLGISIGVTQILAMILTITLLWALYYDRREPGTDQM
MSLKNDNSQHLSCPSVELLKPSLSRIFEHTSMANSFNTHFEMEEL

Signal peptide:
amino acids 1-33

Transmembrane domains:
amino acids 12-35, 57-86, 94-114, 226-248

FIGURE 109

```
CCAAGGCCAGAGCTGTGGACACCTTATCCCACTCATCCTCATCCTCTTCCTCTGATAAAGCCCCTACCAGTGCT
GATAAAGTCTTTCTCGTGAGAGCCTAGAGGCCTTAAAAAAAAAAGTGCTTGAAAGAGAAGGGGACAAAGGAACA
CCAGTATTAAGAGGATTTTCCAGTGTTTCTGGCAGTTGGTCCAGAAGG<u>ATG</u>CCTCCATTCCTGCTTCTCACCTG
CCTCTTCATCACAGGCACCTCCGTGTCACCCGTGGCCCTAGATCCTTGTTCTGCTTACATCAGCCTGAATGAGC
CCTGGAGGAACACTGACCACCAGTTGGATGAGTCTCAAGGTCCTCCTCTATGTGACAACCATGTGAATGGGGAG
TGGTACCACTTCACGGGCATGGCGGGAGATGCCATGCCTACCTTCTGCATACCAGAAAACCACTGTGGAACCCA
CGCACCTGTCTGGCTCAATGGCAGCCACCCCCTAGAAGGCGACGGCATTGTGCAACGCCAGGCTTGTGCCAGCT
TCAATGGGAACTGCTGTCTCTGGAACACCACGGTGGAAGTCAAGGCTTGCCCTGGAGGCTACTATGTGTATCGT
CTGACCAAGCCCAGCGTCTGCTTCCACGTCTACTGTGGTCATTTTTATGACATCTGCGACGAGGACTGCCATGG
CAGCTGCTCAGATACCAGCGAGTGCACATGCGCTCCAGGAACTGTGCTAGGCCCTGACAGGCAGACATGCTTTG
ATGAAAATGAATGTGAGCAAAACAACGGTGGCTGCAGTGAGATCTGTGTGAACCTCAAAAACTCCTACCGCTGT
GAGTGTGGGGTTGGCCGTGTGCTAAGAAGTGATGGCAAGACTTGTGAAGACGTTGAAGGATGCCACAATAACAA
TGGTGGCTGCAGCCACTCTTGCCTTGGATCTGAGAAAGGCTACCAGTGTGAATGTCCCGGGGCCTGGTGCTGT
CTGAGGATAACCACACTTGCCAAGTCCCTGTGTTGTGCAAATCAAATGCCATTGAAGTGAACATCCCCAGGGAG
CTGGTTGGTGGCCTGGAGCTCTTCCTGACCAACACCTCCTGCCGAGGAGTGTCCAACGGCACCCATGTCAACAT
CCTCTTCTCTCTCAAGACATGTGGTACAGTGGTCGATGTGGTGAATGACAAGATTGTGGCCAGCAACCTCGTGA
CAGGTCTACCCAAGCAGACCCCGGGGAGCAGCGGGGACTTCATCATCCGAACCAGCAAGCTGCTGATCCCGGTG
ACCTGCGAGTTTCCACGCCTGTACACCATTTCTGAAGGATACGTTCCCAACCTTCGAAACTCCCCACTGGAAAT
CATGAGCCGAAATCATGGGATCTTCCCATTCACTCTGGAGATCTTCAAGGACAATGAGTTTGAAGAGCCTTACC
GGGAAGCTCTGCCCACCCTCAAGCTTCGTGACTCCCTCTACTTTGGCATTGAGCCCGTGGTGCACGTGAGCGGC
TTGGAAAGCTTGGTGGAGAGCTGCTTTGCCACCCCCACCTCCAAGATCGACGAGGTCCTGAAATACTACCTCAT
CCGGGATGGCTGTGTTTCAGATGACTCGGTAAAGCAGTACACATCCCGGGATCACCTAGCAAAGCACTTCCAGG
TCCCTGTCTTCAAGTTTGTGGGCAAAGACCACAAGGAAGTGTTTCTGCACTGCCGGGTCTTGTCTGTGGAGTG
TTGGACGAGCGTTCCCGCTGTGCCCAGGGTTGCCACCGGCGAATGCGTCGTGGGGCAGGAGGAGAGGACTCAGC
CGGTCTACAGGGCCAGACGCTAACAGGCGGCCCGATCCGCATCGACTGGGAGGAC<u>TAG</u>TTCGTAGCCATACCTC
GAGTCCCTGCATTGGACGGCTCTGCTCTTTGGAGCTTCTCCCCCCACCGCCCTCTAAGAACATCTGCCAACAGC
TGGGTTCAGACTTCACACTGTGAGTTCAGACTCCCAGCACCAACTCACTCTGATTCTGGTCCATTCAGTGGGCA
CAGGTCACAGCACTGCTGAACAATGTGGCCTGGGTGGGGTTTCATCTTTCTAGGGTTGAAAACTAAACTGTCCA
CCCAGAAAGACACTCACCCCATTTCCCTCATTTCTTTCCTACACTTAAATACCTCGTGTATGGTGCAATCAGAC
CACAAAATCAGAAGCTGGGTATAATATTTCAAGTTACAAACCCTAGAAAAATTAAACAGTTACTGAAATTATGA
CTTAAATACCCAATGACTCCTTAAATATGTAAATTATAGTTATACCTTGAAATTTCAATTCAAATGCAGACTAA
TTATAGGGAATTTGGAAGTGTATCAATAAAACAGTATATAATTTT
```

FIGURE 110

```
MPPFLLLTCLFITGTSVSPVALDPCSAYISLNEPWRNTDHQLDESQGPPLCDNHVNGEWYHFTGMAGDAMP
TFCIPENHCGTHAPVWLNGSHPLEGDGIVQRQACASFNGNCCLWNTTVEVKACPGGYYVYRLTKPSVCFHV
YCGHFYDICDEDCHGSCSDTSECTCAPGTVLGPDRQTCFDENECEQNNGGCSEICVNLKNSYRCECGVGRV
LRSDGKTCEDVEGCHNNNGGCSHSCLGSEKGYQCECPRGLVLSEDNHTCQVPVLCKSNAIEVNIPRELVGG
LELFLTNTSCRGVSNGTHVNILFSLKTCGTVVDVVNDKIVASNLVTGLPKQTPGSSGDFIIRTSKLLIPVT
CEFPRLYTISEGYVPNLRNSPLEIMSRNHGIFPFTLEIFKDNEFEEPYREALPTLKLRDSLYFGIEPVVHV
SGLESLVESCFATPTSKIDEVLKYYLIRDGCVSDDSVKQYTSRDHLAKHFQVPVFKFVGKDHKEVFLHCRV
LVCGVLDERSRCAQGCHRRMRRGAGGEDSAGLQGQTLTGGPIRIDWED
```

Important features of the protein:

Signal peptide:

amino acids 1-16

N-glycosylation sites.

amino acids 89-93, 116-120, 259-263, 291-295, 299-303

Tyrosine kinase phosphorylation sites.

amino acids 411-418, 443-451

N-myristoylation sites.

amino acids 226-232, 233-239, 240-246, 252-258, 296-302, 300-306, 522-528, 531-537

Aspartic acid and asparagine hydroxylation site.

amino acids 197-209

ZP domain proteins.

amino acids 431-457

Calcium-binding EGF-like proteins.

amino acids 191-212, 232-253

FIGURE 111

GAGAGAGGCAGCAGCTTGCTCAGCGGACAAGGATGCTGGGCGTGAGGGACCAAGGCCTGCCCTGCACTCGG
GCCTCCTCCAGCCAGTGCTGACCAGGGACTTCTGACCTGCTGGCCAGCCAGGACCTGTGTGGGGAGGCCCT
CCTGCTGCCTTGGGGTGACAATCTCAGCTCCAGGCTACAGGGAGACCGGGAGGATCACAGAGCCAGCATGT
TACAGGATCCTGACAGTGATCAACCTCTGAACAGCCTCGATGTCAAACCCCTGCGCAAACCCCGTATCCCC
ATGGAGACCTTCAGAAAGGTGGGGATCCCCATCATCATAGCACTACTGAGCCTGGCGAGTATCATCATTGT
GGTTGTCCTCATCAAGGTGATTCTGGATAAATACTACTTCCTCTGCGGGCAGCCTCTCCACTTCATCCCGA
GGAAGCAGCTGTGTGACGGAGAGCTGGACTGTCCCTTGGGGGAGGACGAGGAGCACTGTGTCAAGAGCTTC
CCCGAAGGGCCTGCAGTGGCAGTCCGCCTCTCCAAGGACCGATCCACACTGCAGGTGCTGGACTCGGCCAC
AGGGAACTGGTTCTCTGCCTGTTTCGACAACTTCACAGAAGCTCTCGCTGAGACAGCCTGTAGGCAGATGG
GCTACAGCAGAGCTGTGGAGATTGGCCCAGACCAGGATCTGGATGTTGTTGAAATCACAGAAAACAGCCAG
GAGCTTCGCATGCGGAACTCAAGTGGGCCCTGTCTCTCAGGCTCCCTGGTCTCCCTGCACTGTCTTGCCTG
TGGGAAGAGCCTGAAGACCCCCCGTGTGGTGGGTGGGGAGGAGGCCTCTGTGGATTCTTGGCCTTGGCAGG
TCAGCATCCAGTACGACAAACAGCACGTCTGTGGAGGGAGCATCCTGGACCCCCACTGGGTCCTCACGGCA
GCCCACTGCTTCAGGAAACATACCGATGTGTTCAACTGGAAGGTGCGGGCAGGCTCAGACAAACTGGGCAG
CTTCCCATCCCTGGCTGTGGCCAAGATCATCATCATTGAATTCAACCCCATGTACCCCAAAGACAATGACA
TCGCCCTCATGAAGCTGCAGTTCCCACTCACTTTCTCAGGCACAGTCAGGCCCATCTGTCTGCCCTTCTTT
GATGAGGAGCTCACTCCAGCCACCCCACTCTGGATCATTGGATGGGGCTTTACGAAGCAGAATGGAGGGAA
GATGTCTGACATACTGCTGCAGGCGTCAGTCCAGGTCATTGACAGCACACGGTGCAATGCAGACGATGCGT
ACCAGGGGGAAGTCACCGAGAAGATGATGTGTGCAGGCATCCCGGAAGGGGGTGTGGACACCTGCCAGGGT
GACAGTGGTGGGCCCCTGATGTACCAATCTGACCAGTGGCATGTGGTGGGCATCGTTAGCTGGGGCTATGG
CTGCGGGGGCCCGAGCACCCCAGGAGTATACACCAAGGTCTCAGCCTATCTCAACTGGATCTACAATGTCT
GGAAGGCTGAGCTGTAATGCTGCTGCCCCTTTGCAGTGCTGGGAGCCGCTTCCTTCCTGCCCTGCCCACCT
GGGGATCCCCCAAAGTCAGACACAGAGCAAGAGTCCCCTTGGGTACACCCCTCTGCCCACAGCCTCAGCAT
TTCTTGGAGCAGCAAAGGGCCTCAATTCCTGTAAGAGACCCTCGCAGCCCAGAGGCGCCCAGAGGAAGTCA
GCAGCCCTAGCTCGGCCACACTTGGTGCTCCCAGCATCCCAGGGAGAGACACAGCCCACTGAACAAGGTCT
CAGGGGTATTGCTAAGCCAAGAAGGAACTTTCCCACACTACTGAATGGAAGCAGGCTGTCTTGTAAAAGCC
CAGATCACTGTGGGCTGGAGAGGAGAAGGAAAGGGTCTGCGCCAGCCCTGTCCGTCTTCACCCATCCCCAA
GCCTACTAGAGCAAGAAACCAGTTGTAATATAAAATGCACTGCCCTACTGTTGGTATGACTACCGTTACCT
ACTGTTGTCATTGTTATTACAGCTATGGCCACTATTATTAAAGAGCTGTGTAACATCTCTGGCAAAAAAA
AAAA

FIGURE 112

MLQDPDSDQPLNSLDVKPLRKPRIPMETFRKVGIPIIIALLSLASIIIVVVLIKVILDKYYFLCG
QPLHFIPRKQLCDGELDCPLGEDEEHCVKSFPEGPAVAVRLSKDRSTLQVLDSATGNWFSACFDN
FTEALAETACRQMGYSRAVEIGPDQDLDVVEITENSQELRMRNSSGPCLSGSLVSLHCLACGKSL
KTPRVVGGEEASVDSWPWQVSIQYDKQHVCGGSILDPHWVLTAAHCFRKHTDVFNWKVRAGSDKL
GSFPSLAVAKIIIIEFNPMYPKDNDIALMKLQFPLTFSGTVRPICLPFFDEELTPATPLWIIGWG
FTKQNGGKMSDILLQASVQVIDSTRCNADDAYQGEVTEKMMCAGIPEGGVDTCQGDSGGPLMYQS
DQWHVVGIVSWGYGCGGPSTPGVYTKVSAYLNWIYNVWKAEL

Transmembrane domain:
amino acids 32-53 (typeII)

FIGURE 113

```
GGCTGGACTGGAACTCCTGGTCCCAAGTGATCCACCCGCCTCAGCCTCCCAAGGTGCTGTGATTA
TAGGTGTAAGCCACCGTGTCTGGCCTCTGAACAACTTTTTCAGCAACTAAAAAAGCCACAGGAGT
TGAACTGCTAGGATTCTGACTATGCTGTGGTGGCTAGTGCTCCTACTCCTACCTACATTAAAATC
TGTTTTTTGTTCTCTTGTAACTAGCCTTTACCTTCCTAACACAGAGGATCTGTCACTGTGGCTCT
GGCCCAAACCTGACCTTCACTCTGGAACGAGAACAGAGGTTTCTACCCACACCGTCCCCTCGAAG
CCGGGGACAGCCTCACCTTGCTGGCCTCTCGCTGGAGCAGTGCCCTCACCAACTGTCTCACGTCT
GGAGGCACTGACTCGGGCAGTGCAGGTAGCTGAGCCTCTTGGTAGCTGCGGCTTTCAAGGTGGGC
CTTGCCCTGGCCGTAGAAGGGATTGACAAGCCCGAAGATTTCATAGGCGATGGCTCCCACTGCCC
AGGCATCAGCCTTGCTGTAGTCAATCACTGCCCTGGGGCCAGGACGGGCCGTGGACACCTGCTCA
GAAGCAGTGGGTGAGACATCACGCTGCCCGCCCATCTAACCTTTTCATGTCCTGCACATCACCTG
ATCCATGGGCTAATCTGAACTCTGTCCCAAGGAACCCAGAGCTTGAGTGAGCTGTGGCTCAGACC
CAGAAGGGGTCTGCTTAGACCACCTGGTTTATGTGACAGGACTTGCATTCTCCTGGAACATGAGG
GAACGCCGGAGGAAAGCAAAGTGGCAGGGAAGGAACTTGTGCCAAATTATGGGTCAGAAAAGATG
GAGGTGTTGGGTTATCACAAGGCATCGAGTCTCCTGCATTCAGTGGACATGTGGGGAAGGGCTG
CCGATGGCGCATGACACACTCGGGACTCACCTCTGGGGCCATCAGACAGCCGTTTCCGCCCCGAT
CCACGTACCAGCTGCTGAAGGGCAACTGCAGGCCGATGCTCTCATCAGCCAGGCAGCAGCCAAAA
TCTGCGATCACCAGCCAGGGGCAGCCGTCTGGGAAGGAGCAAGCAAAGTGACCATTTCTCCTCCC
CTCCTTCCCTCTGAGAGGCCCTCCTATGTCCCTACTAAAGCCACCAGCAAGACATAGCTGACAGG
GGCTAATGGCTCAGTGTTGGCCCAGGAGGTCAGCAAGGCCTGAGAGCTGATCAGAAGGGCCTGCT
GTGCGAACACGGAAATGCCTCCAGTAAGCACAGGCTGCAAAATCCCCAGGCAAAGGACTGTGTGG
CTCAATTTAAATCATGTTCTAGTAATTGGAGCTGTCCCCAAGACCAAAGGAGCTAGAGCTTGGTT
CAAATGATCTCCAAGGGCCCTTATACCCCAGGAGACTTTGATTTGAATTTGAAACCCCAAATCCA
AACCTAAGAACCAGGTGCATTAAGAATCAGTTATTGCCGGGTGTGGTGGCCTGTAATGCCAACAT
TTTGGGAGGCCGAGGCGGGTAGATCACCTGAGGTCAGGAGTTCAAGACCAGCCTGGCCAACATGG
TGAAACCCCTGTCTCTACTAAAAATACAAAAAAACTAGCCAGGCATGGTGGTGTGTGCCTGTATC
CCAGCTACTCGGGAGGCTGAGACAGGAGAATTACTTGAACCTGGGAGGTGAAGGAGGCTGAGACA
GGAGAATCACTTCAGCCTGAGCAACACAGCGAGACTCTGTCTCAGAAAAAATAAAAAAAGAATTA
TGGTTATTTGTAA
```

FIGURE 114

MLWWLVLLLLPTLKSVFCSLVTSLYLPNTEDLSLWLWPKPDLHSGTRTEVSTHTVPSKPGTASPC
WPLAGAVPSPTVSRLEALTRAVQVAEPLGSCGFQGGPCPGRRRD

Signal peptide:

amino acids 1-15

FIGURE 115

CAGCAGTGGTCTCTCAGTCCTCTCAAAGCAAGGAAAGAGTACTGTGTGCTGAGAGACCATGGCAA
AGAATCCTCCAGAGAATTGTGAAGACTGTCACATTCTAAATGCAGAAGCTTTTAAATCCAAGAAA
ATATGTAAATCACTTAAGATTTGTGGACTGGTGTTTGGTATCCTGGCCCTAACTCTAATTGTCCT
GTTTTGGGGGAGCAAGCACTTCTGGCCGGAGGTACCCAAAAAAGCCTATGACATGGAGCACACTT
TCTACAGCAATGGAGAGAAGAAGAAGATTTACATGGAAATTGATCCTGTGACCAGAACTGAAATA
TTCAGAAGCGGAAATGGCACTGATGAAACATTGGAAGTGCACGACTTTAAAAACGGATACACTGG
CATCTACTTCGTGGGTCTTCAAAAATGTTTTATCAAAACTCAGATTAAAGTGATTCCTGAATTTT
CTGAACCAGAAGAGGAAATAGATGAGAATGAAGAAATTACCACAACTTTCTTTGAACAGTCAGTG
ATTTGGGTCCCAGCAGAAAAGCCTATTGAAACCGAGATTTTCTTAAAAATTCCAAAATTCTGGA
GATTTGTGATAACGTGACCATGTATTGGATCAATCCCACTCTAATATCAGTTTCTGAGTTACAAG
ACTTTGAGGAGGAGGGAGAAGATCTTCACTTTCCTGCCAACGAAAAAAAGGGATTGAACAAAAT
GAACAGTGGGTGGTCCCTCAAGTGAAAGTAGAGAAGACCCGTCACGCCAGACAAGCAAGTGAGGA
AGAACTTCCAATAAATGACTATACTGAAAATGGAATAGAATTTGATCCCATGCTGGATGAGAGAG
GTTATTGTTGTATTTACTGCCGTCGAGGCAACCGCTATTGCCGCCGCGTCTGTGAACCTTTACTA
GGCTACTACCCATATCCATACTGCTACCAAGGAGGACGAGTCATCTGTCGTGTCATCATGCCTTG
TAACTGGTGGGTGGCCCGCATGCTGGGGAGGGTCTAATAGGAGGTTTGAGCTCAAATGCTTAAAC
TGCTGGCAACATATAATAAATGCATGCTATTCAATGAATTTCTGCCTATGAGGCATCTGGCCCCT
GGTAGCCAGCTCTCCAGAATTACTTGTAGGTAATTCCTCTCTTCATGTTCTAATAAACTTCTACA
TTATCACCAAAAAAAAAAAAAAAAAAAA

FIGURE 116

MAKNPPENCEDCHILNAEAFKSKKICKSLKICGLVFGILALTLIVLFWGSKHFWPEVPKKAYDME
HTFYSNGEKKKIYMEIDPVTRTEIFRSGNGTDETLEVHDFKNGYTGIYFVGLQKCFIKTQIKVIP
EFSEPEEEIDENEEITTTFFEQSVIWVPAEKPIENRDFLKNSKILEICDNVTMYWINPTLISVSE
LQDFEEEGEDLHFPANEKKGIEQNEQWVVPQVKVEKTRHARQASEEELPINDYTENGIEFDPMLD
ERGYCCIYCRRGNRYCRRVCEPLLGYYPYPYCYQGGRVICRVIMPCNWWVARMLGRV

Important features of the protein:

Signal peptide:

amino acids 1-40

Transmembrane domain:

amino acids 25-47 (type II)

N-glycosylation sites.

amino acids 94-97, 180-183

Glycosaminoglycan attachment sites.

amino acids 92-95, 70-73, 85-88, 133-136, 148-151, 192-195, 239-242

N-myristoylation sites.

amino acids 33-38, 95-100, 116-121, 215-220, 272-277

Microbodies C-terminal targeting signal.

amino acids 315-317

Cytochrome c family heme-binding site signature.

amino acids 9-14

FIGURE 117

```
GAGCTCCCCTCAGGAGCGCGTTAGCTTCACACCTTCGGCAGCAGGAGGGCGGCAGCTTCTCGCAGGCGGCA
GGGCGGGCGGCCAGGATCATGTCCACCACCACATGCCAAGTGGTGGCGTTCCTCCTGTCCATCCTGGGGCT
GGCCGGCTGCATCGCGGCCACCGGGATGGACATGTGGAGCACCCAGGACCTGTACGACAACCCCGTCACCT
CCGTGTTCCAGTACGAAGGGCTCTGGAGGAGCTGCGTGAGGCAGAGTTCAGGCTTCACCGAATGCAGGCCC
TATTTCACCATCCTGGGACTTCCAGCCATGCTGCAGGCAGTGCGAGCCCTGATGATCGTAGGCATCGTCCT
GGGTGCCATTGGCCTCCTGGTATCCATCTTTGCCCTGAAATGCATCCGCATTGGCAGCATGGAGGACTCTG
CCAAAGCCAACATGACACTGACCTCCGGGATCATGTTCATTGTCTCAGGTCTTTGTGCAATTGCTGGAGTG
TCTGTGTTTGCCAACATGCTGGTGACTAACTTCTGGATGTCCACAGCTAACATGTACACCGGCATGGGTGG
GATGGTGCAGACTGTTCAGACCAGGTACACATTTGGTGCGGCTCTGTTCGTGGGCTGGGTCGCTGGAGGCC
TCACACTAATTGGGGGTGTGATGATGTGCATCGCCTGCCGGGGCCTGGCACCAGAAGAAACCAACTACAAA
GCCGTTTCTTATCATGCCTCAGGCCACAGTGTTGCCTACAAGCCTGGAGGCTTCAAGGCCAGCACTGGCTT
TGGGTCCAACACCAAAAACAAGAAGATATACGATGGAGGTGCCCGCACAGAGGACGAGGTACAATCTTATC
CTTCCAAGCACGACTATGTGTAATGCTCTAAGACCTCTCAGCACGGGCGGAAGAAACTCCCGGAGAGCTCA
CCCAAAAAACAAGGAGATCCCATCTAGATTTCTTCTTGCTTTTGACTCACAGCTGGAAGTTAGAAAAGCCT
CGATTTCATCTTTGGAGAGGCCAAATGGTCTTAGCCTCAGTCTCTGTCTCTAAATATTCCACCATAAAACA
GCTGAGTTATTTATGAATTAGAGGCTATAGCTCACATTTTCAATCCTCTATTTCTTTTTTTAAATATAACT
TTCTACTCTGATGAGAGAATGTGGTTTTAATCTCTCTCTCACATTTTGATGATTTAGACAGACTCCCCCTC
TTCCTCCTAGTCAATAAACCCATTGATGATCTATTTCCCAGCTTATCCCCAAGAAAACTTTTGAAAGGAAA
GAGTAGACCCAAAGATGTTATTTTCTGCTGTTTGAATTTTGTCTCCCCACCCCCAACTTGGCTAGTAATAA
ACACTTACTGAAGAAGAAGCAATAAGAGAAAGATATTTGTAATCTCTCCAGCCCATGATCTCGGTTTTCTT
ACACTGTGATCTTAAAAGTTACCAAACCAAAGTCATTTTCAGTTTGAGGCAACCAAACCTTTCTACTGCTG
TTGACATCTTCTTATTACAGCAACACCATTCTAGGAGTTTCCTGAGCTCTCCACTGGAGTCCTCTTTCTGT
CGCGGGTCAGAAATTGTCCCTAGATGAATGAGAAAATTATTTTTTTTAATTTAAGTCCTAAATATAGTTAA
AATAAATAATGTTTTAGTAAAATGATACACTATCTCTGTGAAATAGCCTCACCCCTACATGTGGATAGAAG
GAAATGAAAAAATAATTGCTTTGACATTGTCTATATGGTACTTTGTAAAGTCATGCTTAAGTACAAATTCC
ATGAAAAGCTCACACCTGTAATCCTAGCACTTTGGGAGGCTGAGGAGGAAGGATCACTTGAGCCCAGAAGT
TCGAGACTAGCCTGGGCAACATGGAGAAGCCCTGTCTCTACAAAATACAGAGAGAAAAAATCAGCCAGTCA
TGGTGGCATACACCTGTAGTCCCAGCATTCCGGGAGGCTGAGGTGGGAGGATCACTTGAGCCCAGGGAGGT
TGGGGCTGCAGTGAGCCATGATCACACCACTGCACTCCAGCCAGGTGACATAGCGAGATCCTGTCTAAAAA
AATAAAAAATAAATAATGGAACACAGCAAGTCCTAGGAAGTAGGTTAAAACTAATTCTTTAA
```

FIGURE 118

MSTTTCQVVAFLLSILGLAGCIAATGMDMWSTQDLYDNPVTSVFQYEGLWRSCVRQSSGFTECRP
YFTILGLPAMLQAVRALMIVGIVLGAIGLLVSIFALKCIRIGSMEDSAKANMTLTSGIMFIVSGL
CAIAGVSVFANMLVTNFWMSTANMYTGMGGMVQTVQTRYTFGAALFVGWVAGGLTLIGGVMMCIA
CRGLAPEETNYKAVSYHASGHSVAYKPGGFKASTGFGSNTKNKKIYDGGARTEDEVQSYPSKHDY
V

Signal peptide:

amino acids 1-23

Transmembrane domains:

amino acids 81-100, 121-141, 173-194

FIGURE 119

```
GGAAAAACTGTTCTCTTCTGTGGCACAGAGAACCCTGCTTCAAAGCAGAAGTAGCAGTTCCGGAGTCC
AGCTGGCTAAAACTCATCCCAGAGGATAATGGCAACCCATGCCTTAGAAATCGCTGGGCTGTTTCTTG
GTGGTGTTGGAATGGTGGGCACAGTGGCTGTCACTGTCATGCCTCAGTGGAGAGTGTCGGCCTTCATT
GAAAACAACATCGTGGTTTTTGAAAACTTCTGGGAAGGACTGTGGATGAATTGCGTGAGGCAGGCTAA
CATCAGGATGCAGTGCAAAATCTATGATTCCCTGCTGGCTCTTTCTCCGGACCTACAGGCAGCCAGAG
GACTGATGTGTGCTGCTTCCGTGATGTCCTTCTTGGCTTTCATGATGGCCATCCTTGGCATGAAATGC
ACCAGGTGCACGGGGGACAATGAGAAGGTGAAGGCTCACATTCTGCTGACGGCTGGAATCATCTTCAT
CATCACGGGCATGGTGGTGCTCATCCCTGTGAGCTGGGTTGCCAATGCCATCATCAGAGATTTCTATA
ACTCAATAGTGAATGTTGCCCAAAAACGTGAGCTTGGAGAAGCTCTCTACTTAGGATGGACCACGGCA
CTGGTGCTGATTGTTGGAGGAGCTCTGTTCTGCTGCGTTTTTTGTTGCAACGAAAAGAGCAGTAGCTA
CAGATACTCGATACCTTCCCATCGCACAACCCAAAAAAGTTATCACACCGGAAAGAAGTCACCGAGCG
TCTACTCCAGAAGTCAGTATGTGTAGTTGTGTATGTTTTTTTAACTTTACTATAAAGCCATGCAAATG
ACAAAAATCTATATTACTTTCTCAAAATGGACCCCAAAGAAACTTTGATTTACTGTTCTTAACTGCCT
AATCTTAATTACAGGAACTGTGCATCAGCTATTTATGATTCTATAAGCTATTTCAGCAGAATGAGATA
TTAAACCCAATGCTTTGATTGTTCTAGAAAGTATAGTAATTTGTTTTCTAAGGTGGTTCAAGCATCTA
CTCTTTTTATCATTTACTTCAAAATGACATTGCTAAAGACTGCATTATTTTACTACTGTAATTTCTCC
ACGACATAGCATTATGTACATAGATGAGTGTAACATTTATATCTCACATAGAGACATGCTTATATGGT
TTTATTTAAAATGAAATGCCAGTCCATTACACTGAATAAATAGAACTCAACTATTGCTTTTCAGGGAA
ATCATGGATAGGGTTGAAGAAGGTTACTATTAATTGTTTAAAAACAGCTTAGGGATTAATGTCCTCCA
TTTATAATGAAGATTAAAATGAAGGCTTTAATCAGCATTGTAAAGGAAATTGAATGGCTTTCTGATAT
GCTGTTTTTTAGCCTAGGAGTTAGAAATCCTAACTTCTTTATCCTCTTCTCCCAGAGGCTTTTTTTTT
CTTGTGTATTAAATTAACATTTTTAAAACGCAGATATTTTGTCAAGGGGCTTTGCATTCAAACTGCTT
TTCCAGGGCTATACTCAGAAGAAAGATAAAAGTGTGATCTAAGAAAAAGTGATGGTTTTAGGAAAGTG
AAAATATTTTTGTTTTTGTATTTGAAGAAGAATGATGCATTTTGACAAGAAATCATATATGTATGGAT
ATATTTTAATAAGTATTTGAGTACAGACTTTGAGGTTTCATCAATATAAATAAAAGAGCAGAAAAATA
TGTCTTGGTTTTCATTTGCTTACCAAAAAAACAACAACAAAAAAAGTTGTCCTTTGAGAACTTCACCT
GCTCCTATGTGGGTACCTGAGTCAAAATTGTCATTTTGTTCTGTGAAAAATAAATTTCCTTCTTGTA
CCATTTCTGTTTAGTTTTACTAAAATCTGTAAATACTGTATTTTTCTGTTTATTCCAAATTTGATGAA
ACTGACAATCCAATTTGAAAGTTTGTGTCGACGTCTGTCTAGCTTAAATGAATGTGTTCTATTTGCTT
TATACATTTATATTAATAAATTGTACATTTTTCTAATT
```

FIGURE 120

MATHALEIAGLFLGGVGMVGTVAVTVMPQWRVSAFIENNIVVFENFWEGLWMNCVRQANIRMQCK
IYDSLLALSPDLQAARGLMCAASVMSFLAFMMAILGMKCTRCTGDNEKVKAHILLTAGIIFIITG
MVVLIPVSWVANAIIRDFYNSIVNVAQKRELGEALYLGWTTALVLIVGGALFCCVFCCNEKSSSY
RYSIPSHRTTQKSYHTGKKSPSVYSRSQYV

Signal peptide:
amino acids 1-17

Transmembrane domains:
amino acids 82-101, 118-145, 164-188

FIGURE 121

```
GGAGAGAGGCGCGCGGGTGAAAGGCGCATTGATGCAGCCTGCGGCGGCCTCGGAGCGCGGCGGAG
CCAGACGCTGACCACGTTCCTCTCCTCGGTCTCCTCCGCCTCCAGCTCCGCGCTGCCCGGCAGCC
GGGAGCCATGCGACCCCAGGGCCCCGCCGCCTCCCCGCAGCGGCTCCGCGGCCTCCTGCTGCTCC
TGCTGCTGCAGCTGCCCGCGCCGTCGAGCGCCTCTGAGATCCCCAAGGGGAAGCAAAAGGCGCAG
CTCCGGCAGAGGGAGGTGGTGGACCTGTATAATGGAATGTGCTTACAAGGGCCAGCAGGAGTGCC
TGGTCGAGACGGGAGCCCTGGGGCCAATGTTATTCCGGGTACACCTGGGATCCCAGGTCGGGATG
GATTCAAAGGAGAAAAGGGGGAATGTCTGAGGGAAAGCTTTGAGGAGTCCTGGACACCCAACTAC
AAGCAGTGTTCATGGAGTTCATTGAATTATGGCATAGATCTTGGGAAAATTGCGGAGTGTACATT
TACAAAGATGCGTTCAAATAGTGCTCTAAGAGTTTTGTTCAGTGGCTCACTTCGGCTAAAATGCA
GAAATGCATGCTGTCAGCGTTGGTATTTCACATTCAATGGAGCTGAATGTTCAGGACCTCTTCCC
ATTGAAGCTATAATTTATTTGGACCAAGGAAGCCCTGAAATGAATTCAACAATTAATATTCATCG
CACTTCTTCTGTGGAAGGACTTTGTGAAGGAATTGGTGCTGGATTAGTGGATGTTGCTATCTGGG
TTGGCACTTGTTCAGATTACCCAAAAGGAGATGCTTCTACTGGATGGAATTCAGTTTCTCGCATC
ATTATTGAAGAACTACCAAAATAAATGCTTTAATTTTCATTTGCTACCTCTTTTTTTATTATGCC
TTGGAATGGTTCACTTAAATGACATTTTAAATAAGTTTATGTATACATCTGAATGAAAGCAAAG
CTAAATATGTTTACAGACCAAAGTGTGATTTCACACTGTTTTAAATCTAGCATTATTCATTTTG
CTTCAATCAAAAGTGGTTTCAATATTTTTTTAGTTGGTTAGAATACTTTCTTCATAGTCACATT
CTCTCAACCTATAATTTGGAATATTGTTGTGGTCTTTTGTTTTTTCTCTTAGTATAGCATTTTTA
AAAAATATAAAAGCTACCAATCTTTGTACAATTTGTAAATGTTAAGAATTTTTTTTATATCTGT
TAAATAAAAATTATTTCCAACA
```

FIGURE 122

MRPQGPAASPQRLRGLLLLLLLQLPAPSSASEIPKGKQKAQLRQREVVDLYNGMCLQGPAGVPGR
DGSPGANVIPGTPGIPGRDGFKGEKGECLRESFEESWTPNYKQCSWSSLNYGIDLGKIAECTFTK
MRSNSALRVLFSGSLRLKCRNACCQRWYFTFNGAECSGPLPIEAIIYLDQGSPEMNSTINIHRTS
SVEGLCEGIGAGLVDVAIWVGTCSDYPKGDASTGWNSVSRIIIEELPK

Signal peptide:

amino acids 1-30

Transmembrane domain:

amino acids 195-217

FIGURE 123

```
GCTGAGCGTGTGCGCGGTACGGGGCTCTCCTGCCTTCTGGGCTCCAACGCAGCTCTGTGGCTGAA
CTGGGTGCTCATCACGGGAACTGCTGGGCTATGGAATACAGATGTGGCAGCTCAGGTAGCCCCAA
ATTGCCTGGAAGAATACATCATGTTTTTCGATAAGAAGAAATTGTAGGATCCAGTTTTTTTTTA
ACCGCCCCCTCCCCACCCCCAAAAAAACTGTAAAGATGCAAAAACGTAATATCCATGAAGATCC
TATTACCTAGGAAGATTTTGATGTTTTGCTGCGAATGCGGTGTTGGGATTTATTTGTTCTTGGAG
TGTTCTGCGTGGCTGGCAAAGAATAATGTTCCAAAATCGGTCCATCTCCCAAGGGGTCCAATTTT
TCTTCCTGGGTGTCAGCGAGCCCTGACTCACTACAGTGCAGCTGACAGGGGCTGTCATGCAACTG
GCCCCTAAGCCAAAGCAAAAGACCTAAGGACGACCTTTGAACAATACAAAGGATGGGTTTCAATG
TAATTAGGCTACTGAGCGGATCAGCTGTAGCACTGGTTATAGCCCCCACTGTCTTACTGACAATG
CTTTCTTCTGCCGAACGAGGATGCCCTAAGGGCTGTAGGTGTGAAGGCAAAATGGTATATTGTGA
ATCTCAGAAATTACAGGAGATACCCTCAAGTATATCTGCTGGTTGCTTAGGTTTGTCCCTTCGCT
ATAACAGCCTTCAAAAACTTAAGTATAATCAATTTAAAGGGCTCAACCAGCTCACCTGGCTATAC
CTTGACCATAACCATATCAGCAATATTGACGAAAATGCTTTTAATGGAATACGCAGACTCAAAGA
GCTGATTCTTAGTTCCAATAGAATCTCCTATTTTCTTAACAATACCTTCAGACCTGTGACAAATT
TACGGAACTTGGATCTGTCCTATAATCAGCTGCATTCTCTGGGATCTGAACAGTTTCGGGGCTTG
CGGAAGCTGCTGAGTTTACATTTACGGTCTAACTCCCTGAGAACCATCCCTGTGCGAATATTCCA
AGACTGCCGCAACCTGGAACTTTTGGACCTGGGATATAACCGGATCCGAAGTTTAGCCAGGAATG
TCTTTGCTGGCATGATCAGACTCAAAGAACTTCACCTGGAGCACAATCAATTTTCCAAGCTCAAC
CTGGCCCTTTTTCCAAGGTTGGTCAGCCTTCAGAACCTTTACTTGCAGTGGAATAAAATCAGTGT
CATAGGACAGACCATGTCCTGGACCTGGAGCTCCTTACAAAGGCTTGATTTATCAGGCAATGAGA
TCGAAGCTTTCAGTGGACCCAGTGTTTTCCAGTGTGTCCCGAATCTGCAGCGCCTCAACCTGGAT
TCCAACAAGCTCACATTTATTGGTCAAGAGATTTTGGATTCTTGGATATCCCTCAATGACATCAG
TCTTGCTGGGAATATATGGGAATGCAGCAGAAATATTTGCTCCCTTGTAAACTGGCTGAAAAGTT
TTAAAGGTCTAAGGGAGAATACAATTATCTGTGCCAGTCCCAAAGAGCTGCAAGGAGTAAATGTG
ATCGATGCAGTGAAGAACTACAGCATCTGTGGCAAAAGTACTACAGAGAGGTTTGATCTGGCCAG
GGCTCTCCCAAAGCCGACGTTTAAGCCCAAGCTCCCCAGGCCGAAGCATGAGAGCAAACCCCCTT
TGCCCCCGACGGTGGGAGCCACAGAGCCCGGCCCAGAGACCGATGCTGACGCCGAGCACATCTCT
TTCCATAAAATCATCGCGGGCAGCGTGGCGCTTTTCCTGTCCGTGCTCGTCATCCTGCTGGTTAT
CTACGTGTCATGGAAGCGGTACCCTGCGAGCATGAAGCAGCTGCAGCAGCGCTCCCTCATGCGAA
GGCACAGGAAAAGAAAAGACAGTCCCTAAAGCAAATGACTCCCAGCACCCAGGAATTTTATGTA
GATTATAAACCCACCAACACGGAGACCAGCGAGATGCTGCTGAATGGGACGGGACCCTGCACCTA
TAACAAATCGGGCTCCAGGGAGTGTGAGGTATGAACCATTGTGATAAAAGAGCTCTTAAAAGCT
GGGAAATAAGTGGTGCTTTATTGAACTCTGGTGACTATCAAGGGAACGCGATGCCCCCCTCCCC
TTCCCTCTCCCTCTCACTTTGGTGGCAAGATCCTTCCTTGTCCGTTTTAGTGCATTCATAATACT
GGTCATTTTCCTCTCATACATAATCAACCCATTGAAATTTAAATACCACAATCAATGTGAAGCTT
GAACTCCGGTTTAATATAATACCTATTGTATAAGACCCTTTACTGATTCCATTAATGTCGCATTT
GTTTTAAGATAAAACTTCTTTCATAGGTAAAAAAAAAA
```

FIGURE 124

```
MGFNVIRLLSGSAVALVIAPTVLLTMLSSAERGCPKGCRCEGKMVYCESQKLQEIPSSISAGCLG
LSLRYNSLQKLKYNQFKGLNQLTWLYLDHNHISNIDENAFNGIRRLKELILSSNRISYFLNNTFR
PVTNLRNLDLSYNQLHSLGSEQFRGLRKLLSLHLRSNSLRTIPVRIFQDCRNLELLDLGYNRIRS
LARNVFAGMIRLKELHLEHNQFSKLNLALFPRLVSLQNLYLQWNKISVIGQTMSWTWSSLQRLDL
SGNEIEAFSGPSVFQCVPNLQRLNLDSNKLTFIGQEILDSWISLNDISLAGNIWECSRNICSLVN
WLKSFKGLRENTIICASPKELQGVNVIDAVKNYSICGKSTTERFDLARALPKPTFKPKLPRPKHE
SKPPLPPTVGATEPGPETDADAEHISFHKIIAGSVALFLSVLVILLVIYVSWKRYPASMKQLQQR
SLMRRHRKKKRQSLKQMTPSTQEFYVDYKPTNTETSEMLLNGTGPCTYNKSGSRECEV
```

Important features of the protein:

Signal peptide:

amino acids 1-33

Transmembrane domain:

amino acids 420-442

N-glycosylation sites.

amino acids 126-129, 357-360, 496-499, 504-507 cAMP- and cGMP-dependent protein kinase phosphorylation site.

amino acids 465-468

Tyrosine kinase phosphorylation site.

amino acids 136-142

N-myristoylation sites.

amino acids 11-16, 33-38, 245-250, 332-337, 497-502, 507-512

FIGURE 125

CCGTTATCGTCTTGCGCTACTGCTGAATGTCCGTCCCGGAGGAGGAGGAGAGGCTTTTGCCGCTG
ACCCAGAGATGGCCCCGAGCGAGCAAATTCCTACTGTCCGGCTGCGCGGCTACCGTGGCCGAGCT
AGCAACCTTTCCCCTGGATCTCACAAAAACTCGACTCCAAATGCAAGGAGAAGCAGCTCTTGCTC
GGTTGGGAGACGGTGCAAGAGAATCTGCCCCCTATAGGGGAATGGTGCGCACAGCCCTAGGGATC
ATTGAAGAGGAAGGCTTTCTAAAGCTTTGGCAAGGAGTGACACCCGCCATTTACAGACACGTAGT
GTATTCTGGAGGTCGAATGGTCACATATGAACATCTCCGAGAGGTTGTGTTTGGCAAAAGTGAAG
ATGAGCATTATCCCCTTTGGAAATCAGTCATTGGAGGGATGATGGCTGGTGTTATTGGCCAGTTT
TTAGCCAATCCAACTGACCTAGTGAAGGTTCAGATGCAAATGGAAGGAAAAGGAAACTGGAAGG
AAAACCATTGCGATTTCGTGGTGTACATCATGCATTTGCAAAAATCTTAGCTGAAGGAGGAATAC
GAGGGCTTTGGGCAGGCTGGGTACCCAATATACAAAGAGCAGCACTGGTGAATATGGGAGATTTA
ACCACTTATGATACAGTGAAACACTACTTGGTATTGAATACACCACTTGAGGACAATATCATGAC
TCACGGTTTATCAAGTTTATGTTCTGGACTGGTAGCTTCTATTCTGGGAACACCAGCCGATGTCA
TCAAAAGCAGAATAATGAATCAACCACGAGATAAACAAGGAAGGGGACTTTTGTATAAATCATCG
ACTGACTGCTTGATTCAGGCTGTTCAAGGTGAAGGATTCATGAGTCTATATAAAGGCTTTTTACC
ATCTTGGCTGAGAATGACCCCTTGGTCAATGGTGTTCTGGCTTACTTATGAAAAAATCAGAGAGA
TGAGTGGAGTCAGTCCATTTTAA

FIGURE 126

MSVPEEEERLLPLTQRWPRASKFLLSGCAATVAELATFPLDLTKTRLQMQGEAALARLGDGARES
APYRGMVRTALGIIEEEGFLKLWQGVTPAIYRHVVYSGGRMVTYEHLREVVFGKSEDEHYPLWKS
VIGGMMAGVIGQFLANPTDLVKVQMQMEGKRKLEGKPLRFRGVHHAFAKILAEGGIRGLWAGWVP
NIQRAALVNMGDLTTYDTVKHYLVLNTPLEDNIMTHGLSSLCSGLVASILGTPADVIKSRIMNQP
RDKQGRGLLYKSSTDCLIQAVQGEGFMSLYKGFLPSWLRMTPWSMVFWLTYEKIREMSGVSPF

Transmembrane domains:
amino acids 25-38, 130-147, 233-248

FIGURE 127

CGCGGATCGGACCCAAGCAGGTCGGCGGCGGCGGCAGGAGAGCGGCCGGGCGTCAGCTCCTCGAC
CCCCGTGTCGGGCTAGTCCAGCGAGGCGGACGGGCGGCGTGGGCCATGGCCAGGCCCGGCATGG
AGCGGTGGCGCGACCGGCTGGCGCTGGTGACGGGGGCCTCGGGGGGCATCGGCGCGGCCGTGGCC
CGGGCCCTGGTCCAGCAGGGACTGAAGGTGGTGGGCTGCGCCCGCACTGTGGGCAACATCGAGGA
GCTGGCTGCTGAATGTAAGAGTGCAGGCTACCCCGGGACTTTGATCCCCTACAGATGTGACCTAT
CAAATGAAGAGGACATCCTCTCCATGTTCTCAGCTATCCGTTCTCAGCACAGCGGTGTAGACATC
TGCATCAACAATGCTGGCTTGGCCCGGCCTGACACCCTGCTCTCAGGCAGCACCAGTGGTTGGAA
GGACATGTTCAATGTGAACGTGCTGGCCCTCAGCATCTGCACACGGGAAGCCTACCAGTCCATGA
AGGAGCGGAATGTGGACGATGGGCACATCATTAACATCAATAGCATGTCTGGCCACCGAGTGTTA
CCCCTGTCTGTGACCCACTTCTATAGTGCCACCAAGTATGCCGTCACTGCGCTGACAGAGGGACT
GAGGCAAGAGCTTCGGGAGGCCCAGACCCACATCCGAGCCACGTGCATCTCCAGGTGTGGTGG
AGACACAATTCGCCTTCAAACTCCACGACAAGGACCCTGAGAAGGCAGCTGCCACCTATGAGCAA
ATGAAGTGTCTCAAACCCGAGGATGTGGCCGAGGCTGTTATCTACGTCCTCAGCACCCCCGCACA
CATCCAGATTGGAGACATCCAGATGAGGCCCACGGAGCAGGTGACCTAGTGACTGTGGGAGCTCC
TCCTTCCCTCCCCACCCTTCATGGCTTGCCTCCTGCCTCTGGATTTTAGGTGTTGATTTCTGGAT
CACGGGATACCACTTCCTGTCCACACCCCGACCAGGGGCTAGAAAATTTGTTTGAGATTTTTATA
TCATCTTGTCAAATTGCTTCAGTTGTAAATGTGAAAAATGGGCTGGGGAAAGGAGGTGGTGTCCC
TAATTGTTTTACTTGTTAACTTGTTCTTGTGCCCCTGGGCACTTGGCCTTTGTCTGCTCTCAGTG
TCTTCCCTTTGACATGGGAAAGGAGTTGTGGCCAAAATCCCCATCTTCTTGCACCTCAACGTCTG
TGGCTCAGGGCTGGGGTGGCAGAGGGAGGCCTTCACCTTATATCTGTGTTGTTATCCAGGGCTCC
AGACTTCCTCCTCTGCCTGCCCCACTGCACCCTCTCCCCCTTATCTATCTCCTTCTCGGCTCCCC
AGCCCAGTCTTGGCTTCTTGTCCCCTCCTGGGGTCATCCCTCCACTCTGACTCTGACTATGGCAG
CAGAACACCAGGGCCTGGCCCAGTGGATTTCATGGTGATCATTAAAAAAGAAAAATCGCAACCAA
AAAAAAAAA

FIGURE 128

MARPGMERWRDRLALVTGASGGIGAAVARALVQQGLKVVGCARTVGNIEELAAECKSAGYPGTLI
PYRCDLSNEEDILSMFSAIRSQHSGVDICINNAGLARPDTLLSGSTSGWKDMFNVNVLALSICTR
EAYQSMKERNVDDGHIININSMSGHRVLPLSVTHFYSATKYAVTALTEGLRQELREAQTHIRATC
ISPGVVETQFAFKLHDKDPEKAAATYEQMKCLKPEDVAEAVIYVLSTPAHIQIGDIQMRPTEQVT

Important features of the protein:

Signal peptide:

amino acids 1-17

N-myristoylation sites.

amino acids 18-24, 21-27, 22-28, 24-30, 40-46, 90-96, 109-115, 199-205

Short-chain alcohol dehyrogenase.

amino acids 30-42, 104-114

FIGURE 129

AACTTCTACATGGGCCTCCTGCTGCTGGTGCTCTTCCTCAGCCTCCTGCCGGTGGCCTACACCAT
CATGTCCCTCCCACCCTCCTTTGACTGCGGGCCGTTCAGGTGCAGAGTCTCAGTTGCCCGGGAGC
ACCTCCCCTCCCGAGGCAGTCTGCTCAGAGGGCCTCGGCCCAGAATTCCAGTTCTGGTTTCATGC
CAGCCTGTAAAAGGCCATGGAACTTTGGGTGAATCACCGATGCCATTTAAGAGGGTTTTCTGCCA
GGATGGAAATGTTAGGTCGTTCTGTGTCTGCGCTGTTCATTTCAGTAGCCACCAGCCACCTGTGG
CCGTTGAGTGCTTGAAATGAGGAACTGAGAAAATTAATTTCTCATGTATTTTCTCATTTATTTA
TTAATTTTTAACTGATAGTTGTACATATTTGGGGGTACATGTGATATTTGGATACATGTATACAA
TATATAATGATCAAATCAGGGTAACTGGGATATCCATCACATCAAACATTTATTTTTATTCTTT
TTAGACAGAGTCTCACTCTGTCACCCAGGCTGGAGTGCAGTGGTGCCATCTCAGCTTACTGCAAC
CTCTGCCTGCCAGGTTCAAGCGATTCTCATGCCTCCACCTCCCAAGTAGCTGGGACTACAGGCAT
GCACCACAATGCCCAACTAATTTTTGTATTTTAGTAGAGACGGGGTTTTGCCATGTTGCCCAGG
CTGGCCTTGAACTCCTGGCCTCAAACAATCCACTTGCCTCGGCCTCCCAAAGTGTTATGATTACA
GGCGTGAGCCACCGTGCCTGGCCTAAACATTTATCTTTTCTTTGTGTTGGGAACTTTGAAATTAT
ACAATGAATTATTGTTAACTGTCATCTCCCTGCTGTGCTATGGAACACTGGGACTTCTTCCCTCT
ATCTAACTGTATATTTGTACCAGTTAACCAACCGTACTTCATCCCCACTCCTCTCTATCCTTCCC
AACCTCTGATCACCTCATTCTACTCTCTACCTCCATGAGATCCACTTTTTTAGCTCCCACATGTG
AGTAAGAAAATGCAATATTTGTCTTTCTGTGCCTGGCTTATTTCACTTAACATAATGACTTCCTG
TTCCATCCATGTTGCTGCAAATGACAGGATTTCGTTCTTAATTTCAATTAAAATAACCACACATG
GCAAAAA

FIGURE 130

MGLLLLVLFLSLLPVAYTIMSLPPSFDCGPFRCRVSVAREHLPSRGSLLRGPRPRIPVLVSCQPV
KGHGTLGESPMPFKRVFCQDGNVRSFCVCAVHFSSHQPPVAVECLK

Important features of the protein:

Signal peptide:

amino acids 1-18

N-myristoylation site.

amino acids 86-92

Zinc carboxypeptidases, zinc-binding region 2 signature.

amino acids 68-79

FIGURE 131

TTCTGAAGTAACGGAAGCTACCTTGTATAAAGACCTCAACACTGCTGACCATGATCAGCGCAGCCTGGAGC
ATCTTCCTCATCGGGACTAAAATTGGGCTGTTCCTTCAAGTAGCACCTCTATCAGTTATGGCTAAATCCTG
TCCATCTGTGTGTCGCTGCGATGCGGGTTTCATTTACTGTAATGATCGCTTTCTGACATCCATTCCAACAG
GAATACCAGAGGATGCTACAACTCTCTACCTTCAGAACAACCAAATAAATAATGCTGGGATTCCTTCAGAT
TTGAAAAACTTGCTGAAAGTAGAAAGAATATACCTATACCACAACAGTTTAGATGAATTTCCTACCAACCT
CCCAAAGTATGTAAAAGAGTTACATTTGCAAGAAAATAACATAAGGACTATCACTTATGATTCACTTTCAA
AAATTCCCTATCTGGAAGAATTACATTTAGATGACAACTCTGTCTCTGCAGTTAGCATAGAAGAGGGAGCA
TTCCGAGACAGCAACTATCTCCGACTGCTTTTCCTGTCCCGTAATCACCTTAGCACAATTCCCTGGGGTTT
GCCCAGGACTATAGAAGAACTACGCTTGGATGATAATCGCATATCCACTATTTCATCACCATCTCTTCAAG
GTCTCACTAGTCTAAAACGCCTGGTTCTAGATGGAAACCTGTTGAACAATCATGGTTTAGGTGACAAAGTT
TTCTTCAACCTAGTTAATTTGACAGAGCTGTCCCTGGTGCGGAATTCCCTGACTGCTGCACCAGTAAACCT
TCCAGGCACAAACCTGAGGAAGCTTTATCTTCAAGATAACCACATCAATCGGGTGCCCCCAAATGCTTTTT
CTTATCTAAGGCAGCTCTATCGACTGGATATGTCCAATAATAACCTAAGTAATTTACCTCAGGGTATCTTT
GATGATTTGGACAATATAACACAACTGATTCTTCGCAACAATCCCTGGTATTGCGGGTGCAAGATGAAATG
GGTACGTGACTGGTTACAATCACTACCTGTGAAGGTCAACGTGCGTGGGCTCATGTGCCAAGCCCCAGAAA
AGGTTCGTGGGATGGCTATTAAGGATCTCAATGCAGAACTGTTTGATTGTAAGGACAGTGGGATTGTAAGC
ACCATTCAGATAACCACTGCAATACCCAACACAGTGTATCCTGCCCAAGGACAGTGGCCAGCTCCAGTGAC
CAAACAGCCAGATATTAAGAACCCCAAGCTCACTAAGGATCAACAAACCACAGGGAGTCCCTCAAGAAAAA
CAATTACAATTACTGTGAAGTCTGTCACCTCTGATACCATTCATATCTCTTGGAAACTTGCTCTACCTATG
ACTGCTTTGAGACTCAGCTGGCTTAAACTGGGCCATAGCCCGGCATTTGGATCTATAACAGAAACAATTGT
AACAGGGGAACGCAGTGAGTACTTGGTCACAGCCCTGGAGCCTGATTCACCCTATAAAGTATGCATGGTTC
CCATGGAAACCAGCAACCTCTACCTATTTGATGAAACTCCTGTTTGTATTGAGACTGAAACTGCACCCCTT
CGAATGTACAACCCTACAACCACCCTCAATCGAGAGCAAGAGAAAGAACCTTACAAAAACCCCAATTTACC
TTTGGCTGCCATCATTGGTGGGCTGTGGCCCTGGTTACCATTGCCCTTCTTGCTTTAGTGTGTTGGTATG
TTCATAGGAATGGATCGCTCTTCTCAAGGAACTGTGCATATAGCAAAGGGAGGAGAAGAAAGGATGACTAT
GCAGAAGCTGGCACTAAGAAGGACAACTCTATCCTGGAAATCAGGGAAACTTCTTTTCAGATGTTACCAAT
AAGCAATGAACCCATCTCGAAGGAGGAGTTTGTAATACACACCATATTTCCTCCTAATGGAATGAATCTGT
ACAAAAACAATCACAGTGAAAGCAGTAGTAACCGAAGCTACAGAGACAGTGGTATTCCAGACTCAGATCAC
TCACACTCATGATGCTGAAGGACTCACAGCAGACTTGTGTTTTGGGTTTTTTAAACCTAAGGGAGGTGATG
GT

FIGURE 132

MISAAWSIFLIGTKIGLFLQVAPLSVMAKSCPSVCRCDAGFIYCNDRFLTSIPTGIPEDATTLYL
QNNQINNAGIPSDLKNLLKVERIYLYHNSLDEFPTNLPKYVKELHLQENNIRTITYDSLSKIPYL
EELHLDDNSVSAVSIEEGAFRDSNYLRLLFLSRNHLSTIPWGLPRTIEELRLDDNRISTISSPSL
QGLTSLKRLVLDGNLLNNHGLGDKVFFNLVNLTELSLVRNSLTAAPVNLPGTNLRKLYLQDNHIN
RVPPNAFSYLRQLYRLDMSNNNLSNLPQGIFDDLDNITQLILRNNPWYCGCKMKWVRDWLQSLPV
KVNVRGLMCQAPEKVRGMAIKDLNAELFDCKDSGIVSTIQITTAIPNTVYPAQGQWPAPVTKQPD
IKNPKLTKDQQTTGSPSRKTITITVKSVTSDTIHISWKLALPMTALRLSWLKLGHSPAFGSITET
IVTGERSEYLVTALEPDSPYKVCMVPMETSNLYLFDETPVCIETETAPLRMYNPTTTLNREQEKE
PYKNPNLPLAAIIGGAVALVTIALLALVCWYVHRNGSLFSRNCAYSKGRRRKDDYAEAGTKKDNS
ILEIRETSFQMLPISNEPISKEEFVIHTIFPPNGMNLYKNNHSESSSNRSYRDSGIPDSDHSHS

Important features of the protein:

Signal peptide:

amino acids 1-28

Transmembrane domain:

amino acids 531-552

N-glycosylation sites.

amino acids 226-229, 282-285, 296-299, 555-558, 626-629, 633-636

Tyrosine kinase phosphorylation site.

amino acids 515-522

N-myristoylation sites.

amino acids 12-17, 172-177, 208-213, 359-364, 534-539, 556-561, 640-645

Amidation site.

amino acids 567-570

Leucine zipper pattern.

amino acids 159-180

Phospholipase A2 aspartic acid active site.

amino acids 34-44

FIGURE 133

```
CCGTCATCCCCCTGCAGCCACCCTTCCCAGAGTCCTTTGCCCAGGCCACCCCAGGCTTCTTGGCA
GCCCTGCCGGGCCACTTGTCTTCATGCTGCCAGGGGGAGGTGGGAAGGAGGTGGGAGGAGGGCG
TGCAGAGGCAGTCTGGGCTTGGCCAGAGCTCAGGGTGCTGAGCGTGTGACCAGCAGTGAGCAGAG
GCCGGCCATGGCCAGCCTGGGGCTGCTGCTCCTGCTCTTACTGACAGCACTGCCACCGCTGTGGT
CCTCCTCACTGCCTGGGCTGGACACTGCTGAAAGTAAAGCCACCATTGCAGACCTGATCCTGTCT
GCGCTGGAGAGAGCCACCGTCTTCCTAGAACAGAGGCTGCCTGAAATCAACCTGGATGGCATGGT
GGGGGTCCGAGTGCTGGAAGAGCAGCTAAAAAGTGTCCGGGAGAAGTGGGCCCAGGAGCCCCTGC
TGCAGCCGCTGAGCCTGCGCGTGGGGATGCTGGGGGAGAAGCTGGAGGCTGCCATCCAGAGATCC
CTCCACTACCTCAAGCTGAGTGATCCCAAGTACCTAAGAGAGTTCCAGCTGACCCTCCAGCCCGG
GTTTTGGAAGCTCCCACATGCCTGGATCCACACTGATGCCTCCTTGGTGTACCCCACGTTCGGGC
CCCAGGACTCATTCTCAGAGGAGAGAAGTGACGTGTGCCTGGTGCAGCTGCTGGGAACCGGGACG
GACAGCAGCGAGCCCTGCGGCCTCTCAGACCTCTGCAGGAGCCTCATGACCAAGCCCGGCTGCTC
AGGCTACTGCCTGTCCCACCAACTGCTCTTCTTCCTCTGGGCCAGAATGAGGGGATGCACACAGG
GACCACTCCAACAGAGCCAGGACTATATCAACCTCTTCTGCGCCAACATGATGGACTTGAACCGC
AGAGCTGAGGCCATCGGATACGCCTACCCTACCCGGGACATCTTCATGGAAAACATCATGTTCTG
TGGAATGGGCGGCTTCTCCGACTTCTACAAGCTCCGGTGGCTGGAGGCCATTCTCAGCTGGCAGA
AACAGCAGGAAGGATGCTTCGGGGAGCCTGATGCTGAAGATGAAGAATTATCTAAAGCTATTCAA
TATCAGCAGCATTTTTCGAGGAGAGTGAAGAGGCGAGAAAAACAATTTCCAGATTCTCGCTCTGT
TGCTCAGGCTGGAGTACAGTGGCGCAATCTCGGCTCACTGCAACCTTTGCCTCCTGGGTTCAAGC
AATTCTCTTGCCTCATCCTCCCGAGTAGCTGGGACTACAGGAGCGTGCCACCATACCTGGCTAAT
TTTTATATTTTTTTAGTAGAGACAGGGTTTCATCATGTTGCTCATGCTGGTCTCGAACTCCTGAT
CTCAAGAGATCCGCCCACCTCAGGCTCCCAAAGTGTGGGATTATAGGTGTGAGCCACCGTGTCTG
GCTGAAAAGCACTTTCAAAGAGACTGTGTTGAATAAAGGGCCAAGGTTCTTGCCACCCAGCACTC
ATGGGGGCTCTCTCCCCTAGATGGCTGCTCCTCCCACAACACAGCCACAGCAGTGGCAGCCCTGG
GTGGCTTCCTATACATCCTGGCAGAATACCCCCAGCAAACAGAGAGCCACACCCATCCACACCG
CCACCACCAAGCAGCCGCTGAGACGGACGGTTCCATGCCAGCTGCCTGGAGGAGGAACAGACCCC
TTTAGTCCTCATCCCTTAGATCCTGGAGGGCACGGATCACATCCTGGGAAGAAGGCATCTGGAGG
ATAAGCAAAGCCACCCCGACACCCAATCTTGGAAGCCCTGAGTAGGCAGGGCCAGGGTAGGTGGG
GGCCGGGAGGGACCCAGGTGTGAACGGATGAATAAAGTTCAACTGCAACTGAAAAAAAAAAA
```

FIGURE 134

MSARGRWEGGGRRACRGSLGLARAQGAERVTSSEQRPAMASLGLLLLLLLTALPPLWSSSLPGLD
TAESKATIADLILSALERATVFLEQRLPEINLDGMVGVRVLEEQLKSVREKWAQEPLLQPLSLRV
GMLGEKLEAAIQRSLHYLKLSDPKYLREFQLTLQPGFWKLPHAWIHTDASLVYPTFGPQDSFSEE
RSDVCLVQLLGTGTDSSEPCGLSDLCRSLMTKPGCSGYCLSHQLLFFLWARMRGCTQGPLQQSQD
YINLFCANMMDLNRRAEAIGYAYPTRDIFMENIMFCGMGGFSDFYKLRWLEAILSWQKQQEGCFG
EPDAEDEELSKAIQYQQHFSRRVKRREKQFPDSRSVAQAGVQWRNLGSLQPLPPGFKQFSCLILP
SSWDYRSVPPYLANFYIFLVETGFHHVAHAGLELLISRDPPTSGSQSVGL

Important features of the protein:

Signal peptide:

amino acids 1-26

Transmembrane domain:

amino acids 39-56

Tyrosine kinase phosphorylation sites.

amino acids 149-156, 274-282

N-myristoylation sites.

amino acids 10-16, 20-26, 63-69, 208-214

Amidation site.

amino acids 10-14

Glycoprotein hormones beta chain signature 1.

amino acids 230-237

FIGURE 135

GGTCTGAGTGCAGAGCTGCTGTCATGGCGGCCGCTCTGTGGGGCTTCTTTCCCGTCCTGCTGCTG
CTGCTGCTATCGGGGGATGTCCAGAGCTCGGAGGTGCCCGGGGCTGCTGCTGAGGGATCGGGAGG
GAGTGGGGTCGGCATAGGAGATCGCTTCAAGATTGAGGGGCGTGCAGTTGTTCCAGGGGTGAAGC
CTCAGGACTGGATCTCGGCGGCCCGAGTGCTGGTAGACGGAGAAGAGCACGTCGGTTTCCTTAAG
ACAGATGGGAGTTTTGTGGTTCATGATATACCTTCTGGATCTTATGTAGTGGAAGTTGTATCTCC
AGCTTACAGATTTGATCCCGTTCGAGTGGATATCACTTCGAAAGGAAAAATGAGAGCAAGATATG
TGAATTACATCAAAACATCAGAGGTTGTCAGACTGCCCTATCCTCTCCAAATGAAATCTTCAGGT
CCACCTTCTTACTTTATTAAAAGGGAATCGTGGGGCTGGACAGACTTTCTAATGAACCCAATGGT
TATGATGATGGTTCTTCCTTTATTGATATTTGTGCTTCTGCCTAAAGTGGTCAACACAAGTGATC
CTGACATGAGACGGGAAATGGAGCAGTCAATGAATATGCTGAATTCCAACCATGAGTTGCCTGAT
GTTTCTGAGTTCATGACAAGACTCTTCTCTTCAAAATCATCTGGCAAATCTAGCAGCGGCAGCAG
TAAAACAGGCAAAAGTGGGGCTGGCAAAAGGAGGTAGTCAGGCCGTCCAGAGCTGGCATTTGCAC
AAACACGGCAACACTGGGTGGCATCCAAGTCTTGGAAAACCGTGTGAAGCAACTACTATAAACTT
GAGTCATCCCGACGTTGATCTCTTACAACTGTGTATGTT
AACTTTTTAGCACATGTTTTGTACTTGGTACACGAGAAAACCCAGCTTTCATCTTTTGTCTGTAT
GAGGTCAATATTGATGTCACTGAATTAATTACAGTGTCCTATAGAAAATGCCATTAATAAATTAT
ATGAACTACTATACATTATGTATATTAATTAAAACATCTTAATCCAGAAATCAAAAAAAAAAAA
AAAAAAAAAAAAAA

FIGURE 136

MAAALWGFFPVLLLLLLSGDVQSSEVPGAAAEGSGGSGVGIGDRFKIEGRAVVPGVKPQDWISAA
RVLVDGEEHVGFLKTDGSFVVHDIPSGSYVVEVVSPAYRFDPVRVDITSKGKMRARYVNYIKTSE
VVRLPYPLQMKSSGPPSYFIKRESWGWTDFLMNPMVMMMVLPLLIFVLLPKVVNTSDPDMRREME
QSMNMLNSNHELPDVSEFMTRLFSSKSSGKSSSGSSKTGKSGAGKRR

Important features of the protein:

Signal sequence:

amino acids 1-23

Transmembrane domain:

amino acids 161-182

N-glycosylation site.

amino acids 184-187

Glycosaminoglycan attachment sites.

amino acids 37-40, 236-239 cAMP- and cGMP-dependent protein kinase phosphorylation site.

amino acids 151-154

N-myristoylation sites.

amino acids 33-38, 36-41, 38-44, 229-234

Amidation site.

amino acids 238-241

ATP/GTP-binding site motif A (P-loop).

amino acids 229-236

FIGURE 137

```
GATGGCGCAGCCACAGCTTCTGTGAGATTCGATTTCTCCCCAGTTCCCCTGTGGGTCTGAGGGGA
CCAGAAGGGTGAGCTACGTTGGCTTTCTGGAAGGGGAGGCTATATGCGTCAATTCCCCAAAACAA
GTTTTGACATTTCCCCTGAAATGTCATTCTCTATCTATTCACTGCAAGTGCCTGCTGTTCCAGGC
CTTACCTGCTGGGCACTAACGGCGGAGCCAGGATGGGGACAGAATAAAGGAGCCACGACCTGTGC
CACCAACTCGCACTCAGACTCTGAACTCAGACCTGAAATCTTCTCTTCACGGGAGGCTTGGCAGT
TTTTCTTACTCCTGTGGTCTCCAGATTTCAGGCCTAAGATGAAAGCCTCTAGTCTTGCCTTCAGC
CTTCTCTCTGCTGCGTTTTATCTCCTATGGACTCCTTCCACTGGACTGAAGACACTCAATTTGGG
AAGCTGTGTGATCGCCACAAACCTTCAGGAAATACGAAATGGATTTTCTGAGATACGGGCAGTG
TGCAAGCCAAAGATGGAAACATTGACATCAGAATCTTAAGGAGGACTGAGTCTTTGCAAGACACA
AAGCCTGCGAATCGATGCTGCCTCCTGCGCCATTTGCTAAGACTCTATCTGGACAGGGTATTTAA
AAACTACCAGACCCCTGACCATTATACTCTCCGGAAGATCAGCAGCCTCGCCAATTCCTTTCTTA
CCATCAAGAAGGACCTCCGGCTCTCTCATGCCCACATGACATGCCATTGTGGGGAGGAAGCAATG
AAGAAATACAGCCAGATTCTGAGTCACTTTGAAAAGCTGGAACCTCAGGCAGCAGTTGTGAAGGC
TTTGGGGAACTAGACATTCTTCTGCAATGGATGGAGGAGACAGAATAGGAGGAAAGTGATGCTG
CTGCTAAGAATATTCGAGGTCAAGAGCTCCAGTCTTCAATACCTGCAGAGGAGGCATGACCCCAA
ACCACCATCTCTTTACTGTACTAGTCTTGTGCTGGTCACAGTGTATCTTATTTATGCATTACTTG
CTTCCTTGCATGATTGTCTTTATGCATCCCCAATCTTAATTGAGACCATACTTGTATAAGATTTT
TGTAATATCTTTCTGCTATTGGATATATTTATTAGTTAATATATTTATTTATTTTTGCTATTTA
ATGTATTTATTTTTTACTTGGACATGAAACTTTAAAAAAATTCACAGATTATATTTATAACCTG
ACTAGAGCAGGTGATGTATTTTATACAGTAAAAAAAAAAAACCTTGTAAATTCTAGAAGAGTGG
CTAGGGGGGTTATTCATTTGTATTCAACTAAGGACATATTTACTCATGCTGATGCTCTGTGAGAT
ATTTGAAATTGAACCAATGACTACTTAGGATGGGTTGTGGAATAAGTTTTGATGTGGAATTGCAC
ATCTACCTTACAATTACTGACCATCCCCAGTAGACTCCCCAGTCCCATAATTGTGTATCTTCCAG
CCAGGAATCCTACACGGCCAGCATGTATTTCTACAAATAAGTTTTCTTTGCATACCAAAAAAAA
AAAAAAAAAA
```

FIGURE 138

MRQFPKTSFDISPEMSFSIYSLQVPAVPGLTCWALTAEPGWGQNKGATTCATNSHSDSELRPEIF
SSREAWQFFLLLWSPDFRPKMKASSLAFSLLSAAFYLLWTPSTGLKTLNLGSCVIATNLQEIRNG
FSEIRGSVQAKDGNIDIRILRRTESLQDTKPANRCCLLRHLLRLYLDRVFKNYQTPDHYTLRKIS
SLANSFLTIKKDLRLSHAHMTCHCGEEAMKKYSQILSHFEKLEPQAAVVKALGELDILLQWMEET
E

Important features of the protein:

Signal peptide:

amino acids 1-42 cAMP- and cGMP-dependent protein kinase phosphorylation sites.

amino acids 192-195, 225-228

N-myristoylation sites.

amino acids 42-47, 46-51, 136-141

FIGURE 139

```
CCTGGAGCCGGAAGCGCGGCTGCAGCAGGGCGAGGCTCCAGGTGGGGTCGGTTCCGCATCCAGCC
TAGCGTGTCCACGATGCGGCTGGGCTCCGGGACTTTCGCTACCTGTTGCGTAGCGATCGAGGTGC
TAGGGATCGCGGTCTTCCTTCGGGGATTCTTCCCGGCTCCCGTTCGTTCCTCTGCCAGAGCGGAA
CACGGAGCGGAGCCCCCAGCGCCCGAACCCTCGGCTGGAGCCAGTTCTAACTGGACCACGCTGCC
ACCACCTCTCTTCAGTAAAGTTGTTATTGTTCTGATAGATGCCTTGAGAGATGATTTTGTGTTTG
GGTCAAAGGGTGTGAAATTTATGCCCTACACAACTTACCTTGTGGAAAAAGGAGCATCTCACAGT
TTTGTGGCTGAAGCAAAGCCACCTACAGTTACTATGCCTCGAATCAAGGCATTGATGACGGGGAG
CCTTCCTGGCTTTGTCGACGTCATCAGGAACCTCAATTCTCCTGCACTGCTGGAAGACAGTGTGA
TAAGACAAGCAAAAGCAGCTGGAAAAAGAATAGTCTTTTATGGAGATGAAACCTGGGTTAAATTA
TTCCCAAAGCATTTGTGGAATATGATGGAACAACCTCATTTTCGTGTCAGATTACACAGAGGT
GGATAATAATGTCACGAGGCATTTGGATAAAGTATTAAAAGAGGAGATTGGGACATATTAATCC
TCCACTACCTGGGGCTGGACCACATTGGCCACATTTCAGGGCCCAACAGCCCCTGATTGGGCAG
AAGCTGAGCGAGATGGACAGCGTGCTGATGAAGATCCACACCTCACTGCAGTCGAAGGAGAGAGA
GACGCCTTTACCCAATTTGCTGGTTCTTTGTGGTGACCATGGCATGTCTGAAACAGGAAGTCACG
GGGCCTCCTCCACCGAGGAGGTGAATACACCTCTGATTTTAATCAGTTCTGCGTTTGAAAGGAAA
CCCGGTGATATCCGACATCCAAAGCACGTCCAATAGACGGATGTGGCTGCGACACTGGCGATAGC
ACTTGGCTTACCGATTCCAAAAGACAGTGTAGGGAGCCTCCTATTCCCAGTTGTGGAAGGAAGAC
CAATGAGAGAGCAGTTGAGATTTTACATTTGAATACAGTGCAGCTTAGTAAACTGTTGCAAGAG
AATGTGCCGTCATATGAAAAGATCCTGGGTTTGAGCAGTTTAAAATGTCAGAAAGATTGCATGG
GAACTGGATCAGACTGTACTTGGAGGAAAAGCATTCAGAAGTCCTATTCAACCTGGGCTCCAAGG
TTCTCAGGCAGTACCTGGATGCTCTGAAGACGCTGAGCTTGTCCCTGAGTGCACAAGTGGCCCAG
TTCTCACCCTGCTCCTGCTCAGCGTCCCACAGGCACTGCACAGAAAGGCTGAGCTGGAAGTCCCA
CTGTCATCTCCTGGGTTTTCTCTGCTCTTTTATTTGGTGATCCTGGTTCTTTCGGCCGTTCACGT
CATTGTGTGCACCTCAGCTGAAAGTTCGTGCTACTTCTGTGGCCTCTCGTGGCTGGCGGCAGGCT
GCCTTTCGTTTACCAGACTCTGGTTGAACACCTGGTGTGTGCCAAGTGCTGGCAGTGCCCTGGAC
AGGGGGCCTCAGGGAAGGACGTGGAGCAGCCTTATCCCAGGCCTCTGGGTGTCCCGACACAGGTG
TTCACATCTGTGCTGTCAGGTCAGATGCCTCAGTTCTTGGAAAGCTAGGTTCCTGCGACTGTTAC
CAAGGTGATTGTAAAGAGCTGGCGGTCACAGAGGAACAAGCCCCCAGCTGAGGGGTGTGTGAA
TCGGACAGCCTCCCAGCAGAGGTGTGGGAGCTGCAGCTGAGGGAAGAAGAGACAATCGGCCTGGA
CACTCAGGAGGGTCAAAAGGAGACTTGGTCGCACCACTCATCCTGCCACCCCAGAATGCATCCT
GCCTCATCAGGTCCAGATTTCTTTCCAAGGCGGACGTTTTCTGTTGGAATTCTTAGTCCTTGGCC
TCGGACACCTTCATTCGTTAGCTGGGGAGTGGTGGTGAGGCAGTGAAGAAGAGGCGGATGGTCAC
ACTCAGATCCACAGAGCCCAGGATCAAGGGACCCACTGCAGTGGCAGCAGGACTGTTGGGCCCCC
ACCCCAACCCTGCACAGCCCTCATCCCTCTTGGCTTGAGCCGTCAGAGGCCCTGTGCTGAGTGT
CTGACCGAGACACTCACAGCTTTGTCATCAGGGCACAGGCTTCCTCGGAGCCAGGATGATCTGTG
CCACGCTTGCACCTCGGGCCCATCTGGGCTCATGCTCTCTCCTGCTATTGAATTAGTACCTAG
CTGCACACAGTATGTAGTTACCAAAAGAATAAACGGCAATAATTGAGAAAAAAA
```

FIGURE 140

MRLGSGTFATCCVAIEVLGIAVFLRGFFPAPVRSSARAEHGAEPPAPEPSAGASSNWTTLPPPLF
SKVVIVLIDALRDDFVFGSKGVKFMPYTTYLVEKGASHSFVAEAKPPTVTMPRIKALMTGSLPGF
VDVIRNLNSPALLEDSVIRQAKAAGKRIVFYGDETWVKLFPKHFVEYDGTTSFFVSDYTEVDNNV
TRHLDKVLKRGDWDILILHYLGLDHIGHISGPNSPLIGQKLSEMDSVLMKIHTSLQSKERETPLP
NLLVLCGDHGMSETGSHGASSTEEVNTPLILISSAFERKPGDIRHPKHVQ

Important features of the protein:

Signal peptide:

amino acids 1-34

Transmembrane domain:

amino acids 58-76

N-glycosylation sites.

amino acids 56-60, 194-198

N-myristoylation sites.

amino acids 6-12, 52-58, 100-106, 125-131, 233-239, 270-276, 275-281, 278-284

Amidation site.

amino acids 154-158

Cell attachment sequence.

amino acids 205-208

FIGURE 141

GGCACGAGGCAAGCCTTCCAGGTTATCGTGACGCACCTTGAAAGTCTGAGAGCTACTGCCCTACA
GAAAGTTACTAGTGCCCTAAAGCTGGCGCTGGCACTG<u>ATG</u>TTACTGCTGCTGTTGGAGTACAACT
TCCCTATAGAAAACAACTGCCAGCACCTTAAGACCACTCACACCTTCAGAGTGAAGAACTTAAAC
CCGAAGAAATTCAGCATTCATGACCAGGATCACAAAGTACTGGTCCTGGACTCTGGGAATCTCAT
AGCAGTTCCAGATAAAAACTACATACGCCCAGAGATCTTCTTTGCATTAGCCTCATCCTTGAGCT
CAGCCTCTGCGGAGAAAGGAAGTCCGATTCTCCTGGGGGTCTCTAAAGGGGAGTTTTGTCTCTAC
TGTGACAAGGATAAAGGACAAAGTCATCCATCCCTTCAGCTGAAGAAGGAGAAACTGATGAAGCT
GGCTGCCCAAAAGGAATCAGCACGCCGGCCCTTCATCTTTTATAGGGCTCAGGTGGGCTCCTGGA
ACATGCTGGAGTCGGCGGCTCACCCCGGATGGTTCATCTGCACCTCCTGCAATTGTAATGAGCCT
GTTGGGGTGACAGATAAATTTGAGAACAGGAAACACATTGAATTTTCATTTCAACCAGTTTGCAA
AGCTGAAATGAGCCCCAGTGAGGTCAGCGAT<u>TAG</u>GAAACTGCCCCATTGAACGCCTTCCTCGCTA
ATTTGAACTAATTGTATAAAAACACCAAACCTGCTCACT

FIGURE 142

MLLLLLEYNFPIENNCQHLKTTHTFRVKNLNPKKFSIHDQDHKVLVLDSGNLIAVPDKNYIRPEI
FFALASSLSSASAEKGSPILLGVSKGEFCLYCDKDKGQSHPSLQLKKEKLMKLAAQKESARRPFI
FYRAQVGSWNMLESAAHPGWFICTSCNCNEPVGVTDKFENRKHIEFSFQPVCKAEMSPSEVSD cAMP- and cGMP-dependent protein kinase phosphorylation site.

amino acids 33-36

N-myristoylation site.

amino acids 50-55, 87-92

Interleukin-1 amino acids 37-182

FIGURE 143

CTAGAGAGTATAGGGCAGAAGGATGGCAGATGAGTGACTCCACATCCAGAGCTGCCTCCCTTTAA
TCCAGGATCCTGTCCTTCCTGTCCTGTAGGAGTGCCTGTTGCCAGTGTGGGGTGAGACAAGTTTG
TCCCACAGGGCTGTCTGAGCAGATAAGATTAAGGGCTGGGTCTGTGCTCAATTAACTCCTGTGGG
CACGGGGGCTGGGAAGAGCAAAGTCAGCGGTGCCTACAGTCAGCACCATGCTGGGCCTGCCGTGG
AAGGGAGGTCTGTCCTGGGCGCTGCTGCTGCTTCTCTTAGGCTCCCAGATCCTGCTGATCTATGC
CTGGCATTTCCACGAGCAAAGGGACTGTGATGAACACAATGTCATGGCTCGTTACCTCCCTGCCA
CAGTGGAGTTTGCTGTCCACACATTCAACCAACAGAGCAAGGACTACTATGCCTACAGACTGGGG
CACATCTTGAATTCCTGGAAGGAGCAGGTGGAGTCCAAGACTGTATTCTCAATGGAGCTACTGCT
GGGGAGAACTAGGTGTGGGAAATTTGAAGACGACATTGACAACTGCCATTTCCAAGAAAGCACAG
AGCTGAACAATACTTTCACCTGCTTCTTCACCATCAGCACCAGGCCCTGGATGACTCAGTTCAGC
CTCCTGAACAAGACCTGCTTGGAGGGATTCCACTGAGTGAAACCCACTCACAGGCTTGTCCATGT
GCTGCTCCCACATTCCGTGGACATCAGCACTACTCTCCTGAGGACTCTTCAGTGGCTGAGCAGCT
TTGGACTTGTTTGTTATCCTATTTTGCATGTGTTTGAGATCTCAGATCAGTGTTTTAGAAAATCC
ACACATCTTGAGCCTAATCATGTAGTGTAGATCATTAAACATCAGCATTTTAAGAAAAAAAAAA
AAAAAAAAAAAAAAAAAAAAAAAAAAAAAAAAAAAAAAAAAAAA

FIGURE 144

MLGLPWKGGLSWALLLLLLGSQILLIYAWHFHEQRDCDEHNVMARYLPATVEFAVHTFNQQSKDY
YAYRLGHILNSWKEQVESKTVFSMELLLGRTRCGKFEDDIDNCHFQESTELNNTFTCFFTISTRP
WMTQFSLLNKTCLEGFH

Important features of the protein:

Signal peptide:

amino acids 1-25

N-glycosylation sites.

amino acids 117-121, 139-143

N-myristoylation site.

amino acids 9-15

FIGURE 145

CTGTGCAGCTCGAGGCTCCAGAGGCACACTCCAGAGAGAGCCAAGGTTCTGACGCG<u>ATG</u>AGGAAG
CACCTGAGCTGGTGGTGGCTGGCCACTGTCTGCATGCTGCTCTTCAGCCACCTCTCTGCGGTCCA
GACGAGGGGCATCAAGCACAGAATCAAGTGGAACCGGAAGGCCCTGCCCAGCACTGCCCAGATCA
CTGAGGCCCAGGTGGCTGAGAACCGCCCGGGAGCCTTCATCAAGCAAGGCCGCAAGCTCGACATT
GACTTCGGAGCCGAGGGCAACAGGTACTACGAGGCCAACTACTGGCAGTTCCCCGATGGCATCCA
CTACAACGGCTGCTCTGAGGCTAATGTGACCAAGGAGGCATTTGTCACCGGCTGCATCAATGCCA
CCCAGGCGGCGAACCAGGGGGAGTTCCAGAAGCCAGACAACAAGCTCCACCAGCAGGTGCTCTGG
CGGCTGGTCCAGGAGCTCTGCTCCCTCAAGCATTGCGAGTTTTGGTTGGAGAGGGGCGCAGGACT
TCGGGTCACCATGCACCAGCCAGTGCTCCTCTGCCTTCTGGCTTTGATCTGGCTCATGGTGAAA<u>T</u>
<u>AA</u>GCTTGCCAGGAGGCTGGCAGTACAGAGCGCAGCAGCGAGCAAATCCTGGCAAGTGACCCAGCT
CTTCTCCCCCAAACCCACGCGTGTTCTGAAGGTGCCCAGGAGCGGCGATGCACTCGCACTGCAAA
TGCCGCTCCCACGTATGCGCCCTGGTATGTGCCTGCGTTCTGATAGATGGGGGACTGTGGCTTCT
CCGTCACTCCATTCTCAGCCCCTAGCAGAGCGTCTGGCACACTAGATTAGTAGTAAATGCTTGAT
GAGAAGAACACATCAGGCACTGCGCCACCTGCTTCACAGTACTTCCCAACAACTCTTAGAGGTAG
GTGTATTCCCGTTTTACAGATAAGGAAACTGAGGCCCAGAGAGCTGAAGTACTGCACCCAGCATC
ACCAGCTAGAAAGTGGCAGAGCCAGGATTCAACCCTGGCTTGTCTAACCCCAGGTTTTCTGCTCT
GTCCAATTCCAGAGCTGTCTGGTGATCACTTTATGTCTCACAGGGACCCACATCCAAACATGTAT
CTCTAATGAAATTGTGAAAGCTCCATGTTTAGAAATAAATGAAAACACCTGA

FIGURE 146

```
MRKHLSWWWLATVCMLLFSHLSAVQTRGIKHRIKWNRKALPSTAQITEAQVAENRPGAFIKQGRK
LDIDFGAEGNRYYEANYWQFPDGIHYNGCSEANVTKEAFVTGCINATQAANQGEFQKPDNKLHQQ
VLWRLVQELCSLKHCEFWLERGAGLRVTMHQPVLLCLLALIWLMVK
```

Important features of the protein:

Signal peptide:

amino acids 1-26

Transmembrane domain:

amino acids 157-171

N-glycosylation sites.

amino acids 98-102, 110-114

Tyrosine kinase phosphorylation site.

amino acids 76-83

N-myristoylation sites.

amino acids 71-77, 88-94, 93-99, 107-113, 154-160

Amidation site.

amino acids 62-66

FIGURE 147

```
GCCTTGGCCTCCCAAAGGGCTGGGATTATAGGCGTGACCACCATGTCTGGTCCAGAGTCTCATTT
CCTGATGATTTATAGACTCAAAGAAAACTCATGTTCAGAAGCTCTCTTCTCTTCTGGCCTCCTCT
CTGTCTTCTTTCCCTCTTTCTTCTTATTTTAATTAGTAGCATCTACTCAGAGTCATGCAAGCTGG
AAATCTTTCATTTTGCTTGTCAGTGGGGTAGGTCACTGAGTCTTAGTTTTTATTTTTGAAATTT
CAACTTTCAGATTCAGGGGGTACATGTGAAGGTTTGTTTTATGAGTATATTGCATGATGCTGAGG
TTTGGGGT
```

FIGURE 148

MFRSSLLFWPPLCLLSLFLLILISSIYSESCKLEIFHFACQWGRSLSLSFYFLKFQLSDSGGTCE
GLFYEYIA

Important features of the protein:

Signal peptide:

amino acids 1-25

N-myristoylation site.

amino acids 62-68

FIGURE 149

GTCTCCGCGTCACAGGAACTTCAGCACCCACAGGGCGGACAGCGCTCCCCTCTACCTGGAGACTTGAC
TCCCGCGCGCCCCAACCCTGCTTATCCCTTGACCGTCGAGTGTCAGAGATCCTGCAGCCGCCCAGTCC
CGGCCCCTCTCCCGCCCCACACCCACCCTCCTGGCTCTTCCTGTTTTTACTCCTCCTTTTCATTCATA
ACAAAAGCTACAGCTCCAGGAGCCCAGCGCCGGCTGTGACCCAAGCCGAGCGTGGAAGA<u>ATG</u>GGGTT
CCTCGGGACCGGCACTTGGATTCTGGTGTTAGTGCTCCCGATTCAAGCTTTCCCCAAACCTGGAGGAA
GCCAAGACAAATCTCTACATAATAGAGAATTAAGTGCAGAAAGACCTTTGAATGAACAGATTGCTGAA
GCAGAAGAAGACAAGATTAAAAAAACATATCCTCCAGAAAACAAGCCAGGTCAGAGCAACTATTCTTT
TGTTGATAACTTGAACCTGCTAAAGGCAATAACAGAAAAGGAAAAAATTGAGAAAGAAAGACAATCTA
TAAGAAGCTCCCCACTTGATAATAAGTTGAATGTGGAAGATGTTGATTCAACCAAGAATCGAAAACTG
ATCGATGATTATGACTCTACTAAGAGTGGATTGGATCATAAATTTCAAGATGATCCAGATGGTCTTCA
TCAACTAGACGGGACTCCTTTAACCGCTGAAGACATTGTCCATAAAATCGCTGCCAGGATTTATGAAG
AAAATGACAGAGCCGTGTTTGACAAGATTGTTTCTAAACTACTTAATCTCGGCCTTATCACAGAAAGC
CAAGCACATACACTGGAAGATGAAGTAGCAGAGGTTTTACAAAAATTAATCTCAAAGGAAGCCAACAA
TTATGAGGAGGATCCCAATAAGCCCACAAGCTGGACTGAGAATCAGGCTGGAAAAATACCAGAGAAAG
TGACTCCAATGGCAGCAATTCAAGATGGTCTTGCTAAGGGAGAAAACGATGAAACAGTATCTAACACA
TTAACCTTGACAAATGGCTTGGAAAGGAGAACTAAAACCTACAGTGAAGACAACTTTGAGGAACTCCA
ATATTTCCCAAATTTCTATGCGCTACTGAAAAGTATTGATTCAGAAAAAGAAGCAAAAGAGAAAGAAA
CACTGATTACTATCATGAAAACACTGATTGACTTTGTGAAGATGATGGTGAAATATGGAACAATATCT
CCAGAAGAAGGTGTTTCCTACCTTGAAAACTTGGATGAAATGATTGCTCTTCAGACCAAAAACAAGCT
AGAAAAAAATGCTACTGACAATATAAGCAAGCTTTTCCCAGCACCATCAGAGAAGAGTCATGAAGAAA
CAGACAGTACCAAGGAAGAAGCAGCTAAGATGGAAAAGGAATATGGAAGCTTGAAGGATTCCACAAAA
GATGATAACTCCAACCCAGGAGGAAAGACAGATGAACCCAAAGGAAAAACAGAAGCCTATTTGGAAGC
CATCAGAAAAAATATTGAATGGTTGAAGAAACATGACAAAAAGGGAAATAAAGAAGATTATGACCTTT
CAAAGATGAGAGACTTCATCAATAAACAAGCTGATGCTTATGTGGAGAAAGGCATCCTTGACAAGGAA
GAAGCCGAGGCCATCAAGCGCATTTATAGCAGCCTG<u>TAA</u>AAATGGCAAAAGATCCAGGAGTCTTTCAA
CTGTTTCAGAAAACATAATATAGCTTAAAACACTTCTAATTCTGTGATTAAAATTTTTTGACCCAAGG
GTTATTAGAAAGTGCTGAATTTACAGTAGTTAACCTTTTACAAGTGGTTAAAACATAGCTTTCTTCCC
GTAAAAACTATCTGAAAGTAAAGTTGTATGTAAGCTGAAAAAAAAAAAAAAAAAAA

FIGURE 150

MGFLGTGTWILVLVLPIQAFPKPGGSQDKSLHNRELSAERPLNEQIAEAEEDKIKKTYPPENKPG
QSKYSFVDKLNLLKAITEKEKIEKERQSIRSSPLDKKLNVEDVDSTKNRKLIDDYDSTKSGLDHK
FQDDPDGLHQLDGTPLTAEDIVHKIAARIYEENDRAVFDKIVSKLLNLGLITESQAHTLEDEVAE
VLQKLISKEANNYEEDPNKPTSWTENQAGKIPEKVTPMAAIQDGLAKGENDETVSNTLTLTNGLE
RRTKTYSEDNFEELQYFPNFYALLKSIDSEKEAKEKETLITIMKTLIDFVKMMVKYGTISPEEGV
SYLENLDEMIALQTKNKLEKNATDNISKLFPAPSEKSHEETDSTKEEAAKMEKEYGSLKDSTKDD
NSNPGGKTDEPKGKTEAYLEAIRKNIEWLKKHDKKGNKEDYDLSKMRDFINKQADAYVEKGILDK
EEAEAIKRIYSSL

N-glycosylation sites:
amino acids 68-71, 346-349, 350-353

Casein kinase II phosphorylation site:
amino acids 70-73, 82-85, 97-100, 125-128, 147-150, 188-191, 217-220, 265-268, 289-292, 305-308, 320-323, 326-329, 362-365, 368-341, 369-372, 382-385, 386-389, 387-390

N-myristoylation sites:
amino acids 143-148, 239-244

FIGURE 151

CGGCTCGAGGCTCCCGCCAGGAGAAAGGAACATTCTGAGGGGAGTCTACACCCTGTGGAGCTCAA
GA<u>TGG</u>TCCTGAGTGGGGCGCTGTGCTTCCGAATGAAGGACTCGGCATTGAAGGTGCTTTATCTGC
ATAATAACCAGCTTCTAGCTGGAGGGCTGCATGCAGGGAAGGTCATTAAAGGTGAAGAGATCAGC
GTGGTCCCCAATCGGTGGCTGGATGCCAGCCTGTCCCCGTCATCCTGGGTGTCCAGGGTGGAAG
CCAGTGCCTGTCATGTGGGGTGGGGCAGGAGCCGACTCTAACACTAGAGCCAGTGAACATCATGG
AGCTCTATCTTGGTGCCAAGGAATCCAAGAGCTTCACCTTCTACCGGCGGGACATGGGGCTCACC
TCCAGCTTCGAGTCGGCTGCCTACCCGGGCTGGTTCCTGTGCACGGTGCCTGAAGCCGATCAGCC
TGTCAGACTCACCCAGCTTCCCGAGAATGGTGGCTGGAATGCCCCCATCACAGACTTCTACTTCC
AGCAGTGTGAC<u>TAG</u>GGCAACGTGCCCCCCAGAACTCCCTGGGCAGAGCCAGCTCGGGTGAGGGT
GAGTGGAGGAGACCCATGGCGGACAATCACTCTCTCTGCTCTCAGGACCCCCACGTCTGACTTAG
TGGGCACCTGACCACTTTGTCTTCTGGTTCCCAGTTTGGATAAATTCTGAGATTTGGAGCTCAGT
CCACGGTCCTCCCCACTGGATGGTGCTACTGCTGTGGAACCTTGTAAAAACCATGTGGGGTAAA
CTGGGAATAACATGAAAAGATTTCTGTGGGGGTGGGGTGGGGAGTGGTGGGAATCATTCCTGCT
TAATGGTAACTGACAAGTGTTACCCTGAGCCCCGCAGGCCAACCCATCCCCAGTTGAGCCTTATA
GGGTCAGTAGCTCTCCACATGAAGTCCTGTCACTCACCACTGTGCAGGAGAGGGAGCTGGTCATA
GAGTCAGGGATCTATGGCCCTTGGCCCAGCCCCACCCCCTTCCCTTTAATCCTGCCACTGTCATA
TGCTACCTTTCCTATCTCTTCCCTCATCATCTTGTTGTGGGCATGAGGAGGTGGTGATGTCAGAA
GAAATGGCTCGAGCTCAGAAGATAAAAGATAAGTAGGGTATGCTGATCCTCTTTTAAAAACCCAA
GATACAATCAAAATCCCAGATGCTGGTCTCTATTCCCATGAAAAAGTGCTCATGACATATTGAGA
AGACCTACTTACAAAGTGGCATATATTGCAATTTATTTTAATTAAAAGATACCTATTTATATATT
TCTTTATAGAAAAAGTCTGGAAGAGTTTACTTCAATTGTAGCAATGTCAGGGTGGTGGCAGTAT
AGGTGATTTTTCTTTTAATTCTGTTAATTTATCTGTATTTCCTAATTTTCTACAATGAAGATGA
ATTCCTTGTATAAAAATAAGAAAAGAAATTAATCTTGAGGTAAGCAGAGCAGACATCATCTCTGA
TTGTCCTCAGCCTCCACTTCCCCAGAGTAAATTCAAATTGAATCGAGCTCTGCTGCTCTGGTTGG
TTGTAGTAGTGATCAGGAAACAGATCTCAGCAAAGCCACTGAGGAGGAGGCTGTGCTGAGTTTGT
GTGGCTGGAATCTCTGGGTAAGGAACTTAAAGAACAAAAATCATCTGGTAATTCTTTCCTAGAAG
GATCACAGCCCCTGGGATTCCAAGGCATTGGATCCAGTCTCTAAGAAGGCTGCTGTACTGGTTGA
ATTGTGTCCCCTCAAATTCACATCCTTCTTGGAATCTCAGTCTGTGAGTTTATTTGGAGATAAG
GTCTCTGCAGATGTAGTTAGTTAAGACAAGGTCATGCTGGATGAAGGTAGACCTAAATTCAATAT
GACTGGTTTCCTTGTATGAAAGGAGAGGACACAGAGACAGAGGAGACGCGGGGAAGACTATGTA
AAGATGAAGGCAGAGATCGGAGTTTTGCAGCCACAAGCTAAGAAACACCAAGGATTGTGGCAACC
ATCAGAAGCTTGGAAGAGGCAAAGAAGAATTCTTCCCTAGAGGCTTTAGAGGGATAACGGCTCTG
CTGAAACCTTAATCTCAGACTTCCAGCCTCCTGAACGAAGAAAGAATAAATTTCGGCTGTTTTAA
GCCACCAAGGATAATTGGTTACAGCAGCTCTAGGAAACTAATACAGCTGCTAAAATGATCCCTGT
CTCCTCGTGTTTACATTCTGTGTGTGTCCCCTCCCACAATGTACCAAAGTTGTCTTTGTGACCAA
TAGAATATGGCAGAAGTGATGGCATGCCACTTCCAAGATTAGGTTATAAAAGACACTGCAGCTTC
TACTTGAGCCCTCTCTCTCTGCCACCCACCGCCCCAATCTATCTTGGCTCACTCGCTCTGGGGG
AAGCTAGCTGCCATGCTATGAGCAGGCCTATAAAGAGACTTACGTGGTAAAAAATGAAGTCTCCT
GCCCACAGCCACATTAGTGAACCTAGAAGCAGAGACTCTGTGAGATAATCGATGTTTGTTGTTTT
AAGTTGCTCAGTTTTGGTCTAACTTGTTATGCAGCAATAGATAAATAATATGCAGAGAAAGAG

FIGURE 152

MVLSGALCFRMKDSALKVLYLHNNQLLAGGLHAGKVIKGEEISVVPNRWLDASLSPVILGVQGGS
QCLSCGVGQEPTLTLEPVNIMELYLGAKESKSFTFYRRDMGLTSSFESAAYPGWFLCTVPEADQP
VRLTQLPENGGWNAPITDFYFQQCD

N-myristoylation sites.

amino acids 29-34, 30-35, 60-65, 63-68, 73-78, 91-96, 106-111

Interleukin-1 signature.

amino acids 111-131

Interleukin-1 proteins.

amino acids 8-29, 83-120, 95-134, 64-103

FIGURE 153

CTTCAGAACAGGTTCTCCTTCCCCAGTCACCAGTTGCTCGAGTTAGAATTGTCTGCAATGGCCGC
CCTGCAGAAATCTGTGAGCTCTTTCCTTATGGGGACCCTGGCCACCAGCTGCCTCCTTCTCTTGG
CCCTCTTGGTACAGGGAGGAGCAGCTGCGCCCATCAGCTCCCACTGCAGGCTTGACAAGTCCAAC
TTCCAGCAGCCCTATATCACCAACCGCACCTTCATGCTGGCTAAGGAGGCTAGCTTGGCTGATAA
CAACACAGACGTTCGTCTCATTGGGGAGAAACTGTTCCACGGAGTCAGTATGAGTGAGCGCTGCT
ATCTGATGAAGCAGGTGCTGAACTTCACCCTTGAAGAAGTGCTGTTCCCTCAATCTGATAGGTTC
CAGCCTTATATGCAGGAGGTGGTGCCCTTCCTGGCCAGGCTCAGCAACAGGCTAAGCACATGTCA
TATTGAAGGTGATGACCTGCATATCCAGAGGAATGTGCAAAAGCTGAAGGACACAGTGAAAAAGC
TTGGAGAGAGTGGAGAGATCAAAGCAATTGGAGAACTGGATTTGCTGTTTATGTCTCTGAGAAAT
GCCTGCATTTGACCAGAGCAAAGCTGAAAAATGAATAACTAACCCCCTTTCCTGCTAGAAATAA
CAATTAGATGCCCCAAAGCGATTTTTTTTAACCAAAAGGAAGATGGGAAGCCAAACTCCATCATG
ATGGGTGGATTCCAAATGAACCCCTGCGTTAGTTACAAAGGAAACCAATGCCACTTTTGTTTATA
AGACCAGAAGGTAGACTTTCTAAGCATAGATATTTATTGATAACATTTCATTGTAACTGGTGTTC
TATACACAGAAAACAATTTATTTTTAAATAATTGTCTTTTTCCATAAAAAAGATTACTTTCCAT
TCCTTTAGGGGAAAAAACCCCTAAATAGCTTCATGTTTCCATAATCAGTACTTTATATTTATAAA
TGTATTTATTATTATTATAAGACTGCATTTTATTTATATCATTTATTAATATGGATTTATTTAT
AGAAACATCATTCGATATTGCTACTTGAGTGTAAGGCTAATATTGATATTTATGACAATAATTAT
AGAGCTATAACATGTTTATTTGACCTCAATAAACACTTGGATATCCC

FIGURE 154

MAALQKSVSSFLMGTLATSCLLLLALLVQGGAAAPISSHCRLDKSNFQQPYITNRTFMLAKEASL
ADNNTDVRLIGEKLFHGVSMSERCYLMKQVLNFTLEEVLFPQSDRFQPYMQEVVPFLARLSNRLS
TCHIEGDDLHIQRNVQKLKDTVKKLGESGEIKAIGELDLLFMSLRNACI

Important features of the protein:

Signal peptide:

amino acids 1-33

N-glycosylation sites.

amino acids 54-58, 68-72, 97-101

N-myristoylation sites.

amino acids 14-20, 82-88

Prokaryotic membrane lipoprotein lipid attachment site.

amino acids 10-21

FIGURE 155

GGCTTGCTGAAAATAAAATCAGGACTCCTAACCTGCTCCAGTCAGCCTGCTTCCACGAGGCCTGT
CAGTCAGTGCCCGACTTGTGACTGAGTGTGCAGTGCCCAGCATGTACCAGGTCAGTGCAGAGGGC
TGCCTGAGGGCTGTGCTGAGAGGGAGAGGAGCAGAGATGCTGCTGAGGGTGGAGGGAGGCCAAGC
TGCCAGGTTTGGGGCTGGGGGCCAAGTGGAGTGAGAAACTGGGATCCCAGGGGGAGGGTGCAG**AT
G**AGGGAGCGACCCAGATTAGGTGAGGACAGTTCTCTCATTAGCCTTTTCCTACAGGTGGTTGCAT
TCTTGGCAATGGTCATGGGAACCCACACCTACAGCCACTGGCCCAGCTGCTGCCCCAGCAAAGGG
CAGGACACCTCTGAGGAGCTGCTGAGGTGGAGCACTGTGCCTGTGCCTCCCCTAGAGCCTGCTAG
GCCCAACCGCCACCCAGAGTCCTGTAGGGCCAGTGAAGATGGACCCCTCAACAGCAGGGCCATCT
CCCCCTGGAGATATGAGTTGGACAGAGACTTGAACCGGCTCCCCCAGGACCTGTACCACGCCCGT
TGCCTGTGCCCGCACTGCGTCAGCCTACAGACAGGCTCCCACATGGACCCCGGGGCAACTCGGA
GCTGCTCTACCACAACCAGACTGTCTTCTACAGGCGGCCATGCCATGGCGAGAAGGGCACCCACA
AGGGCTACTGCCTGGAGCGCAGGCTGTACCGTGTTTCCTTAGCTTGTGTGTGTGTGCGGCCCCGT
GTGATGGGCTAGCCGGACCTGCTGGAGGCTGGTCCCTTTTGGGAAACCTGGAGCCAGGTGTACA
ACCACTTGCCATGAAGGGCCAGGATGCCCAGATGCTTGGCCCCTGTGAAGTGCTGTCTGGAGCAG
CAGGATCCCGGGACAGGATGGGGGGCTTTGGGGAAAACCTGCACTTCTGCACATTTTGAAAAGAG
CAGCTGCTGCTTAGGGCCGCCGGAAGCTGGTGTCCTGTCATTTTCTCTCAGGAAAGGTTTTCAAA
GTTCTGCCCATTTCTGGAGGCCACCACTCCTGTCTCTTCCTCTTTTCCCATCCCCTGCTACCCTG
GCCCAGCACAGGCACTTTCTAGATATTTCCCCCTTGCTGGAGAAGAAAGAGCCCCTGGTTTTATT
TGTTTGTTTACTCATCACTCAGTGAGCATCTACTTTGGGTGCATTCTAGTGTAGTTACTAGTCTT
TTGACATGGATGATTCTGAGGAGGAAGCTGTTATTGAATGTATAGAGATTTATCCAAATAAATAT
CTTTATTTAAAAATGAAAAA

FIGURE 156

MRERPRLGEDSSLISLFLQVVAFLAMVMGTHTYSHWPSCCPSKGQDTSEELLRWSTVPVPPLEPA
RPNRHPESCRASEDGPLNSRAISPWRYELDRDLNRLPQDLYHARCLCPHCVSLQTGSHMDPRGNS
ELLYHNQTVFYRRPCHGEKGTHKGYCLERRLYRVSLACVCVRPRVMG

Important features of the protein:

Signal peptide:

amino acids 1-32

N-glycosylation site.

amino acids 136-140

Tyrosine kinase phosphorylation site.

amino acids 127-135

N-myristoylation sites.

amino acids 44-50, 150-156

FIGURE 157

```
CCGGCGATGTCGCTCGTGCTGCTAAGCCTGGCCGCGCTGTGCAGGAGCGCCGTACCCCGAGAGCC
GACCGTTCAATGTGGCTCTGAAACTGGGCATCTCCAGAGTGGATGCTACAACATGATCTAATCC
CCGGAGACTTGAGGGACCTCCGAGTAGAACCTGTTACAACTAGTGTTGCAACAGGGGACTATTCA
ATTTTGATGAATGTAAGCTGGGTACTCCGGGCAGATGCCAGCATCCGCTTGTTGAAGGCCACCAA
GATTTGTGTGACGGGCAAAAGCAACTTCCAGTCCTACAGCTGTGTGAGGTGCAATTACACAGAGG
CCTTCCAGACTCAGACCAGACCCTCTGGTGGTAAATGGACATTTTCCTACATCGGCTTCCCTGTA
GAGCTGAACACAGTCTATTTCATTGGGGCCCATAATATTCCTAATGCAAATATGAATGAAGATGG
CCCTTCCATGTCTGTGAATTTCACCTCACCAGGCTGCCTAGACCACATAATGAAATATAAAAAAA
AGTGTGTCAAGGCCGGAAGCCTGTGGGATCCGAACATCACTGCTTGTAAGAAGAATGAGGAGACA
GTAGAAGTGAACTTCACAACCACTCCCCTGGGAAACAGATACATGGCTCTTATCCAACACAGCAC
TATCATCGGGTTTTCTCAGGTGTTTGAGCCACACCAGAAGAAACAAACGCGAGCTTCAGTGGTGA
TTCCAGTGACTGGGGATAGTGAAGGTGCTACGGTGCAGCTGACTCCATATTTTCCTACTTGTGGC
AGCGACTGCATCCGACATAAAGGAACAGTTGTGCTCTGCCCACAAACAGGCGTCCCTTTCCCTCT
GGATAACAACAAAAGCAAGCCGGGAGGCTGGCTGCCTCTCCTCCTGCTGTCTCTGCTGGTGGCCA
CATGGGTGCTGGTGGCAGGGATCTATCTAATGTGGAGGCACGAAAGGATCAAGAAGACTTCCTTT
TCTACCACCACACTACTGCCCCCCATTAAGGTTCTTGTGGTTTACCCATCTGAAATATGTTTCCA
TCACACAATTTGTTACTTCACTGAATTTCTTCAAAACCATTGCAGAAGTGAGGTCATCCTTGAAA
AGTGGCAGAAAAAGAAAATAGCAGAGATGGGTCCAGTGCAGTGGCTTGCCACTCAAAAGAAGGCA
GCAGACAAAGTCGTCTTCCTTCTTTCCAATGACGTCAACAGTGTGTGCGATGGTACCTGTGGCAA
GAGCGAGGGCAGTCCCAGTGAGAACTCTCAAGACCTCTTCCCCCTTGCCTTTAACCTTTTCTGCA
GTGATCTAAGAAGCCAGATTCATCTGCACAAATACGTGGTGGTCTACTTTAGAGAGATTGATACA
AAAGACGATTACAATGCTCTCAGTGTCTGCCCCAAGTACCACCTCATGAAGGATGCCACTGCTTT
CTGTGCAGAACTTCTCCATGTCAAGCAGCAGGTGTCAGCAGGAAAAGATCACAAGCCTGCCACG
ATGGCTGCTGCTCCTTGTAG
```

FIGURE 158

MSLVLLSLAALCRSAVPREPTVQCGSETGPSPEWMLQHDLIPGDLRDLRVEPVTTSVATGDYSILMNVSWV
LRADASIRLLKATKICVTGKSNFQSYSCVRCNYTEAFQTQTRPSGGKWTFSYIGFPVELNTVYFIGAHNIP
NANMNEDGPSMSVNFTSPGCLDHIMKYKKKCVKAGSLWDPNITACKKNEETVEVNFTTTPLGNRYMALIQH
STIIGFSQVFEPHQKKQTRASVVIPVTGDSEGATVQLTPYFPICGSDCIRHKGTVVLCPQTGVPFPLDNNK
SKPGGWLPLLLLSLLVATWVLVAGIYLMWRHERIKKTSFSTTTLLPPIKVLVVYPSEICFHHTICYFTEFL
QNHCRSEVILEKWQKKKIAEMGPVQWLATQKKAADKVVFLLSNDVNSVCDGTCGKSEGSPSENSQDLFPLA
FNLFCSDLRSQIHLHKYVVVYFREIDTKDDYNALSVCPKYHLMKDATAFCAELLHVKQQVSAGKRSQACHD
GCCSL

Important features of the protein:
Signal peptide:
amino acids 1-14

Transmembrane domain:
amino acids 290-309

N-glycosylation sites.
amino acids 67 - 71, 103 - 107, 156 - 160, 183 - 187, 197 - 201 and 283 - 287 cAMP- and cGMP-dependent protein kinase phosphorylation sites.
amino acids 228 - 232 and 319 - 323

Casein kinase II phosphorylation sites.
amino acids 178 - 182, 402 - 406, 414 - 418 and 453 - 457

N-myristoylation site.
amino acids 116-122

Amidation site.
amino acids 488-452

FIGURE 159

AGCCACCAGCGCAAC<u>ATG</u>ACAGTGAAGACCCTGCATGGCCCAGCCATGGTCAAGTACTTGCTGCT
GTCGATATTGGGGCTTGCCTTTCTGAGTGAGGCGGCAGCTCGGAAAATCCCCAAAGTAGGACATA
CTTTTTTCCAAAAGCCTGAGAGTTGCCCGCCTGTGCCAGGAGGTAGTATGAAGCTTGACATTGGC
ATCATCAATGAAAACCAGCGCGTTTCCATGTCACGTAACATCGAGAGCCGCTCCACCTCCCCCTG
GAATTACACTGTCACTTGGGACCCCAACCGGTACCCTCGGAAGTTGTACAGGCCCAGTGTAGGA
ACTTGGGCTGCATCAATGCTCAAGGAAAGGAAGACATCTCCATGAATTCCGTTCCCATCCAGCAA
GAGACCCTGGTCGTCCGGAGGAAGCACCAAGGCTGCTCTGTTTCTTTCCAGTTGGAGAAGGTGCT
GGTGACTGTTGGCTGCACCTGCGTCACCCCTGTCATCCACCATGTGCAG<u>TAA</u>GAGGTGCATATCC
ACTCAGCTGAAGAAG

FIGURE 160

MTVKTLHGPAMVKYLLLSILGLAFLSEAAARKIPKVGHTFFQKPESCPPVPGGSMKLDIGIINEN
QRVSMSRNIESRSTSPWNYTVTWDPNRYPSEVVQAQCRNLGCINAQGKEDISMNSVPIQQETLVV
RRKHQGCSVSFQLEKVLVTVGCTCVTPVIHHVQ

Signal sequence:

amino acids 1-30

N-glycosylation site.

amino acids 83-87

N-myristoylation sites.

amino acids 106-111, 136-141

FIGURE 161

```
ACACTGGCCAAACAAAAACGAAAGCACTCCGTGCTGGAAGTAGGAGGAGAGTCAGGACTCCCAGG
ACAGAGAGTGCACAAACTACCCAGCACAGCCCCCTCCGCCCCCTCTGGAGGCTGAAGAGGGATTC
CAGCCCCTGCCACCCACAGACACGGGCTGACTGGGGTGTCTGCCCCCCTTGGGGGGGGGCAGCAC
AGGGCCTCAGGCCTGGGTGCCACCTGGCACCTAGAAGATGCCTGTGCCCTGGTTCTTGCTGTCCT
TGGCACTGGGCCGAAGCCCAGTGGTCCTTTCTCTGGAGAGGCTTGTGGGGCCTCAGGACGCTACC
CACTGCTCTCCGGGCCTCTCCTGCCGCCTCTGGGACAGTGACATACTCTGCCTGCCTGGGGACAT
CGTGCCTGCTCCGGGCCCCGTGCTGGCGCCTACGCACCTGCAGACAGAGCTGGTGCTGAGGTGCC
AGAAGGAGACCGACTGTGACCTCTGTCTGCGTGTGGCTGTCCACTTGGCCGTGCATGGGCACTGG
GAAGAGCCTGAAGATGAGGAAAAGTTTGGAGGAGCAGCTGACTCAGGGGTGGAGGAGCCTAGGAA
TGCCTCTCTCCAGGCCCAAGTCGTGCTCTCCTTCCAGGCCTACCCTACTGCCCGCTGCGTCCTGC
TGGAGGTGCAAGTGCCTGCTGCCCTTGTGCAGTTTGGTCAGTCTGTGGGCTCTGTGGTATATGAC
TGCTTCGAGGCTGCCCTAGGGAGTGAGGTACGAATCTGGTCCTATACTCAGCCCAGGTACGAGAA
GGAACTCAACCACACACAGCAGCTGCCTGCCCTGCCCTGGCTCAACGTGTCAGCAGATGGTGACA
ACGTGCATCTGGTTCTGAATGTCTCTGAGGAGCAGCACTTCGGCCTCTCCCTGTACTGGAATCAG
GTCCAGGGCCCCCCAAAACCCCGGTGGCACAAAAACCTGACTGGACCGCAGATCATTACCTTGAA
CCACACAGACCTGGTTCCCTGCCTCTGTATTCAGGTGTGGCCTCTGGAACCTGACTCCGTTAGGA
CGAACATCTGCCCCTTCAGGGAGGACCCCCGCGCACACCAGAACCTCTGGCAAGCCGCCCGACTG
CGACTGCTGACCCTGCAGAGCTGGCTGCTGGACGCACCGTGCTCGCTGCCCGCAGAAGCGGCACT
GTGCTGGCGGGCTCCGGGTGGGGACCCCTGCCAGCCACTGGTCCCACCGCTTTCCTGGGAGAACG
TCACTGTGGACAAGGTTCTCGAGTTCCCATTGCTGAAAGGCCACCCTAACCTCTGTGTTCAGGTG
AACAGCTCGGAGAAGCTGCAGCTGCAGGAGTGCTTGTGGGCTGACTCCCTGGGGCCTCTCAAAGA
CGATGTGCTACTGTTGGAGACACGAGGCCCCCAGGACAACAGATCCCTCTGTGCCTTGGAACCCA
GTGGCTGTACTTCACTACCCAGCAAAGCCTCCACGAGGGCAGCTCGCCTTGGAGAGTACTTACTA
CAAGACCTGCAGTCAGGCCAGTGTCTGCAGCTATGGGACGATGACTTGGGAGCGCTATGGGCCTG
CCCCATGGACAAATACATCCACAAGCGCTGGGCCCTCGTGTGGCTGGCCTGCCTACTCTTTGCCG
CTGCGCTTTCCCTCATCCTCCTTCTCAAAAAGGATCACGCGAAAGGGTGGCTGAGGCTCTTGAAA
CAGGACGTCCGCTCGGGGCGGCCGCCAGGGGCCGCGCGGCTCTGCTCCTCTACTCAGCCGATGA
CTCGGGTTTCGAGCGCCTGGTGGGCGCCCTGGCGTCGGCCCTGTGCCAGCTGCCGCTGCGCGTGG
CCGTAGACCTGTGGAGCCGTCGTGAACTGAGCGCGCAGGGCCCGTGGCTTGGTTTCACGCGCAG
CGGCGCCAGACCCTGCAGGAGGGCGGCGTGGTGGTCTTGCTCTTCTCTCCCGGTGCGGTGGCGCT
GTGCAGCGAGTGGCTACAGGATGGGGTGTCCGGGCCCGGGGCGCACGGCCCGCACGACGCCTTCC
GCGCCTCGCTCAGCTGCGTGCTGCCCGACTTCTTGCAGGGCCGGGCGCCCGGCAGCTACGTGGGG
GCCTGCTTCGACAGGCTGCTCCACCCGGACGCCGTACCCGCCCTTTTCCGCACCGTGCCCGTCTT
CACACTGCCCTCCCAACTGCCAGACTTCCTGGGGGCCCTGCAGCAGCCTCGCGCCCCGCGTTCCG
GCGGCTCCAAGAGAGAGCGGAGCAAGTGTCCCGGGCCCTTCAGCCAGCCCTGGATAGCTACTTC
CATCCCCGGGGACTCCCGCGCCGGGACGCGGGGTGGGACCAGGGCGGGACCTGGGCGGGGA
CGGGACTTAAATAAAGGCAGACGCTGTTTTCTAAAAAAA
```

FIGURE 162

MPVPWFLLSLALGRSPVVLSLERLVGPQDATHCSPGLSCRLWDSDILCLPGDIVPAPGPVLAPTHLQTELV
LRCQKETDCDLCLRVAVHLAVHGHWEEPEDEEKFGGAADSGVEEPRNASLQAQVVLSFQAYPTARCVLLEV
QVPAALVQFGQSVGSVVYDCFEAALGSEVRIWSYTQPRYEKELNHTQQLPALPWLNVSADGDNVHLVLNVS
EEQHFGLSLYWNQVQGPPKPRWHKNLTGPQIITLNHTDLVPCLCIQVWPLEPDSVRTNICPFREDPRAHQN
LWQAARLRLLTLQSWLLDAPCSLPAEAALCWRAPGGDPCQPLVPPLSWENVTVDKVLEFPLLKGHPNLCVQ
VNSSEKLQLQECLWADSLGPLKDDVLLLETRGPQDNRSLCALEPSGCTSLPSKASTRAARLGEYLLQDLQS
GQCLQLWDDDLGALWACPMDKYIHKRWALVWLACLLFAAALSLILLLKKDHAKGWLRLLKQDVRSGAAARG
RAALLLYSADDSGFERLVGALASALCQLPLRVAVDLWSRRELSAQGPVAWFHAQRRQTLQEGGVVVLLFSP
GAVALCSEWLQDGVSGPGAHGPHDAFRASLSCVLPDFLQGRAPGSYVGACFDRLLHPDAVPALFRTVPVFT
LPSQLPDFLGALQQPRAPRSGRLQERAEQVSRALQPALDSYFHPPGTPAPGRGVGPGAGPGAGDGT

Signal sequence:

amino acids 1-20

Transmembrane domain amino acids 453-475

N-glycosylation sites.

amino acids 118-121, 186-189, 198-201, 211-214, 238-241, 248-251, 334-337, 357-360, 391-394

Glycosaminoglycan attachment site.

amino acids 583-586 cAMP- and cGMP-dependent protein kinase phosphorylation site.

amino acids 552-555

N-myristoylation sites.

amino acids 107-112, 152-157, 319-324, 438-443, 516-521, 612-617, 692-697, 696-701, 700-705

FIGURE 163

```
GGGAGGGCTCTGTGCCAGCCCCGATGAGGACGCTGCTGACCATCTTGACTGTGGGATCCCTGGCT
GCTCACGCCCTGAGGACCCCTCGGATCTGCTCCAGCACGTGAAATTCCAGTCCAGCAACTTTGA
AAACATCCTGACGTGGGACAGCGGGCCAGAGGGCACCCCAGACACGGTCTACAGCATCGAGTATA
AGACGTACGGAGAGAGGGACTGGGTGGCAAAGAAGGGCTGTCAGCGGATCACCCGGAAGTCCTGC
AACCTGACGGTGGAGACGGGCAACCTCACGGAGCTCTACTATGCCAGGGTCACCGCT
GTCAGTGCGGGAGGCCGGTCAGCCACCAAGATGACTGACAGGTTCAGCTCTCTGCAGCACACTAC
CCTCAAGCCACCTGATGTGACCTGTATCTCCAAAGTGAGATCGATTCAGATGATTGTTCATCCTA
CCCCCACGCCAATCCGTGCAGGCGATGGCCACCGGCTAACCCTGGAAGACATCTTCCATGACCTG
TTCTACCACTTAGAGCTCCAGGTCAACCGCACCTACCAAATGCACCTTGGAGGGAAGCAGAGAGA
ATATGAGTTCTTCGGCCTGACCCCTGACACAGAGTTCCTTGGCACCATCATGATTTGCGTTCCCA
CCTGGGCCAAGGAGAGTGCCCCCTACATGTGCCGAGTGAAGACACTGCCAGACCGGACATGGACC
TACTCCTTCTCCGGAGCCTTCCTGTTCTCCATGGGCTTCCTCGTCGCAGTACTCTGCTACCTGAG
CTACAGATATGTCACCAAGCCGCCTGCACCTCCCAACTCCCTGAACGTCCAGCGAGTCCTGACTT
TCCAGCCGCTGCGCTTCATCCAGGAGCACGTCCTGATCCCTGTCTTTGACCTCAGCGGCCCCAGC
AGTCTGGCCCAGCCTGTCCAGTACTCCCAGATCAGGGTGTCTGGACCCAGGGAGCCCGCAGGAGC
TCCACAGCGGCATAGCCTGTCCGAGATCACCTACTTAGGGCAGCCAGACATCTCCATCCTCCAGC
CCTCCAACGTGCCACCTCCCCAGATCCTCTCCCCACTGTCCTATGCCCCAAACGCTGCCCCTGAG
GTCGGGCCCCCATCCTATGCACCTCAGGTGACCCCCGAAGCTCAATTCCCATTCTACGCCCCACA
GGCCATCTCTAAGGTCCAGCCTTCCTCCTATGCCCCTCAAGCCACTCCGGACAGCTGGCCTCCCT
CCTATGGGGTATGCATGGAAGGTTCTGGCAAAGACTCCCCCACTGGGACACTTTCTAGTCCTAAA
CACCTTAGGCCTAAAGGTCAGCTTCAGAAAGAGCCACCAGCTGGAAGCTGCATGTTAGGTGGCCT
TTCTCTGCAGGAGGTGACCTCCTTGGCTATGGAGGAATCCCAAGAAGCAAAATCATTGCACCAGC
CCCTGGGGATTTGCACAGACAGAACATCTGACCCAAATGTGCTACACAGTGGGGAGGAAGGGACA
CCACAGTACCTAAAGGGCCAGCTCCCCCTCCTCTCCTCAGTCCAGATCGAGGGCCACCCCATGTC
CCTCCCTTTGCAACCTCCTTCCGGTCCATGTTCCCCCTCGGACCAAGGTCCAAGTCCCTGGGGCC
TGCTGGAGTCCCTTGTGTGTCCCAAGGATGAAGCCAAGAGCCCAGCCCTGAGACCTCAGACCTG
GAGCAGCCCACAGAACTGGATTCTCTTTTCAGAGGCCTGGCCCTGACTGTGCAGTGGGAGTCCTG
AGGGGAATGGGAAAGGCTTGGTGCTTCCTCCCTGTCCCTACCCAGTGTCACATCCTTGGCTGTCA
ATCCCATGCCTGCCCATGCCACACACTCTGCGATCTGGCCTCAGACGGGTGCCCTTGAGAGAAGC
AGAGGGAGTGGCATGCAGGGCCCCTGCCATGGGTGCGCTCCTCACCGGAACAAAGCAGCATGATA
AGGACTGCAGCGGGGGAGCTCTGGGGAGCAGCTTGTGTAGACAAGCGCGTGCTCGCTGAGCCCTG
CAAGGCAGAAATGACAGTGCAAGGAGGAAATGCAGGGAAACTCCCGAGGTCCAGAGCCCCACCTC
CTAACACCATGGATTCAAAGTGCTCAGGGAATTTGCCTCTCCTTGCCCCATTCCTGGCCAGTTTC
ACAATCTAGCTCGACAGAGCATGAGGCCCCTGCCTCTTCTGTCATTGTTCAAAGGTGGGAAGAGA
GCCTGGAAAAGAACCAGGCCTGGAAAAGAACCAGAAGGAGGCTGGGCAGAACCAGAACAACCTGC
ACTTCTGCCAAGGCCAGGGCCAGCAGGACGGCAGGACTCTAGGGAGGGGTGTGGCCTGCAGCTCA
TTCCCAGCCAGGGCAACTGCCTGACGTTGCACGATTTCAGCTTCATTCCTCTGATAGAACAAAGC
GAAATGCAGGTCCACCAGGGAGGGAGACACACAAGCCTTTTCTGCAGGCAGGAGTTTCAGACCCT
ATCCTGAGAATGGGGTTTGAAAGGAAGGTGAGGGCTGTGGCCCCTGGACGGGTACAATAACACAC
TGTACTGATGTCACAACTTTGCAAGCTCTGCCTTGGGTTCAGCCCATCTGGGCTCAAATTCCAGC
CTCACCACTCACAAGCTGTGTGACTTCAAACAAATGAAATCAGTGCCCAGAACCTCGGTTTCCTC
ATCTGTAATGTGGGGATCATAACACCTACCTCATGGAGTTGTGGTGAAGATGAAATGAAGTCATG
TCTTTAAAGTGCTTAATAGTGCCTGGTACATGGGCAGTGCCCAATAAACGGTAGCTATTTAAAAA
AAAAAAAA
```

FIGURE 164

MRTLLTILTVGSLAAHAPEDPSDLLQHVKFQSSNFENILTWDSGPEGTPDTVYSIEYKTYGERDW
VAKKGCQRITRKSCNLTVETGNLTELYYARVTAVSAGGRSATKMTDRFSSLQHTTLKPPDVTCIS
KVRSIQMIVHPTPTPIRAGDGHRLTLEDIFHDLFYHLELQVNRTYQMHLGGKQREYEFFGLTPDT
EFLGTIMICVPTWAKESAPYMCRVKTLPDRTWTYSFSGAFLFSMGFLVAVLCYLSYRYVTKPPAP
PNSLNVQRVLTFQPLRFIQEHVLIPVFDLSGPSSLAQPVQYSQIRVSGPREPAGAPQRHSLSEIT
YLGQPDISILQPSNVPPPQILSPLSYAPNAAPEVGPPSYAPQVTPEAQFPFYAPQAISKVQPSSY
APQATPDSWPPSYGVCMEGSGKDSPTGTLSSPKHLRPKGQLQKEPPAGSCMLGGLSLQEVTSLAM
EESQEAKSLHQPLGICTDRTSDPNVLHSGEEGTPQYLKGQLPLLSSVQIEGHPMSLPLQPPSGPC
SPSDQGPSPWGLLESLVCPKDEAKSPAPETSDLEQPTELDSLFRGLALTVQWES

Signal sequence.
amino acids 1-17

Transmembrane domain.
amino acids 233-250

N-glycosylation sites.
amino acids 80-83, 87-90, 172-175

N-myristoylation sites.
amino acids 11-16, 47-52, 102-107, 531-536, 565-570

FIGURE 165

TGGCCTACTGGAAAAAAAAAAAAAAAAAAAAAAGTCACCCGGGCCCGCGGTGGCCACAAC<u>ATGG</u>
CTGCGGCGCCGGGGCTGCTCTTCTGGCTGTTCGTGCTGGGGGCGCTCTGGTGGGTCCCGGGCCAG
TCGGATCTCAGCCACGGACGGCGTTTCTCGGACCTCAAAGTGTGCGGGGACGAAGAGTGCAGCAT
GTTAATGTACCGTGGGAAAGCTCTTGAAGACTTCACGGGCCCTGATTGTCGTTTTGTGAATTTTA
AAAAAGGTGACGATGTATATGTCTACTACAAACTGGCAGGGGGATCCCTTGAACTTTGGGCTGGA
AGTGTTGAACACAGTTTTGGATATTTTCCAAAAGATTTGATCAAGGTACTTCATAAATACACGGA
AGAAGAGCTACATATTCCAGCAGATGAGACAGACTTTGTCTGCTTTGAAGGAGGAAGAGATGATT
TTAATAGTTATAATGTAGAAGAGCTTTTAGGATCTTTGGAACTGGAGGACTCTGTACCTGAAGAG
TCGAAGAAAGCTGAAGAAGTTTCTCAGCACAGAGAGAAATCTCCTGAGGAGTCTCGGGGGCGTGA
ACTTGACCCTGTGCCTGAGCCCGAGGCATTCAGAGCTGATTCAGAGGATGGAGAAGGTGCTTTCT
CAGAGAGCACCGAGGGGCTGCAGGGACAGCCCTCAGCTCAGGAGAGCCACCCTCACACCAGCGGT
CCTGCGGCTAACGCTCAGGGAGTGCAGTCTTCGTTGGACACTTTTGAAGAAATTCTGCACGATAA
ATTGAAAGTGCCGGGAAGCGAAAGCAGAACTGGCAATAGTTCTCCTGCCTCGGTGGAGCGGGAGA
AGACAGATGCTTACAAAGTCCTGAAAACAGAAATGAGTCAGAGAGGAAGTGGACAGTGCGTTATT
CATTACAGCAAAGGATTTCGTTGGCATCAAAATCTAAGTTTGTTTTACAAAGATTGTTTT<u>TAGTA</u>
CTAAGCTGCCTTGGCAGTTTGCATTTTTGAGCCAAACAAAAATATATTATTTTCCCTTCTAAGTA
AAAAAAAAAAAAAAAAAA

FIGURE 166

MAAAPGLLFWLFVLGALWWVPGQSDLSHGRRFSDLKVCGDEECSMLMYRGKALEDFTGPDCRFVN
FKKGDDVYVYYKLAGGSLELWAGSVEHSFGYFPKDLIKVLHKYTEEELHIPADETDFVCFEGGRD
DFNSYNVEELLGSLELEDSVPEESKKAEEVSQHREKSPEESRGRELDPVPEPEAFRADSEDGEGA
FSESTEGLQGQPSAQESHPHTSGPAANAQGVQSSLDTFEEILHDKLKVPGSESRTGNSSPASVER
EKTDAYKVLKTEMSQRGSGQCVIHYSKGFRWHQNLSLFYKDCF

Important features of the protein:

Signal peptide:
amino acids 1-22

N-glycosylation site.
amino acids 294-298 cAMP- and cGMP-dependent protein kinase phosphorylation site.
amino acids 30-34

Tyrosine kinase phosphorylation site.
amino acids 67-76

N-myristoylation sites.
amino acids 205-211, 225-231, 277-283

Amidation site.
amino acids 28-32

FIGURE 167

```
CCAGGACCAGGGCGCACCGGCTCAGCCTCTCACTTGTCAGAGGCCGGGGAAGAGAAGCAAAGCGC
AACGGTGTGGTCCAAGCCGGGGCTTCTGCTTCGCCTCTAGGACATACACGGGACCCCCTAACTTC
AGTCCCCCAAACGCGCACCCTCGAAGTCTTGAACTCCAGCCCCGCACATCCACGCGCGGCACAGG
CGCGGCAGGCGGCAGGTCCCGGCCGAAGGCGATGCGCGCAGGGGTCGGGCAGCTGGGCTCGGGC
GGCGGGAGTAGGGCCCGGCAGGGAGGCAGGGAGGCTGCATATTCAGAGTCGCGGGCTGCGCCCTG
GGCAGAGGCCGCCCTCGCTCCACGCAACACCTGCTGCTGCCACCGCGCCGCGATGAGCCGCGTGG
TCTCGCTGCTGCTGGGCGCCGCGCTGCTCTGCGGCCACGGAGCCTTCTGCCGCCGCGTGGTCAGC
GGCCAAAAGGTGTGTTTTGCTGACTTCAAGCATCCCTGCTACAAAATGGCCTACTTCCATGAACT
GTCCAGCCGAGTGAGCTTTCAGGAGGCACGCCTGGCTTGTGAGAGTGAGGGAGGAGTCCTCCTCA
GCCTTGAGAATGAAGCAGAACAGAAGTTAATAGAGAGCATGTTGCAAAACCTGACAAAACCCGGG
ACAGGGATTTCTGATGGTGATTTCTGGATAGGGCTTTGGAGGAATGGAGATGGGCAAACATCTGG
TGCCTGCCCAGATCTCTACCAGTGGTCTGATGGAAGCAATTCCCAGTACCGAAACTGGTACACAG
ATGAACCTTCCTGCGGAAGTGAAAAGTGTGTTGTGATGTATCACCAACCAACTGCCAATCCTGGC
CTTGGGGGTCCCTACCTTTACCAGTGGAATGATGACAGGTGTAACATGAAGCACAATTATATTTG
CAAGTATGAACCAGAGATTAATCCAACAGCCCTGTAGAAAAGCCTTATCTTACAAATCAACCAG
GAGACACCCATCAGAATGTGGTTGTTACTGAAGCAGGTATAATTCCCAATCTAATTTATGTTGTT
ATACCAACAATACCCCTGCTCTTACTGATACTGGTTGCTTTTGGAACCTGTTGTTTCCAGATGCT
GCATAAAAGTAAAGGAAGAACAAAAACTAGTCCAAACCAGTCTACACTGTGGATTTCAAAGAGTA
CCAGAAAAGAAAGTGGCATGGAAGTATAATAACTCATTGACTTGGTTCCAGAATTTTGTAATTCT
GGATCTGTATAAGGAATGGCATCAGAACAATAGCTTGGAATGGCTTGAAATCACAAAGGATCTGC
AAGATGAACTGTAAGCTCCCCCTTGAGGCAAATATTAAAGTAATTTTTATATGTCTATTATTTCA
TTTAAAGAATATGCTGTGCTAATAATGGAGTGAGACATGCTTATTTTGCTAAAGGATGCACCCAA
ACTTCAAACTTCAAGCAAATGAAATGGACAATGCAGATAAAGTTGTTATCAACACGTCGGGAGTA
TGTGTGTTAGAAGCAATTCCTTTTATTTCTTTCACCTTTCATAAGTTGTTATCTAGTCAATGTAA
TGTATATTGTATTGAAATTTACAGTGTGCAAAAGTATTTTACCTTTGCATAAGTGTTTGATAAAA
ATGAACTGTTCTAATATTTATTTTATGGCATCTCATTTTTCAATACATGCTCTTTTGATTAAAG
AAACTTATTACTGTTGTCAACTGAATTCACACACACACAAATATAGTACCATAGAAAAAGTTTGT
TTTCTCGAAATAATTCATCTTTCAGCTTCTCTGCTTTTGGTCAATGTCTAGGAAATCTCTTCAGA
AATAAGAAGCTATTTCATTAAGTGTGATATAAACCTCCTCAAACATTTTACTTAGAGGCAAGGAT
TGTCTAATTTCAATTGTGCAAGACATGTGCCTTATAATTATTTTTAGCTTAAAATTAAACAGATT
TTGTAATAATGTAACTTTGTTAATAGGTGCATAAACACTAATGCAGTCAATTTGAACAAAAGAAG
TGACATACACAATATAAATCATATGTCTTCACACGTTGCCTATATAATGAGAAGCAGCTCTCTGA
GGGTTCTGAAATCAATGTGGTCCCTCTCTTGCCCACTAAACAAAGATGGTTGTTCGGGGTTTGGG
ATTGACACTGGAGGCAGATAGTTGCAAAGTTAGTCTAAGGTTTCCCTAGCTGTATTTAGCCTCTG
ACTATATTAGTATACAAAGAGGTCATGTGGTTGAGACCAGGTGAATAGTCACTATCAGTGTGGAG
ACAAGCACAGCACACAGACATTTTAGGAAGGAAAGGAACTACGAAATCGTGTGAAAATGGGTTGG
AACCCATCAGTGATCGCATATTCATTGATGAGGGTTTGCTTGAGATAGAAAATGGTGGCTCCTTT
CTGTCTTATCTCCTAGTTTCTTCAATGCTTACGCCTTGTTCTTCTCAAGAGAAAGTTGTAACTCT
CTGGTCTTCATATGTCCCTGTGCTCCTTTTAACCAAATAAAGAGTTCTTGTTTCTGGGGAAAAA
AAAAAAAAAAAAAAAAAAAAAAAAAAAAAAAA
```

FIGURE 168

MSRVVSLLLGAALLCGHGAFCRRVVSGQKVCFADFKHPCYKMAYFHELSSRVSFQEARLACESE
GGVLLSLENEAEQKLIESMLQNLTKPGTGISDGDFWIGLWRNGDGQTSGACPDLYQWSDGSNSQ
YRNWYTDEPSCGSEKCVVMYHQPTANPGLGGPYLYQWNDDRCNMKHNYICKYEPEINPTAPVEK
PYLTNQPGDTHQNVVVTEAGIIPNLIYVVIPTIPLLLLILVAFGTCCFQMLHKSKGRTKTSPNQ
STLWISKSTRKESGMEV

Important features of the protein:

Signal peptide:

amino acids 1-21

Transmembrane domain:

amino acids 214-235

N-glycosylation sites.

amino acids 86-89, 255-258 cAMP- and cGMP-dependent protein kinase phosphorylation site.

amino acids 266-269

N-myristoylation sites.

amino acids 27-32, 66-71, 91-96, 93-98, 102-107, 109-114, 140-145, 212-217

SEQUENCE LISTING

<160> NUMBER OF SEQ ID NOS: 170

<210> SEQ ID NO 1
<211> LENGTH: 1173
<212> TYPE: DNA
<213> ORGANISM: Homo Sapien

<400> SEQUENCE: 1

| | | | | | |
|---|---|---|---|---|---|
| ggggcttcgg | cgccagcggc | cagcgctagt | cggtctggta | aggatttaca | 50 |
| aaaggtgcag | gtatgagcag | gtctgaagac | taacattttg | tgaagttgta | 100 |
| aaacagaaaa | cctgttagaa | atgtggtggt | ttcagcaagg | cctcagtttc | 150 |
| cttccttcag | cccttgtaat | ttggacatct | gctgctttca | tattttcata | 200 |
| cattactgca | gtaacactcc | accatataga | cccggcttta | ccttatatca | 250 |
| gtgacactgg | tacagtagct | ccagaaaaat | gcttatttgg | ggcaatgcta | 300 |
| aatattgcgg | cagttttatg | cattgctacc | atttatgttc | gttataagca | 350 |
| agttcatgct | ctgagtcctg | aagagaacgt | tatcatcaaa | ttaaacaagg | 400 |
| ctggccttgt | acttggaata | ctgagttgtt | taggactttc | tattgtggca | 450 |
| aacttccaga | aaacaaccct | ttttgctgca | catgtaagtg | gagctgtgct | 500 |
| tacctttggt | atgggctcat | tatatatgtt | tgttcagacc | atcctttcct | 550 |
| accaaatgca | gcccaaaatc | catggcaaac | aagtcttctg | gatcagactg | 600 |
| ttgttggtta | tctggtgtgg | agtaagtgca | cttagcatgc | tgacttgctc | 650 |
| atcagttttg | cacagtggca | attttgggac | tgatttagaa | cagaaactcc | 700 |
| attggaaccc | cgaggacaaa | ggttatgtgc | ttcacatgat | cactactgca | 750 |
| gcagaatggt | ctatgtcatt | ttccttcttt | ggttttttcc | tgacttacat | 800 |
| tcgtgatttt | cagaaaattt | ctttacgggt | ggaagccaat | ttacatggat | 850 |
| taaccctcta | tgacactgca | ccttgcccta | ttaacaatga | acgaacacgg | 900 |
| ctactttcca | gagatatttg | atgaaaggat | aaaatatttc | tgtaatgatt | 950 |
| atgattctca | gggattgggg | aaaggttcac | agaagttgct | tattcttctc | 1000 |
| tgaaatttc | aaccacttaa | tcaaggctga | cagtaacact | gatgaatgct | 1050 |
| gataatcagg | aaacatgaaa | gaagccattt | gatagattat | tctaaaggat | 1100 |
| atcatcaaga | agactattaa | aaacacctat | gcctatactt | ttttatctca | 1150 |
| gaaaataaag | tcaaaagact | atg | | | 1173 |

<210> SEQ ID NO 2
<211> LENGTH: 266
<212> TYPE: PRT
<213> ORGANISM: Homo Sapien

<400> SEQUENCE: 2

Met Trp Trp Phe Gln Gln Gly Leu Ser Phe Leu Pro Ser Ala Leu
 1               5                   10                  15

Val Ile Trp Thr Ser Ala Ala Phe Ile Phe Ser Tyr Ile Thr Ala
                20                  25                  30

Val Thr Leu His His Ile Asp Pro Ala Leu Pro Tyr Ile Ser Asp
                35                  40                  45

Thr Gly Thr Val Ala Pro Glu Lys Cys Leu Phe Gly Ala Met Leu
                50                  55                  60

```
Asn Ile Ala Ala Val Leu Cys Ile Ala Thr Ile Tyr Val Arg Tyr
             65                  70                  75
Lys Gln Val His Ala Leu Ser Pro Glu Glu Asn Val Ile Ile Lys
         80                  85                  90
Leu Asn Lys Ala Gly Leu Val Leu Gly Ile Leu Ser Cys Leu Gly
         95                 100                 105
Leu Ser Ile Val Ala Asn Phe Gln Lys Thr Thr Leu Phe Ala Ala
            110                 115                 120
His Val Ser Gly Ala Val Leu Thr Phe Gly Met Gly Ser Leu Tyr
            125                 130                 135
Met Phe Val Gln Thr Ile Leu Ser Tyr Gln Met Gln Pro Lys Ile
            140                 145                 150
His Gly Lys Gln Val Phe Trp Ile Arg Leu Leu Val Ile Trp
            155                 160                 165
Cys Gly Val Ser Ala Leu Ser Met Leu Thr Cys Ser Ser Val Leu
            170                 175                 180
His Ser Gly Asn Phe Gly Thr Asp Leu Glu Gln Lys Leu His Trp
            185                 190                 195
Asn Pro Glu Asp Lys Gly Tyr Val Leu His Met Ile Thr Thr Ala
            200                 205                 210
Ala Glu Trp Ser Met Ser Phe Ser Phe Gly Phe Phe Leu Thr
            215                 220                 225
Tyr Ile Arg Asp Phe Gln Lys Ile Ser Leu Arg Val Glu Ala Asn
            230                 235                 240
Leu His Gly Leu Thr Leu Tyr Asp Thr Ala Pro Cys Pro Ile Asn
            245                 250                 255
Asn Glu Arg Thr Arg Leu Leu Ser Arg Asp Ile
            260                 265

<210> SEQ ID NO 3
<211> LENGTH: 2037
<212> TYPE: DNA
<213> ORGANISM: Homo Sapien

<400> SEQUENCE: 3
cggacgcgtg gcggacgcg tgggggagag ccgcagtccc ggctgcagca         50
cctgggagaa ggcagaccgt gtgagggggc ctgtggcccc agcgtgctgt        100
ggcctcgggg agtgggaagt ggaggcagga gccttcctta cacttcgcca        150
tgagtttcct catcgactcc agcatcatga ttacctccca gatactattt        200
tttggatttg ggtggctttt cttcatgcgc caattgttta agactatga         250
gatacgtcag tatgttgtac aggtgatctt ctccgtgacg tttgcatttt        300
cttgcaccat gtttgagctc atcatctttg aaatcttagg agtattgaat        350
agcagctccc gttattttca ctggaaaatg aacctgtgtg taattctgct        400
gatcctggtt ttcatggtgc ctttttacat tggctatttt attgtgagca        450
atatccgact actgcataaa caacgactgc tttttttcctg tctcttatgg       500
ctgacccttta tgtatttctt ctggaaacta ggagatccct ttcccattct      550
cagcccaaaa catgggatct tatccataga acagctcatc agccgggttg        600
gtgtgattgg agtgactctc atggctcttc tttctggatt tggtgctgtc        650
aactgcccat acacttacat gtcttacttc ctcaggaatg tgactgacac        700
```

-continued

| | |
|---|---|
| ggatattcta gccctggaac ggcgactgct gcaaaccatg gatatgatca | 750 |
| taagcaaaaa gaaaaggatg gcaatggcac ggagaacaat gttccagaag | 800 |
| ggggaagtgc ataacaaacc atcaggtttc tggggaatga taaaaagtgt | 850 |
| taccacttca gcatcaggaa gtgaaaatct tactcttatt caacaggaag | 900 |
| tggatgcttt ggaagaatta gcaggcagc ttttctgga aacagctgat | 950 |
| ctatatgcta ccaaggagag aatagaatac tccaaaacct tcaaggggaa | 1000 |
| atattttaat tttcttggtt acttttctc tatttactgt gtttggaaaa | 1050 |
| ttttcatggc taccatcaat attgtttttg atcgagttgg gaaaacggat | 1100 |
| cctgtcacaa gaggcattga gatcactgtg aattatctgg gaatccaatt | 1150 |
| tgatgtgaag ttttggtccc aacacatttc cttcattctt gttggaataa | 1200 |
| tcatcgtcac atccatcaga ggattgctga tcactcttac caagttcttt | 1250 |
| tatgccatct ctagcagtaa gtcctccaat gtcattgtcc tgctattagc | 1300 |
| acagataatg ggcatgtact ttgtctcctc tgtgctgctg atccgaatga | 1350 |
| gtatgccttt agaataccgc accataatca ctgaagtcct tggagaactg | 1400 |
| cagttcaact tctatcaccg ttggtttgat gtgatcttcc tggtcagcgc | 1450 |
| tctctctagc atactcttcc tctatttggc tcacaaacag gcaccagaga | 1500 |
| agcaaatggc accttgaact taagcctact acagactgtt agaggccagt | 1550 |
| ggtttcaaaa tttagatata agaggggga aaaatggaac cagggcctga | 1600 |
| cattttataa acaaacaaaa tgctatggta gcatttttca ccttcatagc | 1650 |
| atactccttc cccgtcaggt gatactatga ccatgagtag catcagccag | 1700 |
| aacatgagag ggagaactaa ctcaagacaa tactcagcag agagcatccc | 1750 |
| gtgtggatat gaggctggtg tagaggcgga gaggagccaa gaaactaaag | 1800 |
| gtgaaaaata cactggaact ctggggcaag acatgtctat ggtagctgag | 1850 |
| ccaaacacgt aggatttccg ttttaaggtt cacatggaaa aggttatagc | 1900 |
| tttgccttga gattgactca ttaaaatcag agactgtaac aaaaaaaaaa | 1950 |
| aaaaaaaaaa agggcggccg cgactctaga gtcgacctgc agaagcttgg | 2000 |
| ccgccatggc ccaacttgtt tattgcagct tataatg | 2037 |

<210> SEQ ID NO 4
<211> LENGTH: 455
<212> TYPE: PRT
<213> ORGANISM: Homo Sapien

<400> SEQUENCE: 4

Met Ser Phe Leu Ile Asp Ser Ser Ile Met Ile Thr Ser Gln Ile
 1               5                  10                  15

Leu Phe Phe Gly Phe Gly Trp Leu Phe Phe Met Arg Gln Leu Phe
                20                  25                  30

Lys Asp Tyr Glu Ile Arg Gln Tyr Val Val Gln Val Ile Phe Ser
                35                  40                  45

Val Thr Phe Ala Phe Ser Cys Thr Met Phe Glu Leu Ile Ile Phe
                50                  55                  60

Glu Ile Leu Gly Val Leu Asn Ser Ser Ser Arg Tyr Phe His Trp
                65                  70                  75

Lys Met Asn Leu Cys Val Ile Leu Leu Ile Leu Val Phe Met Val
                80                  85                  90

-continued

```
Pro Phe Tyr Ile Gly Tyr Phe Ile Val Ser Asn Ile Arg Leu Leu
                 95                 100                 105

His Lys Gln Arg Leu Leu Phe Ser Cys Leu Leu Trp Leu Thr Phe
            110                 115                 120

Met Tyr Phe Phe Trp Lys Leu Gly Asp Pro Phe Pro Ile Leu Ser
            125                 130                 135

Pro Lys His Gly Ile Leu Ser Ile Glu Gln Leu Ile Ser Arg Val
            140                 145                 150

Gly Val Ile Gly Val Thr Leu Met Ala Leu Leu Ser Gly Phe Gly
            155                 160                 165

Ala Val Asn Cys Pro Tyr Thr Tyr Met Ser Tyr Phe Leu Arg Asn
            170                 175                 180

Val Thr Asp Thr Asp Ile Leu Ala Leu Glu Arg Arg Leu Leu Gln
            185                 190                 195

Thr Met Asp Met Ile Ile Ser Lys Lys Lys Arg Met Ala Met Ala
            200                 205                 210

Arg Arg Thr Met Phe Gln Lys Gly Glu Val His Asn Lys Pro Ser
            215                 220                 225

Gly Phe Trp Gly Met Ile Lys Ser Val Thr Thr Ser Ala Ser Gly
            230                 235                 240

Ser Glu Asn Leu Thr Leu Ile Gln Gln Glu Val Asp Ala Leu Glu
            245                 250                 255

Glu Leu Ser Arg Gln Leu Phe Leu Glu Thr Ala Asp Leu Tyr Ala
            260                 265                 270

Thr Lys Glu Arg Ile Glu Tyr Ser Lys Thr Phe Lys Gly Lys Tyr
            275                 280                 285

Phe Asn Phe Leu Gly Tyr Phe Phe Ser Ile Tyr Cys Val Trp Lys
            290                 295                 300

Ile Phe Met Ala Thr Ile Asn Ile Val Phe Asp Arg Val Gly Lys
            305                 310                 315

Thr Asp Pro Val Thr Arg Gly Ile Glu Ile Thr Val Asn Tyr Leu
            320                 325                 330

Gly Ile Gln Phe Asp Val Lys Phe Trp Ser Gln His Ile Ser Phe
            335                 340                 345

Ile Leu Val Gly Ile Ile Val Thr Ser Ile Arg Gly Leu Leu
            350                 355                 360

Ile Thr Leu Thr Lys Phe Phe Tyr Ala Ile Ser Ser Ser Lys Ser
            365                 370                 375

Ser Asn Val Ile Val Leu Leu Ala Gln Ile Met Gly Met Tyr
            380                 385                 390

Phe Val Ser Ser Val Leu Leu Ile Arg Met Ser Met Pro Leu Glu
            395                 400                 405

Tyr Arg Thr Ile Ile Thr Glu Val Leu Gly Glu Leu Gln Phe Asn
            410                 415                 420

Phe Tyr His Arg Trp Phe Asp Val Ile Phe Leu Val Ser Ala Leu
            425                 430                 435

Ser Ser Ile Leu Phe Leu Tyr Leu Ala His Lys Gln Ala Pro Glu
            440                 445                 450

Lys Gln Met Ala Pro
            455
```

<210> SEQ ID NO 5
<211> LENGTH: 2372

<212> TYPE: DNA
<213> ORGANISM: Homo Sapien

<400> SEQUENCE: 5

| | |
|---|---|
| agcagggaaa tccggatgtc tcggttatga agtggagcag tgagtgtgag | 50 |
| cctcaacata gttccagaac tctccatccg gactagttat tgagcatctg | 100 |
| cctctcatat caccagtggc catctgaggt gtttccctgg ctctgaaggg | 150 |
| gtaggcacga tggccaggtg cttcagcctg tgttgcttc tcacttccat | 200 |
| ctggaccacg aggctcctgg tccaaggctc tttgcgtgca gaagagcttt | 250 |
| ccatccaggt gtcatgcaga attatgggga tcacccttgt gagcaaaaag | 300 |
| gcgaaccagc agctgaattt cacagaagct aaggaggcct gtaggctgct | 350 |
| gggactaagt ttggccggca aggaccaagt tgaaacagcc ttgaaagcta | 400 |
| gctttgaaac ttgcagctat ggctgggttg gagatggatt cgtggtcatc | 450 |
| tctaggatta gcccaaaccc caagtgtggg aaaaatgggg tgggtgtcct | 500 |
| gatttggaag gttccagtga gccgacagtt tgcagcctat tgttacaact | 550 |
| catctgatac ttggactaac tcgtgcattc cagaaattat caccaccaaa | 600 |
| gatcccatat tcaacactca aactgcaaca caaacaacag aatttattgt | 650 |
| cagtgacagt acctactcgg tggcatcccc ttactctaca atacctgccc | 700 |
| ctactactac tcctcctgct ccagcttcca cttctattcc acggagaaaa | 750 |
| aaattgattt gtgtcacaga agtttttatg gaaactagca ccatgtctac | 800 |
| agaaactgaa ccatttgttg aaaataaagc agcattcaag aatgaagctg | 850 |
| ctgggtttgg aggtgtcccc acggctctgc tagtgcttgc tctcctcttc | 900 |
| tttggtgctg cagctggtct tggattttgc tatgtcaaaa ggtatgtgaa | 950 |
| ggccttccct tttacaaaca gaatcagca gaaggaaatg atcgaaacca | 1000 |
| aagtagtaaa ggaggagaag gccaatgata gcaaccctaa tgaggaatca | 1050 |
| aagaaaactg ataaaaaccc agaagagtcc aagagtccaa gcaaaactac | 1100 |
| cgtgcgatgc ctggaagctg aagtttagat gagacagaaa tgaggagaca | 1150 |
| cacctgaggc tggtttcttt catgctcctt accctgcccc agctggggaa | 1200 |
| atcaaaaggg ccaaagaacc aaagaagaaa gtccaccctt ggttcctaac | 1250 |
| tggaatcagc tcaggactgc cattggacta tggagtgcac caaagagaat | 1300 |
| gcccttctcc ttattgtaac cctgtctgga tcctatcctc ctacctccaa | 1350 |
| agcttcccac ggccttttcta gcctggctat gtcctaataa tatcccactg | 1400 |
| ggagaaagga gttttgcaaa gtgcaaggac ctaaaacatc tcatcagtat | 1450 |
| ccagtggtaa aaaggcctcc tggctgtctg aggctaggtg ggttgaaagc | 1500 |
| caaggagtca ctgagaccaa ggctttctct actgattccg cagctcagac | 1550 |
| cctttcttca gctctgaaag agaaacacgt atcccacctg acatgtcctt | 1600 |
| ctgagcccgg taagagcaaa agaatggcag aaaagtttag cccctgaaag | 1650 |
| ccatggagat tctcataact tgagacctaa tctctgtaaa gctaaaataa | 1700 |
| agaaatagaa caaggctgag gatacgacag tacactgtca gcagggactg | 1750 |
| taaacacaga cagggtcaaa gtgttttctc tgaacacatt gagttggaat | 1800 |
| cactgtttag aacacacaca cttactttttt ctggtctcta ccactgctga | 1850 |

-continued

| | |
|---|---|
| tattttctct aggaaatata cttttacaag taacaaaaat aaaaactctt | 1900 |
| ataaatttct atttttatct gagttacaga aatgattact aaggaagatt | 1950 |
| actcagtaat ttgtttaaaa agtaataaaa ttcaacaaac atttgctgaa | 2000 |
| tagctactat atgtcaagtg ctgtgcaagg tattacactc tgtaattgaa | 2050 |
| tattattcct caaaaaattg cacatagtag aacgctatct gggaagctat | 2100 |
| tttttttcagt tttgatattt ctagcttatc tacttccaaa ctaattttta | 2150 |
| tttttgctga gactaatctt attcattttc tctaatatgg caaccattat | 2200 |
| aaccttaatt tattattaac atacctaaga agtacattgt tacctctata | 2250 |
| taccaaagca cattttaaaa gtgccattaa caaatgtatc actagccctc | 2300 |
| cttttttccaa caagaaggga ctgagagatg cagaaatatt tgtgacaaaa | 2350 |
| aattaaagca tttagaaaac tt | 2372 |

<210> SEQ ID NO 6
<211> LENGTH: 322
<212> TYPE: PRT
<213> ORGANISM: Homo Sapien

<400> SEQUENCE: 6

Met Ala Arg Cys Phe Ser Leu Val Leu Leu Thr Ser Ile Trp
 1               5                  10                  15

Thr Thr Arg Leu Leu Val Gln Gly Ser Leu Arg Ala Glu Glu Leu
                20                  25                  30

Ser Ile Gln Val Ser Cys Arg Ile Met Gly Ile Thr Leu Val Ser
                35                  40                  45

Lys Lys Ala Asn Gln Gln Leu Asn Phe Thr Glu Ala Lys Glu Ala
                50                  55                  60

Cys Arg Leu Leu Gly Leu Ser Leu Ala Gly Lys Asp Gln Val Glu
                65                  70                  75

Thr Ala Leu Lys Ala Ser Phe Glu Thr Cys Ser Tyr Gly Trp Val
                80                  85                  90

Gly Asp Gly Phe Val Val Ile Ser Arg Ile Ser Pro Asn Pro Lys
                95                  100                 105

Cys Gly Lys Asn Gly Val Gly Val Leu Ile Trp Lys Val Pro Val
                110                 115                 120

Ser Arg Gln Phe Ala Ala Tyr Cys Tyr Asn Ser Ser Asp Thr Trp
                125                 130                 135

Thr Asn Ser Cys Ile Pro Glu Ile Ile Thr Thr Lys Asp Pro Ile
                140                 145                 150

Phe Asn Thr Gln Thr Ala Thr Gln Thr Thr Glu Phe Ile Val Ser
                155                 160                 165

Asp Ser Thr Tyr Ser Val Ala Ser Pro Tyr Ser Thr Ile Pro Ala
                170                 175                 180

Pro Thr Thr Thr Pro Pro Ala Pro Ala Ser Thr Ser Ile Pro Arg
                185                 190                 195

Arg Lys Lys Leu Ile Cys Val Thr Glu Val Phe Met Glu Thr Ser
                200                 205                 210

Thr Met Ser Thr Glu Thr Glu Pro Phe Val Glu Asn Lys Ala Ala
                215                 220                 225

Phe Lys Asn Glu Ala Ala Gly Phe Gly Gly Val Pro Thr Ala Leu
                230                 235                 240

Leu Val Leu Ala Leu Leu Phe Phe Gly Ala Ala Ala Gly Leu Gly

```
                    245                 250                 255
        Phe Cys Tyr Val Lys Arg Tyr Val Lys Ala Phe Pro Phe Thr Asn
                        260                 265                 270

Lys Asn Gln Gln Lys Glu Met Ile Glu Thr Lys Val Val Lys Glu
                    275                 280                 285

Glu Lys Ala Asn Asp Ser Asn Pro Asn Glu Glu Ser Lys Lys Thr
                    290                 295                 300

Asp Lys Asn Pro Glu Glu Ser Lys Ser Pro Ser Lys Thr Thr Val
                    305                 310                 315

Arg Cys Leu Glu Ala Glu Val
                    320

<210> SEQ ID NO 7
<211> LENGTH: 2586
<212> TYPE: DNA
<213> ORGANISM: Homo Sapien

<400> SEQUENCE: 7
cgccgcgctc cgcacccgc ggcccgccca ccgcgccgct cccgcatctg            50
cacccgcagc ccggcggcct cccggcggga gcgagcagat ccagtccggc           100
ccgcagcgca actcggtcca gtcggggcgg cggctgcggg cgcagagcgg           150
agatgcagcg gcttggggcc accctgctgt gcctgctgct ggcggcggcg           200
gtccccacgg ccccccgcgc cgctccgacg gcgacctcgg ctccagtcaa           250
gcccggcccg gctctcagct acccgcagga ggaggccacc ctcaatgaga           300
tgttccgcga ggttgaggaa ctgatggagg acacgcagca caaattgcgc           350
agcgcggtgg aagagatgga ggcagaagaa gctgctgcta agcatcatc            400 agaagtgaac ctggcaaact tacctcccag ctatcacaat gagaccaaca           450
cagacacgaa ggttggaaat aataccatcc atgtgcaccg agaaattcac           500
aagataacca caaccagac tggacaaatg gtcttttcag agacagttat            550
cacatctgtg ggagacgaag aaggcagaag gagccacgtg tgcatcatcg           600
acgaggactg tgggcccagc atgtactgcc agtttgccag cttccagtac           650
acctgccagc catgccgggg ccagaggatg ctctgcaccc gggacagtga           700
gtgctgtgga gaccagctgt gtgtctgggg tcactgcacc aaaatggcca           750 ccagggcag caatgggacc atctgtgaca accagaggga ctgccagccg            800
gggctgtgct gtgccttcca gagaggcctg ctgttccctg tgtgcacacc           850 cctgccgtg gagggcgagc tttgccatga ccccgccagc cggcttctgg            900
acctcatcac ctgggagcta gagcctgatg gagccttgga ccgatgccct           950
tgtgccagtg gcctcctctg ccagccccac agccacagcc tggtgtatgt          1000
gtgcaagccg accttcgtgg ggagccgtga ccaagatggg gagatcctgc          1050
tgcccagaga ggtccccgat gagtatgaag ttggcagctt catggaggag          1100
gtgcgccagg agctggagga cctggagagg agcctgactg aagagatggc          1150
gctgggggag cctgcggctg ccgccgctgc actgctggga ggggaagaga          1200
tttagatctg gaccaggctg tgggtagatg tgcaatagaa atagctaatt          1250
tatttcccca ggtgtgtgct ttaggcgtgg gctgaccagg cttcttccta          1300
catcttcttc ccagtaagtt tccctctgg cttgacagca tgaggtgttg           1350
```

-continued

| | |
|---|---|
| tgcatttgtt cagctccccc aggctgttct ccaggcttca cagtctggtg | 1400 |
| cttgggagag tcaggcaggg ttaaactgca ggagcagttt gccacccctg | 1450 |
| tccagattat tggctgcttt gcctctacca gttggcagac agccgtttgt | 1500 |
| tctacatggc tttgataatt gtttgagggg aggagatgga acaatgtgg | 1550 |
| agtctccctc tgattggttt tggggaaatg tggagaagag tgccctgctt | 1600 |
| tgcaaacatc aacctggcaa aaatgcaaca atgaattttt ccacgcagtt | 1650 |
| ctttccatgg gcataggtaa gctgtgcctt cagctgttgc agatgaaatg | 1700 |
| ttctgttcac cctgcattac atgtgtttat tcatccagca gtgttgctca | 1750 |
| gctcctacct ctgtgccagg gcagcatttt catatccaag atcaattccc | 1800 |
| tctctcagca cagcctgggg aggggtcat tgttctcctc gtccatcagg | 1850 |
| gatctcagag gctcagagac tgcaagctgc ttgcccaagt cacacagcta | 1900 |
| gtgaagacca gagcagtttc atctggttgt gactctaagc tcagtgctct | 1950 |
| ctccactacc ccacaccagc cttggtgcca ccaaaagtgc tccccaaaag | 2000 |
| gaaggagaat gggatttttc ttgaggcatg cacatctgga attaaggtca | 2050 |
| aactaattct cacatccctc taaaagtaaa ctactgttag gaacagcagt | 2100 |
| gttctcacag tgtggggcag ccgtccttct aatgaagaca atgatattga | 2150 |
| cactgtccct ctttggcagt tgcattagta actttgaaag gtatatgact | 2200 |
| gagcgtagca tacaggttaa cctgcagaaa cagtacttag gtaattgtag | 2250 |
| ggcgaggatt ataaatgaaa tttgcaaaat cacttagcag caactgaaga | 2300 |
| caattatcaa ccacgtggag aaaatcaaac cgagcagggc tgtgtgaaac | 2350 |
| atggttgtaa tatgcgactg cgaacactga actctacgcc actccacaaa | 2400 |
| tgatgttttc aggtgtcatg gactgttgcc accatgtatt catccagagt | 2450 |
| tcttaaagtt taagttgca catgattgta taagcatgct ttctttgagt | 2500 |
| tttaaattat gtataaacat aagttgcatt tagaaatcaa gcataaatca | 2550 |
| cttcaactgc aaaaaaaaaa aaaaaaaaaa aaaaaa | 2586 |

<210> SEQ ID NO 8
<211> LENGTH: 350
<212> TYPE: PRT
<213> ORGANISM: Homo Sapien

<400> SEQUENCE: 8

Met Gln Arg Leu Gly Ala Thr Leu Leu Cys Leu Leu Leu Ala Ala
1               5                   10                  15

Ala Val Pro Thr Ala Pro Ala Pro Ala Pro Thr Ala Thr Ser Ala
                20                  25                  30

Pro Val Lys Pro Gly Pro Ala Leu Ser Tyr Pro Gln Glu Glu Ala
                35                  40                  45

Thr Leu Asn Glu Met Phe Arg Glu Val Glu Glu Leu Met Glu Asp
                50                  55                  60

Thr Gln His Lys Leu Arg Ser Ala Val Glu Glu Met Glu Ala Glu
                65                  70                  75

Glu Ala Ala Ala Lys Ala Ser Ser Glu Val Asn Leu Ala Asn Leu
                80                  85                  90

Pro Pro Ser Tyr His Asn Glu Thr Asn Thr Asp Thr Lys Val Gly
                95                  100                 105

-continued

```
Asn Asn Thr Ile His Val His Arg Glu Ile His Lys Ile Thr Asn
            110                 115                 120

Asn Gln Thr Gly Gln Met Val Phe Ser Glu Thr Val Ile Thr Ser
        125                 130                 135

Val Gly Asp Glu Glu Gly Arg Arg Ser His Glu Cys Ile Ile Asp
        140                 145                 150

Glu Asp Cys Gly Pro Ser Met Tyr Cys Gln Phe Ala Ser Phe Gln
        155                 160                 165

Tyr Thr Cys Gln Pro Cys Arg Gly Gln Arg Met Leu Cys Thr Arg
        170                 175                 180

Asp Ser Glu Cys Cys Gly Asp Gln Leu Cys Val Trp Gly His Cys
        185                 190                 195

Thr Lys Met Ala Thr Arg Gly Ser Asn Gly Thr Ile Cys Asp Asn
        200                 205                 210

Gln Arg Asp Cys Gln Pro Gly Leu Cys Cys Ala Phe Gln Arg Gly
        215                 220                 225

Leu Leu Phe Pro Val Cys Thr Pro Leu Pro Val Glu Gly Glu Leu
        230                 235                 240

Cys His Asp Pro Ala Ser Arg Leu Leu Asp Leu Ile Thr Trp Glu
        245                 250                 255

Leu Glu Pro Asp Gly Ala Leu Asp Arg Cys Pro Cys Ala Ser Gly
        260                 265                 270

Leu Leu Cys Gln Pro His Ser His Ser Leu Val Tyr Val Cys Lys
        275                 280                 285

Pro Thr Phe Val Gly Ser Arg Asp Gln Asp Gly Glu Ile Leu Leu
        290                 295                 300

Pro Arg Glu Val Pro Asp Glu Tyr Glu Val Gly Ser Phe Met Glu
        305                 310                 315

Glu Val Arg Gln Glu Leu Glu Asp Leu Glu Arg Ser Leu Thr Glu
        320                 325                 330

Glu Met Ala Leu Gly Glu Pro Ala Ala Ala Ala Ala Leu Leu
        335                 340                 345

Gly Gly Glu Glu Ile
        350

<210> SEQ ID NO 9
<211> LENGTH: 1395
<212> TYPE: DNA
<213> ORGANISM: Homo Sapien

<400> SEQUENCE: 9
cggacgcgtg gcggacgcg tgggggctgt gagaaagtgc aataaatac          50 atcatgcaac cccacggccc accttgtgaa ctcctcgtgc ccagggctga        100
tgtgcgtctt ccaggctac tcatccaaag gcctaatcca acgttctgtc        150
ttcaatctgc aaatctatgg ggtcctgggg ctcttctgga cccttaactg       200
ggtactggcc ctgggccaat gcgtcctcgc tggagccttt gcctccttct       250
actgggcctt ccacaagccc caggacatcc ctaccttccc cttaatctct      300
gccttcatcc gcacactccg ttaccacact gggtcattgg catttggagc      350
cctcatcctg acccttgtgc agatagcccg ggtcatcttg gagtatattg       400
accacaagct cagaggagtg cagaaccctg tagcccgctg catcatgtgc      450
tgtttcaagt gctgcctctg gtgtctggaa aaatttatca agttcctaaa     500
```

-continued

| | |
|---|---|
| ccgcaatgca tacatcatga tcgccatcta cgggaagaat ttctgtgtct | 550 |
| cagccaaaaa tgcgttcatg ctactcatgc gaaacattgt cagggtggtc | 600 |
| gtcctggaca aagtcacaga cctgctgctg ttctttggga agctgctggt | 650 |
| ggtcggaggc gtgggggtcc tgtccttctt ttttttctcc ggtcgcatcc | 700 |
| cggggctggg taaagacttt aagagccccc acctcaacta ttactggctg | 750 |
| cccatcatga cctccatcct gggggcctat gtcatcgcca gcggcttctt | 800 |
| cagcgttttc ggcatgtgtg tggacacgct cttcctctgc ttcctggaag | 850 |
| acctggagcg gaacaacggc tccctggacc ggccctacta catgtccaag | 900 |
| agccttctaa agattctggg caagaagaac gaggcgcccc cggacaacaa | 950 |
| gaagaggaag aagtgacagc tccggccctg atccaggact gcaccccacc | 1000 |
| cccaccgtcc agccatccaa cctcacttcg ccttacaggt ctccattttg | 1050 |
| tggtaaaaaa aggttttagg ccaggcgccg tggctcacgc ctgtaatcca | 1100 |
| acactttgag aggctgaggc gggcggatca cctgagtcag gagttcgaga | 1150 |
| ccagcctggc caacatggtg aaacctccgt ctctattaaa aatacaaaaa | 1200 |
| ttagccgaga gtggtggcat gcacctgtca tcccagctac tcgggaggct | 1250 |
| gaggcaggag aatcgcttga acccgggagg cagaggttgc agtgagccga | 1300 |
| gatcgcgcca ctgcactcca acctgggtga cagactctgt ctccaaaaca | 1350 |
| aaacaaacaa acaaaaagat tttattaaag atattttgtt aactc | 1395 |

<210> SEQ ID NO 10
<211> LENGTH: 321
<212> TYPE: PRT
<213> ORGANISM: Homo Sapien

<400> SEQUENCE: 10

Arg Thr Arg Gly Arg Thr Arg Gly Gly Cys Glu Lys Val Pro Ile
 1               5                  10                  15

Asn Thr Ser Cys Asn Pro Thr Ala His Leu Val Asn Ser Ser Cys
                20                  25                  30

Pro Gly Leu Met Cys Val Phe Gln Gly Tyr Ser Ser Lys Gly Leu
            35                  40                  45

Ile Gln Arg Ser Val Phe Asn Leu Gln Ile Tyr Gly Val Leu Gly
        50                  55                  60

Leu Phe Trp Thr Leu Asn Trp Val Leu Ala Leu Gly Gln Cys Val
    65                  70                  75

Leu Ala Gly Ala Phe Ala Ser Phe Tyr Trp Ala Phe His Lys Pro
80                  85                  90

Gln Asp Ile Pro Thr Phe Pro Leu Ile Ser Ala Phe Ile Arg Thr
            95                  100                 105

Leu Arg Tyr His Thr Gly Ser Leu Ala Phe Gly Ala Leu Ile Leu
            110                 115                 120

Thr Leu Val Gln Ile Ala Arg Val Ile Leu Glu Tyr Ile Asp His
            125                 130                 135

Lys Leu Arg Gly Val Gln Asn Pro Val Ala Arg Cys Ile Met Cys
            140                 145                 150

Cys Phe Lys Cys Cys Leu Trp Cys Leu Glu Lys Phe Ile Lys Phe
            155                 160                 165

Leu Asn Arg Asn Ala Tyr Ile Met Ile Ala Ile Tyr Gly Lys Asn
            170                 175                 180

```
Phe Cys Val Ser Ala Lys Asn Ala Phe Met Leu Leu Met Arg Asn
                185                 190                 195
Ile Val Arg Val Val Leu Asp Lys Val Thr Asp Leu Leu Leu
            200                 205                 210
Phe Phe Gly Lys Leu Leu Val Val Gly Gly Val Leu Ser
        215                 220                 225
Phe Phe Phe Phe Ser Gly Arg Ile Pro Gly Leu Gly Lys Asp Phe
                230                 235                 240
Lys Ser Pro His Leu Asn Tyr Tyr Trp Leu Pro Ile Met Thr Ser
                245                 250                 255
Ile Leu Gly Ala Tyr Val Ile Ala Ser Gly Phe Phe Ser Val Phe
                260                 265                 270
Gly Met Cys Val Asp Thr Leu Phe Leu Cys Phe Leu Glu Asp Leu
                275                 280                 285
Glu Arg Asn Asn Gly Ser Leu Asp Arg Pro Tyr Tyr Met Ser Lys
                290                 295                 300
Ser Leu Leu Lys Ile Leu Gly Lys Lys Asn Glu Ala Pro Pro Asp
                305                 310                 315
Asn Lys Lys Arg Lys Lys
                320

<210> SEQ ID NO 11
<211> LENGTH: 1901
<212> TYPE: DNA
<213> ORGANISM: Homo Sapien

<400> SEQUENCE: 11
gccccgcgcc cggcgccggg cgcccgaagc cgggagccac cgccatgggg          50
gcctgcctgg gagcctgctc cctgctcagc tgcgcgtcct gcctctgcgg         100
ctctgccccc tgcatcctgt gcagctgctg ccccgccagc cgcaactcca         150
ccgtgagccg cctcatcttc acgttcttcc tcttcctggg ggtgctggtg         200
tccatcatta tgctgagccc gggcgtggag agtcagctct acaagctgcc         250
ctgggtgtgt gaggaggggg ccgggatccc caccgtcctg cagggccaca         300
tcgactgtgg ctccctgctt ggctaccgcg ctgtctaccg catgtgcttc         350
gccacggcgg ccttcttctt cttctttttc accctgctca tgctctgcgt         400
gagcagcagc cggaccccc gggctgccat ccagaatggg ttttggttct          450
ttaagttcct gatcctggtg ggcctcaccg tgggtgcctt ctacatccct         500
gacggctcct tcaccaacat ctggttctac ttcggcgtcg tgggctcctt         550
cctcttcatc ctcatccagc tggtgctgct catcgacttt gcgcactcct         600
ggaaccagcg gtggctgggc aaggccgagg agtgcgattc ccgtgcctgg         650
tacgcaggcc tcttcttctt cactctcctc ttctacttgc tgtcgatcgc         700
ggccgtggcg ctgatgttca gtactacac tgagcccagc ggctgccacg         750
agggcaaggt cttcatcagc ctcaacctca ccttctgtgt ctgcgtgtcc         800
atcgctgctg tcctgcccaa ggtccaggac gcccagccca actcgggtct         850
gctgcaggcc tcggtcatca ccctctacac catgtttgtc acctggtcag         900
ccctatccag tatccctgaa cagaaatgca accccatttt gccaaccccag         950
ctgggcaacg agacagttgt ggcaggcccc gagggctatg agacccagtg        1000
```

-continued

| | |
|---|---|
| gtgggatgcc ccgagcattg tgggcctcat catcttcctc ctgtgcaccc | 1050 |
| tcttcatcag tctgcgctcc tcagaccacc ggcaggtgaa cagcctgatg | 1100 |
| cagaccgagg agtgcccacc tatgctagac gccacacagc agcagcagca | 1150 |
| gcaggtggca gcctgtgagg gccgggcctt tgacaacgag caggacggcg | 1200 |
| tcacctacag ctactccttc ttccacttct gcctggtgct ggcctcactg | 1250 |
| cacgtcatga tgacgctcac caactggtac aagcccggtg agacccggaa | 1300 |
| gatgatcagc acgtggaccg ccgtgtgggt gaagatctgt gccagctggg | 1350 |
| cagggctgct cctctacctg tggaccctgg tagcccact cctcctgcgc | 1400 |
| aaccgcgact tcagctgagg cagcctcaca gcctgccatc tggtgcctcc | 1450 |
| tgccacctgg tgcctctcgg ctcggtgaca gccaacctgc cccctcccca | 1500 |
| caccaatcag ccaggctgag ccccacccc tgccccagct ccaggacctg | 1550 |
| cccctgagcc gggccttcta gtcgtagtgc cttcagggtc cgaggagcat | 1600 |
| caggctcctg cagagcccca tcccccgcc acccacac ggtggagctg | 1650 |
| cctcttcctt cccctcctcc ctgttgccca tactcagcat ctcggatgaa | 1700 |
| agggctccct tgtcctcagg ctccacggga gcggggctgc tggagagagc | 1750 |
| ggggaactcc caccacagtg gggcatccgg cactgaagcc ctggtgttcc | 1800 |
| tggtcacgtc ccccagggga ccctgccccc ttcctggact tcgtgcctta | 1850 |
| ctgagtctct aagacttttt ctaataaaca agccagtgcg tgtaaaaaaa | 1900 |
| a | 1901 |

<210> SEQ ID NO 12
<211> LENGTH: 457
<212> TYPE: PRT
<213> ORGANISM: Homo Sapien

<400> SEQUENCE: 12

```
Met Gly Ala Cys Leu Gly Ala Cys Ser Leu Leu Ser Cys Ala Ser
  1               5                  10                  15

Cys Leu Cys Gly Ser Ala Pro Cys Ile Leu Ser Cys Cys Pro
                 20                  25                  30

Ala Ser Arg Asn Ser Thr Val Ser Arg Leu Ile Phe Thr Phe Phe
                 35                  40                  45

Leu Phe Leu Gly Val Leu Val Ser Ile Ile Met Leu Ser Pro Gly
                 50                  55                  60

Val Glu Ser Gln Leu Tyr Lys Leu Pro Trp Val Cys Glu Glu Gly
                 65                  70                  75

Ala Gly Ile Pro Thr Val Leu Gln Gly His Ile Asp Cys Gly Ser
                 80                  85                  90

Leu Leu Gly Tyr Arg Ala Val Tyr Arg Met Cys Phe Ala Thr Ala
                 95                 100                 105

Ala Phe Phe Phe Phe Phe Phe Thr Leu Leu Met Leu Cys Val Ser
                110                 115                 120

Ser Ser Arg Asp Pro Arg Ala Ala Ile Gln Asn Gly Phe Trp Phe
                125                 130                 135

Phe Lys Phe Leu Ile Leu Val Gly Leu Thr Val Gly Ala Phe Tyr
                140                 145                 150

Ile Pro Asp Gly Ser Phe Thr Asn Ile Trp Phe Tyr Phe Gly Val
                155                 160                 165
```

-continued

```
Val Gly Ser Phe Leu Phe Ile Leu Ile Gln Leu Val Leu Leu Ile
            170                 175                 180

Asp Phe Ala His Ser Trp Asn Gln Arg Trp Leu Gly Lys Ala Glu
            185                 190                 195

Glu Cys Asp Ser Arg Ala Trp Tyr Ala Gly Leu Phe Phe Phe Thr
            200                 205                 210

Leu Leu Phe Tyr Leu Leu Ser Ile Ala Val Ala Leu Met Phe
            215                 220                 225

Met Tyr Tyr Thr Glu Pro Ser Gly Cys His Glu Gly Lys Val Phe
            230                 235                 240

Ile Ser Leu Asn Leu Thr Phe Cys Val Cys Val Ser Ile Ala Ala
            245                 250                 255

Val Leu Pro Lys Val Gln Asp Ala Gln Pro Asn Ser Gly Leu Leu
            260                 265                 270

Gln Ala Ser Val Ile Thr Leu Tyr Thr Met Phe Val Thr Trp Ser
            275                 280                 285

Ala Leu Ser Ser Ile Pro Glu Gln Lys Cys Asn Pro His Leu Pro
            290                 295                 300

Thr Gln Leu Gly Asn Glu Thr Val Val Ala Gly Pro Glu Gly Tyr
            305                 310                 315

Glu Thr Gln Trp Trp Asp Ala Pro Ser Ile Val Gly Leu Ile Ile
            320                 325                 330

Phe Leu Leu Cys Thr Leu Phe Ile Ser Leu Arg Ser Ser Asp His
            335                 340                 345

Arg Gln Val Asn Ser Leu Met Gln Thr Glu Glu Cys Pro Pro Met
            350                 355                 360

Leu Asp Ala Thr Gln Gln Gln Gln Gln Gln Val Ala Ala Cys Glu
            365                 370                 375

Gly Arg Ala Phe Asp Asn Glu Gln Asp Gly Val Thr Tyr Ser Tyr
            380                 385                 390

Ser Phe Phe His Phe Cys Leu Val Leu Ala Ser Leu His Val Met
            395                 400                 405

Met Thr Leu Thr Asn Trp Tyr Lys Pro Gly Glu Thr Arg Lys Met
            410                 415                 420

Ile Ser Thr Trp Thr Ala Val Trp Val Lys Ile Cys Ala Ser Trp
            425                 430                 435

Ala Gly Leu Leu Leu Tyr Leu Trp Thr Leu Val Ala Pro Leu Leu
            440                 445                 450

Leu Arg Asn Arg Asp Phe Ser
            455
```

<210> SEQ ID NO 13
<211> LENGTH: 1572
<212> TYPE: DNA
<213> ORGANISM: Homo Sapien

<400> SEQUENCE: 13

| | | |
|---|---|---|
| cgggccagcc tggggcggcc ggccaggaac cacccgttaa ggtgtcttct | 50 |
| ctttagggat ggtgaggttg gaaaaagact cctgtaaccc tcctccagga | 100 |
| tgaaccacct gccagaagac atggagaacg ctctcaccgg gagccagagc | 150 |
| tcccatgctt ctctgcgcaa tatccattcc atcaacccca cacaactcat | 200 |
| ggccaggatt gagtcctatg aaggaaggga aagaaaggc atatctgatg | 250 |
| tcaggaggac tttctgtttg tttgtcacct ttgacctctt attcgtaaca | 300 |

-continued

| | |
|---|---|
| ttactgtgga taatagagtt aaatgtgaat ggaggcattg agaacacatt | 350 |
| agagaaggag gtgatgcagt atgactacta ttcttcatat tttgatatat | 400 |
| ttcttctggc agttttcga tttaaagtgt taatacttgc atatgctgtg | 450 |
| tgcagactgc gccattggtg ggcaatagcg ttgacaacgg cagtgaccag | 500 |
| tgccttttta ctagcaaaag tgatcctttc gaagcttttc tctcaagggg | 550 |
| cttttggcta tgtgctgccc atcatttcat tcatccttgc ctggattgag | 600 |
| acgtggttcc tggatttcaa agtgttacct caagaagcag aagaagaaaa | 650 |
| cagactcctg atagttcagg atgcttcaga gagggcagca cttatacctg | 700 |
| gtggtctttc tgatggtcag ttttattccc ctcctgaatc cgaagcagga | 750 |
| tctgaagaag ctgaagaaaa acaggacagt gagaaaccac tttagaact | 800 |
| atgagtacta cttttgttaa atgtgaaaaa ccctcacaga aagtcatcga | 850 |
| ggcaaaaaga ggcaggcagt ggagtctccc tgtcgacagt aaagttgaaa | 900 |
| tggtgacgtc cactgctggc tttattgaac agctaataaa gatttattta | 950 |
| ttgtaatacc tcacaaacgt tgtaccatat ccatgcacat ttagttgcct | 1000 |
| gcctgtggct ggtaaggtaa tgtcatgatt catcctctct tcagtgagac | 1050 |
| tgagcctgat gtgttaacaa ataggtgaag aaagtcttgt gctgtattcc | 1100 |
| taatcaaaag acttaatata ttgaagtaac acttttttag taagcaagat | 1150 |
| acctttttat ttcaattcac agaatggaat ttttttgttt catgtctcag | 1200 |
| atttatttg tatttctttt taacactct acatttccct tgtttttaa | 1250 |
| ctcatgcaca tgtgctcttt gtacagtttt aaaaagtgta ataaaatctg | 1300 |
| acatgtcaat gtggctagtt ttattttct tgttttgcat tatgtgtatg | 1350 |
| gcctgaagtg ttggacttgc aaaaggggaa gaaaggaatt gcgaatacat | 1400 |
| gtaaaatgtc accagacatt tgtattattt ttatcatgaa atcatgtttt | 1450 |
| tctctgattg ttctgaaatg ttctaaatac tcttattttg aatgcacaaa | 1500 |
| atgacttaaa ccattcatat catgtttcct ttgcgttcag ccaatttcaa | 1550 |
| ttaaaatgaa ctaaattaaa aa | 1572 |

<210> SEQ ID NO 14
<211> LENGTH: 234
<212> TYPE: PRT
<213> ORGANISM: Homo Sapien

<400> SEQUENCE: 14

```
Met Asn His Leu Pro Glu Asp Met Glu Asn Ala Leu Thr Gly Ser
 1               5                  10                  15

Gln Ser Ser His Ala Ser Leu Arg Asn Ile His Ser Ile Asn Pro
                20                  25                  30

Thr Gln Leu Met Ala Arg Ile Glu Ser Tyr Glu Gly Arg Glu Lys
                35                  40                  45

Lys Gly Ile Ser Asp Val Arg Arg Thr Phe Cys Leu Phe Val Thr
                50                  55                  60

Phe Asp Leu Leu Phe Val Thr Leu Leu Trp Ile Glu Leu Asn
                65                  70                  75

Val Asn Gly Gly Ile Glu Asn Thr Leu Glu Lys Glu Val Met Gln
                80                  85                  90
```

-continued

```
Tyr Asp Tyr Tyr Ser Ser Tyr Phe Asp Ile Phe Leu Leu Ala Val
             95                  100                 105

Phe Arg Phe Lys Val Leu Ile Leu Ala Tyr Ala Val Cys Arg Leu
            110                 115                 120

Arg His Trp Trp Ala Ile Ala Leu Thr Thr Ala Val Thr Ser Ala
            125                 130                 135

Phe Leu Leu Ala Lys Val Ile Leu Ser Lys Leu Phe Ser Gln Gly
            140                 145                 150

Ala Phe Gly Tyr Val Leu Pro Ile Ile Ser Phe Ile Leu Ala Trp
            155                 160                 165

Ile Glu Thr Trp Phe Leu Asp Phe Lys Val Leu Pro Gln Glu Ala
            170                 175                 180

Glu Glu Glu Asn Arg Leu Leu Ile Val Gln Asp Ala Ser Glu Arg
            185                 190                 195

Ala Ala Leu Ile Pro Gly Gly Leu Ser Asp Gly Gln Phe Tyr Ser
            200                 205                 210

Pro Pro Glu Ser Glu Ala Gly Ser Glu Glu Ala Glu Glu Lys Gln
            215                 220                 225

Asp Ser Glu Lys Pro Leu Leu Glu Leu
            230
```

```
<210> SEQ ID NO 15
<211> LENGTH: 2768
<212> TYPE: DNA
<213> ORGANISM: Homo Sapien

<400> SEQUENCE: 15
actcgaacgc agttgcttcg ggacccagga cccctcggg cccgaccgc            50 caggaaagac tgaggccgcg gcctgccccg cccggctccc tgcgccgccg          100
ccgcctcccg ggacagaaga tgtgctccag ggtccctctg ctgctgccgc          150
tgctcctgct actggccctg ggcctgggg tgcagggctg cccatccggc           200
tgccagtgca gccagccaca gacagtcttc tgcactgccc gccagggac            250 cacggtgccc cgagacgtgc caccccgacac ggtggggctg tacgtctttg         300
agaacggcat caccatgctc gacgcaggca gctttgccgg cctgccgggc          350
ctgcagctcc tggacctgtc acagaaccag atcgccagcc tgcccagcgg          400
ggtcttccag ccactcgcca acctcagcaa cctggacctg acggccaaca          450
ggctgcatga atcaccaat gagaccttcc gtggcctgcg cgcctcgag            500 cgcctctacc tgggcaagaa ccgcatccgc acatccagc ctggtgcctt           550 cgacacgctc gaccgcctcc tggagctcaa gctgcaggac aacgagctgc          600 ggcactgcc ccgctgcgc ctgcccgcc tgctgctgct ggacctcagc             650
cacaacagcc tcctggccct ggagcccggc atcctggaca ctgccaacgt          700
ggaggcgctg cggctggctg tctggggct gcagcagctg gacgaggggc           750
tcttcagccg cttgcgcaac ctccacgacc tggatgtgtc cgacaaccag          800
ctggagcgag tgccacctgt gatccgaggc ctccggggcc tgacgcgcct          850
gcggctggcc ggcaacaccc gcattgccca gctgcggccc gaggacctgg          900
ccggcctggc tgccctgcag gagctggatg tgagcaacct aagcctgcag          950
gccctgcctg cgacctctc gggcctcttc cccgcctgc ggctgctggc           1000 agctgcccgc aaccccttca actgcgtgtg ccccctgagc tggtttggcc         1050
```

-continued

```
cctgggtgcg cgagagccac gtcacactgg ccagccctga ggagacgcgc      1100
tgccacttcc cgcccaagaa cgctggccgg ctgctcctgg agcttgacta      1150
cgccgacttt ggctgcccag ccaccaccac cacagccaca gtgcccacca      1200
cgaggcccgt ggtgcgggag cccacagcct tgtcttctag cttggctcct      1250
acctggctta gccccacagc gccggccact gaggccccca gcccgccctc      1300
cactgcccca ccgactgtag ggcctgtccc ccagcccag gactgcccac       1350
cgtccacctg cctcaatggg ggcacatgcc acctggggac acggcaccac      1400
ctggcgtgct tgtgccccga aggcttcacg ggcctgtact gtgagagcca      1450
gatgggcag gggacacggc ccagccctac accagtcacg ccgaggccac       1500
cacggtccct gaccctgggc atcgagccgg tgagcccac ctccctgcgc       1550
gtggggctgc agcgctacct ccaggggagc tccgtgcagc tcaggagcct      1600
ccgtctcacc tatcgcaacc tatcgggccc tgataagcgg ctggtgacgc      1650
tgcgactgcc tgcctcgctc gctgagtaca cggtcaccca gctgcggccc      1700
aacgccactt actccgtctg tgtcatgcct ttggggcccg ggcgggtgcc      1750
ggagggcgag gaggcctgcg gggaggccca tacaccccca gccgtccact      1800
ccaaccacgc cccagtcacc caggcccgcg agggcaacct gccgctcctc      1850
attgcgcccg ccctggccgc ggtgctcctg gccgcgctgg ctgcggtggg      1900
ggcagcctac tgtgtgcggc gggggcgggc catggcagca cgggctcagg      1950
acaaagggca ggtggggcca ggggctgggc ccctggaact ggagggagtg      2000
aaggtccect tggagccagg cccgaaggca acagagggcg gtggagaggc       2050
cctgcccagc gggtctgagt gtgaggtgcc actcatgggc ttcccagggc      2100
ctggcctcca gtcaccccctc cacgcaaagc cctacatcta agccagagag      2150
agacagggca gctggggccg ggctctcagc cagtgagatg gccagccccc      2200
tcctgctgcc acaccacgta agttctcagt cccaacctcg gggatgtgtg      2250
cagacagggc tgtgtgacca cagctgggcc ctgttccctc tggacctcgg      2300
tctcctcatc tgtgagatgc tgtggcccag ctgacgagcc ctaacgtccc      2350
cagaaccgag tgcctatgag gacagtgtcc gccctgccct ccgcaacgtg      2400
cagtccctgg gcacggcggg ccctgccatg tgctggtaac gcatgcctgg      2450
gtcctgctgg gctctcccac tccaggcgga ccctgggggc cagtgaagga      2500
agctcccgga aagagcagag ggagagcggg taggcggctg tgtgactcta      2550
gtcttggccc caggaagcga aggaacaaaa gaaactggaa aggaagatgc      2600
tttaggaaca tgttttgctt ttttaaaata tatatattta taagagatcc      2650
tttcccattt attctgggaa gatgtttttc aaactcagag acaaggactt      2700
tggttttgt aagacaaacg atgatatgaa ggccttttgt aagaaaaaat       2750
aaaagatgaa gtgtgaaa                                         2768
```

<210> SEQ ID NO 16
<211> LENGTH: 673
<212> TYPE: PRT
<213> ORGANISM: Homo Sapien

<400> SEQUENCE: 16

-continued

```
Met Cys Ser Arg Val Pro Leu Leu Pro Leu Leu Leu Leu
 1               5                  10                  15

Ala Leu Gly Pro Gly Val Gln Gly Cys Pro Ser Gly Cys Gln Cys
                20                  25                  30

Ser Gln Pro Gln Thr Val Phe Cys Thr Ala Arg Gln Gly Thr Thr
                35                  40                  45

Val Pro Arg Asp Val Pro Pro Asp Thr Val Gly Leu Tyr Val Phe
                50                  55                  60

Glu Asn Gly Ile Thr Met Leu Asp Ala Gly Ser Phe Ala Gly Leu
                65                  70                  75

Pro Gly Leu Gln Leu Leu Asp Leu Ser Gln Asn Gln Ile Ala Ser
                80                  85                  90

Leu Pro Ser Gly Val Phe Gln Pro Leu Ala Asn Leu Ser Asn Leu
                95                 100                 105

Asp Leu Thr Ala Asn Arg Leu His Glu Ile Thr Asn Glu Thr Phe
               110                 115                 120

Arg Gly Leu Arg Arg Leu Glu Arg Leu Tyr Leu Gly Lys Asn Arg
               125                 130                 135

Ile Arg His Ile Gln Pro Gly Ala Phe Asp Thr Leu Asp Arg Leu
               140                 145                 150

Leu Glu Leu Lys Leu Gln Asp Asn Glu Leu Arg Ala Leu Pro Pro
               155                 160                 165

Leu Arg Leu Pro Arg Leu Leu Leu Asp Leu Ser His Asn Ser
               170                 175                 180

Leu Leu Ala Leu Glu Pro Gly Ile Leu Asp Thr Ala Asn Val Glu
               185                 190                 195

Ala Leu Arg Leu Ala Gly Leu Gly Leu Gln Gln Leu Asp Glu Gly
               200                 205                 210

Leu Phe Ser Arg Leu Arg Asn Leu His Asp Leu Asp Val Ser Asp
               215                 220                 225

Asn Gln Leu Glu Arg Val Pro Pro Val Ile Arg Gly Leu Arg Gly
               230                 235                 240

Leu Thr Arg Leu Arg Leu Ala Gly Asn Thr Arg Ile Ala Gln Leu
               245                 250                 255

Arg Pro Glu Asp Leu Ala Gly Leu Ala Ala Leu Gln Glu Leu Asp
               260                 265                 270

Val Ser Asn Leu Ser Leu Gln Ala Leu Pro Gly Asp Leu Ser Gly
               275                 280                 285

Leu Phe Pro Arg Leu Arg Leu Leu Ala Ala Arg Asn Pro Phe
               290                 295                 300

Asn Cys Val Cys Pro Leu Ser Trp Phe Gly Pro Trp Val Arg Glu
               305                 310                 315

Ser His Val Thr Leu Ala Ser Pro Glu Glu Thr Arg Cys His Phe
               320                 325                 330

Pro Pro Lys Asn Ala Gly Arg Leu Leu Leu Glu Leu Asp Tyr Ala
               335                 340                 345

Asp Phe Gly Cys Pro Ala Thr Thr Thr Thr Ala Thr Val Pro Thr
               350                 355                 360

Thr Arg Pro Val Val Arg Glu Pro Thr Ala Leu Ser Ser Ser Leu
               365                 370                 375

Ala Pro Thr Trp Leu Ser Pro Thr Ala Pro Ala Thr Glu Ala Pro
               380                 385                 390

Ser Pro Pro Ser Thr Ala Pro Pro Thr Val Gly Pro Val Pro Gln
```

```
                        395                 400                 405
Pro Gln Asp Cys Pro Pro Ser Thr Cys Leu Asn Gly Gly Thr Cys
                410                 415                 420
His Leu Gly Thr Arg His His Leu Ala Cys Leu Cys Pro Glu Gly
                425                 430                 435
Phe Thr Gly Leu Tyr Cys Glu Ser Gln Met Gly Gln Gly Thr Arg
                440                 445                 450
Pro Ser Pro Thr Pro Val Thr Pro Arg Pro Arg Ser Leu Thr
                455                 460                 465
Leu Gly Ile Glu Pro Val Ser Pro Thr Ser Leu Arg Val Gly Leu
                470                 475                 480
Gln Arg Tyr Leu Gln Gly Ser Val Gln Leu Arg Ser Leu Arg
                485                 490                 495
Leu Thr Tyr Arg Asn Leu Ser Gly Pro Asp Lys Arg Leu Val Thr
                500                 505                 510
Leu Arg Leu Pro Ala Ser Leu Ala Glu Tyr Thr Val Thr Gln Leu
                515                 520                 525
Arg Pro Asn Ala Thr Tyr Ser Val Cys Val Met Pro Leu Gly Pro
                530                 535                 540
Gly Arg Val Pro Glu Gly Glu Glu Ala Cys Gly Glu Ala His Thr
                545                 550                 555
Pro Pro Ala Val His Ser Asn His Ala Pro Val Thr Gln Ala Arg
                560                 565                 570
Glu Gly Asn Leu Pro Leu Leu Ile Ala Pro Ala Leu Ala Ala Val
                575                 580                 585
Leu Leu Ala Ala Leu Ala Ala Val Gly Ala Ala Tyr Cys Val Arg
                590                 595                 600
Arg Gly Arg Ala Met Ala Ala Ala Gln Asp Lys Gly Gln Val
                605                 610                 615
Gly Pro Gly Ala Gly Pro Leu Glu Leu Glu Gly Val Lys Val Pro
                620                 625                 630
Leu Glu Pro Gly Pro Lys Ala Thr Glu Gly Gly Gly Glu Ala Leu
                635                 640                 645
Pro Ser Gly Ser Glu Cys Glu Val Pro Leu Met Gly Phe Pro Gly
                650                 655                 660
Pro Gly Leu Gln Ser Pro Leu His Ala Lys Pro Tyr Ile
                665                 670

<210> SEQ ID NO 17
<211> LENGTH: 1672
<212> TYPE: DNA
<213> ORGANISM: Homo Sapien

<400> SEQUENCE: 17
gcagcggcga ggcggcggtg gtggctgagt ccgtggtggc agaggcgaag          50
gcgacagctc atgcgggtcc ggatagggct gacgctgctg ctgtgtgcgg         100
tgctgctgag cttggcctcg gcgtcctcgg atgaagaagg cagccaggat         150
gaatccttag attccaagac tactttgaca tcagatgagt cagtaaagga         200
ccatactact gcaggcagag tagttgctgg tcaaatattt cttgattcag         250
aagaatctga attagaatcc tctattcaag aagaggaaga cagcctcaag         300
agccaagagg gggaaagtgt cacagaagat atcagctttc tagagtctcc         350
aaatccagaa aacaaggact atgaagagcc aaagaaagta cggaaaccag         400
```

-continued

| | |
|---|---|
| ctttgaccgc cattgaaggc acagcacatg gggagccctg ccacttccct | 450 |
| tttcttttcc tagataagga gtatgatgaa tgtacatcag atgggaggga | 500 |
| agatggcaga ctgtggtgtg ctacaaccta tgactacaaa gcagatgaaa | 550 |
| agtggggctt ttgtgaaact gaagaagagg ctgctaagag acggcagatg | 600 |
| caggaagcag aaatgatgta tcaaactgga atgaaaatcc ttaatggaag | 650 |
| caataagaaa agccaaaaaa gagaagcata tcggtatctc caaaaggcag | 700 |
| caagcatgaa ccataccaaa gccctggaga gagtgtcata tgctctttta | 750 |
| tttggtgatt acttgccaca gaatatccag gcagcgagag agatgtttga | 800 |
| gaagctgact gaggaaggct ctcccaaggg acagactgct cttggctttc | 850 |
| tgtatgcctc tggacttggt gttaattcaa gtcaggcaaa ggctcttgta | 900 |
| tattatacat ttggagctct tgggggcaat ctaatagccc acatggtttt | 950 |
| ggtaagtaga ctttagtgga aggctaataa tattaacatc agaagaattt | 1000 |
| gtggtttata gcggccacaa cttttttcagc tttcatgatc cagatttgct | 1050 |
| tgtattaaga ccaaatattc agttgaactt ccttcaaatt cttgttaatg | 1100 |
| gatataacac atggaatcta catgtaaatg aaagttggtg gagtccacaa | 1150 |
| tttttctttta aaatgattag tttggctgat tgcccctaaa aagagagatc | 1200 |
| tgataaatgg ctctttttaa attttctctg agttggaatt gtcagaatca | 1250 |
| tttttttacat tagattatca taattttaaa aattttttctt tagttttttca | 1300 |
| aaattttgta aatggtggct atagaaaaac aacatgaaat attatacaat | 1350 |
| attttgcaac aatgccctaa gaattgttaa aattcatgga gttatttgtg | 1400 |
| cagaatgact ccagagagct ctactttctg ttttttactt ttcatgattg | 1450 |
| gctgtcttcc catttattct ggtcatttat tgctagtgac actgtgcctg | 1500 |
| cttccagtag tctcattttc cctatttttgc taatttgtta cttttttcttt | 1550 |
| gctaatttgg aagattaact cattttttaat aaaattatgt ctaagattaa | 1600 |
| aaaaaaaaaa aaaaaaaaaa aaaaaaaaaa aaaaaaaaaa aaaaaaaaaa | 1650 |
| aaaaaaaaaa aaaaaaaaaa aa | 1672 |

<210> SEQ ID NO 18
<211> LENGTH: 301
<212> TYPE: PRT
<213> ORGANISM: Homo Sapien

<400> SEQUENCE: 18

```
Met Arg Val Arg Ile Gly Leu Thr Leu Leu Leu Cys Ala Val Leu
 1               5                  10                  15

Leu Ser Leu Ala Ser Ala Ser Ser Asp Glu Glu Gly Ser Gln Asp
                20                  25                  30

Glu Ser Leu Asp Ser Lys Thr Thr Leu Thr Ser Asp Glu Ser Val
                35                  40                  45

Lys Asp His Thr Thr Ala Gly Arg Val Val Ala Gly Gln Ile Phe
                50                  55                  60

Leu Asp Ser Glu Glu Ser Glu Leu Glu Ser Ser Ile Gln Glu Glu
                65                  70                  75

Glu Asp Ser Leu Lys Ser Gln Glu Gly Glu Ser Val Thr Glu Asp
                80                  85                  90
```

```
Ile Ser Phe Leu Glu Ser Pro Asn Pro Glu Asn Lys Asp Tyr Glu
                95                 100                 105
Glu Pro Lys Lys Val Arg Lys Pro Ala Leu Thr Ala Ile Glu Gly
            110                 115                 120
Thr Ala His Gly Glu Pro Cys His Phe Pro Phe Leu Phe Leu Asp
            125                 130                 135
Lys Glu Tyr Asp Glu Cys Thr Ser Asp Gly Arg Glu Asp Gly Arg
            140                 145                 150
Leu Trp Cys Ala Thr Thr Tyr Asp Tyr Lys Ala Asp Glu Lys Trp
            155                 160                 165
Gly Phe Cys Glu Thr Glu Glu Glu Ala Ala Lys Arg Arg Gln Met
            170                 175                 180
Gln Glu Ala Glu Met Met Tyr Gln Thr Gly Met Lys Ile Leu Asn
            185                 190                 195
Gly Ser Asn Lys Lys Ser Gln Lys Arg Glu Ala Tyr Arg Tyr Leu
            200                 205                 210
Gln Lys Ala Ala Ser Met Asn His Thr Lys Ala Leu Glu Arg Val
            215                 220                 225
Ser Tyr Ala Leu Leu Phe Gly Asp Tyr Leu Pro Gln Asn Ile Gln
            230                 235                 240
Ala Ala Arg Glu Met Phe Glu Lys Leu Thr Glu Glu Gly Ser Pro
            245                 250                 255
Lys Gly Gln Thr Ala Leu Gly Phe Leu Tyr Ala Ser Gly Leu Gly
            260                 265                 270
Val Asn Ser Ser Gln Ala Lys Ala Leu Val Tyr Tyr Thr Phe Gly
            275                 280                 285
Ala Leu Gly Gly Asn Leu Ile Ala His Met Val Leu Val Ser Arg
            290                 295                 300
Leu

<210> SEQ ID NO 19
<211> LENGTH: 1508
<212> TYPE: DNA
<213> ORGANISM: Homo Sapien

<400> SEQUENCE: 19
aattcagatt ttaagcccat tctgcagtgg aatttcatga actagcaaga         50
ggacaccatc ttcttgtatt atacaagaaa ggagtgtacc tatcacacac        100
agggggaaaa atgctctttt gggtgctagg cctcctaatc ctctgtggtt        150
ttctgtggac tcgtaaagga aaactaaaga ttgaagacat cactgataag        200
tacattttta tcactggatg tgactcgggc tttggaaact ggcagccag         250
aacttttgat aaaagggat ttcatgtaat cgctgcctgt ctgactgaat          300
caggatcaac agctttaaag gcagaaacct cagagagact tcgtactgtg        350
cttctggatg tgaccgaccc agagaatgtc aagaggactg cccagtgggt        400
gaagaaccaa gttggggaga aggtctctg ggtctgatc aataatgctg           450
gtgttcccgg cgtgctggct cccactgact ggctgacact agaggactac        500
agagaaccta ttgaagtgaa cctgtttgga ctcatcagtg tgcactaaa         550
tatgcttcct ttggtcaaga agctcaagg gagagttatt aatgtctcca         600
gtgttggagg tcgccttgca atcgttggag gggctatac tccatccaaa         650
tatgcagtgg aaggtttcaa tgacagctta agacgggaca tgaaagcttt        700
```

```
tggtgtgcac gtctcatgca ttgaaccagg attgttcaaa acaaacttgg       750
cagatccagt aaaggtaatt gaaaaaaaac tcgccatttg ggagcagctg       800
tctccagaca tcaaacaaca atatggagaa ggttacattg aaaaaagtct       850
agacaaactg aaaggcaata atcctatgt gaacatggac ctctctccgg        900
tggtagagtg catggaccac gctctaacaa gtctcttccc taagactcat       950
tatgccgctg aaaagatgc caaaattttc tggatacctc tgtctcacat       1000
gccagcagct ttgcaagact ttttattgtt gaaacagaaa gcagagctgg       1050
ctaatcccaa ggcagtgtga ctcagctaac cacaaatgtc tcctccaggc       1100
tatgaaattg ccgatttca gaacacatc tccttttcaa ccccattcct         1150
tatctgctcc aacctggact catttagatc gtgcttattt ggattgcaaa       1200
agggagtccc accatcgctg gtggtatccc agggtccctg ctcaagtttt       1250 cttttgaaaag gagggctgga atggtacatc acataggcaa gtcctgccct      1300
gtatttaggc tttgcctgct tggtgtgatg taagggaaat tgaaagactt       1350
gcccattcaa aatgatcttt accgtggcct gccccatgct tatggtcccc       1400
agcatttaca gtaacttgtg aatgttaagt atcatctctt atctaaatat       1450
taaaagataa gtcaacccaa aaaaaaaaaa aaaaaaaaaa aaaaaaaaaa       1500
aaaaaaaa                                                     1508
```

<210> SEQ ID NO 20
<211> LENGTH: 319
<212> TYPE: PRT
<213> ORGANISM: Homo Sapien

<400> SEQUENCE: 20

```
Met Leu Phe Trp Val Gly Leu Leu Ile Leu Cys Gly Phe Leu
 1               5                  10                  15

Trp Thr Arg Lys Gly Lys Leu Lys Ile Glu Asp Ile Thr Asp Lys
                20                  25                  30

Tyr Ile Phe Ile Thr Gly Cys Asp Ser Gly Phe Gly Asn Leu Ala
                35                  40                  45

Ala Arg Thr Phe Asp Lys Lys Gly Phe His Val Ile Ala Ala Cys
                50                  55                  60

Leu Thr Glu Ser Gly Ser Thr Ala Leu Lys Ala Glu Thr Ser Glu
                65                  70                  75

Arg Leu Arg Thr Val Leu Leu Asp Val Thr Asp Pro Glu Asn Val
                80                  85                  90

Lys Arg Thr Ala Gln Trp Val Lys Asn Gln Val Gly Glu Lys Gly
                95                  100                 105

Leu Trp Gly Leu Ile Asn Asn Ala Gly Val Pro Gly Val Leu Ala
                110                 115                 120

Pro Thr Asp Trp Leu Thr Leu Glu Asp Tyr Arg Glu Pro Ile Glu
                125                 130                 135

Val Asn Leu Phe Gly Leu Ile Ser Val Thr Leu Asn Met Leu Pro
                140                 145                 150

Leu Val Lys Lys Ala Gln Gly Arg Val Ile Asn Val Ser Ser Val
                155                 160                 165

Gly Gly Arg Leu Ala Ile Val Gly Gly Gly Tyr Thr Pro Ser Lys
                170                 175                 180
```

```
Tyr Ala Val Glu Gly Phe Asn Asp Ser Leu Arg Arg Asp Met Lys
            185                 190                 195

Ala Phe Gly Val His Val Ser Cys Ile Glu Pro Gly Leu Phe Lys
        200                 205                 210

Thr Asn Leu Ala Asp Pro Val Lys Val Ile Glu Lys Lys Leu Ala
            215                 220                 225

Ile Trp Glu Gln Leu Ser Pro Asp Ile Lys Gln Gln Tyr Gly Glu
        230                 235                 240

Gly Tyr Ile Glu Lys Ser Leu Asp Lys Leu Lys Gly Asn Lys Ser
            245                 250                 255

Tyr Val Asn Met Asp Leu Ser Pro Val Val Glu Cys Met Asp His
        260                 265                 270

Ala Leu Thr Ser Leu Phe Pro Lys Thr His Tyr Ala Ala Gly Lys
            275                 280                 285

Asp Ala Lys Ile Phe Trp Ile Pro Leu Ser His Met Pro Ala Ala
        290                 295                 300

Leu Gln Asp Phe Leu Leu Leu Lys Gln Lys Ala Glu Leu Ala Asn
            305                 310                 315

Pro Lys Ala Val

<210> SEQ ID NO 21
<211> LENGTH: 1849
<212> TYPE: DNA
<213> ORGANISM: Homo Sapien

<400> SEQUENCE: 21
ctgaggcggc ggtagcatgg agggggagag tacgtcggcg gtgctctcgg              50
gctttgtgct cggcgcactc gctttccagc acctcaacac ggactcggac             100
acggaaggtt ttcttcttgg ggaagtaaaa ggtgaagcca agaacagcat             150
tactgattcc caaatggatg atgttgaagt tgtttataca attgacattc             200
agaaatatat tccatgctat cagcttttta gcttttataa ttcttcaggc             250
gaagtaaatg agcaagcact gaagaaaata ttatcaaatg tcaaaaagaa             300
tgtggtaggt tggtacaaat tccgtcgtca ttcagatcag atcatgacgt             350
ttagagagag gctgcttcac aaaaacttgc aggagcattt ttcaaaccaa             400
gaccttgttt ttctgctatt aacaccaagt ataataacag aaagctgctc             450
tactcatcga ctggaacatt ccttatataa acctcaaaaa ggacttttc              500 acagggtacc tttagtggtt gccaatctgg gcatgtctga caactgggt              550 tataaaactg tatcaggttc ctgtatgtcc actggttta gccgagcagt              600 acaaacacac agctctaaat tttttgaaga agatggatcc ttaaaggagg              650
tacataagat aaatgaaatg tatgcttcat tacaagagga attaaagagt              700
atatgcaaaa aagtggaaga cagtgaacaa gcagtagata aactagtaaa              750
ggatgtaaac agattaaaac gagaaattga gaaaggaga ggagcacaga             800 ttcaggcagc aagagagaag aacatccaaa aagaccctca ggagaacatt              850
tttctttgtc aggcattacg gaccttttt ccaaattctg aatttcttca              900
ttcatgtgtt atgtctttaa aaaatagaca tgtttctaaa agtagctgta              950
actacaacca ccatctcgat gtagtagaca atctgacctt aatggtagaa             1000
cacactgaca ttcctgaagc tagtccagct agtacaccac aaatcattaa             1050
```

```
gcataaagcc ttagacttag atgacagatg gcaattcaag agatctcggt         1100
tgttagatac acaagacaaa cgatctaaag caaatactgg tagtagtaac         1150
caagataaag catccaaaat gagcagccca gaaacagatg aagaaattga         1200
aaagatgaag ggttttggtg aatattcacg gtctcctaca ttttgatcct         1250
tttaacctta caaggagatt ttttatttg gctgatgggt aaagccaaac          1300
atttctattg ttttactat gttgagctac ttgcagtaag ttcatttgtt          1350
tttactatgt tcacctgttt gcagtaatac acagataact cttagtgcat         1400
ttacttcaca aagtactttt tcaaacatca gatgctttta tttccaaacc         1450 ttttttttcac ctttcactaa gttgttgagg ggaaggctta cacagacaca        1500
ttctttagaa ttggaaaagt gagaccaggc acagtggctc acacctgtaa         1550
tcccagcact tagggaagac aagtcaggag gattgattga agctaggagt         1600
tagagaccag cctgggcaac gtattgagac catgtctatt aaaaaataaa         1650
atggaaaagc aagaatagcc ttatttcaa aatatggaaa gaatttata           1700 tgaaaattta tctgagtcat taaaattctc cttaagtgat acttttttag         1750
aagtacatta tggctagagt tgccagataa aatgctggat atcatgcaat         1800
aaatttgcaa aacatcatct aaaatttaaa aaaaaaaaaa aaaaaaaa           1849
```

<210> SEQ ID NO 22
<211> LENGTH: 409
<212> TYPE: PRT
<213> ORGANISM: Homo Sapien

<400> SEQUENCE: 22

```
Met Glu Gly Glu Ser Thr Ser Ala Val Leu Ser Gly Phe Val Leu
 1               5                  10                  15

Gly Ala Leu Ala Phe Gln His Leu Asn Thr Asp Ser Asp Thr Glu
                20                  25                  30

Gly Phe Leu Leu Gly Glu Val Lys Gly Glu Ala Lys Asn Ser Ile
                35                  40                  45

Thr Asp Ser Gln Met Asp Asp Val Glu Val Val Tyr Thr Ile Asp
                50                  55                  60

Ile Gln Lys Tyr Ile Pro Cys Tyr Gln Leu Phe Ser Phe Tyr Asn
                65                  70                  75

Ser Ser Gly Glu Val Asn Glu Gln Ala Leu Lys Lys Ile Leu Ser
                80                  85                  90

Asn Val Lys Lys Asn Val Val Gly Trp Tyr Lys Phe Arg Arg His
                95                 100                 105

Ser Asp Gln Ile Met Thr Phe Arg Glu Arg Leu Leu His Lys Asn
               110                 115                 120

Leu Gln Glu His Phe Ser Asn Gln Asp Leu Val Phe Leu Leu Leu
               125                 130                 135

Thr Pro Ser Ile Ile Thr Glu Ser Cys Ser Thr His Arg Leu Glu
               140                 145                 150

His Ser Leu Tyr Lys Pro Gln Lys Gly Leu Phe His Arg Val Pro
               155                 160                 165

Leu Val Val Ala Asn Leu Gly Met Ser Glu Gln Leu Gly Tyr Lys
               170                 175                 180

Thr Val Ser Gly Ser Cys Met Ser Thr Gly Phe Ser Arg Ala Val
               185                 190                 195
```

-continued

```
Gln Thr His Ser Ser Lys Phe Phe Glu Glu Asp Gly Ser Leu Lys
                200                 205                 210
Glu Val His Lys Ile Asn Glu Met Tyr Ala Ser Leu Gln Glu Glu
                215                 220                 225
Leu Lys Ser Ile Cys Lys Lys Val Glu Asp Ser Glu Gln Ala Val
                230                 235                 240
Asp Lys Leu Val Lys Asp Val Asn Arg Leu Lys Arg Glu Ile Glu
                245                 250                 255
Lys Arg Arg Gly Ala Gln Ile Gln Ala Ala Arg Glu Lys Asn Ile
                260                 265                 270
Gln Lys Asp Pro Gln Glu Asn Ile Phe Leu Cys Gln Ala Leu Arg
                275                 280                 285
Thr Phe Phe Pro Asn Ser Glu Phe Leu His Ser Cys Val Met Ser
                290                 295                 300
Leu Lys Asn Arg His Val Ser Lys Ser Ser Cys Asn Tyr Asn His
                305                 310                 315
His Leu Asp Val Val Asp Asn Leu Thr Leu Met Val Glu His Thr
                320                 325                 330
Asp Ile Pro Glu Ala Ser Pro Ala Ser Thr Pro Gln Ile Ile Lys
                335                 340                 345
His Lys Ala Leu Asp Leu Asp Asp Arg Trp Gln Phe Lys Arg Ser
                350                 355                 360
Arg Leu Leu Asp Thr Gln Asp Lys Arg Ser Lys Ala Asn Thr Gly
                365                 370                 375
Ser Ser Asn Gln Asp Lys Ala Ser Lys Met Ser Ser Pro Glu Thr
                380                 385                 390
Asp Glu Glu Ile Glu Lys Met Lys Gly Phe Gly Glu Tyr Ser Arg
                395                 400                 405
Ser Pro Thr Phe
```

<210> SEQ ID NO 23
<211> LENGTH: 2651
<212> TYPE: DNA
<213> ORGANISM: Homo Sapien

<400> SEQUENCE: 23

| | |
|---|---|
| ggcacagccg cgcggcggag ggcagagtca gccgagccga gtccagccgg | 50 |
| acgagcggac cagcgcaggg cagcccaagc agcgcgcagc gaacgcccgc | 100 |
| cgccgcccac accctctgcg gtccccgcgg cgcctgccac ccttccctcc | 150 |
| ttccccgcgt ccccgcctcg ccggccagtc agcttgccgg gttcgctgcc | 200 |
| ccgcgaaacc ccgaggtcac cagcccgcgc ctctgcttcc ctgggccgcg | 250 |
| cgccgcctcc acgccctcct tctcccctgg cccggcgcct ggcaccgggg | 300 |
| accgttgcct gacgcgaggc ccagctctac ttttcgcccc gcgtctcctc | 350 |
| cgcctgctcg cctcttccac caactccaac tccttctccc tccagctcca | 400 |
| ctcgctagtc cccgactccg ccagccctcg gcccgctgcc gtagcgccgc | 450 |
| ttcccgtccg gtcccaaagg tgggaacgcg tccgccccgg ccgcaccat | 500 |
| ggcacggttc ggcttgcccg cgcttctctg caccctggca gtgctcagcg | 550 |
| ccgcgctgct ggctgccgag ctcaagtcga aagttgctc ggaagtgcga | 600 |
| cgtctttacg tgtccaaagg cttcaacaag aacgatgccc cctccacga | 650 |
| gatcaacggt gatcatttga agatctgtcc ccagggttct acctgctgct | 700 |

-continued

| | |
|---|---|
| ctcaagagat ggaggagaag tacagcctgc aaagtaaaga tgatttcaaa | 750 |
| agtgtggtca gcgaacagtg caatcatttg caagctgtct ttgcttcacg | 800 |
| ttacaagaag tttgatgaat tcttcaaaga actacttgaa aatgcagaga | 850 |
| aatccctgaa tgatatgttt gtgaagacat atggccattt atacatgcaa | 900 |
| aattctgagc tatttaaaga tctcttcgta gagttgaaac gttactacgt | 950 |
| ggtgggaaat gtgaacctgg aagaaatgct aaatgacttc tgggctcgcc | 1000 |
| tcctggagcg gatgttccgc ctggtgaact cccagtacca ctttacagat | 1050 |
| gagtatctgg aatgtgtgag caagtatacg gagcagctga agcccttcgg | 1100 |
| agatgtccct cgcaaattga agctccaggt tactcgtgct tttgtagcag | 1150 |
| cccgtacttt cgctcaaggc ttagcggttg cgggagatgt cgtgagcaag | 1200 |
| gtctccgtgg taaaccccac agcccagtgt acccatgccc tgttgaagat | 1250 |
| gatctactgc tcccactgcc ggggtctcgt gactgtgaag ccatgttaca | 1300 |
| actactgctc aaacatcatg agaggctgtt tggccaacca aggggatctc | 1350 |
| gattttgaat ggaacaattt catagatgct atgctgatgg tggcagagag | 1400 |
| gctagagggt cctttcaaca ttgaatcggt catggatccc atcgatgtga | 1450 |
| agatttctga tgctattatg aacatgcagg ataatagtgt tcaagtgtct | 1500 |
| cagaaggttt tccagggatg tggacccccc aagcccctcc cagctggacg | 1550 |
| aatttctcgt tccatctctg aaagtgcctt cagtgctcgc ttcagaccac | 1600 |
| atcaccccga ggaacgccca accacagcag ctggcactag ttggaccga | 1650 |
| ctggttactg atgtcaagga gaactgaaa caggccaaga aattctggtc | 1700 |
| ctcccttccg agcaacgttt gcaacgatga gaggatggct gcaggaaacg | 1750 |
| gcaatgagga tgactgttgg aatgggaaag gcaaaagcag gtacctgttt | 1800 |
| gcagtgacag gaaatggatt agccaaccag ggcaacaacc cagaggtcca | 1850 |
| ggttgacacc agcaaaccag acatactgat ccttcgtcaa atcatggctc | 1900 |
| ttcgagtgat gaccagcaag atgaagaatg catacaatgg gaacgacgtg | 1950 |
| gacttctttg atatcagtga tgaaagtagt ggagaaggaa gtggaagtgg | 2000 |
| ctgtgagtat cagcagtgcc cttcagagtt tgactacaat gccactgacc | 2050 |
| atgctgggaa gagtgccaat gagaaagccg acagtgctgg tgtccgtcct | 2100 |
| ggggcacagg cctacctcct cactgtcttc tgcatcttgt tcctggttat | 2150 |
| gcagagagag tggagataat tctcaaactc tgagaaaaag tgttcatcaa | 2200 |
| aaagttaaaa ggcaccagtt atcacttttc taccatccta gtgactttgc | 2250 |
| ttttttaaatg aatggacaac aatgtacagt ttttactatg tggccactgg | 2300 |
| tttaagaagt gctgactttg ttttctcatt cagttttggg aggaaaaggg | 2350 |
| actgtgcatt gagttggttc ctgctccccc aaaccatgtt aaacgtggct | 2400 |
| aacagtgtag gtacagaact atagttagtt gtgcatttgt gattttatca | 2450 |
| ctctattatt tgtttgtatg ttttttttctc atttcgtttg tgggtttttt | 2500 |
| tttccaactg tgatctcgcc ttgtttctta caagcaaacc agggtccctt | 2550 |
| cttggcacgt aacatgtacg tatttctgaa atattaaata gctgtacaga | 2600 |
| agcaggtttt atttatcatg ttatcttatt aaaagaaaaa gcccaaaaag | 2650 |

-continued

<210> SEQ ID NO 24
<211> LENGTH: 556
<212> TYPE: PRT
<213> ORGANISM: Homo Sapien

<400> SEQUENCE: 24

Met Ala Arg Phe Gly Leu Pro Ala Leu Leu Cys Thr Leu Ala Val
1               5                   10                  15

Leu Ser Ala Ala Leu Leu Ala Ala Glu Leu Lys Ser Lys Ser Cys
            20                  25                  30

Ser Glu Val Arg Arg Leu Tyr Val Ser Lys Gly Phe Asn Lys Asn
            35                  40                  45

Asp Ala Pro Leu His Glu Ile Asn Gly Asp His Leu Lys Ile Cys
            50                  55                  60

Pro Gln Gly Ser Thr Cys Cys Ser Gln Glu Met Glu Glu Lys Tyr
            65                  70                  75

Ser Leu Gln Ser Lys Asp Asp Phe Lys Ser Val Val Ser Glu Gln
            80                  85                  90

Cys Asn His Leu Gln Ala Val Phe Ala Ser Arg Tyr Lys Lys Phe
            95                  100                 105

Asp Glu Phe Phe Lys Glu Leu Leu Glu Asn Ala Glu Lys Ser Leu
            110                 115                 120

Asn Asp Met Phe Val Lys Thr Tyr Gly His Leu Tyr Met Gln Asn
            125                 130                 135

Ser Glu Leu Phe Lys Asp Leu Phe Val Glu Leu Lys Arg Tyr Tyr
            140                 145                 150

Val Val Gly Asn Val Asn Leu Glu Glu Met Leu Asn Asp Phe Trp
            155                 160                 165

Ala Arg Leu Leu Glu Arg Met Phe Arg Leu Val Asn Ser Gln Tyr
            170                 175                 180

His Phe Thr Asp Glu Tyr Leu Glu Cys Val Ser Lys Tyr Thr Glu
            185                 190                 195

Gln Leu Lys Pro Phe Gly Asp Val Pro Arg Lys Leu Lys Leu Gln
            200                 205                 210

Val Thr Arg Ala Phe Val Ala Arg Thr Phe Ala Gln Gly Leu
            215                 220                 225

Ala Val Ala Gly Asp Val Val Ser Lys Val Ser Val Val Asn Pro
            230                 235                 240

Thr Ala Gln Cys Thr His Ala Leu Leu Lys Met Ile Tyr Cys Ser
            245                 250                 255

His Cys Arg Gly Leu Val Thr Val Lys Pro Cys Tyr Asn Tyr Cys
            260                 265                 270

Ser Asn Ile Met Arg Gly Cys Leu Ala Asn Gln Gly Asp Leu Asp
            275                 280                 285

Phe Glu Trp Asn Asn Phe Ile Asp Ala Met Leu Met Val Ala Glu
            290                 295                 300

Arg Leu Glu Gly Pro Phe Asn Ile Glu Ser Val Met Asp Pro Ile
            305                 310                 315

Asp Val Lys Ile Ser Asp Ala Ile Met Asn Met Gln Asp Asn Ser
            320                 325                 330

Val Gln Val Ser Gln Lys Val Phe Gln Gly Cys Gly Pro Pro Lys
            335                 340                 345

-continued

| | | | | | | | | | | |
|---|---|---|---|---|---|---|---|---|---|---|
|Pro|Leu|Pro|Ala|Gly<br>350|Arg|Ile|Ser|Arg|Ser<br>355|Ile Ser Glu Ser Ala<br>360|

Pro Leu Pro Ala Gly Arg Ile Ser Arg Ser Ile Ser Glu Ser Ala
                  350                           355                   360

Phe Ser Ala Arg Phe Arg Pro His His Pro Glu Glu Arg Pro Thr
                  365                           370                   375

Thr Ala Ala Gly Thr Ser Leu Asp Arg Leu Val Thr Asp Val Lys
                  380                           385                   390

Glu Lys Leu Lys Gln Ala Lys Lys Phe Trp Ser Ser Leu Pro Ser
                  395                           400                   405

Asn Val Cys Asn Asp Glu Arg Met Ala Ala Gly Asn Gly Asn Glu
                  410                           415                   420

Asp Asp Cys Trp Asn Gly Lys Gly Lys Ser Arg Tyr Leu Phe Ala
                  425                           430                   435

Val Thr Gly Asn Gly Leu Ala Asn Gln Gly Asn Asn Pro Glu Val
                  440                           445                   450

Gln Val Asp Thr Ser Lys Pro Asp Ile Leu Ile Leu Arg Gln Ile
                  455                           460                   465

Met Ala Leu Arg Val Met Thr Ser Lys Met Lys Asn Ala Tyr Asn
                  470                           475                   480

Gly Asn Asp Val Asp Phe Phe Asp Ile Ser Asp Glu Ser Ser Gly
                  485                           490                   495

Glu Gly Ser Gly Ser Gly Cys Glu Tyr Gln Gln Cys Pro Ser Glu
                  500                           505                   510

Phe Asp Tyr Asn Ala Thr Asp His Ala Gly Lys Ser Ala Asn Glu
                  515                           520                   525

Lys Ala Asp Ser Ala Gly Val Arg Pro Gly Ala Gln Ala Tyr Leu
                  530                           535                   540

Leu Thr Val Phe Cys Ile Leu Phe Leu Val Met Gln Arg Glu Trp
                  545                           550                   555

Arg

<210> SEQ ID NO 25
<211> LENGTH: 870
<212> TYPE: DNA
<213> ORGANISM: Homo Sapien

<400> SEQUENCE: 25

| | | |
|---|---|---|
|ctcgccctca aatgggaacg ctggcctggg actaaagcat agaccaccag|  |50|
|gctgagtatc ctgacctgag tcatccccag ggatcaggag cctccagcag|  |100|
|ggaaccttcc attatattct tcaagcaact tacagctgca ccgacagttg|  |150|
|cgatgaaagt tctaatctct tccctcctcc tgttgctgcc actaatgctg|  |200|
|atgtccatgg tctctagcag cctgaatcca ggggtcgcca gaggccacag|  |250|
|ggaccgaggc caggcttcta ggagatggct ccaggaaggc ggccaagaat|  |300|
|gtgagtgcaa agattggttc ctgagagccc cgagaagaaa attcatgaca|  |350|
|gtgtctgggc tgccaaagaa gcagtgcccc tgtgatcatt tcaagggcaa|  |400|
|tgtgaagaaa acaagacacc aaaggcacca cagaaagcca acaagcatt|  |450|
|ccagagcctg ccagcaattt ctcaaacaat gtcagctaag aagctttgct|  |500|
|ctgcctttgt aggagctctg agcgcccact cttccaatta acattctca|  |550|
|gccaagaaga cagtgagcac acctaccaga cactcttctt ctcccacctc|  |600|
|actctcccac tgtacccacc ctaaatcat tccagtgctc tcaaaagca|  |650|
|tgttttttcaa gatcattttg tttgttgctc tctctagtgt cttcttctct|  |700|

| | |
|---|---|
| cgtcagtctt agcctgtgcc ctccccttac ccaggcttag gcttaattac | 750 |
| ctgaaagatt ccaggaaact gtagcttcct agctagtgtc atttaacctt | 800 |
| aaatgcaatc aggaaagtag caaacagaag tcaataaata tttttaaatg | 850 |
| tcaaaaaaaa aaaaaaaaa | 870 |

<210> SEQ ID NO 26
<211> LENGTH: 119
<212> TYPE: PRT
<213> ORGANISM: Homo Sapien

<400> SEQUENCE: 26

```
Met Lys Val Leu Ile Ser Ser Leu Leu Leu Pro Leu Met
 1               5                  10              15

Leu Met Ser Met Val Ser Ser Leu Asn Pro Gly Val Ala Arg
                20                  25              30

Gly His Arg Asp Arg Gly Gln Ala Ser Arg Arg Trp Leu Gln Glu
                35                  40              45

Gly Gly Gln Glu Cys Glu Cys Lys Asp Trp Phe Leu Arg Ala Pro
        50                  55                      60

Arg Arg Lys Phe Met Thr Val Ser Gly Leu Pro Lys Lys Gln Cys
        65                      70                      75

Pro Cys Asp His Phe Lys Gly Asn Val Lys Lys Thr Arg His Gln
                80                      85              90

Arg His His Arg Lys Pro Asn Lys His Ser Arg Ala Cys Gln Gln
                95                      100             105

Phe Leu Lys Gln Cys Gln Leu Arg Ser Phe Ala Leu Pro Leu
                110                     115
```

<210> SEQ ID NO 27
<211> LENGTH: 1371
<212> TYPE: DNA
<213> ORGANISM: Homo Sapien

<400> SEQUENCE: 27

| | |
|---|---|
| ggacgccagc gcctgcagag gctgagcagg gaaaaagcca gtgccccagc | 50 |
| ggaagcacag ctcagagctg gtctgccatg acatcctgg tcccactcct | 100 |
| gcagctgctg gtgctgcttc ttaccctgcc cctgcacctc atggctctgc | 150 |
| tgggctgctg gcagcccctg tgcaaaagct acttccccta cctgatggcc | 200 |
| gtgctgactc ccaagagcaa ccgcaagatg gagagcaaga acgggagct | 250 |
| cttcagccag ataaagggggc ttacaggagc ctccgggaaa gtggccctac | 300 |
| tggagctggg ctgcggaacc ggagccaact ttcagttcta cccaccgggc | 350 |
| tgcagggtca cctgcctaga cccaaatccc cactttgaga agttcctgac | 400 |
| aaagagcatg gctgagaaca ggcacctcca atatgagcgg tttgtggtgg | 450 |
| ctcctggaga ggacatgaga cagctggctg atggctccat ggatgtggtg | 500 |
| gtctgcactc tggtgctgtg ctctgtgcag agcccaagga aggtcctgca | 550 |
| ggaggtccgg agagtactga gaccgggagg tgtgctcttt ttctgggagc | 600 |
| atgtggcaga accatatgga agctgggcct tcatgtggca gcaagttttc | 650 |
| gagcccacct ggaaacacat tgggatggc tgctgcctca ccagagagac | 700 |
| ctggaaggat cttgagaacg cccagttctc cgaaatccaa atggaacgac | 750 |

-continued

| | |
|---|---|
| agcccctcc cttgaagtgg ctacctgttg ggccccacat catgggaaag | 800 |
| gctgtcaaac aatctttccc aagctccaag gcactcattt gctccttccc | 850 |
| cagcctccaa ttagaacaag ccacccacca gcctatctat cttccactga | 900 |
| gagggaccta gcagaatgag agaagacatt catgtaccac ctactagtcc | 950 |
| ctctctcccc aacctctgcc agggcaatct ctaacttcaa tcccgccttc | 1000 |
| gacagtgaaa aagctctact tctacgctga cccagggagg aaacactagg | 1050 |
| accctgttgt atcctcaact gcaagtttct ggactagtct cccaacgttt | 1100 |
| gcctcccaat gttgtcccttt tccttcgttc ccatggtaaa gctcctctcg | 1150 |
| ctttcctcct gaggctacac ccatgcgtct ctaggaactg gtcacaaaag | 1200 |
| tcatggtgcc tgcatccctg ccaagccccc ctgaccctct ctccccacta | 1250 |
| ccaccttctt cctgagctgg gggcaccagg gagaatcaga gatgctgggg | 1300 |
| atgccagagc aagactcaaa gaggcagagg ttttgttctc aaatattttt | 1350 |
| taataaatag acgaaaccac g | 1371 |

<210> SEQ ID NO 28
<211> LENGTH: 277
<212> TYPE: PRT
<213> ORGANISM: Homo Sapien

<400> SEQUENCE: 28

```
Met Asp Ile Leu Val Pro Leu Gln Leu Leu Val Leu Leu
  1               5                  10              15

Thr Leu Pro Leu His Leu Met Ala Leu Leu Gly Cys Trp Gln Pro
             20                  25                  30

Leu Cys Lys Ser Tyr Phe Pro Tyr Leu Met Ala Val Leu Thr Pro
             35                  40                  45

Lys Ser Asn Arg Lys Met Glu Ser Lys Lys Arg Glu Leu Phe Ser
             50                  55                  60

Gln Ile Lys Gly Leu Thr Gly Ala Ser Gly Lys Val Ala Leu Leu
             65                  70                  75

Glu Leu Gly Cys Gly Thr Gly Ala Asn Phe Gln Phe Tyr Pro Pro
             80                  85                  90

Gly Cys Arg Val Thr Cys Leu Asp Pro Asn Pro His Phe Glu Lys
             95                 100                 105

Phe Leu Thr Lys Ser Met Ala Glu Asn Arg His Leu Gln Tyr Glu
            110                 115                 120

Arg Phe Val Val Ala Pro Gly Glu Asp Met Arg Gln Leu Ala Asp
            125                 130                 135

Gly Ser Met Asp Val Val Cys Thr Leu Val Leu Cys Ser Val
            140                 145                 150

Gln Ser Pro Arg Lys Val Leu Gln Glu Val Arg Arg Val Leu Arg
            155                 160                 165

Pro Gly Gly Val Leu Phe Phe Trp Glu His Val Ala Glu Pro Tyr
            170                 175                 180

Gly Ser Trp Ala Phe Met Trp Gln Gln Val Phe Glu Pro Thr Trp
            185                 190                 195

Lys His Ile Gly Asp Gly Cys Cys Leu Thr Arg Glu Thr Trp Lys
            200                 205                 210

Asp Leu Glu Asn Ala Gln Phe Ser Glu Ile Gln Met Glu Arg Gln
            215                 220                 225
```

```
Pro Pro Pro Leu Lys Trp Leu Pro Val Gly Pro His Ile Met Gly
            230                 235                 240

Lys Ala Val Lys Gln Ser Phe Pro Ser Ser Lys Ala Leu Ile Cys
            245                 250                 255

Ser Phe Pro Ser Leu Gln Leu Glu Gln Ala Thr His Gln Pro Ile
            260                 265                 270

Tyr Leu Pro Leu Arg Gly Thr
            275

<210> SEQ ID NO 29
<211> LENGTH: 494
<212> TYPE: DNA
<213> ORGANISM: Homo Sapien

<400> SEQUENCE: 29
caatgtttgc ctatccacct cccccaagcc cctttaccta tgctgctgct        50
aacgctgctg ctgctgctgc tgctgcttaa aggctcatgc ttggagtggg       100
gactggtcgg tgcccagaaa gtctcttctg ccactgacgc ccccatcagg       150
gattgggcct tctttccccc ttcctttctg tgtctcctgc ctcatcggcc       200
tgccatgacc tgcagccaag cccagccccg tggggaaggg gagaaagtgg       250
gggatggcta gaaagctgga gatagggaa acagaagagg gtagtgggtg       300
ggctaggggg gctgccttat ttaaagtggt tgtttatgat tcttatacta       350
atttatacaa agatattaag gccctgttca ttaagaaatt gttcccttcc       400
cctgtgttca atgtttgtaa agattgttct gtgtaaatat gtctttataa       450
taaacagtta aaagctgaaa aaaaaaaaaa aaaaaaaaaa aaaa            494

<210> SEQ ID NO 30
<211> LENGTH: 73
<212> TYPE: PRT
<213> ORGANISM: Homo Sapien

<400> SEQUENCE: 30

Met Leu Leu Leu Thr Leu Leu Leu Leu Leu Leu Leu Leu Lys Gly
 1               5                  10                  15

Ser Cys Leu Glu Trp Gly Leu Val Gly Ala Gln Lys Val Ser Ser
                20                  25                  30

Ala Thr Asp Ala Pro Ile Arg Asp Trp Ala Phe Phe Pro Pro Ser
                35                  40                  45

Phe Leu Cys Leu Leu Pro His Arg Pro Ala Met Thr Cys Ser Gln
                50                  55                  60

Ala Gln Pro Arg Gly Glu Gly Glu Lys Val Gly Asp Gly
                65                  70

<210> SEQ ID NO 31
<211> LENGTH: 1660
<212> TYPE: DNA
<213> ORGANISM: Homo Sapien

<400> SEQUENCE: 31
gtttgaattc cttcaactat acccacagtc caaaagcaga ctcactgtgt        50
cccaggctac cagttcctcc aagcaagtca tttcccttat ttaaccgatg       100
tgtccctcaa acacctgagt gctactccct atttgcatct gttttgataa       150
atgatgttga caccctccac cgaattctaa gtggaatcat gtcgggaaga       200
```

-continued

| | |
|---|---|
| gatacaatcc ttggcctgtg tatcctcgca ttagccttgt ctttggccat | 250 |
| gatgtttacc ttcagattca tcaccaccct tctggttcac attttcattt | 300 |
| cattggttat tttgggattg ttgtttgtct gcggtgtttt atggtggctg | 350 |
| tattatgact ataccaacga cctcagcata gaattggaca cagaaaggga | 400 |
| aaatatgaag tgcgtgctgg ggtttgctat cgtatccaca ggcatcacgg | 450 |
| cagtgctgct cgtcttgatt tttgttctca gaaagagaat aaaattgaca | 500 |
| gttgagcttt tccaaatcac aaataaagcc atcagcagtg ctcccttcct | 550 |
| gctgttccag ccactgtgga catttgccat cctcattttc ttctgggtcc | 600 |
| tctgggtggc tgtgctgctg agcctgggaa ctgcaggagc tgcccaggtt | 650 |
| atggaaggcg gccaagtgga atataagccc ctttcgggca ttcggtacat | 700 |
| gtggtcgtac catttaattg gcctcatctg gactagtgaa ttcatccttg | 750 |
| cgtgccagca aatgactata gctggggcag tggttacttg ttatttcaac | 800 |
| agaagtaaaa atgatcctcc tgatcatccc atcctttcgt ctctctccat | 850 |
| tctcttcttc taccatcaag gaaccgttgt gaaagggtta ttttaatct | 900 |
| ctgtggtgag gattccgaga atcattgtca tgtacatgca aaacgcactg | 950 |
| aaagaacagc agcatggtgc attgtccagg tacctgttcc gatgctgcta | 1000 |
| ctgctgtttc tggtgtcttg acaaatacct gctccatctc aaccagaatg | 1050 |
| catatactac aactgctatt aatgggacag atttctgtac atcagcaaaa | 1100 |
| gatgcattca aaatcttgtc caagaactca agtcacttta catctattaa | 1150 |
| ctgctttgga gacttcataa ttttttctagg aaaggtgtta gtggtgtgtt | 1200 |
| tcactgtttt tggaggactc atggctttta actacaatcg ggcattccag | 1250 |
| gtgtgggcag tccctctgtt attggtagct ttttttgcct acttagtagc | 1300 |
| ccatagtttt ttatctgtgt ttgaaactgt gctggatgca cttttcctgt | 1350 |
| gttttgctgt tgatctggaa acaaatgatg gatcgtcaga aaagccctac | 1400 |
| tttatggatc aagaatttct gagtttcgta aaaaggagca acaaattaaa | 1450 |
| caatgcaagg gcacagcagg acaagcactc attaaggaat gaggagggaa | 1500 |
| cagaactcca ggccattgtg agatagatac ccatttaggt atctgtacct | 1550 |
| ggaaaacatt tccttctaag agccatttac agaatagaag atgagaccac | 1600 |
| tagagaaaag ttagtgaatt ttttttttaaa agacctaata aaccctattc | 1650 |
| ttcctcaaaa | 1660 |

<210> SEQ ID NO 32
<211> LENGTH: 445
<212> TYPE: PRT
<213> ORGANISM: Homo Sapien

<400> SEQUENCE: 32

```
Met Ser Gly Arg Asp Thr Ile Leu Gly Leu Cys Ile Leu Ala Leu
 1               5                  10                  15

Ala Leu Ser Leu Ala Met Met Phe Thr Phe Arg Phe Ile Thr Thr
                20                  25                  30

Leu Leu Val His Ile Phe Ile Ser Leu Val Ile Leu Gly Leu Leu
                35                  40                  45

Phe Val Cys Gly Val Leu Trp Trp Leu Tyr Tyr Asp Tyr Thr Asn
                50                  55                  60
```

-continued

```
Asp Leu Ser Ile Glu Leu Asp Thr Arg Glu Asn Met Lys Cys
             65                  70                  75

Val Leu Gly Phe Ala Ile Val Ser Thr Gly Ile Thr Ala Val Leu
                 80                  85                  90

Leu Val Leu Ile Phe Val Leu Arg Lys Arg Ile Lys Leu Thr Val
                 95                 100                 105

Glu Leu Phe Gln Ile Thr Asn Lys Ala Ile Ser Ser Ala Pro Phe
                110                 115                 120

Leu Leu Phe Gln Pro Leu Trp Thr Phe Ala Ile Leu Ile Phe Phe
                125                 130                 135

Trp Val Leu Trp Val Ala Val Leu Leu Ser Leu Gly Thr Ala Gly
                140                 145                 150

Ala Ala Gln Val Met Glu Gly Gly Gln Val Glu Tyr Lys Pro Leu
                155                 160                 165

Ser Gly Ile Arg Tyr Met Trp Ser Tyr His Leu Ile Gly Leu Ile
                170                 175                 180

Trp Thr Ser Glu Phe Ile Leu Ala Cys Gln Gln Met Thr Ile Ala
                185                 190                 195

Gly Ala Val Val Thr Cys Tyr Phe Asn Arg Ser Lys Asn Asp Pro
                200                 205                 210

Pro Asp His Pro Ile Leu Ser Ser Leu Ser Ile Leu Phe Phe Tyr
                215                 220                 225

His Gln Gly Thr Val Val Lys Gly Ser Phe Leu Ile Ser Val Val
                230                 235                 240

Arg Ile Pro Arg Ile Ile Val Met Tyr Met Gln Asn Ala Leu Lys
                245                 250                 255

Glu Gln Gln His Gly Ala Leu Ser Arg Tyr Leu Phe Arg Cys Cys
                260                 265                 270

Tyr Cys Cys Phe Trp Cys Leu Asp Lys Tyr Leu Leu His Leu Asn
                275                 280                 285

Gln Asn Ala Tyr Thr Thr Thr Ala Ile Asn Gly Thr Asp Phe Cys
                290                 295                 300

Thr Ser Ala Lys Asp Ala Phe Lys Ile Leu Ser Lys Asn Ser Ser
                305                 310                 315

His Phe Thr Ser Ile Asn Cys Phe Gly Asp Phe Ile Ile Phe Leu
                320                 325                 330

Gly Lys Val Leu Val Val Cys Phe Thr Val Phe Gly Gly Leu Met
                335                 340                 345

Ala Phe Asn Tyr Asn Arg Ala Phe Gln Val Trp Ala Val Pro Leu
                350                 355                 360

Leu Leu Val Ala Phe Phe Ala Tyr Leu Val Ala His Ser Phe Leu
                365                 370                 375

Ser Val Phe Glu Thr Val Leu Asp Ala Leu Phe Leu Cys Phe Ala
                380                 385                 390

Val Asp Leu Glu Thr Asn Asp Gly Ser Ser Glu Lys Pro Tyr Phe
                395                 400                 405

Met Asp Gln Glu Phe Leu Ser Phe Val Lys Arg Ser Asn Lys Leu
                410                 415                 420

Asn Asn Ala Arg Ala Gln Gln Asp Lys His Ser Leu Arg Asn Glu
                425                 430                 435

Glu Gly Thr Glu Leu Gln Ala Ile Val Arg
                440                 445
```

-continued

<210> SEQ ID NO 33
<211> LENGTH: 2773
<212> TYPE: DNA
<213> ORGANISM: Homo Sapien

<400> SEQUENCE: 33

| | |
|---|---|
| gttcgattag ctcctctgag aagaagagaa aaggttcttg gacctctccc | 50 |
| tgtttcttcc ttagaataat ttgtatggga tttgtgatgc aggaaagcct | 100 |
| aagggaaaaa gaatattcat tctgtgtggt gaaaattttt tgaaaaaaaa | 150 |
| attgccttct tcaaacaagg gtgtcattct gatatttatg aggactgttg | 200 |
| ttctcactat gaaggcatct gttattgaaa tgttccttgt tttgctggtg | 250 |
| actggagtac attcaaacaa agaaacggca agaagatta aaaggcccaa | 300 |
| gttcactgtg cctcagatca actgcgatgt caaagccgga agatcatcg | 350 |
| atcctgagtt cattgtgaaa tgtccagcag gatgccaaga ccccaaatac | 400 |
| catgtttatg gcactgacgt gtatgcatcc tactccagtg tgtgtggcgc | 450 |
| tgccgtacac agtggtgtgc ttgataattc aggagggaaa atacttgttc | 500 |
| ggaaggttgc tggacagtct ggttacaaag ggagttattc caacggtgtc | 550 |
| caatcgttat ccctaccacg atggagagaa tcctttatcg tcttagaaag | 600 |
| taaacccaaa aagggtgtaa cctacccatc agctcttaca tactcatcat | 650 |
| cgaaaagtcc agctgcccaa gcaggtgaga ccacaaaagc ctatcagagg | 700 |
| ccacctattc cagggacaac tgcacagccg gtcactctga tgcagcttct | 750 |
| ggctgtcact gtagctgtgg ccacccccac caccttgcca aggccatccc | 800 |
| cttctgctgc ttctaccacc agcatcccca gaccacaatc agtgggccac | 850 |
| aggagccagg agatggatct ctggtccact gccacctaca caagcagcca | 900 |
| aaacaggccc agagctgatc caggtatcca aaggcaagat ccttcaggag | 950 |
| ctgccttcca gaaacctgtt ggagcggatg tcagcctggg acttgttcca | 1000 |
| aaagaagaat tgagcacaca gtctttggag ccagtatccc tgggagatcc | 1050 |
| aaactgcaaa attgacttgt cgttttaat tgatgggagc accagcattg | 1100 |
| gcaaacggcg attccgaatc cagaagcagc tcctggctga tgttgcccaa | 1150 |
| gctcttgaca ttggccctgc cggtccactg atgggtgttg tccagtatgg | 1200 |
| agacaaccct gctactcact ttaacctcaa gacacacacg aattctcgag | 1250 |
| atctgaagac agccatagag aaaattactc agagaggagg actttctaat | 1300 |
| gtaggtcggg ccatctcctt tgtgaccaag aacttctttt ccaaagccaa | 1350 |
| tggaaacaga agcggggctc ccaatgtggt ggtggtgatg gtggatggct | 1400 |
| ggcccacgga caaagtggag gaggcttcaa gacttgcgag agagtcagga | 1450 |
| atcaacattt tcttcatcac cattgaaggt gctgctgaaa atgagaagca | 1500 |
| gtatgtggtg gagcccaact tgcaaacaa ggccgtgtgc agaacaaacg | 1550 |
| gcttctactc gctccacgtg cagagctggt ttggcctcca caagaccctg | 1600 |
| cagcctctgg tgaagcgggt ctgcgacact gaccgcctgg cctgcagcaa | 1650 |
| gacctgcttg aactcggctg acattggctt cgtcatcgac ggctccagca | 1700 |
| gtgtggggac gggcaacttc cgcaccgtcc tccagtttgt gaccaaccct | 1750 |
| accaaagagt ttgagatttc cgacacggac acgcgcatcg gggccgtgca | 1800 |

```
gtacacctac gaacagcggc tggagtttgg gttcgacaag tacagcagca         1850
agcctgacat cctcaacgcc atcaagaggg tgggctactg gagtggtggc         1900
accagcacgg gggctgccat caacttcgcc ctggagcagc tcttcaagaa         1950
gtccaagccc aacaagagga agttaatgat cctcatcacc gacgggaggt         2000
cctacgacga cgtccggatc ccagccatgg ctgcccatct gaagggagtg         2050
atcacctatg cgataggcgt tgcctgggct gcccaagagg agctagaagt         2100
cattgccact caccccgcca gagaccactc cttctttgtg gacgagtttg         2150
acaacctcca tcagtatgtc cccaggatca tccagaacat ttgtacagag         2200
ttcaactcac agcctcggaa ctgaattcag agcaggcaga gcaccagcaa         2250
gtgctgcttt actaactgac gtgttggacc accccaccgc ttaatggggc         2300
acgcacggtg catcaagtct tgggcagggc atggagaaac aaatgtcttg         2350
ttattattct ttgccatcat gcttttcat attccaaaac ttggagttac          2400
aaagatgatc acaaacgtat agaatgagcc aaaaggctac atcatgttga         2450
gggtgctgga gattttacat tttgacaatt gttttcaaaa taaatgttcg         2500
gaatacagtg cagcccttac gacaggctta cgtagagctt ttgtgagatt         2550
tttaagttgt tatttctgat ttgaactctg taaccctcag caagtttcat         2600
ttttgtcatg acaatgtagg aattgctgaa ttaaatgttt agaaggatga         2650
aaaataaaaa aaaaaaaaaa aaaaaaaaaa aaaaaaaaaa aaaaaaaaaa         2700
aaaaaaaaaa aaaaaaaaaa aaaaaaaaaa aaaaaaaaaa aaaaaaaaaa         2750
aaaaaaaaaa aaaaaaaaaa aag                                      2773

<210> SEQ ID NO 34
<211> LENGTH: 678
<212> TYPE: PRT
<213> ORGANISM: Homo Sapien

<400> SEQUENCE: 34

Met Arg Thr Val Val Leu Thr Met Lys Ala Ser Val Ile Glu Met
 1               5                  10                  15

Phe Leu Val Leu Leu Val Thr Gly Val His Ser Asn Lys Glu Thr
                20                  25                  30

Ala Lys Lys Ile Lys Arg Pro Lys Phe Thr Val Pro Gln Ile Asn
                35                  40                  45

Cys Asp Val Lys Ala Gly Lys Ile Ile Asp Pro Glu Phe Ile Val
                50                  55                  60

Lys Cys Pro Ala Gly Cys Gln Asp Pro Lys Tyr His Val Tyr Gly
                65                  70                  75

Thr Asp Val Tyr Ala Ser Tyr Ser Ser Val Cys Gly Ala Ala Val
                80                  85                  90

His Ser Gly Val Leu Asp Asn Ser Gly Gly Lys Ile Leu Val Arg
                95                 100                 105

Lys Val Ala Gly Gln Ser Gly Tyr Lys Gly Ser Tyr Ser Asn Gly
               110                 115                 120

Val Gln Ser Leu Ser Leu Pro Arg Trp Arg Glu Ser Phe Ile Val
               125                 130                 135

Leu Glu Ser Lys Pro Lys Lys Gly Val Thr Tyr Pro Ser Ala Leu
               140                 145                 150
```

```
Thr Tyr Ser Ser Ser Lys Ser Pro Ala Ala Gln Ala Gly Glu Thr
                155                 160                 165

Thr Lys Ala Tyr Gln Arg Pro Pro Ile Pro Gly Thr Thr Ala Gln
            170                 175                 180

Pro Val Thr Leu Met Gln Leu Leu Ala Val Thr Val Ala Val Ala
        185                 190                 195

Thr Pro Thr Thr Leu Pro Arg Pro Ser Pro Ala Ala Ser Thr
    200                 205                 210

Thr Ser Ile Pro Arg Pro Gln Ser Val Gly His Arg Ser Gln Glu
            215                 220                 225

Met Asp Leu Trp Ser Thr Ala Thr Tyr Thr Ser Ser Gln Asn Arg
            230                 235                 240

Pro Arg Ala Asp Pro Gly Ile Gln Arg Gln Asp Pro Ser Gly Ala
            245                 250                 255

Ala Phe Gln Lys Pro Val Gly Ala Asp Val Ser Leu Gly Leu Val
            260                 265                 270

Pro Lys Glu Glu Leu Ser Thr Gln Ser Leu Glu Pro Val Ser Leu
            275                 280                 285

Gly Asp Pro Asn Cys Lys Ile Asp Leu Ser Phe Leu Ile Asp Gly
            290                 295                 300

Ser Thr Ser Ile Gly Lys Arg Arg Phe Arg Ile Gln Lys Gln Leu
            305                 310                 315

Leu Ala Asp Val Ala Gln Ala Leu Asp Ile Gly Pro Ala Gly Pro
            320                 325                 330

Leu Met Gly Val Val Gln Tyr Gly Asp Asn Pro Ala Thr His Phe
            335                 340                 345

Asn Leu Lys Thr His Thr Asn Ser Arg Asp Leu Lys Thr Ala Ile
            350                 355                 360

Glu Lys Ile Thr Gln Arg Gly Gly Leu Ser Asn Val Gly Arg Ala
            365                 370                 375

Ile Ser Phe Val Thr Lys Asn Phe Phe Ser Lys Ala Asn Gly Asn
            380                 385                 390

Arg Ser Gly Ala Pro Asn Val Val Val Met Val Asp Gly Trp
            395                 400                 405

Pro Thr Asp Lys Val Glu Glu Ala Ser Arg Leu Ala Arg Glu Ser
            410                 415                 420

Gly Ile Asn Ile Phe Phe Ile Thr Ile Glu Gly Ala Ala Glu Asn
            425                 430                 435

Glu Lys Gln Tyr Val Val Glu Pro Asn Phe Ala Asn Lys Ala Val
            440                 445                 450

Cys Arg Thr Asn Gly Phe Tyr Ser Leu His Val Gln Ser Trp Phe
            455                 460                 465

Gly Leu His Lys Thr Leu Gln Pro Leu Val Lys Arg Val Cys Asp
            470                 475                 480

Thr Asp Arg Leu Ala Cys Ser Lys Thr Cys Leu Asn Ser Ala Asp
            485                 490                 495

Ile Gly Phe Val Ile Asp Gly Ser Ser Val Gly Thr Gly Asn
            500                 505                 510

Phe Arg Thr Val Leu Gln Phe Val Thr Asn Leu Thr Lys Glu Phe
            515                 520                 525

Glu Ile Ser Asp Thr Asp Thr Arg Ile Gly Ala Val Gln Tyr Thr
            530                 535                 540

Tyr Glu Gln Arg Leu Glu Phe Gly Phe Asp Lys Tyr Ser Ser Lys
```

-continued

```
                    545                 550                 555
Pro Asp Ile Leu Asn Ala Ile Lys Arg Val Gly Tyr Trp Ser Gly
                560                 565                 570
Gly Thr Ser Thr Gly Ala Ala Ile Asn Phe Ala Leu Glu Gln Leu
                575                 580                 585
Phe Lys Lys Ser Lys Pro Asn Lys Arg Lys Leu Met Ile Leu Ile
                590                 595                 600
Thr Asp Gly Arg Ser Tyr Asp Asp Val Arg Ile Pro Ala Met Ala
                605                 610                 615
Ala His Leu Lys Gly Val Ile Thr Tyr Ala Ile Gly Val Ala Trp
                620                 625                 630
Ala Ala Gln Glu Glu Leu Glu Val Ile Ala Thr His Pro Ala Arg
                635                 640                 645
Asp His Ser Phe Phe Val Asp Glu Phe Asp Asn Leu His Gln Tyr
                650                 655                 660
Val Pro Arg Ile Ile Gln Asn Ile Cys Thr Glu Phe Asn Ser Gln
                665                 670                 675
Pro Arg Asn

<210> SEQ ID NO 35
<211> LENGTH: 2095
<212> TYPE: DNA
<213> ORGANISM: Homo Sapien

<400> SEQUENCE: 35
ccgagcacag gagattgcct gcgtttagga ggtggctgcg ttgtgggaaa              50
agctatcaag gaagaaattg ccaaaccatg tcttttttc tgttttcaga             100 gtagttcaca acagatctga gtgttttaat taagcatgga atacagaaaa            150
caacaaaaaa cttaagcttt aatttcatct ggaattccac agttttctta            200
gctccctgga cccggttgac ctgttggctc ttcccgctgg ctgctctatc            250
acgtggtgct ctccgactac tcaccccgag tgtaaagaac cttcggctcg            300
cgtgcttctg agctgctgtg gatggcctcg gctctctgga ctgtccttcc            350
gagtaggatg tcactgagat ccctcaaatg gagcctcctg ctgctgtcac            400
tcctgagttt ctttgtgatg tggtacctca gccttcccca ctacaatgtg            450
atagaacgcg tgaactggat gtacttctat gagtatgagc cgatttacag            500
acaagacttt cacttcacac ttcgagagca ttcaaactgc tctcatcaaa            550
atccatttct ggtcattctg gtgacctccc acccttcaga tgtgaaagcc            600
aggcaggcca ttagagttac ttgggggtgaa aaaagtctt ggtggggata            650 tgaggttctt acatttttct tattaggcca agaggctgaa aaggaagaca            700
aaatgttggc attgtcctta gaggatgaac accttcttta tggtgacata            750
atccgacaag atttttaga cacatataat aacctgacct tgaaaaccat            800 tatgcattc aggtgggtaa ctgagttttg ccccaatgcc aagtacgtaa             850
tgaagacaga cactgatgtt ttcatcaata ctggcaattt agtgaagtat            900
cttttaaacc taaccactc agagaagttt tcacaggtt atcctctaat             950 tgataattat tcctatagag gattttacca aaaacccat atttcttacc            1000 aggagtatcc tttcaaggtg ttccctccat actgcagtgg gttgggttat           1050
ataatgtcca gagatttggt gccaaggatc tatgaaatga tgggtcacgt           1100
```

-continued

```
aaaacccatc aagtttgaag atgtttatgt cgggatctgt ttgaatttat        1150
taaaagtgaa cattcatatt ccagaagaca caaatctttt ctttctatat        1200
agaatccatt tggatgtctg tcaactgaga cgtgtgattg cagcccatgg        1250
cttttcttcc aaggagatca tcactttttg gcaggtcatg ctaaggaaca        1300
ccacatgcca ttattaactt cacattctac aaaaagccta aaggacagg         1350 ataccttgtg gaaagtgtta aataaagtag gtactgtgga aaattcatgg        1400
ggaggtcagt gtgctggctt acactgaact gaaactcatg aaaaacccag        1450
actggagact ggagggttac acttgtgatt tattagtcag gcccttcaaa        1500
gatgatatgt ggaggaatta aatataaagg aattggaggt ttttgctaaa        1550
gaaattaata ggaccaaaca atttggacat gtcattctgt agactagaat        1600
ttcttaaaag ggtgttactg agttataagc tcactaggct gtaaaaacaa        1650
aacaatgtag agttttattt attgaacaat gtagtcactt gaaggttttg        1700
tgtatatctt atgtggatta ccaatttaaa aatatatgta gttctgtgtc        1750
aaaaaacttc ttcactgaag ttatactgaa caaaatttta cctgtttttg        1800
gtcatttata aagtacttca agatgttgca gtatttcaca gttattatta        1850
tttaaaatta cttcaacttt gtgtttttaa atgttttgac gatttcaata        1900
caagataaaa aggatagtga atcattcttt acatgcaaac attttccagt        1950
tacttaactg atcagtttat tattgataca tcactccatt aatgtaaagt        2000
cataggtcat tattgcatat cagtaatctc ttggactttg ttaaatattt        2050
tactgtggta atatagagaa gaattaaagc aagaaaatct gaaaa            2095
```

<210> SEQ ID NO 36
<211> LENGTH: 331
<212> TYPE: PRT
<213> ORGANISM: Homo Sapien

<400> SEQUENCE: 36

```
Met Ala Ser Ala Leu Trp Thr Val Leu Pro Ser Arg Met Ser Leu
 1               5                  10                  15

Arg Ser Leu Lys Trp Ser Leu Leu Leu Ser Leu Leu Ser Phe
                20                  25                  30

Phe Val Met Trp Tyr Leu Ser Leu Pro His Tyr Asn Val Ile Glu
                35                  40                  45

Arg Val Asn Trp Met Tyr Phe Tyr Glu Tyr Glu Pro Ile Tyr Arg
                50                  55                  60

Gln Asp Phe His Phe Thr Leu Arg Glu His Ser Asn Cys Ser His
                65                  70                  75

Gln Asn Pro Phe Leu Val Ile Leu Val Thr Ser His Pro Ser Asp
                80                  85                  90

Val Lys Ala Arg Gln Ala Ile Arg Val Thr Trp Gly Glu Lys Lys
                95                 100                 105

Ser Trp Trp Gly Tyr Glu Val Leu Thr Phe Phe Leu Leu Gly Gln
               110                 115                 120

Glu Ala Glu Lys Glu Asp Lys Met Leu Ala Leu Ser Leu Glu Asp
               125                 130                 135

Glu His Leu Leu Tyr Gly Asp Ile Ile Arg Gln Asp Phe Leu Asp
               140                 145                 150
```

-continued

```
Thr Tyr Asn Asn Leu Thr Leu Lys Thr Ile Met Ala Phe Arg Trp
            155                 160                 165
Val Thr Glu Phe Cys Pro Asn Ala Lys Tyr Val Met Lys Thr Asp
        170                 175                 180
Thr Asp Val Phe Ile Asn Thr Gly Asn Leu Val Lys Tyr Leu Leu
    185                 190                 195
Asn Leu Asn His Ser Glu Lys Phe Phe Thr Gly Tyr Pro Leu Ile
200                 205                 210
Asp Asn Tyr Ser Tyr Arg Gly Phe Tyr Gln Lys Thr His Ile Ser
            215                 220                 225
Tyr Gln Glu Tyr Pro Phe Lys Val Phe Pro Tyr Cys Ser Gly
        230                 235                 240
Leu Gly Tyr Ile Met Ser Arg Asp Leu Val Pro Arg Ile Tyr Glu
    245                 250                 255
Met Met Gly His Val Lys Pro Ile Lys Phe Glu Asp Val Tyr Val
260                 265                 270
Gly Ile Cys Leu Asn Leu Leu Lys Val Asn Ile His Ile Pro Glu
            275                 280                 285
Asp Thr Asn Leu Phe Phe Leu Tyr Arg Ile His Leu Asp Val Cys
        290                 295                 300
Gln Leu Arg Arg Val Ile Ala Ala His Gly Phe Ser Ser Lys Glu
    305                 310                 315
Ile Ile Thr Phe Trp Gln Val Met Leu Arg Asn Thr Thr Cys His
320                 325                 330
Tyr
```

<210> SEQ ID NO 37
<211> LENGTH: 2846
<212> TYPE: DNA
<213> ORGANISM: Homo Sapien

<400> SEQUENCE: 37

```
cgctcgggca ccagccgcgg caaggatgga gctgggttgc tggacgcagt        50
tggggctcac ttttcttcag ctccttctca tctcgtcctt gccaagagag       100
tacacagtca ttaatgaagc tgccctgga gcagagtgga atatcatgtg        150
tcgggagtgc tgtgaatatg atcagattga gtgcgtctgc cccggaaaga       200
gggaagtcgt gggttatacc atcccttgct gcaggaatga ggagaatgag       250
tgtgactcct gcctgatcca cccaggttgt accatctttg aaaactgcaa       300
gagctgccga aatggctcat gggggggtac cttggatgac ttctatgtga       350
aggggttcta ctgtgcagag tgccgagcag gctggtacgg aggagactgc       400
atgcgatgtg gccaggttct gcgagcccca aagggtcaga ttttgttgga       450
aagctatccc ctaaatgctc actgtgaatg gaccattcat gctaaacctg       500
ggtttgtcat ccaactaaga tttgtcatgt tgagtctgga gtttgactac       550
atgtgccagt atgactatgt tgaggttcgt gatggagaca accgcgatgg       600
ccagatcatc aagcgtgtct gtggcaacga gcggccagct cctatccaga       650
gcataggatc tcactccac gtcctcttcc actccgatgg ctccaagaat       700
tttgacggtt ccatgccat ttatgaggag atcacagcat gctcctcatc       750
cccttgtttc catgacggca cgtgcgtcct tgacaaggct ggatcttaca       800
agtgtgcctg cttggcaggc tatactgggc agcgctgtga aaatctcctt       850
```

```
gaagaaagaa actgctcaga ccctgggggc ccagtcaatg ggtaccagaa        900
aataacaggg ggccctgggc ttatcaacgg acgccatgct aaaattggca        950
ccgtggtgtc tttcttttgt aacaactcct atgttcttag tggcaatgag       1000
aaaagaactt gccagcagaa tggagagtgg tcagggaaac agcccatctg       1050
cataaaagcc tgccgagaac caaagatttc agacctggtg agaaggagag       1100
ttcttccgat gcaggttcag tcaagggaga caccattaca ccagctatac       1150
tcagcggcct tcagcaagca gaaactgcag agtgcccta ccaagaagcc        1200
agcccttccc tttggagatc tgcccatggg ataccaacat ctgcataccc       1250
agctccagta tgagtgcatc tcacccttct accgccgcct gggcagcagc       1300
aggaggacat gtctgaggac tgggaagtgg agtgggcggg caccatcctg       1350
catccctatc tgcgggaaaa ttgagaacat cactgctcca aagacccaag       1400
ggttgcgctg gccgtggcag gcagccatct acaggaggac cagcggggtg       1450
catgacggca gcctacacaa gggagcgtgg ttcctagtct gcagcggtgc       1500
cctggtgaat gagcgcactg tggtggtggc tgcccactgt gttactgacc       1550
tggggaaggt caccatgatc aagacagcag acctgaaagt tgttttgggg       1600
aaattctacc gggatgatga ccgggatgag aagaccatcc agagcctaca       1650
gatttctgct atcattctgc atcccaacta tgaccccatc ctgcttgatg       1700
ctgacatcgc catcctgaag ctcctagaca aggcccgtat cagcacccga       1750
gtccagccca tctgcctcgc tgccagtcgg gatctcagca cttccttcca       1800
ggagtcccac atcactgtgg ctggctggaa tgtcctggca gacgtgagga       1850
gccctggctt caagaacgac acactgcgct ctggggtggt cagtgtggtg       1900
gactcgctgc tgtgtgagga gcagcatgag gaccatggca tcccagtgag       1950
tgtcactgat aacatgttct gtgccagctg ggaacccact gccccttctg       2000
atatctgcac tgcagagaca ggaggcatcg cggctgtgtc cttcccggga       2050
cgagcatctc ctgagccacg ctggcatctg atgggactgg tcagctggag       2100
ctatgataaa acatgcagcc acaggctctc cactgccttc accaaggtgc       2150
tgccttttaa agactggatt gaaagaaata tgaaatgaac catgctcatg       2200
cactccttga gaagtgtttc tgtatatccg tctgtacgtg tgtcattgcg       2250
tgaagcagtg tgggcctgaa gtgtgatttg gcctgtgaac ttggctgtgc       2300
cagggcttct gacttcaggg acaaaactca gtgaagggtg agtagacctc       2350
cattgctggt aggctgatgc cgcgtccact actaggacag ccaattggaa       2400
gatgccaggg cttgcaagaa gtaagttttct tcaaagaaga ccatatacaa      2450
aacctctcca ctccactgac ctggtggtct tccccaactt tcagttatac       2500
gaatgccatc agcttgacca gggaagatct gggcttcatg aggcccctttt      2550
tgaggctctc aagttctaga gagctgcctg tgggacagcc agggcagca        2600
gagctgggat gtggtgcatg cctttgtgta catggccaca gtacagtctg       2650
gtcctttttcc ttccccatct cttgtacaca ttttaataaa ataagggttg      2700
gcttctgaac tacaaaaaaa aaaaaaaaaa aaaaaaaaaa aaaaaaaaaa       2750
aaaaaaaaaa aaaaaaaaaa aaaaaaaaaa aaaaaaaaaa aaaaaaaaaa       2800
```
aaaaaaaaaa aaaaaaaaaa aaaaaaaaaa aaaaaaaaaa aaaaaa    2846

<210> SEQ ID NO 38
<211> LENGTH: 720
<212> TYPE: PRT
<213> ORGANISM: Homo Sapien

<400> SEQUENCE: 38

Met Glu Leu Gly Cys Trp Thr Gln Leu Gly Leu Thr Phe Leu Gln
1               5                   10                  15

Leu Leu Leu Ile Ser Ser Leu Pro Arg Glu Tyr Thr Val Ile Asn
                20                  25                  30

Glu Ala Cys Pro Gly Ala Glu Trp Asn Ile Met Cys Arg Glu Cys
                35                  40                  45

Cys Glu Tyr Asp Gln Ile Glu Cys Val Cys Pro Gly Lys Arg Glu
                50                  55                  60

Val Val Gly Tyr Thr Ile Pro Cys Cys Arg Asn Glu Glu Asn Glu
                65                  70                  75

Cys Asp Ser Cys Leu Ile His Pro Gly Cys Thr Ile Phe Glu Asn
                80                  85                  90

Cys Lys Ser Cys Arg Asn Gly Ser Trp Gly Gly Thr Leu Asp Asp
                95                  100                 105

Phe Tyr Val Lys Gly Phe Tyr Cys Ala Glu Cys Arg Ala Gly Trp
                110                 115                 120

Tyr Gly Gly Asp Cys Met Arg Cys Gly Gln Val Leu Arg Ala Pro
                125                 130                 135

Lys Gly Gln Ile Leu Leu Glu Ser Tyr Pro Leu Asn Ala His Cys
                140                 145                 150

Glu Trp Thr Ile His Ala Lys Pro Gly Phe Val Ile Gln Leu Arg
                155                 160                 165

Phe Val Met Leu Ser Leu Glu Phe Asp Tyr Met Cys Gln Tyr Asp
                170                 175                 180

Tyr Val Glu Val Arg Asp Gly Asp Asn Arg Asp Gly Gln Ile Ile
                185                 190                 195

Lys Arg Val Cys Gly Asn Glu Arg Pro Ala Pro Ile Gln Ser Ile
                200                 205                 210

Gly Ser Ser Leu His Val Leu Phe His Ser Asp Gly Ser Lys Asn
                215                 220                 225

Phe Asp Gly Phe His Ala Ile Tyr Glu Glu Ile Thr Ala Cys Ser
                230                 235                 240

Ser Ser Pro Cys Phe His Asp Gly Thr Cys Val Leu Asp Lys Ala
                245                 250                 255

Gly Ser Tyr Lys Cys Ala Cys Leu Ala Gly Tyr Thr Gly Gln Arg
                260                 265                 270

Cys Glu Asn Leu Leu Glu Glu Arg Asn Cys Ser Asp Pro Gly Gly
                275                 280                 285

Pro Val Asn Gly Tyr Gln Lys Ile Thr Gly Pro Gly Leu Ile
                290                 295                 300

Asn Gly Arg His Ala Lys Ile Gly Thr Val Ser Phe Phe Cys
                305                 310                 315

Asn Asn Ser Tyr Val Leu Ser Gly Asn Glu Lys Arg Thr Cys Gln
                320                 325                 330

Gln Asn Gly Glu Trp Ser Gly Lys Gln Pro Ile Cys Ile Lys Ala
                335                 340                 345

-continued

```
Cys Arg Glu Pro Lys Ile Ser Asp Leu Val Arg Arg Val Leu
            350                 355                 360

Pro Met Gln Val Gln Ser Arg Glu Thr Pro Leu His Gln Leu Tyr
            365                 370                 375

Ser Ala Ala Phe Ser Lys Gln Lys Leu Gln Ser Ala Pro Thr Lys
            380                 385                 390

Lys Pro Ala Leu Pro Phe Gly Asp Leu Pro Met Gly Tyr Gln His
            395                 400                 405

Leu His Thr Gln Leu Gln Tyr Glu Cys Ile Ser Pro Phe Tyr Arg
            410                 415                 420

Arg Leu Gly Ser Ser Arg Arg Thr Cys Leu Arg Thr Gly Lys Trp
            425                 430                 435

Ser Gly Arg Ala Pro Ser Cys Ile Pro Ile Cys Gly Lys Ile Glu
            440                 445                 450

Asn Ile Thr Ala Pro Lys Thr Gln Gly Leu Arg Trp Pro Trp Gln
            455                 460                 465

Ala Ala Ile Tyr Arg Arg Thr Ser Gly Val His Asp Gly Ser Leu
            470                 475                 480

His Lys Gly Ala Trp Phe Leu Val Cys Ser Gly Ala Leu Val Asn
            485                 490                 495

Glu Arg Thr Val Val Ala Ala His Cys Val Thr Asp Leu Gly
            500                 505                 510

Lys Val Thr Met Ile Lys Thr Ala Asp Leu Lys Val Val Leu Gly
            515                 520                 525

Lys Phe Tyr Arg Asp Asp Arg Asp Glu Lys Thr Ile Gln Ser
            530                 535                 540

Leu Gln Ile Ser Ala Ile Ile Leu His Pro Asn Tyr Asp Pro Ile
            545                 550                 555

Leu Leu Asp Ala Asp Ile Ala Ile Leu Lys Leu Leu Asp Lys Ala
            560                 565                 570

Arg Ile Ser Thr Arg Val Gln Pro Ile Cys Leu Ala Ala Ser Arg
            575                 580                 585

Asp Leu Ser Thr Ser Phe Gln Glu Ser His Ile Thr Val Ala Gly
            590                 595                 600

Trp Asn Val Leu Ala Asp Val Arg Ser Pro Gly Phe Lys Asn Asp
            605                 610                 615

Thr Leu Arg Ser Gly Val Val Ser Val Val Asp Ser Leu Leu Cys
            620                 625                 630

Glu Glu Gln His Glu Asp His Gly Ile Pro Val Ser Val Thr Asp
            635                 640                 645

Asn Met Phe Cys Ala Ser Trp Glu Pro Thr Ala Pro Ser Asp Ile
            650                 655                 660

Cys Thr Ala Glu Thr Gly Gly Ile Ala Ala Val Ser Phe Pro Gly
            665                 670                 675

Arg Ala Ser Pro Glu Pro Arg Trp His Leu Met Gly Leu Val Ser
            680                 685                 690

Trp Ser Tyr Asp Lys Thr Cys Ser His Arg Leu Ser Thr Ala Phe
            695                 700                 705

Thr Lys Val Leu Pro Phe Lys Asp Trp Ile Glu Arg Asn Met Lys
            710                 715                 720
```

<210> SEQ ID NO 39
<211> LENGTH: 2571
<212> TYPE: DNA

<213> ORGANISM: Homo Sapien

<400> SEQUENCE: 39

| | | | | |
|---|---|---|---|---|
| ggttcctaca | tcctctcatc | tgagaatcag | agagcataat | cttcttacgg | 50 |
| gcccgtgatt | tattaacgtg | gcttaatctg | aaggttctca | gtcaaattct | 100 |
| ttgtgatcta | ctgattgtgg | gggcatggca | aggtttgctt | aaaggagctt | 150 |
| ggctggtttg | ggcccttgta | gctgacagaa | ggtggccagg | gagaatgcag | 200 |
| cacactgctc | ggagaatgaa | ggcgcttctg | ttgctggtct | tgccttggct | 250 |
| cagtcctgct | aactacattg | acaatgtggg | caacctgcac | ttcctgtatt | 300 |
| cagaactctg | taaaggtgcc | tcccactacg | gcctgaccaa | agataggaag | 350 |
| aggcgctcac | aagatggctg | tccagacggc | tgtgcgagcc | tcacagccac | 400 |
| ggctccctcc | ccagaggttt | ctgcagctgc | caccatctcc | ttaatgacag | 450 |
| acgagcctgg | cctagacaac | cctgcctacg | tgtcctcggc | agaggacggg | 500 |
| cagccagcaa | tcagcccagt | ggactctggc | cggagcaacc | gaactagggc | 550 |
| acggcccttt | gagagatcca | ctattagaag | cagatcattt | aaaaaaataa | 600 |
| atcgagcttt | gagtgttctt | cgaaggacaa | agagcgggag | tgcagttgcc | 650 |
| aaccatgccg | accagggcag | ggaaaattct | gaaaacacca | ctgcccctga | 700 |
| agtctttcca | aggttgtacc | acctgattcc | agatggtgaa | attaccagca | 750 |
| tcaagatcaa | tcgagtagat | cccagtgaaa | gcctctctat | taggctggtg | 800 |
| ggaggtagcg | aaacccact | ggtccatatc | attatccaac | acatttatcg | 850 |
| tgatggggtg | atcgccagag | acggccggct | actgccagga | gacatcattc | 900 |
| taaaggtcaa | cgggatggac | atcagcaatg | tccctcacaa | ctacgctgtg | 950 |
| cgtctcctgc | ggcagccctg | ccaggtgctg | tggctgactg | tgatgcgtga | 1000 |
| acagaagttc | cgcagcagga | acaatggaca | ggccccggat | gcctacagac | 1050 |
| cccgagatga | cagctttcat | gtgattctca | acaaaagtag | ccccgaggag | 1100 |
| cagcttggaa | taaaactggt | gcgcaaggtg | gatgagcctg | ggttttcat | 1150 |
| cttcaatgtg | ctggatggcg | gtgtggcata | tcgacatggt | cagcttgagg | 1200 |
| agaatgaccg | tgtgttagcc | atcaatggac | atgatcttcg | atatggcagc | 1250 |
| ccagaaagtg | cggctcatct | gattcaggcc | agtgaaagac | gtgttcacct | 1300 |
| cgtcgtgtcc | cgccaggttc | ggcagcggag | ccctgacatc | tttcaggaag | 1350 |
| ccggctggaa | cagcaatggc | agctggtccc | cagggccagg | ggagaggagc | 1400 |
| aacactccca | agcccctcca | tcctacaatt | acttgtcatg | agaaggtggt | 1450 |
| aaatatccaa | aaagaccccg | gtgaatctct | cggcatgacc | gtcgcagggg | 1500 |
| gagcatcaca | tagagaatgg | gatttgccta | tctatgtcat | cagtgttgag | 1550 |
| cccggaggag | tcataagcag | agatggaaga | ataaaaacag | gtgacatttt | 1600 |
| gttgaatgtg | gatgggtcg | aactgacaga | ggtcagccgg | agtgaggcag | 1650 |
| tggcattatt | gaaagaaca | tcatcctcga | tagtactcaa | agctttggaa | 1700 |
| gtcaaagagt | atgagcccca | ggaagactgc | agcagcccag | cagccctgga | 1750 |
| ctccaaccac | aacatggccc | cacccagtga | ctggtcccca | tcctgggtca | 1800 |
| tgtggctgga | attccacgg | tgcttgtata | actgtaaaga | tattgtatta | 1850 |
| cgaagaaaca | cagctggaag | tctgggcttc | tgcattgtag | gaggttatga | 1900 |

| | |
|---|---:|
| agaatacaat ggaaacaaac cttttttcat caaatccatt gttgaaggaa | 1950 |
| caccagcata caatgatgga agaattagat gtggtgatat tcttcttgct | 2000 |
| gtcaatggta gaagtacatc aggaatgata catgcttgct tggcaagact | 2050 |
| gctgaaagaa cttaaaggaa gaattactct aactattgtt tcttggcctg | 2100 |
| gcactttttt atagaatcaa tgatgggtca gaggaaaaca gaaaaatcac | 2150 |
| aaataggcta agaagttgaa acactatatt tatcttgtca gtttttatat | 2200 |
| ttaaagaaag aatacattgt aaaaatgtca ggaaaagtat gatcatctaa | 2250 |
| tgaaagccag ttacacctca gaaaatatga ttccaaaaaa attaaaacta | 2300 |
| ctagtttttt ttcagtgtgg aggatttctc attactctac aacattgttt | 2350 |
| atattttttc tattcaataa aaagccctaa acaactaaa atgattgatt | 2400 |
| tgtataccc actgaattca agctgattta aatttaaaat ttggtatatg | 2450 |
| ctgaagtctg ccaagggtac attatggcca tttttaattt acagctaaaa | 2500 |
| tatttttta aatgcattgc tgagaaacgt tgctttcatc aaacaagaat | 2550 |
| aaatatttt cagaagttaa a | 2571 |

<210> SEQ ID NO 40
<211> LENGTH: 632
<212> TYPE: PRT
<213> ORGANISM: Homo Sapien

<400> SEQUENCE: 40

```
Met Lys Ala Leu Leu Leu Val Leu Pro Trp Leu Ser Pro Ala
  1               5                  10                  15

Asn Tyr Ile Asp Asn Val Gly Asn Leu His Phe Leu Tyr Ser Glu
                 20                  25                  30

Leu Cys Lys Gly Ala Ser His Tyr Gly Leu Thr Lys Asp Arg Lys
             35                  40                  45

Arg Arg Ser Gln Asp Gly Cys Pro Asp Gly Cys Ala Ser Leu Thr
         50                  55                  60

Ala Thr Ala Pro Ser Pro Glu Val Ser Ala Ala Thr Ile Ser
     65                  70                  75

Leu Met Thr Asp Glu Pro Gly Leu Asp Asn Pro Ala Tyr Val Ser
 80                  85                  90

Ser Ala Glu Asp Gly Gln Pro Ala Ile Ser Pro Val Asp Ser Gly
             95                 100                 105

Arg Ser Asn Arg Thr Arg Ala Arg Pro Phe Glu Arg Ser Thr Ile
            110                 115                 120

Arg Ser Arg Ser Phe Lys Lys Ile Asn Arg Ala Leu Ser Val Leu
            125                 130                 135

Arg Arg Thr Lys Ser Gly Ser Ala Val Ala Asn His Ala Asp Gln
            140                 145                 150

Gly Arg Glu Asn Ser Glu Asn Thr Thr Ala Pro Glu Val Phe Pro
            155                 160                 165

Arg Leu Tyr His Leu Ile Pro Asp Gly Glu Ile Thr Ser Ile Lys
            170                 175                 180

Ile Asn Arg Val Asp Pro Ser Glu Ser Leu Ser Ile Arg Leu Val
            185                 190                 195

Gly Gly Ser Glu Thr Pro Leu Val His Ile Ile Gln His Ile
            200                 205                 210
```

-continued

```
Tyr Arg Asp Gly Val Ile Ala Arg Asp Gly Arg Leu Leu Pro Gly
            215                 220                 225

Asp Ile Ile Leu Lys Val Asn Gly Met Asp Ile Ser Asn Val Pro
            230                 235                 240

His Asn Tyr Ala Val Arg Leu Leu Arg Gln Pro Cys Gln Val Leu
            245                 250                 255

Trp Leu Thr Val Met Arg Glu Gln Lys Phe Arg Ser Arg Asn Asn
            260                 265                 270

Gly Gln Ala Pro Asp Ala Tyr Arg Pro Arg Asp Asp Ser Phe His
            275                 280                 285

Val Ile Leu Asn Lys Ser Ser Pro Glu Glu Gln Leu Gly Ile Lys
            290                 295                 300

Leu Val Arg Lys Val Asp Glu Pro Gly Val Phe Ile Phe Asn Val
            305                 310                 315

Leu Asp Gly Gly Val Ala Tyr Arg His Gly Gln Leu Glu Glu Asn
            320                 325                 330

Asp Arg Val Leu Ala Ile Asn Gly His Asp Leu Arg Tyr Gly Ser
            335                 340                 345

Pro Glu Ser Ala Ala His Leu Ile Gln Ala Ser Glu Arg Arg Val
            350                 355                 360

His Leu Val Val Ser Arg Gln Val Arg Gln Arg Ser Pro Asp Ile
            365                 370                 375

Phe Gln Glu Ala Gly Trp Asn Ser Asn Gly Ser Trp Ser Pro Gly
            380                 385                 390

Pro Gly Glu Arg Ser Asn Thr Pro Lys Pro Leu His Pro Thr Ile
            395                 400                 405

Thr Cys His Glu Lys Val Val Asn Ile Gln Lys Asp Pro Gly Glu
            410                 415                 420

Ser Leu Gly Met Thr Val Ala Gly Gly Ala Ser His Arg Glu Trp
            425                 430                 435

Asp Leu Pro Ile Tyr Val Ile Ser Val Glu Pro Gly Gly Val Ile
            440                 445                 450

Ser Arg Asp Gly Arg Ile Lys Thr Gly Asp Ile Leu Leu Asn Val
            455                 460                 465

Asp Gly Val Glu Leu Thr Glu Val Ser Arg Ser Glu Ala Val Ala
            470                 475                 480

Leu Leu Lys Arg Thr Ser Ser Ser Ile Val Leu Lys Ala Leu Glu
            485                 490                 495

Val Lys Glu Tyr Glu Pro Gln Glu Asp Cys Ser Ser Pro Ala Ala
            500                 505                 510

Leu Asp Ser Asn His Asn Met Ala Pro Pro Ser Asp Trp Ser Pro
            515                 520                 525

Ser Trp Val Met Trp Leu Glu Leu Pro Arg Cys Leu Tyr Asn Cys
            530                 535                 540

Lys Asp Ile Val Leu Arg Arg Asn Thr Ala Gly Ser Leu Gly Phe
            545                 550                 555

Cys Ile Val Gly Gly Tyr Glu Glu Tyr Asn Gly Asn Lys Pro Phe
            560                 565                 570

Phe Ile Lys Ser Ile Val Glu Gly Thr Pro Ala Tyr Asn Asp Gly
            575                 580                 585

Arg Ile Arg Cys Gly Asp Ile Leu Leu Ala Val Asn Gly Arg Ser
            590                 595                 600

Thr Ser Gly Met Ile His Ala Cys Leu Ala Arg Leu Leu Lys Glu
```

|  | 605 |  |  | 610 |  |  | 615 |  |  |  |
|---|---|---|---|---|---|---|---|---|---|---|
| Leu | Lys | Gly | Arg | Ile | Thr | Leu | Thr | Ile | Val | Ser | Trp | Pro | Gly | Thr |
|  |  | 620 |  |  |  | 625 |  |  |  | 630 |

Phe Leu

<210> SEQ ID NO 41
<211> LENGTH: 1964
<212> TYPE: DNA
<213> ORGANISM: Homo Sapien

<400> SEQUENCE: 41

```
accaggcatt gtatcttcag ttgtcatcaa gttcgcaatc agattggaaa           50
agctcaactt gaagctttct tgcctgcagt gaagcagaga gatagatatt          100
attcacgtaa taaaaaacat gggcttcaac ctgactttcc acctttccta          150
caaattccga ttactgttgc tgttgacttt gtgcctgaca gtggttgggt          200
gggccaccag taactacttc gtgggtgcca ttcaagagat tcctaaagca          250
aaggagttca tggctaattt ccataagacc ctcattttgg ggaagggaaa          300
aactctgact aatgaagcat ccacgaagaa ggtagaactt gacaactgtc          350
cttctgtgtc tccttacctc agaggccaga gcaagctcat tttcaaacca          400
gatctcactt tggaagaggt acaggcagaa atcccaaag tgtccagagg           450
ccggtatcgc cctcaggaat gtaaagcttt acagagggtc gccatcctcg          500
ttccccaccg aacagagag aaacacctga tgtacctgct ggaacatctg           550
catcccttcc tgcagaggca gcagctggat tatggcatct acgtcatcca          600
ccaggctgaa ggtaaaaagt ttaatcgagc caaactcttg aatgtgggct          650
atctagaagc cctcaaggaa gaaaattggg actgctttat attccacgat          700
gtggacctgg tacccgagaa tgactttaac ctttacaagt gtgaggagca          750
tcccaagcat ctggtggttg caggaacag cactgggtac aggttacgtt           800
acagtggata ttttgggggt gttactgccc taagcagaga gcagttttc            850
aaggtgaatg gattctctaa caactactgg ggatggggag gcgaagacga          900
tgacctcaga ctcagggttg agctccaaag aatgaaaatt tcccggcccc          950
tgcctgaagt gggtaaatat acaatggtct ccacactag agacaaaggc          1000
aatgaggtga acgcagaacg gatgaagctc ttacaccaag tgtcacgagt         1050
ctggagaaca gatgggttga gtagttgttc ttataaatta gtatctgtgg         1100
aacacaatcc tttatatatc aacatcacag tggatttctg gtttggtgca         1150
tgaccctgga tcttttggtg atgtttggaa gaactgattc tttgtttgca         1200
ataattttgg cctagagact tcaaatagta gcacacatta gaacctgtt          1250
acagctcatt gttgagctga atttttcctt tttgtatttt cttagcagag         1300
ctcctggtga tgtagagtat aaaacagttg taacaagaca gctttcttag         1350
tcattttgat catgagggtt aaatattgta atatggatac ttgaaggact         1400
ttatataaaa ggatgactca aaggataaaa tgaacgctat ttgaggactc         1450
tggttgaagg agatttattt aaatttgaag taatatatta tgggataaaa         1500
ggccacagga aataagactg ctgaatgtct gagagaacca gagttgttct         1550
cgtccaaggt agaaaggtac gaagatacaa tactgttatt catttatcct         1600
```

-continued

```
gtacaatcat ctgtgaagtg gtggtgtcag gtgagaaggc gtccacaaaa           1650
gaggggagaa aaggcgacga atcaggacac agtgaacttg ggaatgaaga           1700
ggtagcagga gggtggagtg tcggctgcaa aggcagcagt agctgagctg           1750
gttgcaggtg ctgatagcct tcaggggagg acctgcccag gtatgccttc           1800
cagtgatgcc caccagagaa tacattctct attagttttt aaagagtttt           1850
tgtaaaatga ttttgtacaa gtaggatatg aattagcagt ttacaagttt           1900
acatattaac taataataaa tatgtctatc aaatacctct gtagtaaaat           1950
gtgaaaaagc aaaa                                                  1964
```

<210> SEQ ID NO 42
<211> LENGTH: 344
<212> TYPE: PRT
<213> ORGANISM: Homo Sapien

<400> SEQUENCE: 42

```
Met Gly Phe Asn Leu Thr Phe His Leu Ser Tyr Lys Phe Arg Leu
 1               5                  10                  15

Leu Leu Leu Leu Thr Leu Cys Leu Thr Val Val Gly Trp Ala Thr
                20                  25                  30

Ser Asn Tyr Phe Val Gly Ala Ile Gln Glu Ile Pro Lys Ala Lys
                35                  40                  45

Glu Phe Met Ala Asn Phe His Lys Thr Leu Ile Leu Gly Lys Gly
                50                  55                  60

Lys Thr Leu Thr Asn Glu Ala Ser Thr Lys Lys Val Glu Leu Asp
                65                  70                  75

Asn Cys Pro Ser Val Ser Pro Tyr Leu Arg Gly Gln Ser Lys Leu
                80                  85                  90

Ile Phe Lys Pro Asp Leu Thr Leu Glu Glu Val Gln Ala Glu Asn
                95                  100                 105

Pro Lys Val Ser Arg Gly Arg Tyr Arg Pro Gln Glu Cys Lys Ala
                110                 115                 120

Leu Gln Arg Val Ala Ile Leu Val Pro His Arg Asn Arg Glu Lys
                125                 130                 135

His Leu Met Tyr Leu Leu Glu His Leu His Pro Phe Leu Gln Arg
                140                 145                 150

Gln Gln Leu Asp Tyr Gly Ile Tyr Val Ile His Gln Ala Glu Gly
                155                 160                 165

Lys Lys Phe Asn Arg Ala Lys Leu Leu Asn Val Gly Tyr Leu Glu
                170                 175                 180

Ala Leu Lys Glu Glu Asn Trp Asp Cys Phe Ile Phe His Asp Val
                185                 190                 195

Asp Leu Val Pro Glu Asn Asp Phe Asn Leu Tyr Lys Cys Glu Glu
                200                 205                 210

His Pro Lys His Leu Val Val Gly Arg Asn Ser Thr Gly Tyr Arg
                215                 220                 225

Leu Arg Tyr Ser Gly Tyr Phe Gly Gly Val Thr Ala Leu Ser Arg
                230                 235                 240

Glu Gln Phe Phe Lys Val Asn Gly Phe Ser Asn Asn Tyr Trp Gly
                245                 250                 255

Trp Gly Gly Glu Asp Asp Asp Leu Arg Leu Arg Val Glu Leu Gln
                260                 265                 270

Arg Met Lys Ile Ser Arg Pro Leu Pro Glu Val Gly Lys Tyr Thr
```

```
                    275                 280                 285
Met Val Phe His Thr Arg Asp Lys Gly Asn Glu Val Asn Ala Glu
                290                 295                 300

Arg Met Lys Leu Leu His Gln Val Ser Arg Val Trp Arg Thr Asp
                305                 310                 315

Gly Leu Ser Ser Cys Ser Tyr Lys Leu Val Ser Val Glu His Asn
                320                 325                 330

Pro Leu Tyr Ile Asn Ile Thr Val Asp Phe Trp Phe Gly Ala
                335                 340

<210> SEQ ID NO 43
<211> LENGTH: 485
<212> TYPE: DNA
<213> ORGANISM: Homo Sapien

<400> SEQUENCE: 43
gctcaagacc cagcagtggg acagccagac agacggcacg atggcactga          50
gctcccagat ctgggccgct tgcctcctgc tcctcctcct cctcgccagc         100
ctgaccagtg gctctgtttt cccacaacag acgggacaac ttgcagagct         150 gcaacccag acagagctg agccagggc agctggatg cccatgttcc             200 agaggcgaag gaggcgagac acccacttcc ccatctgcat tttctgctgc         250
ggctgctgtc atcgatcaaa gtgtgggatg tgctgcaaga cgtagaacct         300
acctgccctg ccccgtccc ctcccttcct tatttattcc tgctgcccca          350
gaacataggt cttggaataa aatggctggt tcttttgttt tccaaaaaaa         400
aaaaaaaaaa aaaaaaaaaa aaaaaaaaaa aaaaaaaaaa aaaaaaaaaa         450
aaaaaaaaaa aaaaaaaaa aaaaaaaaaa aaaaa                          485

<210> SEQ ID NO 44
<211> LENGTH: 84
<212> TYPE: PRT
<213> ORGANISM: Homo Sapien

<400> SEQUENCE: 44

Met Ala Leu Ser Ser Gln Ile Trp Ala Ala Cys Leu Leu Leu Leu
  1               5                  10                  15

Leu Leu Leu Ala Ser Leu Thr Ser Gly Ser Val Phe Pro Gln Gln
                 20                  25                  30

Thr Gly Gln Leu Ala Glu Leu Gln Pro Gln Asp Arg Ala Gly Ala
                 35                  40                  45

Arg Ala Ser Trp Met Pro Met Phe Gln Arg Arg Arg Arg Arg Asp
                 50                  55                  60

Thr His Phe Pro Ile Cys Ile Phe Cys Cys Gly Cys Cys His Arg
                 65                  70                  75

Ser Lys Cys Gly Met Cys Cys Lys Thr
                 80

<210> SEQ ID NO 45
<211> LENGTH: 1076
<212> TYPE: DNA
<213> ORGANISM: Homo Sapien

<400> SEQUENCE: 45
gtggcttcat ttcagtggct gacttccaga gagcaatatg gctggttccc          50
caacatgcct caccctcatc tatatccttt ggcagctcac agggtcagca         100
```

-continued

```
gcctctggac ccgtgaaaga gctggtcggt tccgttggtg gggccgtgac      150 tttcccctg aagtccaaag taaagcaagt tgactctatt gtctggacct       200
tcaacacaac ccctcttgtc accatacagc cagaagggg cactatcata       250 gtgacccaaa atcgtaatag ggagagagta gacttcccag atggaggcta      300
ctccctgaag ctcagcaaac tgaagaagaa tgactcaggg atctactatg      350
tggggatata cagctcatca ctccagcagc cctccaccca ggagtacgtg      400
ctgcatgtct acgagcacct gtcaaagcct aaagtcacca tgggtctgca      450
gagcaataag aatggcacct gtgtgaccaa tctgacatgc tgcatggaac      500
atggggaaga ggatgtgatt tatacctgga aggccctggg gcaagcagcc      550
aatgagtccc ataatgggtc catcctcccc atctcctgga gatggggaga      600
aagtgatatg accttcatct gcgttgccag gaaccctgtc agcagaaact      650
tctcaagccc catccttgcc aggaagctct gtgaaggtgc tgctgatgac      700
ccagattcct ccatggtcct cctgtgtctc ctgttggtgc ccctcctgct      750
cagtctcttt gtactggggc tatttctttg gtttctgaag agagagagac      800
aagaagagta cattgaagag aagaagagag tggacatttg tcgggaaact      850
cctaacatat gccccattc tggagagaac acagagtacg acacaatccc       900
tcacactaat agaacaatcc taaaggaaga tccagcaaat acggtttact      950
ccactgtgga ataccgaaa agatggaaa atccccactc actgctcacg       1000
atgccagaca caccaaggct atttgcctat gagaatgtta tctagacagc      1050
agtgcactcc cctaagtctc tgctca                                1076
```

<210> SEQ ID NO 46
<211> LENGTH: 335
<212> TYPE: PRT
<213> ORGANISM: Homo Sapien

<400> SEQUENCE: 46

```
Met Ala Gly Ser Pro Thr Cys Leu Thr Leu Ile Tyr Ile Leu Trp
 1               5                  10                  15

Gln Leu Thr Gly Ser Ala Ala Ser Gly Pro Val Lys Glu Leu Val
                20                  25                  30

Gly Ser Val Gly Gly Ala Val Thr Phe Pro Leu Lys Ser Lys Val
                35                  40                  45

Lys Gln Val Asp Ser Ile Val Trp Thr Phe Asn Thr Thr Pro Leu
                50                  55                  60

Val Thr Ile Gln Pro Glu Gly Gly Thr Ile Ile Val Thr Gln Asn
                65                  70                  75

Arg Asn Arg Glu Arg Val Asp Phe Pro Asp Gly Gly Tyr Ser Leu
                80                  85                  90

Lys Leu Ser Lys Leu Lys Lys Asn Asp Ser Gly Ile Tyr Tyr Val
                95                 100                 105

Gly Ile Tyr Ser Ser Ser Leu Gln Gln Pro Ser Thr Gln Glu Tyr
               110                 115                 120

Val Leu His Val Tyr Glu His Leu Ser Lys Pro Lys Val Thr Met
               125                 130                 135

Gly Leu Gln Ser Asn Lys Asn Gly Thr Cys Val Thr Asn Leu Thr
               140                 145                 150
```

```
Cys Cys Met Glu His Gly Glu Asp Val Ile Tyr Thr Trp Lys
            155                 160                 165

Ala Leu Gly Gln Ala Ala Asn Glu Ser His Asn Gly Ser Ile Leu
            170                 175                 180

Pro Ile Ser Trp Arg Trp Gly Ser Asp Met Thr Phe Ile Cys
            185                 190                 195

Val Ala Arg Asn Pro Val Ser Arg Asn Phe Ser Ser Pro Ile Leu
            200                 205                 210

Ala Arg Lys Leu Cys Glu Gly Ala Ala Asp Pro Asp Ser Ser
            215                 220                 225

Met Val Leu Leu Cys Leu Leu Val Pro Leu Leu Leu Ser Leu
            230                 235                 240

Phe Val Leu Gly Leu Phe Leu Trp Phe Leu Lys Arg Glu Arg Gln
            245                 250                 255

Glu Glu Tyr Ile Glu Glu Lys Lys Arg Val Asp Ile Cys Arg Glu
            260                 265                 270

Thr Pro Asn Ile Cys Pro His Ser Gly Glu Asn Thr Glu Tyr Asp
            275                 280                 285

Thr Ile Pro His Thr Asn Arg Thr Ile Leu Lys Glu Asp Pro Ala
            290                 295                 300

Asn Thr Val Tyr Ser Thr Val Glu Ile Pro Lys Lys Met Glu Asn
            305                 310                 315

Pro His Ser Leu Leu Thr Met Pro Asp Thr Pro Arg Leu Phe Ala
            320                 325                 330

Tyr Glu Asn Val Ile
            335

<210> SEQ ID NO 47
<211> LENGTH: 766
<212> TYPE: DNA
<213> ORGANISM: Homo Sapien

<400> SEQUENCE: 47
ggctcgagcg tttctgagcc agggtgacc atgacctgct gcgaaggatg         50
gacatcctgc aatggattca gcctgctggt tctactgctg ttaggagtag        100
ttctcaatgc gataccctcta attgtcagct tagttgagga agaccaattt       150
tctcaaaacc ccatctcttg cttttgagtgg tggttcccag gaattatagg       200
agcaggtctg atggccattc cagcaacaac aatgtccttg acagcaagaa        250
aaagagcgtg ctgcaacaac agaactggaa tgtttctttc atcatttttc        300
agtgtgatca cagtcattgg tgctctgtat tgcatgctga tatccatcca        350
ggctctctta aaggtcctc tcatgtgtaa ttctccaagc aacagtaatg         400
ccaattgtga attttcattg aaaaacatca gtgacattca tccagaatcc        450
ttcaacttgc agtggttttt caatgactct tgtgcacctc ctactggttt        500
caataaaccc accagtaacg acaccatggc gagtggctgg agagcatcta        550
gtttccactt cgattctgaa gaaaacaaac ataggcttat ccacttctca        600
gtatttttag gtctattgct tgttggaatt ctggaggtcc tgtttgggct        650
cagtcagata gtcatcggtt ccttggctg tctgtgtgga gtctctaagc         700
gaagaagtca aattgtgtag tttaatggga ataaaatgta agtatcagta        750
gtttgaaaaa aaaaaa                                              766
```

<210> SEQ ID NO 48
<211> LENGTH: 229
<212> TYPE: PRT
<213> ORGANISM: Homo Sapien

<400> SEQUENCE: 48

```
Met Thr Cys Cys Glu Gly Trp Thr Ser Cys Asn Gly Phe Ser Leu
 1               5                  10                  15

Leu Val Leu Leu Leu Gly Val Val Leu Asn Ala Ile Pro Leu
                20                  25                  30

Ile Val Ser Leu Val Glu Glu Asp Gln Phe Ser Gln Asn Pro Ile
                35                  40                  45

Ser Cys Phe Glu Trp Trp Phe Pro Gly Ile Ile Gly Ala Gly Leu
                50                  55                  60

Met Ala Ile Pro Ala Thr Thr Met Ser Leu Thr Ala Arg Lys Arg
                65                  70                  75

Ala Cys Cys Asn Asn Arg Thr Gly Met Phe Leu Ser Ser Phe Phe
                80                  85                  90

Ser Val Ile Thr Val Ile Gly Ala Leu Tyr Cys Met Leu Ile Ser
                95                 100                 105

Ile Gln Ala Leu Leu Lys Gly Pro Leu Met Cys Asn Ser Pro Ser
               110                 115                 120

Asn Ser Asn Ala Asn Cys Glu Phe Ser Leu Lys Asn Ile Ser Asp
               125                 130                 135

Ile His Pro Glu Ser Phe Asn Leu Gln Trp Phe Phe Asn Asp Ser
               140                 145                 150

Cys Ala Pro Pro Thr Gly Phe Asn Lys Pro Thr Ser Asn Asp Thr
               155                 160                 165

Met Ala Ser Gly Trp Arg Ala Ser Ser Phe His Phe Asp Ser Glu
               170                 175                 180

Glu Asn Lys His Arg Leu Ile His Phe Ser Val Phe Leu Gly Leu
               185                 190                 195

Leu Leu Val Gly Ile Leu Glu Val Leu Phe Gly Leu Ser Gln Ile
               200                 205                 210

Val Ile Gly Phe Leu Gly Cys Leu Cys Gly Val Ser Lys Arg Arg
               215                 220                 225

Ser Gln Ile Val
```

<210> SEQ ID NO 49
<211> LENGTH: 636
<212> TYPE: DNA
<213> ORGANISM: Homo Sapien

<400> SEQUENCE: 49

| | | | |
|---|---|---|---|
| atccgttctc tgcgctgcca gctcaggtga gccctcgcca aggtgacctc | | | 50 |
| gcaggacact ggtgaaggag cagtgaggaa cctgcagagt cacacagttg | | | 100 |
| ctgaccaatt gagctgtgag cctggagcag atccgtgggc tgcagacccc | | | 150 |
| cgccccagtg cctctccccc tgcagccctg cccctcgaac tgtgacatgg | | | 200 |
| agagagtgac cctggccctt ctcctactgg caggcctgac tgccttggaa | | | 250 |
| gccaatgacc catttgccaa taaagacgat cccttctact atgactggaa | | | 300 |
| aaacctgcag ctgagcggac tgatctgcgg agggctcctg gccattgctg | | | 350 |
| ggatcgcggc agttctgagt ggcaaatgca aatacaagag cagccagaag | | | 400 |

| | |
|---|---|
| cagcacagtc ctgtacctga aaggccatc ccactcatca ctccaggctc | 450 |
| tgccactact tgctgagcac aggactggcc tccaggatg gcctgaagcc | 500 |
| taacactggc ccccagcacc tcctcccctg ggaggcctta tcctcaagga | 550 |
| aggacttctc tccaagggca ggctgttagg ccccttcctg atcaggaggc | 600 |
| ttctttatga attaaactcg ccccaccacc ccctca | 636 |

<210> SEQ ID NO 50
<211> LENGTH: 89
<212> TYPE: PRT
<213> ORGANISM: Homo Sapien

<400> SEQUENCE: 50

Met Glu Arg Val Thr Leu Ala Leu Leu Leu Ala Gly Leu Thr
 1               5                  10                  15
Ala Leu Glu Ala Asn Asp Pro Phe Ala Asn Lys Asp Asp Pro Phe
                20                  25                  30
Tyr Tyr Asp Trp Lys Asn Leu Gln Leu Ser Gly Leu Ile Cys Gly
                35                  40                  45
Gly Leu Leu Ala Ile Ala Gly Ile Ala Ala Val Leu Ser Gly Lys
                50                  55                  60
Cys Lys Tyr Lys Ser Ser Gln Lys Gln His Ser Pro Val Pro Glu
 65                  70                                  75
Lys Ala Ile Pro Leu Ile Thr Pro Gly Ser Ala Thr Thr Cys
                80                  85

<210> SEQ ID NO 51
<211> LENGTH: 1734
<212> TYPE: DNA
<213> ORGANISM: Homo Sapien

<400> SEQUENCE: 51

| | |
|---|---|
| gtggactctg agaagcccag gcagttgagg acaggagaga gaaggctgca | 50 |
| gacccagagg gagggaggac agggagtcgg aaggaggagg acagaggagg | 100 |
| gcacagagac gcagagcaag ggcggcaagg aggagaccct ggtgggagga | 150 |
| agacactctg gagagagagg gggctgggca gagatgaagt tccagggcc | 200 |
| cctggcctgc ctcctgctgg ccctctgcct gggcagtggg gaggctggcc | 250 |
| ccctgcagag cggagaggaa agcactggga caaatattgg ggaggccctt | 300 |
| ggacatggcc tgggagacgc cctgagcgaa ggggtgggaa aggccattgg | 350 |
| caaagaggcc ggaggggcag ctggctctaa agtcagtgag gcccttggcc | 400 |
| aagggaccag agaagcagtt ggcactggag tcaggcaggt tccaggcttt | 450 |
| ggcgcagcag atgctttggg caacagggtc ggggaagcag cccatgctct | 500 |
| gggaaacact gggcacgaga ttggcagaca ggcagaagat gtcattcgac | 550 |
| acggagcaga tgctgtccgc ggctcctggc aggggtgcc tggccacagt | 600 |
| ggtgcttggg aaacttctgg aggccatggc atctttggct ctcaaggtgg | 650 |
| ccttggaggc cagggccagg gcaatcctgg aggtctgggg actccgtggg | 700 |
| tccacggata ccccggaaac tcagcaggca gctttggaat gaatcctcag | 750 |
| ggagctccct ggggtcaagg aggcaatgga gggccaccaa actttgggac | 800 |
| caacactcag ggagctgtgg cccagcctgg ctatggttca gtgagagcca | 850 |
| gcaaccagaa tgaagggtgc acgaatcccc caccatctgg ctcaggtgga | 900 |

-continued

```
ggctccagca actctggggg aggcagcggc tcacagtcgg gcagcagtgg         950
cagtggcagc aatggtgaca acaacaatgg cagcagcagt ggtggcagca        1000
gcagtggcag cagcagtggc agcagcagtg gcggcagcag tggcggcagc        1050
agtggtggca gcagtggcaa cagtggtggc agcagaggtg acagcggcag        1100
tgagtcctcc tggggatcca gcaccggctc ctcctccggc aaccacggtg        1150
ggagcggcgg aggaaatgga cataaacccg ggtgtgaaaa gccagggaat        1200
gaagcccgcg ggagcgggga atctgggatt cagggcttca gaggacaggg        1250
agtttccagc aacatgaggg aaataagcaa agagggcaat cgcctccttg        1300
gaggctctgg agacaattat cgggggcaag ggtcgagctg ggcagtgga         1350 ggaggtgacg ctgttggtgg agtcaatact gtgaactctg agacgtctcc        1400
tgggatgttt aactttgaca ctttctggaa gaattttaaa tccaagctgg        1450
gtttcatcaa ctgggatgcc ataaacaagg accagagaag ctctcgcatc        1500
ccgtgacctc cagacaagga gccaccagat tggatgggag cccccacact        1550
ccctccttaa acaccaccc tctcatcact aatctcagcc cttgcccttg         1600
aaataaacct tagctgcccc acaaaaaaaa aaaaaaaaaa aaaaaaaaaa        1650
aaaaaaaaaa aaaaaaaaaa aaaaaaaaaa aaaaaaaaaa aaaaaaaaaa        1700
aaaaaaaaaa aaaaaaaaaa aaaaaaaaaa aaaa                         1734
```

<210> SEQ ID NO 52
<211> LENGTH: 440
<212> TYPE: PRT
<213> ORGANISM: Homo Sapien

<400> SEQUENCE: 52

```
Met Lys Phe Gln Gly Pro Leu Ala Cys Leu Leu Ala Leu Cys
 1               5                  10                  15

Leu Gly Ser Gly Glu Ala Gly Pro Leu Gln Ser Gly Glu Glu Ser
            20                  25                  30

Thr Gly Thr Asn Ile Gly Glu Ala Leu Gly His Gly Leu Gly Asp
            35                  40                  45

Ala Leu Ser Glu Gly Val Gly Lys Ala Ile Gly Lys Glu Ala Gly
            50                  55                  60

Gly Ala Ala Gly Ser Lys Val Ser Glu Ala Leu Gly Gln Gly Thr
            65                  70                  75

Arg Glu Ala Val Gly Thr Gly Val Arg Gln Val Pro Gly Phe Gly
            80                  85                  90

Ala Ala Asp Ala Leu Gly Asn Arg Val Gly Glu Ala Ala His Ala
            95                 100                 105

Leu Gly Asn Thr Gly His Glu Ile Gly Arg Gln Ala Glu Asp Val
           110                 115                 120

Ile Arg His Gly Ala Asp Ala Val Arg Gly Ser Trp Gln Gly Val
           125                 130                 135

Pro Gly His Ser Gly Ala Trp Glu Thr Ser Gly Gly His Gly Ile
           140                 145                 150

Phe Gly Ser Gln Gly Gly Leu Gly Gly Gln Gln Gly Asn Pro
           155                 160                 165

Gly Gly Leu Gly Thr Pro Trp Val His Gly Tyr Pro Gly Asn Ser
           170                 175                 180
```

-continued

```
Ala Gly Ser Phe Gly Met Asn Pro Gln Gly Ala Pro Trp Gly Gln
            185                 190                 195
Gly Gly Asn Gly Gly Pro Pro Asn Phe Gly Thr Asn Thr Gln Gly
            200                 205                 210
Ala Val Ala Gln Pro Gly Tyr Gly Ser Val Arg Ala Ser Asn Gln
            215                 220                 225
Asn Glu Gly Cys Thr Asn Pro Pro Ser Gly Ser Gly Gly
            230                 235                 240
Ser Ser Asn Ser Gly Gly Gly Ser Gln Ser Gly Ser Ser
            245                 250                 255
Gly Ser Gly Ser Asn Gly Asp Asn Asn Gly Ser Ser Gly
            260                 265                 270
Gly Ser Ser Ser Gly Ser Ser Ser Gly Ser Ser Gly Gly Ser
            275                 280                 285
Ser Gly Gly Ser Gly Gly Ser Ser Gly Asn Ser Gly Gly Ser
            290                 295                 300
Arg Gly Asp Ser Gly Ser Glu Ser Ser Trp Gly Ser Ser Thr Gly
            305                 310                 315
Ser Ser Ser Gly Asn His Gly Gly Ser Gly Gly Asn Gly His
            320                 325                 330
Lys Pro Gly Cys Glu Lys Pro Gly Asn Glu Ala Arg Gly Ser Gly
            335                 340                 345
Glu Ser Gly Ile Gln Gly Phe Arg Gly Gln Gly Val Ser Ser Asn
            350                 355                 360
Met Arg Glu Ile Ser Lys Glu Gly Asn Arg Leu Leu Gly Gly Ser
            365                 370                 375
Gly Asp Asn Tyr Arg Gly Gln Gly Ser Ser Trp Gly Ser Gly Gly
            380                 385                 390
Gly Asp Ala Val Gly Gly Val Asn Thr Val Asn Ser Glu Thr Ser
            395                 400                 405
Pro Gly Met Phe Asn Phe Asp Thr Phe Trp Lys Asn Phe Lys Ser
            410                 415                 420
Lys Leu Gly Phe Ile Asn Trp Asp Ala Ile Asn Lys Asp Gln Arg
            425                 430                 435
Ser Ser Arg Ile Pro
            440

<210> SEQ ID NO 53
<211> LENGTH: 1676
<212> TYPE: DNA
<213> ORGANISM: Homo Sapien

<400> SEQUENCE: 53
ggagaagagg ttgtgtggga caagctgctc ccgacagaag gatgtcgctg              50
ctgagcctgc cctggctggg cctcagaccg gtggcaatgt ccccatggct             100
actcctgctg ctggttgtgg gctcctggct actcgcccgc atcctggctt             150
ggacctatgc cttctataac aactgccgcc ggctccagtg tttcccacag             200 ccccaaaac ggaactggtt tggggtcac ctgggcctga tcactcctac              250
agaggagggc ttgaaggact cgacccagat gtcggccacc tattcccagg             300
gctttacggt atgctgggt cccatcatcc ccttcatcgt tttatgccac              350
cctgacacca tccggtctat caccaatgcc tcagctgcca ttgcacccaa             400
ggataatctc ttcatcaggt tcctgaagcc ctggctggga gaagggatac             450
```

```
tgctgagtgg cggtgacaag tggagccgcc accgtcggat gctgacgccc        500
gccttccatt tcaacatcct gaagtcctat ataacgatct tcaacaagag        550
tgcaaacatc atgcttgaca agtggcagca cctggcctca gagggcagca        600
gtcgtctgga catgtttgag cacatcagcc tcatgacctt ggacagtcta        650
cagaaatgca tcttcagctt tgacagccat tgtcaggaga ggcccagtga        700
atatattgcc accatcttgg agctcagtgc ccttgtagag aaaagaagcc        750
agcatatcct ccagcacatg gactttctgt attacctctc ccatgacggg        800
cggcgcttcc acagggcctg ccgcctggtg catgacttca cagacgctgt        850
catccgggag cggcgtcgca ccctccccac tcagggtatt gatgattttt        900
tcaaagacaa agccaagtcc aagactttgg atttcattga tgtgcttctg        950
ctgagcaagg atgaagatgg gaaggcattg tcagatgagg atataagagc        1000
agaggctgac accttcatgt tggaggcca tgacaccacg gccagtggcc         1050
tctcctgggt cctgtacaac cttgcgaggc acccagaata ccaggagcgc        1100
tgccgacagg aggtgcaaga gcttctgaag gaccgcgatc ctaaagagat        1150
tgaatgggac gacctggccc agctgcccct cctgaccatg tgcgtgaagg        1200
agagcctgag gttacatccc ccagctccct tcatctcccg atgctgcacc        1250
caggacattg ttctcccaga tggccgagtc atccccaaag gcattacctg        1300
cctcatcgat attataggg tccatcacaa cccaactgtg tggccggatc         1350
ctgaggtcta cgacccttc cgctttgacc agagaacag caaggggagg          1400 tcacctctgg cttttattcc tttctccgca gggcccagga actgcatcgg        1450
gcaggcgttc gccatggcgg agatgaaagt ggtcctggcg ttgatgctgc        1500
tgcacttccg gttcctgcca gaccacactg agccccgcag gaagctggaa        1550
ttgatcatgc gcgccgaggg cgggctttgg ctgcgggtgg agcccctgaa        1600
tgtaggcttg cagtgacttt ctgacccatc cacctgtttt tttgcagatt        1650
gtcatgaata aaacggtgct gtcaaa                                  1676
```

<210> SEQ ID NO 54
<211> LENGTH: 524
<212> TYPE: PRT
<213> ORGANISM: Homo Sapien

<400> SEQUENCE: 54

```
Met Ser Leu Leu Ser Leu Pro Trp Leu Gly Leu Arg Pro Val Ala
 1               5                  10                  15

Met Ser Pro Trp Leu Leu Leu Leu Val Val Gly Ser Trp Leu
                20                  25                  30

Leu Ala Arg Ile Leu Ala Trp Thr Tyr Ala Phe Tyr Asn Asn Cys
                35                  40                  45

Arg Arg Leu Gln Cys Phe Pro Gln Pro Lys Arg Asn Trp Phe
                50                  55                  60

Trp Gly His Leu Gly Leu Ile Thr Pro Thr Glu Glu Gly Leu Lys
                65                  70                  75

Asp Ser Thr Gln Met Ser Ala Thr Tyr Ser Gln Gly Phe Thr Val
                80                  85                  90

Trp Leu Gly Pro Ile Ile Pro Phe Ile Val Leu Cys His Pro Asp
                95                 100                 105
```

```
Thr Ile Arg Ser Ile Thr Asn Ala Ser Ala Ile Ala Pro Lys
            110                 115                 120

Asp Asn Leu Phe Ile Arg Phe Leu Lys Pro Trp Leu Gly Glu Gly
            125                 130                 135

Ile Leu Leu Ser Gly Gly Asp Lys Trp Ser Arg His Arg Arg Met
            140                 145                 150

Leu Thr Pro Ala Phe His Phe Asn Ile Leu Lys Ser Tyr Ile Thr
            155                 160                 165

Ile Phe Asn Lys Ser Ala Asn Ile Met Leu Asp Lys Trp Gln His
            170                 175                 180

Leu Ala Ser Glu Gly Ser Ser Arg Leu Asp Met Phe Glu His Ile
            185                 190                 195

Ser Leu Met Thr Leu Asp Ser Leu Gln Lys Cys Ile Phe Ser Phe
            200                 205                 210

Asp Ser His Cys Gln Glu Arg Pro Ser Glu Tyr Ile Ala Thr Ile
            215                 220                 225

Leu Glu Leu Ser Ala Leu Val Glu Lys Arg Ser Gln His Ile Leu
            230                 235                 240

Gln His Met Asp Phe Leu Tyr Tyr Leu Ser His Asp Gly Arg Arg
            245                 250                 255

Phe His Arg Ala Cys Arg Leu Val His Asp Phe Thr Asp Ala Val
            260                 265                 270

Ile Arg Glu Arg Arg Arg Thr Leu Pro Thr Gln Gly Ile Asp Asp
            275                 280                 285

Phe Phe Lys Asp Lys Ala Lys Ser Lys Thr Leu Asp Phe Ile Asp
            290                 295                 300

Val Leu Leu Leu Ser Lys Asp Glu Asp Gly Lys Ala Leu Ser Asp
            305                 310                 315

Glu Asp Ile Arg Ala Glu Ala Asp Thr Phe Met Phe Gly Gly His
            320                 325                 330

Asp Thr Thr Ala Ser Gly Leu Ser Trp Val Leu Tyr Asn Leu Ala
            335                 340                 345

Arg His Pro Glu Tyr Gln Glu Arg Cys Arg Gln Glu Val Gln Glu
            350                 355                 360

Leu Leu Lys Asp Arg Asp Pro Lys Glu Ile Glu Trp Asp Asp Leu
            365                 370                 375

Ala Gln Leu Pro Phe Leu Thr Met Cys Val Lys Glu Ser Leu Arg
            380                 385                 390

Leu His Pro Pro Ala Pro Phe Ile Ser Arg Cys Cys Thr Gln Asp
            395                 400                 405

Ile Val Leu Pro Asp Gly Arg Val Ile Pro Lys Gly Ile Thr Cys
            410                 415                 420

Leu Ile Asp Ile Ile Gly Val His His Asn Pro Thr Val Trp Pro
            425                 430                 435

Asp Pro Glu Val Tyr Asp Pro Phe Arg Phe Asp Pro Glu Asn Ser
            440                 445                 450

Lys Gly Arg Ser Pro Leu Ala Phe Ile Pro Phe Ser Ala Gly Pro
            455                 460                 465

Arg Asn Cys Ile Gly Gln Ala Phe Ala Met Ala Glu Met Lys Val
            470                 475                 480

Val Leu Ala Leu Met Leu Leu His Phe Arg Phe Leu Pro Asp His
            485                 490                 495
```

```
Thr Glu Pro Arg Arg Lys Leu Glu Leu Ile Met Arg Ala Glu Gly
            500                 505                 510
Gly Leu Trp Leu Arg Val Glu Pro Leu Asn Val Gly Leu Gln
            515                 520

<210> SEQ ID NO 55
<211> LENGTH: 644
<212> TYPE: DNA
<213> ORGANISM: Homo Sapien

<400> SEQUENCE: 55
atcgcatcaa ttgggagtac catcttcctc atgggaccag tgaaacagct           50
gaagcgaatg tttgagccta ctcgtttgat tgcaactatc atggtgctgt          100
tgtgttttgc acttaccctg tgttctgcct tttggtggca taacaaggga          150
cttgcactta tcttctgcat tttgcagtct ttggcattga cgtggtacag          200
cctttccttc ataccatttg caagggatgc tgtgaagaag tgttttgccg          250
tgtgtcttgc ataattcatg ccagttttta tgaagctttg gaaggcacta          300
tggacagaag ctggtggaca gttttgtaac tatcttcgaa acctctgtct          350
tacagacatg tgcctttat cttgcagcaa tgtgttgctt gtgattcgaa           400
catttgaggg ttacttttgg aagcaacaat acattctcga acctgaatgt          450
cagtagcaca ggatgagaag tgggttctgt atcttgtgga gtggaatctt          500
cctcatgtac ctgtttcctc tctggatgtt gtcccactga attcccatga          550
atacaaacct attcagcaac agcaaaaaaa aaaaaaaaaa aaaaaaaaa           600 aaaaaaaaa aaaaaaaaaa aaaaaaaaaa aaaaaaaaaa aaaa                 644

<210> SEQ ID NO 56
<211> LENGTH: 77
<212> TYPE: PRT
<213> ORGANISM: Homo Sapien

<400> SEQUENCE: 56

Met Gly Pro Val Lys Gln Leu Lys Arg Met Phe Glu Pro Thr Arg
  1               5                  10                  15

Leu Ile Ala Thr Ile Met Val Leu Leu Cys Phe Ala Leu Thr Leu
             20                  25                  30

Cys Ser Ala Phe Trp Trp His Asn Lys Gly Leu Ala Leu Ile Phe
             35                  40                  45

Cys Ile Leu Gln Ser Leu Ala Leu Thr Trp Tyr Ser Leu Ser Phe
             50                  55                  60

Ile Pro Phe Ala Arg Asp Ala Val Lys Lys Cys Phe Ala Val Cys
             65                  70                  75

Leu Ala

<210> SEQ ID NO 57
<211> LENGTH: 3334
<212> TYPE: DNA
<213> ORGANISM: Homo Sapien

<400> SEQUENCE: 57
cggctcgagc tcgagccgaa tcggctcgag ggcagtgga gcacccagca            50 ggccgccaac atgctctgtc tgtgcctgta cgtgccggtc atcggggaag          100
cccagaccga gttccagtac tttgagtcga aggggctccc tgccgagctg          150
```

-continued

| | |
|---|---|
| aagtccattt tcaagctcag tgtcttcatc ccctcccagg aattctccac | 200 |
| ctaccgccag tggaagcaga aaattgtaca agctggagat aaggaccttg | 250 |
| atgggcagct agactttgaa gaatttgtcc attatctcca agatcatgag | 300 |
| aagaagctga ggctggtgtt taagattttg acaaaaaga atgatggacg | 350 |
| cattgacgcg caggagatca tgcagtccct gcgggacttg ggagtcaaga | 400 |
| tatctgaaca gcaggcagaa aaaattctca agagcatgga taaaaacggc | 450 |
| acgatgacca tcgactggaa cgagtggaga gactaccacc tcctccaccc | 500 |
| cgtggaaaac atccccgaga tcatcctcta ctggaagcat tccacgatct | 550 |
| ttgatgtggg tgagaatcta acggtcccgg atgagttcac agtggaggag | 600 |
| aggcagacgg ggatgtggtg gagacacctg gtggcaggag gtggggcagg | 650 |
| ggccgtatcc agaacctgca cggccccccct ggacaggctc aaggtgctca | 700 |
| tgcaggtcca tgcctcccgc agcaacaaca tgggcatcgt tggtggcttc | 750 |
| actcagatga ttcgagaagg aggggccagg tcactctggc ggggcaatgg | 800 |
| catcaacgtc ctcaaaattg ccccccgaatc agccatcaaa ttcatggcct | 850 |
| atgagcagat caagcgcctt gttggtagtg accaggagac tctgaggatt | 900 |
| cacgagaggc ttgtgcagg gtccttggca ggggccatcg cccagagcag | 950 |
| catctaccca atggaggtcc tgaagacccg gatggcgctg cggaagacag | 1000 |
| gccagtactc aggaatgctg gactgcgcca ggagggatcct ggccagagag | 1050 |
| ggggtggccg ccttctacaa aggctatgtc cccaacatgc tgggcatcat | 1100 |
| cccctatgcc ggcatcgacc ttgcagtcta cgagacgctc aagaatgcct | 1150 |
| ggctgcagca ctatgcagtg aacagcgcgg accccggcgt gtttgtgctc | 1200 |
| ctggcctgtg gcaccatgtc cagtacctgt ggccagctgg ccagctaccc | 1250 |
| cctggcccta gtcaggaccc ggatgcaggc gcaagcctct attgagggcg | 1300 |
| ctccggaggt gaccatgagc agcctcttca acatatcct gcggaccgag | 1350 |
| ggggccttcg ggctgtacag ggggctggcc cccaacttca tgaaggtcat | 1400 |
| cccagctgtg agcatcagct acgtggtcta cgagaacctg aagatcaccc | 1450 |
| tgggcgtgca gtcgcggtga cgggggggagg gccgcccggc agtggactcg | 1500 |
| ctgatcctgg gccgcagcct ggggtgtgca gccatctcat tctgtgaatg | 1550 |
| tgccaacact aagctgtctc gagccaagct gtgaaaaccc tagacgcacc | 1600 |
| cgcaggagg gtggggagag ctggcaggcc cagggcttgt cctgctgacc | 1650 |
| ccagcagacc ctcctgttgg ttccagcgaa gaccacaggc attccttagg | 1700 |
| gtccagggtc agcaggctcc gggctcacat gtgtaaggac aggacattt | 1750 |
| ctgcagtgcc tgccaatagt gagcttggag cctggaggcc ggcttagttc | 1800 |
| ttccatttca cccttgcagc cagctgttgg ccacggcccc tgccctctgg | 1850 |
| tctgccgtgc atccccctgt gccctcttgc tgcctgcctg tctgctgagg | 1900 |
| taaggtggga ggagggctac agcccacatc ccaccccctc gtccaatccc | 1950 |
| ataatccatg atgaaggtg aggtcacgtg cctcccagg cctgacttcc | 2000 |
| caacctacag cattgacgcc aacttggctg tgaaggaaga ggaaaggatc | 2050 |
| tggccttgtg gtcactggca tctgagccct gctgatggct gggctctcg | 2100 |
| ggcatgcttg ggagtgcagg gggctcgggc tgcctggcct ggctgcacag | 2150 |

-continued

```
aaggcaagtg ctggggctca tggtgctctg agctggcctg gaccctgtca         2200
ggatgggccc cacctcagaa ccaaactcac tgtccccact gtggcatgag         2250
ggcagtggag caccatgttt gagggcgaag ggcagagcgt ttgtgtgttc         2300
tggggaggga aggaaaaggt gttggaggcc ttaattatgg actgttggga         2350
aaagggtttt gtccagaagg acaagccgga caaatgagcg acttctgtgc         2400
ttccagagga agacgaggga gcaggagctt ggctgactgc tcagagtctg         2450
ttctgacgcc ctgggggttc ctgtccaacc ccagcagggg cgcagcggga         2500
ccagccccac attccacttg tgtcactgct tggaacctat ttattttgta         2550
tttatttgaa cagagttatg tcctaactat ttttatagat ttgtttaatt         2600
aatagcttgt cattttcaag ttcattttt attcatattt atgttcatgg          2650
ttgattgtac cttcccaagc ccgcccagtg ggatgggagg aggaggagaa         2700 gggggggcctt gggccgctgc agtcacatct gtccagagaa attccttttg       2750
ggactggagg cagaaaagcg gccagaaggc agcagccctg gctcctttcc         2800
tttggcaggt tggggaaggg cttgccccca gccttaggat ttcagggttt         2850 gactggggc gtggagagag agggaggaac ctcaataacc ttgaaggtgg         2900
aatccagtta tttcctgcgc tgcgagggtt tctttatttc actcttttct         2950
gaatgtcaag gcagtgaggt gcctctcact gtgaatttgt ggtgggcggg         3000
ggctggagga gagggtgggg ggctggctcc gtccctccca gccttctgct         3050
gcccttgctt aacaatgccg gccaactggc gacctcacgg ttgcacttcc         3100
attccaccag aatgacctga tgaggaaatc ttcaatagga tgcaaagatc         3150
aatgcaaaaa ttgttatata tgaacatata actggagtcg tcaaaaagca         3200
aattaagaaa gaattggacg ttagaagttg tcatttaaag cagccttcta         3250
ataaagttgt ttcaaagctg aaaaaaaaaa aaaaaaaaa aaaaaaaaa            3300 aaaaaaaaaa aaaaaaaaaa aaaaaaaaaa aaaa                          3334
```

<210> SEQ ID NO 58
<211> LENGTH: 469
<212> TYPE: PRT
<213> ORGANISM: Homo Sapien

<400> SEQUENCE: 58

```
Met Leu Cys Leu Cys Leu Tyr Val Pro Val Ile Gly Glu Ala Gln
  1               5                  10                  15

Thr Glu Phe Gln Tyr Phe Glu Ser Lys Gly Leu Pro Ala Glu Leu
                 20                  25                  30

Lys Ser Ile Phe Lys Leu Ser Val Phe Ile Pro Ser Gln Glu Phe
                 35                  40                  45

Ser Thr Tyr Arg Gln Trp Lys Gln Lys Ile Val Gln Ala Gly Asp
                 50                  55                  60

Lys Asp Leu Asp Gly Gln Leu Asp Phe Glu Glu Phe Val His Tyr
                 65                  70                  75

Leu Gln Asp His Glu Lys Lys Leu Arg Leu Val Phe Lys Ile Leu
                 80                  85                  90

Asp Lys Lys Asn Asp Gly Arg Ile Asp Ala Gln Glu Ile Met Gln
                 95                 100                 105

Ser Leu Arg Asp Leu Gly Val Lys Ile Ser Glu Gln Gln Ala Glu
```

```
            110                 115                 120
Lys Ile Leu Lys Ser Met Asp Lys Asn Gly Thr Met Thr Ile Asp
        125                 130                 135
Trp Asn Glu Trp Arg Asp Tyr His Leu His Pro Val Glu Asn
        140                 145                 150
Ile Pro Glu Ile Ile Leu Tyr Trp Lys His Ser Thr Ile Phe Asp
        155                 160                 165
Val Gly Glu Asn Leu Thr Val Pro Asp Glu Phe Thr Val Glu Glu
        170                 175                 180
Arg Gln Thr Gly Met Trp Trp Arg His Leu Val Ala Gly Gly
        185                 190                 195
Ala Gly Ala Val Ser Arg Thr Cys Thr Ala Pro Leu Asp Arg Leu
        200                 205                 210
Lys Val Leu Met Gln Val His Ala Ser Arg Ser Asn Asn Met Gly
        215                 220                 225
Ile Val Gly Gly Phe Thr Gln Met Ile Arg Glu Gly Gly Ala Arg
        230                 235                 240
Ser Leu Trp Arg Gly Asn Gly Ile Asn Val Leu Lys Ile Ala Pro
        245                 250                 255
Glu Ser Ala Ile Lys Phe Met Ala Tyr Glu Gln Ile Lys Arg Leu
        260                 265                 270
Val Gly Ser Asp Gln Glu Thr Leu Arg Ile His Glu Arg Leu Val
        275                 280                 285
Ala Gly Ser Leu Ala Gly Ala Ile Ala Gln Ser Ser Ile Tyr Pro
        290                 295                 300
Met Glu Val Leu Lys Thr Arg Met Ala Leu Arg Lys Thr Gly Gln
        305                 310                 315
Tyr Ser Gly Met Leu Asp Cys Ala Arg Arg Ile Leu Ala Arg Glu
        320                 325                 330
Gly Val Ala Ala Phe Tyr Lys Gly Tyr Val Pro Asn Met Leu Gly
        335                 340                 345
Ile Ile Pro Tyr Ala Gly Ile Asp Leu Ala Val Tyr Glu Thr Leu
        350                 355                 360
Lys Asn Ala Trp Leu Gln His Tyr Ala Val Asn Ser Ala Asp Pro
        365                 370                 375
Gly Val Phe Val Leu Leu Ala Cys Gly Thr Met Ser Ser Thr Cys
        380                 385                 390
Gly Gln Leu Ala Ser Tyr Pro Leu Ala Leu Val Arg Thr Arg Met
        395                 400                 405
Gln Ala Gln Ala Ser Ile Glu Gly Ala Pro Glu Val Thr Met Ser
        410                 415                 420
Ser Leu Phe Lys His Ile Leu Arg Thr Glu Gly Ala Phe Gly Leu
        425                 430                 435
Tyr Arg Gly Leu Ala Pro Asn Phe Met Lys Val Ile Pro Ala Val
        440                 445                 450
Ser Ile Ser Tyr Val Val Tyr Glu Asn Leu Lys Ile Thr Leu Gly
        455                 460                 465
Val Gln Ser Arg

<210> SEQ ID NO 59
<211> LENGTH: 1658
<212> TYPE: DNA
<213> ORGANISM: Homo Sapien
```

<400> SEQUENCE: 59

| | | | | |
|---|---|---|---|---|
| ggaaggcagc | ggcagctcca | ctcagccagt | acccagatac | gctgggaacc | 50 |
| ttccccagcc | atggcttccc | tggggcagat | cctcttctgg | agcataatta | 100 |
| gcatcatcat | tattctggct | ggagcaattg | cactcatcat | tggctttggt | 150 |
| atttcaggga | gacactccat | cacagtcact | actgtcgcct | cagctgggaa | 200 |
| cattggggag | gatggaatcc | tgagctgcac | ttttgaacct | gacatcaaac | 250 |
| tttctgatat | cgtgatacaa | tggctgaagg | aaggtgtttt | aggcttggtc | 300 |
| catgagttca | aagaaggcaa | agatgagctg | tcggagcagg | atgaaatgtt | 350 |
| cagaggccgg | acagcagtgt | ttgctgatca | agtgatagtt | ggcaatgcct | 400 |
| ctttgcggct | gaaaaacgtg | caactcacag | atgctggcac | ctacaaatgt | 450 |
| tatatcatca | cttctaaagg | caaggggaat | gctaaccttg | agtataaaac | 500 |
| tggagccttc | agcatgccgg | aagtgaatgt | ggactataat | gccagctcag | 550 |
| agaccttgcg | gtgtgaggct | ccccgatggt | tcccccagcc | cacagtggtc | 600 |
| tgggcatccc | aagttgacca | gggagccaac | ttctcggaag | tctccaatac | 650 |
| cagctttgag | ctgaactctg | agaatgtgac | catgaaggtt | gtgtctgtgc | 700 |
| tctacaatgt | tacgatcaac | aacacatact | cctgtatgat | tgaaaatgac | 750 |
| attgccaaag | caacagggga | tatcaaagtg | acagaatcgg | agatcaaaag | 800 |
| gcggagtcac | ctacagctgc | taaactcaaa | ggcttctctg | tgtgtctctt | 850 |
| ctttctttgc | catcagctgg | gcacttctgc | ctctcagccc | ttacctgatg | 900 |
| ctaaaataat | gtgccttggc | cacaaaaaag | catgcaaagt | cattgttaca | 950 |
| acagggatct | acagaactat | ttcaccacca | gatatgacct | agtttatat | 1000 |
| ttctgggagg | aaatgaattc | atatctagaa | gtctggagtg | agcaaacaag | 1050 |
| agcaagaaac | aaaaagaagc | caaaagcaga | aggctccaat | atgaacaaga | 1100 |
| taaatctatc | ttcaaagaca | tattagaagt | tgggaaaata | attcatgtga | 1150 |
| actagacaag | tgtgttaaga | gtgataagta | aaatgcacgt | ggagacaagt | 1200 |
| gcatccccag | atctcaggga | cctcccctg | cctgtcacct | ggggagtgag | 1250 |
| aggacaggat | agtgcatgtt | ctttgtctct | gaattttag | ttatatgtgc | 1300 |
| tgtaatgttg | ctctgaggaa | gcccctggaa | agtctatccc | aacatatcca | 1350 |
| catcttatat | tccacaaatt | aagctgtagt | atgtacccta | agacgctgct | 1400 |
| aattgactgc | cacttcgcaa | ctcagggggcg | gctgcatttt | agtaatgggt | 1450 |
| caaatgattc | actttttatg | atgcttccaa | aggtgccttg | gcttctcttc | 1500 |
| ccaactgaca | aatgccaaag | ttgagaaaaa | tgatcataat | tttagcataa | 1550 |
| acagagcagt | cggggacacc | gattttataa | ataaactgag | caccttcttt | 1600 |
| ttaaacaaaa | aaaaaaaaaa | aaaaaaaaaa | aaaaaaaaaa | aaaaaaaaaa | 1650 |
| aaaaaaaa | | | | | 1658 |

<210> SEQ ID NO 60
<211> LENGTH: 282
<212> TYPE: PRT
<213> ORGANISM: Homo Sapien

<400> SEQUENCE: 60

Met Ala Ser Leu Gly Gln Ile Leu Phe Trp Ser Ile Ile Ser Ile

```
                  1               5              10              15
Ile Ile Ile Leu Ala Gly Ala Ala Leu Ile Ile Gly Phe Gly
                 20                              25                              30

Ile Ser Gly Arg His Ser Ile Thr Val Thr Val Ala Ser Ala
                 35                              40                              45

Gly Asn Ile Gly Glu Asp Gly Ile Leu Ser Cys Thr Phe Glu Pro
                 50                              55                              60

Asp Ile Lys Leu Ser Asp Ile Val Ile Gln Trp Leu Lys Glu Gly
                 65                              70                              75

Val Leu Gly Leu Val His Glu Phe Lys Glu Gly Lys Asp Glu Leu
                 80                              85                              90

Ser Glu Gln Asp Glu Met Phe Arg Gly Arg Thr Ala Val Phe Ala
                 95                             100                             105

Asp Gln Val Ile Val Gly Asn Ala Ser Leu Arg Leu Lys Asn Val
                110                             115                             120

Gln Leu Thr Asp Ala Gly Thr Tyr Lys Cys Tyr Ile Ile Thr Ser
                125                             130                             135

Lys Gly Lys Gly Asn Ala Asn Leu Glu Tyr Lys Thr Gly Ala Phe
                140                             145                             150

Ser Met Pro Glu Val Asn Val Asp Tyr Asn Ala Ser Ser Glu Thr
                155                             160                             165

Leu Arg Cys Glu Ala Pro Arg Trp Phe Pro Gln Pro Thr Val Val
                170                             175                             180

Trp Ala Ser Gln Val Asp Gln Gly Ala Asn Phe Ser Glu Val Ser
                185                             190                             195

Asn Thr Ser Phe Glu Leu Asn Ser Glu Asn Val Thr Met Lys Val
                200                             205                             210

Val Ser Val Leu Tyr Asn Val Thr Ile Asn Asn Thr Tyr Ser Cys
                215                             220                             225

Met Ile Glu Asn Asp Ile Ala Lys Ala Thr Gly Asp Ile Lys Val
                230                             235                             240

Thr Glu Ser Glu Ile Lys Arg Arg Ser His Leu Gln Leu Leu Asn
                245                             250                             255

Ser Lys Ala Ser Leu Cys Val Ser Ser Phe Phe Ala Ile Ser Trp
                260                             265                             270

Ala Leu Leu Pro Leu Ser Pro Tyr Leu Met Leu Lys
                275                             280

<210> SEQ ID NO 61
<211> LENGTH: 1617
<212> TYPE: DNA
<213> ORGANISM: Homo Sapien

<400> SEQUENCE: 61
tgacgtcaga atcaccatgg ccagctatcc ttaccggcag ggctgcccag        50
gagctgcagg acaagcacca ggagcccctc cgggtagcta ctaccctgga       100 cccccaata gtgagggca gtatggtagt gggctacccc ctggtggtgg         150
ttatgggggt cctgcccctg gagggcctta tggaccacca gctggtggag      200
ggccctatgg acaccccaat cctgggatgt tccctctgg aactccagga       250 ggaccatatg gcggtgcagc tcccgggggc cctatggtc agccacctcc       300 aagttcctac ggtgcccagc agcctgggct ttatggacag gtggcgccc       350 ctcccaatgt ggatcctgag gcctactcct ggttccagtc ggtggactca      400
```

```
gatcacagtg gctatatctc catgaaggag ctaaagcagg ccctggtcaa        450
ctgcaattgg tcttcattca atgatgagac ctgcctcatg atgataaaca        500
tgtttgacaa gaccaagtca ggccgcatcg atgtctacgg cttctcagcc        550
ctgtggaaat tcatccagca gtggaagaac ctcttccagc agtatgaccg        600
ggaccgctcg ggctccatta gctacacaga gctgcagcaa gctctgtccc        650
aaatgggcta caacctgagc ccccagttca cccagcttct ggtctcccgc        700
tactgcccac gctctgccaa tcctgccatg cagcttgacc gcttcatcca        750
ggtgtgcacc cagctgcagg tgctgacaga ggccttccgg gagaaggaca        800
cagctgtaca aggcaacatc cggctcagct tcgaggactt cgtcaccatg        850
acagcttctc ggatgctatg acccaaccat ctgtggagag tggagtgcac        900
cagggaccct tcctggcttc ttagagtgag agaagtatgt ggacatctct        950
tcttttcctg tccctctaga agaacattct cccttgcttg atgcaacact       1000
gttccaaaag agggtggaga gtcctgcatc atagccacca aatagtgagg       1050
accggggctg aggccacaca gatagggggcc tgatggagga gaggatagaa      1100
gttgaatgtc ctgatggcca tgagcagttg agtggcacag cctggcacca       1150
ggagcaggtc cttgtaatgg agttagtgtc cagtcagctg agctccaccc       1200
tgatgccagt ggtgagtgtt catcggcctg ttaccgttag tacctgtgtt       1250
ccctcaccag gccatcctgt caaacgagcc cattttctcc aaagtggaat       1300
ctgaccaagc atgagagaga tctgtctatg ggaccagtgg cttggattct       1350
gccacaccca taaatccttg tgtgttaact tctagctgcc tggggctggc       1400
cctgctcaga caaatctgct ccctgggcat cttttggccag gcttctgccc      1450 cctgcagctg ggaccctca cttgcctgcc atgctctgct cggcttcagt        1500
ctccaggaga cagtggtcac ctctccctgc caatacttt tttaatttgc        1550 attttttttc atttggggcc aaaagtccag tgaaattgta agcttcaata       1600
aaaggatgaa actctga                                           1617
```

<210> SEQ ID NO 62
<211> LENGTH: 284
<212> TYPE: PRT
<213> ORGANISM: Homo Sapien

<400> SEQUENCE: 62

```
Met Ala Ser Tyr Pro Tyr Arg Gln Gly Cys Pro Gly Ala Ala Gly
  1               5                  10                  15

Gln Ala Pro Gly Ala Pro Pro Gly Ser Tyr Tyr Pro Gly Pro Pro
                 20                  25                  30

Asn Ser Gly Gly Gln Tyr Gly Ser Gly Leu Pro Pro Gly Gly Gly
                 35                  40                  45

Tyr Gly Gly Pro Ala Pro Gly Gly Pro Tyr Gly Pro Ala Gly
                 50                  55                  60

Gly Gly Pro Tyr Gly His Pro Asn Pro Gly Met Phe Pro Ser Gly
                 65                  70                  75

Thr Pro Gly Gly Pro Tyr Gly Gly Ala Ala Pro Gly Gly Pro Tyr
                 80                  85                  90

Gly Gln Pro Pro Pro Ser Ser Tyr Gly Ala Gln Gln Pro Gly Leu
                 95                 100                 105
```

-continued

```
Tyr Gly Gln Gly Gly Ala Pro Pro Asn Val Asp Pro Glu Ala Tyr
            110                 115                 120

Ser Trp Phe Gln Ser Val Asp Ser Asp His Ser Gly Tyr Ile Ser
        125                 130                 135

Met Lys Glu Leu Lys Gln Ala Leu Val Asn Cys Asn Trp Ser Ser
    140                 145                 150

Phe Asn Asp Glu Thr Cys Leu Met Met Ile Asn Met Phe Asp Lys
155                 160                 165

Thr Lys Ser Gly Arg Ile Asp Val Tyr Gly Phe Ser Ala Leu Trp
        170                 175                 180

Lys Phe Ile Gln Gln Trp Lys Asn Leu Phe Gln Gln Tyr Asp Arg
    185                 190                 195

Asp Arg Ser Gly Ser Ile Ser Tyr Thr Glu Leu Gln Gln Ala Leu
        200                 205                 210

Ser Gln Met Gly Tyr Asn Leu Ser Pro Gln Phe Thr Gln Leu Leu
    215                 220                 225

Val Ser Arg Tyr Cys Pro Arg Ser Ala Asn Pro Ala Met Gln Leu
        230                 235                 240

Asp Arg Phe Ile Gln Val Cys Thr Gln Leu Gln Val Leu Thr Glu
    245                 250                 255

Ala Phe Arg Glu Lys Asp Thr Ala Val Gln Gly Asn Ile Arg Leu
        260                 265                 270

Ser Phe Glu Asp Phe Val Thr Met Thr Ala Ser Arg Met Leu
    275                 280
```

<210> SEQ ID NO 63
<211> LENGTH: 1234
<212> TYPE: DNA
<213> ORGANISM: Homo Sapien

<400> SEQUENCE: 63

| | |
|---|---:|
| caggatgcag ggccgcgtgg cagggagctg cgctcctctg ggcctgctcc | 50 |
| tggtctgtct tcatctccca ggcctctttg cccggagcat cggtgttgtg | 100 |
| gaggagaaag tttcccaaaa cttcgggacc aacttgcctc agctcggaca | 150 |
| accttcctcc actggcccct ctaactctga acatccgcag cccgctctgg | 200 |
| accctaggtc taatgacttg gcaagggttc ctctgaagct cagcgtgcct | 250 |
| ccatcagatg gcttcccacc tgcaggaggt tctgcagtgc agaggtggcc | 300 |
| tccatcgtgg gggctgcctg ccatggattc ctggcccct gaggatcctt | 350 |
| ggcagatgat ggctgctgcg gctgaggacc gcctggggga agcgctgcct | 400 |
| gaagaactct cttacctctc cagtgctgcg gccctcgctc cgggcagtgg | 450 |
| cccttttgcct ggggagtctt ctcccgatgc acaggcctc tcacctgagg | 500 |
| cttcactcct ccaccaggac tcggagtcca gacgactgcc ccgttctaat | 550 |
| tcactgggag ccggggggaaa aatcctttcc aacgccctc cctggtctct | 600 |
| catccacagg gttctgcctg atcacccctg gggtaccctg aatcccagtg | 650 |
| tgtcctgggg aggtggaggc cctgggactg gttggggaac gaggcccatg | 700 |
| ccacaccctg agggaatctg gggtatcaat atcaacccc caggtaccag | 750 |
| ctggggaaat attaatcggt atccaggagg cagctgggga atattaatc | 800 |
| ggtatccagg aggcagctgg gggaatatta atcggtatcc aggaggcagc | 850 |

-continued

```
tgggggaata ttcatctata cccaggtatc aataacccat ttcctcctgg         900
agttctccgc cctcctggct cttcttggaa catcccagct ggcttcccta         950
atcctccaag ccctaggttg cagtggggct agagcacgat agagggaaac        1000
ccaacattgg gagttagagt cctgctcccg cccttgctg tgtgggctca         1050 atccaggccc tgttaacatg tttccagcac tatccccact tttcagtgcc        1100
tcccctgctc atctccaata aaataaaagc acttatgaaa aaaaaaaaa         1150 aaaaaaaaaa aaaaaaaaa aaaaaaaaaa aaaaaaaaaa aaaaaaaaaa         1200
aaaaaaaaaa aaaaaaaaa aaaaaaaaaa aaaa                          1234
```

<210> SEQ ID NO 64
<211> LENGTH: 325
<212> TYPE: PRT
<213> ORGANISM: Homo Sapien

<400> SEQUENCE: 64

```
Met Gln Gly Arg Val Ala Gly Ser Cys Ala Pro Leu Gly Leu Leu
 1               5                  10                  15

Leu Val Cys Leu His Leu Pro Gly Leu Phe Ala Arg Ser Ile Gly
                20                  25                  30

Val Val Glu Glu Lys Val Ser Gln Asn Phe Gly Thr Asn Leu Pro
            35                  40                  45

Gln Leu Gly Gln Pro Ser Ser Thr Gly Pro Ser Asn Ser Glu His
        50                  55                  60

Pro Gln Pro Ala Leu Asp Pro Arg Ser Asn Asp Leu Ala Arg Val
    65                  70                  75

Pro Leu Lys Leu Ser Val Pro Pro Ser Asp Gly Phe Pro Pro Ala
            80                  85                  90

Gly Gly Ser Ala Val Gln Arg Trp Pro Pro Ser Trp Gly Leu Pro
            95                 100                 105

Ala Met Asp Ser Trp Pro Pro Glu Asp Pro Trp Gln Met Met Ala
           110                 115                 120

Ala Ala Ala Glu Asp Arg Leu Gly Glu Ala Leu Pro Glu Glu Leu
           125                 130                 135

Ser Tyr Leu Ser Ser Ala Ala Ala Leu Ala Pro Gly Ser Gly Pro
           140                 145                 150

Leu Pro Gly Glu Ser Ser Pro Asp Ala Thr Gly Leu Ser Pro Glu
           155                 160                 165

Ala Ser Leu Leu His Gln Asp Ser Glu Ser Arg Arg Leu Pro Arg
           170                 175                 180

Ser Asn Ser Leu Gly Ala Gly Gly Lys Ile Leu Ser Gln Arg Pro
           185                 190                 195

Pro Trp Ser Leu Ile His Arg Val Leu Pro Asp His Pro Trp Gly
           200                 205                 210

Thr Leu Asn Pro Ser Val Ser Trp Gly Gly Gly Pro Gly Thr
           215                 220                 225

Gly Trp Gly Thr Arg Pro Met Pro His Pro Glu Gly Ile Trp Gly
           230                 235                 240

Ile Asn Asn Gln Pro Pro Gly Thr Ser Trp Gly Asn Ile Asn Arg
           245                 250                 255

Tyr Pro Gly Gly Ser Trp Gly Asn Ile Asn Arg Tyr Pro Gly Gly
           260                 265                 270

Ser Trp Gly Asn Ile Asn Arg Tyr Pro Gly Gly Ser Trp Gly Asn
```

```
                275                 280                 285
Ile His Leu Tyr Pro Gly Ile Asn Asn Pro Phe Pro Pro Gly Val
                290                 295                 300
Leu Arg Pro Pro Gly Ser Ser Trp Asn Ile Pro Ala Gly Phe Pro
                305                 310                 315
Asn Pro Pro Ser Pro Arg Leu Gln Trp Gly
                320                 325

<210> SEQ ID NO 65
<211> LENGTH: 422
<212> TYPE: DNA
<213> ORGANISM: Homo Sapien

<400> SEQUENCE: 65
aaggagaggc caccgggact tcagtgtctc ctccatccca ggagcgcagt        50
ggccactatg gggtctgggc tgccccttgt cctcctcttg accctccttg       100
gcagctcaca tggaacaggg ccgggtatga ctttgcaact gaagctgaag       150 gagtctttc tgacaaattc ctcctatgag tccagcttcc tggaattgct        200
tgaaaagctc tgcctcctcc tccatctccc ttcagggacc agcgtcaccc       250
tccaccatgc aagatctcaa caccatgttg tctgcaacac atgacagcca       300
ttgaagcctg tgtccttctt ggcccgggct tttgggccgg ggatgcagga       350
ggcaggcccc gaccctgtct ttcagcaggc ccccaccctc ctgagtggca       400
ataaataaaa ttcggtatgc tg                                    422

<210> SEQ ID NO 66
<211> LENGTH: 78
<212> TYPE: PRT
<213> ORGANISM: Homo Sapien

<400> SEQUENCE: 66

Met Gly Ser Gly Leu Pro Leu Val Leu Leu Leu Thr Leu Leu Gly
  1               5                  10                  15
Ser Ser His Gly Thr Gly Pro Gly Met Thr Leu Gln Leu Lys Leu
                 20                  25                  30
Lys Glu Ser Phe Leu Thr Asn Ser Ser Tyr Glu Ser Ser Phe Leu
                 35                  40                  45
Glu Leu Leu Glu Lys Leu Cys Leu Leu Leu His Leu Pro Ser Gly
                 50                  55                  60
Thr Ser Val Thr Leu His His Ala Arg Ser Gln His His Val Val
                 65                  70                  75
Cys Asn Thr

<210> SEQ ID NO 67
<211> LENGTH: 744
<212> TYPE: DNA
<213> ORGANISM: Homo Sapien

<400> SEQUENCE: 67
acggaccgag ggttcgaggg agggacacgg accaggaacc tgagctaggt        50
caaagacgcc cgggccaggt gccccgtcgc aggtgcccct ggccggagat       100
gcggtaggag gggcgagcgc gagaagcccc ttcctcggcg ctgccaaccc       150
gccacccagc ccatggcgaa ccccgggctg ggctgcttc tggcgctggg       200 cctgccgttc ctgctggccc gctggggccg agcctggggg caaatacaga       250
```

-continued

```
ccacttctgc aaatgagaat agcactgttt tgccttcatc caccagctcc        300
agctccgatg gcaacctgcg tccggaagcc atcactgcta tcatcgtggt        350
cttctccctc ttggctgcct tgctcctggc tgtggggctg gcactgttgg        400
tgcggaagct tcgggagaag cggcagacgg agggcaccta ccggcccagt        450
agcgaggagc agttctccca tgcagccgag gcccgggccc ctcaggactc        500
caaggagacg gtgcagggct gcctgcccat ctaggtcccc tctcctgcat        550
ctgtctccct tcattgctgt gtgaccttgg ggaaaggcag tgccctctct        600
gggcagtcag atccacccag tgcttaatag cagggaagaa ggtacttcaa        650
agactctgcc cctgaggtca agagaggatg gggctattca cttttatata        700
tttatataaa attagtagtg agatgtaaaa aaaaaaaaaa aaaa             744
```

<210> SEQ ID NO 68
<211> LENGTH: 123
<212> TYPE: PRT
<213> ORGANISM: Homo Sapien

<400> SEQUENCE: 68

```
Met Ala Asn Pro Gly Leu Gly Leu Leu Ala Leu Gly Leu Pro
  1               5                  10                  15

Phe Leu Leu Ala Arg Trp Gly Arg Ala Trp Gly Gln Ile Gln Thr
                 20                  25                  30

Thr Ser Ala Asn Glu Asn Ser Thr Val Leu Pro Ser Ser Thr Ser
                 35                  40                  45

Ser Ser Ser Asp Gly Asn Leu Arg Pro Glu Ala Ile Thr Ala Ile
                 50                  55                  60

Ile Val Val Phe Ser Leu Leu Ala Ala Leu Leu Ala Val Gly
             65                  70                  75

Leu Ala Leu Leu Val Arg Lys Leu Arg Glu Lys Arg Gln Thr Glu
                 80                  85                  90

Gly Thr Tyr Arg Pro Ser Ser Glu Glu Gln Phe Ser His Ala Ala
                 95                 100                 105

Glu Ala Arg Ala Pro Gln Asp Ser Lys Glu Thr Val Gln Gly Cys
                110                 115                 120

Leu Pro Ile
```

<210> SEQ ID NO 69
<211> LENGTH: 3265
<212> TYPE: DNA
<213> ORGANISM: Homo Sapien

<400> SEQUENCE: 69

```
gccaggaata actagagagg aacaatgggg ttattcagag gttttgtttt         50
cctcttagtt ctgtgcctgc tgcaccagtc aaatacttcc ttcattaagc        100
tgaataataa tggctttgaa gatattgtca ttgttataga tcctagtgtg        150
ccagaagatg aaaaaataat tgaacaaata gaggatatgg tgactacagc        200
ttctacgtac ctgttttgaag ccacagaaaa aagatttttt ttcaaaaatg        250
tatctatatt aattcctgag aattggaagg aaaatcctca gtacaaaagg        300
ccaaaacatg aaaaccataa acatgctgat gttatagttg caccacctac        350
actcccaggt agagatgaac catacaccaa gcagttcaca gaatgtggag        400
```

-continued

| | |
|---|---|
| agaaaggcga atacattcac ttcacccctg accttctact tggaaaaaaa | 450 |
| caaaatgaat atgaccacc aggcaaactg tttgtccatg agtgggctca | 500 |
| cctccggtgg ggagtgtttg atgagtacaa tgaagatcag cctttctacc | 550 |
| gtgctaagtc aaaaaaaatc gaagcaacaa ggtgttccgc aggtatctct | 600 |
| ggtagaaata gagtttataa gtgtcaagga ggcagctgtc ttagtagagc | 650 |
| atgcagaatt gattctacaa caaaactgta tggaaaagat tgtcaattct | 700 |
| ttcctgataa agtacaaaca gaaaagcat ccataatgtt tatgcaaagt | 750 |
| attgattctg ttgttgaatt ttgtaacgaa aaaacccata atcaagaagc | 800 |
| tccaagccta caaaacataa agtgcaattt tagaagtaca tgggaggtga | 850 |
| ttagcaattc tgaggatttt aaaaacacca tacccatggt gacaccacct | 900 |
| cctccacctg tcttctcatt gctgaagatc agtcaaagaa ttgtgtgctt | 950 |
| agttcttgat aagtctggaa gcatggggg taaggaccgc ctaaatcgaa | 1000 |
| tgaatcaagc agcaaaacat ttcctgctgc agactgttga aaatggatcc | 1050 |
| tgggtgggga tggttcactt tgatagtact gccactattg taaataagct | 1100 |
| aatccaaata aaaagcagtg atgaaagaaa cacactcatg gcaggattac | 1150 |
| ctacatatcc tctgggagga acttccatct gctctggaat taaatatgca | 1200 |
| tttcaggtga ttggagagct acattcccaa ctcgatggat ccgaagtact | 1250 |
| gctgctgact gatggggagg ataacactgc aagttcttgt attgatgaag | 1300 |
| tgaaacaaag tggggccatt gttcatttta ttgctttggg aagagctgct | 1350 |
| gatgaagcag taatagagat gagcaagata acaggaggaa gtcatttta | 1400 |
| tgtttcagat gaagctcaga acaatggcct cattgatgct tttggggctc | 1450 |
| ttacatcagg aaatactgat ctctcccaga agtcccttca gctcgaaagt | 1500 |
| aagggattaa cactgaatag taatgcctgg atgaacgaca ctgtcataat | 1550 |
| tgatagtaca gtgggaaagg acacgttctt tctcatcaca tggaacagtc | 1600 |
| tgcctcccag tatttctctc tgggatccca gtggaacaat aatggaaaat | 1650 |
| ttcacagtgg atgcaacttc caaaatggcc tatctcagta ttccaggaac | 1700 |
| tgcaaaggtg ggcacttggg catacaatct tcaagccaaa gcgaacccag | 1750 |
| aaacattaac tattacagta acttctcgag cagcaaattc ttctgtgcct | 1800 |
| ccaatcacag tgaatgctaa aatgaataag gacgtaaaca gtttccccag | 1850 |
| cccaatgatt gtttacgcag aaattctaca aggatatgta cctgttcttg | 1900 |
| gagccaatgt gactgctttc attgaatcac agaatggaca tacagaagtt | 1950 |
| ttggaacttt tggataatgg tgcaggcgct gattctttca agaatgatgg | 2000 |
| agtctactcc aggtatttta cagcatatac agaaaatggc agatatagct | 2050 |
| taaaagttcg ggctcatgga ggagcaaaca ctgccaggct aaaattacgg | 2100 |
| cctccactga atagagccgc gtacatacca ggctgggtag tgaacgggga | 2150 |
| aattgaagca aacccgccaa gacctgaaat tgatgaggat actcagacca | 2200 |
| ccttggagga tttcagccga acagcatccg gaggtgcatt tgtggtatca | 2250 |
| caagtcccaa gccttcctt gcctgaccaa tacccaccaa gtcaaatcac | 2300 |
| agaccttgat gccacagttc atgaggataa gattattctt acatggacag | 2350 |
| caccaggaga taattttgat gttggaaaag ttcaacgtta tatcataaga | 2400 |

-continued

```
ataagtgcaa gtattcttga tctaagagac agttttgatg atgctcttca      2450
agtaaatact actgatctgt caccaaagga ggccaactcc aaggaaagct      2500
ttgcatttaa accagaaaat atctcagaag aaaatgcaac ccacatattt      2550
attgccatta aaagtataga taaaagcaat ttgacatcaa aagtatccaa      2600
cattgcacaa gtaactttgt ttatccctca agcaaatcct gatgacattg      2650
atcctacacc tactcctact cctactccta ctcctgataa aagtcataat      2700
tctggagtta atatttctac gctggtattg tctgtgattg ggtctgttgt      2750
aattgttaac tttatttaa gtaccaccat ttgaaccta acgaagaaaa        2800 aaatcttcaa gtagacctag aagagagttt taaaaaacaa aacaatgtaa      2850
gtaaaggata tttctgaatc ttaaaattca tcccatgtgt gatcataaac      2900
tcataaaaat aattttaaga tgtcggaaaa ggatactttg attaaataaa      2950
aacactcatg gatatgtaaa aactgtcaag attaaaattt aatagtttca      3000
tttatttgtt atttttatttg taagaaatag tgatgaacaa agatccttt     3050 tcatactgat acctggttgt atattatttg atgcaacagt tttctgaaat      3100
gatatttcaa attgcatcaa gaaattaaaa tcatctatct gagtagtcaa      3150
aatacaagta aaggagagca aataaacaac atttggaaaa aaaaaaaaa       3200 aaaaaaaaaa aaaaaaaaaa aaaaaaaaaa aaaaaaaaaa aaaaaaaaaa      3250
aaaaaaaaaa aaaaa                                            3265
```

<210> SEQ ID NO 70
<211> LENGTH: 919
<212> TYPE: PRT
<213> ORGANISM: Homo Sapien

<400> SEQUENCE: 70

```
Met Gly Leu Phe Arg Gly Phe Val Phe Leu Leu Val Leu Cys Leu
 1               5                  10                  15

Leu His Gln Ser Asn Thr Ser Phe Ile Lys Leu Asn Asn Asn Gly
                20                  25                  30

Phe Glu Asp Ile Val Ile Val Asp Pro Ser Val Pro Glu Asp
                35                  40                  45

Glu Lys Ile Ile Glu Gln Ile Glu Asp Met Val Thr Thr Ala Ser
                50                  55                  60

Thr Tyr Leu Phe Glu Ala Thr Glu Lys Arg Phe Phe Lys Asn
                65                  70                  75

Val Ser Ile Leu Ile Pro Glu Asn Trp Lys Glu Asn Pro Gln Tyr
                80                  85                  90

Lys Arg Pro Lys His Glu Asn His Lys His Ala Asp Val Ile Val
                95                  100                 105

Ala Pro Pro Thr Leu Pro Gly Arg Asp Glu Pro Tyr Thr Lys Gln
                110                 115                 120

Phe Thr Glu Cys Gly Glu Lys Gly Glu Tyr Ile His Phe Thr Pro
                125                 130                 135

Asp Leu Leu Gly Lys Lys Gln Asn Glu Tyr Gly Pro Pro Gly
                140                 145                 150

Lys Leu Phe Val His Glu Trp Ala His Leu Arg Trp Gly Val Phe
                155                 160                 165

Asp Glu Tyr Asn Glu Asp Gln Pro Phe Tyr Arg Ala Lys Ser Lys
```

-continued

```
            170                 175                 180
Lys Ile Glu Ala Thr Arg Cys Ser Ala Gly Ile Ser Gly Arg Asn
        185                 190                 195
Arg Val Tyr Lys Cys Gln Gly Gly Ser Cys Leu Ser Arg Ala Cys
        200                 205                 210
Arg Ile Asp Ser Thr Thr Lys Leu Tyr Gly Lys Asp Cys Gln Phe
        215                 220                 225
Phe Pro Asp Lys Val Gln Thr Glu Lys Ala Ser Ile Met Phe Met
        230                 235                 240
Gln Ser Ile Asp Ser Val Val Glu Phe Cys Asn Glu Lys Thr His
        245                 250                 255
Asn Gln Glu Ala Pro Ser Leu Gln Asn Ile Lys Cys Asn Phe Arg
        260                 265                 270
Ser Thr Trp Glu Val Ile Ser Asn Ser Glu Asp Phe Lys Asn Thr
        275                 280                 285
Ile Pro Met Val Thr Pro Pro Pro Pro Val Phe Ser Leu Leu
        290                 295                 300
Lys Ile Ser Gln Arg Ile Val Cys Leu Val Leu Asp Lys Ser Gly
        305                 310                 315
Ser Met Gly Gly Lys Asp Arg Leu Asn Arg Met Asn Gln Ala Ala
        320                 325                 330
Lys His Phe Leu Leu Gln Thr Val Glu Asn Gly Ser Trp Val Gly
        335                 340                 345
Met Val His Phe Asp Ser Thr Ala Thr Ile Val Asn Lys Leu Ile
        350                 355                 360
Gln Ile Lys Ser Ser Asp Glu Arg Asn Thr Leu Met Ala Gly Leu
        365                 370                 375
Pro Thr Tyr Pro Leu Gly Gly Thr Ser Ile Cys Ser Gly Ile Lys
        380                 385                 390
Tyr Ala Phe Gln Val Ile Gly Glu Leu His Ser Gln Leu Asp Gly
        395                 400                 405
Ser Glu Val Leu Leu Leu Thr Asp Gly Glu Asp Asn Thr Ala Ser
        410                 415                 420
Ser Cys Ile Asp Glu Val Lys Gln Ser Gly Ala Ile Val His Phe
        425                 430                 435
Ile Ala Leu Gly Arg Ala Ala Asp Glu Ala Val Ile Glu Met Ser
        440                 445                 450
Lys Ile Thr Gly Gly Ser His Phe Tyr Val Ser Asp Glu Ala Gln
        455                 460                 465
Asn Asn Gly Leu Ile Asp Ala Phe Gly Ala Leu Thr Ser Gly Asn
        470                 475                 480
Thr Asp Leu Ser Gln Lys Ser Leu Gln Leu Glu Ser Lys Gly Leu
        485                 490                 495
Thr Leu Asn Ser Asn Ala Trp Met Asn Asp Thr Val Ile Ile Asp
        500                 505                 510
Ser Thr Val Gly Lys Asp Thr Phe Phe Leu Ile Thr Trp Asn Ser
        515                 520                 525
Leu Pro Pro Ser Ile Ser Leu Trp Asp Pro Ser Gly Thr Ile Met
        530                 535                 540
Glu Asn Phe Thr Val Asp Ala Thr Ser Lys Met Ala Tyr Leu Ser
        545                 550                 555
Ile Pro Gly Thr Ala Lys Val Gly Thr Trp Ala Tyr Asn Leu Gln
        560                 565                 570
```

```
Ala Lys Ala Asn Pro Glu Thr Leu Thr Ile Thr Val Thr Ser Arg
            575                 580                 585

Ala Ala Asn Ser Ser Val Pro Pro Ile Thr Val Asn Ala Lys Met
            590                 595                 600

Asn Lys Asp Val Asn Ser Phe Pro Ser Pro Met Ile Val Tyr Ala
            605                 610                 615

Glu Ile Leu Gln Gly Tyr Val Pro Val Leu Gly Ala Asn Val Thr
            620                 625                 630

Ala Phe Ile Glu Ser Gln Asn Gly His Thr Glu Val Leu Glu Leu
            635                 640                 645

Leu Asp Asn Gly Ala Gly Ala Asp Ser Phe Lys Asn Asp Gly Val
            650                 655                 660

Tyr Ser Arg Tyr Phe Thr Ala Tyr Thr Glu Asn Gly Arg Tyr Ser
            665                 670                 675

Leu Lys Val Arg Ala His Gly Gly Ala Asn Thr Ala Arg Leu Lys
            680                 685                 690

Leu Arg Pro Pro Leu Asn Arg Ala Ala Tyr Ile Pro Gly Trp Val
            695                 700                 705

Val Asn Gly Glu Ile Glu Ala Asn Pro Pro Arg Pro Glu Ile Asp
            710                 715                 720

Glu Asp Thr Gln Thr Thr Leu Glu Asp Phe Ser Arg Thr Ala Ser
            725                 730                 735

Gly Gly Ala Phe Val Val Ser Gln Val Pro Ser Leu Pro Leu Pro
            740                 745                 750

Asp Gln Tyr Pro Pro Ser Gln Ile Thr Asp Leu Asp Ala Thr Val
            755                 760                 765

His Glu Asp Lys Ile Ile Leu Thr Trp Thr Ala Pro Gly Asp Asn
            770                 775                 780

Phe Asp Val Gly Lys Val Gln Arg Tyr Ile Ile Arg Ile Ser Ala
            785                 790                 795

Ser Ile Leu Asp Leu Arg Asp Ser Phe Asp Asp Ala Leu Gln Val
            800                 805                 810

Asn Thr Thr Asp Leu Ser Pro Lys Glu Ala Asn Ser Lys Glu Ser
            815                 820                 825

Phe Ala Phe Lys Pro Glu Asn Ile Ser Glu Glu Asn Ala Thr His
            830                 835                 840

Ile Phe Ile Ala Ile Lys Ser Ile Asp Lys Ser Asn Leu Thr Ser
            845                 850                 855

Lys Val Ser Asn Ile Ala Gln Val Thr Leu Phe Ile Pro Gln Ala
            860                 865                 870

Asn Pro Asp Asp Ile Asp Pro Thr Pro Thr Pro Thr Pro Thr Pro
            875                 880                 885

Thr Pro Asp Lys Ser His Asn Ser Gly Val Asn Ile Ser Thr Leu
            890                 895                 900

Val Leu Ser Val Ile Gly Ser Val Val Ile Val Asn Phe Ile Leu
            905                 910                 915

Ser Thr Thr Ile

<210> SEQ ID NO 71
<211> LENGTH: 3877
<212> TYPE: DNA
<213> ORGANISM: Homo Sapien

<400> SEQUENCE: 71
```

```
ctccttaggt ggaaaccctg ggagtagagt actgacagca aagaccggga        50
aagaccatac gtccccgggc aggggtgaca acaggtgtca tcttttttgat      100
ctcgtgtgtg gctgccttcc tatttcaagg aaagacgcca aggtaatttt       150
gacccagagg agcaatgatg tagccacctc ctaaccttcc cttcttgaac       200
ccccagttat gccaggattt actagagagt gtcaactcaa ccagcaagcg       250
gctccttcgg cttaacttgt ggttggagga gagaaccttt gtggggctgc       300
gttctcttag cagtgctcag aagtgacttg cctgagggtg gaccagaaga       350
aaggaaaggt cccctcttgc tgttggctgc acatcaggaa ggctgtgatg       400
ggaatgaagg tgaaaacttg gagatttcac ttcagtcatt gcttctgcct       450
gcaagatcat cctttaaaag tagagaagct gctctgtgtg gtggttaact       500
ccaagaggca gaactcgttc tagaaggaaa tggatgcaag cagctccggg       550
ggccccaaac gcatgcttcc tgtggtctag cccagggaag cccttccgtg       600
gggcccccgg ctttgaggga tgccaccggt tctggacgca tggctgattc       650
ctgaatgatg atggttcgcc gggggctgct tgcgtggatt tcccgggtgg       700
tggttttgct ggtgctcctc tgctgtgcta tctctgtcct gtacatgttg       750
gcctgcaccc caaaggtga cgaggagcag ctggcactgc ccagggccaa        800
cagccccacg gggaaggagg ggtaccaggc cgtccttcag gagtgggagg       850
agcagcaccg caactacgtg agcagcctga agcggcagat cgcacagctc       900
aaggaggagc tgcaggagag gagtgagcag ctcaggaatg ggcagtacca       950
agccagcgat gctgctggcc tgggtctgga caggagcccc ccagagaaaa      1000
cccaggccga cctcctggcc ttcctgcact cgcaggtgga caaggcagag      1050
gtgaatgctg gcgtcaagct ggccacagag tatgcagcga tgcctttcga      1100
tagctttact ctacagaagg tgtaccagct ggagactggc cttacccgcc      1150
accccgagga gaagcctgtg aggaaggaca agcgggatga gttggtggaa      1200
gccattgaat cagccttgga gaccctgaac aatcctgcag agaacagccc      1250
caatcaccgt ccttacacgg cctctgattt catagaaggg atctaccgaa      1300
cagaaaggga caaagggaca ttgtatgagc tcaccttcaa aggggaccac      1350
aaacacgaat tcaaacggct catcttattt cgaccattca gccccatcat      1400
gaaagtgaaa aatgaaaagc tcaacatggc caacacgctt atcaatgtta      1450
tcgtgcctct agcaaaaagg gtggacaagt tccggcagtt catgcagaat      1500
ttcagggaga tgtgcattga gcaggatggg agagtccatc tcactgttgt      1550
ttactttggg aaagaagaaa taatgaagt caaaggaata cttgaaaaca      1600
cttccaaagc tgccaacttc aggaacttta ccttcatcca gctgaatgga      1650
gaattttctc ggggaaaggg acttgatgtt ggagcccgct tctggaaggg      1700
aagcaacgtc cttctctttt tctgtgatgt ggacatctac ttcacatctg      1750
aattcctcaa tacgtgtagg ctgaatacac agccagggaa gaaggtatt       1800
tatccagttc ttttcagtca gtacaatcct ggcataatat acggccacca      1850
tgatgcagtc cctcccttgg aacagcagct ggtcataaag aaggaaactg      1900
gattttggag agactttgga tttgggatga cgtgtcagta tcggtcagac      1950
```

| | |
|---|---|
| ttcatcaata taggtgggtt tgatctggac atcaaaggct ggggcggaga | 2000 |
| ggatgtgcac ctttatcgca agtatctcca cagcaacctc atagtggtac | 2050 |
| ggacgcctgt gcgaggactc ttccacctct ggcatgagaa gcgctgcatg | 2100 |
| gacgagctga cccccgagca gtacaagatg tgcatgcagt ccaaggccat | 2150 |
| gaacgaggca tcccacggcc agctgggcat gctggtgttc aggcacgaga | 2200 |
| tagaggctca ccttcgcaaa cagaaacaga agacaagtag caaaaaaaca | 2250 |
| tgaactccca gagaaggatt gtgggagaca cttttcttt cttttgcaa | 2300 |
| ttactgaaag tggctgcaac agagaaaaga cttccataaa ggacgacaaa | 2350 |
| agaattggac tgatgggtca gagatgagaa agcctccgat ttctctctgt | 2400 |
| tgggcttttt acaacagaaa tcaaaatctc cgctttgcct gcaaaagtaa | 2450 |
| cccagttgca ccctgtgaag tgtctgacaa aggcagaatg cttgtgagat | 2500 |
| tataagccta atggtgtgga ggttttgatg gtgtttacaa tacactgaga | 2550 |
| cctgttgttt tgtgtgctca ttgaaatatt catgatttaa gagcagtttt | 2600 |
| gtaaaaaatt cattagcatg aaaggcaagc atatttctcc tcatatgaat | 2650 |
| gagcctatca gcagggctct agtttctagg aatgctaaaa tatcagaagg | 2700 |
| caggagagga gataggctta ttatgatact agtgagtaca ttaagtaaaa | 2750 |
| taaaatggac cagaaaagaa aagaaaccat aaatatcgtg tcatattttc | 2800 |
| cccaagatta accaaaaata atctgcttat cttttggtt gtccttttaa | 2850 |
| ctgtctccgt tttttctttt tatttaaaaa tgcacttttt ttcccttgtg | 2900 |
| agttatagtc tgcttattta attaccactt tgcaagcctt acaagagagc | 2950 |
| acaagttggc ctacattttt atattttta agaagatact ttgagatgca | 3000 |
| ttatgagaac tttcagttca aagcatcaaa ttgatgccat atccaaggac | 3050 |
| atgccaaatg ctgattctgt caggcactga atgtcaggca ttgagacata | 3100 |
| gggaaggaat ggtttgtact aatacagacg tacagatact ttctctgaag | 3150 |
| agtattttcg aagaggagca actgaacact ggaggaaaag aaaatgacac | 3200 |
| tttctgcttt acagaaaagg aaactcattc agactggtga tatcgtgatg | 3250 |
| tacctaaaag tcagaaacca catttctcc tcagaagtag ggaccgcttt | 3300 |
| cttacctgtt taaataaacc aaagtatacc gtgtgaacca acaatctct | 3350 |
| tttcaaaaca gggtgctcct cctggcttct ggcttccata agaagaaatg | 3400 |
| gagaaaaata tatatatata tatatatatt gtgaaagatc aatccatctg | 3450 |
| ccagaatcta gtgggatgga agttttgct acatgttatc caccccaggc | 3500 |
| caggtggaag taactgaatt atttttaaa ttaagcagtt ctactcaatc | 3550 |
| accaagatgc ttctgaaaat tgcattttat taccatttca aactatttt | 3600 |
| taaaaataaa tacagttaac atagagtggt ttcttcattc atgtgaaaat | 3650 |
| tattagccag caccagatgc atgagctaat tatctctttg agtccttgct | 3700 |
| tctgtttgct cacagtaaac tcattgttta aaagcttcaa gaacattcaa | 3750 |
| gctgttggtg tgttaaaaaa tgcattgtat tgatttgtac tggtagttta | 3800 |
| tgaaattaa ttaaaacaca ggccatgaat ggaaggtggt attgcacagc | 3850 |
| taataaaata tgatttgtgg atatgaa | 3877 |

```
<210> SEQ ID NO 72
<211> LENGTH: 532
<212> TYPE: PRT
<213> ORGANISM: Homo Sapien

<400> SEQUENCE: 72

Met Met Met Val Arg Arg Gly Leu Leu Ala Trp Ile Ser Arg Val
 1               5                  10                  15

Val Val Leu Leu Val Leu Leu Cys Cys Ala Ile Ser Val Leu Tyr
                20                  25                  30

Met Leu Ala Cys Thr Pro Lys Gly Asp Glu Glu Gln Leu Ala Leu
                35                  40                  45

Pro Arg Ala Asn Ser Pro Thr Gly Lys Glu Gly Tyr Gln Ala Val
                50                  55                  60

Leu Gln Glu Trp Glu Gln His Arg Asn Tyr Val Ser Ser Leu
 65                  70                  75

Lys Arg Gln Ile Ala Gln Leu Lys Glu Glu Leu Gln Glu Arg Ser
                80                  85                  90

Glu Gln Leu Arg Asn Gly Gln Tyr Gln Ala Ser Asp Ala Ala Gly
                95                 100                 105

Leu Gly Leu Asp Arg Ser Pro Pro Glu Lys Thr Gln Ala Asp Leu
                110                 115                 120

Leu Ala Phe Leu His Ser Gln Val Asp Lys Ala Glu Val Asn Ala
                125                 130                 135

Gly Val Lys Leu Ala Thr Glu Tyr Ala Ala Val Pro Phe Asp Ser
                140                 145                 150

Phe Thr Leu Gln Lys Val Tyr Gln Leu Glu Thr Gly Leu Thr Arg
                155                 160                 165

His Pro Glu Glu Lys Pro Val Arg Lys Asp Lys Arg Asp Glu Leu
                170                 175                 180

Val Glu Ala Ile Glu Ser Ala Leu Glu Thr Leu Asn Asn Pro Ala
                185                 190                 195

Glu Asn Ser Pro Asn His Arg Pro Tyr Thr Ala Ser Asp Phe Ile
                200                 205                 210

Glu Gly Ile Tyr Arg Thr Glu Arg Asp Lys Gly Thr Leu Tyr Glu
                215                 220                 225

Leu Thr Phe Lys Gly Asp His Lys His Glu Phe Lys Arg Leu Ile
                230                 235                 240

Leu Phe Arg Pro Phe Ser Pro Ile Met Lys Val Lys Asn Glu Lys
                245                 250                 255

Leu Asn Met Ala Asn Thr Leu Ile Asn Val Ile Val Pro Leu Ala
                260                 265                 270

Lys Arg Val Asp Lys Phe Arg Gln Phe Met Gln Asn Phe Arg Glu
                275                 280                 285

Met Cys Ile Glu Gln Asp Gly Arg Val His Leu Thr Val Val Tyr
                290                 295                 300

Phe Gly Lys Glu Glu Ile Asn Glu Val Lys Gly Ile Leu Glu Asn
                305                 310                 315

Thr Ser Lys Ala Ala Asn Phe Arg Asn Phe Thr Phe Ile Gln Leu
                320                 325                 330

Asn Gly Glu Phe Ser Arg Gly Lys Gly Leu Asp Val Gly Ala Arg
                335                 340                 345

Phe Trp Lys Gly Ser Asn Val Leu Leu Phe Phe Cys Asp Val Asp
                350                 355                 360
```

-continued

```
Ile Tyr Phe Thr Ser Glu Phe Leu Asn Thr Cys Arg Leu Asn Thr
            365                 370                 375

Gln Pro Gly Lys Lys Val Phe Tyr Pro Val Leu Phe Ser Gln Tyr
        380                 385                 390

Asn Pro Gly Ile Ile Tyr Gly His His Asp Ala Val Pro Pro Leu
        395                 400                 405

Glu Gln Gln Leu Val Ile Lys Lys Glu Thr Gly Phe Trp Arg Asp
        410                 415                 420

Phe Gly Phe Gly Met Thr Cys Gln Tyr Arg Ser Asp Phe Ile Asn
        425                 430                 435

Ile Gly Gly Phe Asp Leu Asp Ile Lys Gly Trp Gly Gly Glu Asp
        440                 445                 450

Val His Leu Tyr Arg Lys Tyr Leu His Ser Asn Leu Ile Val Val
        455                 460                 465

Arg Thr Pro Val Arg Gly Leu Phe His Leu Trp His Glu Lys Arg
        470                 475                 480

Cys Met Asp Glu Leu Thr Pro Glu Gln Tyr Lys Met Cys Met Gln
        485                 490                 495

Ser Lys Ala Met Asn Glu Ala Ser His Gly Gln Leu Gly Met Leu
        500                 505                 510

Val Phe Arg His Glu Ile Glu Ala His Leu Arg Lys Gln Lys Gln
        515                 520                 525

Lys Thr Ser Ser Lys Lys Thr
        530
```

<210> SEQ ID NO 73
<211> LENGTH: 1701
<212> TYPE: DNA
<213> ORGANISM: Homo Sapien
<220> FEATURE:
<221> NAME/KEY: unsure
<222> LOCATION: 1528
<223> OTHER INFORMATION: unknown base

<400> SEQUENCE: 73

```
gagactgcag agggagataa agagagaggg caaagaggca gcaagagatt        50
tgtcctgggg atccagaaac ccatgatacc ctactgaaca ccgaatcccc       100
tggaagccca cagagacaga gacagcaaga gaagcagaga taaatacact       150
cacgccagga gctcgctcgc tctctctctc tctctctcac tcctccctcc       200
ctctctctct gcctgtccta gtcctctagt cctcaaattc ccagtcccct       250
gcaccccttc ctgggacact atgttgttct ccgccctcct gctggaggtg       300
atttggatcc tggctgcaga tggggtcaa cactggacgt atgagggccc        350
acatggtcag gaccattggc cagcctctta ccctgagtgt ggaaacaatg       400
cccagtcgcc atcgatatt cagacagaca gtgtgacatt tgaccctgat        450
ttgcctgctc tgcagcccca cggatatgac cagcctggca ccgagccttt       500
ggacctgcac aacaatggcc acacagtgca actctctctg ccctctaccc       550
tgtatctggg tggacttccc cgaaaatatg tagctgccca gctccacctg       600
cactggggtc agaaaggatc cccagggggg tcagaacacc agatcaacag       650
tgaagccaca tttgcagagc tccacattgt acattatgac tctgattcct       700
atgacagctt gagtgaggct gctgagaggc ctcaggggct ggctgtcctg       750
ggcatcctaa ttgaggtggg tgagactaag aatatagctt atgaacacat       800
```

```
tctgagtcac ttgcatgaag tcaggcataa agatcagaag acctcagtgc         850
ctcccttcaa cctaagagag ctgctcccca acagctgggg gcagtacttc         900
cgctacaatg gctcgctcac aactcccct tgctaccaga gtgtgctctg          950
gacagttttt tatagaaggt cccagatttc aatggaacag ctggaaaagc        1000
ttcaggggac attgttctcc acagaagagg agccctctaa gcttctggta        1050
cagaactacc gagcccttca gcctctcaat cagcgcatgg tctttgcttc        1100
tttcatccaa gcaggatcct cgtataccac aggtgaaatg ctgagtctag        1150
gtgtaggaat cttggttggc tgtctctgcc ttctcctggc tgtttatttc        1200
attgctagaa agattcggaa gaagaggctg gaaaaccgaa agagtgtggt        1250
cttcacctca gcacaagcca cgactgaggc ataaattcct tctcagatac        1300
catggatgtg gatgacttcc cttcatgcct atcaggaagc ctctaaaatg        1350
gggtgtagga tctggccaga acactgtag gagtagtaag cagatgtcct         1400
ccttcccctg gacatctctt agagaggaat ggacccaggc tgtcattcca        1450
ggaagaactg cagagccttc agcctctcca acatgtagg aggaaatgag         1500
gaaatcgctg tgttgttaat gcagaganca aactctgttt agttgcaggg        1550
gaagtttggg atataccca agtcctcta ccccctcact tttatggccc          1600
tttccctaga tatactgcgg gatctctcct taggataaag agttgctgtt        1650
gaagttgtat attttgatc aatatatttg gaaattaaag tttctgactt         1700
t                                                             1701
```

<210> SEQ ID NO 74
<211> LENGTH: 337
<212> TYPE: PRT
<213> ORGANISM: Homo Sapien

<400> SEQUENCE: 74

```
Met Leu Phe Ser Ala Leu Leu Leu Glu Val Ile Trp Ile Leu Ala
 1               5                   10                  15

Ala Asp Gly Gly Gln His Trp Thr Tyr Glu Gly Pro His Gly Gln
                20                  25                  30

Asp His Trp Pro Ala Ser Tyr Pro Glu Cys Gly Asn Asn Ala Gln
                35                  40                  45

Ser Pro Ile Asp Ile Gln Thr Asp Ser Val Thr Phe Asp Pro Asp
                50                  55                  60

Leu Pro Ala Leu Gln Pro His Gly Tyr Asp Gln Pro Gly Thr Glu
                65                  70                  75

Pro Leu Asp Leu His Asn Asn Gly His Thr Val Gln Leu Ser Leu
                80                  85                  90

Pro Ser Thr Leu Tyr Leu Gly Gly Leu Pro Arg Lys Tyr Val Ala
                95                  100                 105

Ala Gln Leu His Leu His Trp Gly Gln Lys Gly Ser Pro Gly Gly
                110                 115                 120

Ser Glu His Gln Ile Asn Ser Glu Ala Thr Phe Ala Glu Leu His
                125                 130                 135

Ile Val His Tyr Asp Ser Asp Ser Tyr Asp Ser Leu Ser Glu Ala
                140                 145                 150

Ala Glu Arg Pro Gln Gly Leu Ala Val Leu Gly Ile Leu Ile Glu
                155                 160                 165
```

-continued

```
Val Gly Glu Thr Lys Asn Ile Ala Tyr Glu His Ile Leu Ser His
                170                 175                 180
Leu His Glu Val Arg His Lys Asp Gln Lys Thr Ser Val Pro Pro
            185                 190                 195
Phe Asn Leu Arg Glu Leu Leu Pro Lys Gln Leu Gly Gln Tyr Phe
        200                 205                 210
Arg Tyr Asn Gly Ser Leu Thr Thr Pro Pro Cys Tyr Gln Ser Val
            215                 220                 225
Leu Trp Thr Val Phe Tyr Arg Arg Ser Gln Ile Ser Met Glu Gln
        230                 235                 240
Leu Glu Lys Leu Gln Gly Thr Leu Phe Ser Thr Glu Glu Pro
            245                 250                 255
Ser Lys Leu Leu Val Gln Asn Tyr Arg Ala Leu Gln Pro Leu Asn
        260                 265                 270
Gln Arg Met Val Phe Ala Ser Phe Ile Gln Ala Gly Ser Ser Tyr
            275                 280                 285
Thr Thr Gly Glu Met Leu Ser Leu Gly Val Gly Ile Leu Val Gly
        290                 295                 300
Cys Leu Cys Leu Leu Leu Ala Val Tyr Phe Ile Ala Arg Lys Ile
            305                 310                 315
Arg Lys Lys Arg Leu Glu Asn Arg Lys Ser Val Val Phe Thr Ser
        320                 325                 330
Ala Gln Ala Thr Thr Glu Ala
            335
```

<210> SEQ ID NO 75
<211> LENGTH: 1743
<212> TYPE: DNA
<213> ORGANISM: Homo Sapien

<400> SEQUENCE: 75

| | |
|---|---:|
| tgccgctgcc gccgctgctg ctgttgctcc tggcggcgcc ttggggacgg | 50 |
| gcagttccct gtgtctctgg tggtttgcct aaacctgcaa acatcacctt | 100 |
| cttatccatc aacatgaaga atgtcctaca atggactcca ccagagggtc | 150 |
| ttcaaggagt taagttact tacactgtgc agtatttcat cacaaattgg | 200 |
| cccaccagag gtggcactga ctacagatga aagtccatt tctgttgtcc | 250 |
| tgacagctcc agagaagtgg aagagaaatc cagaagacct tcctgtttcc | 300 |
| atgcaacaaa tatactccaa tctgaagtat aacgtgtctg tgttgaatac | 350 |
| taaatcaaac agaacgtggt cccagtgtgt gaccaaccac acgctggtgc | 400 |
| tcacctggct ggagccgaac actctttact gcgtacacgt ggagtccttc | 450 |
| gtcccagggc cccctcgccg tgctcagcct tctgagaagc agtgtgccag | 500 |
| gactttgaaa gatcaatcat cagagttcaa ggctaaaatc atcttctggt | 550 |
| atgttttgcc catatctatt accgtgtttc ttttttctgt gatgggctat | 600 |
| tccatctacc gatatatcca cgttggcaaa gagaaacacc cagcaaattt | 650 |
| gattttgatt tatggaaatg aatttgacaa aagattcttt gtgcctgctg | 700 |
| aaaaaatcgt gattaacttt atcaccctca atatctcgga tgattctaaa | 750 |
| atttctcatc aggatatgag tttactggga aaaagcagtg atgtatccag | 800 |
| ccttaatgat cctcagccca gcgggaacct gaggcccct caggaggaag | 850 |

-continued

| | |
|---|---|
| aggaggtgaa acatttaggg tatgcttcgc atttgatgga aattttttgt | 900 |
| gactctgaag aaaacacgga aggtacttct ctcacccagc aagagtccct | 950 |
| cagcagaaca ataccccgg ataaaacagt cattgaatat gaatatgatg | 1000 |
| tcagaaccac tgacatttgt gcggggcctg aagagcagga gctcagtttg | 1050 |
| caggaggagg tgtccacaca aggaacatta ttggagtcgc aggcagcgtt | 1100 |
| ggcagtcttg ggcccgcaaa cgttacagta ctcatacacc cctcagctcc | 1150 |
| aagacttaga cccctggcg caggagcaca cagactcgga ggaggggccg | 1200 |
| gaggaagagc catcgacgac cctggtcgac tgggatcccc aaactggcag | 1250 |
| gctgtgtatt ccttcgctgt ccagcttcga ccaggattca gagggctgcg | 1300 |
| agccttctga gggggatggg ctcggagagg agggtcttct atctagactc | 1350 |
| tatgaggagc cggctccaga caggccacca ggagaaaatg aaacctatct | 1400 |
| catgcaattc atggaggaat ggggttata tgtgcagatg gaaaactgat | 1450 |
| gccaacactt ccttttgcct tttgtttcct gtgcaaacaa gtgagtcacc | 1500 |
| cctttgatcc cagccataaa gtacctggga tgaaagaagt tttttccagt | 1550 |
| ttgtcagtgt ctgtgagaat tacttatttc ttttctctat tctcatagca | 1600 |
| cgtgtgtgat tggttcatgc atgtaggtct cttaacaatg atggtgggcc | 1650 |
| tctggagtcc aggggctggc cggttgttct atgcagagaa agcagtcaat | 1700 |
| aaatgtttgc cagactgggt gcagaattta ttcaggtggg tgt | 1743 |

<210> SEQ ID NO 76
<211> LENGTH: 442
<212> TYPE: PRT
<213> ORGANISM: Homo Sapien

<400> SEQUENCE: 76

```
Met Ser Tyr Asn Gly Leu His Gln Arg Val Phe Lys Glu Leu Lys
  1               5                  10                  15

Leu Leu Thr Leu Cys Ser Ile Ser Ser Gln Ile Gly Pro Pro Glu
             20                  25                  30

Val Ala Leu Thr Thr Asp Glu Lys Ser Ile Ser Val Val Leu Thr
             35                  40                  45

Ala Pro Glu Lys Trp Lys Arg Asn Pro Glu Asp Leu Pro Val Ser
             50                  55                  60

Met Gln Gln Ile Tyr Ser Asn Leu Lys Tyr Asn Val Ser Val Leu
             65                  70                  75

Asn Thr Lys Ser Asn Arg Thr Trp Ser Gln Cys Val Thr Asn His
             80                  85                  90

Thr Leu Val Leu Thr Trp Leu Glu Pro Asn Thr Leu Tyr Cys Val
             95                 100                 105

His Val Glu Ser Phe Val Pro Gly Pro Pro Arg Arg Ala Gln Pro
            110                 115                 120

Ser Glu Lys Gln Cys Ala Arg Thr Leu Lys Asp Gln Ser Ser Glu
            125                 130                 135

Phe Lys Ala Lys Ile Ile Phe Trp Tyr Val Leu Pro Ile Ser Ile
            140                 145                 150

Thr Val Phe Leu Phe Ser Val Met Gly Tyr Ser Ile Tyr Arg Tyr
            155                 160                 165

Ile His Val Gly Lys Glu Lys His Pro Ala Asn Leu Ile Leu Ile
            170                 175                 180
```

-continued

```
Tyr Gly Asn Glu Phe Asp Lys Arg Phe Phe Val Pro Ala Glu Lys
            185                 190                 195
Ile Val Ile Asn Phe Ile Thr Leu Asn Ile Ser Asp Asp Ser Lys
            200                 205                 210
Ile Ser His Gln Asp Met Ser Leu Leu Gly Lys Ser Ser Asp Val
            215                 220                 225
Ser Ser Leu Asn Asp Pro Gln Pro Ser Gly Asn Leu Arg Pro Pro
            230                 235                 240
Gln Glu Glu Glu Val Lys His Leu Gly Tyr Ala Ser His Leu
            245                 250                 255
Met Glu Ile Phe Cys Asp Ser Glu Glu Asn Thr Glu Gly Thr Ser
            260                 265                 270
Leu Thr Gln Gln Glu Ser Leu Ser Arg Thr Ile Pro Pro Asp Lys
            275                 280                 285
Thr Val Ile Glu Tyr Glu Tyr Asp Val Arg Thr Thr Asp Ile Cys
            290                 295                 300
Ala Gly Pro Glu Glu Gln Glu Leu Ser Leu Gln Glu Glu Val Ser
            305                 310                 315
Thr Gln Gly Thr Leu Leu Glu Ser Gln Ala Ala Leu Ala Val Leu
            320                 325                 330
Gly Pro Gln Thr Leu Gln Tyr Ser Tyr Thr Pro Gln Leu Gln Asp
            335                 340                 345
Leu Asp Pro Leu Ala Gln Glu His Thr Asp Ser Glu Glu Gly Pro
            350                 355                 360
Glu Glu Glu Pro Ser Thr Thr Leu Val Asp Trp Pro Gln Thr
            365                 370                 375
Gly Arg Leu Cys Ile Pro Ser Leu Ser Ser Phe Asp Gln Asp Ser
            380                 385                 390
Glu Gly Cys Glu Pro Ser Glu Gly Asp Gly Leu Gly Glu Glu Gly
            395                 400                 405
Leu Leu Ser Arg Leu Tyr Glu Glu Pro Ala Pro Asp Arg Pro Pro
            410                 415                 420
Gly Glu Asn Glu Thr Tyr Leu Met Gln Phe Met Glu Glu Trp Gly
            425                 430                 435
Leu Tyr Val Gln Met Glu Asn
            440
```

<210> SEQ ID NO 77
<211> LENGTH: 1636
<212> TYPE: DNA
<213> ORGANISM: Homo Sapien

<400> SEQUENCE: 77

| | | | |
|---|---|---|---|
| gaggagcggg ccgaggactc cagcgtgccc aggtctggca tcctgcactt | 50 |
| gctgccctct gacacctggg aagatggccg gcccgtggac cttcacccctt | 100 |
| ctctgtggtt tgctggcagc caccttgatc caagccaccc tcagtcccac | 150 |
| tgcagttctc atcctcggcc caaaagtcat caaagaaaag ctgacacagg | 200 |
| agctgaagga ccacaacgcc accagcatcc tgcagcagct gccgctgctc | 250 |
| agtgccatgc gggaaaagcc agccggaggc atccctgtgc tgggcagcct | 300 |
| ggtgaacacc gtcctgaagc acatcatctg gctgaaggtc atcacagcta | 350 |
| acatcctcca gctgcaggtg aagccctcgg ccaatgacca ggagctgcta | 400 |

-continued

| | |
|---|---|
| gtcaagatcc ccctggacat ggtggctgga ttcaacacgc ccctggtcaa | 450 |
| gaccatcgtg gagttccaca tgacgactga ggcccaagcc accatccgca | 500 |
| tggacaccag tgcaagtggc cccacccgcc tggtcctcag tgactgtgcc | 550 |
| accagccatg ggagcctgcg catccaactg ctgtataagc tctccttcct | 600 |
| ggtgaacgcc ttagctaagc aggtcatgaa cctcctagtg ccatccctgc | 650 |
| ccaatctagt gaaaaaccag ctgtgtcccg tgatcgagcc ttccttcaat | 700 |
| ggcatgtatg cagacctcct gcagctggtg aaggtgccca tttccctcag | 750 |
| cattgaccgt ctggagtttg accttctgta tcctgccatc aagggtgaca | 800 |
| ccattcagct ctacctgggg gccaagttgt tggactcaca gggaaaggtg | 850 |
| accaagtggt tcaataactc tgcagcttcc ctgacaatgc ccaccctgga | 900 |
| caacatcccg ttcagcctca tcgtgagtca ggacgtggtg aaagctgcag | 950 |
| tggctgctgt gctctctcca gaagaattca tggtcctgtt ggactctgtg | 1000 |
| cttcctgaga gtgcccatcg gctgaagtca agcatcgggc tgatcaatga | 1050 |
| aaaggctgca gataagctgg gatctaccca gatcgtgaag atcctaactc | 1100 |
| aggacactcc cgagtttttt atagaccaag gccatgccaa ggtggcccaa | 1150 |
| ctgatcgtgc tggaagtgtt tccctccagt gaagccctcc gcccttttgtt | 1200 |
| caccctgggc atcgaagcca gctcggaagc tcagttttac accaaaggtg | 1250 |
| accaacttat actcaacttg aataacatca gctctgatcg gatccagctg | 1300 |
| atgaactctg ggattggctg gttccaacct gatgttctga aaacatcat | 1350 |
| cactgagatc atccactcca tcctgctgcc gaaccagaat ggcaaattaa | 1400 |
| gatctggggt cccagtgtca ttggtgaagg ccttgggatt cgaggcagct | 1450 |
| gagtcctcac tgaccaagga tgcccttgtg cttactccag cctccttgtg | 1500 |
| gaaacccagc tctcctgtct cccagtgaag acttggatgg cagccatcag | 1550 |
| ggaaggctgg gtcccagctg ggagtatggg tgtgagctct atagaccatc | 1600 |
| cctctctgca atcaataaac acttgcctgt gaaaaa | 1636 |

<210> SEQ ID NO 78
<211> LENGTH: 484
<212> TYPE: PRT
<213> ORGANISM: Homo Sapien

<400> SEQUENCE: 78

```
Met Ala Gly Pro Trp Thr Phe Thr Leu Leu Cys Gly Leu Leu Ala
 1               5                  10                  15

Ala Thr Leu Ile Gln Ala Thr Leu Ser Pro Thr Ala Val Leu Ile
                20                  25                  30

Leu Gly Pro Lys Val Ile Lys Glu Lys Leu Thr Gln Glu Leu Lys
                35                  40                  45

Asp His Asn Ala Thr Ser Ile Leu Gln Gln Leu Pro Leu Leu Ser
                50                  55                  60

Ala Met Arg Glu Lys Pro Ala Gly Gly Ile Pro Val Leu Gly Ser
                65                  70                  75

Leu Val Asn Thr Val Leu Lys His Ile Ile Trp Leu Lys Val Ile
                80                  85                  90

Thr Ala Asn Ile Leu Gln Leu Gln Val Lys Pro Ser Ala Asn Asp
                95                  100                 105
```

```
Gln Glu Leu Leu Val Lys Ile Pro Leu Asp Met Val Ala Gly Phe
            110                 115                 120

Asn Thr Pro Leu Val Lys Thr Ile Val Glu Phe His Met Thr Thr
            125                 130                 135

Glu Ala Gln Ala Thr Ile Arg Met Asp Thr Ser Ala Ser Gly Pro
            140                 145                 150

Thr Arg Leu Val Leu Ser Asp Cys Ala Thr Ser His Gly Ser Leu
            155                 160                 165

Arg Ile Gln Leu Leu Tyr Lys Leu Ser Phe Leu Val Asn Ala Leu
            170                 175                 180

Ala Lys Gln Val Met Asn Leu Leu Val Pro Ser Leu Pro Asn Leu
            185                 190                 195

Val Lys Asn Gln Leu Cys Pro Val Ile Glu Ala Ser Phe Asn Gly
            200                 205                 210

Met Tyr Ala Asp Leu Leu Gln Leu Val Lys Val Pro Ile Ser Leu
            215                 220                 225

Ser Ile Asp Arg Leu Glu Phe Asp Leu Leu Tyr Pro Ala Ile Lys
            230                 235                 240

Gly Asp Thr Ile Gln Leu Tyr Leu Gly Ala Lys Leu Leu Asp Ser
            245                 250                 255

Gln Gly Lys Val Thr Lys Trp Phe Asn Asn Ser Ala Ala Ser Leu
            260                 265                 270

Thr Met Pro Thr Leu Asp Asn Ile Pro Phe Ser Leu Ile Val Ser
            275                 280                 285

Gln Asp Val Val Lys Ala Ala Val Ala Ala Val Leu Ser Pro Glu
            290                 295                 300

Glu Phe Met Val Leu Leu Asp Ser Val Leu Pro Glu Ser Ala His
            305                 310                 315

Arg Leu Lys Ser Ser Ile Gly Leu Ile Asn Glu Lys Ala Ala Asp
            320                 325                 330

Lys Leu Gly Ser Thr Gln Ile Val Lys Ile Leu Thr Gln Asp Thr
            335                 340                 345

Pro Glu Phe Phe Ile Asp Gln Gly His Ala Lys Val Ala Gln Leu
            350                 355                 360

Ile Val Leu Glu Val Phe Pro Ser Ser Glu Ala Leu Arg Pro Leu
            365                 370                 375

Phe Thr Leu Gly Ile Glu Ala Ser Ser Glu Ala Gln Phe Tyr Thr
            380                 385                 390

Lys Gly Asp Gln Leu Ile Leu Asn Leu Asn Asn Ile Ser Ser Asp
            395                 400                 405

Arg Ile Gln Leu Met Asn Ser Gly Ile Gly Trp Phe Gln Pro Asp
            410                 415                 420

Val Leu Lys Asn Ile Ile Thr Glu Ile His Ser Ile Leu Leu
            425                 430                 435

Pro Asn Gln Asn Gly Lys Leu Arg Ser Gly Val Pro Val Ser Leu
            440                 445                 450

Val Lys Ala Leu Gly Phe Glu Ala Ala Glu Ser Ser Leu Thr Lys
            455                 460                 465

Asp Ala Leu Val Leu Thr Pro Ala Ser Leu Trp Lys Pro Ser Ser
            470                 475                 480

Pro Val Ser Gln

<210> SEQ ID NO 79
```

<211> LENGTH: 1475
<212> TYPE: DNA
<213> ORGANISM: Homo Sapien

<400> SEQUENCE: 79

| | |
|---|---|
| gagagaagtc agcctggcag agagactctg aaatgaggga ttagaggtgt | 50 |
| tcaaggagca agagcttcag cctgaagaca agggagcagt ccctgaagac | 100 |
| gcttctactg agaggtctgc catggcctct cttggcctcc aacttgtggg | 150 |
| ctacatccta ggccttctgg ggcttttggg cacactggtt gccatgctgc | 200 |
| tccccagctg gaaaacaagt tcttatgtcg gtgccagcat tgtgacagca | 250 |
| gttggcttct ccaagggcct ctggatggaa tgtgccacac acagcacagg | 300 |
| catcacccag tgtgacatct atagcaccct tctgggcctg cccgctgaca | 350 |
| tccaggctgc ccaggccatg atggtgacat ccagtgcaat ctcctccctg | 400 |
| gcctgcatta tctctgtggt gggcatgaga tgcacagtct tctgccagga | 450 |
| atcccgagcc aaagacagag tggcggtagc aggtggagtc tttttcatcc | 500 |
| ttggaggcct cctgggattc attcctgttg cctggaatct tcatgggatc | 550 |
| ctacgggact tctactcacc actggtgcct gacagcatga aatttgagat | 600 |
| tggagaggct ctttacttgg gcattatttc ttccctgttc tccctgatag | 650 |
| ctggaatcat cctctgcttt tcctgctcat cccagagaaa tcgctccaac | 700 |
| tactacgatg cctaccaagc ccaacctctt gccacaagga gctctccaag | 750 |
| gcctggtcaa cctcccaaag tcaagagtga gttcaattcc tacagcctga | 800 |
| cagggtatgt gtgaagaacc aggggccaga gctgggggggt ggctgggtct | 850 |
| gtgaaaaaca gtggacagca ccccgagggc cacaggtgag ggacactacc | 900 |
| actggatcgt gtcagaaggt gctgctgagg atagactgac tttggccatt | 950 |
| ggattgagca aaggcagaaa tgggggctag tgtaacagca tgcaggttga | 1000 |
| attgccaagg atgctcgcca tgccagcctt tctgttttcc tcaccttgct | 1050 |
| gctcccctgc cctaagtccc caaccctcaa cttgaaaccc cattccctta | 1100 |
| agccaggact cagaggatcc ctttgccctc tggtttacct gggactccat | 1150 |
| ccccaaaccc actaatcaca tcccactgac tgaccctctg tgatcaaaga | 1200 |
| ccctctctct ggctgaggtt ggctcttagc tcattgctgg ggatgggaag | 1250 |
| gagaagcagt ggcttttgtg ggcattgctc taacctactt ctcaagcttc | 1300 |
| cctccaaaga aactgattgg ccctggaacc tccatcccac tcttgttatg | 1350 |
| actccacagt gtccagacta atttgtgcat gaactgaaat aaaaccatcc | 1400 |
| tacggtatcc agggaacaga aagcaggatg caggatggga ggacaggaag | 1450 |
| gcagcctggg acatttaaaa aaata | 1475 |

<210> SEQ ID NO 80
<211> LENGTH: 230
<212> TYPE: PRT
<213> ORGANISM: Homo Sapien

<400> SEQUENCE: 80

Met Ala Ser Leu Gly Leu Gln Leu Val Gly Tyr Ile Leu Gly Leu
1               5                   10                  15

Leu Gly Leu Leu Gly Thr Leu Val Ala Met Leu Leu Pro Ser Trp
            20                  25                  30

Lys Thr Ser Ser Tyr Val Gly Ala Ser Ile Val Thr Ala Val Gly
                35                  40                  45

Phe Ser Lys Gly Leu Trp Met Glu Cys Ala Thr His Ser Thr Gly
            50                  55                  60

Ile Thr Gln Cys Asp Ile Tyr Ser Thr Leu Leu Gly Leu Pro Ala
        65                  70                  75

Asp Ile Gln Ala Ala Gln Ala Met Met Val Thr Ser Ser Ala Ile
    80                  85                  90

Ser Ser Leu Ala Cys Ile Ile Ser Val Val Gly Met Arg Cys Thr
                95                 100                 105

Val Phe Cys Gln Glu Ser Arg Ala Lys Asp Arg Val Ala Val Ala
               110                 115                 120

Gly Gly Val Phe Phe Ile Leu Gly Gly Leu Leu Gly Phe Ile Pro
           125                 130                 135

Val Ala Trp Asn Leu His Gly Ile Leu Arg Asp Phe Tyr Ser Pro
       140                 145                 150

Leu Val Pro Asp Ser Met Lys Phe Glu Ile Gly Glu Ala Leu Tyr
   155                 160                 165

Leu Gly Ile Ile Ser Ser Leu Phe Ser Leu Ile Ala Gly Ile Ile
               170                 175                 180

Leu Cys Phe Ser Cys Ser Ser Gln Arg Asn Arg Ser Asn Tyr Tyr
           185                 190                 195

Asp Ala Tyr Gln Ala Gln Pro Leu Ala Thr Arg Ser Ser Pro Arg
       200                 205                 210

Pro Gly Gln Pro Pro Lys Val Lys Ser Glu Phe Asn Ser Tyr Ser
   215                 220                 225

Leu Thr Gly Tyr Val
           230

<210> SEQ ID NO 81
<211> LENGTH: 1732
<212> TYPE: DNA
<213> ORGANISM: Homo Sapien

<400> SEQUENCE: 81

| | |
|---|---:|
| cccacgcgtc cgcgcctctc ccttctgctg gaccttcctt cgtctctcca | 50 |
| tctctccctc ctttccccgc gttctctttc caccttTctc ttcttcccac | 100 |
| cttagacctc ccttcctgcc ctcctttcct gcccaccgct gcttcctggc | 150 |
| ccttctccga ccccgctcta gcagcagacc tcctggggtc tgtgggttga | 200 |
| tctgtggccc ctgtgcctcc gtgtccttTt cgtctccctt cctcccgact | 250 |
| ccgctcccgg accagcggcc tgaccctggg gaaaggatgg ttcccgaggt | 300 |
| gagggtcctc tcctccttgc tgggactcgc gctgctctgg ttccccctgg | 350 |
| actcccacgc tcgagcccgc ccagacatgt tctgcctttt ccatgggaag | 400 |
| agatactccc ccggcgagag ctggcacccc tacttggagc cacaaggcct | 450 |
| gatgtactgc ctgcgctgta cctgctcaga gggcgcccat gtgagttgtt | 500 |
| accgcctcca ctgtccgcct gtccactgcc ccagcctgt gacggagcca | 550 |
| cagcaatgct gtcccaagtg tgtggaacct cacactccct ctggactccg | 600 |
| ggccccacca aagtcctgcc agcacaacgg gaccatgtac caaacggag | 650 |
| agatcttcag tgcccatgag ctgttcccct cccgcctgcc caaccagtgt | 700 |

-continued

| | |
|---|---|
| gtcctctgca gctgcacaga gggccagatc tactgcggcc tcacaacctg | 750 |
| ccccgaacca ggctgcccag caccoctccc actgccagac tcctgctgcc | 800 |
| aagcctgcaa agatgaggca agtgagcaat cggatgaaga ggacagtgtg | 850 |
| cagtcgctcc atgggggtgag acatcctcag gatccatgtt ccagtgatgc | 900 |
| tgggagaaag agaggcccgg gcaccccagc ccccactggc ctcagcgccc | 950 |
| ctctgagctt catccctcgc cacttcagac ccaagggagc aggcagcaca | 1000 |
| actgtcaaga tcgtcctgaa ggagaaacat aagaaagcct gtgtgcatgg | 1050 |
| cgggaagacg tactcccacg gggaggtgtg gcacccggcc ttccgtgcct | 1100 |
| tcggccccct gccctgcatc ctatgcacct gtgaggatgg ccgccaggac | 1150 |
| tgccagcgtg tgacctgtcc caccgagtac ccctgccgtc accccgagaa | 1200 |
| agtggctggg aagtgctgca agatttgccc agaggacaaa gcagaccctg | 1250 |
| gccacagtga gatcagttct accaggtgtc caaggcacc gggccgggtc | 1300 |
| ctcgtccaca catcggtatc cccaagccca dacaacctgc gtcgctttgc | 1350 |
| cctggaacac gaggcctcgg acttggtgga gatctacctc tggaagctgg | 1400 |
| taaaagatga ggaaactgag gctcagagag gtgaagtacc tggcccaagg | 1450 |
| ccacacagcc agaatcttcc acttgactca gatcaagaaa gtcaggaagc | 1500 |
| aagacttcca gaaagaggca cagcacttcc gactgctcgc tggcccccac | 1550 |
| gaaggtcact ggaacgtctt cctagcccag accctggagc tgaaggtcac | 1600 |
| ggccagtcca gacaaagtga ccaagacata acaaagacct aacagttgca | 1650 |
| gatatgagct gtataattgt tgttattata tattaataaa taagaagttg | 1700 |
| cattaccctc aaaaaaaaaa aaaaaaaaaa aa | 1732 |

<210> SEQ ID NO 82
<211> LENGTH: 451
<212> TYPE: PRT
<213> ORGANISM: Homo Sapien

<400> SEQUENCE: 82

```
Met Val Pro Glu Val Arg Val Leu Ser Leu Leu Gly Leu Ala
  1               5                  10                  15

Leu Leu Trp Phe Pro Leu Asp Ser His Ala Arg Ala Arg Pro Asp
                 20                  25                  30

Met Phe Cys Leu Phe His Gly Lys Arg Tyr Ser Pro Gly Glu Ser
                 35                  40                  45

Trp His Pro Tyr Leu Glu Pro Gln Gly Leu Met Tyr Cys Leu Arg
                 50                  55                  60

Cys Thr Cys Ser Glu Gly Ala His Val Ser Cys Tyr Arg Leu His
             65                  70                  75

Cys Pro Pro Val His Cys Pro Gln Pro Val Thr Glu Pro Gln Gln
             80                  85                  90

Cys Cys Pro Lys Cys Val Glu Pro His Thr Pro Ser Gly Leu Arg
             95                 100                 105

Ala Pro Pro Lys Ser Cys Gln His Asn Gly Thr Met Tyr Gln His
            110                 115                 120

Gly Glu Ile Phe Ser Ala His Glu Leu Phe Pro Ser Arg Leu Pro
            125                 130                 135

Asn Gln Cys Val Leu Cys Ser Cys Thr Glu Gly Gln Ile Tyr Cys
            140                 145                 150
```

```
Gly Leu Thr Thr Cys Pro Glu Pro Gly Cys Ala Pro Leu Pro
            155                 160                 165
Leu Pro Asp Ser Cys Cys Gln Ala Cys Lys Asp Glu Ala Ser Glu
            170                 175                 180
Gln Ser Asp Glu Glu Asp Ser Val Gln Ser Leu His Gly Val Arg
            185                 190                 195
His Pro Gln Asp Pro Cys Ser Ser Asp Ala Gly Arg Lys Arg Gly
            200                 205                 210
Pro Gly Thr Pro Ala Pro Thr Gly Leu Ser Ala Pro Leu Ser Phe
            215                 220                 225
Ile Pro Arg His Phe Arg Pro Lys Gly Ala Gly Ser Thr Thr Val
            230                 235                 240
Lys Ile Val Leu Lys Glu Lys His Lys Lys Ala Cys Val His Gly
            245                 250                 255
Gly Lys Thr Tyr Ser His Gly Glu Val Trp His Pro Ala Phe Arg
            260                 265                 270
Ala Phe Gly Pro Leu Pro Cys Ile Leu Cys Thr Cys Glu Asp Gly
            275                 280                 285
Arg Gln Asp Cys Gln Arg Val Thr Cys Pro Thr Glu Tyr Pro Cys
            290                 295                 300
Arg His Pro Glu Lys Val Ala Gly Lys Cys Cys Lys Ile Cys Pro
            305                 310                 315
Glu Asp Lys Ala Asp Pro Gly His Ser Glu Ile Ser Ser Thr Arg
            320                 325                 330
Cys Pro Lys Ala Pro Gly Arg Val Leu Val His Thr Ser Val Ser
            335                 340                 345
Pro Ser Pro Asp Asn Leu Arg Arg Phe Ala Leu Glu His Glu Ala
            350                 355                 360
Ser Asp Leu Val Glu Ile Tyr Leu Trp Lys Leu Val Lys Asp Glu
            365                 370                 375
Glu Thr Glu Ala Gln Arg Gly Glu Val Pro Gly Pro Arg Pro His
            380                 385                 390
Ser Gln Asn Leu Pro Leu Asp Ser Asp Gln Glu Ser Gln Glu Ala
            395                 400                 405
Arg Leu Pro Glu Arg Gly Thr Ala Leu Pro Thr Ala Arg Trp Pro
            410                 415                 420
Pro Arg Arg Ser Leu Glu Arg Leu Pro Ser Pro Asp Pro Gly Ala
            425                 430                 435
Glu Gly His Gly Gln Ser Arg Gln Ser Asp Gln Asp Ile Thr Lys
            440                 445                 450
Thr

<210> SEQ ID NO 83
<211> LENGTH: 2052
<212> TYPE: DNA
<213> ORGANISM: Homo Sapien

<400> SEQUENCE: 83
gacagctgtg tctcgatgga gtagactctc agaacagcgc agtttgccct          50
ccgctcacgc agagcctctc cgtggcttcc gcaccttgag cattaggcca         100
gttctcctct tctctctaat ccatccgtca cctctcctgt catccgtttc         150
catgccgtga ggtccattca cagaacacat ccatggctct catgctcagt         200
```

-continued

| | |
|---|---|
| ttggttctga gtctcctcaa gctgggatca gggcagtggc aggtgtttgg | 250 |
| gccagacaag cctgtccagg ccttggtggg ggaggacgca gcattctcct | 300 |
| gtttcctgtc tcctaagacc aatgcagagg ccatggaagt gcggttcttc | 350 |
| agggccagt tctctagcgt ggtccacctc tacagggacg ggaaggacca | 400 |
| gccattatg cagatgccac agtatcaagg caggacaaaa ctggtgaagg | 450 |
| attctattgc ggaggggcgc atctctctga ggctggaaaa cattactgtg | 500 |
| ttggatgctg gcctctatgg gtgcaggatt agttcccagt cttactacca | 550 |
| gaaggccatc tgggagctac aggtgtcagc actgggctca gttcctctca | 600 |
| tttccatcac gggatatgtt gatagagaca tccagctact ctgtcagtcc | 650 |
| tcgggctggt tcccccggcc acagcgaag tggaaaggtc cacaaggaca | 700 |
| ggatttgtcc acagactcca ggacaaacag agacatgcat ggcctgtttg | 750 |
| atgtggagat ctctctgacc gtccaagaga acgccgggag catatcctgt | 800 |
| tccatgcggc atgctcatct gagccgagag gtggaatcca gggtacagat | 850 |
| aggagatacc tttttcgagc ctatatcgtg gcacctggct accaaagtac | 900 |
| tgggaatact ctgctgtggc ctatttttg gcattgttgg actgaagatt | 950 |
| tcttctccca aattccagtg gaaaatccag gcggaactgg actggagaag | 1000 |
| aaagcacgga caggcagaat tgagagacgc ccggaaacac gcagtggagg | 1050 |
| tgactctgga tccagagacg gctcacccga agctctgcgt ttctgatctg | 1100 |
| aaaactgtaa cccatagaaa agctccccag gaggtgcctc actctgagaa | 1150 |
| gagatttaca aggaagagtg tggtggcttc tcagagtttc caagcaggga | 1200 |
| aacattactg ggaggtggac ggaggacaca ataaaaggtg gcgcgtggga | 1250 |
| gtgtgccggg atgatgtgga caggaggaag gagtacgtga cttttgtctcc | 1300 |
| cgatcatggg tactgggtcc tcagactgaa tggagaacat ttgtatttca | 1350 |
| cattaaatcc ccgttttatc agcgtcttcc ccaggacccc acctacaaaa | 1400 |
| atagggtct tcctggacta tgagtgtggg accatctcct tcttcaacat | 1450 |
| aaatgaccag tcccttattt taccctgac atgtcggttt gaaggcttat | 1500 |
| tgaggcccta cattgagtat ccgtcctata atgagcaaaa tggaactccc | 1550 |
| atagtcatct gcccagtcac ccaggaatca gagaaagagg cctcttggca | 1600 |
| aagggcctct gcaatcccag agacaagcaa cagtgagtcc tcctcacagg | 1650 |
| caaccacgcc cttcctcccc agggtgaaa tgtaggatga atcacatccc | 1700 |
| acattcttct ttagggatat taaggtctct ctcccagatc caaagtcccg | 1750 |
| cagcagccgg ccaaggtggc ttccagatga agggggactg gcctgtccac | 1800 |
| atgggagtca ggtgtcatgg ctgccctgag ctggagggga agaaggctga | 1850 |
| cattacattt agtttgctct cactccatct ggctaagtga tcttgaaata | 1900 |
| ccacctctca ggtgaagaac cgtcaggaat tcccatctca caggctgtgg | 1950 |
| tgtagattaa gtagacaagg aatgtgaata atgcttagat cttattgatg | 2000 |
| acagagtgta tcctaatggt ttgttcatta tattacactt tcagtaaaaa | 2050 |
| aa | 2052 |

<210> SEQ ID NO 84
<211> LENGTH: 500

```
<212> TYPE: PRT
<213> ORGANISM: Homo Sapien

<400> SEQUENCE: 84

Met Ala Leu Met Leu Ser Leu Val Leu Ser Leu Leu Lys Leu Gly
 1               5                  10                  15

Ser Gly Gln Trp Gln Val Phe Gly Pro Asp Lys Pro Val Gln Ala
            20                  25                  30

Leu Val Gly Glu Asp Ala Ala Phe Ser Cys Phe Leu Ser Pro Lys
        35                  40                  45

Thr Asn Ala Glu Ala Met Glu Val Arg Phe Phe Arg Gly Gln Phe
    50                  55                  60

Ser Ser Val Val His Leu Tyr Arg Asp Gly Lys Asp Gln Pro Phe
            65                  70                  75

Met Gln Met Pro Gln Tyr Gln Gly Arg Thr Lys Leu Val Lys Asp
        80                  85                  90

Ser Ile Ala Glu Gly Arg Ile Ser Leu Arg Leu Glu Asn Ile Thr
            95                 100                 105

Val Leu Asp Ala Gly Leu Tyr Gly Cys Arg Ile Ser Ser Gln Ser
           110                 115                 120

Tyr Tyr Gln Lys Ala Ile Trp Glu Leu Gln Val Ser Ala Leu Gly
           125                 130                 135

Ser Val Pro Leu Ile Ser Ile Thr Gly Tyr Val Asp Arg Asp Ile
           140                 145                 150

Gln Leu Leu Cys Gln Ser Ser Gly Trp Phe Pro Arg Pro Thr Ala
           155                 160                 165

Lys Trp Lys Gly Pro Gln Gly Gln Asp Leu Ser Thr Asp Ser Arg
           170                 175                 180

Thr Asn Arg Asp Met His Gly Leu Phe Asp Val Glu Ile Ser Leu
           185                 190                 195

Thr Val Gln Glu Asn Ala Gly Ser Ile Ser Cys Ser Met Arg His
           200                 205                 210

Ala His Leu Ser Arg Glu Val Glu Ser Arg Val Gln Ile Gly Asp
           215                 220                 225

Thr Phe Phe Glu Pro Ile Ser Trp His Leu Ala Thr Lys Val Leu
           230                 235                 240

Gly Ile Leu Cys Cys Gly Leu Phe Gly Ile Val Gly Leu Lys
           245                 250                 255

Ile Phe Phe Ser Lys Phe Gln Trp Lys Ile Gln Ala Glu Leu Asp
           260                 265                 270

Trp Arg Arg Lys His Gly Gln Ala Glu Leu Arg Asp Ala Arg Lys
           275                 280                 285

His Ala Val Glu Val Thr Leu Asp Pro Glu Thr Ala His Pro Lys
           290                 295                 300

Leu Cys Val Ser Asp Leu Lys Thr Val Thr His Arg Lys Ala Pro
           305                 310                 315

Gln Glu Val Pro His Ser Glu Lys Arg Phe Thr Arg Lys Ser Val
           320                 325                 330

Val Ala Ser Gln Ser Phe Gln Ala Gly Lys His Tyr Trp Glu Val
           335                 340                 345

Asp Gly Gly His Asn Lys Arg Trp Arg Val Gly Val Cys Arg Asp
           350                 355                 360

Asp Val Asp Arg Arg Lys Glu Tyr Val Thr Leu Ser Pro Asp His
           365                 370                 375
```

```
Gly Tyr Trp Val Leu Arg Leu Asn Gly Glu His Leu Tyr Phe Thr
            380                 385                 390
Leu Asn Pro Arg Phe Ile Ser Val Phe Pro Arg Thr Pro Pro Thr
        395                 400                 405
Lys Ile Gly Val Phe Leu Asp Tyr Glu Cys Gly Thr Ile Ser Phe
            410                 415                 420
Phe Asn Ile Asn Asp Gln Ser Leu Ile Tyr Thr Leu Thr Cys Arg
            425                 430                 435
Phe Glu Gly Leu Leu Arg Pro Tyr Ile Glu Tyr Pro Ser Tyr Asn
            440                 445                 450
Glu Gln Asn Gly Thr Pro Ile Val Ile Cys Pro Val Thr Gln Glu
            455                 460                 465
Ser Glu Lys Glu Ala Ser Trp Gln Arg Ala Ser Ala Ile Pro Glu
            470                 475                 480
Thr Ser Asn Ser Glu Ser Ser Ser Gln Ala Thr Thr Pro Phe Leu
            485                 490                 495
Pro Arg Gly Glu Met
            500
```

<210> SEQ ID NO 85
<211> LENGTH: 1665
<212> TYPE: DNA
<213> ORGANISM: Homo Sapien

<400> SEQUENCE: 85

| | | |
|---|---|---|
| aacagacgtt ccctcgcggc cctggcacct ctaaccccag acatgctgct | 50 |
| gctgctgctg cccctgctct gggggaggga gagggcggaa ggacagacaa | 100 |
| gtaaactgct gacgatgcag agttccgtga cggtgcagga aggcctgtgt | 150 |
| gtccatgtgc cctgctcctt ctcctacccc tcgcatggct ggatttaccc | 200 |
| tggcccagta gttcatggct actggttccg ggaagggggcc aatacagacc | 250 |
| aggatgctcc agtggccaca acaacccag ctcgggcagt gtgggaggag | 300 |
| actcgggacc gattccacct ccttggggac ccacatacca agaattgcac | 350 |
| cctgagcatc agagatgcca gaagaagtga tgcggggaga tacttctttc | 400 |
| gtatggagaa aggaagtata aaatggaatt ataaacatca ccggctctct | 450 |
| gtgaatgtga cagccttgac ccacaggccc aacatcctca tcccaggcac | 500 |
| cctggagtcc ggctgccccc agaatctgac ctgctctgtg ccctgggcct | 550 |
| gtgagcaggg gacacccct atgatctcct ggataggggac ctccgtgtcc | 600 |
| cccctggacc cctccaccac ccgctcctcg gtgctcaccc tcatcccaca | 650 |
| gccccaggac catggcacca gcctcacctg tcaggtgacc ttccctgggg | 700 |
| ccagcgtgac cacgaacaag accgtccatc tcaacgtgtc ctacccgcct | 750 |
| cagaacttga ccatgactgt cttccaagga gacggcacag tatccacagt | 800 |
| cttgggaaat ggctcatctc tgtcactccc agagggccag tctctgcgcc | 850 |
| tggtctgtgc agttgatgca gttgacagca tcccctgc caggctgagc | 900 |
| ctgagctgga gaggcctgac cctgtgcccc tcacagccct caaacccggg | 950 |
| ggtgctggag ctgcccttggg tgcacctgag ggatgcagct gaattcacct | 1000 |
| gcagagctca gaaccctctc ggctctcagc aggtctacct gaacgtctcc | 1050 |
| ctgcagagca aagccacatc aggagtgact caggggggtgg tcggggagc | 1100 |

-continued

```
tggagccaca gccctggtct tcctgtcctt ctgcgtcatc ttcgttgtag      1150
tgaggtcctg caggaagaaa tcggcaaggc cagcagcggg cgtgggagat      1200
acgggcatag aggatgcaaa cgctgtcagg ggttcagcct ctcagggcc       1250 cctgactgaa ccttgggcag aagacagtcc cccagaccag cctcccccag      1300
cttctgcccg ctcctcagtg ggggaaggag agctccagta tgcatccctc      1350
agcttccaga tggtgaagcc ttgggactcg cggggacagg aggccactga      1400
caccgagtac tcggagatca agatccacag atgagaaact gcagagactc      1450
accctgattg agggatcaca gcccctccag gcaagggaga agtcagaggc      1500
tgattcttgt agaattaaca gccctcaacg tgatgagcta tgataacact      1550
atgaattatg tgcagagtga aaagcacaca ggctttagag tcaaagtatc      1600
tcaaacctga atccacactg tgccctccct tttattttt taactaaaag       1650 acagacaaat tccta                                           1665
```

<210> SEQ ID NO 86
<211> LENGTH: 463
<212> TYPE: PRT
<213> ORGANISM: Homo Sapien

<400> SEQUENCE: 86

```
Met Leu Leu Leu Leu Pro Leu Leu Trp Gly Arg Glu Arg Ala
  1               5                  10                  15

Glu Gly Gln Thr Ser Lys Leu Leu Thr Met Gln Ser Ser Val Thr
             20                  25                  30

Val Gln Glu Gly Leu Cys Val His Val Pro Cys Ser Phe Ser Tyr
         35                  40                  45

Pro Ser His Gly Trp Ile Tyr Pro Gly Pro Val Val His Gly Tyr
         50                  55                  60

Trp Phe Arg Glu Gly Ala Asn Thr Asp Gln Asp Ala Pro Val Ala
     65                  70                  75

Thr Asn Asn Pro Ala Arg Ala Val Trp Glu Thr Arg Asp Arg
         80                  85                  90

Phe His Leu Leu Gly Asp Pro His Thr Lys Asn Cys Thr Leu Ser
         95                 100                 105

Ile Arg Asp Ala Arg Arg Ser Asp Ala Gly Arg Tyr Phe Phe Arg
        110                 115                 120

Met Glu Lys Gly Ser Ile Lys Trp Asn Tyr Lys His His Arg Leu
        125                 130                 135

Ser Val Asn Val Thr Ala Leu Thr His Arg Pro Asn Ile Leu Ile
        140                 145                 150

Pro Gly Thr Leu Glu Ser Gly Cys Pro Gln Asn Leu Thr Cys Ser
        155                 160                 165

Val Pro Trp Ala Cys Glu Gln Gly Thr Pro Pro Met Ile Ser Trp
        170                 175                 180

Ile Gly Thr Ser Val Ser Pro Leu Asp Pro Ser Thr Thr Arg Ser
        185                 190                 195

Ser Val Leu Thr Leu Ile Pro Gln Pro Gln Asp His Gly Thr Ser
        200                 205                 210

Leu Thr Cys Gln Val Thr Phe Pro Gly Ala Ser Val Thr Thr Asn
        215                 220                 225

Lys Thr Val His Leu Asn Val Ser Tyr Pro Pro Gln Asn Leu Thr
```

```
                           230                 235                 240
Met Thr Val Phe Gln Gly Asp Gly Thr Val Ser Thr Val Leu Gly
                245                 250                 255
Asn Gly Ser Ser Leu Ser Leu Pro Glu Gly Gln Ser Leu Arg Leu
                260                 265                 270
Val Cys Ala Val Asp Ala Val Asp Ser Asn Pro Pro Ala Arg Leu
                275                 280                 285
Ser Leu Ser Trp Arg Gly Leu Thr Leu Cys Pro Ser Gln Pro Ser
                290                 295                 300
Asn Pro Gly Val Leu Glu Leu Pro Trp Val His Leu Arg Asp Ala
                305                 310                 315
Ala Glu Phe Thr Cys Arg Ala Gln Asn Pro Leu Gly Ser Gln Gln
                320                 325                 330
Val Tyr Leu Asn Val Ser Leu Gln Ser Lys Ala Thr Ser Gly Val
                335                 340                 345
Thr Gln Gly Val Val Gly Gly Ala Gly Ala Thr Ala Leu Val Phe
                350                 355                 360
Leu Ser Phe Cys Val Ile Phe Val Val Arg Ser Cys Arg Lys
                365                 370                 375
Lys Ser Ala Arg Pro Ala Ala Gly Val Gly Asp Thr Gly Ile Glu
                380                 385                 390
Asp Ala Asn Ala Val Arg Gly Ser Ala Ser Gln Gly Pro Leu Thr
                395                 400                 405
Glu Pro Trp Ala Glu Asp Ser Pro Pro Asp Gln Pro Pro Ala
                410                 415                 420
Ser Ala Arg Ser Ser Val Gly Glu Gly Glu Leu Gln Tyr Ala Ser
                425                 430                 435
Leu Ser Phe Gln Met Val Lys Pro Trp Asp Ser Arg Gly Gln Glu
                440                 445                 450
Ala Thr Asp Thr Glu Tyr Ser Glu Ile Lys Ile His Arg
                455                 460

<210> SEQ ID NO 87
<211> LENGTH: 1176
<212> TYPE: DNA
<213> ORGANISM: Homo Sapien

<400> SEQUENCE: 87
agaaagctgc actctgttga gctccagggc gcagtggagg gagggagtga              50
aggagctctc tgtacccaag gaaagtgcag ctgagactca gacaagatta             100
caatgaacca actcagcttc ctgctgtttc tcatagcgac caccagagga             150
tggagtacag atgaggctaa tacttacttc aaggaatgga cctgttcttc             200
gtctccatct ctgcccagaa gctgcaagga aatcaaagac gaatgtccta             250
gtgcatttga tggcctgtat tttctccgca ctgagaatgg tgttatctac             300
cagaccttct gtgacatgac ctctgggggt ggcggctgga ccctggtggc             350
cagcgtgcat gagaatgaca tgcgtgggaa gtgcacggtg ggcgatcgct             400
ggtccagtca gcaggcagc aaagcagact acccagaggg ggacggcaac              450
tgggccaact acaacacctt tggatctgca gaggcggcca cgagcgatga             500
ctacaagaac cctggctact acgacatcca ggccaaggac ctgggcatct             550
ggcacgtgcc aataagtcc cccatgcagc actggagaaa cagctccctg              600
```

```
ctgaggtacc gcacggacac tggcttcctc cagacactgg gacataatct         650
gtttggcatc taccagaaat atccagtgaa atatggagaa ggaaagtgtt         700
ggactgacaa cggcccggtg atccctgtgg tctatgattt tggcgacgcc         750
cagaaaacag catcttatta ctcaccctat ggccagcggg aattcactgc         800
gggatttgtt cagttcaggg tatttaataa cgagagagca gccaacgcct         850
tgtgtgctgg aatgagggtc accggatgta acactgagca tcactgcatt         900
ggtggaggag gatactttcc agaggccagt ccccagcagt gtggagattt         950
ttctggtttt gattggagtg gatatggaac tcatgttggt tacagcagca        1000
gccgtgagat aactgaggca gctgtgcttc tattctatcg ttgagagttt        1050
tgtgggaggg aacccagacc tctcctccca accatgagat cccaaggatg        1100
gagaacaact tacccagtag ctagaatgtt aatggcagaa gagaaaacaa        1150
taaatcatat tgactcaaga aaaaaa                                  1176
```

<210> SEQ ID NO 88
<211> LENGTH: 313
<212> TYPE: PRT
<213> ORGANISM: Homo Sapien

<400> SEQUENCE: 88

```
Met Asn Gln Leu Ser Phe Leu Leu Phe Leu Ile Ala Thr Thr Arg
 1               5                  10                  15

Gly Trp Ser Thr Asp Glu Ala Asn Thr Tyr Phe Lys Glu Trp Thr
                20                  25                  30

Cys Ser Ser Ser Pro Ser Leu Pro Arg Ser Cys Lys Glu Ile Lys
                35                  40                  45

Asp Glu Cys Pro Ser Ala Phe Asp Gly Leu Tyr Phe Leu Arg Thr
                50                  55                  60

Glu Asn Gly Val Ile Tyr Gln Thr Phe Cys Asp Met Thr Ser Gly
                65                  70                  75

Gly Gly Gly Trp Thr Leu Val Ala Ser Val His Glu Asn Asp Met
                80                  85                  90

Arg Gly Lys Cys Thr Val Gly Asp Arg Trp Ser Ser Gln Gln Gly
                95                 100                 105

Ser Lys Ala Asp Tyr Pro Glu Gly Asp Gly Asn Trp Ala Asn Tyr
               110                 115                 120

Asn Thr Phe Gly Ser Ala Glu Ala Thr Ser Asp Asp Tyr Lys
               125                 130                 135

Asn Pro Gly Tyr Tyr Asp Ile Gln Ala Lys Asp Leu Gly Ile Trp
               140                 145                 150

His Val Pro Asn Lys Ser Pro Met Gln His Trp Arg Asn Ser Ser
               155                 160                 165

Leu Leu Arg Tyr Arg Thr Asp Thr Gly Phe Leu Gln Thr Leu Gly
               170                 175                 180

His Asn Leu Phe Gly Ile Tyr Gln Lys Tyr Pro Val Lys Tyr Gly
               185                 190                 195

Glu Gly Lys Cys Trp Thr Asp Asn Gly Pro Val Ile Pro Val Val
               200                 205                 210

Tyr Asp Phe Gly Asp Ala Gln Lys Thr Ala Ser Tyr Tyr Ser Pro
               215                 220                 225

Tyr Gly Gln Arg Glu Phe Thr Ala Gly Phe Val Gln Phe Arg Val
               230                 235                 240
```

```
Phe Asn Asn Glu Arg Ala Ala Asn Ala Leu Cys Ala Gly Met Arg
                245                 250                 255

Val Thr Gly Cys Asn Thr Glu His His Cys Ile Gly Gly Gly Gly
            260                 265                 270

Tyr Phe Pro Glu Ala Ser Pro Gln Gln Cys Gly Asp Phe Ser Gly
        275                 280                 285

Phe Asp Trp Ser Gly Tyr Gly Thr His Val Gly Tyr Ser Ser Ser
            290                 295                 300

Arg Glu Ile Thr Glu Ala Ala Val Leu Leu Phe Tyr Arg
                305                 310
```

<210> SEQ ID NO 89
<211> LENGTH: 759
<212> TYPE: DNA
<213> ORGANISM: Homo Sapien

<400> SEQUENCE: 89

```
ctagatttgt cggcttgcgg ggagacttca ggagtcgctg tctctgaact          50
tccagcctca gagaccgccg cccttgtccc cgagggccat gggccgggtc         100
tcagggcttg tgccctctcg cttcctgacg ctcctggcgc atctggtggt         150
cgtcatcacc ttattctggt cccgggacag caacatacag gcctgcctgc         200
ctctcacgtt caccccgag gagtatgaca agcaggacat tcagctggtg          250
gccgcgctct ctgtcaccct gggcctcttt gcagtggagc tggccggttt         300
cctctcagga gtctccatgt tcaacagcac ccagagcctc atctccattg         350
gggctcactg tagtgcatcc gtggccctgt ccttcttcat attcgagcgt         400
tgggagtgca ctacgtattg gtacatttt gtcttctgca gtgcccttcc          450
agctgtcact gaaatggctt tattcgtcac cgtctttggg ctgaaaaaga         500
aaccttctg attaccttca tgacgggaac ctaaggacga agcctacagg          550
ggcaagggcc gcttcgtatt cctggaagaa ggaaggcata ggcttcggtt         600
ttcccctcgg aaactgcttc tgctggagga tatgtgttgg aataattacg         650
tcttgagtct gggattatcc gcattgtatt tagtgctttg taataaaata         700
tgttttgtag taacattaag acttatatac agttttaggg gacaattaaa         750
aaaaaaaa                                                      759
```

<210> SEQ ID NO 90
<211> LENGTH: 140
<212> TYPE: PRT
<213> ORGANISM: Homo Sapien

<400> SEQUENCE: 90

```
Met Gly Arg Val Ser Gly Leu Val Pro Ser Arg Phe Leu Thr Leu
  1               5                  10                  15

Leu Ala His Leu Val Val Ile Thr Leu Phe Trp Ser Arg Asp
            20                  25                  30

Ser Asn Ile Gln Ala Cys Leu Pro Leu Thr Phe Thr Pro Glu Glu
            35                  40                  45

Tyr Asp Lys Gln Asp Ile Gln Leu Val Ala Ala Leu Ser Val Thr
            50                  55                  60

Leu Gly Leu Phe Ala Val Glu Leu Ala Gly Phe Leu Ser Gly Val
            65                  70                  75
```

-continued

```
Ser Met Phe Asn Ser Thr Gln Ser Leu Ile Ser Ile Gly Ala His
        80                  85                  90

Cys Ser Ala Ser Val Ala Leu Ser Phe Phe Ile Phe Glu Arg Trp
        95                  100                 105

Glu Cys Thr Thr Tyr Trp Tyr Ile Phe Val Phe Cys Ser Ala Leu
        110                 115                 120

Pro Ala Val Thr Glu Met Ala Leu Phe Val Thr Val Phe Gly Leu
        125                 130                 135

Lys Lys Lys Pro Phe
        140
```

<210> SEQ ID NO 91
<211> LENGTH: 1871
<212> TYPE: DNA
<213> ORGANISM: Homo Sapien

<400> SEQUENCE: 91

```
ctgggacccc gaaaagagaa ggggagagcg aggggacgag agcggaggag        50
gaagatgcaa ctgactcgct gctgcttcgt gttcctggtg cagggtagcc       100
tctatctggt catctgtggc caggatgatg gtcctcccgg ctcagaggac       150
cctgagcgtg atgaccacga gggccagccc cggccccggg tgcctcggaa       200
gcggggccac atctcaccta gtcccgccc catggccaat ccactctcc        250
tagggctgct ggccccgcct ggggaggctt ggggcattct tgggcagccc       300
cccaaccgcc cgaaccacag cccccaccc tcagccaagg tgaagaaaat       350
ctttggctgg ggcgacttct actccaacat caagacggtg ccctgaacc       400
tgctcgtcac agggaagatt gtggaccatg caatgggac cttcagcgtc       450
cacttccaac acaatgccac aggccaggga acatctcca tcagcctcgt       500
gcccccagt aaagctgtag agttccacca ggaacagcag atcttcatcg       550
aagccaaggc ctccaaaatc ttcaactgcc ggatggagtg ggagaaggta       600
gaacggggcc gccggacctc gctttgcacc cacgacccag ccaagatctg       650
ctcccgagac cacgctcaga gctcagccac ctggagctgc tcccagccct       700
tcaaagtcgt ctgtgtctac atcgccttct acagcacgga ctatcggctg       750
gtccagaagg tgtgcccaga ttacaactac catagtgata ccccctacta       800
cccatctggg tgacccgggg caggccacag aggccaggcc agggctggaa       850
ggacaggcct gcccatgcag gagaccatct ggacaccggg cagggaaggg       900
gttgggcctc aggcagggag gggggtggag acgaggagat gccaagtggg       950
gccagggcca agtctcaagt ggcagagaaa gggtcccaag tgctggtccc      1000
aacctgaagc tgtggagtga ctagatcaca ggagcactgg aggaggagtg      1050
ggctctctgt gcagcctcac agggctttgc cacggagcca cagagagatg      1100
ctgggtcccc gaggcctgtg gcaggccga tcagtgtggc cccagatcaa       1150
gtcatgggag gaagctaagc ccttggttct tgccatcctg aggaaagata      1200
gcaacaggga gggggagatt tcatcagtgt ggacagcctg tcaacttagg      1250
atggatggct gagagggctt cctaggagcc agtcagcagg gtggggtggg      1300
gccagaggag ctctccagcc ctgcctagtg ggcgccctga gcccttgtc       1350
gtgtgctgag catggcatga ggctgaagtg gcaaccctgg ggtctttgat      1400
```

-continued

```
gtcttgacag attgaccatc tgtctccagc caggccaccc ctttccaaaa          1450
ttccctcttc tgccagtact cccccctgtac cacccattgc tgatggcaca         1500
cccatcctta agctaagaca ggacgattgt ggtcctccca cactaaggcc          1550
acagcccatc cgcgtgctgt gtgtccctct tccaccccaa ccctgctgg           1600 ctcctctggg agcatccatg tcccggagag gggtccctca acagtcagcc          1650
tcacctgtca gaccggggtt ctcccggatc tggatggcgc cgccctctca          1700
gcagcgggca cgggtggggc ggggccgggc cgcagagcat gtgctggatc          1750
tgttctgtgt gtctgtctgt gggtgggggg aggggaggga agtcttgtga          1800
aaccgctgat tgctgacttt tgtgtgaaga atcgtgttct tggagcagga          1850
aataaagctt gccccggggc a                                         1871
```

<210> SEQ ID NO 92
<211> LENGTH: 252
<212> TYPE: PRT
<213> ORGANISM: Homo Sapien

<400> SEQUENCE: 92

```
Met Gln Leu Thr Arg Cys Cys Phe Val Phe Leu Val Gln Gly Ser
  1               5                  10                  15

Leu Tyr Leu Val Ile Cys Gly Gln Asp Asp Gly Pro Pro Gly Ser
                 20                  25                  30

Glu Asp Pro Glu Arg Asp Asp His Glu Gly Gln Pro Arg Pro Arg
                 35                  40                  45

Val Pro Arg Lys Arg Gly His Ile Ser Pro Lys Ser Arg Pro Met
                 50                  55                  60

Ala Asn Ser Thr Leu Leu Gly Leu Leu Ala Pro Pro Gly Glu Ala
                 65                  70                  75

Trp Gly Ile Leu Gly Gln Pro Pro Asn Arg Pro Asn His Ser Pro
                 80                  85                  90

Pro Pro Ser Ala Lys Val Lys Lys Ile Phe Gly Trp Gly Asp Phe
                 95                 100                 105

Tyr Ser Asn Ile Lys Thr Val Ala Leu Asn Leu Leu Val Thr Gly
                110                 115                 120

Lys Ile Val Asp His Gly Asn Gly Thr Phe Ser Val His Phe Gln
                125                 130                 135

His Asn Ala Thr Gly Gln Gly Asn Ile Ser Ile Ser Leu Val Pro
                140                 145                 150

Pro Ser Lys Ala Val Glu Phe His Gln Glu Gln Gln Ile Phe Ile
                155                 160                 165

Glu Ala Lys Ala Ser Lys Ile Phe Asn Cys Arg Met Glu Trp Glu
                170                 175                 180

Lys Val Glu Arg Gly Arg Arg Thr Ser Leu Cys Thr His Asp Pro
                185                 190                 195

Ala Lys Ile Cys Ser Arg Asp His Ala Gln Ser Ser Ala Thr Trp
                200                 205                 210

Ser Cys Ser Gln Pro Phe Lys Val Val Cys Val Tyr Ile Ala Phe
                215                 220                 225

Tyr Ser Thr Asp Tyr Arg Leu Val Gln Lys Val Cys Pro Asp Tyr
                230                 235                 240

Asn Tyr His Ser Asp Thr Pro Tyr Tyr Pro Ser Gly
                245                 250
```

<210> SEQ ID NO 93
<211> LENGTH: 902
<212> TYPE: DNA
<213> ORGANISM: Homo Sapien

<400> SEQUENCE: 93

```
cggtggccat gactgcggcc gtgttcttcg gctgcgcctt cattgccttc         50
gggcctgcgc tcgcccttta tgtcttcacc atcgccatcg agccgttgcg        100
tatcatcttc ctcatcgccg gagctttctt ctggttggtg tctctactga        150
tttcgtccct tgtttggttc atggcaagag tcattattga caacaaagat        200
ggaccaacac agaaatatct gctgatcttt ggagcgtttg tctctgtcta        250
tatccaagaa atgttccgat tgcatatta taaactctta aaaaaagcca         300
gtgaaggttt gaagagtata aacccaggtg agacagcacc ctctatgcga        350
ctgctgccct atgtttctgg cttgggcttt ggaatcatga gtggagtatt        400
ttcctttgtg aataccctat ctgactcctt ggggccaggc acagtgggca        450
ttcatggaga ttctcctcaa ttcttccttt attcagcttt catgacgctg        500
gtcattatct tgctgcatgt attctggggc attgtatttt ttgatggctg        550
tgagaagaaa aagtggggca tcctccttat cgttctcctg acccacctgc        600
tggtgtcagc ccagaccttc ataagttctt attatggaat aaacctggcg        650
tcagcattta taatcctggt gctcatgggc acctgggcat tcttagctgc        700
gggaggcagc tgccgaagcc tgaaactctg cctgctctgc aagacaaga         750
actttcttct ttacaaccag cgctccagat aacctcaggg aaccagcact        800
tcccaaaccg cagactacat ctttagagga agcacaactg tgccttttc         850
tgaaaatccc tttttctggt ggaattgaga agaaataaa actatgcaga         900
ta                                                             902
```

<210> SEQ ID NO 94
<211> LENGTH: 257
<212> TYPE: PRT
<213> ORGANISM: Homo Sapien

<400> SEQUENCE: 94

```
Met Thr Ala Ala Val Phe Phe Gly Cys Ala Phe Ile Ala Phe Gly
  1               5                  10                  15

Pro Ala Leu Ala Leu Tyr Val Phe Thr Ile Ala Ile Glu Pro Leu
                 20                  25                  30

Arg Ile Ile Phe Leu Ile Ala Gly Ala Phe Phe Trp Leu Val Ser
                 35                  40                  45

Leu Leu Ile Ser Ser Leu Val Trp Phe Met Ala Arg Val Ile Ile
                 50                  55                  60

Asp Asn Lys Asp Gly Pro Thr Gln Lys Tyr Leu Leu Ile Phe Gly
                 65                  70                  75

Ala Phe Val Ser Val Tyr Ile Gln Glu Met Phe Arg Phe Ala Tyr
                 80                  85                  90

Tyr Lys Leu Leu Lys Lys Ala Ser Glu Gly Leu Lys Ser Ile Asn
                 95                 100                 105

Pro Gly Glu Thr Ala Pro Ser Met Arg Leu Leu Ala Tyr Val Ser
                110                 115                 120

Gly Leu Gly Phe Gly Ile Met Ser Gly Val Phe Ser Phe Val Asn
```

```
                125                 130                 135
Thr Leu Ser Asp Ser Leu Gly Pro Gly Thr Val Gly Ile His Gly
                140                 145                 150
Asp Ser Pro Gln Phe Phe Leu Tyr Ser Ala Phe Met Thr Leu Val
                155                 160                 165
Ile Ile Leu Leu His Val Phe Trp Gly Ile Val Phe Asp Gly
                170                 175                 180
Cys Glu Lys Lys Lys Trp Gly Ile Leu Ile Val Leu Leu Thr
                185                 190                 195
His Leu Leu Val Ser Ala Gln Thr Phe Ile Ser Ser Tyr Tyr Gly
                200                 205                 210
Ile Asn Leu Ala Ser Ala Phe Ile Ile Leu Val Leu Met Gly Thr
                215                 220                 225
Trp Ala Phe Leu Ala Ala Gly Gly Ser Cys Arg Ser Leu Lys Leu
                230                 235                 240
Cys Leu Leu Cys Gln Asp Lys Asn Phe Leu Leu Tyr Asn Gln Arg
                245                 250                 255
Ser Arg

<210> SEQ ID NO 95
<211> LENGTH: 1073
<212> TYPE: DNA
<213> ORGANISM: Homo Sapien

<400> SEQUENCE: 95 aattttcac cagagtaaac ttgagaaacc aactggacct tgagtattgt            50
acattttgcc tcgtggaccc aaaggtagca atctgaaaca tgaggagtac          100
gattctactg ttttgtcttc taggatcaac tcggtcatta ccacagctca          150
aacctgcttt gggactccct cccacaaaac tggctccgga tcaggaaca           200
ctaccaaacc aacagcagtc aaatcaggtc tttccttctt taagtctgat          250
accattaaca cagatgctca cactggggcc agatctgcat ctgttaaatc          300
ctgctgcagg aatgacacct ggtacccaga cccacccatt gaccctggga          350
gggttgaatg tacaacagca actgcaccca catgtgttac caattttttgt         400
cacacaactt ggagcccagg gcactatcct aagctcagag gaattgccac          450
aaatcttcac gagcctcatc atccattcct tgttcccggg aggcatcctg          500
cccaccagtc aggcagggc taatccagat gtccaggatg gaagccttcc           550
agcaggagga gcaggtgtaa atcctgccac ccagggaacc ccagcaggcc          600
gcctcccaac tcccagtggc acagatgacg actttgcagt gaccaccct           650
gcaggcatcc aaaggagcac acatgccatc gaggaagcca ccacagaatc          700
agcaaatgga attcagtaag ctgtttcaaa ttttttcaac taagctgcct          750
cgaatttggt gatacatgtg aatctttatc attgattata ttatgaaata          800
gattgagaca cattggatag tcttagaaga aattaattct taatttacct          850
gaaaatattc ttgaaatttc agaaaatatg ttctatgtag agaatcccaa          900
cttttaaaaa caataattca atggataaat ctgtctttga aatataacat          950
tatgctgcct ggatgatatg catattaaaa catatttgga aaactggaaa         1000
aaaaaaaaaa aaaaaaaaaa aaaaaaaaaa aaaaaaaaaa aaaaaaaaaa         1050
aaaaaaaaaa aaaaaaaaaa aaa                                      1073
```

<210> SEQ ID NO 96
<211> LENGTH: 209
<212> TYPE: PRT
<213> ORGANISM: Homo Sapien

<400> SEQUENCE: 96

```
Met Arg Ser Thr Ile Leu Leu Phe Cys Leu Leu Gly Ser Thr Arg
  1               5                  10                  15

Ser Leu Pro Gln Leu Lys Pro Ala Leu Gly Leu Pro Pro Thr Lys
                 20                  25                  30

Leu Ala Pro Asp Gln Gly Thr Leu Pro Asn Gln Gln Ser Asn
             35                  40                  45

Gln Val Phe Pro Ser Leu Ser Leu Ile Pro Leu Thr Gln Met Leu
             50                  55                  60

Thr Leu Gly Pro Asp Leu His Leu Leu Asn Pro Ala Ala Gly Met
             65                  70                  75

Thr Pro Gly Thr Gln Thr His Pro Leu Thr Leu Gly Gly Leu Asn
             80                  85                  90

Val Gln Gln Gln Leu His Pro His Val Leu Pro Ile Phe Val Thr
             95                 100                 105

Gln Leu Gly Ala Gln Gly Thr Ile Leu Ser Ser Glu Glu Leu Pro
            110                 115                 120

Gln Ile Phe Thr Ser Leu Ile Ile His Ser Leu Phe Pro Gly Gly
            125                 130                 135

Ile Leu Pro Thr Ser Gln Ala Gly Ala Asn Pro Asp Val Gln Asp
            140                 145                 150

Gly Ser Leu Pro Ala Gly Gly Ala Gly Val Asn Pro Ala Thr Gln
            155                 160                 165

Gly Thr Pro Ala Gly Arg Leu Pro Thr Pro Ser Gly Thr Asp Asp
            170                 175                 180

Asp Phe Ala Val Thr Thr Pro Ala Gly Ile Gln Arg Ser Thr His
            185                 190                 195

Ala Ile Glu Glu Ala Thr Thr Glu Ser Ala Asn Gly Ile Gln
            200                 205
```

<210> SEQ ID NO 97
<211> LENGTH: 2848
<212> TYPE: DNA
<213> ORGANISM: Homo Sapien

<400> SEQUENCE: 97

```
gctcaagtgc cctgccttgc cccacccagc ccagcctggc cagagccccc           50
tggagaagga gctctcttct tgcttggcag ctggaccaag ggagccagtc          100
ttgggcgctg gagggcctgt cctgaccatg gtccctgcct ggctgtggct          150
gctttgtgtc tccgtccccc aggctctccc caaggcccag cctgcagagc          200
tgtctgtgga agttccagaa aactatggtg gaaatttccc tttatacctg          250
accaagttgc cgctgccccg tgagggggct gaaggccaga tcgtgctgtc          300 agggggactca ggcaaggcaa ctgagggccc atttgctatg gatccagatt         350
ctggcttcct gctggtgacc agggccctgg accgagagga gcaggcagag          400
taccagctac aggtcaccct ggagatgcag gatggacatg tcttgtgggg          450
tccacagcct gtgcttgtgc acgtgaagga tgagaatgac caggtgcccc          500
```

-continued

| | |
|---|---|
| atttctctca agccatctac agagctcggc tgagccgggg taccaggcct | 550 |
| ggcatcccct tcctcttcct tgaggcttca gaccgggatg agccaggcac | 600 |
| agccaactcg gatcttcgat tccacatcct gagccaggct ccagcccagc | 650 |
| cttccccaga catgttccag ctggagcctc ggctgggggc tctggccctc | 700 |
| agccccaagg ggagcaccag ccttgaccac gccctggaga ggacctacca | 750 |
| gctgttggta caggtcaagg acatgggtga ccaggcctca ggccaccagg | 800 |
| ccactgccac cgtggaagtc tccatcatag agagcacctg ggtgtcccta | 850 |
| gagcctatcc acctggcaga gaatctcaaa gtcctatacc cgcaccacat | 900 |
| ggcccaggta cactggagtg ggggtgatgt gcactatcac ctggagagcc | 950 |
| atcccccggg acccttttgaa gtgaatgcag agggaaacct ctacgtgacc | 1000 |
| agagagctgg acagagaagc ccaggctgag tacctgctcc aggtgcgggc | 1050 |
| tcagaattcc catggcgagg actatgcggc ccctctggag ctgcacgtgc | 1100 |
| tggtgatgga tgagaatgac aacgtgccta tctgccctcc ccgtgacccc | 1150 |
| acagtcagca tccctgagct cagtccacca ggtactgaag tgactagact | 1200 |
| gtcagcagag gatgcagatg cccccggctc ccccaattcc cacgttgtgt | 1250 |
| atcagctcct gagccctgag cctgaggatg gggtagaggg gagagccttc | 1300 |
| caggtggacc ccacttcagg cagtgtgacg ctggggggtgc tcccactccg | 1350 |
| agcaggccaa acatcctgc ttctggtgct ggccatggac ctggcaggcg | 1400 |
| cagagggtgg cttcagcagc acgtgtgaag tcgaagtcgc agtcacagat | 1450 |
| atcaatgatc acgcccctga gttcatcact tcccagattg ggcctataag | 1500 |
| cctccctgag gatgtggagc ccgggactct ggtggccatg ctaacagcca | 1550 |
| ttgatgctga cctcgagccc gccttccgcc tcatggattt tgccattgag | 1600 |
| agggagacag cagaagggac ttttggcctg gattgggagc cagactctgg | 1650 |
| gcatgttaga ctcagactct gcaagaacct cagttatgag gcagctccaa | 1700 |
| gtcatgaggt ggtggtggtg gtgcagagtg tggcgaagct ggtggggcca | 1750 |
| ggcccaggcc ctggagccac cgccacggtg actgtgctag tggagagagt | 1800 |
| gatgccaccc cccaagttgg accaggagag ctacgaggcc agtgtcccca | 1850 |
| tcagtgcccc agccggctct ttcctgctga ccatccagcc ctccgacccc | 1900 |
| atcagccgaa ccctcaggtt ctccctagtc aatgactcag agggctggct | 1950 |
| ctgcattgag aaattctccg gggaggtgca caccgcccag tccctgcagg | 2000 |
| gcgcccagcc tgggacacc tacacggtgc ttgtggaggc ccaggataca | 2050 |
| gccctgactc ttgcccctgt gccctcccaa tacctctgca caccccgcca | 2100 |
| agaccatggc ttgatcgtga gtggacccag caaggacccc gatctggcca | 2150 |
| gtgggcacgg tccctacagc ttcacccttg gtcccaaccc cacggtgcaa | 2200 |
| cgggattggc gcctccagac tctcaatggt tcccatgcct acctcacctt | 2250 |
| ggccctgcat tgggtggagc cacgtgaaca cataatcccc gtggtggtca | 2300 |
| gccacaatgc ccagatgtgg cagctcctgg ttcgagtgat cgtgtgtcgc | 2350 |
| tgcaacgtgg aggggcagtg catgcgcaag gtgggccgca tgaagggcat | 2400 |
| gcccacgaag ctgtcggcag tgggcatcct tgtaggcacc ctggtagcaa | 2450 |
| taggaatctt cctcatcctc attttcaccc actggaccat gtcaaggaag | 2500 |

| | | |
|---|---|---|
| aaggacccgg atcaaccagc agacagcgtg cccctgaagg cgactgtctg | | 2550 |
| aatggcccag gcagctctag ctgggagctt ggcctctggc tccatctgag | | 2600 |
| tcccctggga gagagcccag cacccaagat ccagcagggg acaggacaga | | 2650 |
| gtagaagccc ctccatctgc cctggggtgg aggcaccatc accatcacca | | 2700 |
| ggcatgtctg cagagcctgg acaccaactt tatggactgc ccatgggagt | | 2750 |
| gctccaaatg tcagggtgtt tgcccaataa taaagcccca gagaactggg | | 2800 |
| ctgggcccta tgggaaaaaa aaaaaaaaaa aaaaaaaaaa aaaaaaag | | 2848 |

<210> SEQ ID NO 98
<211> LENGTH: 807
<212> TYPE: PRT
<213> ORGANISM: Homo Sapien

<400> SEQUENCE: 98

```
Met Val Pro Ala Trp Leu Trp Leu Leu Cys Val Ser Val Pro Gln
 1               5                  10                  15

Ala Leu Pro Lys Ala Gln Pro Ala Glu Leu Ser Val Glu Val Pro
                20                  25                  30

Glu Asn Tyr Gly Gly Asn Phe Pro Leu Tyr Leu Thr Lys Leu Pro
                35                  40                  45

Leu Pro Arg Glu Gly Ala Glu Gly Gln Ile Val Leu Ser Gly Asp
                50                  55                  60

Ser Gly Lys Ala Thr Glu Gly Pro Phe Ala Met Asp Pro Asp Ser
                65                  70                  75

Gly Phe Leu Leu Val Thr Arg Ala Leu Asp Arg Glu Glu Gln Ala
                80                  85                  90

Glu Tyr Gln Leu Gln Val Thr Leu Glu Met Gln Asp Gly His Val
                95                 100                 105

Leu Trp Gly Pro Gln Pro Val Leu Val His Val Lys Asp Glu Asn
               110                 115                 120

Asp Gln Val Pro His Phe Ser Gln Ala Ile Tyr Arg Ala Arg Leu
               125                 130                 135

Ser Arg Gly Thr Arg Pro Gly Ile Pro Phe Leu Phe Leu Glu Ala
               140                 145                 150

Ser Asp Arg Asp Glu Pro Gly Thr Ala Asn Ser Asp Leu Arg Phe
               155                 160                 165

His Ile Leu Ser Gln Ala Pro Ala Gln Pro Ser Pro Asp Met Phe
               170                 175                 180

Gln Leu Glu Pro Arg Leu Gly Ala Leu Ala Leu Ser Pro Lys Gly
               185                 190                 195

Ser Thr Ser Leu Asp His Ala Leu Glu Arg Thr Tyr Gln Leu Leu
               200                 205                 210

Val Gln Val Lys Asp Met Gly Asp Gln Ala Ser Gly His Gln Ala
               215                 220                 225

Thr Ala Thr Val Glu Val Ser Ile Ile Glu Ser Thr Trp Val Ser
               230                 235                 240

Leu Glu Pro Ile His Leu Ala Glu Asn Leu Lys Val Leu Tyr Pro
               245                 250                 255

His His Met Ala Gln Val His Trp Ser Gly Gly Asp Val His Tyr
               260                 265                 270

His Leu Glu Ser His Pro Pro Gly Pro Phe Glu Val Asn Ala Glu
               275                 280                 285
```

-continued

```
Gly Asn Leu Tyr Val Thr Arg Glu Leu Asp Arg Glu Ala Gln Ala
            290                 295                 300
Glu Tyr Leu Leu Gln Val Arg Ala Gln Asn Ser His Gly Glu Asp
            305                 310                 315
Tyr Ala Ala Pro Leu Glu Leu His Val Leu Val Met Asp Glu Asn
            320                 325                 330
Asp Asn Val Pro Ile Cys Pro Pro Arg Asp Pro Thr Val Ser Ile
            335                 340                 345
Pro Glu Leu Ser Pro Pro Gly Thr Glu Val Thr Arg Leu Ser Ala
            350                 355                 360
Glu Asp Ala Asp Ala Pro Gly Ser Pro Asn Ser His Val Val Tyr
            365                 370                 375
Gln Leu Leu Ser Pro Glu Pro Glu Asp Gly Val Glu Gly Arg Ala
            380                 385                 390
Phe Gln Val Asp Pro Thr Ser Gly Ser Val Thr Leu Gly Val Leu
            395                 400                 405
Pro Leu Arg Ala Gly Gln Asn Ile Leu Leu Val Leu Ala Met
            410                 415                 420
Asp Leu Ala Gly Ala Glu Gly Gly Phe Ser Ser Thr Cys Glu Val
            425                 430                 435
Glu Val Ala Val Thr Asp Ile Asn Asp His Ala Pro Glu Phe Ile
            440                 445                 450
Thr Ser Gln Ile Gly Pro Ile Ser Leu Pro Glu Asp Val Glu Pro
            455                 460                 465
Gly Thr Leu Val Ala Met Leu Thr Ala Ile Asp Ala Asp Leu Glu
            470                 475                 480
Pro Ala Phe Arg Leu Met Asp Phe Ala Ile Glu Arg Gly Asp Thr
            485                 490                 495
Glu Gly Thr Phe Gly Leu Asp Trp Glu Pro Asp Ser Gly His Val
            500                 505                 510
Arg Leu Arg Leu Cys Lys Asn Leu Ser Tyr Glu Ala Ala Pro Ser
            515                 520                 525
His Glu Val Val Val Val Gln Ser Val Ala Lys Leu Val Gly
            530                 535                 540
Pro Gly Pro Gly Pro Gly Ala Thr Ala Thr Val Thr Val Leu Val
            545                 550                 555
Glu Arg Val Met Pro Pro Lys Leu Asp Gln Glu Ser Tyr Glu
            560                 565                 570
Ala Ser Val Pro Ile Ser Ala Pro Ala Gly Ser Phe Leu Leu Thr
            575                 580                 585
Ile Gln Pro Ser Asp Pro Ile Ser Arg Thr Leu Arg Phe Ser Leu
            590                 595                 600
Val Asn Asp Ser Glu Gly Trp Leu Cys Ile Glu Lys Phe Ser Gly
            605                 610                 615
Glu Val His Thr Ala Gln Ser Leu Gln Gly Ala Gln Pro Gly Asp
            620                 625                 630
Thr Tyr Thr Val Leu Val Glu Ala Gln Asp Thr Ala Leu Thr Leu
            635                 640                 645
Ala Pro Val Pro Ser Gln Tyr Leu Cys Thr Pro Arg Gln Asp His
            650                 655                 660
Gly Leu Ile Val Ser Gly Pro Ser Lys Asp Pro Asp Leu Ala Ser
            665                 670                 675
```

```
Gly His Gly Pro Tyr Ser Phe Thr Leu Gly Pro Asn Pro Thr Val
            680                 685                 690

Gln Arg Asp Trp Arg Leu Gln Thr Leu Asn Gly Ser His Ala Tyr
            695                 700                 705

Leu Thr Leu Ala Leu His Trp Val Glu Pro Arg Glu His Ile Ile
            710                 715                 720

Pro Val Val Val Ser His Asn Ala Gln Met Trp Gln Leu Leu Val
            725                 730                 735

Arg Val Ile Val Cys Arg Cys Asn Val Glu Gly Gln Cys Met Arg
            740                 745                 750

Lys Val Gly Arg Met Lys Gly Met Pro Thr Lys Leu Ser Ala Val
            755                 760                 765

Gly Ile Leu Val Gly Thr Leu Val Ala Ile Gly Ile Phe Leu Ile
            770                 775                 780

Leu Ile Phe Thr His Trp Thr Met Ser Arg Lys Lys Asp Pro Asp
            785                 790                 795

Gln Pro Ala Asp Ser Val Pro Leu Lys Ala Thr Val
            800                 805
```

<210> SEQ ID NO 99
<211> LENGTH: 2436
<212> TYPE: DNA
<213> ORGANISM: Homo Sapien

<400> SEQUENCE: 99

```
ggctgaccgt gctacattgc ctggaggaag cctaaggaac ccaggcatcc         50
agctgcccac gcctgagtcc aagattcttc ccaggaacac aaacgtagga        100
gacccacgct cctggaagca ccagccttta tctcttcacc ttcaagtccc        150
ctttctcaag aatcctctgt tctttgccct ctaaagtctt ggtacatcta        200
ggacccaggc atcttgcttt ccagccacaa agagacagat gaagatgcag        250
aaaggaaatg ttctccttat gtttggtcta ctattgcatt tagaagctgc        300
aacaaattcc aatgagacta gcacctctgc caacactgga tccagtgtga        350
tctccagtgg agccagcaca gccaccaact ctgggtccag tgtgacctcc        400
agtggggtca gcacagccac catctcaggg tccagcgtga cctccaatgg        450
ggtcagcata gtcaccaact ctgagttcca tacaacctcc agtgggatca        500
gcacagccac caactctgag ttcagcacag cgtccagtgg gatcagcata        550
gccaccaact ctgagtccag cacaacctcc agtggggcca gcacagccac        600
caactctgag tccagcacac cctccagtgg ggccagcaca gtcaccaact        650
ctgggtccag tgtgacctcc agtggagcca gcactgccac caactctgag        700
tccagcacag tgtccagtag ggccagcact gccaccaact ctgagtctag        750
cacactctcc agtggggcca gcacagccac caactctgac tccagcacaa        800
cctccagtgg ggctagcaca gccaccaact ctgagtccag cacaacctcc        850
agtggggcca gcacagccac caactctgag tccagcacag tgtccagtag        900
ggccagcact gccaccaact ctgagtccag cacaacctcc agtggggcca        950
gcacagccac caactctgag tccagaacga cctccaatgg ggctggcaca       1000
gccaccaact ctgagtccag cacgacctcc agtggggcca gcacagccac       1050
caactctgac tccagcacag tgtccagtgg ggccagcact gccaccaact       1100
```

-continued

| | |
|---|---|
| ctgagtccag cacgacctcc agtggggcca gcacagccac caactctgag | 1150 |
| tccagcacga cctccagtgg ggctagcaca gccaccaact ctgactccag | 1200 |
| cacaacctcc agtggggccg gcacagccac caactctgag tccagcacag | 1250 |
| tgtccagtgg gatcagcaca gtcaccaatt ctgagtccag cacaccctcc | 1300 |
| agtggggcca acacagccac caactctgag tccagtacga cctccagtgg | 1350 |
| ggccaacaca gccaccaact ctgagtccag cacagtgtcc agtggggcca | 1400 |
| gcactgccac caactctgag tccagcacaa cctccagtgg ggtcagcaca | 1450 |
| gccaccaact ctgagtccag cacaacctcc agtgggccta gcacagccac | 1500 |
| caactctgac tccagcacaa cctccagtga ggccagcaca gccaccaact | 1550 |
| ctgagtctag cacagtgtcc agtgggatca gcacagtcac caattctgag | 1600 |
| tccagcacaa cctccagtgg ggccaacaca gccaccaact ctgggtccag | 1650 |
| tgtgacctct gcaggctctg aacagcagc tctgactgga atgcacacaa | 1700 |
| cttcccatag tgcatctact gcagtgagtg aggcaaagcc tggtgggtcc | 1750 |
| ctggtgccgt gggaaatctt cctcatcacc tggtctcgg ttgtggcggc | 1800 |
| cgtggggctc tttgctgggc tcttcttctg tgtgagaaac agcctgtccc | 1850 |
| tgagaaacac ctttaacaca gctgtctacc accctcatgg cctcaaccat | 1900 |
| ggccttggtc caggccctgg agggaatcat ggagcccccc acaggcccag | 1950 |
| gtggagtcct aactggttct ggaggagacc agtatcatcg atagccatgg | 2000 |
| agatgagcgg gaggaacagc gggccctgag cagccccgga agcaagtgcc | 2050 |
| gcattcttca ggaaggaaga gacctgggca cccaagacct ggtttccttt | 2100 |
| cattcatccc aggagacccc tcccagcttt gtttgagatc ctgaaaatct | 2150 |
| tgaagaaggt attcctcacc tttcttgcct ttaccagaca ctggaaagag | 2200 |
| aatactatat tgctcattta gctaagaaat aaatacatct catctaacac | 2250 |
| acacgacaaa gagaagctgt gcttgcccccg gggtgggtat ctagctctga | 2300 |
| gatgaactca gttataggag aaaacctcca tgctggactc catctggcat | 2350 |
| tcaaaatctc cacagtaaaa tccaaagacc tcaaaaaaaa aaaaaaaaaa | 2400 |
| aaaaaaaaaa aaaaaaaaaa aaaaaaaaaa aaaaaa | 2436 |

<210> SEQ ID NO 100
<211> LENGTH: 596
<212> TYPE: PRT
<213> ORGANISM: Homo Sapien

<400> SEQUENCE: 100

```
Met Lys Met Gln Lys Gly Asn Val Leu Leu Met Phe Gly Leu Leu
 1               5                  10                  15

Leu His Leu Glu Ala Ala Thr Asn Ser Asn Glu Thr Ser Thr Ser
                20                  25                  30

Ala Asn Thr Gly Ser Ser Val Ile Ser Gly Ala Ser Thr Ala
                35                  40                  45

Thr Asn Ser Gly Ser Ser Val Thr Ser Ser Gly Val Ser Thr Ala
                50                  55                  60

Thr Ile Ser Gly Ser Ser Val Thr Ser Asn Gly Val Ser Ile Val
                65                  70                  75

Thr Asn Ser Glu Phe His Thr Ser Ser Gly Ile Ser Thr Ala
                80                  85                  90
```

-continued

```
Thr Asn Ser Glu Phe Ser Thr Ala Ser Ser Gly Ile Ser Ile Ala
                95                 100                 105
Thr Asn Ser Glu Ser Ser Thr Thr Ser Ser Gly Ala Ser Thr Ala
               110                 115                 120
Thr Asn Ser Glu Ser Ser Thr Pro Ser Ser Gly Ala Ser Thr Val
               125                 130                 135
Thr Asn Ser Gly Ser Ser Val Thr Ser Ser Gly Ala Ser Thr Ala
               140                 145                 150
Thr Asn Ser Glu Ser Ser Thr Val Ser Arg Ala Ser Thr Ala
               155                 160                 165
Thr Asn Ser Glu Ser Ser Thr Leu Ser Ser Gly Ala Ser Thr Ala
               170                 175                 180
Thr Asn Ser Asp Ser Ser Thr Thr Ser Ser Gly Ala Ser Thr Ala
               185                 190                 195
Thr Asn Ser Glu Ser Ser Thr Thr Ser Ser Gly Ala Ser Thr Ala
               200                 205                 210
Thr Asn Ser Glu Ser Ser Thr Val Ser Ser Arg Ala Ser Thr Ala
               215                 220                 225
Thr Asn Ser Glu Ser Ser Thr Thr Ser Ser Gly Ala Ser Thr Ala
               230                 235                 240
Thr Asn Ser Glu Ser Arg Thr Thr Ser Asn Gly Ala Gly Thr Ala
               245                 250                 255
Thr Asn Ser Glu Ser Ser Thr Thr Ser Ser Gly Ala Ser Thr Ala
               260                 265                 270
Thr Asn Ser Asp Ser Ser Thr Val Ser Ser Gly Ala Ser Thr Ala
               275                 280                 285
Thr Asn Ser Glu Ser Ser Thr Thr Ser Ser Gly Ala Ser Thr Ala
               290                 295                 300
Thr Asn Ser Glu Ser Ser Thr Thr Ser Ser Gly Ala Ser Thr Ala
               305                 310                 315
Thr Asn Ser Asp Ser Ser Thr Thr Ser Ser Gly Ala Gly Thr Ala
               320                 325                 330
Thr Asn Ser Glu Ser Ser Thr Val Ser Ser Gly Ile Ser Thr Val
               335                 340                 345
Thr Asn Ser Glu Ser Ser Thr Pro Ser Ser Gly Ala Asn Thr Ala
               350                 355                 360
Thr Asn Ser Glu Ser Ser Thr Thr Ser Ser Gly Ala Asn Thr Ala
               365                 370                 375
Thr Asn Ser Glu Ser Ser Thr Val Ser Ser Gly Ala Ser Thr Ala
               380                 385                 390
Thr Asn Ser Glu Ser Ser Thr Thr Ser Ser Gly Val Ser Thr Ala
               395                 400                 405
Thr Asn Ser Glu Ser Ser Thr Thr Ser Ser Gly Ala Ser Thr Ala
               410                 415                 420
Thr Asn Ser Asp Ser Ser Thr Thr Ser Ser Glu Ala Ser Thr Ala
               425                 430                 435
Thr Asn Ser Glu Ser Ser Thr Val Ser Ser Gly Ile Ser Thr Val
               440                 445                 450
Thr Asn Ser Glu Ser Ser Thr Thr Ser Ser Gly Ala Asn Thr Ala
               455                 460                 465
Thr Asn Ser Gly Ser Ser Val Thr Ser Ala Gly Ser Gly Thr Ala
               470                 475                 480
```

```
Ala Leu Thr Gly Met His Thr Thr Ser His Ser Ala Ser Thr Ala
            485                 490                 495
Val Ser Glu Ala Lys Pro Gly Gly Ser Leu Val Pro Trp Glu Ile
            500                 505                 510
Phe Leu Ile Thr Leu Val Ser Val Val Ala Ala Val Gly Leu Phe
            515                 520                 525
Ala Gly Leu Phe Phe Cys Val Arg Asn Ser Leu Ser Leu Arg Asn
            530                 535                 540
Thr Phe Asn Thr Ala Val Tyr His Pro His Gly Leu Asn His Gly
            545                 550                 555
Leu Gly Pro Gly Pro Gly Gly Asn His Gly Ala Pro His Arg Pro
            560                 565                 570
Arg Trp Ser Pro Asn Trp Phe Trp Arg Arg Pro Val Ser Ser Ile
            575                 580                 585
Ala Met Glu Met Ser Gly Arg Asn Ser Gly Pro
            590                 595

<210> SEQ ID NO 101
<211> LENGTH: 1728
<212> TYPE: DNA
<213> ORGANISM: Homo Sapien

<400> SEQUENCE: 101
ggccggacgc ctccgcgtta cgggatgaat taacggcggg ttccgcacgg              50
aggttgtgac ccctacggag ccccagcttg cccacgcacc ccactcggcg             100
tcgcgcggcg tgccctgctt gtcacaggtg ggaggctgga actatcaggc             150
tgaaaaacag agtgggtact ctcttctggg aagctggcaa caaatggatg             200
atgtgatata tgcattccag gggaagggaa attgtggtgc ttctgaaccc             250
atggtcaatt aacgaggcag tttctagcta ctgcacgtac ttcataaagc             300
aggactctaa aagctttgga atcatggtgt catggaaagg gatttacttt             350
atactgactc tgttttgggg aagcttttt ggaagcattt tcatgctgag              400
tcccttttta cctttgatgt tgtaaaccc atcttggtat cgctggatca              450
acaaccgcct tgtggcaaca tggctcaccc tacctgtggc attattggag             500
accatgtttg gtgtaaaagt gattataact ggggatgcat tgttcctgg              550 agaaagaagt gtcattatca tgaaccatcg acaagaatg gactggatgt              600 tcctgtggaa ttgcctgatg cgatatagct acctcagatt ggagaaaatt             650
tgcctcaaag cgagtctcaa aggtgttcct ggatttggtt gggccatgca             700
ggctgctgcc tatatcttca ttcataggaa atggaaggat gacaagagcc             750
atttcgaaga catgattgat tacttttgtg atattcacga accacttcaa             800
ctcctcatat tcccagaagg gactgatctc acagaaaaca gcaagtctcg             850
aagtaatgca tttgctgaaa aaaatggact tcagaaatat gaatatgttt             900
tacatccaag aactacaggc tttacttttg tggtagaccg tctaagagaa             950
ggtaagaacc ttgatgctgt ccatgatatc actgtggcgt atcctcacaa            1000
cattcctcaa tcagagaagc acctcctcca aggagacttt ccagggaaa             1050 tccactttca cgtccaccgg tatccaatag acaccctccc cacatccaag            1100
gaggaccttc aactctggtg ccacaaacgg tgggaagaga aagaagagag            1150
gctgcgttcc ttctatcaag gggagaagaa ttttatttt accggacaga            1200
```

| | |
|---|---|
| gtgtcattcc accttgcaag tctgaactca gggtccttgt ggtcaaattg | 1250 |
| ctctctatac tgtattggac cctgttcagc cctgcaatgt gcctactcat | 1300 |
| atatttgtac agtcttgtta agtggtattt tataatcacc attgtaatct | 1350 |
| ttgtgctgca agagagaata tttggtggac tggagatcat agaacttgca | 1400 |
| tgttaccgac ttttacacaa acagccacat ttaaattcaa agaaaaatga | 1450 |
| gtaagattat aaggtttgcc atgtgaaaac ctagagcata ttttggaaat | 1500 |
| gttctaaacc tttctaagct cagatgcatt tttgcatgac tatgtcgaat | 1550 |
| atttcttact gccatcatta tttgttaaag atattttgca cttaattttg | 1600 |
| tgggaaaaat attgctacaa ttttttttaa tctctgaatg taatttcgat | 1650 |
| actgtgtaca tagcagggag tgatcggggt gaaataactt gggccagaat | 1700 |
| attattaaac aatcatcagg cttttaaa | 1728 |

<210> SEQ ID NO 102
<211> LENGTH: 414
<212> TYPE: PRT
<213> ORGANISM: Homo Sapien

<400> SEQUENCE: 102

Met His Ser Arg Gly Arg Glu Ile Val Val Leu Leu Asn Pro Trp
 1               5                  10                  15

Ser Ile Asn Glu Ala Val Ser Ser Tyr Cys Thr Tyr Phe Ile Lys
                20                  25                  30

Gln Asp Ser Lys Ser Phe Gly Ile Met Val Ser Trp Lys Gly Ile
                35                  40                  45

Tyr Phe Ile Leu Thr Leu Phe Trp Gly Ser Phe Gly Ser Ile
                50                  55                  60

Phe Met Leu Ser Pro Phe Leu Pro Leu Met Phe Val Asn Pro Ser
                65                  70                  75

Trp Tyr Arg Trp Ile Asn Asn Arg Leu Val Ala Thr Trp Leu Thr
                80                  85                  90

Leu Pro Val Ala Leu Leu Glu Thr Met Phe Gly Val Lys Val Ile
                95                 100                 105

Ile Thr Gly Asp Ala Phe Val Pro Gly Glu Arg Ser Val Ile Ile
               110                 115                 120

Met Asn His Arg Thr Arg Met Asp Trp Met Phe Leu Trp Asn Cys
               125                 130                 135

Leu Met Arg Tyr Ser Tyr Leu Arg Leu Glu Lys Ile Cys Leu Lys
               140                 145                 150

Ala Ser Leu Lys Gly Val Pro Gly Phe Gly Trp Ala Met Gln Ala
               155                 160                 165

Ala Ala Tyr Ile Phe Ile His Arg Lys Trp Lys Asp Asp Lys Ser
               170                 175                 180

His Phe Glu Asp Met Ile Asp Tyr Phe Cys Asp Ile His Glu Pro
               185                 190                 195

Leu Gln Leu Leu Ile Phe Pro Glu Gly Thr Asp Leu Thr Glu Asn
               200                 205                 210

Ser Lys Ser Arg Ser Asn Ala Phe Ala Glu Lys Asn Gly Leu Gln
               215                 220                 225

Lys Tyr Glu Tyr Val Leu His Pro Arg Thr Thr Gly Phe Thr Phe
               230                 235                 240

-continued

```
Val Val Asp Arg Leu Arg Glu Gly Lys Asn Leu Asp Ala Val His
            245                 250                 255

Asp Ile Thr Val Ala Tyr Pro His Asn Ile Pro Gln Ser Glu Lys
        260                 265                 270

His Leu Leu Gln Gly Asp Phe Pro Arg Glu Ile His Phe His Val
    275                 280                 285

His Arg Tyr Pro Ile Asp Thr Leu Pro Thr Ser Lys Glu Asp Leu
290                 295                 300

Gln Leu Trp Cys His Lys Arg Trp Glu Glu Lys Glu Arg Leu
        305                 310                 315

Arg Ser Phe Tyr Gln Gly Glu Lys Asn Phe Tyr Phe Thr Gly Gln
            320                 325                 330

Ser Val Ile Pro Pro Cys Lys Ser Glu Leu Arg Val Leu Val Val
                335                 340                 345

Lys Leu Leu Ser Ile Leu Tyr Trp Thr Leu Phe Ser Pro Ala Met
                    350                 355                 360

Cys Leu Leu Ile Tyr Leu Tyr Ser Leu Val Lys Trp Tyr Phe Ile
                        365                 370                 375

Ile Thr Ile Val Ile Phe Val Leu Gln Glu Arg Ile Phe Gly Gly
                            380                 385                 390

Leu Glu Ile Ile Glu Leu Ala Cys Tyr Arg Leu Leu His Lys Gln
                                395                 400                 405

Pro His Leu Asn Ser Lys Lys Asn Glu
                410
```

<210> SEQ ID NO 103
<211> LENGTH: 2403
<212> TYPE: DNA
<213> ORGANISM: Homo Sapien

<400> SEQUENCE: 103

```
cggctcgagc ggctcgagtg aagagcctct ccacggctcc tgcgcctgag          50
acagctggcc tgacctccaa atcatccatc caccccctgct gtcatctgtt         100
ttcatagtgt gagatcaacc cacaggaata tccatggctt ttgtgctcat         150
tttggttctc agtttctacg agctggtgtc aggacagtgg caagtcactg         200
gaccgggcaa gtttgtccag gccttggtgg gggaggacgc cgtgttctcc         250
tgctccctct ttcctgagac cagtgcagag gctatggaag tgcggttctt         300
caggaatcag ttccatgctg tggtccacct ctacagagat ggggaagact         350
gggaatctaa gcagatgcca cagtatcgag ggagaactga gtttgtgaag         400
gactccattg cagggggggcg tgtctctcta aggctaaaaa acatcactcc         450
ctcggacatc ggcctgtatg ggtgctggtt cagttcccag atttacgatg         500
aggaggccac ctgggagctg cgggtggcag cactgggctc acttcctctc         550
atttccatcg tgggatatgt tgacggaggt atccagttac tctgcctgtc         600
ctcaggctgg ttcccccagc ccacagccaa gtggaaaggt ccacaaggac         650
aggatttgtc ttcagactcc agagcaaatg cagatgggta cagcctgtat         700
gatgtggaga tctccattat agtccaggaa aatgctggga gcatattgtg         750
ttccatccac cttgctgagc agagtcatga ggtggaatcc aaggtattga         800
taggagagac gttttttccag ccctcacctt ggcgcctggc ttctatttta         850
ctcgggttac tctgtggtgc cctgtgtggt gttgtcatgg ggatgataat         900
```

-continued

| | |
|---|---|
| tgttttcttc aaatccaaag ggaaaatcca ggcggaactg gactggagaa | 950 |
| gaaagcacgg acaggcagaa ttgagagacg cccggaaaca cgcagtggag | 1000 |
| gtgactctgg atccagagac ggctcacccg aagctctgcg tttctgatct | 1050 |
| gaaaactgta acccatagaa aagctcccca ggaggtgcct cactctgaga | 1100 |
| agagatttac aaggaagagt gtggtggctt ctcagggttt ccaagcaggg | 1150 |
| agacattact gggaggtgga cgtgggacaa aatgtagggt ggtatgtggg | 1200 |
| agtgtgtcgg gatgacgtag acaggggaa gaacaatgtg actttgtctc | 1250 |
| ccaacaatgg gtattgggtc ctcagactga caacagaaca tttgtatttc | 1300 |
| acattcaatc cccattttat cagcctcccc cccagcaccc ctcctacacg | 1350 |
| agtaggggtc ttcctggact atgaggtgg gaccatctcc ttcttcaata | 1400 |
| caaatgacca gtcccttatt tataccctgc tgacatgtca gtttgaaggc | 1450 |
| ttgttgagac cctatatcca gcatgcgatg tatgacgagg aaaaggggac | 1500 |
| tcccatattc atatgtccag tgtcctgggg atgagacaga gaagaccctg | 1550 |
| cttaaagggc cccacaccac agacccagac acagccaagg gagagtgctc | 1600 |
| ccgacaggtg gccccagctt cctctccgga gcctgcgcac agagagtcac | 1650 |
| gcccccact ctcctttagg gagctgaggt tcttctgccc tgagccctgc | 1700 |
| agcagcggca gtcacagctt ccagatgagg ggggattggc ctgaccctgt | 1750 |
| gggagtcaga agccatggct gccctgaagt ggggacggaa tagactcaca | 1800 |
| ttaggtttag tttgtgaaaa ctccatccag ctaagcgatc ttgaacaagt | 1850 |
| cacaacctcc caggctcctc atttgctagt cacggacagt gattcctgcc | 1900 |
| tcacaggtga agattaaaga gacaacgaat gtgaatcatg cttgcaggtt | 1950 |
| tgagggcaca gtgtttgcta atgatgtgtt tttatattat acattttccc | 2000 |
| accataaact ctgtttgctt attccacatt aatttacttt tctctatacc | 2050 |
| aaatcaccca tggaatagtt attgaacacc tgctttgtga ggctcaaaga | 2100 |
| ataaagagga ggtaggattt ttcactgatt ctataagccc agcattacct | 2150 |
| gataccaaaa ccaggcaaag aaaacagaag aagaggaagg aaaactacag | 2200 |
| gtccatatcc ctcattaaca cagacacaaa aattctaaat aaaattttaa | 2250 |
| caaattaaac taaacaatat atttaaagat gatatataac tactcagtgt | 2300 |
| ggtttgtccc acaaatgcag agttggttta atatttaaat atcaaccagt | 2350 |
| gtaattcagc acattaataa agtaaaaaag aaaaccataa aaaaaaaaa | 2400 |
| aaa | 2403 |

<210> SEQ ID NO 104
<211> LENGTH: 466
<212> TYPE: PRT
<213> ORGANISM: Homo Sapien

<400> SEQUENCE: 104

Met Ala Phe Val Leu Ile Leu Val Leu Ser Phe Tyr Glu Leu Val
1               5                   10                  15

Ser Gly Gln Trp Gln Val Thr Gly Pro Gly Lys Phe Val Gln Ala
                20                  25                  30

Leu Val Gly Glu Asp Ala Val Phe Ser Cys Ser Leu Phe Pro Glu
                35                  40                  45

-continued

Thr Ser Ala Glu Ala Met Glu Val Arg Phe Phe Arg Asn Gln Phe
            50                  55                  60

His Ala Val Val His Leu Tyr Arg Asp Gly Glu Asp Trp Glu Ser
            65                  70                  75

Lys Gln Met Pro Gln Tyr Arg Gly Arg Thr Glu Phe Val Lys Asp
            80                  85                  90

Ser Ile Ala Gly Arg Val Ser Leu Arg Leu Lys Asn Ile Thr
        95                 100                 105

Pro Ser Asp Ile Gly Leu Tyr Gly Cys Trp Phe Ser Ser Gln Ile
            110                 115                 120

Tyr Asp Glu Glu Ala Thr Trp Glu Leu Arg Val Ala Ala Leu Gly
            125                 130                 135

Ser Leu Pro Leu Ile Ser Ile Val Gly Tyr Val Asp Gly Gly Ile
            140                 145                 150

Gln Leu Leu Cys Leu Ser Ser Gly Trp Phe Pro Gln Pro Thr Ala
            155                 160                 165

Lys Trp Lys Gly Pro Gln Gly Gln Asp Leu Ser Ser Asp Ser Arg
            170                 175                 180

Ala Asn Ala Asp Gly Tyr Ser Leu Tyr Asp Val Glu Ile Ser Ile
            185                 190                 195

Ile Val Gln Glu Asn Ala Gly Ser Ile Leu Cys Ser Ile His Leu
            200                 205                 210

Ala Glu Gln Ser His Glu Val Glu Ser Lys Val Leu Ile Gly Glu
            215                 220                 225

Thr Phe Phe Gln Pro Ser Pro Trp Arg Leu Ala Ser Ile Leu Leu
            230                 235                 240

Gly Leu Leu Cys Gly Ala Leu Cys Gly Val Val Met Gly Met Ile
            245                 250                 255

Ile Val Phe Phe Lys Ser Lys Gly Lys Ile Gln Ala Glu Leu Asp
            260                 265                 270

Trp Arg Arg Lys His Gly Gln Ala Glu Leu Arg Asp Ala Arg Lys
            275                 280                 285

His Ala Val Glu Val Thr Leu Asp Pro Glu Thr Ala His Pro Lys
            290                 295                 300

Leu Cys Val Ser Asp Leu Lys Thr Val Thr His Arg Lys Ala Pro
            305                 310                 315

Gln Glu Val Pro His Ser Glu Lys Arg Phe Thr Arg Lys Ser Val
            320                 325                 330

Val Ala Ser Gln Gly Phe Gln Ala Gly Arg His Tyr Trp Glu Val
            335                 340                 345

Asp Val Gly Gln Asn Val Gly Trp Tyr Val Gly Val Cys Arg Asp
            350                 355                 360

Asp Val Asp Arg Gly Lys Asn Asn Val Thr Leu Ser Pro Asn Asn
            365                 370                 375

Gly Tyr Trp Val Leu Arg Leu Thr Thr Glu His Leu Tyr Phe Thr
            380                 385                 390

Phe Asn Pro His Phe Ile Ser Leu Pro Pro Ser Thr Pro Thr
            395                 400                 405

Arg Val Gly Val Phe Leu Asp Tyr Glu Gly Gly Thr Ile Ser Phe
            410                 415                 420

Phe Asn Thr Asn Asp Gln Ser Leu Ile Tyr Thr Leu Leu Thr Cys
            425                 430                 435

```
Gln Phe Glu Gly Leu Leu Arg Pro Tyr Ile Gln His Ala Met Tyr
                440                 445                 450

Asp Glu Glu Lys Gly Thr Pro Ile Phe Ile Cys Pro Val Ser Trp
            455                 460                 465

Gly

<210> SEQ ID NO 105
<211> LENGTH: 2103
<212> TYPE: DNA
<213> ORGANISM: Homo Sapien

<400> SEQUENCE: 105
ccttcacagg actcttcatt gctggttggc aatgatgtat cggccagatg          50
tggtgagggc taggaaaaga gtttgttggg aaccctgggt tatcggcctc         100
gtcatcttca tatccctgat tgtcctggca gtgtgcattg gactcactgt         150
tcattatgtg agatataatc aaaagaagac ctacaattac tatagcacat         200
tgtcatttac aactgacaaa ctatatgctg agtttggcag agaggcttct         250
aacaatttta cagaaatgag ccagagactt gaatcaatgg tgaaaaatgc         300
attttataaa tctccattaa gggaagaatt tgtcaagtct caggttatca         350
agttcagtca acagaagcat ggagtgttgg ctcatatgct gttgatttgt         400
agatttcact ctactgagga tcctgaaact gtagataaaa ttgttcaact         450
tgttttacat gaaaagctgc aagatgctgt aggacccccct aaagtagatc         500 ctcactcagt taaaattaaa aaaatcaaca agacagaaac agacagctat         550
ctaaaccatt gctgcggaac acgaagaagt aaaactctag gtcagagtct         600
caggatcgtt ggtgggacag aagtagaaga gggtgaatgg ccctggcagg         650
ctagcctgca gtgggatggg agtcatcgct gtggagcaac cttaattaat         700
gccacatggc ttgtgagtgc tgctcactgt tttacaacat ataagaaccc         750
tgccagatgg actgcttcct ttggagtaac aataaaacct tcgaaaatga         800 acgggtct ccggagaata attgtccatg aaaaatacaa acacccatca          850
catgactatg atatttctct tgcagagctt tctagccctg ttccctacac         900
aaatgcagta catagagttt gtctccctga tgcatcctat gagtttcaac         950
caggtgatgt gatgtttgtg acaggatttg gagcactgaa aaatgatggt        1000
tacagtcaaa atcatcttcg acaagcacag gtgactctca tagacgctac        1050
aacttgcaat gaacctcaag cttacaatga cgccataact cctagaatgt        1100
tatgtgctgg ctccttagaa ggaaaaacag atgcatgcca gggtgactct        1150
ggaggaccac tggttagttc agatgctaga gatatctggt accttgctgg        1200
aatagtgagc tggggagatg aatgtgcgaa acccaacaag cctggtgttt        1250
atactagagt tacggccttg cgggactgga ttacttcaaa aactggtatc        1300
taagagacaa aagcctcatg aacagataa cattttttt tgttttttgg         1350 gtgtggaggc cattttaga gatacagaat tggagaagac ttgcaaaaca         1400
gctagatttg actgatctca ataaactgtt tgcttgatgc atgtattttc        1450
ttcccagctc tgttccgcac gtaagcatcc tgcttctgcc agatcaactc        1500
tgtcatctgt gagcaatagt tgaaacttta tgtacataga gaaatagata        1550
atacaatatt acattacagc ctgtattcat ttgttctcta gaagttttgt        1600
```

-continued

```
cagaattttg acttgttgac ataaatttgt aatgcatata tacaatttga         1650
agcactcctt ttcttcagtt cctcagctcc tctcatttca gcaaatatcc         1700
attttcaagg tgcagaacaa ggagtgaaag aaaatataag aagaaaaaaa         1750
tcccctacat tttattggca cagaaaagta ttaggtgttt ttcttagtgg         1800
aatattagaa atgatcatat tcattatgaa aggtcaagca aagacagcag         1850
aataccaatc acttcatcat ttaggaagta tgggaactaa gttaaggaag         1900
tccagaaaga agccaagata tatccttatt ttcatttcca aacaactact         1950
atgataaatg tgaagaagat tctgttttttt tgtgacctat aataattata         2000
caaacttcat gcaatgtact tgttctaagc aaattaaagc aaatatttat         2050
ttaacattgt tactgaggat gtcaacatat aacaataaaa tataaatcac         2100
cca                                                            2103
```

<210> SEQ ID NO 106
<211> LENGTH: 423
<212> TYPE: PRT
<213> ORGANISM: Homo Sapien

<400> SEQUENCE: 106

```
Met Met Tyr Arg Pro Asp Val Val Arg Ala Arg Lys Arg Val Cys
  1               5                  10                  15

Trp Glu Pro Trp Val Ile Gly Leu Val Ile Phe Ile Ser Leu Ile
                 20                  25                  30

Val Leu Ala Val Cys Ile Gly Leu Thr Val His Tyr Val Arg Tyr
                 35                  40                  45

Asn Gln Lys Lys Thr Tyr Asn Tyr Tyr Ser Thr Leu Ser Phe Thr
                 50                  55                  60

Thr Asp Lys Leu Tyr Ala Glu Phe Gly Arg Glu Ala Ser Asn Asn
                 65                  70                  75

Phe Thr Glu Met Ser Gln Arg Leu Glu Ser Met Val Lys Asn Ala
                 80                  85                  90

Phe Tyr Lys Ser Pro Leu Arg Glu Glu Phe Val Lys Ser Gln Val
                 95                 100                 105

Ile Lys Phe Ser Gln Gln Lys His Gly Val Leu Ala His Met Leu
                110                 115                 120

Leu Ile Cys Arg Phe His Ser Thr Glu Asp Pro Glu Thr Val Asp
                125                 130                 135

Lys Ile Val Gln Leu Val Leu His Glu Lys Leu Gln Asp Ala Val
                140                 145                 150

Gly Pro Pro Lys Val Asp Pro His Ser Val Lys Ile Lys Lys Ile
                155                 160                 165

Asn Lys Thr Glu Thr Asp Ser Tyr Leu Asn His Cys Cys Gly Thr
                170                 175                 180

Arg Arg Ser Lys Thr Leu Gly Gln Ser Leu Arg Ile Val Gly Gly
                185                 190                 195

Thr Glu Val Glu Glu Gly Glu Trp Pro Trp Gln Ala Ser Leu Gln
                200                 205                 210

Trp Asp Gly Ser His Arg Cys Gly Ala Thr Leu Ile Asn Ala Thr
                215                 220                 225

Trp Leu Val Ser Ala Ala His Cys Phe Thr Thr Tyr Lys Asn Pro
                230                 235                 240
```

-continued

```
Ala Arg Trp Thr Ala Ser Phe Gly Val Thr Ile Lys Pro Ser Lys
            245                 250                 255
Met Lys Arg Gly Leu Arg Arg Ile Ile Val His Glu Lys Tyr Lys
            260                 265                 270
His Pro Ser His Asp Tyr Asp Ile Ser Leu Ala Glu Leu Ser Ser
            275                 280                 285
Pro Val Pro Tyr Thr Asn Ala Val His Arg Val Cys Leu Pro Asp
            290                 295                 300
Ala Ser Tyr Glu Phe Gln Pro Gly Asp Val Met Phe Val Thr Gly
            305                 310                 315
Phe Gly Ala Leu Lys Asn Asp Gly Tyr Ser Gln Asn His Leu Arg
            320                 325                 330
Gln Ala Gln Val Thr Leu Ile Asp Ala Thr Thr Cys Asn Glu Pro
            335                 340                 345
Gln Ala Tyr Asn Asp Ala Ile Thr Pro Arg Met Leu Cys Ala Gly
            350                 355                 360
Ser Leu Glu Gly Lys Thr Asp Ala Cys Gln Gly Asp Ser Gly Gly
            365                 370                 375
Pro Leu Val Ser Ser Asp Ala Arg Asp Ile Trp Tyr Leu Ala Gly
            380                 385                 390
Ile Val Ser Trp Gly Asp Glu Cys Ala Lys Pro Asn Lys Pro Gly
            395                 400                 405
Val Tyr Thr Arg Val Thr Ala Leu Arg Asp Trp Ile Thr Ser Lys
            410                 415                 420
Thr Gly Ile

<210> SEQ ID NO 107
<211> LENGTH: 2397
<212> TYPE: DNA
<213> ORGANISM: Homo Sapien

<400> SEQUENCE: 107
agagaaagaa gcgtctccag ctgaagccaa tgcagccctc cggctctccg         50
cgaagaagtt ccctgccccg atgagccccc gccgtgcgtc ccgactatc         100
cccaggcggg cgtggggcac cgggcccagc gccgacgatc gctgccgttt        150
tgcccttggg agtaggatgt ggtgaaagga tggggcttct cccttacggg        200
gctcacaatg ccagagaag attccgtgaa gtgtctgcgc tgcctgctct         250
acgccctcaa tctgctcttt tggttaatgt ccatcagtgt gttggcagtt        300
tctgcttgga tgagggacta cctaaataat gttctcactt taactgcaga        350
aacgagggta gaggaagcag tcattttgac ttactttcct gtggttcatc        400
cggtcatgat gctgtttgc tgtttcctta tcattgtggg gatgttagga         450
tattgtggaa cggtgaaaag aaatctgttg cttcttgcat ggtactttgg        500
aagtttgctt gtcattttct gtgtagaact ggcttgtggc gtttggacat        550
atgaacagga acttatggtt ccagtacaat ggtcagatat ggtcactttg        600
aaagccagga tgacaaatta tggattacct agatatcggt ggcttactca        650
tgcttggaat ttttttcaga gagagtttaa gtgctgtgga gtagtatatt        700
tcactgactg gttggaaatg acagagatgg actggccccc agattcctgc        750
tgtgttagag aattcccagg atgttccaaa caggcccacc aggaagatct        800
cagtgacctt tatcaagagg gttgtgggaa gaaaatgtat tccttttga         850
```

-continued

```
gaggaaccaa acaactgcag gtgctgaggt ttctgggaat ctccattggg        900
gtgacacaaa tcctggccat gattctcacc attactctgc tctgggctct        950
gtattatgat agaagggagc ctgggacaga ccaaatgatg tccttgaaga       1000
atgacaactc tcagcacctg tcatgtccct cagtagaact gttgaaacca       1050
agcctgtcaa gaatctttga acacacatcc atggcaaaca gctttaatac       1100
acactttgag atggaggagt tataaaaaga aatgtcacag aagaaaacca       1150
caaacttgtt ttattggact tgtgaatttt tgagtacata ctatgtgttt       1200
cagaaatatg tagaaataaa aatgttgcca taaaataaca cctaagcata       1250
tactattcta tgctttaaaa tgaggatgga aaagtttcat gtcataagtc       1300
accacctgga caataattga tgcccttaaa atgctgaaga cagatgtcat       1350
acccactgtg tagcctgtgt atgactttta ctgaacacag ttatgttttg       1400
aggcagcatg gtttgattag catttccgca tccatgcaaa cgagtcacat       1450
atggtgggac tggagccata gtaaaggttg atttacttct accaactagt       1500
atataaagta ctaattaaat gctaacatag gaagttagaa aatactaata       1550
acttttatta ctcagcgatc tattcttctg atgctaaata aattatatat       1600
cagaaaactt tcaatattgg tgactaccta aatgtgattt ttgctggtta       1650
ctaaatatt cttaccactt aaaagagcaa gctaacacat tgtcttaagc        1700
tgatcaggga tttttttgtat ataagtctgt gttaaatctg tataattcag      1750
tcgatttcag ttctgataat gttaagaata accattatga aaaggaaaat       1800
ttgtcctgta tagcatcatt attttttagcc tttcctgtta ataaagcttt      1850
actattctgt cctgggctta tattacacat ataactgtta tttaaatact       1900
taaccactaa ttttgaaaat taccagtgtg atacatagga atcattattc       1950
agaatgtagt ctggtcttta ggaagtatta ataagaaaat ttgcacataa       2000
cttagttgat tcagaaagga cttgtatgct gttttctcc caaatgaaga        2050
ctctttttga cactaaacac tttttaaaaa gcttatcttt gccttctcca       2100
aacaagaagc aatagtctcc aagtcaatat aaattctaca gaaaatagtg      2150
ttcttttttct ccagaaaaat gcttgtgaga atcattaaaa catgtgacaa      2200
tttagagatt ctttgttta tttcactgat taatatactg tggcaaatta       2250
cacagattat taaatttttt tacaagagta tagtatattt atttgaaatg      2300
ggaaaagtgc attttactgt attttgtgta ttttgtttat ttctcagaat       2350
atggaaagaa aattaaaatg tgtcaataaa tattttctag agagtaa         2397
```

<210> SEQ ID NO 108
<211> LENGTH: 305
<212> TYPE: PRT
<213> ORGANISM: Homo Sapien

<400> SEQUENCE: 108

```
Met Ala Arg Glu Asp Ser Val Lys Cys Leu Arg Cys Leu Leu Tyr
 1               5                  10                  15

Ala Leu Asn Leu Leu Phe Trp Leu Met Ser Ile Ser Val Leu Ala
                20                  25                  30

Val Ser Ala Trp Met Arg Asp Tyr Leu Asn Asn Val Leu Thr Leu
                35                  40                  45
```

-continued

Thr Ala Glu Thr Arg Val Glu Ala Val Ile Leu Thr Tyr Phe
            50                  55                  60

Pro Val Val His Pro Val Met Ile Ala Val Cys Cys Phe Leu Ile
            65                  70                  75

Ile Val Gly Met Leu Gly Tyr Cys Gly Thr Val Lys Arg Asn Leu
            80                  85                  90

Leu Leu Leu Ala Trp Tyr Phe Gly Ser Leu Val Ile Phe Cys
            95                 100                 105

Val Glu Leu Ala Cys Gly Val Trp Thr Tyr Glu Gln Glu Leu Met
           110                 115                 120

Val Pro Val Gln Trp Ser Asp Met Val Thr Leu Lys Ala Arg Met
           125                 130                 135

Thr Asn Tyr Gly Leu Pro Arg Tyr Arg Trp Leu Thr His Ala Trp
           140                 145                 150

Asn Phe Phe Gln Arg Glu Phe Lys Cys Cys Gly Val Val Tyr Phe
           155                 160                 165

Thr Asp Trp Leu Glu Met Thr Glu Met Asp Trp Pro Pro Asp Ser
           170                 175                 180

Cys Cys Val Arg Glu Phe Pro Gly Cys Ser Lys Gln Ala His Gln
           185                 190                 195

Glu Asp Leu Ser Asp Leu Tyr Gln Glu Gly Cys Gly Lys Lys Met
           200                 205                 210

Tyr Ser Phe Leu Arg Gly Thr Lys Gln Leu Gln Val Leu Arg Phe
           215                 220                 225

Leu Gly Ile Ser Ile Gly Val Thr Gln Ile Leu Ala Met Ile Leu
           230                 235                 240

Thr Ile Thr Leu Leu Trp Ala Leu Tyr Tyr Asp Arg Arg Glu Pro
           245                 250                 255

Gly Thr Asp Gln Met Met Ser Leu Lys Asn Asp Asn Ser Gln His
           260                 265                 270

Leu Ser Cys Pro Ser Val Glu Leu Leu Lys Pro Ser Leu Ser Arg
           275                 280                 285

Ile Phe Glu His Thr Ser Met Ala Asn Ser Phe Asn Thr His Phe
           290                 295                 300

Glu Met Glu Glu Leu
           305

<210> SEQ ID NO 109
<211> LENGTH: 2339
<212> TYPE: DNA
<213> ORGANISM: Homo Sapien

<400> SEQUENCE: 109
ccaaggccag agctgtggac acctatccc actcatcctc atcctcttcc         50
tctgataaag cccctaccag tgctgataaa gtctttctcg tgagagccta        100
gaggccttaa aaaaaaagt gcttgaaaga aaggggaca aaggaacacc          150 agtattaaga ggattttcca gtgtttctgg cagttggtcc agaaggatgc        200
ctccattcct gcttctcacc tgcctcttca tcacaggcac ctccgtgtca        250
cccgtggccc tagatccttg ttctgcttac atcagcctga atgagccctg        300
gaggaacact gaccaccagt tggatgagtc tcaaggtcct cctctatgtg        350
acaaccatgt gaatggggag tggtaccact tcacgggcat ggcgggagat        400

-continued

| | |
|---|---|
| gccatgccta ccttctgcat accagaaaac cactgtggaa cccacgcacc | 450 |
| tgtctggctc aatggcagcc accccctaga aggcgacggc attgtgcaac | 500 |
| gccaggcttg tgccagcttc aatgggaact gctgtctctg aacaccacg | 550 |
| gtggaagtca aggcttgccc tggaggctac tatgtgtatc gtctgaccaa | 600 |
| gcccagcgtc tgcttccacg tctactgtgg tcatttttat gacatctgcg | 650 |
| acgaggactg ccatggcagc tgctcagata ccagcgagtg cacatgcgct | 700 |
| ccaggaactg tgctaggccc tgacaggcag acatgctttg atgaaaatga | 750 |
| atgtgagcaa acaacggtg gctgcagtga gatctgtgtg aacctcaaaa | 800 |
| actcctaccg ctgtgagtgt ggggttggcc gtgtgctaag aagtgatggc | 850 |
| aagacttgtg aagacgttga aggatgccac aataacaatg gtggctgcag | 900 |
| ccactcttgc cttggatctg agaaaggcta ccagtgtgaa tgtcccgggg | 950 |
| gcctggtgct gtctgaggat aaccacactt gccaagtccc tgtgttgtgc | 1000 |
| aaatcaaatg ccattgaagt gaacatcccc agggagctgg ttggtggcct | 1050 |
| ggagctcttc ctgaccaaca cctcctgccg aggagtgtcc aacggcaccc | 1100 |
| atgtcaacat cctcttctct ctcaagacat gtggtacagt ggtcgatgtg | 1150 |
| gtgaatgaca agattgtggc cagcaacctc gtgacaggtc tacccaagca | 1200 |
| gaccccgggg agcagcgggg acttcatcat ccgaaccagc aagctgctga | 1250 |
| tcccggtgac ctgcgagttt ccacgcctgt acaccatttc tgaaggatac | 1300 |
| gttcccaacc ttcgaaactc cccactggaa atcatgagcc gaaatcatgg | 1350 |
| gatcttccca ttcactctgg agatcttcaa ggacaatgag tttgaagagc | 1400 |
| cttaccggga agctctgccc accctcaagc ttcgtgactc cctctacttt | 1450 |
| ggcattgagc ccgtggtgca cgtgagcggc ttggaaaagct tggtggagag | 1500 |
| ctgctttgcc accccccacct ccaagatcga cgaggtcctg aaatactacc | 1550 |
| tcatccggga tggctgtgtt tcagatgact cggtaaagca gtacacatcc | 1600 |
| cgggatcacc tagcaaagca cttccaggtc cctgtcttca gtttgtggg | 1650 |
| caaagaccac aaggaagtgt ttctgcactg ccgggttctt gtctgtggag | 1700 |
| tgttggacga gcgttccgc tgtgcccagg gttgccaccg gcgaatgcgt | 1750 |
| cgtggggcag gaggagagga ctcagccggt ctacagggcc agacgctaac | 1800 |
| aggcggcccg atccgcatcg actgggagga ctagttcgta gccataccts | 1850 |
| gagtccctgc attggacggc tctgctcttt ggagcttctc cccccaccgc | 1900 |
| cctctaagaa catctgccaa cagctgggtt cagacttcac actgtgagtt | 1950 |
| cagactccca gcaccaactc actctgattc tggtccattc agtgggcaca | 2000 |
| ggtcacagca ctgctgaaca atgtggcctg ggtggggttt catctttcta | 2050 |
| gggttgaaaa ctaaactgtc cacccagaaa gacactcacc ccatttccct | 2100 |
| catttctttc ctcacttaa atacctcgtg tatggtgcaa tcagaccaca | 2150 |
| aaatcagaag ctgggtataa tatttcaagt tacaaaccct agaaaaatta | 2200 |
| aacagttact gaaattatga cttaaatacc caatgactcc ttaaatatgt | 2250 |
| aaattatagt tataccttga aatttcaatt caaatgcaga ctaattatag | 2300 |
| ggaatttgga agtgtatcaa taaaacagta tataatttt | 2339 |

<210> SEQ ID NO 110
<211> LENGTH: 545
<212> TYPE: PRT
<213> ORGANISM: Homo Sapien

<400> SEQUENCE: 110

```
Met Pro Pro Phe Leu Leu Leu Thr Cys Leu Phe Ile Thr Gly Thr
 1               5                  10                  15

Ser Val Ser Pro Val Ala Leu Asp Pro Cys Ser Ala Tyr Ile Ser
             20                  25                  30

Leu Asn Glu Pro Trp Arg Asn Thr Asp His Gln Leu Asp Glu Ser
             35                  40                  45

Gln Gly Pro Pro Leu Cys Asp Asn His Val Asn Gly Glu Trp Tyr
             50                  55                  60

His Phe Thr Gly Met Ala Gly Asp Ala Met Pro Thr Phe Cys Ile
             65                  70                  75

Pro Glu Asn His Cys Gly Thr His Ala Pro Val Trp Leu Asn Gly
             80                  85                  90

Ser His Pro Leu Glu Gly Asp Gly Ile Val Gln Arg Gln Ala Cys
             95                 100                 105

Ala Ser Phe Asn Gly Asn Cys Cys Leu Trp Asn Thr Thr Val Glu
            110                 115                 120

Val Lys Ala Cys Pro Gly Gly Tyr Tyr Val Tyr Arg Leu Thr Lys
            125                 130                 135

Pro Ser Val Cys Phe His Val Tyr Cys Gly His Phe Tyr Asp Ile
            140                 145                 150

Cys Asp Glu Asp Cys His Gly Ser Cys Ser Asp Thr Ser Glu Cys
            155                 160                 165

Thr Cys Ala Pro Gly Thr Val Leu Gly Pro Asp Arg Gln Thr Cys
            170                 175                 180

Phe Asp Glu Asn Glu Cys Glu Gln Asn Asn Gly Gly Cys Ser Glu
            185                 190                 195

Ile Cys Val Asn Leu Lys Asn Ser Tyr Arg Cys Glu Cys Gly Val
            200                 205                 210

Gly Arg Val Leu Arg Ser Asp Gly Lys Thr Cys Glu Asp Val Glu
            215                 220                 225

Gly Cys His Asn Asn Asn Gly Gly Cys Ser His Ser Cys Leu Gly
            230                 235                 240

Ser Glu Lys Gly Tyr Gln Cys Glu Cys Pro Arg Gly Leu Val Leu
            245                 250                 255

Ser Glu Asp Asn His Thr Cys Gln Val Pro Val Leu Cys Lys Ser
            260                 265                 270

Asn Ala Ile Glu Val Asn Ile Pro Arg Glu Leu Val Gly Gly Leu
            275                 280                 285

Glu Leu Phe Leu Thr Asn Thr Ser Cys Arg Gly Val Ser Asn Gly
            290                 295                 300

Thr His Val Asn Ile Leu Phe Ser Leu Lys Thr Cys Gly Thr Val
            305                 310                 315

Val Asp Val Val Asn Asp Lys Ile Val Ala Ser Asn Leu Val Thr
            320                 325                 330

Gly Leu Pro Lys Gln Thr Pro Gly Ser Ser Gly Asp Phe Ile Ile
            335                 340                 345

Arg Thr Ser Lys Leu Leu Ile Pro Val Thr Cys Glu Phe Pro Arg
            350                 355                 360
```

-continued

```
Leu Tyr Thr Ile Ser Glu Gly Tyr Val Pro Asn Leu Arg Asn Ser
            365                 370                 375
Pro Leu Glu Ile Met Ser Arg Asn His Gly Ile Phe Pro Phe Thr
            380                 385                 390
Leu Glu Ile Phe Lys Asp Asn Glu Phe Glu Pro Tyr Arg Glu
            395                 400                 405
Ala Leu Pro Thr Leu Lys Leu Arg Asp Ser Leu Tyr Phe Gly Ile
            410                 415                 420
Glu Pro Val Val His Val Ser Gly Leu Glu Ser Leu Val Glu Ser
            425                 430                 435
Cys Phe Ala Thr Pro Thr Ser Lys Ile Asp Glu Val Leu Lys Tyr
            440                 445                 450
Tyr Leu Ile Arg Asp Gly Cys Val Ser Asp Asp Ser Val Lys Gln
            455                 460                 465
Tyr Thr Ser Arg Asp His Leu Ala Lys His Phe Gln Val Pro Val
            470                 475                 480
Phe Lys Phe Val Gly Lys Asp His Lys Glu Val Phe Leu His Cys
            485                 490                 495
Arg Val Leu Val Cys Gly Val Leu Asp Glu Arg Ser Arg Cys Ala
            500                 505                 510
Gln Gly Cys His Arg Arg Met Arg Arg Gly Ala Gly Gly Glu Asp
            515                 520                 525
Ser Ala Gly Leu Gln Gly Gln Thr Leu Thr Gly Gly Pro Ile Arg
            530                 535                 540
Ile Asp Trp Glu Asp
            545

<210> SEQ ID NO 111
<211> LENGTH: 2063
<212> TYPE: DNA
<213> ORGANISM: Homo Sapien

<400> SEQUENCE: 111
gagagaggca gcagcttgct cagcggacaa ggatgctggg cgtgagggac           50
caaggcctgc cctgcactcg ggcctcctcc agccagtgct gaccagggac          100
ttctgacctg ctggccagcc aggacctgtg tggggaggcc ctcctgctgc          150
cttggggtga caatctcagc tccaggctac agggagaccg ggaggatcac          200
agagccagca tgttacagga tcctgacagt gatcaacctc tgaacagcct          250
cgatgtcaaa cccctgcgca aacccgtat ccccatggag accttcagaa           300
aggtggggat cccatcatc atagcactac tgagcctggc gagtatcatc           350
attgtggttg tcctcatcaa ggtgattctg ataaatact acttcctctg           400 cgggcagcct ctccacttca tcccgaggaa gcagctgtgt gacggagagc          450
tggactgtcc cttgggggag gacgaggagc actgtgtcaa gagcttcccc          500
gaagggcctg cagtggcagt ccgcctctcc aaggaccgat ccacactgca          550
ggtgctggac tcggccacag ggaactggtt ctctgcctgt ttcgacaact          600
tcacagaagc tctcgctgag acagcctgta ggcagatggg ctacagcaga          650
gctgtggaga ttgccccaga ccaggatctg atgttgttg aaatcacaga           700 aaacagccag gagcttcgca tgcggaactc aagtgggccc tgtctctcag          750
gctccctggt ctccctgcac tgtcttgcct gtgggaagag cctgaagacc          800
```

-continued

| | |
|---|---|
| cccgtgtgg tgggtgggga ggaggcctct gtggattctt ggccttggca | 850 |
| ggtcagcatc cagtacgaca acagcacgt ctgtggaggg agcatcctgg | 900 |
| accccactg gtcctcacg gcagcccact gcttcaggaa ataccgat | 950 |
| gtgttcaact ggaaggtgcg ggcaggctca gacaaactgg gcagcttccc | 1000 |
| atccctggct gtggccaaga tcatcatcat tgaattcaac cccatgtacc | 1050 |
| ccaaagacaa tgacatcgcc ctcatgaagc tgcagttccc actcactttc | 1100 |
| tcaggcacag tcaggcccat ctgtctgccc ttctttgatg aggagctcac | 1150 |
| tccagccacc ccactctgga tcattggatg gggctttacg aagcagaatg | 1200 |
| gagggaagat gtctgacata ctgctgcagg cgtcagtcca ggtcattgac | 1250 |
| agcacacggt gcaatgcaga cgatgcgtac caggggaag tcaccgagaa | 1300 |
| gatgatgtgt gcaggcatcc cggaaggggg tgtggacacc tgccagggtg | 1350 |
| acagtggtgg gccctgatg taccaatctg accagtggca tgtggtgggc | 1400 |
| atcgttagct ggggctatgg ctgcgggggc ccgagcaccc aggagtata | 1450 |
| caccaaggtc tcagcctatc tcaactggat ctacaatgtc tggaaggctg | 1500 |
| agctgtaatg ctgctgcccc tttgcagtgc tgggagccgc ttccttcctg | 1550 |
| ccctgcccac ctgggatcc cccaaagtca gacacagagc aagagtcccc | 1600 |
| ttgggtacac ccctctgccc acagcctcag catttcttgg agcagcaaag | 1650 |
| ggcctcaatt cctgtaagag accctcgcag cccagaggcg cccagaggaa | 1700 |
| gtcagcagcc ctagctcggc cacacttggt gctcccagca tcccagggag | 1750 |
| agacacagcc cactgaacaa ggtctcaggg gtattgctaa gccaagaagg | 1800 |
| aactttccca cactactgaa tggaagcagg ctgtcttgta aaagcccaga | 1850 |
| tcactgtggg ctggagagga gaaggaaagg gtctgcgcca gccctgtccg | 1900 |
| tcttcacca tccccaagcc tactagagca agaaaccagt tgtaatataa | 1950 |
| aatgcactgc cctactgttg gtatgactac cgttacctac tgttgtcatt | 2000 |
| gttattacag ctatggccac tattattaaa gagctgtgta acatctctgg | 2050 |
| caaaaaaaaa aaa | 2063 |

<210> SEQ ID NO 112
<211> LENGTH: 432
<212> TYPE: PRT
<213> ORGANISM: Homo Sapien

<400> SEQUENCE: 112

```
Met Leu Gln Asp Pro Asp Ser Asp Gln Pro Leu Asn Ser Leu Asp
 1               5                  10                  15

Val Lys Pro Leu Arg Lys Pro Arg Ile Pro Met Glu Thr Phe Arg
                20                  25                  30

Lys Val Gly Ile Pro Ile Ile Ala Leu Leu Ser Leu Ala Ser
                35                  40                  45

Ile Ile Ile Val Val Val Leu Ile Lys Val Ile Leu Asp Lys Tyr
                50                  55                  60

Tyr Phe Leu Cys Gly Gln Pro Leu His Phe Ile Pro Arg Lys Gln
                65                  70                  75

Leu Cys Asp Gly Glu Leu Asp Cys Pro Leu Gly Glu Asp Glu
                80                  85                  90

His Cys Val Lys Ser Phe Pro Glu Gly Pro Ala Val Ala Val Arg
```

```
                95                  100                 105
Leu Ser Lys Asp Arg Ser Thr Leu Gln Val Leu Asp Ser Ala Thr
            110                 115                 120
Gly Asn Trp Phe Ser Ala Cys Phe Asp Asn Phe Thr Glu Ala Leu
            125                 130                 135
Ala Glu Thr Ala Cys Arg Gln Met Gly Tyr Ser Arg Ala Val Glu
            140                 145                 150
Ile Gly Pro Asp Gln Asp Leu Asp Val Glu Ile Thr Glu Asn
            155                 160                 165
Ser Gln Glu Leu Arg Met Arg Asn Ser Ser Gly Pro Cys Leu Ser
            170                 175                 180
Gly Ser Leu Val Ser Leu His Cys Leu Ala Cys Gly Lys Ser Leu
            185                 190                 195
Lys Thr Pro Arg Val Val Gly Gly Glu Ala Ser Val Asp Ser
            200                 205                 210
Trp Pro Trp Gln Val Ser Ile Gln Tyr Asp Lys Gln His Val Cys
            215                 220                 225
Gly Gly Ser Ile Leu Asp Pro His Trp Val Leu Thr Ala Ala His
            230                 235                 240
Cys Phe Arg Lys His Thr Asp Val Phe Asn Trp Lys Val Arg Ala
            245                 250                 255
Gly Ser Asp Lys Leu Gly Ser Phe Pro Ser Leu Ala Val Ala Lys
            260                 265                 270
Ile Ile Ile Ile Glu Phe Asn Pro Met Tyr Pro Lys Asp Asn Asp
            275                 280                 285
Ile Ala Leu Met Lys Leu Gln Phe Pro Leu Thr Phe Ser Gly Thr
            290                 295                 300
Val Arg Pro Ile Cys Leu Pro Phe Phe Asp Glu Glu Leu Thr Pro
            305                 310                 315
Ala Thr Pro Leu Trp Ile Ile Gly Trp Gly Phe Thr Lys Gln Asn
            320                 325                 330
Gly Gly Lys Met Ser Asp Ile Leu Leu Gln Ala Ser Val Gln Val
            335                 340                 345
Ile Asp Ser Thr Arg Cys Asn Ala Asp Asp Ala Tyr Gln Gly Glu
            350                 355                 360
Val Thr Glu Lys Met Met Cys Ala Gly Ile Pro Glu Gly Gly Val
            365                 370                 375
Asp Thr Cys Gln Gly Asp Ser Gly Gly Pro Leu Met Tyr Gln Ser
            380                 385                 390
Asp Gln Trp His Val Val Gly Ile Val Ser Trp Gly Tyr Gly Cys
            395                 400                 405
Gly Gly Pro Ser Thr Pro Gly Val Tyr Thr Lys Val Ser Ala Tyr
            410                 415                 420
Leu Asn Trp Ile Tyr Asn Val Trp Lys Ala Glu Leu
            425                 430

<210> SEQ ID NO 113
<211> LENGTH: 1768
<212> TYPE: DNA
<213> ORGANISM: Homo Sapien

<400> SEQUENCE: 113
ggctggactg gaactcctgg tcccaagtga tccacccgcc tcagcctccc              50
aaggtgctgt gattataggt gtaagccacc gtgtctggcc tctgaacaac             100
```

```
tttttcagca actaaaaaag ccacaggagt tgaactgcta ggattctgac         150
tatgctgtgg tggctagtgc tcctactcct acctacatta aaatctgttt         200
tttgttctct tgtaactagc ctttaccttc ctaacacaga ggatctgtca         250
ctgtggctct ggcccaaacc tgaccttcac tctggaacga aacagaggt          300
ttctacccac accgtcccct cgaagccggg acagcctca ccttgctggc          350
ctctcgctgg agcagtgccc tcaccaactg tctcacgtct ggaggcactg         400
actcgggcag tgcaggtagc tgagcctctt ggtagctgcg gctttcaagg         450
tgggccttgc cctggccgta aagggattg acaagcccga agatttcata          500
ggcgatggct cccactgccc aggcatcagc cttgctgtag tcaatcactg         550
ccctggggcc aggacgggcc gtggacacct gctcagaagc agtgggtgag         600
acatcacgct gcccgcccat ctaacctttt catgtcctgc acatcacctg         650
atccatgggc taatctgaac tctgtcccaa ggaacccaga gcttgagtga         700
gctgtggctc agaccagaa ggggtctgct tagaccacct ggtttatgtg          750
acaggacttg cattctcctg aacatgagg gaacgccgga ggaaagcaaa          800
gtggcaggga aggaacttgt gccaaattat gggtcagaaa agatggaggt         850
gttgggttat cacaaggcat cgagtctcct gcattcagtg gacatgtggg         900
ggaagggctg ccgatggcgc atgacacact cgggactcac ctctgggcc          950
atcagacagc cgtttccgcc ccgatccacg taccagctgc tgaagggcaa         1000
ctgcaggccg atgctctcat cagccaggca gcagccaaaa tctgcgatca         1050
ccagccaggg gcagccgtct gggaaggagc aagcaaagtg accatttctc         1100
ctccctcct tccctctgag aggccctcct atgtccctac taaagccacc          1150
agcaagacat agctgacagg ggctaatggc tcagtgttgg cccaggaggt         1200
cagcaaggcc tgagagctga tcagaagggc ctgctgtgcg aacacggaaa         1250
tgcctccagt aagcacaggc tgcaaaatcc ccaggcaaag gactgtgtgg         1300
ctcaatttaa atcatgttct agtaattgga gctgtcccca agaccaaagg         1350
agctagagct tggttcaaat gatctccaag ggcccttata ccccaggaga         1400
ctttgatttg aatttgaaac cccaaatcca aacctaagaa ccaggtgcat         1450
taagaatcag ttattgccgg gtgtggtggc ctgtaatgcc acatttttgg         1500
gaggccgagg cgggtagatc acctgaggtc aggagttcaa gaccagcctg         1550
gccaacatgg tgaaaccccct gtctctacta aaaatacaaa aaaactagcc         1600
aggcatggtg gtgtgtgcct gtatcccagc tactcgggag gctgagacag         1650
gagaattact tgaacctggg aggtgaagga ggctgagaca ggagaatcac         1700
ttcagcctga gcaacacagc gagactctgt ctcagaaaaa ataaaaaaag         1750
aattatggtt atttgtaa                                            1768
```

<210> SEQ ID NO 114
<211> LENGTH: 109
<212> TYPE: PRT
<213> ORGANISM: Homo Sapien

<400> SEQUENCE: 114

Met Leu Trp Trp Leu Val Leu Leu Leu Pro Thr Leu Lys Ser
1               5                   10                  15

```
Val Phe Cys Ser Leu Val Thr Ser Leu Tyr Leu Pro Asn Thr Glu
            20                  25                  30

Asp Leu Ser Leu Trp Leu Trp Pro Lys Pro Asp Leu His Ser Gly
            35                  40                  45

Thr Arg Thr Glu Val Ser Thr His Thr Val Pro Ser Lys Pro Gly
            50                  55                  60

Thr Ala Ser Pro Cys Trp Pro Leu Ala Gly Ala Val Pro Ser Pro
            65                  70                  75

Thr Val Ser Arg Leu Glu Ala Leu Thr Arg Ala Val Gln Val Ala
            80                  85                  90

Glu Pro Leu Gly Ser Cys Gly Phe Gln Gly Gly Pro Cys Pro Gly
            95                 100                 105

Arg Arg Arg Asp

<210> SEQ ID NO 115
<211> LENGTH: 1197
<212> TYPE: DNA
<213> ORGANISM: Homo Sapien

<400> SEQUENCE: 115
cagcagtggt ctctcagtcc tctcaaagca aggaaagagt actgtgtgct              50
gagagaccat ggcaaagaat cctccagaga attgtgaaga ctgtcacatt             100
ctaaatgcag aagcttttaa atccaagaaa atatgtaaat cacttaagat             150
ttgtggactg gtgtttggta tcctggccct aactctaatt gtcctgtttt             200
gggggagcaa gcacttctgg ccggaggtac ccaaaaaagc ctatgacatg             250
gagcacactt tctacagcaa tggagagaag aagaagattc acatggaaat             300
tgatcctgtg accagaactg aaatattcag aagcggaaat ggcactgatg             350
aaacattgga agtgcacgac tttaaaaacg atacactgg catctacttc              400 gtgggtcttc aaaaatgttt tatcaaaact cagattaaag tgattcctga             450
attttctgaa ccagaagagg aaatagatga gaatgaagaa attaccacaa             500 cttttctttga acagtcagtg atttgggtcc cagcagaaaa gcctattgaa            550
aaccgagatt tcttaaaaa ttccaaaatt ctggagattt gtgataacgt              600
gaccatgtat tggatcaatc ccactctaat atcagtttct gagttacaag             650
actttgagga ggagggagaa gatcttcact ttcctgccaa cgaaaaaaaa             700
gggattgaac aaaatgaaca gtgggtggtc cctcaagtga agtagagaa               750 gacccgtcac gccagacaag caagtgagga agaacttcca ataaatgact             800
atactgaaaa tggaatagaa tttgatccca tgctggatga gagaggttat             850
tgttgtattt actgccgtcg aggcaaccgc tattgccgcc gcgtctgtga             900
acctttacta ggctactacc catatccata ctgctaccaa ggaggacgag             950
tcatctgtcg tgtcatcatg ccttgtaact ggtgggtggc ccgcatgctg            1000
gggagggtct aataggaggt ttgagctcaa atgcttaaac tgctggcaac            1050
atataataaa tgcatgctat tcaatgaatt tctgcctatg aggcatctgg            1100
cccctggtag ccagctctcc agaattactt gtaggtaatt cctctcttca            1150
tgttctaata aacttctaca ttatcaccaa aaaaaaaaaa aaaaaaa               1197

<210> SEQ ID NO 116
```

```
<211> LENGTH: 317
<212> TYPE: PRT
<213> ORGANISM: Homo Sapien

<400> SEQUENCE: 116

Met Ala Lys Asn Pro Pro Glu Asn Cys Glu Asp Cys His Ile Leu
 1               5                  10                  15

Asn Ala Glu Ala Phe Lys Ser Lys Lys Ile Cys Lys Ser Leu Lys
                20                  25                  30

Ile Cys Gly Leu Val Phe Gly Ile Leu Ala Leu Thr Leu Ile Val
                35                  40                  45

Leu Phe Trp Gly Ser Lys His Phe Trp Pro Glu Val Pro Lys Lys
                50                  55                  60

Ala Tyr Asp Met Glu His Thr Phe Tyr Ser Asn Gly Glu Lys Lys
                65                  70                  75

Lys Ile Tyr Met Glu Ile Asp Pro Val Thr Arg Thr Glu Ile Phe
                80                  85                  90

Arg Ser Gly Asn Gly Thr Asp Glu Thr Leu Glu Val His Asp Phe
                95                 100                 105

Lys Asn Gly Tyr Thr Gly Ile Tyr Phe Val Gly Leu Gln Lys Cys
               110                 115                 120

Phe Ile Lys Thr Gln Ile Lys Val Ile Pro Glu Phe Ser Glu Pro
               125                 130                 135

Glu Glu Glu Ile Asp Glu Asn Glu Glu Ile Thr Thr Thr Phe Phe
               140                 145                 150

Glu Gln Ser Val Ile Trp Val Pro Ala Glu Lys Pro Ile Glu Asn
               155                 160                 165

Arg Asp Phe Leu Lys Asn Ser Lys Ile Leu Glu Ile Cys Asp Asn
               170                 175                 180

Val Thr Met Tyr Trp Ile Asn Pro Thr Leu Ile Ser Val Ser Glu
               185                 190                 195

Leu Gln Asp Phe Glu Glu Gly Glu Asp Leu His Phe Pro Ala
               200                 205                 210

Asn Glu Lys Lys Gly Ile Glu Gln Asn Glu Gln Trp Val Pro
               215                 220                 225

Gln Val Lys Val Glu Lys Thr Arg His Ala Arg Gln Ala Ser Glu
               230                 235                 240

Glu Glu Leu Pro Ile Asn Asp Tyr Thr Glu Asn Gly Ile Glu Phe
               245                 250                 255

Asp Pro Met Leu Asp Glu Arg Gly Tyr Cys Cys Ile Tyr Cys Arg
               260                 265                 270

Arg Gly Asn Arg Tyr Cys Arg Arg Val Cys Glu Pro Leu Leu Gly
               275                 280                 285

Tyr Tyr Pro Tyr Pro Tyr Cys Tyr Gln Gly Gly Arg Val Ile Cys
               290                 295                 300

Arg Val Ile Met Pro Cys Asn Trp Trp Val Ala Arg Met Leu Gly
               305                 310                 315

Arg Val

<210> SEQ ID NO 117
<211> LENGTH: 2121
<212> TYPE: DNA
<213> ORGANISM: Homo Sapien

<400> SEQUENCE: 117
```

-continued

| | |
|---|---|
| gagctcccct caggagcgcg ttagcttcac accttcggca gcaggagggc | 50 |
| ggcagcttct cgcaggcggc agggcgggcg gccaggatca tgtccaccac | 100 |
| cacatgccaa gtggtggcgt tcctcctgtc catcctgggg ctggccggct | 150 |
| gcatcgcggc caccgggatg gacatgtgga gcacccagga cctgtacgac | 200 |
| aaccccgtca cctccgtgtt ccagtacgaa gggctctgga ggagctgcgt | 250 |
| gaggcagagt tcaggcttca ccgaatgcag gccctatttc accatcctgg | 300 |
| gacttccagc catgctgcag gcagtgcgag ccctgatgat cgtaggcatc | 350 |
| gtcctgggtg ccattggcct cctggtatcc atctttgccc tgaaatgcat | 400 |
| ccgcattggc agcatggagg actctgccaa agccaacatg acactgacct | 450 |
| ccgggatcat gttcattgtc tcaggtcttt gtgcaattgc tggagtgtct | 500 |
| gtgtttgcca acatgctggt gactaacttc tggatgtcca cagctaacat | 550 |
| gtacaccggc atgggtggga tggtgcagac tgttcagacc aggtacacat | 600 |
| ttggtgcggc tctgttcgtg ggctgggtcg ctggaggcct cacactaatt | 650 |
| gggggtgtga tgatgtgcat cgcctgccgg ggcctggcac cagaagaaac | 700 |
| caactacaaa gccgtttctt atcatgcctc aggccacagt gttgcctaca | 750 |
| agcctggagc cttcaaggcc agcactggct ttgggtccaa caccaaaaac | 800 |
| aagaagatat acgatggagg tgcccgcaca gaggacgagg tacaatctta | 850 |
| tccttccaag cacgactatg tgtaatgctc taagacctct cagcacgggc | 900 |
| ggaagaaact cccggagagc tcacccaaaa acaaggaga tcccatctag | 950 |
| atttcttctt gcttttgact cacagctgga agttagaaaa gcctcgattt | 1000 |
| catctttgga gaggccaaat ggtcttagcc tcagtctctg tctctaaata | 1050 |
| ttccaccata aaacagctga gttatttatg aattagaggc tatagctcac | 1100 |
| attttcaatc ctctatttct tttttttaaat ataactttct actctgatga | 1150 |
| gagaatgtgg ttttaatctc tctctcacat tttgatgatt tagacagact | 1200 |
| cccccctcttc ctcctagtca ataaacccat tgatgatcta tttcccagct | 1250 |
| tatccccaag aaaactttttg aaaggaaaga gtagacccaa agatgttatt | 1300 |
| ttctgctgtt tgaattttgt ctccccaccc ccaacttggc tagtaataaa | 1350 |
| cacttactga agaagaagca ataagagaaa gatatttgta atctctccag | 1400 |
| cccatgatct cggttttctt acactgtgat cttaaaagtt accaaaccaa | 1450 |
| agtcattttc agtttgaggc aaccaaacct ttctactgct gttgacatct | 1500 |
| tcttattaca gcaacaccat tctaggagtt tcctgagctc tccactggag | 1550 |
| tcctctttct gtcgcgggtc agaaattgtc cctagatgaa tgagaaaatt | 1600 |
| atttttttta atttaagtcc taaatatagt taaaataaat aatgttttag | 1650 |
| taaaatgata cactatctct gtgaaatagc ctcaccccta catgtggata | 1700 |
| gaaggaaatg aaaaaataat tgctttgaca ttgtctatat ggtactttgt | 1750 |
| aaagtcatgc ttaagtacaa attccatgaa aagctcacac ctgtaatcct | 1800 |
| agcactttgg gaggctgagg aggaaggatc acttgagccc agaagttcga | 1850 |
| gactagcctg gcaacatgg agaagccctg tctctacaaa atacagagag | 1900 |
| aaaaaatcag ccagtcatgg tggcatacac ctgtagtccc agcattccgg | 1950 |
| gaggctgagg tgggaggatc acttgagccc agggaggttg gggctgcagt | 2000 |

```
gagccatgat cacaccactg cactccagcc aggtgacata gcgagatcct           2050
gtctaaaaaa ataaaaaata aataatggaa cacagcaagt cctaggaagt           2100
aggttaaaac taattcttta a                                          2121
```

<210> SEQ ID NO 118
<211> LENGTH: 261
<212> TYPE: PRT
<213> ORGANISM: Homo Sapien

<400> SEQUENCE: 118

```
Met Ser Thr Thr Thr Cys Gln Val Val Ala Phe Leu Leu Ser Ile
  1               5                  10                  15

Leu Gly Leu Ala Gly Cys Ile Ala Ala Thr Gly Met Asp Met Trp
                 20                  25                  30

Ser Thr Gln Asp Leu Tyr Asp Asn Pro Val Thr Ser Val Phe Gln
                 35                  40                  45

Tyr Glu Gly Leu Trp Arg Ser Cys Val Arg Gln Ser Ser Gly Phe
                 50                  55                  60

Thr Glu Cys Arg Pro Tyr Phe Thr Ile Leu Gly Leu Pro Ala Met
                 65                  70                  75

Leu Gln Ala Val Arg Ala Leu Met Ile Val Gly Ile Val Leu Gly
                 80                  85                  90

Ala Ile Gly Leu Leu Val Ser Ile Phe Ala Leu Lys Cys Ile Arg
                 95                 100                 105

Ile Gly Ser Met Glu Asp Ser Ala Lys Ala Asn Met Thr Leu Thr
                110                 115                 120

Ser Gly Ile Met Phe Ile Val Ser Gly Leu Cys Ala Ile Ala Gly
                125                 130                 135

Val Ser Val Phe Ala Asn Met Leu Val Thr Asn Phe Trp Met Ser
                140                 145                 150

Thr Ala Asn Met Tyr Thr Gly Met Gly Gly Met Val Gln Thr Val
                155                 160                 165

Gln Thr Arg Tyr Thr Phe Gly Ala Ala Leu Phe Val Gly Trp Val
                170                 175                 180

Ala Gly Gly Leu Thr Leu Ile Gly Gly Val Met Met Cys Ile Ala
                185                 190                 195

Cys Arg Gly Leu Ala Pro Glu Glu Thr Asn Tyr Lys Ala Val Ser
                200                 205                 210

Tyr His Ala Ser Gly His Ser Val Ala Tyr Lys Pro Gly Gly Phe
                215                 220                 225

Lys Ala Ser Thr Gly Phe Gly Ser Asn Thr Lys Asn Lys Lys Ile
                230                 235                 240

Tyr Asp Gly Gly Ala Arg Thr Glu Asp Glu Val Gln Ser Tyr Pro
                245                 250                 255

Ser Lys His Asp Tyr Val
                260
```

<210> SEQ ID NO 119
<211> LENGTH: 2010
<212> TYPE: DNA
<213> ORGANISM: Homo Sapien

<400> SEQUENCE: 119

```
ggaaaaactg ttctcttctg tggcacagag aaccctgctt caaagcagaa            50
```

-continued

| | |
|---|---|
| gtagcagttc cggagtccag ctggctaaaa ctcatcccag aggataatgg | 100 |
| caacccatgc cttagaaatc gctgggctgt tccttggtgg tgttggaatg | 150 |
| gtgggcacag tggctgtcac tgtcatgcct cagtggagag tgtcggcctt | 200 |
| cattgaaaac aacatcgtgg ttttttgaaaa cttctgggaa ggactgtgga | 250 |
| tgaattgcgt gaggcaggct aacatcagga tgcagtgcaa aatctatgat | 300 |
| tccctgctgg ctctttctcc ggacctacag gcagccagag gactgatgtg | 350 |
| tgctgcttcc gtgatgtcct tcttggcttt catgatggcc atccttggca | 400 |
| tgaaatgcac caggtgcacg ggggacaatg agaaggtgaa ggctcacatt | 450 |
| ctgctgacgg ctggaatcat cttcatcatc acgggcatgg tggtgctcat | 500 |
| ccctgtgagc tgggttgcca atgccatcat cagagatttc tataactcaa | 550 |
| tagtgaatgt tgcccaaaaa cgtgagcttg agaagctctc ctacttagga | 600 |
| tggaccacgg cactggtgct gattgttgga ggagctctgt tctgctgcgt | 650 |
| tttttgttgc aacgaaaaga gcagtagcta cagatactcg ataccttccc | 700 |
| atcgcacaac ccaaaaaagt tatcacaccg gaaagaagtc accgagcgtc | 750 |
| tactccagaa gtcagtatgt gtagttgtgt atgtttttttt aactttacta | 800 |
| taaagccatg caaatgacaa aaatctatat tactttctca aaatggaccc | 850 |
| caaagaaact ttgatttact gttcttaact gcctaatctt aattacagga | 900 |
| actgtgcatc agctatttat gattctataa gctatttcag cagaatgaga | 950 |
| tattaaaccc aatgctttga ttgttctaga aagtatagta atttgttttc | 1000 |
| taaggtggtt caagcatcta ctcttttat catttacttc aaaatgacat | 1050 |
| tgctaaagac tgcattattt tactactgta atttctccac gacatagcat | 1100 |
| tatgtacata gatgagtgta acatttatat ctcacataga gacatgctta | 1150 |
| tatggtttta tttaaaatga aatgccagtc cattacactg aataaataga | 1200 |
| actcaactat tgcttttcag ggaaatcatg gataggggtg aagaaggtta | 1250 |
| ctattaattg tttaaaaaca gcttagggat taatgtcctc catttataat | 1300 |
| gaagattaaa atgaaggctt taatcagcat tgtaaaggaa attgaatggc | 1350 |
| tttctgatat gctgtttttt agcctaggag ttagaaatcc taacttcttt | 1400 |
| atcctcttct cccagaggct ttttttttct tgtgtattaa attaacattt | 1450 |
| ttaaaacgca gatattttgt caagggcttt tgcattcaaa ctgcttttcc | 1500 |
| agggctatac tcagaagaaa gataaaagtg tgatctaaga aaaagtgatg | 1550 |
| gttttaggaa agtgaaaata ttttttgtttt tgtatttgaa gaagaatgat | 1600 |
| gcattttgac aagaaatcat atatgtatgg atatattttta ataagtattt | 1650 |
| gagtacagac tttgaggttt catcaatata aataaaagag cagaaaaata | 1700 |
| tgtcttggtt ttcatttgct taccaaaaaa acaacaacaa aaaagttgt | 1750 |
| cctttgagaa cttcacctgc tcctatgtgg gtacctgagt caaaattgtc | 1800 |
| attttttgttc tgtgaaaaat aaatttcctt cttgtaccat ttctgtttag | 1850 |
| ttttactaaa atctgtaaat actgtatttt tctgtttatt ccaaatttga | 1900 |
| tgaaactgac aatccaattt gaaagtttgt gtcgacgtct gtctagctta | 1950 |
| aatgaatgtg ttctatttgc tttatacatt tatattaata aattgtacat | 2000 |
| ttttctaatt | 2010 |

<210> SEQ ID NO 120
<211> LENGTH: 225
<212> TYPE: PRT
<213> ORGANISM: Homo Sapien

<400> SEQUENCE: 120

```
Met Ala Thr His Ala Leu Glu Ile Ala Gly Leu Phe Leu Gly Gly
  1               5                  10                  15

Val Gly Met Val Gly Thr Val Ala Val Thr Val Met Pro Gln Trp
                 20                  25                  30

Arg Val Ser Ala Phe Ile Glu Asn Asn Ile Val Val Phe Glu Asn
             35                  40                  45

Phe Trp Glu Gly Leu Trp Met Asn Cys Val Arg Gln Ala Asn Ile
         50                  55                  60

Arg Met Gln Cys Lys Ile Tyr Asp Ser Leu Leu Ala Leu Ser Pro
     65                  70                  75

Asp Leu Gln Ala Ala Arg Gly Leu Met Cys Ala Ala Ser Val Met
 80                  85                  90

Ser Phe Leu Ala Phe Met Met Ala Ile Leu Gly Met Lys Cys Thr
             95                 100                 105

Arg Cys Thr Gly Asp Asn Glu Lys Val Lys Ala His Ile Leu Leu
        110                 115                 120

Thr Ala Gly Ile Ile Phe Ile Ile Thr Gly Met Val Val Leu Ile
    125                 130                 135

Pro Val Ser Trp Val Ala Asn Ala Ile Ile Arg Asp Phe Tyr Asn
    140                 145                 150

Ser Ile Val Asn Val Ala Gln Lys Arg Glu Leu Gly Glu Ala Leu
    155                 160                 165

Tyr Leu Gly Trp Thr Thr Ala Leu Val Leu Ile Val Gly Gly Ala
    170                 175                 180

Leu Phe Cys Cys Val Phe Cys Cys Asn Glu Lys Ser Ser Ser Tyr
    185                 190                 195

Arg Tyr Ser Ile Pro Ser His Arg Thr Thr Gln Lys Ser Tyr His
    200                 205                 210

Thr Gly Lys Lys Ser Pro Ser Val Tyr Ser Arg Ser Gln Tyr Val
    215                 220                 225
```

<210> SEQ ID NO 121
<211> LENGTH: 1257
<212> TYPE: DNA
<213> ORGANISM: Homo Sapien

<400> SEQUENCE: 121

| | | |
|---|---|---|
| ggagagaggc gcgcgggtga aaggcgcatt gatgcagcct gcggcggcct | 50 |
| cggagcgcgg cggagccaga cgctgaccac gttcctctcc tcggtctcct | 100 |
| ccgcctccag ctccgcgctg cccggcagcc gggagccatg cgaccccagg | 150 |
| gccccgccgc ctcccgcag cggctccgcg gcctcctgct gctcctgctg | 200 |
| ctgcagctgc ccgcgccgtc gagcgcctct gagatcccca aggggaagca | 250 |
| aaaggcgcag ctccggcaga gggaggtggt ggacctgtat aatggaatgt | 300 |
| gcttacaagg gccagcagga gtgcctggtc gagacgggag ccctggggcc | 350 |
| aatgttattc cgggtacacc tgggatccca gtcggatg gattcaaagg | 400 |
| agaaaagggg gaatgtctga gggaaagctt tgaggagtcc tggacaccca | 450 |

-continued

```
actacaagca gtgttcatgg agttcattga attatggcat agatcttggg        500
aaaattgcgg agtgtacatt tacaaagatg cgttcaaata gtgctctaag        550
agttttgttc agtggctcac ttcggctaaa atgcagaaat gcatgctgtc        600
agcgttggta tttcacattc aatggagctg aatgttcagg acctcttccc        650
attgaagcta taatttattt ggaccaagga agccctgaaa tgaattcaac        700
aattaatatt catcgcactt cttctgtgga aggactttgt gaaggaattg        750
gtgctggatt agtggatgtt gctatctggg ttggcacttg ttcagattac        800
ccaaaaggag atgcttctac tggatggaat tcagtttctc gcatcattat        850
tgaagaacta ccaaaataaa tgctttaatt ttcatttgct acctcttttt        900
ttattatgcc ttggaatggt tcacttaaat gacattttaa ataagtttat        950
gtatacatct gaatgaaaag caaagctaaa tatgtttaca gaccaaagtg       1000
tgatttcaca ctgtttttaa atctagcatt attcattttg cttcaatcaa       1050
aagtggtttc aatattttttt ttagttggtt agaatacttt cttcatagtc       1100
acattctctc aacctataat ttggaatatt gttgtggtct tttgttttttt       1150 ctcttagtat agcattttta aaaaaatata aaagctacca atctttgtac       1200
aatttgtaaa tgttaagaat ttttttttata tctgttaaat aaaaattatt       1250
tccaaca                                                      1257
```

<210> SEQ ID NO 122
<211> LENGTH: 243
<212> TYPE: PRT
<213> ORGANISM: Homo Sapien

<400> SEQUENCE: 122

```
Met Arg Pro Gln Gly Pro Ala Ala Ser Pro Gln Arg Leu Arg Gly
  1               5                  10                  15

Leu Leu Leu Leu Leu Leu Leu Gln Leu Pro Ala Pro Ser Ser Ala
                 20                  25                  30

Ser Glu Ile Pro Lys Gly Lys Gln Lys Ala Gln Leu Arg Gln Arg
                 35                  40                  45

Glu Val Val Asp Leu Tyr Asn Gly Met Cys Leu Gln Gly Pro Ala
                 50                  55                  60

Gly Val Pro Gly Arg Asp Gly Ser Pro Gly Ala Asn Val Ile Pro
                 65                  70                  75

Gly Thr Pro Gly Ile Pro Gly Arg Asp Gly Phe Lys Gly Glu Lys
                 80                  85                  90

Gly Glu Cys Leu Arg Glu Ser Phe Glu Glu Ser Trp Thr Pro Asn
                 95                 100                 105

Tyr Lys Gln Cys Ser Trp Ser Ser Leu Asn Tyr Gly Ile Asp Leu
                110                 115                 120

Gly Lys Ile Ala Glu Cys Thr Phe Thr Lys Met Arg Ser Asn Ser
                125                 130                 135

Ala Leu Arg Val Leu Phe Ser Gly Ser Leu Arg Leu Lys Cys Arg
                140                 145                 150

Asn Ala Cys Cys Gln Arg Trp Tyr Phe Thr Phe Asn Gly Ala Glu
                155                 160                 165

Cys Ser Gly Pro Leu Pro Ile Glu Ala Ile Ile Tyr Leu Asp Gln
                170                 175                 180
```

-continued

```
Gly Ser Pro Glu Met Asn Ser Thr Ile Asn Ile His Arg Thr Ser
            185                 190                 195

Ser Val Glu Gly Leu Cys Glu Gly Ile Gly Ala Gly Leu Val Asp
            200                 205                 210

Val Ala Ile Trp Val Gly Thr Cys Ser Asp Tyr Pro Lys Gly Asp
            215                 220                 225

Ala Ser Thr Gly Trp Asn Ser Val Ser Arg Ile Ile Ile Glu Glu
            230                 235                 240

Leu Pro Lys

<210> SEQ ID NO 123
<211> LENGTH: 2379
<212> TYPE: DNA
<213> ORGANISM: Homo Sapien

<400> SEQUENCE: 123
```

| | | | |
|---|---|---|---|
| gctgagcgtg tgcgcggtac gggctctcc tgccttctgg gctccaacgc | | | 50 |
| agctctgtgg ctgaactggg tgctcatcac gggaactgct gggctatgga | | | 100 |
| atacagatgt ggcagctcag gtagccccaa attgcctgga agaatacatc | | | 150 |
| atgttttcg ataagaagaa attgtaggat ccagttttt ttttaaccgc | | | 200 |
| ccctcccca ccccaaaa aaactgtaaa gatgcaaaaa cgtaatatcc | | | 250 |
| atgaagatcc tattacctag gaagattttg atgttttgct gcgaatgcgg | | | 300 |
| tgttgggatt tatttgttct tggagtgttc tgcgtggctg caaagaata | | | 350 |
| atgttccaaa atcggtccat ctcccaaggg gtccaatttt tcttcctggg | | | 400 |
| tgtcagcgag ccctgactca ctacagtgca gctgacaggg gctgtcatgc | | | 450 |
| aactggcccc taagccaaag caaaagacct aaggacgacc tttgaacaat | | | 500 |
| acaaaggatg ggtttcaatg taattaggct actgagcgga tcagctgtag | | | 550 |
| cactggttat agccccact gtcttactga caatgctttc ttctgccgaa | | | 600 |
| cgaggatgcc ctaagggctg taggtgtgaa ggcaaaatgg tatattgtga | | | 650 |
| atctcagaaa ttacaggaga taccctcaag tatatctgct ggttgcttag | | | 700 |
| gtttgtccct tcgctataac agccttcaaa aacttaagta taatcaattt | | | 750 |
| aaagggctca accagctcac ctggctatac cttgaccata accatatcag | | | 800 |
| caatattgac gaaaatgctt ttaatggaat acgcagactc aaagagctga | | | 850 |
| ttcttagttc caatagaatc tcctattttc ttaacaatac cttcagacct | | | 900 |
| gtgacaaatt tacggaactt ggatctgtcc tataatcagc tgcattctct | | | 950 |
| gggatctgaa cagtttcggg gcttgcggaa gctgctgagt ttacatttac | | | 1000 |
| ggtctaactc cctgagaacc atccctgtgc gaatattcca agactgccgc | | | 1050 |
| aacctggaac ttttggacct gggatataac cggatccgaa gtttagccag | | | 1100 |
| gaatgtcttt gctggcatga tcagactcaa agaacttcac ctggagcaca | | | 1150 |
| atcaatttc caagctcaac ctggccttt ttccaaggtt ggtcagcctt | | | 1200 |
| cagaaccttt acttgcagtg aataaaatc agtgtcatag acagaccat | | | 1250 |
| gtcctggacc tggagctcct tacaaaggct tgatttatca ggcaatgaga | | | 1300 |
| tcgaagcttt cagtggaccc agtgttttcc agtgtgtccc gaatctgcag | | | 1350 |
| cgcctcaacc tggattccaa caagctcaca tttattggtc aagagatttt | | | 1400 |
| ggattcttgg atatccctca atgacatcag tcttgctggg aatatatggg | | | 1450 |

```
aatgcagcag aaatatttgc tcccttgtaa actggctgaa aagttttaaa      1500
ggtctaaggg agaatacaat tatctgtgcc agtcccaaag agctgcaagg      1550
agtaaatgtg atcgatgcag tgaagaacta cagcatctgt ggcaaaagta      1600
ctacagagag gtttgatctg gccagggctc tcccaaagcc gacgtttaag      1650
cccaagctcc ccaggccgaa gcatgagagc aaaccccctt tgcccccgac      1700
ggtgggagcc acagagcccg gcccagagac cgatgctgac gccgagcaca      1750
tctctttcca taaaatcatc gcgggcagcg tggcgctttt cctgtccgtg      1800
ctcgtcatcc tgctggttat ctacgtgtca tggaagcggt accctgcgag      1850
catgaagcag ctgcagcagc gctccctcat gcgaaggcac aggaaaaaga      1900
aaagacagtc cctaaagcaa atgactccca gcacccagga attttatgta      1950
gattataaac ccaccaacac ggagaccagc gagatgctgc tgaatgggac      2000
gggaccctgc acctataaca aatcgggctc cagggagtgt gaggtatgaa      2050
ccattgtgat aaaagagct cttaaaagct gggaaataag tggtgcttta       2100
ttgaactctg gtgactatca agggaacgcg atgcccccccc tccccttccc    2150 tctccctctc actttggtgg caagatcctt ccttgtccgt tttagtgcat      2200
tcataatact ggtcattttc ctctcataca taatcaaccc attgaaattt      2250
aaataccaca atcaatgtga agcttgaact ccggtttaat ataataccta      2300
ttgtataaga ccctttactg attccattaa tgtcgcattt gttttaagat      2350
aaaacttctt tcataggtaa aaaaaaaaa                             2379
```

```
<210> SEQ ID NO 124
<211> LENGTH: 513
<212> TYPE: PRT
<213> ORGANISM: Homo Sapien

<400> SEQUENCE: 124

Met Gly Phe Asn Val Ile Arg Leu Leu Ser Gly Ser Ala Val Ala
  1               5                  10                  15

Leu Val Ile Ala Pro Thr Val Leu Leu Thr Met Leu Ser Ser Ala
                 20                  25                  30

Glu Arg Gly Cys Pro Lys Gly Cys Arg Cys Glu Gly Lys Met Val
                 35                  40                  45

Tyr Cys Glu Ser Gln Lys Leu Gln Glu Ile Pro Ser Ser Ile Ser
                 50                  55                  60

Ala Gly Cys Leu Gly Leu Ser Leu Arg Tyr Asn Ser Leu Gln Lys
                 65                  70                  75

Leu Lys Tyr Asn Gln Phe Lys Gly Leu Asn Gln Leu Thr Trp Leu
                 80                  85                  90

Tyr Leu Asp His Asn His Ile Ser Asn Ile Asp Glu Asn Ala Phe
                 95                 100                 105

Asn Gly Ile Arg Arg Leu Lys Glu Leu Ile Leu Ser Ser Asn Arg
                110                 115                 120

Ile Ser Tyr Phe Leu Asn Asn Thr Phe Arg Pro Val Thr Asn Leu
                125                 130                 135

Arg Asn Leu Asp Leu Ser Tyr Asn Gln Leu His Ser Leu Gly Ser
                140                 145                 150

Glu Gln Phe Arg Gly Leu Arg Lys Leu Leu Ser Leu His Leu Arg
                155                 160                 165
```

-continued

```
Ser Asn Ser Leu Arg Thr Ile Pro Val Arg Ile Phe Gln Asp Cys
            170                 175                 180

Arg Asn Leu Glu Leu Leu Asp Leu Gly Tyr Asn Arg Ile Arg Ser
            185                 190                 195

Leu Ala Arg Asn Val Phe Ala Gly Met Ile Arg Leu Lys Glu Leu
            200                 205                 210

His Leu Glu His Asn Gln Phe Ser Lys Leu Asn Leu Ala Leu Phe
            215                 220                 225

Pro Arg Leu Val Ser Leu Gln Asn Leu Tyr Leu Gln Trp Asn Lys
            230                 235                 240

Ile Ser Val Ile Gly Gln Thr Met Ser Trp Thr Trp Ser Ser Leu
            245                 250                 255

Gln Arg Leu Asp Leu Ser Gly Asn Glu Ile Glu Ala Phe Ser Gly
            260                 265                 270

Pro Ser Val Phe Gln Cys Val Pro Asn Leu Gln Arg Leu Asn Leu
            275                 280                 285

Asp Ser Asn Lys Leu Thr Phe Ile Gly Gln Glu Ile Leu Asp Ser
            290                 295                 300

Trp Ile Ser Leu Asn Asp Ile Ser Leu Ala Gly Asn Ile Trp Glu
            305                 310                 315

Cys Ser Arg Asn Ile Cys Ser Leu Val Asn Trp Leu Lys Ser Phe
            320                 325                 330

Lys Gly Leu Arg Glu Asn Thr Ile Ile Cys Ala Ser Pro Lys Glu
            335                 340                 345

Leu Gln Gly Val Asn Val Ile Asp Ala Val Lys Asn Tyr Ser Ile
            350                 355                 360

Cys Gly Lys Ser Thr Thr Glu Arg Phe Asp Leu Ala Arg Ala Leu
            365                 370                 375

Pro Lys Pro Thr Phe Lys Pro Lys Leu Pro Arg Pro Lys His Glu
            380                 385                 390

Ser Lys Pro Pro Leu Pro Pro Thr Val Gly Ala Thr Glu Pro Gly
            395                 400                 405

Pro Glu Thr Asp Ala Asp Ala Glu His Ile Ser Phe His Lys Ile
            410                 415                 420

Ile Ala Gly Ser Val Ala Leu Phe Leu Ser Val Leu Val Ile Leu
            425                 430                 435

Leu Val Ile Tyr Val Ser Trp Lys Arg Tyr Pro Ala Ser Met Lys
            440                 445                 450

Gln Leu Gln Gln Arg Ser Leu Met Arg His Arg Lys Lys Lys
            455                 460                 465

Arg Gln Ser Leu Lys Gln Met Thr Pro Ser Thr Gln Glu Phe Tyr
            470                 475                 480

Val Asp Tyr Lys Pro Thr Asn Thr Glu Thr Ser Glu Met Leu Leu
            485                 490                 495

Asn Gly Thr Gly Pro Cys Thr Tyr Asn Lys Ser Gly Ser Arg Glu
            500                 505                 510

Cys Glu Val
```

<210> SEQ ID NO 125
<211> LENGTH: 998
<212> TYPE: DNA
<213> ORGANISM: Homo Sapien

<400> SEQUENCE: 125

-continued

| | |
|---|---|
| ccgttatcgt cttgcgctac tgctgaatgt ccgtcccgga ggaggaggag | 50 |
| aggcttttgc cgctgaccca gagatggccc cgagcgagca aattcctact | 100 |
| gtccggctgc gcggctaccg tggccgagct agcaaccttt ccctggatc | 150 |
| tcacaaaaac tcgactccaa atgcaaggag aagcagctct tgctcggttg | 200 |
| ggagacggtg caagagaatc tgcccctat aggggaatgg tgcgcacagc | 250 |
| cctagggatc attgaagagg aaggctttct aaagctttgg caaggagtga | 300 |
| cacccgccat ttacagacac gtagtgtatt ctggaggtcg aatggtcaca | 350 |
| tatgaacatc tccgagaggt tgtgtttggc aaaagtgaag atgagcatta | 400 |
| tccccttttgg aaatcagtca ttggagggat gatggctggt gttattggcc | 450 |
| agttttttagc caatccaact gacctagtga aggttcagat gcaaatggaa | 500 |
| ggaaaaagga aactggaagg aaaaccattg cgatttcgtg gtgtacatca | 550 |
| tgcatttgca aaaatcttag ctgaaggagg aatacgaggg ctttgggcag | 600 |
| gctgggtacc caatatacaa agagcagcac tggtgaatat gggagattta | 650 |
| accacttatg atacagtgaa acactacttg gtattgaata caccacttga | 700 |
| ggacaatatc atgactcacg gtttatcaag tttatgttct ggactggtag | 750 |
| cttctattct gggaacacca gccgatgtca tcaaaagcag aataatgaat | 800 |
| caaccacgag ataaacaagg aaggggactt ttgtataaat catcgactga | 850 |
| ctgcttgatt caggctgttc aaggtgaagg attcatgagt ctatataaag | 900 |
| gcttttacc atcttggctg agaatgaccc cttggtcaat ggtgttctgg | 950 |
| cttacttatg aaaaaatcag agagatgagt ggagtcagtc cattttaa | 998 |

<210> SEQ ID NO 126
<211> LENGTH: 323
<212> TYPE: PRT
<213> ORGANISM: Homo Sapien

<400> SEQUENCE: 126

```
Met Ser Val Pro Glu Glu Glu Arg Leu Leu Pro Leu Thr Gln
  1               5                  10                  15

Arg Trp Pro Arg Ala Ser Lys Phe Leu Leu Ser Gly Cys Ala Ala
                20                  25                  30

Thr Val Ala Glu Leu Ala Thr Phe Pro Leu Asp Leu Thr Lys Thr
                35                  40                  45

Arg Leu Gln Met Gln Gly Glu Ala Ala Leu Ala Arg Leu Gly Asp
                50                  55                  60

Gly Ala Arg Glu Ser Ala Pro Tyr Arg Gly Met Val Arg Thr Ala
                65                  70                  75

Leu Gly Ile Ile Glu Glu Gly Phe Leu Lys Leu Trp Gln Gly
                80                  85                  90

Val Thr Pro Ala Ile Tyr Arg His Val Val Tyr Ser Gly Gly Arg
                95                  100                 105

Met Val Thr Tyr Glu His Leu Arg Glu Val Val Phe Gly Lys Ser
                110                 115                 120

Glu Asp Glu His Tyr Pro Leu Trp Lys Ser Val Ile Gly Gly Met
                125                 130                 135

Met Ala Gly Val Ile Gly Gln Phe Leu Ala Asn Pro Thr Asp Leu
                140                 145                 150
```

-continued

```
Val Lys Val Gln Met Gln Met Glu Gly Lys Arg Lys Leu Glu Gly
            155                 160                 165
Lys Pro Leu Arg Phe Arg Gly Val His His Ala Phe Ala Lys Ile
        170                 175                 180
Leu Ala Glu Gly Gly Ile Arg Gly Leu Trp Ala Gly Trp Val Pro
    185                 190                 195
Asn Ile Gln Arg Ala Ala Leu Val Asn Met Gly Asp Leu Thr Thr
200                 205                 210
Tyr Asp Thr Val Lys His Tyr Leu Val Leu Asn Thr Pro Leu Glu
            215                 220                 225
Asp Asn Ile Met Thr His Gly Leu Ser Ser Leu Cys Ser Gly Leu
        230                 235                 240
Val Ala Ser Ile Leu Gly Thr Pro Ala Asp Val Ile Lys Ser Arg
    245                 250                 255
Ile Met Asn Gln Pro Arg Asp Lys Gln Gly Arg Gly Leu Leu Tyr
260                 265                 270
Lys Ser Ser Thr Asp Cys Leu Ile Gln Ala Val Gln Gly Glu Gly
            275                 280                 285
Phe Met Ser Leu Tyr Lys Gly Phe Leu Pro Ser Trp Leu Arg Met
        290                 295                 300
Thr Pro Trp Ser Met Val Phe Trp Leu Thr Tyr Glu Lys Ile Arg
    305                 310                 315
Glu Met Ser Gly Val Ser Pro Phe
                320
```

```
<210> SEQ ID NO 127
<211> LENGTH: 1505
<212> TYPE: DNA
<213> ORGANISM: Homo Sapien

<400> SEQUENCE: 127
cgcggatcgg acccaagcag gtcggcggcg gcggcaggag agcggccggg            50
cgtcagctcc tcgaccccg tgtcgggcta gtccagcgag gcggacgggc            100
ggcgtgggcc catggccagg cccggcatgg agcggtggcg cgaccggctg           150
gcgctggtga cggggccctc gggggcatc ggcgcggccg tggcccgggc            200
cctggtccag cagggactga aggtggtggg ctgcgcccgc actgtgggca           250
acatcgagga gctggctgct gaatgtaaga gtgcaggcta ccccgggact           300
ttgatcccct acagatgtga cctatcaaat gaagaggaca tcctctccat           350
gttctcagct atccgttctc agcacagcgg tgtagacatc tgcatcaaca           400
atgctggctt ggcccggcct gacaccctgc tctcaggcag caccagtggt           450
tggaaggaca tgttcaatgt gaacgtgctg gccctcagca tctgcacacg           500
ggaagcctac cagtccatga aggagcggaa tgtggacgat gggcacatca           550
ttaacatcaa tagcatgtct ggccaccgag tgttaccct gtctgtgacc            600 cacttctata gtgccaccaa gtatgccgtc actgcgctga cagagggact           650
gaggcaagag cttcgggagg cccagaccca catccgagcc acgtgcatct           700
ctccaggtgt ggtggagaca caattcgcct tcaaactcca cgacaaggac           750
cctgagaagg cagctgccac ctatgagcaa atgaagtgtc tcaaacccga           800
ggatgtggcc gaggctgtta ctacgtcct cagcaccccc gcacacatcc            850
agattggaga catccagatg aggcccacgg agcaggtgac ctagtgactg           900
```

-continued

```
tgggagctcc tccttccctc cccaccettc atggcttgcc tcctgcctct       950 ggatttagg tgttgatttc tggatcacgg gataccactt cctgtccaca       1000
ccccgaccag gggctagaaa atttgtttga gatttttata tcatcttgtc       1050
aaattgcttc agttgtaaat gtgaaaaatg gctggggaa aggaggtggt       1100 gtccctaatt gttttacttg ttaacttgtt cttgtgcccc tgggcacttg       1150
gcctttgtct gctctcagtg tcttcccttt gacatggaa aggagttgtg       1200 gccaaaatcc ccatcttctt gcacctcaac gtctgtggct cagggctggg       1250
gtggcagagg gaggccttca ccttatatct gtgttgttat ccagggctcc       1300
agacttcctc ctctgcctgc cccactgcac cctctccccc ttatctatct       1350
ccttctcggc tccccagccc agtcttggct tcttgtcccc tcctggggtc       1400
atccctccac tctgactctg actatggcag cagaacacca gggcctggcc       1450
cagtggattt catggtgatc attaaaaaag aaaaatcgca accaaaaaaa       1500
aaaaa                                                       1505
```

<210> SEQ ID NO 128
<211> LENGTH: 260
<212> TYPE: PRT
<213> ORGANISM: Homo Sapien

<400> SEQUENCE: 128

```
Met Ala Arg Pro Gly Met Glu Arg Trp Arg Asp Arg Leu Ala Leu
 1               5                  10                  15

Val Thr Gly Ala Ser Gly Gly Ile Gly Ala Ala Val Ala Arg Ala
                20                  25                  30

Leu Val Gln Gln Gly Leu Lys Val Val Gly Cys Ala Arg Thr Val
                35                  40                  45

Gly Asn Ile Glu Glu Leu Ala Ala Glu Cys Lys Ser Ala Gly Tyr
                50                  55                  60

Pro Gly Thr Leu Ile Pro Tyr Arg Cys Asp Leu Ser Asn Glu Glu
                65                  70                  75

Asp Ile Leu Ser Met Phe Ser Ala Ile Arg Ser Gln His Ser Gly
                80                  85                  90

Val Asp Ile Cys Ile Asn Asn Ala Gly Leu Ala Arg Pro Asp Thr
                95                  100                 105

Leu Leu Ser Gly Ser Thr Ser Gly Trp Lys Asp Met Phe Asn Val
                110                 115                 120

Asn Val Leu Ala Leu Ser Ile Cys Thr Arg Glu Ala Tyr Gln Ser
                125                 130                 135

Met Lys Glu Arg Asn Val Asp Asp Gly His Ile Ile Asn Ile Asn
                140                 145                 150

Ser Met Ser Gly His Arg Val Leu Pro Leu Ser Val Thr His Phe
                155                 160                 165

Tyr Ser Ala Thr Lys Tyr Ala Val Thr Ala Leu Thr Glu Gly Leu
                170                 175                 180

Arg Gln Glu Leu Arg Glu Ala Gln Thr His Ile Arg Ala Thr Cys
                185                 190                 195

Ile Ser Pro Gly Val Val Glu Thr Gln Phe Ala Phe Lys Leu His
                200                 205                 210

Asp Lys Asp Pro Glu Lys Ala Ala Ala Thr Tyr Glu Gln Met Lys
```

|         | 215         |         |         | 220         |         |         | 225 |
| ------- | ----------- | ------- | ------- | ----------- | ------- | ------- | --- |

Cys Leu Lys Pro Glu Asp Val Ala Glu Ala Val Ile Tyr Val Leu
                230                 235                 240

Ser Thr Pro Ala His Ile Gln Ile Gly Asp Ile Gln Met Arg Pro
                245                 250                 255

Thr Glu Gln Val Thr
            260

<210> SEQ ID NO 129
<211> LENGTH: 1177
<212> TYPE: DNA
<213> ORGANISM: Homo Sapien

<400> SEQUENCE: 129

| aacttctaca tgggcctcct gctgctggtg ctcttcctca gcctcctgcc | 50 |
| gtggcctac accatcatgt ccctcccacc ctcctttgac tgcgggccgt | 100 |
| tcaggtgcag agtctcagtt gcccgggagc acctcccctc ccgaggcagt | 150 |
| ctgctcagag ggcctcggcc cagaattcca gttctggttt catgccagcc | 200 |
| tgtaaaaggc catggaactt tgggtgaatc accgatgcca tttaagaggg | 250 |
| ttttctgcca ggatggaaat gttaggtcgt tctgtgtctg cgctgttcat | 300 |
| ttcagtagcc accagccacc tgtggccgtt gagtgcttga aatgaggaac | 350 |
| tgagaaaatt aatttctcat gtattttttct catttattta ttaatttta | 400 |
| actgatagtt gtacatattt gggggtacat gtgatatttg gatacatgta | 450 |
| tacaatatat aatgatcaaa tcagggtaac tgggatatcc atcacatcaa | 500 |
| acatttattt tttattcttt ttagacagag tctcactctg tcacccaggc | 550 |
| tggagtgcag tggtgccatc tcagcttact gcaacctctg cctgccaggt | 600 |
| tcaagcgatt ctcatgcctc acctcccaa gtagctggga ctacaggcat | 650 |
| gcaccacaat gcccaactaa ttttttgtatt tttagtagag acggggtttt | 700 |
| gccatgttgc ccaggctggc cttgaactcc tggcctcaaa caatccactt | 750 |
| gcctcggcct cccaaagtgt tatgattaca ggcgtgagcc accgtgcctg | 800 |
| gcctaaacat ttatcttttc tttgtgttgg aactttgaa attatacaat | 850 |
| gaattattgt taactgtcat ctccctgctg tgctatggaa cactgggact | 900 |
| tcttccctct atctaactgt atatttgtac cagttaacca accgtacttc | 950 |
| atccccactc ctctctatcc ttcccaacct ctgatcacct cattctactc | 1000 |
| tctacctcca tgagatccac ttttttagct cccacatgtg agtaagaaaa | 1050 |
| tgcaatattt gtctttctgt gcctggctta tttcacttaa cataatgact | 1100 |
| tcctgttcca tccatgttgc tgcaaatgac aggatttcgt tcttaatttc | 1150 |
| aattaaaata accacacatg gcaaaaa | 1177 |

<210> SEQ ID NO 130
<211> LENGTH: 111
<212> TYPE: PRT
<213> ORGANISM: Homo Sapien

<400> SEQUENCE: 130

Met Gly Leu Leu Leu Leu Val Leu Phe Leu Ser Leu Leu Pro Val
 1               5                   10                  15

Ala Tyr Thr Ile Met Ser Leu Pro Pro Ser Phe Asp Cys Gly Pro

|  | 20 | 25 | 30 |

Phe Arg Cys Arg Val Ser Val Ala Arg Glu His Leu Pro Ser Arg
　　　　35　　　　　　　　　40　　　　　　　　　45

Gly Ser Leu Leu Arg Gly Pro Arg Pro Arg Ile Pro Val Leu Val
　　　　50　　　　　　　　　55　　　　　　　　　60

Ser Cys Gln Pro Val Lys Gly His Gly Thr Leu Gly Glu Ser Pro
　　　　65　　　　　　　　　70　　　　　　　　　75

Met Pro Phe Lys Arg Val Phe Cys Gln Asp Gly Asn Val Arg Ser
　　　　80　　　　　　　　　85　　　　　　　　　90

Phe Cys Val Cys Ala Val His Phe Ser Ser His Gln Pro Pro Val
　　　　95　　　　　　　　　100　　　　　　　　105

Ala Val Glu Cys Leu Lys
　　　　110

<210> SEQ ID NO 131
<211> LENGTH: 2061
<212> TYPE: DNA
<213> ORGANISM: Homo Sapien

<400> SEQUENCE: 131

| | |
|---|---:|
| ttctgaagta acggaagcta ccttgtataa agacctcaac actgctgacc | 50 |
| atgatcagcg cagcctggag catcttcctc atcgggacta aaattgggct | 100 |
| gttccttcaa gtagcacctc tatcagttat ggctaaatcc tgtccatctg | 150 |
| tgtgtcgctg cgatgcgggt ttcatttact gtaatgatcg ctttctgaca | 200 |
| tccattccaa caggaatacc agaggatgct acaactctct accttcagaa | 250 |
| caaccaaata aataatgctg ggattccttc agatttgaaa acttgctga | 300 |
| aagtagaaag aatataccta taccacaaca gtttagatga atttcctacc | 350 |
| aacctcccaa gtatgtaaa agagttacat ttgcaagaaa ataacataag | 400 |
| gactatcact tatgattcac tttcaaaaat tccctatctg gaagaattac | 450 |
| atttagatga caactctgtc tctgcagtta gcatagaaga gggagcattc | 500 |
| cgagacagca actatctccg actgcttttc ctgtcccgta atcaccttag | 550 |
| cacaattccc tggggtttgc ccaggactat agaagaacta cgcttggatg | 600 |
| ataatcgcat atccactatt tcatcaccat ctcttcaagg tctcactagt | 650 |
| ctaaaacgcc tggttctaga tggaaacctg ttgaacaatc atggtttagg | 700 |
| tgacaaagtt ttcttcaacc tagttaattt gacagagctg tccctggtgc | 750 |
| ggaattccct gactgctgca ccagtaaacc ttccaggcac aaacctgagg | 800 |
| aagctttatc ttcaagataa ccacatcaat cgggtgcccc caaatgcttt | 850 |
| ttcttatcta aggcagctct atcgactgga tatgtccaat aataacctaa | 900 |
| gtaatttacc tcagggtatc tttgatgatt tggacaatat aacacaactg | 950 |
| attcttcgca caatccctg gtattgcggg tgcaagatga atgggtacg | 1000 |
| tgactggtta caatcactac ctgtgaaggt caacgtgcgt gggctcatgt | 1050 |
| gccaagcccc agaaaaggtt cgtgggatgg ctattaagga tctcaatgca | 1100 |
| gaactgtttg attgtaagga cagtgggatt gtaagcacca ttcagataac | 1150 |
| cactgcaata cccaacacag tgtatcctgc ccaaggacag tggccagctc | 1200 |
| cagtgaccaa acagccagat attaagaacc ccaagctcac taaggatcaa | 1250 |
| caaaccacag ggagtccctc aagaaaaaca attacaatta ctgtgaagtc | 1300 |

-continued

```
tgtcacctct gataccattc atatctcttg gaaacttgct ctacctatga         1350
ctgctttgag actcagctgg cttaaactgg gccatagccc ggcatttgga         1400
tctataacag aaacaattgt aacaggggaa cgcagtgagt acttggtcac         1450
agccctggag cctgattcac cctataaagt atgcatggtt cccatggaaa         1500
ccagcaacct ctacctatttt gatgaaactc ctgtttgtat tgagactgaa        1550
actgcacccc ttcgaatgta caaccctaca accaccctca atcgagagca         1600
agagaaagaa ccttacaaaa accccaattt acctttggct gccatcattg         1650
gtggggctgt ggccctggtt accattgccc ttcttgcttt agtgtgttgg         1700
tatgttcata ggaatggatc gctcttctca aggaactgtg catatagcaa         1750
agggaggaga agaaaggatg actatgcaga agctggcact aagaaggaca         1800
actctatcct ggaaatcagg gaaacttctt ttcagatgtt accaataagc         1850
aatgaaccca tctcgaagga ggagtttgta atacacacca tatttcctcc         1900
taatggaatg aatctgtaca aaaacaatca cagtgaaagc agtagtaacc         1950
gaagctacag agacagtggt attccagact cagatcactc acactcatga         2000
tgctgaagga ctcacagcag acttgtgttt tgggtttttt aaacctaagg         2050
gaggtgatgg t                                                    2061
```

<210> SEQ ID NO 132
<211> LENGTH: 649
<212> TYPE: PRT
<213> ORGANISM: Homo Sapien

<400> SEQUENCE: 132

```
Met Ile Ser Ala Ala Trp Ser Ile Phe Leu Ile Gly Thr Lys Ile
 1               5                  10                  15

Gly Leu Phe Leu Gln Val Ala Pro Leu Ser Val Met Ala Lys Ser
                20                  25                  30

Cys Pro Ser Val Cys Arg Cys Asp Ala Gly Phe Ile Tyr Cys Asn
                35                  40                  45

Asp Arg Phe Leu Thr Ser Ile Pro Thr Gly Ile Pro Glu Asp Ala
                50                  55                  60

Thr Thr Leu Tyr Leu Gln Asn Asn Gln Ile Asn Asn Ala Gly Ile
                65                  70                  75

Pro Ser Asp Leu Lys Asn Leu Leu Lys Val Glu Arg Ile Tyr Leu
                80                  85                  90

Tyr His Asn Ser Leu Asp Glu Phe Pro Thr Asn Leu Pro Lys Tyr
                95                 100                 105

Val Lys Glu Leu His Leu Gln Glu Asn Asn Ile Arg Thr Ile Thr
               110                 115                 120

Tyr Asp Ser Leu Ser Lys Ile Pro Tyr Leu Glu Glu Leu His Leu
               125                 130                 135

Asp Asp Asn Ser Val Ser Ala Val Ser Ile Glu Glu Gly Ala Phe
               140                 145                 150

Arg Asp Ser Asn Tyr Leu Arg Leu Leu Phe Leu Ser Arg Asn His
               155                 160                 165

Leu Ser Thr Ile Pro Trp Gly Leu Pro Arg Thr Ile Glu Glu Leu
               170                 175                 180

Arg Leu Asp Asp Asn Arg Ile Ser Thr Ile Ser Ser Pro Ser Leu
               185                 190                 195
```

```
Gln Gly Leu Thr Ser Leu Lys Arg Leu Val Leu Asp Gly Asn Leu
            200                 205                 210

Leu Asn Asn His Gly Leu Gly Asp Lys Val Phe Phe Asn Leu Val
            215                 220                 225

Asn Leu Thr Glu Leu Ser Leu Val Arg Asn Ser Leu Thr Ala Ala
            230                 235                 240

Pro Val Asn Leu Pro Gly Thr Asn Leu Arg Lys Leu Tyr Leu Gln
            245                 250                 255

Asp Asn His Ile Asn Arg Val Pro Pro Asn Ala Phe Ser Tyr Leu
            260                 265                 270

Arg Gln Leu Tyr Arg Leu Asp Met Ser Asn Asn Leu Ser Asn
            275                 280                 285

Leu Pro Gln Gly Ile Phe Asp Asp Leu Asp Asn Ile Thr Gln Leu
            290                 295                 300

Ile Leu Arg Asn Asn Pro Trp Tyr Cys Gly Cys Lys Met Lys Trp
            305                 310                 315

Val Arg Asp Trp Leu Gln Ser Leu Pro Val Lys Val Asn Val Arg
            320                 325                 330

Gly Leu Met Cys Gln Ala Pro Glu Lys Val Arg Gly Met Ala Ile
            335                 340                 345

Lys Asp Leu Asn Ala Glu Leu Phe Asp Cys Lys Asp Ser Gly Ile
            350                 355                 360

Val Ser Thr Ile Gln Ile Thr Thr Ala Ile Pro Asn Thr Val Tyr
            365                 370                 375

Pro Ala Gln Gly Gln Trp Pro Ala Pro Val Thr Lys Gln Pro Asp
            380                 385                 390

Ile Lys Asn Pro Lys Leu Thr Lys Asp Gln Gln Thr Thr Gly Ser
            395                 400                 405

Pro Ser Arg Lys Thr Ile Thr Ile Thr Val Lys Ser Val Thr Ser
            410                 415                 420

Asp Thr Ile His Ile Ser Trp Lys Leu Ala Leu Pro Met Thr Ala
            425                 430                 435

Leu Arg Leu Ser Trp Leu Lys Leu Gly His Ser Pro Ala Phe Gly
            440                 445                 450

Ser Ile Thr Glu Thr Ile Val Thr Gly Glu Arg Ser Glu Tyr Leu
            455                 460                 465

Val Thr Ala Leu Glu Pro Asp Ser Pro Tyr Lys Val Cys Met Val
            470                 475                 480

Pro Met Glu Thr Ser Asn Leu Tyr Leu Phe Asp Glu Thr Pro Val
            485                 490                 495

Cys Ile Glu Thr Glu Thr Ala Pro Leu Arg Met Tyr Asn Pro Thr
            500                 505                 510

Thr Thr Leu Asn Arg Glu Gln Glu Lys Glu Pro Tyr Lys Asn Pro
            515                 520                 525

Asn Leu Pro Leu Ala Ala Ile Ile Gly Gly Ala Val Ala Leu Val
            530                 535                 540

Thr Ile Ala Leu Leu Ala Leu Val Cys Trp Tyr Val His Arg Asn
            545                 550                 555

Gly Ser Leu Phe Ser Arg Asn Cys Ala Tyr Ser Lys Gly Arg Arg
            560                 565                 570

Arg Lys Asp Asp Tyr Ala Glu Ala Gly Thr Lys Lys Asp Asn Ser
            575                 580                 585
```

```
Ile Leu Glu Ile Arg Glu Thr Ser Phe Gln Met Leu Pro Ile Ser
            590                 595                 600

Asn Glu Pro Ile Ser Lys Glu Glu Phe Val Ile His Thr Ile Phe
            605                 610                 615

Pro Pro Asn Gly Met Asn Leu Tyr Lys Asn Asn His Ser Glu Ser
            620                 625                 630

Ser Ser Asn Arg Ser Tyr Arg Asp Ser Gly Ile Pro Asp Ser Asp
            635                 640                 645

His Ser His Ser

<210> SEQ ID NO 133
<211> LENGTH: 1882
<212> TYPE: DNA
<213> ORGANISM: Homo Sapien

<400> SEQUENCE: 133
ccgtcatccc cctgcagcca cccttcccag agtcctttgc ccaggccacc              50
ccaggcttct tggcagccct gccgggccac ttgtcttcat gtctgccagg             100
gggaggtggg aaggaggtgg gaggagggcg tgcagaggca gtctgggctt             150
ggccagagct cagggtgctg agcgtgtgac cagcagtgag cagaggccgg             200
ccatggccag cctggggctg ctgctcctgc tcttactgac agcactgcca             250
ccgctgtggt cctcctcact gcctgggctg acactgctg aaagtaaagc              300 caccattgca gacctgatcc tgtctgcgct ggagagagcc accgtcttcc             350
tagaacagag gctgcctgaa atcaacctgg atggcatggt gggggtccga             400
gtgctggaag agcagctaaa aagtgtccgg gagaagtggg cccaggagcc             450
cctgctgcag ccgctgagcc tgcgcgtggg gatgctgggg gagaagctgg             500
aggctgccat ccagagatcc ctccactacc tcaagctgag tgatcccaag             550
tacctaagag agttccagct gaccctccag cccgggtttt ggaagctccc             600
acatgcctgg atccacactg atgcctcctt ggtgtacccc acgttcgggc             650
cccaggactc attctcagag gagagaagtg acgtgtgcct ggtgcagctg             700
ctgggaaccg ggacggacag cagcgagccc tgcggcctct cagacctctg             750
caggagcctc atgaccaagc ccggctgctc aggctactgc ctgtcccacc             800
aactgctctt cttcctctgg gccagaatga ggggatgcac acagggacca             850
ctccaacaga gccaggacta tatcaacctc ttctgcgcca acatgatgga             900
cttgaaccgc agagctgagg ccatcggata cgcctaccct acccgggaca             950
tcttcatgga aaacatcatg ttctgtggaa tgggcggctt ctccgacttc            1000
tacaagctcc ggtggctgga ggccattctc agctggcaga acagcagga             1050 aggatgcttc ggggagcctg atgctgaaga tgaagaatta tctaaagcta            1100
ttcaatatca gcagcatttt tcgaggagag tgaagaggcg agaaaaacaa            1150
tttccagatt ctcgctctgt tgctcaggct ggagtacagt ggcgcaatct            1200
cggctcactg caacctttgc ctcctgggtt caagcaattc tcttgcctca            1250
tcctcccgag tagctgggac tacaggagcg tgccaccata cctggctaat            1300
ttttatattt ttttagtaga cagggtttt catcatgttg ctcatgctgg             1350
tctcgaactc ctgatctcaa gagatccgcc cacctcaggc tcccaaagtg            1400
tgggattata ggtgtgagcc accgtgtctg gctgaaaagc acttttcaaag           1450
```

```
agactgtgtt gaataaaggg ccaaggttct tgccacccag cactcatggg            1500
ggctctctcc cctagatggc tgctcctccc acaacacagc cacagcagtg            1550
gcagccctgg gtggcttcct atacatcctg gcagaatacc ccccagcaaa            1600
cagagagcca cacccatcca caccgccacc accaagcagc cgctgagacg            1650
gacggttcca tgccagctgc ctggaggagg aacagacccc tttagtcctc            1700
atcccttaga tcctggaggg cacggatcac atcctgggaa gaaggcatct            1750
ggaggataag caaagccacc ccgacaccca atcttggaag ccctgagtag            1800
gcagggccag ggtaggtggg ggccgggagg gacccaggtg tgaacggatg            1850
aataaagttc aactgcaact gaaaaaaaaa aa                               1882
```

<210> SEQ ID NO 134
<211> LENGTH: 440
<212> TYPE: PRT
<213> ORGANISM: Homo Sapien

<400> SEQUENCE: 134

```
Met Ser Ala Arg Gly Arg Trp Glu Gly Gly Arg Arg Ala Cys
  1               5                  10                  15

Arg Gly Ser Leu Gly Leu Ala Arg Ala Gln Gly Ala Glu Arg Val
                 20                  25                  30

Thr Ser Ser Glu Gln Arg Pro Ala Met Ala Ser Leu Gly Leu Leu
                 35                  40                  45

Leu Leu Leu Leu Leu Thr Ala Leu Pro Pro Leu Trp Ser Ser Ser
                 50                  55                  60

Leu Pro Gly Leu Asp Thr Ala Glu Ser Lys Ala Thr Ile Ala Asp
                 65                  70                  75

Leu Ile Leu Ser Ala Leu Glu Arg Ala Thr Val Phe Leu Glu Gln
                 80                  85                  90

Arg Leu Pro Glu Ile Asn Leu Asp Gly Met Val Gly Val Arg Val
                 95                 100                 105

Leu Glu Glu Gln Leu Lys Ser Val Arg Glu Lys Trp Ala Gln Glu
                110                 115                 120

Pro Leu Leu Gln Pro Leu Ser Leu Arg Val Gly Met Leu Gly Glu
                125                 130                 135

Lys Leu Glu Ala Ala Ile Gln Arg Ser Leu His Tyr Leu Lys Leu
                140                 145                 150

Ser Asp Pro Lys Tyr Leu Arg Glu Phe Gln Leu Thr Leu Gln Pro
                155                 160                 165

Gly Phe Trp Lys Leu Pro His Ala Trp Ile His Thr Asp Ala Ser
                170                 175                 180

Leu Val Tyr Pro Thr Phe Gly Pro Gln Asp Ser Phe Ser Glu Glu
                185                 190                 195

Arg Ser Asp Val Cys Leu Val Gln Leu Leu Gly Thr Gly Thr Asp
                200                 205                 210

Ser Ser Glu Pro Cys Gly Leu Ser Asp Leu Cys Arg Ser Leu Met
                215                 220                 225

Thr Lys Pro Gly Cys Ser Gly Tyr Cys Leu Ser His Gln Leu Leu
                230                 235                 240

Phe Phe Leu Trp Ala Arg Met Arg Gly Cys Thr Gln Gly Pro Leu
                245                 250                 255

Gln Gln Ser Gln Asp Tyr Ile Asn Leu Phe Cys Ala Asn Met Met
```

-continued

```
                    260                 265                 270
Asp Leu Asn Arg Arg Ala Glu Ala Ile Gly Tyr Ala Tyr Pro Thr
                275                 280                 285
Arg Asp Ile Phe Met Glu Asn Ile Met Phe Cys Gly Met Gly Gly
                290                 295                 300
Phe Ser Asp Phe Tyr Lys Leu Arg Trp Leu Glu Ala Ile Leu Ser
                305                 310                 315
Trp Gln Lys Gln Glu Gly Cys Phe Gly Glu Pro Asp Ala Glu
                320                 325                 330
Asp Glu Glu Leu Ser Lys Ala Ile Gln Tyr Gln Gln His Phe Ser
                335                 340                 345
Arg Arg Val Lys Arg Glu Lys Gln Phe Pro Asp Ser Arg Ser
                350                 355                 360
Val Ala Gln Ala Gly Val Gln Trp Arg Asn Leu Gly Ser Leu Gln
                365                 370                 375
Pro Leu Pro Pro Gly Phe Lys Gln Phe Ser Cys Leu Ile Leu Pro
                380                 385                 390
Ser Ser Trp Asp Tyr Arg Ser Val Pro Pro Tyr Leu Ala Asn Phe
                395                 400                 405
Tyr Ile Phe Leu Val Glu Thr Gly Phe His His Val Ala His Ala
                410                 415                 420
Gly Leu Glu Leu Leu Ile Ser Arg Asp Pro Pro Thr Ser Gly Ser
                425                 430                 435
Gln Ser Val Gly Leu
                440
```

<210> SEQ ID NO 135
<211> LENGTH: 884
<212> TYPE: DNA
<213> ORGANISM: Homo Sapien

<400> SEQUENCE: 135

```
ggtctgagtg cagagctgct gtcatggcgg ccgctctgtg gggcttcttt          50
cccgtcctgc tgctgctgct gctatcgggg gatgtccaga gctcggaggt         100
gcccggggct gctgctgagg gatcgggagg gagtgggggtc ggcataggag        150
atcgcttcaa gattgagggg cgtgcagttg ttccaggggt gaagcctcag         200
gactggatct cggcggcccg agtgctggta gacggagaag agcacgtcgg         250
tttccttaag acagatggga gttttgtggt tcatgatata ccttctggat         300
cttatgtagt ggaagttgta tctccagctt acagatttga tcccgttcga         350
gtggatatca cttcgaaagg aaaaatgaga gcaagatatg tgaattacat         400
caaaacatca gaggttgtca gactgcccta tcctctccaa atgaaatctt         450
caggtccacc ttcttacttt attaaaaggg aatcgtgggg ctggacagac         500
tttctaatga acccaatggt tatgatgatg gttcttcctt tattgatatt         550
tgtgcttctg cctaaagtgg tcaacacaag tgatcctgac atgagacggg         600
aaatggagca gtcaatgaat atgctgaatt ccaaccatga gttgcctgat         650
gtttctgagt tcatgacaag actcttctct tcaaaatcat ctgcaaatc          700
tagcagcggc agcagtaaaa caggcaaaag tggggctggc aaaaggaggt         750
agtcaggccg tccagagctg gcatttgcac aaacacggca acactgggtg         800
gcatccaagt cttggaaaac cgtgtgaagc aactactata aacttgagtc         850
```

-continued atcccgacgt tgatctctta caactgtgta tgtt 884

<210> SEQ ID NO 136
<211> LENGTH: 242
<212> TYPE: PRT
<213> ORGANISM: Homo Sapien

<400> SEQUENCE: 136

```
Met Ala Ala Ala Leu Trp Gly Phe Phe Pro Val Leu Leu Leu Leu
  1               5                  10                  15
Leu Leu Ser Gly Asp Val Gln Ser Ser Glu Val Pro Gly Ala Ala
                 20                  25                  30
Ala Glu Gly Ser Gly Gly Ser Gly Val Gly Ile Gly Asp Arg Phe
                 35                  40                  45
Lys Ile Glu Gly Arg Ala Val Val Pro Gly Val Lys Pro Gln Asp
                 50                  55                  60
Trp Ile Ser Ala Ala Arg Val Leu Val Asp Gly Glu Glu His Val
                 65                  70                  75
Gly Phe Leu Lys Thr Asp Gly Ser Phe Val Val His Asp Ile Pro
                 80                  85                  90
Ser Gly Ser Tyr Val Val Glu Val Val Ser Pro Ala Tyr Arg Phe
                 95                 100                 105
Asp Pro Val Arg Val Asp Ile Thr Ser Lys Gly Lys Met Arg Ala
                110                 115                 120
Arg Tyr Val Asn Tyr Ile Lys Thr Ser Glu Val Val Arg Leu Pro
                125                 130                 135
Tyr Pro Leu Gln Met Lys Ser Ser Gly Pro Pro Ser Tyr Phe Ile
                140                 145                 150
Lys Arg Glu Ser Trp Gly Trp Thr Asp Phe Leu Met Asn Pro Met
                155                 160                 165
Val Met Met Met Val Leu Pro Leu Leu Ile Phe Val Leu Leu Pro
                170                 175                 180
Lys Val Val Asn Thr Ser Asp Pro Asp Met Arg Arg Glu Met Glu
                185                 190                 195
Gln Ser Met Asn Met Leu Asn Ser Asn His Glu Leu Pro Asp Val
                200                 205                 210
Ser Glu Phe Met Thr Arg Leu Phe Ser Ser Lys Ser Ser Gly Lys
                215                 220                 225
Ser Ser Ser Gly Ser Ser Lys Thr Gly Lys Ser Gly Ala Gly Lys
                230                 235                 240
Arg Arg
```

<210> SEQ ID NO 137
<211> LENGTH: 1571
<212> TYPE: DNA
<213> ORGANISM: Homo Sapien

<400> SEQUENCE: 137
gatggcgcag ccacagcttc tgtgagattc gatttctccc cagttcccct 50
gtgggtctga gggaccaga agggtgagct acgttggctt tctggaaggg 100
gaggctatat gcgtcaattc cccaaaacaa gttttgacat ttcccctgaa 150
atgtcattct ctatctattc actgcaagtg cctgctgttc caggccttac 200
ctgctgggca ctaacggcgg agccaggatg gggacagaat aaaggagcca 250

-continued

| | |
|---|---|
| cgacctgtgc caccaactcg cactcagact ctgaactcag acctgaaatc | 300 |
| ttctcttcac gggaggcttg gcagttttc ttactcctgt ggtctccaga | 350 |
| tttcaggcct aagatgaaag cctctagtct tgccttcagc cttctctctg | 400 |
| ctgcgtttta tctcctatgg actccttcca ctggactgaa acactcaat | 450 |
| ttgggaagct gtgtgatcgc acaaaccttc aggaaatac gaaatggatt | 500 |
| ttctgagata cggggcagtg tgcaagccaa agatggaaac attgacatca | 550 |
| gaatcttaag gaggactgag tctttgcaag acacaaagcc tgcgaatcga | 600 |
| tgctgcctcc tgcgccattt gctaagactc tatctggaca gggtatttaa | 650 |
| aaactaccag accctgacc attatactct ccggaagatc agcagcctcg | 700 |
| ccaattcctt tcttaccatc aagaaggacc tccggctctc tcatgcccac | 750 |
| atgacatgcc attgtgggga ggaagcaatg aagaaataca gccagattct | 800 |
| gagtcacttt gaaaagctgg aacctcaggc agcagttgtg aaggctttgg | 850 |
| gggaactaga cattcttctg caatggatgg aggagacaga ataggaggaa | 900 |
| agtgatgctg ctgctaagaa tattcgaggt caagagctcc agtcttcaat | 950 |
| acctgcagag gaggcatgac cccaaaccac catctcttta ctgtactagt | 1000 |
| cttgtgctgg tcacagtgta tcttatttat gcattacttg cttccttgca | 1050 |
| tgattgtctt tatgcatccc caatcttaat tgagaccata cttgtataag | 1100 |
| attttttgtaa tatctttctg ctattggata tatttattag ttaatatatt | 1150 |
| tatttatttt ttgctatttta atgtatttat tttttactt ggacatgaaa | 1200 |
| ctttaaaaaa attcacagat tatatttata acctgactag agcaggtgat | 1250 |
| gtatttttat acagtaaaaa aaaaaaacct tgtaaattct agaagagtgg | 1300 |
| ctaggggggt tattcatttg tattcaacta aggacatatt tactcatgct | 1350 |
| gatgctctgt gagatatttg aaattgaacc aatgactact taggatgggt | 1400 |
| tgtggaataa gttttgatgt ggaattgcac atctaccta caattactga | 1450 |
| ccatccccag tagactcccc agtcccataa ttgtgtatct tccagccagg | 1500 |
| aatcctacac ggccagcatg tatttctaca aataaagttt tctttgcata | 1550 |
| ccaaaaaaaa aaaaaaaaa a | 1571 |

<210> SEQ ID NO 138
<211> LENGTH: 261
<212> TYPE: PRT
<213> ORGANISM: Homo Sapien

<400> SEQUENCE: 138

```
Met Arg Gln Phe Pro Lys Thr Ser Phe Asp Ile Ser Pro Glu Met
  1               5                  10                  15

Ser Phe Ser Ile Tyr Ser Leu Gln Val Pro Ala Val Pro Gly Leu
                 20                  25                  30

Thr Cys Trp Ala Leu Thr Ala Glu Pro Gly Trp Gly Gln Asn Lys
                 35                  40                  45

Gly Ala Thr Thr Cys Ala Thr Asn Ser His Ser Asp Ser Glu Leu
                 50                  55                  60

Arg Pro Glu Ile Phe Ser Ser Arg Glu Ala Trp Gln Phe Phe Leu
                 65                  70                  75

Leu Leu Trp Ser Pro Asp Phe Arg Pro Lys Met Lys Ala Ser Ser
                 80                  85                  90
```

```
Leu Ala Phe Ser Leu Leu Ser Ala Ala Phe Tyr Leu Leu Trp Thr
             95                  100                 105

Pro Ser Thr Gly Leu Lys Thr Leu Asn Leu Gly Ser Cys Val Ile
        110                 115                 120

Ala Thr Asn Leu Gln Glu Ile Arg Asn Gly Phe Ser Glu Ile Arg
        125                 130                 135

Gly Ser Val Gln Ala Lys Asp Gly Asn Ile Asp Ile Arg Ile Leu
        140                 145                 150

Arg Arg Thr Glu Ser Leu Gln Asp Thr Lys Pro Ala Asn Arg Cys
        155                 160                 165

Cys Leu Leu Arg His Leu Leu Arg Leu Tyr Leu Asp Arg Val Phe
        170                 175                 180

Lys Asn Tyr Gln Thr Pro Asp His Tyr Thr Leu Arg Lys Ile Ser
        185                 190                 195

Ser Leu Ala Asn Ser Phe Leu Thr Ile Lys Lys Asp Leu Arg Leu
        200                 205                 210

Ser His Ala His Met Thr Cys His Cys Gly Glu Glu Ala Met Lys
        215                 220                 225

Lys Tyr Ser Gln Ile Leu Ser His Phe Glu Lys Leu Glu Pro Gln
        230                 235                 240

Ala Ala Val Val Lys Ala Leu Gly Glu Leu Asp Ile Leu Leu Gln
        245                 250                 255

Trp Met Glu Glu Thr Glu
        260
```

<210> SEQ ID NO 139
<211> LENGTH: 2395
<212> TYPE: DNA
<213> ORGANISM: Homo Sapien

<400> SEQUENCE: 139

| | |
|---|---|
| cctggagccg gaagcgcggc tgcagcaggg cgaggctcca ggtggggtcg | 50 |
| gttccgcatc cagcctagcg tgtccacgat gcggctgggc tccgggactt | 100 |
| tcgctacctg ttgcgtagcg atcgaggtgc tagggatcgc ggtcttcctt | 150 |
| cggggattct tcccggctcc cgttcgttcc tctgccagag cggaacacgg | 200 |
| agcggagccc ccagcgcccg aaccctcggc tggagccagt tctaactgga | 250 |
| ccacgctgcc accacctctc ttcagtaaag ttgttattgt tctgatagat | 300 |
| gccttgagag atgattttgt gtttgggtca aagggtgtga aatttatgcc | 350 |
| ctacacaact taccttgtgg aaaaaggagc atctcacagt tttgtggctg | 400 |
| aagcaaagcc acctacagtt actatgcctc gaatcaaggc attgatgacg | 450 |
| gggagccttc ctggctttgt cgacgtcatc aggaacctca attctcctgc | 500 |
| actgctggaa gacagtgtga taagacaagc aaaagcagct ggaaaaagaa | 550 |
| tagtcttta tggagatgaa acctgggtta aattattccc aaagcatttt | 600 |
| gtggaatatg atggaacaac ctcattttc gtgtcagatt acacagaggt | 650 |
| ggataataat gtcacgaggc atttggataa agtattaaaa agaggagatt | 700 |
| gggacatatt aatcctccac tacctgggc tggaccacat tggccacatt | 750 |
| tcagggccca acagcccct gattgggcag aagctgagcg agatggacag | 800 |
| cgtgctgatg aagatccaca cctcactgca gtcgaaggag agagagacgc | 850 |

-continued

| | |
|---|---|
| ctttacccaa tttgctggtt ctttgtggtg accatggcat gtctgaaaca | 900 |
| ggaagtcacg gggcctcctc caccgaggag gtgaatacac ctctgatttt | 950 |
| aatcagttct gcgtttgaaa ggaaacccgg tgatatccga catccaaagc | 1000 |
| acgtccaata gacggatgtg gctgcgacac tggcgatagc acttggctta | 1050 |
| ccgattccaa aagacagtgt agggagcctc ctattcccag ttgtggaagg | 1100 |
| aagaccaatg agagagcagt tgagattttt acatttgaat acagtgcagc | 1150 |
| ttagtaaact gttgcaagag aatgtgccgt catatgaaaa agatcctggg | 1200 |
| tttgagcagt ttaaaatgtc agaaagattg catgggaact ggatcagact | 1250 |
| gtacttggag gaaaagcatt cagaagtcct attcaacctg gctccaaggg | 1300 |
| ttctcaggca gtacctggat gctctgaaga cgctgagctt gtccctgagt | 1350 |
| gcacaagtgg cccagttctc accctgctcc tgctcagcgt cccacaggca | 1400 |
| ctgcacagaa aggctgagct ggaagtccca ctgtcatctc ctgggttttc | 1450 |
| tctgctcttt tatttggtga tcctggttct ttcggccgtt cacgtcattg | 1500 |
| tgtgcacctc agctgaaagt tcgtgctact tctgtggcct ctcgtggctg | 1550 |
| gcggcaggct gcctttcgtt taccagactc tggttgaaca cctggtgtgt | 1600 |
| gccaagtgct ggcagtgccc tggacagggg gcctcaggga aggacgtgga | 1650 |
| gcagccttat cccaggcctc tgggtgtccc gacacaggtg ttcacatctg | 1700 |
| tgctgtcagg tcagatgcct cagttcttgg aaagctaggt tcctgcgact | 1750 |
| gttaccaagg tgattgtaaa gagctggcgg tcacagagga acaagccccc | 1800 |
| cagctgaggg ggtgtgtgaa tcggacagcc tcccagcaga ggtgtgggag | 1850 |
| ctgcagctga gggaagaaga gacaatcggc ctggacactc aggagggtca | 1900 |
| aaaggagact tggtcgcacc actcatcctg ccaccccag aatgcatcct | 1950 |
| gcctcatcag gtccagattt cttccaaggg cggacgtttt ctgttggaat | 2000 |
| tcttagtcct tggcctcgga caccttcatt cgttagctgg ggagtggtgg | 2050 |
| tgaggcagtg aagaagaggc ggatggtcac actcagatcc acagagccca | 2100 |
| ggatcaaggg acccactgca gtggcagcag gactgttggg ccccccccc | 2150 |
| aaccctgcac agccctcatc ccctcttggc ttgagccgtc agaggccctg | 2200 |
| tgctgagtgt ctgaccgaga cactcacagc tttgtcatca gggcacaggc | 2250 |
| ttcctcggag ccaggatgat ctgtgccacg cttgcacctc gggcccatct | 2300 |
| gggctcatgc tctctctcct gctattgaat tagtacctag ctgcacacag | 2350 |
| tatgtagtta ccaaaagaat aaacggcaat aattgagaaa aaaaa | 2395 |

<210> SEQ ID NO 140
<211> LENGTH: 310
<212> TYPE: PRT
<213> ORGANISM: Homo Sapien

<400> SEQUENCE: 140

Met Arg Leu Gly Ser Gly Thr Phe Ala Thr Cys Cys Val Ala Ile
1               5                   10                  15

Glu Val Leu Gly Ile Ala Val Phe Leu Arg Gly Phe Phe Pro Ala
                20                  25                  30

Pro Val Arg Ser Ser Ala Arg Ala Glu His Gly Ala Glu Pro Pro
                35                  40                  45

-continued

```
Ala Pro Glu Pro Ser Ala Gly Ala Ser Asn Trp Thr Thr Leu
                50                  55                  60
Pro Pro Pro Leu Phe Ser Lys Val Val Ile Val Leu Ile Asp Ala
            65                  70                  75
Leu Arg Asp Asp Phe Val Phe Gly Ser Lys Gly Val Lys Phe Met
            80                  85                  90
Pro Tyr Thr Thr Tyr Leu Val Glu Lys Gly Ala Ser His Ser Phe
            95                 100                 105
Val Ala Glu Ala Lys Pro Pro Thr Val Thr Met Pro Arg Ile Lys
           110                 115                 120
Ala Leu Met Thr Gly Ser Leu Pro Gly Phe Val Asp Val Ile Arg
           125                 130                 135
Asn Leu Asn Ser Pro Ala Leu Leu Glu Asp Ser Val Ile Arg Gln
           140                 145                 150
Ala Lys Ala Ala Gly Lys Arg Ile Val Phe Tyr Gly Asp Glu Thr
           155                 160                 165
Trp Val Lys Leu Phe Pro Lys His Phe Val Glu Tyr Asp Gly Thr
           170                 175                 180
Thr Ser Phe Phe Val Ser Asp Tyr Thr Glu Val Asp Asn Asn Val
           185                 190                 195
Thr Arg His Leu Asp Lys Val Leu Lys Arg Gly Asp Trp Asp Ile
           200                 205                 210
Leu Ile Leu His Tyr Leu Gly Leu Asp His Ile Gly His Ile Ser
           215                 220                 225
Gly Pro Asn Ser Pro Leu Ile Gly Gln Lys Leu Ser Glu Met Asp
           230                 235                 240
Ser Val Leu Met Lys Ile His Thr Ser Leu Gln Ser Lys Glu Arg
           245                 250                 255
Glu Thr Pro Leu Pro Asn Leu Leu Val Leu Cys Gly Asp His Gly
           260                 265                 270
Met Ser Glu Thr Gly Ser His Gly Ala Ser Ser Thr Glu Glu Val
           275                 280                 285
Asn Thr Pro Leu Ile Leu Ile Ser Ser Ala Phe Glu Arg Lys Pro
           290                 295                 300
Gly Asp Ile Arg His Pro Lys His Val Gln
           305                 310
```

<210> SEQ ID NO 141
<211> LENGTH: 754
<212> TYPE: DNA
<213> ORGANISM: Homo Sapien

<400> SEQUENCE: 141

| | |
|---|---:|
| ggcacgaggc aagccttcca ggttatcgtg acgcaccttg aaagtctgag | 50 |
| agctactgcc ctacagaaag ttactagtgc cctaaagctg gcgctggcac | 100 |
| tgatgttact gctgctgttg gagtacaact tccctataga aacaactgc | 150 |
| cagcacctta agaccactca caccttcaga gtgaagaact taaacccgaa | 200 |
| gaaattcagc attcatgacc aggatcacaa agtactggtc ctggactctg | 250 |
| ggaatctcat agcagttcca gataaaaact acatacgccc agagatcttc | 300 |
| tttgcattag cctcatcctt gagctcagcc tctgcggaga aggaagtcc | 350 |
| gattctcctg ggggtctcta aaggggagtt ttgtctctac tgtgacaagg | 400 |
| ataaaggaca aagtcatcca tcccttcagc tgaagaagga gaaactgatg | 450 |

```
aagctggctg cccaaaagga atcagcacgc cggcccttca tcttttatag        500
ggctcaggtg ggctcctgga acatgctgga gtcggcggct caccccggat        550
ggttcatctg cacctcctgc aattgtaatg agcctgttgg ggtgacagat        600
aaatttgaga acaggaaaca cattgaattt tcatttcaac cagttttgcaa       650 agctgaaatg agccccagtg aggtcagcga ttaggaaact gccccattga        700
acgccttcct cgctaatttg aactaattgt ataaaaacac caaacctgct        750
cact                                                          754
```

<210> SEQ ID NO 142
<211> LENGTH: 193
<212> TYPE: PRT
<213> ORGANISM: Homo Sapien

<400> SEQUENCE: 142

```
Met Leu Leu Leu Leu Glu Tyr Asn Phe Pro Ile Glu Asn Asn
1               5                   10                  15

Cys Gln His Leu Lys Thr Thr His Thr Phe Arg Val Lys Asn Leu
                20                  25                  30

Asn Pro Lys Lys Phe Ser Ile His Asp Gln Asp His Lys Val Leu
                35                  40                  45

Val Leu Asp Ser Gly Asn Leu Ile Ala Val Pro Asp Lys Asn Tyr
                50                  55                  60

Ile Arg Pro Glu Ile Phe Phe Ala Leu Ala Ser Ser Leu Ser Ser
                65                  70                  75

Ala Ser Ala Glu Lys Gly Ser Pro Ile Leu Leu Gly Val Ser Lys
                80                  85                  90

Gly Glu Phe Cys Leu Tyr Cys Asp Lys Asp Lys Gly Gln Ser His
                95                  100                 105

Pro Ser Leu Gln Leu Lys Lys Glu Lys Leu Met Lys Leu Ala Ala
                110                 115                 120

Gln Lys Glu Ser Ala Arg Arg Pro Phe Ile Phe Tyr Arg Ala Gln
                125                 130                 135

Val Gly Ser Trp Asn Met Leu Glu Ser Ala Ala His Pro Gly Trp
                140                 145                 150

Phe Ile Cys Thr Ser Cys Asn Cys Asn Glu Pro Val Gly Val Thr
                155                 160                 165

Asp Lys Phe Glu Asn Arg Lys His Ile Glu Phe Ser Phe Gln Pro
                170                 175                 180

Val Cys Lys Ala Glu Met Ser Pro Ser Glu Val Ser Asp
                185                 190
```

<210> SEQ ID NO 143
<211> LENGTH: 961
<212> TYPE: DNA
<213> ORGANISM: Homo Sapien

<400> SEQUENCE: 143

```
ctagagagta tagggcagaa ggatggcaga tgagtgactc cacatccaga        50
gctgcctccc tttaatccag gatcctgtcc ttcctgtcct gtaggagtgc        100
ctgttgccag tgtggggtga gacaagtttg tcccacaggg ctgtctgagc        150
agataagatt aagggctggg tctgtgctca attaactcct gtgggcacgg        200
gggctgggaa gagcaaagtc agcggtgcct acagtcagca ccatgctggg        250
```

|  |  |
|---|---|
| cctgccgtgg aagggaggtc tgtcctgggc gctgctgctg cttctcttag | 300 |
| gctcccagat cctgctgatc tatgcctggc atttccacga gcaaagggac | 350 |
| tgtgatgaac acaatgtcat ggctcgttac ctccctgcca cagtggagtt | 400 |
| tgctgtccac acattcaacc aacagagcaa ggactactat gcctacagac | 450 |
| tgggcacat cttgaattcc tggaaggagc aggtggagtc caagactgta | 500 |
| ttctcaatgg agctactgct ggggagaact aggtgtggga atttgaaga | 550 |
| cgacattgac aactgccatt tccaagaaag cacagagctg aacaatactt | 600 |
| tcacctgctt cttcaccatc agcaccaggc cctggatgac tcagttcagc | 650 |
| ctcctgaaca agacctgctt ggagggattc cactgagtga aacccactca | 700 |
| caggcttgtc catgtgctgc tcccacattc cgtggacatc agcactactc | 750 |
| tcctgaggac tcttcagtgg ctgagcagct ttggacttgt ttgttatcct | 800 |
| attttgcatg tgtttgagat ctcagatcag tgttttagaa aatccacaca | 850 |
| tcttgagcct aatcatgtag tgtagatcat taaacatcag cattttaaga | 900 |
| aaaaaaaaaa aaaaaaaaaa aaaaaaaaaa aaaaaaaaaa aaaaaaaaaa | 950 |
| aaaaaaaaaa a | 961 |

```
<210> SEQ ID NO 144
<211> LENGTH: 147
<212> TYPE: PRT
<213> ORGANISM: Homo Sapien

<400> SEQUENCE: 144

Met Leu Gly Leu Pro Trp Lys Gly Gly Leu Ser Trp Ala Leu Leu
  1               5                  10                  15

Leu Leu Leu Leu Gly Ser Gln Ile Leu Leu Ile Tyr Ala Trp His
                 20                  25                  30

Phe His Glu Gln Arg Asp Cys Asp Glu His Asn Val Met Ala Arg
             35                  40                  45

Tyr Leu Pro Ala Thr Val Glu Phe Ala Val His Thr Phe Asn Gln
         50                  55                  60

Gln Ser Lys Asp Tyr Tyr Ala Tyr Arg Leu Gly His Ile Leu Asn
     65                  70                  75

Ser Trp Lys Glu Gln Val Glu Ser Lys Thr Val Phe Ser Met Glu
 80                  85                  90

Leu Leu Leu Gly Arg Thr Arg Cys Gly Lys Phe Glu Asp Asp Ile
                 95                 100                 105

Asp Asn Cys His Phe Gln Glu Ser Thr Glu Leu Asn Asn Thr Phe
            110                 115                 120

Thr Cys Phe Phe Thr Ile Ser Thr Arg Pro Trp Met Thr Gln Phe
        125                 130                 135

Ser Leu Leu Asn Lys Thr Cys Leu Glu Gly Phe His
    140                 145

<210> SEQ ID NO 145
<211> LENGTH: 1157
<212> TYPE: DNA
<213> ORGANISM: Homo Sapien

<400> SEQUENCE: 145
```

|  |  |
|---|---|
| ctgtgcagct cgaggctcca gaggcacact ccagagagag ccaaggttct | 50 |

```
gacgcgatga ggaagcacct gagctggtgg tggctggcca ctgtctgcat      100
gctgctcttc agccacctct ctgcggtcca gacgaggggc atcaagcaca      150
gaatcaagtg gaaccggaag gccctgccca gcactgccca gatcactgag      200
gcccaggtgg ctgagaaccg cccgggagcc ttcatcaagc aaggccgcaa      250
gctcgacatt gacttcggag ccgagggcaa caggtactac gaggccaact      300
actggcagtt ccccgatggc atccactaca acggctgctc tgaggctaat      350
gtgaccaagg aggcatttgt caccggctgc atcaatgcca cccaggcggc      400
gaaccagggg gagttccaga agccagacaa caagctccac cagcaggtgc      450
tctggcggct ggtccaggag ctctgctccc tcaagcattg cgagttttgg      500
ttggagaggg gcgcaggact tcgggtcacc atgcaccagc cagtgctcct      550
ctgccttctg gctttgatct ggctcatggt gaaataagct tgccaggagg      600
ctggcagtac agagcgcagc agcgagcaaa tcctggcaag tgacccagct      650
cttctccccc aaacccacgc gtgttctgaa ggtgcccagg agcggcgatg      700
cactcgcact gcaaatgccg ctcccacgta tgcgccctgg tatgtgcctg      750
cgttctgata gatgggggac tgtggcttct ccgtcactcc attctcagcc      800
cctagcagag cgtctggcac actagattag tagtaaatgc ttgatgagaa      850
gaacacatca ggcactgcgc cacctgcttc acagtacttc ccaacaactc      900
ttagaggtag gtgtattccc gttttacaga taaggaaact gaggcccaga      950
gagctgaagt actgcaccca gcatcaccag ctagaaagtg gcagagccag     1000
gattcaaccc tggcttgtct aaccccaggt tttctgctct gtccaattcc     1050
agagctgtct ggtgatcact ttatgtctca cagggaccca catccaaaca     1100
tgtatctcta atgaaattgt gaaagctcca tgtttagaaa taaatgaaaa     1150
cacctga                                                   1157
```

<210> SEQ ID NO 146
<211> LENGTH: 176
<212> TYPE: PRT
<213> ORGANISM: Homo Sapien

<400> SEQUENCE: 146

```
Met Arg Lys His Leu Ser Trp Trp Leu Ala Thr Val Cys Met
  1               5                  10                  15

Leu Leu Phe Ser His Leu Ser Ala Val Gln Thr Arg Gly Ile Lys
                 20                  25                  30

His Arg Ile Lys Trp Asn Arg Lys Ala Leu Pro Ser Thr Ala Gln
                 35                  40                  45

Ile Thr Glu Ala Gln Val Ala Glu Asn Arg Pro Gly Ala Phe Ile
                 50                  55                  60

Lys Gln Gly Arg Lys Leu Asp Ile Asp Phe Gly Ala Glu Gly Asn
                 65                  70                  75

Arg Tyr Tyr Glu Ala Asn Tyr Trp Gln Phe Pro Asp Gly Ile His
                 80                  85                  90

Tyr Asn Gly Cys Ser Glu Ala Asn Val Thr Lys Glu Ala Phe Val
                 95                 100                 105

Thr Gly Cys Ile Asn Ala Thr Gln Ala Ala Asn Gln Gly Glu Phe
                110                 115                 120

Gln Lys Pro Asp Asn Lys Leu His Gln Gln Val Leu Trp Arg Leu
```

```
                    125                 130                 135
Val Gln Glu Leu Cys Ser Leu Lys His Cys Glu Phe Trp Leu Glu
                140                 145                 150

Arg Gly Ala Gly Leu Arg Val Thr Met His Gln Pro Val Leu Leu
            155                 160                 165

Cys Leu Leu Ala Leu Ile Trp Leu Met Val Lys
        170                 175

<210> SEQ ID NO 147
<211> LENGTH: 333
<212> TYPE: DNA
<213> ORGANISM: Homo Sapien

<400> SEQUENCE: 147
gccttggcct cccaaagggc tgggattata ggcgtgacca ccatgtctgg        50
tccagagtct catttcctga tgatttatag actcaaagaa aactcatgtt       100
cagaagctct cttctcttct ggcctcctct ctgtcttctt tccctctttc       150
ttcttatttt aattagtagc atctactcag agtcatgcaa gctggaaatc       200
tttcattttg cttgtcagtg gggtaggtca ctgagtctta gtttttatt        250 tttgaaattt caactttcag attcaggggg tacatgtgaa ggtttgtttt       300
atgagtatat tgcatgatgc tgaggtttgg ggt                         333

<210> SEQ ID NO 148
<211> LENGTH: 73
<212> TYPE: PRT
<213> ORGANISM: Homo Sapien

<400> SEQUENCE: 148

Met Phe Arg Ser Ser Leu Leu Phe Trp Pro Pro Leu Cys Leu Leu
  1               5                  10                  15

Ser Leu Phe Leu Leu Ile Leu Ile Ser Ser Ile Tyr Ser Glu Ser
                 20                  25                  30

Cys Lys Leu Glu Ile Phe His Phe Ala Cys Gln Trp Gly Arg Ser
             35                  40                  45

Leu Ser Leu Ser Phe Tyr Phe Leu Lys Phe Gln Leu Ser Asp Ser
         50                  55                  60

Gly Gly Thr Cys Glu Gly Leu Phe Tyr Glu Tyr Ile Ala
     65                  70

<210> SEQ ID NO 149
<211> LENGTH: 1893
<212> TYPE: DNA
<213> ORGANISM: Homo Sapien

<400> SEQUENCE: 149
gtctccgcgt cacaggaact tcagcaccca cagggcggac agcgctcccc        50
tctacctgga gacttgactc ccgcgcgccc caaccctgct tatcccttga       100
ccgtcgagtg tcagagatcc tgcagccgcc cagtcccggc ccctctcccg       150
ccccacaccc accctcctgg ctcttcctgt ttttactcct ccttttcatt       200
cataacaaaa gctacagctc caggagccca gcgccgggct gtgacccaag       250
ccgagcgtgg aagaatgggg ttcctcggga ccggcacttg gattctggtg       300
ttagtgctcc cgattcaagc tttccccaaa cctggaggaa gccaagacaa       350
atctctacat aatagagaat taagtgcaga aagacctttg aatgaacaga       400
```

```
ttgctgaagc agaagaagac aagattaaaa aaacatatcc tccagaaaac      450
aagccaggtc agagcaacta ttcttttgtt gataacttga acctgctaaa      500
ggcaataaca gaaaggaaaa aaattgagaa agaaagacaa tctataagaa      550
gctccccact tgataataag ttgaatgtgg aagatgttga ttcaaccaag      600
aatcgaaaac tgatcgatga ttatgactct actaagagtg gattggatca      650
taaatttcaa gatgatccag atggtcttca tcaactagac gggactcctt      700
taaccgctga agacattgtc cataaaatcg ctgccaggat ttatgaagaa      750
aatgacagag ccgtgtttga caagattgtt tctaaactac ttaatctcgg      800
ccttatcaca gaaagccaag cacatacact ggaagatgaa gtagcagagg      850
ttttacaaaa attaatctca aaggaagcca acaattatga ggaggatccc      900
aataagccca aagctggac tgagaatcag gctggaaaaa taccagagaa       950
agtgactcca atggcagcaa ttcaagatgg tcttgctaag ggagaaaacg     1000
atgaaacagt atctaacaca ttaaccttga caaatggctt ggaaaggaga     1050
actaaaaccct acagtgaaga caactttgag gaactccaat atttcccaaa    1100
tttctatgcg ctactgaaaa gtattgattc agaaaaagaa gcaaagagaa     1150
aagaaacact gattactatc atgaaaacac tgattgactt tgtgaagatg     1200
atggtgaaat atggaacaat atctccagaa gaaggtgttt cctaccttga     1250
aaacttggat gaaatgattg ctcttcagac caaaaacaag ctagaaaaaa     1300
atgctactga caatataagc aagcttttcc cagcaccatc agagaagagt     1350
catgaagaaa cagacagtac caaggaagaa gcagctaaga tggaaaagga     1400
atatggaagc ttgaaggatt ccacaaaaga tgataactcc aacccaggag     1450
gaaagacaga tgaacccaaa ggaaaaacag aagcctattt ggaagccatc     1500
agaaaaaata ttgaatggtt gaagaaacat gacaaaaagg gaaataaaga     1550
agattatgac ctttcaaaga tgagagactt catcaataaa caagctgatg     1600
cttatgtgga gaaaggcatc cttgacaagg aagaagccga ggccatcaag     1650
cgcatttata gcagcctgta aaaatggcaa agatccagg agtctttcaa      1700
ctgtttcaga aaacataata tagcttaaaa cacttctaat tctgtgatta     1750
aaatttttg acccaagggt tattagaaag tgctgaattt acagtagtta      1800
accttttaca agtggttaaa acatagcttt cttcccgtaa aaactatctg     1850
aaagtaaagt tgtatgtaag ctgaaaaaaa aaaaaaaaa aaa             1893
```

<210> SEQ ID NO 150
<211> LENGTH: 468
<212> TYPE: PRT
<213> ORGANISM: Homo Sapien

<400> SEQUENCE: 150

Met Gly Phe Leu Gly Thr Gly Thr Trp Ile Leu Val Leu Val Leu
1               5                   10                  15

Pro Ile Gln Ala Phe Pro Lys Pro Gly Gly Ser Gln Asp Lys Ser
                20                  25                  30

Leu His Asn Arg Glu Leu Ser Ala Glu Arg Pro Leu Asn Glu Gln
                35                  40                  45

Ile Ala Glu Ala Glu Glu Asp Lys Ile Lys Lys Thr Tyr Pro Pro

-continued

```
                50                   55                    60
Glu Asn Lys Pro Gly Gln Ser Asn Tyr Ser Phe Val Asp Asn Leu
                65                   70                    75
Asn Leu Leu Lys Ala Ile Thr Glu Lys Glu Lys Ile Glu Lys Glu
                80                   85                    90
Arg Gln Ser Ile Arg Ser Ser Pro Leu Asp Asn Lys Leu Asn Val
                95                  100                   105
Glu Asp Val Asp Ser Thr Lys Asn Arg Lys Leu Ile Asp Asp Tyr
               110                  115                   120
Asp Ser Thr Lys Ser Gly Leu Asp His Lys Phe Gln Asp Asp Pro
               125                  130                   135
Asp Gly Leu His Gln Leu Asp Gly Thr Pro Leu Thr Ala Glu Asp
               140                  145                   150
Ile Val His Lys Ile Ala Ala Arg Ile Tyr Glu Glu Asn Asp Arg
               155                  160                   165
Ala Val Phe Asp Lys Ile Val Ser Lys Leu Leu Asn Leu Gly Leu
               170                  175                   180
Ile Thr Glu Ser Gln Ala His Thr Leu Glu Asp Glu Val Ala Glu
               185                  190                   195
Val Leu Gln Lys Leu Ile Ser Lys Glu Ala Asn Asn Tyr Glu Glu
               200                  205                   210
Asp Pro Asn Lys Pro Thr Ser Trp Thr Glu Asn Gln Ala Gly Lys
               215                  220                   225
Ile Pro Glu Lys Val Thr Pro Met Ala Ala Ile Gln Asp Gly Leu
               230                  235                   240
Ala Lys Gly Glu Asn Asp Glu Thr Val Ser Asn Thr Leu Thr Leu
               245                  250                   255
Thr Asn Gly Leu Glu Arg Arg Thr Lys Thr Tyr Ser Glu Asp Asn
               260                  265                   270
Phe Glu Glu Leu Gln Tyr Phe Pro Asn Phe Tyr Ala Leu Leu Lys
               275                  280                   285
Ser Ile Asp Ser Glu Lys Glu Ala Lys Glu Lys Glu Thr Leu Ile
               290                  295                   300
Thr Ile Met Lys Thr Leu Ile Asp Phe Val Lys Met Met Val Lys
               305                  310                   315
Tyr Gly Thr Ile Ser Pro Glu Glu Gly Val Ser Tyr Leu Glu Asn
               320                  325                   330
Leu Asp Glu Met Ile Ala Leu Gln Thr Lys Asn Lys Leu Glu Lys
               335                  340                   345
Asn Ala Thr Asp Asn Ile Ser Lys Leu Phe Pro Ala Pro Ser Glu
               350                  355                   360
Lys Ser His Glu Glu Thr Asp Ser Thr Lys Glu Glu Ala Ala Lys
               365                  370                   375
Met Glu Lys Glu Tyr Gly Ser Leu Lys Asp Ser Thr Lys Asp Asp
               380                  385                   390
Asn Ser Asn Pro Gly Gly Lys Thr Asp Glu Pro Lys Gly Lys Thr
               395                  400                   405
Glu Ala Tyr Leu Glu Ala Ile Arg Lys Asn Ile Glu Trp Leu Lys
               410                  415                   420
Lys His Asp Lys Lys Gly Asn Lys Glu Asp Tyr Asp Leu Ser Lys
               425                  430                   435
Met Arg Asp Phe Ile Asn Lys Gln Ala Asp Ala Tyr Val Glu Lys
               440                  445                   450
```

```
Gly Ile Leu Asp Lys Glu Glu Ala Glu Ala Ile Lys Arg Ile Tyr
            455                 460                 465
Ser Ser Leu

<210> SEQ ID NO 151
<211> LENGTH: 2598
<212> TYPE: DNA
<213> ORGANISM: Homo Sapien

<400> SEQUENCE: 151
cggctcgagg ctcccgccag gagaaaggaa cattctgagg ggagtctaca        50
ccctgtggag ctcaagatgg tcctgagtgg ggcgctgtgc ttccgaatga       100
aggactcggc attgaaggtg ctttatctgc ataataacca gcttctagct       150
ggagggctgc atgcagggaa ggtcattaaa ggtgaagaga tcagcgtggt       200
ccccaatcgg tggctggatg ccagcctgtc ccccgtcatc ctgggtgtcc       250
agggtggaag ccagtgcctg tcatgtgggg tgggcaggga gccgactcta       300
acactagagc cagtgaacat catggagctc tatcttggtg ccaaggaatc       350
caagagcttc accttctacc ggcgggacat ggggctcacc tccagcttcg       400
agtcggctgc ctacccgggc tggttcctgt gcacggtgcc tgaagccgat       450
cagcctgtca gactcaccca gcttcccgag aatggtggct ggaatgcccc       500
catcacagac ttctacttcc agcagtgtga ctagggcaac gtgcccccca       550
gaactccctg ggcagagcca gctcgggtga ggggtgagtg gaggagaccc       600
atggcggaca tcactctctc tgctctcag gaccccacg tctgacttag        650 tgggcacctg accactttgt cttctggttc ccagtttgga taaattctga       700
gatttggagc tcagtccacg gtcctccccc actggatggt gctactgctg       750
tggaaccttg taaaaaccat gtggggtaaa ctgggaataa catgaaaaga       800
tttctgtggg ggtggggtgg gggagtggtg ggaatcattc ctgcttaatg       850
gtaactgaca agtgttaccc tgagccccgc aggccaaccc atccccagtt       900
gagccttata gggtcagtag ctctccacat gaagtcctgt cactcaccac       950
tgtgcaggag agggaggtgg tcatagagtc agggatctat ggcccttggc      1000
ccagccccac ccccttccct ttaatcctgc cactgtcata tgctaccttt      1050
cctatctctt ccctcatcat cttgttgtgg gcatgaggag gtggtgatgt      1100
cagaagaaat ggctcgagct cagaagataa agataagta gggtatgctg       1150 atcctctttt aaaacccaa gatacaatca aaatcccaga tgctggtctc       1200
tattcccatg aaaagtgct catgacatat tgagaagacc tacttacaaa       1250
gtggcatata ttgcaattta ttttaattaa agataccta tttatatatt       1300 tctttataga aaaagtctg gaagagttta cttcaattgt agcaatgtca       1350
gggtggtggc agtataggtg attttttctt taattctgtt aatttatctg       1400
tatttcctaa tttttctaca atgaagatga attccttgta taaaaataag      1450 aaagaaatt aatcttgagg taagcagagc agacatcatc tctgattgtc       1500
ctcagcctcc acttccccag agtaaattca aattgaatcg agctctgctg       1550 ctctggtttgg ttgtagtagt gatcaggaaa cagatctcag caaagccact     1600
gaggaggagg ctgtgctgag tttgtgtggc tggaatctct gggtaaggaa      1650
```

-continued

| | |
|---|---|
| cttaaagaac aaaaatcatc tggtaattct ttcctagaag gatcacagcc | 1700 |
| cctgggattc caaggcattg gatccagtct ctaagaaggc tgctgtactg | 1750 |
| gttgaattgt gtcccccctca aattcacatc cttcttggaa tctcagtctg | 1800 |
| tgagtttatt tggagataag gtctctgcag atgtagttag ttaagacaag | 1850 |
| gtcatgctgg atgaaggtag acctaaattc aatatgactg gtttccttgt | 1900 |
| atgaaaagga gaggacacag agacagagga gacgcgggga agactatgta | 1950 |
| aagatgaagg cagagatcgg agttttgcag ccacaagcta agaaacacca | 2000 |
| aggattgtgg caaccatcag aagcttggaa gaggcaaaga agaattcttc | 2050 |
| cctagaggct ttagagggat aacggctctg ctgaaaccttt aatctcagac | 2100 |
| ttccagcctc ctgaacgaag aaagaataaa tttcggctgt tttaagccac | 2150 |
| caaggataat tggttacagc agctctagga aactaataca gctgctaaaa | 2200 |
| tgatccctgt ctcctcgtgt ttacattctg tgtgtgtccc ctcccacaat | 2250 |
| gtaccaaagt tgtctttgtg accaatagaa tatggcagaa gtgatggcat | 2300 |
| gccacttcca agattaggtt ataaaagaca ctgcagcttc tacttgagcc | 2350 |
| ctctctctct gccacccacc gcccccaatc tatcttggct cactcgctct | 2400 |
| gggggaagct agctgccatg ctatgagcag gcctataaag agacttacgt | 2450 |
| ggtaaaaaat gaagtctcct gcccacagcc acattagtga acctagaagc | 2500 |
| agagactctg tgagataatc gatgtttgtt gttttaagtt gctcagtttt | 2550 |
| ggtctaactt gttatgcagc aatagataaa taatatgcag agaaagag | 2598 |

<210> SEQ ID NO 152
<211> LENGTH: 155
<212> TYPE: PRT
<213> ORGANISM: Homo Sapien

<400> SEQUENCE: 152

```
Met Val Leu Ser Gly Ala Leu Cys Phe Arg Met Lys Asp Ser Ala
 1               5                  10                  15

Leu Lys Val Leu Tyr Leu His Asn Asn Gln Leu Leu Ala Gly Gly
                20                  25                  30

Leu His Ala Gly Lys Val Ile Lys Gly Glu Glu Ile Ser Val Val
                35                  40                  45

Pro Asn Arg Trp Leu Asp Ala Ser Leu Ser Pro Val Ile Leu Gly
                50                  55                  60

Val Gln Gly Gly Ser Gln Cys Leu Ser Cys Gly Val Gly Gln Glu
                65                  70                  75

Pro Thr Leu Thr Leu Glu Pro Val Asn Ile Met Glu Leu Tyr Leu
                80                  85                  90

Gly Ala Lys Glu Ser Lys Ser Phe Thr Phe Tyr Arg Arg Asp Met
                95                 100                 105

Gly Leu Thr Ser Ser Phe Glu Ser Ala Ala Tyr Pro Gly Trp Phe
               110                 115                 120

Leu Cys Thr Val Pro Glu Ala Asp Gln Pro Val Arg Leu Thr Gln
               125                 130                 135

Leu Pro Glu Asn Gly Gly Trp Asn Ala Pro Ile Thr Asp Phe Tyr
               140                 145                 150

Phe Gln Gln Cys Asp
               155
```

<210> SEQ ID NO 153
<211> LENGTH: 1152
<212> TYPE: DNA
<213> ORGANISM: Homo Sapien

<400> SEQUENCE: 153

| | | | | | |
|---|---|---|---|---|---|
| cttcagaaca | ggttctcctt | ccccagtcac | cagttgctcg | agttagaatt | 50 |
| gtctgcaatg | gccgccctgc | agaaatctgt | gagctctttc | cttatgggga | 100 |
| ccctggccac | cagctgcctc | cttctcttgg | ccctcttggt | acagggagga | 150 |
| gcagctgcgc | ccatcagctc | ccactgcagg | cttgacaagt | ccaacttcca | 200 |
| gcagccctat | atcaccaacc | gcaccttcat | gctggctaag | gaggctagct | 250 |
| tggctgataa | caacacagac | gttcgtctca | ttggggagaa | actgttccac | 300 |
| ggagtcagta | tgagtgagcg | ctgctatctg | atgaagcagg | tgctgaactt | 350 |
| caccccttgaa | gaagtgctgt | tccctcaatc | tgataggttc | cagccttata | 400 |
| tgcaggaggt | ggtgcccttc | ctggccaggc | tcagcaacag | gctaagcaca | 450 |
| tgtcatattg | aaggtgatga | cctgcatatc | cagaggaatg | tgcaaaagct | 500 |
| gaaggacaca | gtgaaaaagc | ttggagagag | tggagagatc | aaagcaattg | 550 |
| gagaactgga | tttgctgttt | atgtctctga | gaaatgcctg | catttgacca | 600 |
| gagcaaagct | gaaaaatgaa | taactaaccc | cctttccctg | ctagaaataa | 650 |
| caattagatg | ccccaaagcg | attttttttta | accaaaagga | agatgggaag | 700 |
| ccaaactcca | tcatgatggg | tggattccaa | atgaacccct | gcgttagtta | 750 |
| caaaggaaac | caatgccact | tttgtttata | agaccagaag | gtagactttc | 800 |
| taagcataga | tatttattga | taacatttca | ttgtaactgg | tgttctatac | 850 |
| acagaaaaca | atttatttttt | taaataattg | tcttttttcca | taaaaaagat | 900 |
| tactttccat | tcctttaggg | gaaaaaccc | ctaaatagct | tcatgttttcc | 950 |
| ataatcagta | ctttatattt | ataaatgtat | ttattattat | tataagactg | 1000 |
| cattttattt | atatcatttt | attaatatgg | atttatttat | agaaacatca | 1050 |
| ttcgatattg | ctacttgagt | gtaaggctaa | tattgatatt | tatgacaata | 1100 |
| attatagagc | tataacatgt | ttatttgacc | tcaataaaca | cttggatatc | 1150 |
| cc | | | | | 1152 |

<210> SEQ ID NO 154
<211> LENGTH: 179
<212> TYPE: PRT
<213> ORGANISM: Homo Sapien

<400> SEQUENCE: 154

```
Met Ala Ala Leu Gln Lys Ser Val Ser Ser Phe Leu Met Gly Thr
 1               5                  10                  15

Leu Ala Thr Ser Cys Leu Leu Leu Ala Leu Leu Val Gln Gly
            20                  25                  30

Gly Ala Ala Ala Pro Ile Ser Ser His Cys Arg Leu Asp Lys Ser
        35                  40                  45

Asn Phe Gln Gln Pro Tyr Ile Thr Asn Arg Thr Phe Met Leu Ala
            50                  55                  60

Lys Glu Ala Ser Leu Ala Asp Asn Asn Thr Asp Val Arg Leu Ile
        65                  70                  75
```

-continued

Gly Glu Lys Leu Phe His Gly Val Ser Met Ser Glu Arg Cys Tyr
                 80                  85                  90

Leu Met Lys Gln Val Leu Asn Phe Thr Leu Glu Glu Val Leu Phe
             95                 100                 105

Pro Gln Ser Asp Arg Phe Gln Pro Tyr Met Gln Glu Val Val Pro
        110                 115                 120

Phe Leu Ala Arg Leu Ser Asn Arg Leu Ser Thr Cys His Ile Glu
        125                 130                 135

Gly Asp Asp Leu His Ile Gln Arg Asn Val Gln Lys Leu Lys Asp
        140                 145                 150

Thr Val Lys Lys Leu Gly Glu Ser Gly Glu Ile Lys Ala Ile Gly
        155                 160                 165

Glu Leu Asp Leu Leu Phe Met Ser Leu Arg Asn Ala Cys Ile
        170                 175

<210> SEQ ID NO 155
<211> LENGTH: 1320
<212> TYPE: DNA
<213> ORGANISM: Homo Sapien

<400> SEQUENCE: 155

| ggcttgctga aaataaaatc aggactccta acctgctcca gtcagcctgc | 50 |
| ttccacgagg cctgtcagtc agtgcccgac ttgtgactga gtgtgcagtg | 100 |
| cccagcatgt accaggtcag tgcagagggc tgcctgaggg ctgtgctgag | 150 |
| agggagagga gcagagatgc tgctgagggt ggagggaggc caagctgcca | 200 |
| ggtttggggc tggggccaa gtggagtgag aaactgggat cccaggggga | 250 |
| gggtgcagat gagggagcga cccagattag gtgaggacag ttctctcatt | 300 |
| agccttttcc tacaggtggt tgcattcttg gcaatggtca tgggaaccca | 350 |
| cacctacagc cactggccca gctgctgccc cagcaaaggg caggacacct | 400 |
| ctgaggagct gctgaggtgg agcactgtgc ctgtgcctcc cctagagcct | 450 |
| gctaggccca accgccaccc agagtcctgt agggccagtg aagatggacc | 500 |
| cctcaacagc agggccatct cccctggag atatgagttg acagagact | 550 |
| tgaaccggct ccccaggac ctgtaccacg cccgttgcct gtgcccgcac | 600 |
| tgcgtcagcc tacagacagg ctcccacatg accccgggg gcaactcgga | 650 |
| gctgctctac cacaaccaga ctgtcttcta caggcggcca tgccatggcg | 700 |
| agaagggcac ccacaagggc tactgcctgg agcgcaggct gtaccgtgtt | 750 |
| tccttagctt gtgtgtgtgt gcggccccgt gtgatgggct agccggacct | 800 |
| gctggaggct ggtcccttt tgggaaacct ggagccaggt gtacaaccac | 850 |
| ttgccatgaa gggccaggat gcccagatgc ttggcccctg tgaagtgctg | 900 |
| tctggagcag caggatcccg ggacaggatg gggggctttg ggaaaacct | 950 |
| gcacttctgc acattttgaa aagagcagct gctgcttagg gccgccggaa | 1000 |
| gctggtgtcc tgtcattttc tctcaggaaa ggttttcaaa gttctgccca | 1050 |
| tttctggagg ccaccactcc tgtctcttcc tcttttccca tccctgcta | 1100 |
| ccctggccca gcacaggcac tttctagata tttccccctt gctggagaag | 1150 |
| aaagagcccc tggttttatt tgtttgttta ctcatcactc agtgagcatc | 1200 |
| tactttgggt gcattctagt gtagttacta gtcttttgac atggatgatt | 1250 |

-continued

```
ctgaggagga agctgttatt gaatgtatag agatttatcc aaataaatat            1300
ctttatttaa aaatgaaaaa                                              1320
```

<210> SEQ ID NO 156
<211> LENGTH: 177
<212> TYPE: PRT
<213> ORGANISM: Homo Sapien

<400> SEQUENCE: 156

```
Met Arg Glu Arg Pro Arg Leu Gly Glu Asp Ser Ser Leu Ile Ser
  1               5                  10                  15

Leu Phe Leu Gln Val Val Ala Phe Leu Ala Met Val Met Gly Thr
                 20                  25                  30

His Thr Tyr Ser His Trp Pro Ser Cys Cys Pro Ser Lys Gly Gln
             35                  40                  45

Asp Thr Ser Glu Glu Leu Leu Arg Trp Ser Thr Val Pro Val Pro
         50                  55                  60

Pro Leu Glu Pro Ala Arg Pro Asn Arg His Pro Glu Ser Cys Arg
     65                  70                  75

Ala Ser Glu Asp Gly Pro Leu Asn Ser Arg Ala Ile Ser Pro Trp
 80                  85                  90

Arg Tyr Glu Leu Asp Arg Asp Leu Asn Arg Leu Pro Gln Asp Leu
                 95                 100                 105

Tyr His Ala Arg Cys Leu Cys Pro His Cys Val Ser Leu Gln Thr
            110                 115                 120

Gly Ser His Met Asp Pro Arg Gly Asn Ser Glu Leu Leu Tyr His
        125                 130                 135

Asn Gln Thr Val Phe Tyr Arg Arg Pro Cys His Gly Glu Lys Gly
    140                 145                 150

Thr His Lys Gly Tyr Cys Leu Glu Arg Arg Leu Tyr Arg Val Ser
                155                 160                 165

Leu Ala Cys Val Cys Val Arg Pro Arg Val Met Gly
            170                 175
```

<210> SEQ ID NO 157
<211> LENGTH: 1515
<212> TYPE: DNA
<213> ORGANISM: Homo Sapien

<400> SEQUENCE: 157

```
ccggcgatgt cgctcgtgct gctaagcctg ccgcgctgt gcaggagcgc              50 cgtaccccga gagccgaccg ttcaatgtgg ctctgaaact gggccatctc            100
cagagtggat gctacaacat gatctaatcc ccggagactt gagggacctc            150
cgagtagaac ctgttacaac tagtgttgca acagggact attcaatttt             200 gatgaatgta agctgggtac tccgggcaga tgccagcatc cgcttgttga            250
aggccaccaa gatttgtgtg acgggcaaaa gcaacttcca gtcctacagc            300
tgtgtgaggt gcaattacac agaggccttc cagactcaga ccagaccctc            350
tggtggtaaa tggacatttt cctacatcgg cttccctgta gagctgaaca            400
cagtctattt cattggggcc cataatattc ctaatgcaaa tatgaatgaa            450
gatggccctt ccatgtctgt gaatttcacc tcaccaggct gcctagacca            500
cataatgaaa tataaaaaaa agtgtgtcaa ggccggaagc ctgtgggatc            550
```

| | | |
|---|---|---|
| cgaacatcac tgcttgtaag aagaatgagg agacagtaga agtgaacttc | | 600 |
| acaaccactc ccctgggaaa cagatacatg gctcttatcc aacacagcac | | 650 |
| tatcatcggg ttttctcagg tgtttgagcc acaccagaag aaacaaacgc | | 700 |
| gagcttcagt ggtgattcca gtgactgggg atagtgaagg tgctacggtg | | 750 |
| cagctgactc catatttccc tacttgtggc agcgactgca tccgacataa | | 800 |
| aggaacagtt gtgctctgcc cacaaacagg cgtccctttc cctctggata | | 850 |
| acaacaaaag caagccggga ggctggctgc ctctcctcct gctgtctctg | | 900 |
| ctggtggcca catgggtgct ggtggcaggg atctatctaa tgtggaggca | | 950 |
| cgaaaggatc aagaagactt cctttttctac caccacacta ctgccccca | | 1000 |
| ttaaggttct tgtggtttac ccatctgaaa tatgtttcca tcacacaatt | | 1050 |
| tgttacttca ctgaatttct tcaaaaccat tgcagaagtg aggtcatcct | | 1100 |
| tgaaagtgg cagaaaaaga aaatagcaga gatgggtcca gtgcagtggc | | 1150 |
| ttgccactca aagaaggca gcagacaaag tcgtcttcct tctttccaat | | 1200 |
| gacgtcaaca gtgtgtgcga tggtacctgt ggcaagagcg agggcagtcc | | 1250 |
| cagtgagaac tctcaagacc tcttcccct tgcctttaac cttttctgca | | 1300 |
| gtgatctaag aagccagatt catctgcaca aatacgtggt ggtctacttt | | 1350 |
| agagagattg atacaaaaga cgattacaat gctctcagtg tctgccccaa | | 1400 |
| gtaccacctc atgaaggatg ccactgcttt ctgtgcagaa cttctccatg | | 1450 |
| tcaagcagca ggtgtcagca ggaaaaagat cacaagcctg ccacgatggc | | 1500 |
| tgctgctcct tgtag | | 1515 |

<210> SEQ ID NO 158
<211> LENGTH: 502
<212> TYPE: PRT
<213> ORGANISM: Homo Sapien

<400> SEQUENCE: 158

Met Ser Leu Val Leu Leu Ser Leu Ala Ala Leu Cys Arg Ser Ala
 1               5                  10                  15

Val Pro Arg Glu Pro Thr Val Gln Cys Gly Ser Glu Thr Gly Pro
                20                  25                  30

Ser Pro Glu Trp Met Leu Gln His Asp Leu Ile Pro Gly Asp Leu
                35                  40                  45

Arg Asp Leu Arg Val Glu Pro Val Thr Thr Ser Val Ala Thr Gly
                50                  55                  60

Asp Tyr Ser Ile Leu Met Asn Val Ser Trp Val Leu Arg Ala Asp
                65                  70                  75

Ala Ser Ile Arg Leu Leu Lys Ala Thr Lys Ile Cys Val Thr Gly
                80                  85                  90

Lys Ser Asn Phe Gln Ser Tyr Ser Cys Val Arg Cys Asn Tyr Thr
                95                  100                 105

Glu Ala Phe Gln Thr Gln Thr Arg Pro Ser Gly Gly Lys Trp Thr
                110                 115                 120

Phe Ser Tyr Ile Gly Phe Pro Val Glu Leu Asn Thr Val Tyr Phe
                125                 130                 135

Ile Gly Ala His Asn Ile Pro Asn Ala Asn Met Asn Glu Asp Gly
                140                 145                 150

Pro Ser Met Ser Val Asn Phe Thr Ser Pro Gly Cys Leu Asp His

```
                        155                 160                 165
Ile Met Lys Tyr Lys Lys Cys Val Lys Ala Gly Ser Leu Trp
        170                 175                 180

Asp Pro Asn Ile Thr Ala Cys Lys Lys Asn Glu Glu Thr Val Glu
            185                 190                 195

Val Asn Phe Thr Thr Thr Pro Leu Gly Asn Arg Tyr Met Ala Leu
            200                 205                 210

Ile Gln His Ser Thr Ile Ile Gly Phe Ser Gln Val Phe Glu Pro
            215                 220                 225

His Gln Lys Lys Gln Thr Arg Ala Ser Val Ile Pro Val Thr
        230                 235                 240

Gly Asp Ser Glu Gly Ala Thr Val Gln Leu Thr Pro Tyr Phe Pro
            245                 250                 255

Thr Cys Gly Ser Asp Cys Ile Arg His Lys Gly Thr Val Val Leu
            260                 265                 270

Cys Pro Gln Thr Gly Val Pro Phe Pro Leu Asp Asn Asn Lys Ser
            275                 280                 285

Lys Pro Gly Gly Trp Leu Pro Leu Leu Leu Ser Leu Val
        290                 295                 300

Ala Thr Trp Val Leu Val Ala Gly Ile Tyr Leu Met Trp Arg His
            305                 310                 315

Glu Arg Ile Lys Lys Thr Ser Phe Ser Thr Thr Thr Leu Leu Pro
            320                 325                 330

Pro Ile Lys Val Leu Val Val Tyr Pro Ser Glu Ile Cys Phe His
            335                 340                 345

His Thr Ile Cys Tyr Phe Thr Glu Phe Leu Gln Asn His Cys Arg
            350                 355                 360

Ser Glu Val Ile Leu Glu Lys Trp Gln Lys Lys Ile Ala Glu
        365                 370                 375

Met Gly Pro Val Gln Trp Leu Ala Thr Gln Lys Lys Ala Ala Asp
            380                 385                 390

Lys Val Val Phe Leu Leu Ser Asn Asp Val Asn Ser Val Cys Asp
            395                 400                 405

Gly Thr Cys Gly Lys Ser Glu Gly Ser Pro Ser Glu Asn Ser Gln
            410                 415                 420

Asp Leu Phe Pro Leu Ala Phe Asn Leu Phe Cys Ser Asp Leu Arg
            425                 430                 435

Ser Gln Ile His Leu His Lys Tyr Val Val Tyr Phe Arg Glu
        440                 445                 450

Ile Asp Thr Lys Asp Asp Tyr Asn Ala Leu Ser Val Cys Pro Lys
            455                 460                 465

Tyr His Leu Met Lys Asp Ala Thr Ala Phe Cys Ala Glu Leu Leu
            470                 475                 480

His Val Lys Gln Gln Val Ser Ala Gly Lys Arg Ser Gln Ala Cys
            485                 490                 495

His Asp Gly Cys Cys Ser Leu
            500

<210> SEQ ID NO 159
<211> LENGTH: 535
<212> TYPE: DNA
<213> ORGANISM: Homo Sapien

<400> SEQUENCE: 159
```

-continued

| | |
|---|---|
| agccaccagc gcaacatgac agtgaagacc ctgcatggcc cagccatggt | 50 |
| caagtacttg ctgctgtcga tattggggct tgcctttctg agtgaggcgg | 100 |
| cagctcggaa aatccccaaa gtaggacata cttttttcca aaagcctgag | 150 |
| agttgcccgc ctgtgccagg aggtagtatg aagcttgaca ttggcatcat | 200 |
| caatgaaaac cagcgcgttt ccatgtcacg taacatcgag agccgctcca | 250 |
| cctcccctg gaattacact gtcacttggg accccaaccg gtaccctcg | 300 |
| gaagttgtac aggcccagtg taggaacttg ggctgcatca atgctcaagg | 350 |
| aaaggaagac atctccatga attccgttcc catccagcaa gagaccctgg | 400 |
| tcgtccggag gaagcaccaa ggctgctctg tttctttcca gttggagaag | 450 |
| gtgctggtga ctgttggctg cacctgcgtc accctgtca tccaccatgt | 500 |
| gcagtaagag gtgcatatcc actcagctga agaag | 535 |

<210> SEQ ID NO 160
<211> LENGTH: 163
<212> TYPE: PRT
<213> ORGANISM: Homo Sapien

<400> SEQUENCE: 160

```
Met Thr Val Lys Thr Leu His Gly Pro Ala Met Val Lys Tyr Leu
  1               5                  10                  15
Leu Leu Ser Ile Leu Gly Leu Ala Phe Leu Ser Glu Ala Ala Ala
                 20                  25                  30
Arg Lys Ile Pro Lys Val Gly His Thr Phe Phe Gln Lys Pro Glu
                 35                  40                  45
Ser Cys Pro Pro Val Pro Gly Gly Ser Met Lys Leu Asp Ile Gly
                 50                  55                  60
Ile Ile Asn Glu Asn Gln Arg Val Ser Met Ser Arg Asn Ile Glu
                 65                  70                  75
Ser Arg Ser Thr Ser Pro Trp Asn Tyr Thr Val Thr Trp Asp Pro
                 80                  85                  90
Asn Arg Tyr Pro Ser Glu Val Val Gln Ala Gln Cys Arg Asn Leu
                 95                 100                 105
Gly Cys Ile Asn Ala Gln Gly Lys Glu Asp Ile Ser Met Asn Ser
                110                 115                 120
Val Pro Ile Gln Gln Glu Thr Leu Val Val Arg Arg Lys His Gln
                125                 130                 135
Gly Cys Ser Val Ser Phe Gln Leu Glu Lys Val Leu Val Thr Val
                140                 145                 150
Gly Cys Thr Cys Val Thr Pro Val Ile His His Val Gln
                155                 160
```

<210> SEQ ID NO 161
<211> LENGTH: 2380
<212> TYPE: DNA
<213> ORGANISM: Homo Sapien

<400> SEQUENCE: 161

| | |
|---|---|
| acactggcca aacaaaaacg aaagcactcc gtgctggaag taggaggaga | 50 |
| gtcaggactc ccaggacaga gagtgcacaa actacccagc acagccccct | 100 |
| ccgcccctc tggaggctga agagggattc cagcccctgc acccacaga | 150 |
| cacgggctga ctgggtgtc tgccccctt gggggggggc agcacagggc | 200 |

-continued

| | |
|---|---|
| ctcaggcctg ggtgccacct ggcacctaga agatgcctgt gccctggttc | 250 |
| ttgctgtcct tggcactggg ccgaagccca gtggtccttt ctctggagag | 300 |
| gcttgtgggg cctcaggacg ctacccactg ctctccgggc ctctcctgcc | 350 |
| gcctctggga cagtgacata tctgcctgc ctggggacat cgtgcctgct | 400 |
| ccgggccccg tgctggcgcc tacgcacctg cagacagagc tggtgctgag | 450 |
| gtgccagaag gagaccgact gtgacctctg tctgcgtgtg gctgtccact | 500 |
| tggccgtgca tgggcactgg gaagagcctg aagatgagga aaagtttgga | 550 |
| ggagcagctg actcagggt ggaggagcct aggaatgcct ctctccaggc | 600 |
| ccaagtcgtg ctctccttcc aggcctaccc tactgcccgc tgcgtcctgc | 650 |
| tggaggtgca agtgcctgct gcccttgtgc agtttggtca gtctgtgggc | 700 |
| tctgtggtat atgactgctt cgaggctgcc ctagggagtg aggtacgaat | 750 |
| ctggtcctat actcagccca ggtacgagaa ggaactcaac cacacacagc | 800 |
| agctgcctgc cctgccctgg ctcaacgtgt cagcagatgg tgacaacgtg | 850 |
| catctggttc tgaatgtctc tgaggagcag cacttcggcc tctccctgta | 900 |
| ctggaatcag gtccagggcc ccccaaaacc ccggtggcac aaaaacctga | 950 |
| ctggaccgca gatcattacc ttgaaccaca cagacctggt tccctgcctc | 1000 |
| tgtattcagg tgtggcctct ggaacctgac tccgttagga cgaacatctg | 1050 |
| cccccttcagg gaggaccccc cgcacaccca gaacctctgg caagccgccc | 1100 |
| gactgcgact gctgaccctg cagagctggc tgctggacgc accgtgctcg | 1150 |
| ctgcccgcag aagcggcact gtgctggcgg gctccgggtg gggaccccctg | 1200 |
| ccagccactg gtcccaccgc tttcctggga gaacgtcact gtggacaagg | 1250 |
| ttctcgagtt cccattgctg aaaggccacc ctaacctctg tgttcaggtg | 1300 |
| aacagctcgg agaagctgca gctgcaggag tgcttgtggg ctgactccct | 1350 |
| ggggcctctc aaagacgatg tgctactgtt ggagacacga ggcccccagg | 1400 |
| acaacagatc cctctgtgcc ttggaaccca gtggctgtac ttcactaccc | 1450 |
| agcaaagcct ccacgagggc agctcgcctt ggagagtact tactacaaga | 1500 |
| cctgcagtca ggccagtgtc tgcagctatg ggacgatgac ttgggagcgc | 1550 |
| tatgggcctg ccccatggac aaatacatcc acaagcgctg ggccctcgtg | 1600 |
| tggctggcct gcctactctt tgccgctgcg cttttccctca tcctccttct | 1650 |
| caaaaaggat cacgcgaaag ggtggctgag gctcttgaaa caggacgtcc | 1700 |
| gctcgggggc ggccgccagg ggccgcgcgg ctctgctcct ctactcagcc | 1750 |
| gatgactcgg gtttcgagcg cctggtgggc gcctggcgt cggccctgtg | 1800 |
| ccagctgccg ctgcgcgtgg ccgtagacct gtggagccgc cgtgaactga | 1850 |
| gcgcgcaggg gcccgtggct tggtttcacg cgcagcggcg ccagaccctg | 1900 |
| caggagggcg gcgtggtggt cttgctcttc tctcccggtg cggtggcgct | 1950 |
| gtgcagcgag tggctacagg atggggtgtc cgggccgggg gcgcacggcc | 2000 |
| cgcacgacgc cttccgcgcc tcgctcagct gcgtgctgcc cgacttcttg | 2050 |
| cagggccggg cgcccggcag ctacgtgggg gcctgcttcg acaggctgct | 2100 |
| ccacccggac gccgtacccg ccttttccg caccgtgccc gtcttcacac | 2150 |
| tgccctccca actgccagac ttcctggggg ccctgcagca gcctcgcgcc | 2200 |

```
ccgcgttccg ggcggctcca agagagagcg gagcaagtgt cccgggccct        2250
tcagccagcc ctggatagct acttccatcc cccggggact cccgcgccgg        2300
gacgcggggt gggaccaggg gcgggacctg gggcggggga cgggacttaa        2350
ataaaggcag acgctgtttt tctaaaaaaa                              2380
```

<210> SEQ ID NO 162
<211> LENGTH: 705
<212> TYPE: PRT
<213> ORGANISM: Homo Sapien

<400> SEQUENCE: 162

```
Met Pro Val Pro Trp Phe Leu Leu Ser Leu Ala Leu Gly Arg Ser
 1               5                  10                  15

Pro Val Val Leu Ser Glu Arg Leu Val Gly Pro Gln Asp Ala
            20                  25                  30

Thr His Cys Ser Pro Gly Leu Ser Cys Arg Leu Trp Asp Ser Asp
            35                  40                  45

Ile Leu Cys Leu Pro Gly Asp Ile Val Pro Ala Pro Gly Pro Val
            50                  55                  60

Leu Ala Pro Thr His Leu Gln Thr Glu Leu Val Leu Arg Cys Gln
            65                  70                  75

Lys Glu Thr Asp Cys Asp Leu Cys Leu Arg Val Ala Val His Leu
            80                  85                  90

Ala Val His Gly His Trp Glu Glu Pro Glu Asp Glu Glu Lys Phe
            95                 100                 105

Gly Gly Ala Ala Asp Ser Gly Val Glu Glu Pro Arg Asn Ala Ser
           110                 115                 120

Leu Gln Ala Gln Val Val Leu Ser Phe Gln Ala Tyr Pro Thr Ala
           125                 130                 135

Arg Cys Val Leu Leu Glu Val Gln Val Pro Ala Ala Leu Val Gln
           140                 145                 150

Phe Gly Gln Ser Val Gly Ser Val Val Tyr Asp Cys Phe Glu Ala
           155                 160                 165

Ala Leu Gly Ser Glu Val Arg Ile Trp Ser Tyr Thr Gln Pro Arg
           170                 175                 180

Tyr Glu Lys Glu Leu Asn His Thr Gln Gln Leu Pro Ala Leu Pro
           185                 190                 195

Trp Leu Asn Val Ser Ala Asp Gly Asp Asn Val His Leu Val Leu
           200                 205                 210

Asn Val Ser Glu Glu Gln His Phe Gly Leu Ser Leu Tyr Trp Asn
           215                 220                 225

Gln Val Gln Gly Pro Pro Lys Pro Arg Trp His Lys Asn Leu Thr
           230                 235                 240

Gly Pro Gln Ile Ile Thr Leu Asn His Thr Asp Leu Val Pro Cys
           245                 250                 255

Leu Cys Ile Gln Val Trp Pro Leu Glu Pro Asp Ser Val Arg Thr
           260                 265                 270

Asn Ile Cys Pro Phe Arg Glu Asp Pro Arg Ala His Gln Asn Leu
           275                 280                 285

Trp Gln Ala Ala Arg Leu Arg Leu Leu Thr Leu Gln Ser Trp Leu
           290                 295                 300

Leu Asp Ala Pro Cys Ser Leu Pro Ala Glu Ala Ala Leu Cys Trp
           305                 310                 315
```

```
Arg Ala Pro Gly Gly Asp Pro Cys Gln Pro Leu Val Pro Pro Leu
            320                 325                 330

Ser Trp Glu Asn Val Thr Val Asp Lys Val Leu Glu Phe Pro Leu
            335                 340                 345

Leu Lys Gly His Pro Asn Leu Cys Val Gln Val Asn Ser Ser Glu
            350                 355                 360

Lys Leu Gln Leu Gln Glu Cys Leu Trp Ala Asp Ser Leu Gly Pro
            365                 370                 375

Leu Lys Asp Asp Val Leu Leu Glu Thr Arg Gly Pro Gln Asp
            380                 385                 390

Asn Arg Ser Leu Cys Ala Leu Glu Pro Ser Gly Cys Thr Ser Leu
            395                 400                 405

Pro Ser Lys Ala Ser Thr Arg Ala Ala Arg Leu Gly Glu Tyr Leu
            410                 415                 420

Leu Gln Asp Leu Gln Ser Gly Gln Cys Leu Gln Leu Trp Asp Asp
            425                 430                 435

Asp Leu Gly Ala Leu Trp Ala Cys Pro Met Asp Lys Tyr Ile His
            440                 445                 450

Lys Arg Trp Ala Leu Val Trp Leu Ala Cys Leu Leu Phe Ala Ala
            455                 460                 465

Ala Leu Ser Leu Ile Leu Leu Lys Lys Asp His Ala Lys Gly
            470                 475                 480

Trp Leu Arg Leu Leu Lys Gln Asp Val Arg Ser Gly Ala Ala Ala
            485                 490                 495

Arg Gly Arg Ala Ala Leu Leu Leu Tyr Ser Ala Asp Asp Ser Gly
            500                 505                 510

Phe Glu Arg Leu Val Gly Ala Leu Ala Ser Ala Leu Cys Gln Leu
            515                 520                 525

Pro Leu Arg Val Ala Val Asp Leu Trp Ser Arg Arg Glu Leu Ser
            530                 535                 540

Ala Gln Gly Pro Val Ala Trp Phe His Ala Gln Arg Arg Gln Thr
            545                 550                 555

Leu Gln Glu Gly Gly Val Val Leu Leu Phe Ser Pro Gly Ala
            560                 565                 570

Val Ala Leu Cys Ser Glu Trp Leu Gln Asp Gly Val Ser Gly Pro
            575                 580                 585

Gly Ala His Gly Pro His Asp Ala Phe Arg Ala Ser Leu Ser Cys
            590                 595                 600

Val Leu Pro Asp Phe Leu Gln Gly Arg Ala Pro Gly Ser Tyr Val
            605                 610                 615

Gly Ala Cys Phe Asp Arg Leu Leu His Pro Asp Ala Val Pro Ala
            620                 625                 630

Leu Phe Arg Thr Val Pro Val Phe Thr Leu Pro Ser Gln Leu Pro
            635                 640                 645

Asp Phe Leu Gly Ala Leu Gln Gln Pro Arg Ala Pro Arg Ser Gly
            650                 655                 660

Arg Leu Gln Glu Arg Ala Glu Gln Val Ser Arg Ala Leu Gln Pro
            665                 670                 675

Ala Leu Asp Ser Tyr Phe His Pro Pro Gly Thr Pro Ala Pro Gly
            680                 685                 690

Arg Gly Val Gly Pro Gly Ala Gly Pro Gly Ala Gly Asp Gly Thr
            695                 700                 705
```

-continued

<210> SEQ ID NO 163
<211> LENGTH: 2478
<212> TYPE: DNA
<213> ORGANISM: Homo Sapien

<400> SEQUENCE: 163

| | | | | | |
|---|---|---|---|---|---|
| gtcagtgcgg | gaggccggtc | agccaccaag | atgactgaca | ggttcagctc | 50 |
| tctgcagcac | actaccctca | agccacctga | tgtgacctgt | atctccaaag | 100 |
| tgagatcgat | tcagatgatt | gttcatccta | ccccacgcc | aatccgtgca | 150 |
| ggcgatggcc | accggctaac | cctggaagac | atcttccatg | acctgttcta | 200 |
| ccacttagag | ctccaggtca | accgcaccta | ccaaatgcac | cttggaggga | 250 |
| agcagagaga | atatgagttc | ttcggcctga | cccctgacac | agagttcctt | 300 |
| ggcaccatca | tgatttgcgt | tcccacctgg | gccaaggaga | gtgccccta | 350 |
| catgtgccga | gtgaagacac | tgccagaccg | gacatggacc | tactccttct | 400 |
| ccggagcctt | cctgttctcc | atgggcttcc | tcgtcgcagt | actctgctac | 450 |
| ctgagctaca | gatatgtcac | caagccgcct | gcacctccca | actccctgaa | 500 |
| cgtccagcga | gtcctgactt | tccagccgct | gcgcttcatc | caggagcacg | 550 |
| tcctgatccc | tgtctttgac | ctcagcggcc | cagcagtct | ggcccagcct | 600 |
| gtccagtact | cccagatcag | ggtgtctgga | cccagggagc | ccgcaggagc | 650 |
| tccacagcgg | catagcctgt | ccgagatcac | ctacttaggg | cagccagaca | 700 |
| tctccatcct | ccagccctcc | aacgtgccac | ctccccagat | cctctcccca | 750 |
| ctgtcctatg | ccccaaacgc | tgcccctgag | gtcgggcccc | catcctatgc | 800 |
| acctcaggtg | acccccgaag | ctcaattccc | attctacgcc | ccacaggcca | 850 |
| tctctaaggt | ccagccttcc | tcctatgccc | tcaagccac | tccggacagc | 900 |
| tggcctccct | cctatgggt | atgcatggaa | ggttctggca | aagactcccc | 950 |
| cactgggaca | ctttctagtc | ctaaacacct | taggcctaaa | ggtcagcttc | 1000 |
| agaaagagcc | accagctgga | agctgcatgt | taggtggcct | ttctctgcag | 1050 |
| gaggtgacct | ccttggctat | ggaggaatcc | caagaagcaa | aatcattgca | 1100 |
| ccagcccctg | gggatttgca | cagacagaac | atctgaccca | aatgtgctac | 1150 |
| acagtgggga | ggaagggaca | ccacagtacc | taaagggcca | gctcccccct | 1200 |
| ctctcctcag | tccagatcga | gggccacccc | atgtccctcc | ctttgcaacc | 1250 |
| tccttccggt | ccatgttccc | cctcggacca | aggtccaagt | ccctggggcc | 1300 |
| tgctggagtc | ccttgtgtgt | cccaaggatg | aagccaagag | cccagcccct | 1350 |
| gagacctcag | acctggagca | gcccacagaa | ctggattctc | ttttcagagg | 1400 |
| cctggccctg | actgtgcagt | gggagtcctg | aggggaatgg | gaaaggcttg | 1450 |
| gtgcttcctc | cctgtcccta | cccagtgtca | catccttggc | tgtcaatccc | 1500 |
| atgcctgccc | atgccacaca | ctctgcgatc | tggcctcaga | cgggtgccct | 1550 |
| tgagagaagc | agagggagtg | gcatgcaggg | ccctgccat | gggtgcgctc | 1600 |
| ctcaccggaa | caaagcagca | tgataaggac | tgcagcgggg | gagctctggg | 1650 |
| gagcagcttg | tgtagacaag | cgcgtgctcg | ctgagccctg | caaggcagaa | 1700 |
| atgacagtgc | aaggaggaaa | tgcagggaaa | ctccgaggt | ccagagcccc | 1750 |
| acctcctaac | accatggatt | caaagtgctc | agggaatttg | cctctccttg | 1800 |

-continued

```
ccccattcct ggccagtttc acaatctagc tcgacagagc atgaggcccc      1850
tgcctcttct gtcattgttc aaaggtggga agagagcctg aaaagaacc       1900 aggcctggaa agaaccaga aggaggctgg gcagaaccag aacaacctgc       1950
acttctgcca aggccagggc cagcaggacg gcaggactct agggaggggt     2000
gtggcctgca gctcattccc agccagggca actgcctgac gttgcacgat     2050
ttcagcttca ttcctctgat agaacaaagc gaaatgcagg tccaccaggg     2100
agggagacac acaagccttt tctgcaggca ggagtttcag accctatcct     2150
gagaatgggg tttgaaagga aggtgagggc tgtggcccct ggacgggtac     2200
aataacacac tgtactgatg tcacaacttt gcaagctctg ccttgggttc     2250
agcccatctg ggctcaaatt ccagcctcac cactcacaag ctgtgtgact     2300
tcaaacaaat gaaatcagtg cccagaacct cggtttcctc atctgtaatg     2350 tgggatcat aacacctacc tcatggagtt gtggtgaaga tgaaatgaag      2400
tcatgtcttt aaagtgctta atagtgcctg gtacatgggc agtgcccaat     2450
aaacggtagc tatttaaaaa aaaaaaaa                             2478
```

<210> SEQ ID NO 164
<211> LENGTH: 574
<212> TYPE: PRT
<213> ORGANISM: Homo Sapien

<400> SEQUENCE: 164

```
Met Arg Thr Leu Leu Thr Ile Leu Thr Val Gly Ser Leu Ala Ala
  1               5                  10                  15

His Ala Pro Glu Asp Pro Ser Asp Leu Leu Gln His Val Lys Phe
                 20                  25                  30

Gln Ser Ser Asn Phe Glu Asn Ile Leu Thr Trp Asp Ser Gly Pro
                 35                  40                  45

Glu Gly Thr Pro Asp Thr Val Tyr Ser Ile Glu Tyr Lys Thr Tyr
                 50                  55                  60

Gly Glu Arg Asp Trp Val Ala Lys Lys Gly Cys Gln Arg Ile Thr
                 65                  70                  75

Arg Lys Ser Cys Asn Leu Thr Val Glu Thr Gly Asn Leu Thr Glu
                 80                  85                  90

Leu Tyr Tyr Ala Arg Val Thr Ala Val Ser Ala Gly Gly Arg Ser
                 95                 100                 105

Ala Thr Lys Met Thr Asp Arg Phe Ser Ser Leu Gln His Thr Thr
                110                 115                 120

Leu Lys Pro Pro Asp Val Thr Cys Ile Ser Lys Val Arg Ser Ile
                125                 130                 135

Gln Met Ile Val His Pro Thr Pro Thr Pro Ile Arg Ala Gly Asp
                140                 145                 150

Gly His Arg Leu Thr Leu Glu Asp Ile Phe His Asp Leu Phe Tyr
                155                 160                 165

His Leu Glu Leu Gln Val Asn Arg Thr Tyr Gln Met His Leu Gly
                170                 175                 180

Gly Lys Gln Arg Glu Tyr Glu Phe Phe Gly Leu Thr Pro Asp Thr
                185                 190                 195

Glu Phe Leu Gly Thr Ile Met Ile Cys Val Pro Thr Trp Ala Lys
                200                 205                 210
```

-continued

```
Glu Ser Ala Pro Tyr Met Cys Arg Val Lys Thr Leu Pro Asp Arg
            215                 220                 225

Thr Trp Thr Tyr Ser Phe Ser Gly Ala Phe Leu Phe Ser Met Gly
            230                 235                 240

Phe Leu Val Ala Val Leu Cys Tyr Leu Ser Tyr Arg Tyr Val Thr
            245                 250                 255

Lys Pro Pro Ala Pro Pro Asn Ser Leu Asn Val Gln Arg Val Leu
            260                 265                 270

Thr Phe Gln Pro Leu Arg Phe Ile Gln Glu His Val Leu Ile Pro
            275                 280                 285

Val Phe Asp Leu Ser Gly Pro Ser Ser Leu Ala Gln Pro Val Gln
            290                 295                 300

Tyr Ser Gln Ile Arg Val Ser Gly Pro Arg Glu Pro Ala Gly Ala
            305                 310                 315

Pro Gln Arg His Ser Leu Ser Glu Ile Thr Tyr Leu Gly Gln Pro
            320                 325                 330

Asp Ile Ser Ile Leu Gln Pro Ser Asn Val Pro Pro Gln Ile
            335                 340                 345

Leu Ser Pro Leu Ser Tyr Ala Pro Asn Ala Ala Pro Glu Val Gly
            350                 355                 360

Pro Pro Ser Tyr Ala Pro Gln Val Thr Pro Glu Ala Gln Phe Pro
            365                 370                 375

Phe Tyr Ala Pro Gln Ala Ile Ser Lys Val Gln Pro Ser Ser Tyr
            380                 385                 390

Ala Pro Gln Ala Thr Pro Asp Ser Trp Pro Pro Ser Tyr Gly Val
            395                 400                 405

Cys Met Glu Gly Ser Gly Lys Asp Ser Pro Thr Gly Thr Leu Ser
            410                 415                 420

Ser Pro Lys His Leu Arg Pro Lys Gly Gln Leu Gln Lys Glu Pro
            425                 430                 435

Pro Ala Gly Ser Cys Met Leu Gly Gly Leu Ser Leu Gln Glu Val
            440                 445                 450

Thr Ser Leu Ala Met Glu Glu Ser Gln Glu Ala Lys Ser Leu His
            455                 460                 465

Gln Pro Leu Gly Ile Cys Thr Asp Arg Thr Ser Asp Pro Asn Val
            470                 475                 480

Leu His Ser Gly Glu Glu Gly Thr Pro Gln Tyr Leu Lys Gly Gln
            485                 490                 495

Leu Pro Leu Leu Ser Ser Val Gln Ile Glu Gly His Pro Met Ser
            500                 505                 510

Leu Pro Leu Gln Pro Pro Ser Gly Pro Cys Ser Pro Ser Asp Gln
            515                 520                 525

Gly Pro Ser Pro Trp Gly Leu Leu Glu Ser Leu Val Cys Pro Lys
            530                 535                 540

Asp Glu Ala Lys Ser Pro Ala Pro Glu Thr Ser Asp Leu Glu Gln
            545                 550                 555

Pro Thr Glu Leu Asp Ser Leu Phe Arg Gly Leu Ala Leu Thr Val
            560                 565                 570

Gln Trp Glu Ser
```

<210> SEQ ID NO 165
<211> LENGTH: 1060
<212> TYPE: DNA
<213> ORGANISM: Homo Sapien -continued

<400> SEQUENCE: 165

| | | |
|---|---|---|
| tggcctactg gaaaaaaaaa aaaaaaaaaa aaaagtcacc cgggcccgcg | 50 |
| gtggccacaa catggctgcg gcgccggggc tgctcttctg gctgttcgtg | 100 |
| ctggggggcgc tctggtgggt cccgggccag tcggatctca gccacggacg | 150 |
| gcgtttctcg gacctcaaag tgtgcgggga cgaagagtgc agcatgttaa | 200 |
| tgtaccgtgg gaaagctctt gaagacttca cgggccctga ttgtcgtttt | 250 |
| gtgaatttta aaaaggtgac gatgtatat gtctactaca aactggcagg | 300 |
| gggatccctt gaactttggg ctggaagtgt tgaacacagt tttggatatt | 350 |
| ttccaaaaga tttgatcaag gtacttcata aatacacgga agaagagcta | 400 |
| catattccag cagatgagac agactttgtc tgctttgaag aggaagaga | 450 |
| tgatttttaat agttataatg tagaagagct tttaggatct ttggaactgg | 500 |
| aggactctgt acctgaagag tcgaagaaag ctgaagaagt ttctcagcac | 550 |
| agagagaaat ctcctgagga gtctcggggg cgtgaacttg accctgtgcc | 600 |
| tgagcccgag gcattcagag ctgattcaga ggatggagaa ggtgctttct | 650 |
| cagagagcac cgaggggctg cagggacagc cctcagctca ggagagccac | 700 |
| cctcacacca gcggtcctgc ggctaacgct cagggagtgc agtcttcgtt | 750 |
| ggacactttt gaagaaattc tgcacgataa attgaaagtg ccgggaagcg | 800 |
| aaagcagaac tggcaatagt tctcctgcct cggtggagcg ggagaagaca | 850 |
| gatgcttaca aagtcctgaa aacagaaatg agtcagagag aagtggaca | 900 |
| gtgcgttatt cattacagca aaggatttcg ttggcatcaa aatctaagtt | 950 |
| tgttttacaa agattgtttt tagtactaag ctgccttggc agtttgcatt | 1000 |
| tttgagccaa acaaaaatat attattttcc cttctaagta aaaaaaaaa | 1050 |
| aaaaaaaaaa | 1060 |

<210> SEQ ID NO 166
<211> LENGTH: 303
<212> TYPE: PRT
<213> ORGANISM: Homo Sapien

<400> SEQUENCE: 166

```
Met Ala Ala Ala Pro Gly Leu Leu Phe Trp Leu Phe Val Leu Gly
  1               5                  10                 15

Ala Leu Trp Trp Val Pro Gly Gln Ser Asp Leu Ser His Gly Arg
 20                  25                 30

Arg Phe Ser Asp Leu Lys Val Cys Gly Asp Glu Cys Ser Met
 35                  40                 45

Leu Met Tyr Arg Gly Lys Ala Leu Glu Asp Phe Thr Gly Pro Asp
 50                  55                 60

Cys Arg Phe Val Asn Phe Lys Lys Gly Asp Val Tyr Val Tyr
 65                  70                 75

Tyr Lys Leu Ala Gly Gly Ser Leu Glu Leu Trp Ala Gly Ser Val
 80                  85                 90

Glu His Ser Phe Gly Tyr Phe Pro Lys Asp Leu Ile Lys Val Leu
 95                 100                105

His Lys Tyr Thr Glu Glu Glu Leu His Ile Pro Ala Asp Glu Thr
110                 115                120
```

-continued

```
Asp Phe Val Cys Phe Glu Gly Gly Arg Asp Asp Phe Asn Ser Tyr
            125                 130                 135

Asn Val Glu Glu Leu Leu Gly Ser Leu Glu Leu Asp Ser Val
        140                 145                 150

Pro Glu Glu Ser Lys Lys Ala Glu Glu Val Ser Gln His Arg Glu
            155                 160                 165

Lys Ser Pro Glu Ser Arg Gly Arg Glu Leu Asp Pro Val Pro
        170                 175                 180

Glu Pro Glu Ala Phe Arg Ala Asp Ser Glu Asp Gly Glu Gly Ala
            185                 190                 195

Phe Ser Glu Ser Thr Glu Gly Leu Gln Gly Gln Pro Ser Ala Gln
            200                 205                 210

Glu Ser His Pro His Thr Ser Gly Pro Ala Ala Asn Ala Gln Gly
            215                 220                 225

Val Gln Ser Ser Leu Asp Thr Phe Glu Glu Ile Leu His Asp Lys
            230                 235                 240

Leu Lys Val Pro Gly Ser Glu Ser Arg Thr Gly Asn Ser Ser Pro
            245                 250                 255

Ala Ser Val Glu Arg Glu Lys Thr Asp Ala Tyr Lys Val Leu Lys
            260                 265                 270

Thr Glu Met Ser Gln Arg Gly Ser Gly Gln Cys Val Ile His Tyr
            275                 280                 285

Ser Lys Gly Phe Arg Trp His Gln Asn Leu Ser Leu Phe Tyr Lys
            290                 295                 300

Asp Cys Phe

<210> SEQ ID NO 167
<211> LENGTH: 2570
<212> TYPE: DNA
<213> ORGANISM: Homo Sapien

<400> SEQUENCE: 167
ccaggaccag ggcgcaccgg ctcagcctct cacttgtcag aggccgggga         50
agagaagcaa agcgcaacgg tgtggtccaa gccggggctt ctgcttcgcc        100
tctaggacat acacgggacc ccctaacttc agtcccccaa acgcgcaccc        150
tcgaagtctt gaactccagc cccgcacatc cacgcgcggc acaggcgcgg        200
caggcggcag gtcccggccg aaggcgatgc gcgcaggggg tcgggcagct        250
gggctcgggc ggcgggagta gggcccggca gggaggcagg gaggctgcat        300
attcagagtc gcgggctgcg ccctgggcag aggccgccct cgctccacgc        350
aacacctgct gctgccaccg cgccgcgatg agccgcgtgg tctcgctgct        400
gctgggcgcc gcgctgctct gcggccacgg agccttctgc cgccgcgtgg        450
tcagcggcca aaaggtgtgt tttgctgact tcaagcatcc ctgctacaaa        500
atggcctact ccatgaact gtccagccga gtgagctttc aggaggcacg        550
cctggcttgt gagagtgagg gaggagtcct cctcagcctt gagaatgaag        600
cagaacagaa gttaatagag agcatgttgc aaaacctgac aaaacccggg        650
acagggattt ctgatggtga tttctggata gggctttgga ggaatggaga        700
tgggcaaaca tctggtgcct gcccagatct ctaccagtgg tctgatggaa        750
gcaattccca gtaccgaaac tggtacacag atgaacttc ctgcggaagt        800 gaaaagtgtg ttgtgatgta tcaccaacca actgccaatc ctggccttgg        850
```

| | | |
|---|---|---|
| gggtccctac ctttaccagt ggaatgatga caggtgtaac atgaagcaca | 900 |
| attatatttg caagtatgaa ccagagatta atccaacagc ccctgtagaa | 950 |
| aagccttatc ttacaaatca accaggagac acccatcaga atgtggttgt | 1000 |
| tactgaagca ggtataattc ccaatctaat ttatgttgtt ataccaacaa | 1050 |
| taccctgct cttactgata ctggttgctt ttggaacctg ttgtttccag | 1100 |
| atgctgcata aaagtaaagg aagaacaaaa actagtccaa accagtctac | 1150 |
| actgtggatt tcaaagagta ccagaaaaga agtggcatg gaagtataat | 1200 |
| aactcattga cttggttcca gaattttgta attctggatc tgtataagga | 1250 |
| atggcatcag aacaatagct tggaatggct tgaaatcaca aaggatctgc | 1300 |
| aagatgaact gtaagctccc ccttgaggca aatattaaag taatttttat | 1350 |
| atgtctatta tttcatttaa agaatatgct gtgctaataa tggagtgaga | 1400 |
| catgcttatt ttgctaaagg atgcacccaa acttcaaact tcaagcaaat | 1450 |
| gaaatggaca atgcagataa agttgttatc aacacgtcgg gagtatgtgt | 1500 |
| gttagaagca attccttta tttctttcac ctttcataag ttgttatcta | 1550 |
| gtcaatgtaa tgtatattgt attgaaattt acagtgtgca aaagtatttt | 1600 |
| acctttgcat aagtgtttga taaaaatgaa ctgttctaat atttattttt | 1650 |
| atggcatctc atttttcaat acatgctctt ttgattaaag aaacttatta | 1700 |
| ctgttgtcaa ctgaattcac acacacacaa atatagtacc atagaaaaag | 1750 |
| tttgttttct cgaaataatt catctttcag cttctctgct tttggtcaat | 1800 |
| gtctaggaaa tctcttcaga aataagaagc tatttcatta agtgtgatat | 1850 |
| aaacctcctc aaacatttta cttagaggca aggattgtct aatttcaatt | 1900 |
| gtgcaagaca tgtgccttat aattatttt agcttaaaat taaacagatt | 1950 |
| ttgtaataat gtaactttgt taataggtgc ataaacacta atgcagtcaa | 2000 |
| tttgaacaaa agaagtgaca tacacaatat aaatcatatg tcttcacacg | 2050 |
| ttgcctatat aatgagaagc agctctctga gggttctgaa atcaatgtgg | 2100 |
| tccctctctt gcccactaaa caaagatggt tgttcgggt ttgggattga | 2150 |
| cactggaggc agatagttgc aaagttagtc taaggtttcc ctagctgtat | 2200 |
| ttagcctctg actatattag tatacaaaga ggtcatgtgg ttgagaccag | 2250 |
| gtgaatagtc actatcagtg tggagacaag cacagcacac agacattta | 2300 |
| ggaaggaaag gaactacgaa atcgtgtgaa aatgggttgg aacccatcag | 2350 |
| tgatcgcata ttcattgatg agggtttgct tgagatagaa aatggtggct | 2400 |
| cctttctgtc ttatctccta gtttcttcaa tgcttacgcc ttgttcttct | 2450 |
| caagagaaag ttgtaactct ctggtcttca tatgtccctg tgctcctttt | 2500 |
| aaccaaataa agagttcttg tttctggggg aaaaaaaaa aaaaaaaaa | 2550 |
| aaaaaaaaa aaaaaaaaa | 2570 |

<210> SEQ ID NO 168
<211> LENGTH: 273
<212> TYPE: PRT
<213> ORGANISM: Homo Sapien

<400> SEQUENCE: 168

```
Met Ser Arg Val Val Ser Leu Leu Gly Ala Ala Leu Leu Cys
 1               5                  10                  15

Gly His Gly Ala Phe Cys Arg Val Ser Gly Gln Lys Val
                20                  25                  30

Cys Phe Ala Asp Phe Lys His Pro Cys Tyr Lys Met Ala Tyr Phe
                35                  40                  45

His Glu Leu Ser Ser Arg Val Ser Phe Gln Glu Ala Arg Leu Ala
                50                  55                  60

Cys Glu Ser Glu Gly Gly Val Leu Leu Ser Leu Glu Asn Glu Ala
                65                  70                  75

Glu Gln Lys Leu Ile Glu Ser Met Leu Gln Asn Leu Thr Lys Pro
                80                  85                  90

Gly Thr Gly Ile Ser Asp Gly Asp Phe Trp Ile Gly Leu Trp Arg
                95                  100                 105

Asn Gly Asp Gly Gln Thr Ser Gly Ala Cys Pro Asp Leu Tyr Gln
                110                 115                 120

Trp Ser Asp Gly Ser Asn Ser Gln Tyr Arg Asn Trp Tyr Thr Asp
                125                 130                 135

Glu Pro Ser Cys Gly Ser Glu Lys Cys Val Val Met Tyr His Gln
                140                 145                 150

Pro Thr Ala Asn Pro Gly Leu Gly Gly Pro Tyr Leu Tyr Gln Trp
                155                 160                 165

Asn Asp Asp Arg Cys Asn Met Lys His Asn Tyr Ile Cys Lys Tyr
                170                 175                 180

Glu Pro Glu Ile Asn Pro Thr Ala Pro Val Glu Lys Pro Tyr Leu
                185                 190                 195

Thr Asn Gln Pro Gly Asp Thr His Gln Asn Val Val Val Thr Glu
                200                 205                 210

Ala Gly Ile Ile Pro Asn Leu Ile Tyr Val Val Ile Pro Thr Ile
                215                 220                 225

Pro Leu Leu Leu Leu Ile Leu Val Ala Phe Gly Thr Cys Cys Phe
                230                 235                 240

Gln Met Leu His Lys Ser Lys Gly Arg Thr Lys Thr Ser Pro Asn
                245                 250                 255

Gln Ser Thr Leu Trp Ile Ser Lys Ser Thr Arg Lys Glu Ser Gly
                260                 265                 270

Met Glu Val

<210> SEQ ID NO 169
<211> LENGTH: 43
<212> TYPE: DNA
<213> ORGANISM: Artificial Sequence
<220> FEATURE:
<223> OTHER INFORMATION: Synthetic oligonucleotide probe

<400> SEQUENCE: 169
tgtaaaacga cggccagtta aatagacctg caattattaa tct           43

<210> SEQ ID NO 170
<211> LENGTH: 41
<212> TYPE: DNA
<213> ORGANISM: Artificial Sequence
```

```
-continued
<220> FEATURE:
<223> OTHER INFORMATION: Synthetic oligonucleotide probe

<400> SEQUENCE: 170
caggaaacag ctatgaccac ctgcacacct gcaaatccat t                    41
```

PRO1557 POLYPEPTIDE ENCODED BY A NUCLEIC ACID HIGHLY EXPRESSED IN ESOPHAGEAL AND KIDNEY TUMORS

RELATED APPLICATIONS

This application is a continuation of, and claims priority under 35 U.S.C. § 120 to, U.S. application Ser. No. 10/006,867 filed Dec. 6, 2001, which is a continuation of, and claims priority under 35 U.S.C. § 120 to, PCT Application PCT/US00/23328 filed Aug. 24, 2000, which is a continuation-in-part of, and claims priority under 35 U.S.C. § 120 to, U.S. application Ser. No. 09/403,297 filed Oct. 18, 1999, now abandoned, which is the National Stage filed under 35 U.S.C. § 371 of PCT Application PCT/US99/20111 filed Sep. 1, 1999, which claims priority under 35 U.S.C. § 119 to U.S. Provisional Application 60/105881 filed Oct. 27, 1998.

On Oct. 27, 2006, a CD submission of the Sequence Listing was filed in compliance with the requirements of 37 C.F.R. 1.821(c). The CD contains one file, with the filename: "Sequence Listing-P3230R1C1.txt", file size: 437 KB, date created: Oct. 24, 2006. The information submitted in this CD is incorporated by reference in its entirety.

BACKGROUND OF THE INVENTION

The present invention relates generally to the identification and isolation of novel DNA and to the recombinant production of novel polypeptides.

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents. Efforts are being undertaken by both industry and academia to identify new, native secreted proteins. Many efforts are focused on the screening of mammalian recombinant DNA libraries to identify the coding sequences for novel secreted proteins. Examples of screening methods and techniques are described in the literature [see, for example, Klein et al., Proc. Natl. Acad. Sci. 93:7108–7113 (1996); U.S. Pat. No. 5,536,637)].

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed screening of potential peptide or small molecule inhibitors of the relevant receptor/ligand interaction.

Efforts are being undertaken by both industry and academia to identify new, native receptor or membrane-bound proteins. Many efforts are focused on the screening of mammalian recombinant DNA libraries to identify the coding sequences for novel receptor or membrane-bound proteins.

SUMMARY OF INVENTION

In one embodiment, the invention provides an isolated nucleic acid molecule comprising a nucleotide sequence that encodes a PRO polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO polypeptide cDNA as disclosed herein, the coding sequence of a PRO polypeptide lacking the signal peptide as disclosed herein, the coding sequence of an extracellular domain of a transmembrane PRO polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another aspect the invention provides an isolated nucleic acid molecule comprising a nucleotide sequence encoding a PRO polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO polypeptides are contemplated.

Another embodiment is directed to fragments of a PRO polypeptide coding sequence, or the complement thereof, that may find use as, for example, hybridization probes, for encoding fragments of a PRO polypeptide that may optionally encode a polypeptide comprising a binding site for an anti-PRO antibody or as antisense oligonucleotide probes. Such nucleic acid fragments are usually at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a PRO polypeptide-encoding nucleotide sequence may be determined in a routine manner by aligning the PRO polypeptide-encoding nucleotide sequence with other known nucleotide sequences using any of a number of well known sequence alignment programs and determining which PRO polypeptide-encoding nucleotide sequence fragment(s) are novel. All of such PRO polypeptide-encoding nucleotide sequences are contemplated herein. Also contemplated are the PRO polypeptide fragments encoded by these nucleotide molecule fragments, preferably those PRO polypeptide fragments that comprise a binding site for an anti-PRO antibody.

In another embodiment, the invention provides isolated PRO polypeptide encoded by any of the isolated nucleic acid sequences hereinabove identified.

In a certain aspect, the invention concerns an isolated PRO polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO polypeptide having a full-length amino acid sequence as disclosed herein, an amino acid sequence lacking the signal peptide as disclosed herein, an extracellular domain of a transmembrane protein, with or without the peptide, as disclosed herein or any other specifically defined fragment of the full-length amino acid sequence as disclosed herein.

In a further aspect, the invention concerns an isolated PRO polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In a specific aspect, the invention provides an isolated PRO polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

Another aspect the invention provides an isolated PRO polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO polypeptide and recovering the PRO polypeptide from the cell culture.

In yet another embodiment, the invention concerns agonists and antagonists of a native PRO polypeptide as defined herein. In a particular embodiment, the agonist or antagonist is an anti-PRO antibody or a small molecule.

In a further embodiment, the invention concerns a method of identifying agonists or antagonists to a PRO polypeptide which comprise contacting the PRO polypeptide with a candidate molecule and monitoring a biological activity mediated by said PRO polypeptide. Preferably, the PRO polypeptide is a native PRO polypeptide.

In a still further embodiment, the invention concerns a composition of matter comprising a PRO polypeptide, or an agonist or antagonist of a PRO polypeptide as herein described, or an anti-PRO antibody, in combination with a carrier. Optionally, the carrier is a pharmaceutically acceptable carrier.

Another embodiment of the present invention is directed to the use of a PRO polypeptide, or an agonist or antagonist thereof as hereinbefore described, or an anti-PRO antibody, for the preparation of a medicament useful in the treatment of a condition which is responsive to the PRO polypeptide, an agonist or antagonist thereof or an anti-PRO antibody.

In other embodiments of the present invention, the invention provides vectors comprising DNA encoding any of the herein described polypeptides. Host cell comprising any such vector are also provided. By way of example, the host cells may be CHO cells, E. coli, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which binds, preferably specifically, to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences or as antisense probes, wherein those probes may be derived from any of the above or below described nucleotide sequences.

In yet other embodiments, the present invention is directed to methods of using the PRO polypeptides of the present invention for a variety of uses based upon the functional biological assay data presented in the Examples below.

BRIEF DESCRIPTION OF DRAWINGS

FIG. 1 shows a nucleotide sequence (SEQ ID NO:1) of a native sequence PRO180 cDNA, wherein SEQ ID NO:1 is a clone designated herein as "DNA26843-1389".

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence PRO218 cDNA, wherein SEQ ID NO:3 is a clone designated herein as "DNA30867-1335".

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence PRO263 cDNA, wherein SEQ ID NO:5 is a clone designated herein as "DNA34431-1177".

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a native sequence PRO295 cDNA, wherein SEQ ID NO:7 is a clone designated herein as "DNA38268-1188".

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a native sequence PRO874 cDNA, wherein SEQ ID NO:9 is a clone designated herein as "DNA40621-1440".

FIG. 10 shows the amino acid sequence (SEQ ID NO:10) derived from the coding sequence of SEQ ID NO:9 shown in FIG. 9.

FIG. 11 shows a nucleotide sequence (SEQ ID NO:11) of a native sequence PRO300 cDNA, wherein SEQ ID NO:11 is a clone designated herein as "DNA40625-1189".

FIG. 12 shows the amino acid sequence (SEQ ID NO:12) derived from the coding sequence of SEQ ID NO:11 shown in FIG. 11.

FIG. 13 shows a nucleotide sequence (SEQ ID NO:13) of a native sequence PRO1864 cDNA, wherein SEQ ID NO:13 is a clone designated herein as "DNA45409-2511".

FIG. 14 shows the amino acid sequence (SEQ ID NO:14) derived from the coding sequence of SEQ ID NO:13 shown in FIG. 13.

FIG. 15 shows a nucleotide sequence (SEQ ID NO:15) of a native sequence PRO1282 cDNA, wherein SEQ ID NO:15 is a clone designated herein as "DNA45495-1550".

FIG. 16 shows the amino acid sequence (SEQ ID NO:16) derived from the coding sequence of SEQ ID NO:15 shown in FIG. 15.

FIG. 17 shows a nucleotide sequence (SEQ ID NO:17) of a native sequence PRO1063 cDNA, wherein SEQ ID NO:17 is a clone designated herein as "DNA49820-1427".

FIG. 18 shows the amino acid sequence (SEQ ID NO:18) derived from the coding sequence of SEQ ID NO:17 shown in FIG. 17.

FIG. 19 shows a nucleotide sequence (SEQ ID NO:19) of a native sequence PRO1773 cDNA, wherein SEQ ID NO:19 is a clone designated herein as "DNA56406-1704".

FIG. 20 shows the amino acid sequence (SEQ ID NO:20) derived from the coding sequence of SEQ ID NO:19 shown in FIG. 19.

FIG. 21 shows a nucleotide sequence (SEQ ID NO:21) of a native sequence PRO1013 cDNA, wherein SEQ ID NO:21 is a clone designated herein as "DNA56410-1414".

FIG. 22 shows the amino acid sequence (SEQ ID NO:22) derived from the coding sequence of SEQ ID NO:21 shown in FIG. 21.

FIG. 23 shows a nucleotide sequence (SEQ ID NO:23) of a native sequence PRO937 cDNA, wherein SEQ ID NO:23 is a clone designated herein as "DNA56436-1448".

FIG. 24 shows the amino acid sequence (SEQ ID NO:24) derived from the coding sequence of SEQ ID NO:23 shown in FIG. 23.

FIG. 25 shows a nucleotide sequence (SEQ ID NO:25) of a native sequence PRO842 cDNA, wherein SEQ ID NO:25 is a clone designated herein as "DNA56855-1447".

FIG. 26 shows the amino acid sequence (SEQ ID NO:26) derived from the coding sequence of SEQ ID NO:25 shown in FIG. 25.

FIG. 27 shows a nucleotide sequence (SEQ ID NO:27) of a native sequence PRO1180 cDNA, wherein SEQ ID NO:27 is a clone designated herein as "DNA56860-1510".

FIG. 28 shows the amino acid sequence (SEQ ID NO:28) derived from the coding sequence of SEQ ID NO:27 shown in FIG. 27.

FIG. 29 shows a nucleotide sequence (SEQ ID NO:29) of a native sequence PRO831 cDNA, wherein SEQ ID NO:29 is a clone designated herein as "DNA56862-1343".

FIG. 30 shows the amino acid sequence (SEQ ID NO:30) derived from the coding sequence of SEQ ID NO:29 shown in FIG. 29.

FIG. 31 shows a nucleotide sequence (SEQ ID NO:31) of a native sequence PRO1115 cDNA, wherein SEQ ID NO:31 is a clone designated herein as "DNA56868-1478".

FIG. 32 shows the amino acid sequence (SEQ ID NO:32) derived from the coding sequence of SEQ ID NO:31 shown in FIG. 31.

FIG. 33 shows a nucleotide sequence (SEQ ID NO:33) of a native sequence PRO1277 cDNA, wherein SEQ ID NO:33 is a clone designated herein as "DNA56869-1545".

FIG. 34 shows the amino acid sequence (SEQ ID NO:34) derived from the coding sequence of SEQ ID NO:33 shown in FIG. 33.

FIG. 35 shows a nucleotide sequence (SEQ ID NO:35) of a native sequence PRO1074 cDNA, wherein SEQ ID NO:35 is a clone designated herein as "DNA57704-1452".

FIG. 36 shows the amino acid sequence (SEQ ID NO:36) derived from the coding sequence of SEQ ID NO:35 shown in FIG. 35.

FIG. 37 shows a nucleotide sequence (SEQ ID NO:37) of a native sequence PRO1344 cDNA, wherein SEQ ID NO:37 is a clone designated herein as "DNA58723-1588".

FIG. 38 shows the amino acid sequence (SEQ ID NO:38) derived from the coding sequence of SEQ ID NO:37 shown in FIG. 37.

FIG. 39 shows a nucleotide sequence (SEQ ID NO:39) of a native sequence PRO1136 cDNA, wherein SEQ ID NO:39 is a clone designated herein as "DNA57827-1493".

FIG. 40 shows the amino acid sequence (SEQ ID NO:40) derived from the coding sequence of SEQ ID NO:39 shown in FIG. 39.

FIG. 41 shows a nucleotide sequence (SEQ ID NO:41) of a native sequence PRO1109 cDNA, wherein SEQ ID NO:41 is a clone designated herein as "DNA58737-1473".

FIG. 42 shows the amino acid sequence (SEQ ID NO:42) derived from the coding sequence of SEQ ID NO:41 shown in FIG. 41.

FIG. 43 shows a nucleotide sequence (SEQ ID NO:43) of a native sequence PRO1003 cDNA, wherein SEQ ID NO:43 is a clone designated herein as "DNA58846-1409".

FIG. 44 shows the amino acid sequence (SEQ ID NO:44) derived from the coding sequence of SEQ ID NO:43 shown in FIG. 43.

FIG. 45 shows a nucleotide sequence (SEQ ID NO:45) of a native sequence PRO1138 cDNA, wherein SEQ ID NO:45 is a clone designated herein as "DNA58850-1495".

FIG. 46 shows the amino acid sequence (SEQ ID NO:46) derived from the coding sequence of SEQ ID NO:45 shown in FIG. 45.

FIG. 47 shows a nucleotide sequence (SEQ ID NO:47) of a native sequence PRO994 cDNA, wherein SEQ ID NO:47 is a clone designated herein as "DNA58855-1422".

FIG. 48 shows the amino acid sequence (SEQ ID NO:48) derived from the coding sequence of SEQ ID NO:47 shown in FIG. 47.

FIG. 49 shows a nucleotide sequence (SEQ ID NO:49) of a native sequence PRO1069 cDNA, wherein SEQ ID NO:49 is a clone designated herein as "DNA59211-1450".

FIG. 50 shows the amino acid sequence (SEQ ID NO:50) derived from the coding sequence of SEQ ID NO:49 shown in FIG. 49.

FIG. 51 shows a nucleotide sequence (SEQ ID NO:51) of a native sequence PRO1411 cDNA, wherein SEQ ID NO:51 is a clone designated herein as "DNA59212-1627".

FIG. 52 shows the amino acid sequence (SEQ ID NO:52) derived from the coding sequence of SEQ ID NO:51 shown in FIG. 51.

FIG. 53 shows a nucleotide sequence (SEQ ID NO:53) of a native sequence PRO1129 cDNA, wherein SEQ ID NO:53 is a clone designated herein as "DNA59213-1487".

FIG. 54 shows the amino acid sequence (SEQ ID NO:54) derived from the coding sequence of SEQ ID NO:53 shown in FIG. 53.

FIG. 55 shows a nucleotide sequence (SEQ ID NO:55) of a native sequence PRO1027 cDNA, wherein SEQ ID NO:55 is a clone designated herein as "DNA59605-1418".

FIG. 56 shows the amino acid sequence (SEQ ID NO:56) derived from the coding sequence of SEQ ID NO:55 shown in FIG. 55.

FIG. 57 shows a nucleotide sequence (SEQ ID NO:57) of a native sequence PRO1106 cDNA, wherein SEQ ID NO:57 is a clone designated herein as "DNA59609-1470".

FIG. 58 shows the amino acid sequence (SEQ ID NO:58) derived from the coding sequence of SEQ ID NO:57 shown in FIG. 57.

FIG. 59 shows a nucleotide sequence (SEQ ID NO:59) of a native sequence PRO1291 cDNA, wherein SEQ ID NO:59 is a clone designated herein as "DNA59610-1556".

FIG. 60 shows the amino acid sequence (SEQ ID NO:60) derived from the coding sequence of SEQ ID NO:59 shown in FIG. 59.

FIG. 61 shows a nucleotide sequence (SEQ ID NO:61) of a native sequence PRO3573 cDNA, wherein SEQ ID NO:61 is a clone designated herein as "DNA59837-2545".

FIG. 62 shows the amino acid sequence (SEQ ID NO:62) derived from the coding sequence of SEQ ID NO:61 shown in FIG. 61.

FIG. 63 shows a nucleotide sequence (SEQ ID NO:63) of a native sequence PRO3566 cDNA, wherein SEQ ID NO:63 is a clone designated herein as "DNA59844-2542".

FIG. 64 shows the amino acid sequence (SEQ ID NO:64) derived from the coding sequence of SEQ ID NO:63 shown in FIG. 63.

FIG. 65 shows a nucleotide sequence (SEQ ID NO:65) of a native sequence PRO1098 cDNA, wherein SEQ ID NO:65 is a clone designated herein as "DNA59854-1459".

FIG. 66 shows the amino acid sequence (SEQ ID NO:66) derived from the coding sequence of SEQ ID NO:65 shown in FIG. 65.

FIG. 67 shows a nucleotide sequence (SEQ ID NO:67) of a native sequence PRO1158 cDNA, wherein SEQ ID NO:67 is a clone designated herein as "DNA60625-1507".

FIG. 68 shows the amino acid sequence (SEQ ID NO:68) derived from the coding sequence of SEQ ID NO:67 shown in FIG. 67.

FIG. 69 shows a nucleotide sequence (SEQ ID NO:69) of a native sequence PRO1124 cDNA, wherein SEQ ID NO:69 is a clone designated herein as "DNA60629-1481".

FIG. 70 shows the amino acid sequence (SEQ ID NO:70) derived from the coding sequence of SEQ ID NO:69 shown in FIG. 69.

FIG. 71 shows a nucleotide sequence (SEQ ID NO:71) of a native sequence PRO1287 cDNA, wherein SEQ ID NO:71 is a clone designated herein as "DNA61755-1554".

FIG. 72 shows the amino acid sequence (SEQ ID NO:72) derived from the coding sequence of SEQ ID NO:71 shown in FIG. 71.

FIG. 73 shows a nucleotide sequence (SEQ ID NO:73) of a native sequence PRO1335 cDNA, wherein SEQ ID NO:73 is a clone designated herein as "DNA62812-1594".

FIG. 74 shows the amino acid sequence (SEQ ID NO:74) derived from the coding sequence of SEQ ID NO:73 shown in FIG. 73.

FIG. 75 shows a nucleotide sequence (SEQ ID NO:75) of a native sequence PRO1315 cDNA, wherein SEQ ID NO:75 is a clone designated herein as "DNA62815-1576".

FIG. 76 shows the amino acid sequence (SEQ ID NO:76) derived from the coding sequence of SEQ ID NO:75 shown in FIG. 75.

FIG. 77 shows a nucleotide sequence (SEQ ID NO:77) of a native sequence PRO1357 cDNA, wherein SEQ ID NO:77 is a clone designated herein as "DNA64881-1602".

FIG. 78 shows the amino acid sequence (SEQ ID NO:78) derived from the coding sequence of SEQ ID NO:77 shown in FIG. 77.

FIG. 79 shows a nucleotide sequence (SEQ ID NO:79) of a native sequence PRO1356 cDNA, wherein SEQ ID NO:79 is a clone designated herein as "DNA64886-1601".

FIG. 80 shows the amino acid sequence (SEQ ID NO:80) derived from the coding sequence of SEQ ID NO:79 shown in FIG. 79.

FIG. 81 shows a nucleotide sequence (SEQ ID NO:81) of a native sequence PRO1557 cDNA, wherein SEQ ID NO:81 is a clone designated herein as "DNA64902-1667".

FIG. 82 shows the amino acid sequence (SEQ ID NO:82) derived from the coding sequence of SEQ ID NO:81 shown in FIG. 81.

FIG. 83 shows a nucleotide sequence (SEQ ID NO:83) of a native sequence PRO1347 cDNA, wherein SEQ ID NO:83 is a clone designated herein as "DNA64950-1590".

FIG. 84 shows the amino acid sequence (SEQ ID NO:84) derived from the coding sequence of SEQ ID NO:83 shown in FIG. 83.

FIG. 85 shows a nucleotide sequence (SEQ ID NO:85) of a native sequence PRO1302 cDNA, wherein SEQ ID NO:85 is a clone designated herein as "DNA65403-1565".

FIG. 86 shows the amino acid sequence (SEQ ID NO:86) derived from the coding sequence of SEQ ID NO:85 shown in FIG. 85.

FIG. 87 shows a nucleotide sequence (SEQ ID NO:87) of a native sequence PRO1270 cDNA, wherein SEQ ID NO:87 is a clone designated herein as "DNA66308-1537".

FIG. 88 shows the amino acid sequence (SEQ ID NO:88) derived from the coding sequence of SEQ ID NO:87 shown in FIG. 87.

FIG. 89 shows a nucleotide sequence (SEQ ID NO:89) of a native sequence PRO1268 cDNA, wherein SEQ ID NO:89 is a clone designated herein as "DNA66519-1535".

FIG. 90 shows the amino acid sequence (SEQ ID NO:90) derived from the coding sequence of SEQ ID NO:89 shown in FIG. 89.

FIG. 91 shows a nucleotide sequence (SEQ ID NO:91) of a native sequence PRO1327 cDNA, wherein SEQ ID NO:91 is a clone designated herein as "DNA66521-1583".

FIG. 92 shows the amino acid sequence (SEQ ID NO:92) derived from the coding sequence of SEQ ID NO:91 shown in FIG. 91.

FIG. 93 shows a nucleotide sequence (SEQ ID NO:93) of a native sequence PRO1328 cDNA, wherein SEQ ID NO:93 is a clone designated herein as "DNA66658-1584".

FIG. 94 shows the amino acid sequence (SEQ ID NO:94) derived from the coding sequence of SEQ ID NO:93 shown in FIG. 93.

FIG. 95 shows a nucleotide sequence (SEQ ID NO:95) of a native sequence PRO1329 cDNA, wherein SEQ ID NO:95 is a clone designated herein as "DNA66660-1585".

FIG. 96 shows the amino acid sequence (SEQ ID NO:96) derived from the coding sequence of SEQ ID NO:95 shown in FIG. 95.

FIG. 97 shows a nucleotide sequence (SEQ ID NO:97) of a native sequence PRO1340 cDNA, wherein SEQ ID NO:97 is a clone designated herein as "DNA66663-1598".

FIG. 98 shows the amino acid sequence (SEQ ID NO:98) derived from the coding sequence of SEQ ID NO:97 shown in FIG. 97.

FIG. 99 shows a nucleotide sequence (SEQ ID NO:99) of a native sequence PRO1342 cDNA, wherein SEQ ID NO:99 is a clone designated herein as "DNA66674-1599".

FIG. 100 shows the amino acid sequence (SEQ ID NO:100) derived from the coding sequence of SEQ ID NO:99 shown in FIG. 99.

FIG. 101 shows a nucleotide sequence (SEQ ID NO:101) of a native sequence PRO3579 cDNA, wherein SEQ ID NO:101 is a clone designated herein as "DNA68862-2546".

FIG. 102 shows the amino acid sequence (SEQ ID NO:102) derived from the coding sequence of SEQ ID NO:101 shown in FIG. 101.

FIG. 103 shows a nucleotide sequence (SEQ ID NO:103) of a native sequence PRO1472 cDNA, wherein SEQ ID NO:103 is a clone designated herein as "DNA68866-1644".

FIG. 104 shows the amino acid sequence (SEQ ID NO:104) derived from the coding sequence of SEQ ID NO:103 shown in FIG. 103.

FIG. 105 shows a nucleotide sequence (SEQ ID NO:105) of a native sequence PRO1461 cDNA, wherein SEQ ID NO:105 is a clone designated herein as "DNA68871-1638".

FIG. 106 shows the amino acid sequence (SEQ ID NO:106) derived from the coding sequence of SEQ ID NO:105 shown in FIG. 105.

FIG. 107 shows a nucleotide sequence (SEQ ID NO:107) of a native sequence PRO1568 cDNA, wherein SEQ ID NO:107 is a clone designated herein as "DNA68880-1676".

FIG. 108 shows the amino acid sequence (SEQ ID NO:108) derived from the coding sequence of SEQ ID NO:107 shown in FIG. 107.

FIG. 109 shows a nucleotide sequence (SEQ ID NO:109) of a native sequence PRO1753 cDNA, wherein SEQ ID NO:109 is a clone designated herein as "DNA68883-1691".

FIG. 110 shows the amino acid sequence (SEQ ID NO:110) derived from the coding sequence of SEQ ID NO:109 shown in FIG. 109.

FIG. 111 shows a nucleotide sequence (SEQ ID NO:111) of a native sequence PRO1570 cDNA, wherein SEQ ID NO:111 is a clone designated herein as "DNA68885-1678".

FIG. 112 shows the amino acid sequence (SEQ ID NO:112) derived from the coding sequence of SEQ ID NO:111 shown in FIG. 111.

FIG. 113 shows a nucleotide sequence (SEQ ID NO:113) of a native sequence PRO1446 cDNA, wherein SEQ ID NO:113 is a clone designated herein as "DNA71277-1636".

FIG. 114 shows the amino acid sequence (SEQ ID NO:114) derived from the coding sequence of SEQ ID NO:113 shown in FIG. 113.

FIG. 115 shows a nucleotide sequence (SEQ ID NO:115) of a native sequence PRO1565 cDNA, wherein SEQ ID NO:115 is a clone designated herein as "DNA73727-1673".

FIG. 116 shows the amino acid sequence (SEQ ID NO:116) derived from the coding sequence of SEQ ID NO:115 shown in FIG. 115.

FIG. 117 shows a nucleotide sequence (SEQ ID NO:117) of a native sequence PRO1572 cDNA, wherein SEQ ID NO:117 is a clone designated herein as "DNA73734-1680".

FIG. 118 shows the amino acid sequence (SEQ ID NO:118) derived from the coding sequence of SEQ ID NO:117 shown in FIG. 117.

FIG. 119 shows a nucleotide sequence (SEQ ID NO:119) of a native sequence PRO1573 cDNA, wherein SEQ ID NO:119 is a clone designated herein as "DNA73735-1681".

FIG. 120 shows the amino acid sequence (SEQ ID NO:120) derived from the coding sequence of SEQ ID NO:119 shown in FIG. 119.

FIG. 121 shows a nucleotide sequence (SEQ ID NO:121) of a native sequence PRO1550 cDNA, wherein SEQ ID NO:121 is a clone designated herein as "DNA76393-1664".

FIG. 122 shows the amino acid sequence (SEQ ID NO:122) derived from the coding sequence of SEQ ID NO:121 shown in FIG. 121.

FIG. 123 shows a nucleotide sequence (SEQ ID NO:123) of a native sequence PRO1693 cDNA, wherein SEQ ID NO:123 is a clone designated herein as "DNA77301-1708".

FIG. 124 shows the amino acid sequence (SEQ ID NO:124) derived from the coding sequence of SEQ ID NO:123 shown in FIG. 123.

FIG. 125 shows a nucleotide sequence (SEQ ID NO:125) of a native sequence PRO1566 cDNA, wherein SEQ ID NO:125 is a clone designated herein as "DNA77568-1626".

FIG. 126 shows the amino acid sequence (SEQ ID NO:126) derived from the coding sequence of SEQ ID NO:125 shown in FIG. 125.

FIG. 127 shows a nucleotide sequence (SEQ ID NO:127) of a native sequence PRO1774 cDNA, wherein SEQ ID NO:127 is a clone designated herein as "DNA77626-1705".

FIG. 128 shows the amino acid sequence (SEQ ID NO:128) derived from the coding sequence of SEQ ID NO:127 shown in FIG. 127.

FIG. 129 shows a nucleotide sequence (SEQ ID NO:129) of a native sequence PRO1928 cDNA, wherein SEQ ID NO:129 is a clone designated herein as "DNA81754-2532".

FIG. 130 shows the amino acid sequence (SEQ ID NO:130) derived from the coding sequence of SEQ ID NO:129 shown in FIG. 129.

FIG. 131 shows a nucleotide sequence (SEQ ID NO:131) of a native sequence PRO1865 cDNA, wherein SEQ ID NO:131 is a clone designated herein as "DNA81757-2512".

FIG. 132 shows the amino acid sequence (SEQ ID NO:132) derived from the coding sequence of SEQ ID NO:131 shown in FIG. 131.

FIG. 133 shows a nucleotide sequence (SEQ ID NO:133) of a native sequence PRO1925 cDNA, wherein SEQ ID NO:133 is a clone designated herein as "DNA82302-2529".

FIG. 134 shows the amino acid sequence (SEQ ID NO:134) derived from the coding sequence of SEQ ID NO:133 shown in FIG. 133.

FIG. 135 shows a nucleotide sequence (SEQ ID NO:135) of a native sequence PRO1926 cDNA, wherein SEQ ID NO:135 is a clone designated herein as "DNA82340-2530".

FIG. 136 shows the amino acid sequence (SEQ ID NO:136) derived from the coding sequence of SEQ ID NO:135 shown in FIG. 135.

FIG. 137 shows a nucleotide sequence (SEQ ID NO:137) of a native sequence PRO1801 cDNA, wherein SEQ ID NO:137 is a clone designated herein as "DNA83500-2506".

FIG. 138 shows the amino acid sequence (SEQ ID NO:138) derived from the coding sequence of SEQ ID NO:137 shown in FIG. 137.

FIG. 139 shows a nucleotide sequence (SEQ ID NO:139) of a native sequence PRO4405 cDNA, wherein SEQ ID NO:139 is a clone designated herein as "DNA84920-2614".

FIG. 140 shows the amino acid sequence (SEQ ID NO:140) derived from the coding sequence of SEQ ID NO:139 shown in FIG. 139.

FIG. 141 shows a nucleotide sequence (SEQ ID NO:141) of a native sequence PRO3435 cDNA, wherein SEQ ID NO:141 is a clone designated herein as "DNA85066-2534".

FIG. 142 shows the amino acid sequence (SEQ ID NO:142) derived from the coding sequence of SEQ ID NO:141 shown in FIG. 141.

FIG. 143 shows a nucleotide sequence (SEQ ID NO:143) of a native sequence PRO3543 cDNA, wherein SEQ ID NO:143 is a clone designated herein as "DNA86571-2551".

FIG. 144 shows the amino acid sequence (SEQ ID NO:144) derived from the coding sequence of SEQ ID NO:143 shown in FIG. 143.

FIG. 145 shows a nucleotide sequence (SEQ ID NO:145) of a native sequence PRO3443 cDNA, wherein SEQ ID NO:145 is a clone designated herein as "DNA87991-2540".

FIG. 146 shows the amino acid sequence (SEQ ID NO:146) derived from the coding sequence of SEQ ID NO:145 shown in FIG. 145.

FIG. 147 shows a nucleotide sequence (SEQ ID NO:147) of a native sequence PRO3442 cDNA, wherein SEQ ID NO:147 is a clone designated herein as "DNA92238-2539".

FIG. 148 shows the amino acid sequence (SEQ ID NO:148) derived from the coding sequence of SEQ ID NO:147 shown in FIG. 147.

FIG. 149 shows a nucleotide sequence (SEQ ID NO:149) of a native sequence PRO5990 cDNA, wherein SEQ ID NO:149 is a clone designated herein as "DNA96042-2682".

FIG. 150 shows the amino acid sequence (SEQ ID NO:150) derived from the coding sequence of SEQ ID NO:149 shown in FIG. 149.

FIG. 151 shows a nucleotide sequence (SEQ ID NO:151) of a native sequence PRO4342 cDNA, wherein SEQ ID NO:151 is a clone designated herein as "DNA96787-2534".

FIG. 152 shows the amino acid sequence (SEQ ID NO:152) derived from the coding sequence of SEQ ID NO:151 shown in FIG. 151.

FIG. 153 shows a nucleotide sequence (SEQ ID NO:153) of a native sequence PRO10096 cDNA, wherein SEQ ID NO:153 is a clone designated herein as "DNA125185-2806".

FIG. 154 shows the amino acid sequence (SEQ ID NO:154) derived from the coding sequence of SEQ ID NO:153 shown in FIG. 153.

FIG. 155 shows a nucleotide sequence (SEQ ID NO:155) of a native sequence PRO10272 cDNA, wherein SEQ ID NO:155 is a clone designated herein as "DNA147531-2821".

FIG. 156 shows the amino acid sequence (SEQ ID NO:156) derived from the coding sequence of SEQ ID NO:155 shown in FIG. 155.

FIG. 157 shows a nucleotide sequence (SEQ ID NO:157) of a native sequence PRO5801 cDNA, wherein SEQ ID NO:157 is a clone designated herein as "DNA115291-2681".

FIG. 158 shows the amino acid sequence (SEQ ID NO:158) derived from the coding sequence of SEQ ID NO:157 shown in FIG. 157.

FIG. 159 shows a nucleotide sequence (SEQ ID NO:159) of a native sequence PRO20110 cDNA, wherein SEQ ID NO:159 is a clone designated herein as "DNA166819".

FIG. 160 shows the amino acid sequence (SEQ ID NO:160) derived from the coding sequence of SEQ ID NO:159 shown in FIG. 159.

FIG. 161 shows a nucleotide sequence (SEQ ID NO:161) of a native sequence PRO20040 cDNA, wherein SEQ ID NO:161 is a clone designated herein as "DNA164625-2890".

FIG. 162 shows the amino acid sequence (SEQ ID NO:162) derived from the coding sequence of SEQ ID NO:161 shown in FIG. 161.

FIG. 163 shows a nucleotide sequence (SEQ ID NO:163) of a native sequence PRO20233 cDNA, wherein SEQ ID NO:163 is a clone designated herein as "DNA165608".

FIG. 164 shows the amino acid sequence (SEQ ID NO:164) derived from the coding sequence of SEQ ID NO:163 shown in FIG. 163.

FIG. 165 shows a nucleotide sequence (SEQ ID NO:165) of a native sequence PRO19670 cDNA, wherein SEQ ID NO:165 is a clone designated herein as "DNA131639-2874".

FIG. 166 shows the amino acid sequence (SEQ ID NO:166) derived from the coding sequence of SEQ ID NO:165 shown in FIG. 165.

FIG. 167 shows a nucleotide sequence (SEQ ID NO:167) of a native sequence PRO1890 cDNA, wherein SEQ ID NO:167 is a clone designated herein as "DNA79230-2525".

FIG. 168 shows the amino acid sequence (SEQ ID NO:168) derived from the coding sequence of SEQ ID NO:167 shown in FIG. 167.

DETAILED DESCRIPTION

I. Definitions

The terms "PRO polypeptide" and "PRO" as used herein and when immediately followed by a numerical designation refer to various polypeptides, wherein the complete designation (i.e., PRO/number) refers to specific polypeptide sequences as described herein. The terms "PRO/number polypeptide" and "PRO/number" wherein the term "number" is provided as an actual numerical designation as used herein encompass native sequence polypeptides and polypeptide variants (which are further defined herein). The PRO polypeptides described herein may be isolated from a variety of sources, such as from human tissue types or from another source, or prepared by recombinant or synthetic methods. The term "PRO polypeptide" refers to each individual PRO/number polypeptide disclosed herein. All disclosures in this specification which refer to the "PRO polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO polypeptide" also includes variants of the PRO/number polypeptides disclosed herein.

A "native sequence PRO polypeptide" comprises a polypeptide having the same amino acid sequence as the corresponding PRO polypeptide derived from nature. Such native sequence PRO polypeptides can be isolated from nature or can be produced by recombinant or synthetic means. The term "native sequence PRO polypeptide" specifically encompasses naturally-occurring truncated or secreted forms of the specific PRO polypeptide (e.g., an extracellular domain sequence), naturally-occurring variant forms (e.g., alternatively spliced forms) and naturally-occurring allelic variants of the polypeptide. In various embodiments of the invention, the native sequence PRO polypeptides disclosed herein are mature or full-length native sequence polypeptides comprising the full-length amino acids sequences shown in the accompanying figures. Start and stop codons are shown in bold font and underlined in the figures. However, while the PRO polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO polypeptides.

The PRO polypeptide "extracellular domain" or "ECD" refers to a form of the PRO polypeptide which is essentially free of the transmembrane and cytoplasmic domains. Ordinarily, a PRO polypeptide ECD will have less than 1% of such transmembrane and/or cytoplasmic domains and preferably, will have less than 0.5% of such domains. It will be understood that any transmembrane domains identified for the PRO polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO polypeptide may contain from about 5 or fewer amino acids on either side of the transmembrane domain/extracellular domain boundary as identified in the Examples or specification and such polypeptides, with or without the associated signal peptide, and nucleic acid encoding them, are comtemplated by the present invention.

The approximate location of the "signal peptides" of the various PRO polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., Prot. Eng. 10:1–6 (1997) and von Heinje et al., Nucl. Acids. Res. 14:4683–4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"PRO polypeptide variant" means an active PRO polypeptide as defined above or below having at least about 80% amino acid sequence identity with a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Such PRO polypeptide variants include, for instance, PRO polypeptides wherein one or more amino acid residues are added, or deleted, at the N- or C-terminus of the full-length native amino acid sequence. Ordinarily, a PRO polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence PRO polypeptide sequence as disclosed herein, a PRO polypeptide sequence lacking the signal peptide as disclosed herein, an extracellular domain of a PRO polypeptide, with or without the signal peptide, as disclosed herein or any other specifically defined fragment of a full-length PRO polypeptide sequence as disclosed herein. Ordinarily, PRO variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the PRO polypeptide sequences identified herein is defined as the percentage of amino acid residues in a candidate sequence that are identical with the amino acid residues in the specific PRO polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO", wherein "PRO" represents the amino acid sequence of a hypothetical PRO polypeptide of interest, "Comparison Protein" represents the amino acid sequence of a polypeptide against which the "PRO" polypeptide of interest is being compared, and "X", "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., Methods in Enzymology 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO polypeptide of interest having a sequence derived from the native PRO polypeptide and the comparison amino acid sequence of interest (i.e., the sequence against which the PRO polypeptide of interest is being compared which may be a PRO variant polypeptide) as determined by WU-BLAST-2 by (b) the total number of amino acid residues of the PRO polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO polypeptide of interest.

Percent amino acid sequence identity may also be determined using the sequence comparison program NCBI-BLAST2 (Altschul et al., Nucleic Acids Res. 25:3389–3402 (1997)). The NCBI-BLAST2 sequence comparison program may be downloaded from the National Institutes of Health website or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO variant polynucleotide" or "PRO variant nucleic acid sequence" means a nucleic acid molecule which encodes an active PRO polypeptide as defined below and which has at least about 80% nucleic acid sequence identity with a nucleotide acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal peptide, as disclosed herein or any other fragment of a full-length PRO polypeptide sequence as disclosed herein. Ordinarily, a PRO variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence PRO polypeptide sequence as disclosed herein, a full-length native sequence PRO polypeptide sequence lacking the signal peptide as disclosed herein, an extracellular domain of a PRO polypeptide, with or without the signal sequence, as disclosed herein or any other fragment of a full-length PRO polypeptide sequence as disclosed herein. Variants do not encompass the native nucleotide sequence.

Ordinarily, PRO variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to PRO-encoding nucleic acid sequences identified herein is defined as the percentage of nucleotides in a candidate sequence that are identical with the nucleotides in the PRO nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO-DNA", wherein "PRO-DNA" represents a hypothetical PRO-encoding nucleic acid sequence of interest, "Comparison DNA" represents the nucleotide sequence of a nucleic acid molecule against which the "PRO-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., Methods in Enzymology 266:460–480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO polypeptide-encoding nucleic acid molecule of interest having a sequence derived from the native sequence PRO polypeptide-encoding nucleic acid and the comparison nucleic acid molecule of interest (i.e., the sequence against which the PRO polypeptide-encoding nucleic acid molecule of interest is being compared which may be a variant PRO polynucleotide) as determined by WU-BLAST-2 by (b) the total number of nucleotides of the PRO polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO polypeptide-encoding nucleic acid molecule of interest.

Percent nucleic acid sequence identity may also be determined using the sequence comparison program NCBI-BLAST2 (Altschul et al., Nucleic Acids Res. 25:3389–3402 (1997)). The NCBI-BLAST2 sequence comparison program may be downloaded from the National Institutes of Health website or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO variant polynucleotides are nucleic acid molecules that encode an active PRO polypeptide and which are capable of hybridizing, preferably under stringent hybridization and wash conditions, to nucleotide sequences encoding a full-length PRO polypeptide as disclosed herein. PRO variant polypeptides may be those that are encoded by a PRO variant polynucleotide.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO polypeptide natural environment will not be present. Ordinarily, however, isolated polypeptide will be prepared by at least one purification step.

An "isolated" PRO polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO monoclonal antibodies (including agonist, antagonist, and neutralizing antibodies), anti-PRO antibody compositions with polyepitopic specificity, single chain anti-PRO antibodies, and fragments of anti-PRO antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a PRO polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a PRO polypeptide which retain a biological and/or an immunological activity of native or naturally-occurring PRO, wherein "biological" activity refers to a biological function (either inhibitory or stimulatory) caused by a native or naturally-occurring PRO other than the ability to induce the production of an antibody against an antigenic epitope possessed by a native or naturally-occurring PRO and an "immunological" activity refers to the ability to induce the production of an antibody against an antigenic epitope possessed by a native or naturally-occurring PRO.

The term "antagonist" is used in the broadest sense, and includes any molecule that partially or fully blocks, inhibits, or neutralizes a biological activity of a native PRO polypeptide disclosed herein. In a similar manner, the term "agonist" is used in the broadest sense and includes any molecule that mimics a biological activity of a native PRO polypeptide disclosed herein. Suitable agonist or antagonist molecules specifically include agonist or antagonist antibodies or antibody fragments, fragments or amino acid sequence variants of native PRO polypeptides, peptides, antisense oligonucleotides, small organic molecules, etc. Methods for identifying agonists or antagonists of a PRO polypeptide may comprise contacting a PRO polypeptide with a candidate agonist or antagonist molecule and measuring a detectable change in one or more biological activities normally associated with the PRO polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., Protein Eng. 8(10): 1057–1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in The Pharmacology of Monoclonal Antibodies, vol.113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444–6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons

Table 1

```
/*
 *
 * C-C increased from 12 to 15
 * Z is average of EQ
 * B is average of ND
 * match with stop is _M; stop-stop = 0; J (joker) match = 0
 */
define  _M    -8      /* value of a match with a stop */ int    _day[26][26] = {
/*     A  B  C  D  E  F  G  H  I  J  K  L  M  N  O  P  Q  R  S  T  U  V  W  X  Y  Z */
/* A */ { 2, 0,-2, 0, 0,-4, 1,-1,-1, 0,-1,-2,-1, 0,_M, 1, 0,-2, 1, 1, 0, 0,-6, 0,-3, 0},
/* B */ { 0, 3, 4, 3, 2,-5, 0, 1,-2, 0, 0,-3,-2, 2,_M,-1, 1, 0, 0, 0, 0,-2,-5, 0,-3, 1},
/* C */ {-2, 4,15,-5,-5, 4,-3,-3,-2, 0,-5,-6,-5, 4,_M, 3,-5, 4, 0,-2, 0,-2,-8, 0, 0,-5},
/* D */ { 0, 3,-5, 4, 3,-6, 1, 1,-2, 0, 0,-4,-3, 2,_M,-1, 2,-1, 0, 0, 0,-2,-7, 0, 4, 2},
/* E */ { 0, 2,-5, 3, 4,-5, 0, 1,-2, 0, 0,-3,-2, 1,_M,-1, 2,-1, 0, 0, 0,-2,-7, 0, 4, 3},
/* F */ {-4,-5,-4,-6,-5, 9,-5,-2, 1, 0,-5, 2, 0, 4,_M,-5,-5,-4,-3,-3, 0,-1, 0, 0, 7,-5},
/* G */ { 1, 0,-3, 1, 0,-5, 5,-2,-3, 0,-2, 4,-3, 0,_M,-1,-1,-3, 1, 0, 0,-1,-7, 0,-5, 0},
/* H */ {-1, 1,-3, 1, 1,-2, 2, 6,-2, 0, 0,-2,-2, 2,_M, 0, 3, 2,-1,-1, 0,-2,-3, 0, 0, 2},
/* I */ {-1,-2,-2,-2, 2, 1, 3,-2, 5, 0,-2, 2, 2,-2,_M,-2,-2,-2,-1, 0, 0, 4,-5, 0,-1,-2},
/* J */ { 0, 0, 0, 0, 0, 0, 0, 0, 0, 0, 0, 0, 0, 0,_M, 0, 0, 0, 0, 0, 0, 0, 0, 0, 0, 0},
/* K */ {-1, 0,-5, 0, 0,-5,-2, 0,-2, 0, 5,-3, 0, 1,_M,-1, 1, 3, 0, 0, 0,-2,-3, 0, 4, 0},
/* L */ {-2,-3,-6,-4,-3, 2, 4,-2, 2, 0,-3, 6, 4,-3,_M,-3,-2,-3,-3,-1, 0, 2,-2, 0,-1, 2},
/* M */ {-1,-2,-5,-3,-2, 0,-3,-2, 2, 0, 0, 4, 6,-2,_M,-2,-1, 0,-2,-1, 0, 2, 4, 0,-2,-1},
/* N */ { 0, 2, 4, 2, 1,-4, 0, 2,-2, 0, 1,-3,-2, 2,_M,-1, 1, 0, 1, 0, 0,-2, 4, 0,-2, 1},
/* O */ {_M,_M,_M,_M,_M,_M,_M,_M,_M,_M,_M,_M,_M,_M, 0,_M,_M,_M,_M,_M,_M,_M,_M,_M,_M,_M},
/* P */ { 1,-1,-3,-1,-1,-5,-1, 0,-2, 0,-1,-3,-2,-1,_M, 6, 0, 0, 1, 0, 0,-1,-6, 0,-5, 0},
/* Q */ { 0, 1,-5, 2, 2,-5,-1, 3,-2, 0, 1,-2,-1, 1,_M, 0, 4, 1,-1,-1, 0,-2,-5, 0,-4, 3},
/* R */ {-2, 0, 4,-1,-1,-4,-3, 2,-2, 0, 3,-3, 0, 0,_M, 0, 1, 6, 0,-1, 0,-2, 2, 0, 4, 0},
/* S */ { 1, 0, 0, 0, 0,-3, 1,-1, 1, 0, 0,-3,-2, 1,_M, 1,-1, 0, 2, 1, 0,-1,-2, 0,-3, 0},
/* T */ { 1, 0,-2, 0, 0,-3, 0,-1, 0, 0, 0,-1,-1, 0,_M, 0,-1,-1, 1, 3, 0, 0,-5, 0,-3, 0},
/* U */ { 0, 0, 0, 0, 0, 0, 0, 0, 0, 0, 0, 0, 0, 0,_M, 0, 0, 0, 0, 0, 0, 0, 0, 0, 0, 0},
/* V */ { 0,-2,-2,-2,-2,-1,-1,-2, 4, 0,-2, 2, 2,-2,_M,-1,-2,-2,-1, 0, 0, 4,-6, 0,-2,-2},
/* W */ {-6,-5,-8,-7,-7, 0,-7,-3,-5, 0,-3,-2, 4, 4,_M,-6,-5, 2,-2,-5, 0,-6,17, 0, 0,-6},
/* X */ { 0, 0, 0, 0, 0, 0, 0, 0, 0, 0, 0, 0, 0, 0,_M, 0, 0, 0, 0, 0, 0, 0, 0, 0, 0, 0},
/* Y */ {-3,-3, 0, 4,-4, 7,-5, 0,-1, 0, 4,-1,-2, 2,_M, 5,-4,-4,-3,-3, 0,-2, 0, 0,10, 4},
/* Z */ { 0, 1,-5, 2, 3,-5, 0, 2,-2, 0, 0,-2,-1, 1,_M, 0, 3, 0, 0, 0, 0,-2,-6, 0, 4, 4}
};
```

Table 1 (cont')

```
/*
*/
#include <stdio.h>
include <ctype.h> define   MAXJMP   16      /* max jumps in a diag */
define   MAXGAP   24      /* don't continue to penalize gaps larger than this */
#define   JMPS     1024    /* max jmps in an path */
define   MX       4       /* save if there's at least MX-1 bases since last jmp */ define   DMAT     3       /* value of matching bases */
define   DMIS     0       /* penalty for mismatched bases */
#define   DINS0    8       /* penalty for a gap */
#define   DINS1    1       /* penalty per base */
#define   PINS0    8       /* penalty for a gap */
define   PINS1    4       /* penalty per residue */ struct jmp {
          short            n[MAXJMP];       /* size of jmp (neg for dely) */
          unsigned short   x[MAXJMP];       /* base no. of jmp in seq x */
};                                          /* limits seq to 2^16 -1 */ struct diag {
          int              score;           /* score at last jmp */
          long             offset;          /* offset of prev block */
          short            ijmp;            /* current jmp index */
          struct jmp       jp;              /* list of jmps */
};

struct path {
          int              spc;             /* number of leading spaces */
          short            n[JMPS];         /* size of jmp (gap) */
          int              x[JMPS];         /* loc of jmp (last elem before gap) */
};

char             *ofile;                    /* output file name */
char             *namex[2];                 /* seq names: getseqs() */
char             *prog;                     /* prog name for err msgs */
char             *seqx[2];                  /* seqs: getseqs() */
int              dmax;                      /* best diag: nw() */
int              dmax0;                     /* final diag */
int              dna;                       /* set if dna: main() */
int              endgaps;                   /* set if penalizing end gaps */
int              gapx, gapy;                /* total gaps in seqs */
int              len0, len1;                /* seq lens */
int              ngapx, ngapy;              /* total size of gaps */
int              smax;                      /* max score: nw() */
int              *xbm;                      /* bitmap for matching */
long             offset;                    /* current offset in jmp file */
struct diag      *dx;                       /* holds diagonals */
struct path      pp[2];                     /* holds path for seqs */ char             *calloc(), *malloc(), *index(), *strcpy();
char             *getseq(), *g_calloc();
```

Table 1 (cont')

```
/* Needleman-Wunsch alignment program
*
* usage: progs file1 file2
* where file1 and file2 are two dna or two protein sequences.
* The sequences can be in upper- or lower-case an may contain ambiguity
* Any lines beginning with ';', '>' or '<' are ignored
* Max file length is 65535 (limited by unsigned short x in the jmp struct)
* A sequence with 1/3 or more of its elements ACGTU is assumed to be DNA
* Output is in the file "align.out"
*
* The program may create a tmp file in /tmp to hold info about traceback.
* Original version developed under BSD 4.3 on a vax 8650
*/
include "nw.h"
#include "day.h"

static      _dbval[26] = {
            1,14,2,13,0,0,4,11,0,0,12,0,3,15,0,0,0,5,6,8,8,7,9,0,10,0
};

static      _pbval[26] = {
            1, 2|(1<<('D'-'A'))|(1<<('N'-'A')), 4, 8, 16, 32, 64,
            128, 256, 0xFFFFFFF, 1<<10, 1<<11, 1<<12, 1<<13, 1<<14,
            1<<15, 1<<16, 1<<17, 1<<18, 1<<19, 1<<20, 1<<21, 1<<22,
            1<<23, 1<<24, 1<<25 |(1<<('E'-'A'))|(1<<('Q'-'A'))
};

main(ac, av)                                                                          main
            int     ac;
            char    *av[];
{
            prog = av[0];
            if (ac != 3) {
                        fprintf(stderr,"usage: %s file1 file2\n", prog);
                        fprintf(stderr,"where file1 and file2 are two dna or two protein sequences.\n");
                        fprintf(stderr,"The sequences can be in upper- or lowercase\n");
                        fprintf(stderr,"Any lines beginning with ';' or '<' are ignored\n");
                        fprintf(stderr,"Output is in the file \"align.out\"\n");
                        exit(1);
            }
            namex[0] = av[1];
            namex[1] = av[2];
            seqx[0] = getseq(namex[0], &len0);
            seqx[1] = getseq(namex[1], &len1);
            xbm = (dna)? _dbval : _pbval;

endgaps = 0;                        /* 1 to penalize endgaps */
            ofile = "align.out";                /* output file */ nw();                               /* fill in the matrix, get the possible jmps */
            readjmps();                         /* get the actual jmps */
            print();                            /* print stats, alignment */ cleanup(0);                         /* unlink any tmp files */
}
```

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()                                                                        nw
{
        char            *px, *py;           /* seqs and ptrs */
        int             *ndely, *dely;      /* keep track of dely */
        int             ndelx, delx;        /* keep track of delx */
        int             *tmp;               /* for swapping row0, row1 */
        int             mis;                /* score for each type */
        int             ins0, ins1;         /* insertion penalties */
        register        id;                 /* diagonal index */
        register        ij;                 /* jmp index */
        register        *col0, *col1;       /* score for curr, last row */
        register        xx, yy;             /* index into seqs */ dx = (struct diag *)g_calloc("to get diags", len0+len1+1, sizeof(struct diag));

ndely = (int *)g_calloc("to get ndely", len1+1, sizeof(int));
        dely  = (int *)g_calloc("to get dely", len1+1, sizeof(int));
        col0  = (int *)g_calloc("to get col0", len1+1, sizeof(int));
        col1  = (int *)g_calloc("to get col1", len1+1, sizeof(int));
        ins0  = (dna)? DINS0 : PINS0;
        ins1  = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;         /* Waterman Bull Math Biol 84 */
        }
        else
                for (yy = 1; yy <= len1; yy++)
                        dely[yy] = -ins0;

/* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Table 1 (cont')

...nw

```
for (px = seqx[1], yy = 1; yy <= len1; px++, yy++) {
    mis = col0[yy-1];
    if (dna)
            mis += (xbm[*px-'A']&xbm[*py-'A'])? DMAT : DMIS;
    else
            mis += _day[*px-'A'][*py-'A'];

/* update penalty for del in x seq;
     * favor new del over ongong del
     * ignore MAXGAP if weighting endgaps
     */
    if (endgaps || ndely[yy] < MAXGAP) {
            if (col0[yy] - ins0 >= dely[yy]) {
                    dely[yy] = col0[yy] - (ins0+ins1);
                    ndely[yy] = 1;
            } else {
                    dely[yy] -= ins1;
                    ndely[yy]++;
            }
    } else {
            if (col0[yy] - (ins0+ins1) >= dely[yy]) {
                    dely[yy] = col0[yy] - (ins0+ins1);
                    ndely[yy] = 1;
            } else
                    ndely[yy]++;
    }

/* update penalty for del in y seq;
     * favor new del over ongong del
     */
    if (endgaps || ndelx < MAXGAP) {
            if (col1[yy-1] - ins0 >= delx) {
                    delx = col1[yy-1] - (ins0+ins1);
                    ndelx = 1;
            } else {
                    delx -= ins1;
                    ndelx++;
            }
    } else {
            if (col1[yy-1] - (ins0+ins1) >= delx) {
                    delx = col1[yy-1] - (ins0+ins1);
                    ndelx = 1;
            } else
                    ndelx++;
    }

/* pick the maximum score; we're favoring
     * mis over any del and delx over dely
     */
```

Table 1 (cont')

```
                        id = xx - yy + len1 - 1;
                        if (mis >= delx && mis >= dely[yy])
                                coll[yy] = mis;
                        else if (delx >= dely[yy]) {
                                coll[yy] = delx;
                                ij = dx[id].ijmp;
                                if (dx[id].jp.n[0] && (!dna || (ndelx >= MAXJMP
                                        && xx > dx[id].jp.x[ij]+MX) || mis > dx[id].score+DINS0)) {
                                        dx[id].ijmp++;
                                        if (++ij >= MAXJMP) {
                                                writejmps(id);
                                                ij = dx[id].ijmp = 0;
                                                dx[id].offset = offset;
                                                offset += sizeof(struct jmp) + sizeof(offset);
                                        }
                                }
                                dx[id].jp.n[ij] = ndelx;
                                dx[id].jp.x[ij] = xx;
                                dx[id].score = delx;
                        }
                        else {
                                coll[yy] = dely[yy];
                                ij = dx[id].ijmp;
        if (dx[id].jp.n[0] && (!dna || (ndely[yy] >= MAXJMP
                        && xx > dx[id].jp.x[ij]+MX) || mis > dx[id].score+DINS0)) {
                                        dx[id].ijmp++;
                                        if (++ij >= MAXJMP) {
                                                writejmps(id);
                                                ij = dx[id].ijmp = 0;
                                                dx[id].offset = offset;
                                                offset += sizeof(struct jmp) + sizeof(offset);
                                        }
                                }
                                dx[id].jp.n[ij] = -ndely[yy];
                                dx[id].jp.x[ij] = xx;
                                dx[id].score = dely[yy];
                        }
                        if (xx == len0 && yy < len1) {
                                /* last col
                                */
                                if (endgaps)
                                        coll[yy] -= ins0+ins1*(len1-yy);
                                if (coll[yy] > smax) {
                                        smax = coll[yy];
                                        dmax = id;
                                }
                        }
                }
                if (endgaps && xx < len0)
                        coll[yy-1] -= ins0+ins1*(len0-xx);
                if (coll[yy-1] > smax) {
                        smax = coll[yy-1];
                        dmax = id;
                }
                tmp = col0; col0 = coll; coll = tmp;
        }
        (void) free((char *)ndely);
        (void) free((char *)dely);
```

```
(void) free((char *)col0);
(void) free((char *)col1);
```

}

Table 1 (cont')

```
/*
*
* print() - only routine visible outside this module
*
* static:
* getmat() - trace back best path, count matches: print()
* pr_align() - print alignment of described in array p[]: print()
* dumpblock() - dump a block of lines with numbers, stars: pr_align()
* nums() - put out a number line: dumpblock()
* putline() - put out a line (name, [num], seq, [num]): dumpblock()
* stars() - put a line of stars: dumpblock()
* stripname() - strip any path and prefix from a seqname
*/ include "nw.h"

define SPC      3
#define P_LINE   256    /* maximum output line */
define P_SPC    3      /* space between name or num and seq */ extern   _day[26][26];
int      olen;          /* set output line length */
FILE     *fx;           /* output file */ print()                                                              print
{
        int     lx, ly, firstgap, lastgap;    /* overlap */ if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {           /* leading gap in x */
                pp[0].spc = firstgap = len1 - dmax - 1;
                ly -= pp[0].spc;
        }
        else if (dmax > len1 - 1) {      /* leading gap in y */
                pp[1].spc = firstgap = dmax - (len1 - 1);
                lx -= pp[1].spc;
        }
        if (dmax0 < len0 - 1) {          /* trailing gap in x */
                lastgap = len0 - dmax0 - 1;
                lx -= lastgap;
        }
        else if (dmax0 > len0 - 1) {     /* trailing gap in y */
                lastgap = dmax0 - (len0 - 1);
                ly -= lastgap;
        }
        getmat(lx, ly, firstgap, lastgap);
        pr_align();
}
```

Table 1 (cont')

```
/*
 * trace back the best path, count matches
 */
static
getmat(lx, ly, firstgap, lastgap)                                               getmat
        int     lx, ly;                 /* "core" (minus endgaps) */
        int     firstgap, lastgap;      /* leading trailing overlap */
{
        int             nm, i0, i1, siz0, siz1;
        char            outx[32];
        double          pct;
        register        n0, n1;
        register char   *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
```

Table 1 (cont')

```
        fprintf(fx, "<gaps in first sequence: %d", gapx);                                    ...getmat
        if (gapx) {
                (void) sprintf(outx, " (%d %s%s)",
                        ngapx, (dna)? "base":"residue", (ngapx == 1)? "":"s");
                fprintf(fx,"%s", outx);
        }
        fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
                "\n<score: %d (Dayhoff PAM 250 matrix, gap penalty = %d + %d per residue)\n",
                smax, PINS0, PINS1);
        if (endgaps)
                fprintf(fx,
                "<endgaps penalized. left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, "<endgaps not penalized\n");
} static          nm;             /* matches in core - for checking */
static          lmax;           /* lengths of stripped file names */
static          ij[2];          /* jmp index for a path */
static          nc[2];          /* number at start of current line */
static          ni[2];          /* current elem number - for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars() */

/*
 * print alignment of described in struct path pp []
 */
static
pr_align()                                                                                   pr_align
{
        int     nn;             /* char count */
        int     more;
        register i;

for (i = 0, lmax = 0; i < 2; i++) {
                nn = stripname(namex[i]);
                if (nn > lmax)
                        lmax = nn;

nc[i] = 1;
                ni[i] = 1;
                siz[i] = ij[i] = 0;
```

```
ps[i] = seqz[i];
po[i] = out[i];
```

}

Table 1 (cont')

```
for (nn = nm = 0, more = 1; more; ) {                              ...pr_align
        for (i = more = 0; i < 2; i++) {
                /*
                 * do we have more of this sequence?
                 */
                if (!*ps[i])
                        continue;

more++;

if (pp[i].spc) {           /* leading space */
                        *po[i]++ = ' ';
                        pp[i].spc--;
                }
                else if (siz[i]) {          /* in a gap */
                        *po[i]++ = ' ';
                        siz[i]--;
                }
                else {                      /* we're putting a seq element
                                             */
                        *po[i] = *ps[i];
                        if (islower(*ps[i]))
                                *ps[i] = toupper(*ps[i]);
                        po[i]++;
                        ps[i]++;

/*
                         * are we at next gap for this seq?
                         */
                        if (ni[i] == pp[i].x[ij[i]]) {
                                /*
                                 * we need to merge all gaps
                                 * at this location
                                 */
                                siz[i] = pp[i].n[ij[i]++];
                                while (ni[i] == pp[i].x[ij[i]])
                                        siz[i] += pp[i].n[ij[i]++];
                        }
                        ni[i]++;
                }
        }
        if (++nn == olen || !more && nn) {
                dumpblock();
                for (i = 0; i < 2; i++)
                        po[i] = out[i];
                nn = 0;
        }
    }
}

/*
 * dump a block of lines, including numbers, stars: pr_align()
 */
static
dumpblock()                                                         dumpblock
{
        register i;
```

```
for (i = 0; i < 2; i++)
        *po[i]-- = '\0';
```

Table 1 (cont')

...dumpblock

```
                (void) putc('\n', fx);
                for (i = 0; i < 2; i++) {
                        if (*out[i] && (*out[i] != ' ' || *(po[i]) != ' ')) {
                                if (i == 0)
                                        nums(i);
                                if (i == 0 && *out[1])
                                        stars();
                                putline(i);
                                if (i == 0 && *out[1])
                                        fprintf(fx, star);
                                if (i == 1)
                                        nums(i);
                        }
                }
        }
}

/*
* put out a number line: dumpblock()
*/
static
nums(ix)                                                                                    nums
        int        ix;        /* index in out[] holding seq line */
{
        char            nline[P_LINE];
        register        i, j;
        register char   *pn, *px, *py;

for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px-)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}

/*
* put out a line (name, [num], seq, [num]): dumpblock()
*/
static
```

```
putline(ix)
    int      ix;           {
``` putline

Table 1 (cont')

...putline

```
        int             i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[] is current element (from 1)
         * nc[] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()                                                                         stars
{
        int             i;
        register char   *p0, *p1, cx, *px;

if ((!*out[0] || (*out[0] == ' ' && *(po[0]) == ' ')) ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) { if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
```

Table 1 (cont')

```
/*
 * strip path or prefix from pn, return len: pr_align()
 */
static
stripname(pn)
        char    *pn;     /* file name (may be path) */
{
        register char   *px, *py;

py = 0;
        for (px = pn; *px; px++)
                if (*px == '/')
                        py = px + 1;
        if (py)
                (void) strcpy(pn, py);
        return(strlen(pn));

}
``` stripname

Table 1 (cont')

```
/*
 * cleanup() - cleanup any tmp file
 * getseq() - read in seq, set dna, len, maxlen
 * g_calloc() - calloc() with error checkin
 * readjmps() - get the good jmps, from tmp file if necessary
 * writejmps() - write a filled array of jmps to a tmp file: nw()
 */
include "nw.h"
include <sys/file.h> char      *jname = "/tmp/homgXXXXXX";      /* tmp file for jmps */
FILE      *fj;

int       cleanup();                       /* cleanup tmp file */
long      lseek();

/*
 * remove any tmp file if we blow
 */
cleanup(i)                                                                      cleanup
      int     i;
{
      if (fj)
            (void) unlink(jname);
      exit(i);
}

/*
 * read, return ptr to seq, set dna, len, maxlen
 * skip lines starting with ';', '<', or '>'
 * seq in upper or lower case
 */
char      *
getseq(file, len)                                                               getseq
      char    *file;     /* file name */
      int     *len;      /* seq len */
{
      char           line[1024], *pseq;
      register char  *px, *py;
      int            natgc, tlen;
      FILE           *fp;

if ((fp = fopen(file,"r")) == 0) {
            fprintf(stderr,"%s: can't read %s\n", prog, file);
            exit(1);
      }
      tlen = natgc = 0;
      while (fgets(line, 1024, fp)) {
            if (*line == ';' || *line == '<' || *line == '>')
                  continue;
            for (px = line; *px != '\n'; px++)
                  if (isupper(*px) || islower(*px))
                        tlen++;
      }
      if ((pseq = malloc((unsigned)(tlen+6))) == 0) {
            fprintf(stderr,"%s: malloc() failed to get %d bytes for %s\n", prog, tlen+6, file);
            exit(1);
      }
      pseq[0] = pseq[1] = pseq[2] = pseq[3] = '\0';
```

Table 1 (cont')

...getseq

```
        py = pseq + 4;
        *len = tlen;
        rewind(fp);

while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return (pseq+4);
} char    *
g_calloc(msg, nx, sz)                                                           g_calloc
        char    *msg;           /* program, calling routine */
        int     nx, sz;         /* number and size of elements */
{
        char    *px, *calloc();

if ((px = calloc((unsigned)nx, (unsigned)sz)) == 0) {
                if (*msg) {
                        fprintf(stderr, "%s: g_calloc() failed %s (n=%d, sz=%d)\n", prog, msg, nx, sz);
                        exit(1);
                }
        }
        return (px);
}

/*
* get final jmps from dx[] or tmp file, set pp[], reset dmax: main()
*/
readjmps()                                                                      readjmps
{
        int             fd = -1;
        int             siz, i0, i1;
        register        i, j, xx;

if (f) {
                (void) fclose(f);
                if ((fd = open(jname, O_RDONLY, 0)) < 0) {
                        fprintf(stderr, "%s: can't open() %s\n", prog, jname);
                        cleanup(1);
                }
        }
        for (i = i0 = i1 = 0, dmax0 = dmax, xx = len0; ; i++) {
                while (1) {
```

```
for (j = dx[dmax].ijmp; j >= 0 && dx[dmax].ip.x[j] >= xx; j--)
    ;
```

Table 1 (cont')

...readjmps

```
                if (j < 0 && dx[dmax].offset && f) {
                        (void) lseek(fd, dx[dmax].offset, 0);
                        (void) read(fd, (char *)&dx[dmax].jp, sizeof(struct jmp));
                        (void) read(fd, (char *)&dx[dmax].offset, sizeof(dx[dmax].offset));
                        dx[dmax].ijmp = MAXJMP-1;
                }
                else
                        break;
        }
        if (i >= JMPS) {
                fprintf(stderr, "%s: too many gaps in alignment\n", prog);
                cleanup(1);
        }
        if (j >= 0) {
                siz = dx[dmax].jp.n[j];
                xx = dx[dmax].jp.x[j];
                dmax += siz;
                if (siz < 0) {                          /* gap in second seq */
                        pp[1].n[i1] = -siz;
                        xx += siz;
                        /* id = xx - yy + len1 - 1
                        */
                        pp[1].x[i1] = xx - dmax + len1 - 1;
                        gapy++;
                        ngapy -= siz;
/* ignore MAXGAP when doing endgaps */
                        siz = (-siz < MAXGAP || endgaps)? -siz : MAXGAP;
                        i1++;
                }
                else if (siz > 0) {     /* gap in first seq */
                        pp[0].n[i0] = siz;
                        pp[0].x[i0] = xx;
                        gapx++;
                        ngapx += siz;
/* ignore MAXGAP when doing endgaps */
                        siz = (siz < MAXGAP || endgaps)? siz : MAXGAP;
                        i0++;
                }
        }
        else
                break;
}

/* reverse the order of jmps
*/
for (j = 0, i0--; j < i0; j++, i0--) {
        i = pp[0].n[j]; pp[0].n[j] = pp[0].n[i0]; pp[0].n[i0] = i;
        i = pp[0].x[j]; pp[0].x[j] = pp[0].x[i0]; pp[0].x[i0] = i;
}
for (j = 0, i1--; j < i1; j++, i1--) {
        i = pp[1].n[j]; pp[1].n[j] = pp[1].n[i1]; pp[1].n[i1] = i;
        i = pp[1].x[j]; pp[1].x[j] = pp[1].x[i1]; pp[1].x[i1] = i;
}
if (fd >= 0)
        (void) close(fd);
if (f) {
        (void) unlink(jname);
        fj = 0;
```

```
    offset = 0;
}
```

```
}
```

Table 1 (cont')

```
/*
 * write a filled jmp struct offset of the prev one (if any); nw()
 */
writejmps(ix)                                                                           writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| | | |
|---|---|---|
| PRO | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO polypeptide) = 5 divided by 15 = 33.3%

TABLE 3

| | | |
|---|---|---|
| PRO | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO polypeptide) = 5 divided by 10 = 50%

TABLE 4

| | | |
|---|---|---|
| PRO-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 6 divided by 14 = 42.9%

TABLE 5

| | | |
|---|---|---|
| PRO-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO-DNA nucleic acid sequence) = 4 divided by 12 = 33.3%

II. Compositions and Methods of the Invention

A. Full-Length PRO Polypeptides

The present invention provides newly identified and isolated nucleotide sequences encoding polypeptides referred to in the present application as PRO polypeptides. In particular, cDNAs encoding various PRO polypeptides have been identified and isolated, as disclosed in further detail in the Examples below. It is noted that proteins produced in separate expression rounds may be given different PRO numbers but the UNQ number is unique for any given DNA and the encoded protein, and will not be changed. However, for sake of simplicity, in the present specification the protein encoded by the full length native nucleic acid molecules disclosed herein as well as all further native homologues and variants included in the foregoing definition of PRO, will be referred to as "PRO/number", regardless of their origin or mode of preparation.

As disclosed in the Examples below, various cDNA clones have been deposited with the ATCC. The actual nucleotide sequences of those clones can readily be determined by the skilled artisan by sequencing of the deposited clone using routine methods in the art. The predicted amino acid sequence can be determined from the nucleotide sequence using routine skill. For the PRO polypeptides and encoding nucleic acids described herein, Applicants have identified what is believed to be the reading frame best identifiable with the sequence information available at the time.

B. PRO Polypeptide Variants

In addition to the full-length native sequence PRO polypeptides described herein, it is contemplated that PRO variants can be prepared. PRO variants can be prepared by introducing appropriate nucleotide changes into the PRO DNA, and/or by synthesis of the desired PRO polypeptide. Those skilled in the art will appreciate that amino acid changes may alter post-translational processes of the PRO, such as changing the number or position of glycosylation sites or altering the membrane anchoring characteristics.

Variations in the native full-length sequence PRO or in various domains of the PRO described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO that results in a change in the amino acid sequence of the PRO as compared with the native sequence PRO. Optionally the variation is by substitution of at least one amino acid with any other amino acid in one or more of the domains of the PRO. Guidance in determining which amino acid residue may be inserted, substituted or deleted without adversely affecting the desired activity may be found by comparing the sequence of the PRO with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO polypeptide.

PRO fragments may be prepared by any of a number of conventional techniques. Desired peptide fragments may be chemically synthesized. An alternative approach involves generating PRO fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO polypeptide fragments share at least one biological and/or immunological activity with the native PRO polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., Nucl. Acids Res., 13:4331 (1986); Zoller et al., Nucl. Acids Res., 10:6487 (1987)], cassette mutagenesis [Wells et al., Gene, 34:315 (1985)], restriction selection mutagenesis [Wells et al., Philos. Trans. R. Soc. London SerA, 317:415 (1986)] or other known techniques can be performed on the cloned DNA to produce the PRO variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, Science, 244: 1081–1085 (1989)]. Alanine is also typically preferred because it is the most common amino acid. Further, it is frequently found in both buried and exposed positions [Creighton, The Proteins, (W. H. Freeman & Co., N.Y.); Chothia, J. Mol. Biol., 150:1 (1976)]. If alanine substitution does not yield adequate amounts of variant, an isoteric amino acid can be used.

C. Modifications of PRO

Covalent modifications of PRO are included within the scope of this invention. One type of covalent modification includes reacting targeted amino acid residues of a PRO polypeptide with an organic derivatizing agent that is capable of reacting with selected side chains or the N- or C-terminal residues of the PRO. Derivatization with bifunctional agents is useful, for instance, for crosslinking PRO to a water-insoluble support matrix or surface for use in the method for purifying anti-PRO antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: Structure and Molecular Properties, W. H. Freeman & Co., San Francisco, pp. 79–86 (1983)], acetylation of the N-terminal amine, and amidation of any C-terminal carboxyl group.

Another type of covalent modification of the PRO polypeptide included within the scope of this invention comprises altering the native glycosylation pattern of the polypeptide. "Altering the native glycosylation pattern" is intended for purposes herein to mean deleting one or more carbohydrate moieties found in native sequence PRO (either by removing the underlying glycosylation site or by deleting the glycosylation by chemical and/or enzymatic means), and/or adding one or more glycosylation sites that are not present in the native sequence PRO. In addition, the phrase includes qualitative changes in the glycosylation of the native proteins, involving a change in the nature and proportions of the various carbohydrate moieties present.

Addition of glycosylation sites to the PRO polypeptide may be accomplished by altering the amino acid sequence. The alteration may be made, for example, by the addition of, or substitution by, one or more serine or threonine residues to the native sequence PRO (for O-linked glycosylation sites). The PRO amino acid sequence may optionally be altered through changes at the DNA level, particularly by mutating the DNA encoding the PRO polypeptide at preselected bases such that codons are generated that will translate into the desired amino acids.

Another means of increasing the number of carbohydrate moieties on the PRO polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259–306 (1981).

Removal of carbohydrate moieties present on the PRO polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of PRO comprises linking the PRO polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO of the present invention may also be modified in a way to form a chimeric molecule comprising PRO fused to another, heterologous polypeptide or amino acid sequence.

In one embodiment, such a chimeric molecule comprises a fusion of the PRO with a tag polypeptide which provides an epitope to which an anti-tag antibody can selectively bind. The epitope tag is generally placed at the amino- or carboxyl-terminus of the PRO. The presence of such epitope-tagged forms of the PRO can be detected using an antibody against the tag polypeptide. Also, provision of the epitope tag enables the PRO to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., BioTechnology, 6:1204–1210 (1988)]; the KT3 epitope peptide [Martin et al., Science, 255:192–194 (1992)]; an α-tubulin epitope peptide [Skinner et al., J. Biol. Chem., 266:15163–15166 (1991)]; and the T7 gene 10 protein peptide tag [Lutz-Freyermuth et al., Proc. Natl. Acad. Sci. USA, 87:6393–6397 (1990)].

In an alternative embodiment, the chimeric molecule may comprise a fusion of the PRO with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO

The description below relates primarily to production of PRO by culturing cells transformed or transfected with a vector containing PRO nucleic acid. It is, of course, contemplated that alternative methods, which are well known in the art, may be employed to prepare PRO. For instance, the PRO sequence, or portions thereof, may be produced by direct peptide synthesis using solid-phase techniques [see, e.g., Stewart et al., Solid-Phase Peptide Synthesis, W. H. Freeman Co., San Francisco, Calif. (1969); Merrifield, J. Am. Chem. Soc., 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO may be chemically synthesized separately and combined using chemical or enzymatic methods to produce the full-length PRO.

1. Isolation of DNA Encoding PRO

DNA encoding PRO may be obtained from a cDNA library prepared from tissue believed to possess the PRO mRNA and to express it at a detectable level. Accordingly, human PRO DNA can be conveniently obtained from a cDNA library prepared from human tissue, such as described in the Examples. The PRO-encoding gene may also be obtained from a genomic library or by known synthetic procedures (e.g., automated nucleic acid synthesis).

Libraries can be screened with probes (such as antibodies to the PRO or oligonucleotides of at least about 20–80 bases) designed to identify the gene of interest or the protein encoded by it. Screening the cDNA or genomic library with the selected probe may be conducted using standard procedures, such as described in Sambrook et al., Molecular Cloning: A Laboratory Manual (New York: Cold Spring Harbor Laboratory Press, 1989). An alternative means to isolate the gene encoding PRO is to use PCR methodology [Sambrook et al., supra; Dieffenbach et al., PCR Primer: A Laboratory Manual (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in Mammalian Cell Biotechnology: a Practical Approach, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., Gene, 23:315 (1983) and WO 89/05859 published Jun. 29, 1989. For mammalian cells without such cell walls, the calcium phosphate precipitation method of Graham and van der Eb, Virology, 52:456–457 (1978) can be employed. General aspects of mammalian cell host system transfections have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., Methods in Enzymology, 185:527–537 (1990) and Mansour et al., Nature, 336:348–352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO-encoding vectors. *Saccharomyces cerevisiae* is a commonly used lower eukaryotic host microorganism. Others include *Schizosaccharomyces pombe* (Beach and Nurse, Nature, 290: 140 [1981]; EP 139,383 published May 2, 1985); *Kluyveromyces* hosts (U.S. Pat. No. 4,943,529; Fleer et al., Bio/Technology, 9:968–975 (1991)) such as, e.g., *K. lactis* (MW98-8C, CBS683, CBS4574; Louvencourt et al., J. Bacteriol., 154(2):737–742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., Bio/Technology, 8:135 (1990)), *K. thermotolerans*, and *K. marxianus*; *yarrowia* (EP 402,226); *Pichia pastoris* (EP 183,070; Sreekrishna et al., J. Basic Microbiol., 28:265–278 [1988]); *Candida*; *Trichoderma reesia* (EP 244,234); *Neurospora crassa* (Case et al., Proc. Natl. Acad. Sci. USA, 76:5259–5263 [1979]); *Schwanniomyces* such as *Schwanniomyces occidentalis* (EP 394,538 published Oct. 31, 1990); and filamentous fungi such as, e.g., *Neurospora*, *Penicillium*, *Tolypocladium* (WO 91/000357 published 10 Jan. 1991), and *Aspergillus* hosts such as *A. nidulans* (Ballance et al., Biochem. Biophys. Res. Commun., 112:284–289 [1983]; Tilburn et al., Gene, 26:205–221 [1983]; Yelton et al., Proc. Natl. Acad. Sci. USA, 81: 1470–1474 [1984]) and *A. niger* (Kelly and Hynes, EMBO J., 4:475–479 [1985]). Methylotropic yeasts are suitable herein and include, but are not limited to, yeast capable of growth on methanol selected from the genera consisting of *Hansenula*, *Candida*, *Kloeckera*, *Pichia*, *Saccharomyces*, *Torulopsis*, and *Rhodotorula*. A list of specific species that are exemplary of this class of yeasts may be found in C. Anthony, The Biochemistry of Methylotrophs, 269 (1982).

Suitable host cells for the expression of glycosylated PRO are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); Chinese hamster ovary cells/-DHFR (CHO, Urlaub and Chasin, Proc. Natl. Acad. Sci. USA, 77:4216 (1980)); mouse sertoli cells (TM4, Mather, Biol. Reprod., 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the PRO-encoding nucleic acid, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980). A suitable selection gene for use in yeast is the trp 1 gene present in the yeast plasmid YRp7 [Stinchcomb et al., Nature, 282:39 (1979); Kingsman et al., Gene, 7:141 (1979); Tschemper et al., Gene, 10:157 (1980)]. The trp 1 gene provides a selection marker for a mutant strain of yeast lacking the ability to grow in tryptophan, for example, ATCC No. 44076 or PEP4-1 [Jones, Genetics, 85:12 (1977)].

Expression and cloning vectors usually contain a promoter operably linked to the PRO-encoding nucleic acid sequence to direct mRNA synthesis. Promoters recognized by a variety of potential host cells are well known. Promoters suitable for use with prokaryotic hosts include the β-lactamase and lactose promoter systems [Chang et al., Nature, 275:615 (1978); Goeddel et al., Nature, 281:544 (1979)], alkaline phosphatase, a tryptophan (trp) promoter system [Goeddel, Nucleic Acids Res., 8:4057 (1980); EP 36,776], and hybrid promoters such as the tac promoter [deBoer et al., Proc. Natl. Acad. Sci. USA, 80:21–25 (1983)]. Promoters for use in bacterial systems also will contain a Shine-Dalgarno (S.D.) sequence operably linked to the DNA encoding PRO.

Examples of suitable promoting sequences for use with yeast hosts include the promoters for 3-phosphoglycerate kinase [Hitzeman et al., J. Biol. Chem., 255:2073 (1980)] or other glycolytic enzymes [Hess et al., J. Adv. Enzyme Reg., 7:149 (1968); Holland, Biochemistry, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the PRO coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO.

Still other methods, vectors, and host cells suitable for adaptation to the synthesis of PRO in recombinant vertebrate cell culture are described in Gething et al., Nature, 293: 620–625 (1981); Mantei et al., Nature, 281:40–46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, Proc. Natl. Acad. Sci. USA, 77:5201 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO polypeptide or against a synthetic peptide based on the DNA sequences provided herein or against exogenous sequence fused to PRO DNA and encoding a specific antibody epitope.

5. Purification of Polypeptide

Forms of PRO may be recovered from culture medium or from host cell lysates. If membrane-bound, it can be released from the membrane using a suitable detergent solution (e.g. Triton-X 100) or by enzymatic cleavage. Cells employed in expression of PRO can be disrupted by various physical or chemical means, such as freeze-thaw cycling, sonication, mechanical disruption, or cell lysing agents.

It may be desired to purify PRO from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, SEPHADEX™ G-75 filtration resin; protein A SEPHAROSE™ columns to remove contaminants such as IgG; and metal chelating columns to bind epitope-tagged forms of the PRO. Various methods of protein purification may be employed and such methods are known in the art and described for example in Deutscher, Methods in Enzymology, 182 (1990); Scopes, Protein Purification: Principles and Practice, Springer-Verlag, New York (1982). The purification step(s) selected will depend, for example, on the nature of the production process used and the particular PRO produced.

E. Uses for PRO

Nucleotide sequences (or their complement) encoding PRO have various applications in the art of molecular biology, including uses as hybridization probes, in chromosome and gene mapping and in the generation of anti-sense RNA and DNA. PRO nucleic acid will also be useful for the preparation of PRO polypeptides by the recombinant techniques described herein.

The full-length native sequence PRO gene, or portions thereof, may be used as hybridization probes for a cDNA library to isolate the full-length PRO cDNA or to isolate still other cDNAs (for instance, those encoding naturally-occurring variants of PRO or PRO from other species) which have a desired sequence identity to the native PRO sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence PRO. By way of example, a screening method will comprise isolating the coding region of the PRO gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the PRO gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the PRO nucleic acids include antisense or sense oligonucleotides comprising a singe-stranded nucleic acid sequence (either RNA or DNA) capable of binding to target PRO mRNA (sense) or PRO DNA (antisense) sequences. Antisense or sense oligonucleotides, according to the present invention, comprise a fragment of the coding region of PRO DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (Cancer Res. 48:2659, 1988) and van der Krol et al. (BioTechniques 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of PRO proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related PRO coding sequences.

Nucleotide sequences encoding a PRO can also be used to construct hybridization probes for mapping the gene which encodes that PRO and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

When the coding sequences for PRO encode a protein which binds to another protein (example, where the PRO is a receptor), the PRO can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor PRO can be used to isolate correlative ligand(s). Screening assays can be designed to find lead compounds that mimic the biological activity of a native PRO or a receptor for PRO. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode PRO or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding PRO can be used to clone genomic DNA encoding PRO in accordance with established techniques and the genomic sequences used to generate transgenic animals that contain cells which express DNA encoding PRO. Methods for generating transgenic animals, particularly animals such as mice or rats, have become conventional in the art and are described, for example, in U.S. Pat. Nos. 4,736,866 and 4,870,009. Typically, particular cells would be targeted for PRO transgene incorporation with tissue-specific enhancers. Transgenic animals that include a copy of a transgene encoding PRO introduced into the germ line of the animal at an embryonic stage can be used to examine the effect of increased expression of DNA encoding PRO. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of PRO can be used to construct a PRO "knock out" animal which has a defective or altered gene encoding PRO as a result of homologous recombination between the endogenous gene encoding PRO and altered genomic DNA encoding PRO introduced into an embryonic stem cell of the animal. For example, cDNA encoding PRO can be used to clone genomic DNA encoding PRO in accordance with established techniques. A portion of the genomic DNA encoding PRO can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knock-out animals can be characterized for instance, for their ability to defend against certain pathological conditions and for their development of pathological conditions due to absence of the PRO polypeptide.

Nucleic acid encoding the PRO polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., Proc. Natl. Acad. Sci. USA 83:4143–4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., Trends in Biotechnology 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429–4432 (1987); and Wagner et al., Proc. Natl. Acad. Sci. USA 87, 3410–3414 (1990). For review of gene marking and gene therapy protocols see Anderson et al., Science 256, 808–813 (1992).

The PRO polypeptides described herein may also be employed as molecular weight markers for protein electrophoresis purposes and the isolated nucleic acid sequences may be used for recombinantly expressing those markers.

The nucleic acid molecules encoding the PRO polypeptides or fragments thereof described herein are useful for chromosome identification. In this regard, there exists an ongoing need to identify new chromosome markers, since relatively few chromosome marking reagents, based upon actual sequence data are presently available. Each PRO nucleic acid molecule of the present invention can be used as a chromosome marker.

The PRO polypeptides and nucleic acid molecules of the present invention may also be used diagnostically for tissue typing, wherein the PRO polypeptides of the present invention may be differentially expressed in one tissue as compared to another, preferably in a diseased tissue as compared to a normal tissue of the same tissue type. PRO nucleic acid molecules will find use for generating probes for PCR, Northern analysis, Southern analysis and Western analysis.

The PRO polypeptides described herein may also be employed as therapeutic agents. The PRO polypeptides of the present invention can be formulated according to known methods to prepare pharmaceutically useful compositions, whereby the PRO product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42–96.

When in vivo administration of a PRO polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of a PRO polypeptide is desired in a formulation with release characteristics suitable for the treatment of any disease or disorder requiring administration of the PRO polypeptide, microencapsulation of the PRO polypeptide is contemplated. Microencapsulation of recombinant proteins for sustained release has been successfully performed with human growth hormone (rhGH), interferon- (rhIFN-), interleukin-2, and MN rgp120. Johnson et al., Nat. Med., 2:795–799 (1996); Yasuda, Biomed. Ther., 27:1221–1223 (1993); Hora et al., Bio/Technology, 8:755–758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439–462; WO 97/03692, WO 96/40072, WO 96/07399; and U.S. Pat. No. 5,654,010.

The sustained-release formulations of these proteins were developed using polylactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp.1–41.

This invention encompasses methods of screening compounds to identify those that mimic the PRO polypeptide (agonists) or prevent the effect of the PRO polypeptide (antagonists). Screening assays for antagonist drug candidates are designed to identify compounds that bind or complex with the PRO polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with a PRO polypeptide encoded by a nucleic acid identified herein under conditions and for a time sufficient to allow these two components to interact.

In binding assays, the interaction is binding and the complex formed can be isolated or detected in the reaction mixture. In a particular embodiment, the PRO polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the PRO polypeptide and drying. Alternatively, an immobilized antibody, e.g., a monoclonal antibody, specific for the PRO polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular PRO polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, Nature (London), 340:245–246 (1989); Chien et al., Proc. Natl. Acad. Sci. USA, 88:9578–9582 (1991)) as disclosed by Chevray and Nathans, Proc. Natl. Acad. Sci. USA, 89: 5789–5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding a PRO polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

To assay for antagonists, the PRO polypeptide may be added to a cell along with the compound to be screened for a particular activity and the ability of the compound to inhibit the activity of interest in the presence of the PRO polypeptide indicates that the compound is an antagonist to the PRO polypeptide. Alternatively, antagonists may be detected by combining the PRO polypeptide and a potential antagonist with membrane-bound PRO polypeptide receptors or recombinant receptors under appropriate conditions for a competitive inhibition assay. The PRO polypeptide can be labeled, such as by radioactivity, such that the number of PRO polypeptide molecules bound to the receptor can be used to determine the effectiveness of the potential antagonist. The gene encoding the receptor can be identified by numerous methods known to those of skill in the art, for example, ligand panning and FACS sorting. Coligan et al., Current Protocols in Immun., 1(2): Chapter 5 (1991). Preferably, expression cloning is employed wherein polyadenylated RNA is prepared from a cell responsive to the PRO polypeptide and a cDNA library created from this RNA is divided into pools and used to transfect COS cells or other cells that are not responsive to the PRO polypeptide. Transfected cells that are grown on glass slides are exposed to labeled PRO polypeptide. The PRO polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled PRO polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled PRO polypeptide in the presence of the candidate compound. The ability of the compound to enhance or block this interaction could then be measured.

More specific examples of potential antagonists include an oligonucleotide that binds to the fusions of immunoglobulin with PRO polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the PRO polypeptide that recognizes the receptor but imparts no effect, thereby competitively inhibiting the action of the PRO polypeptide.

Another potential PRO polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to gene expression through triple-helix formation or antisense DNA or RNA, both of which methods are based on binding of a polynucleotide to DNA or RNA. For example, the 5' coding portion of the polynucleotide sequence, which encodes the mature PRO polypeptides herein, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al., Science, 241: 456 (1988); Dervan et al., Science, 251:1360 (1991)), thereby preventing transcription and the production of the PRO polypeptide. The antisense RNA oligonucleotide hybridizes to the mRNA in vivo and blocks translation of the mRNA molecule into the PRO polypeptide (antisense—Okano, Neurochem., 56:560 (1991); Oligodeoxynucleotides as Antisense Inhibitors of Gene Expression (CRC Press: Boca Raton, Fla., 1988). The oligonucleotides described above can also be delivered to cells such that the antisense RNA or DNA may be expressed in vivo to inhibit production of the PRO polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the PRO polypeptide, thereby blocking the normal biological activity of the PRO polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, Current Biology, 4:469–471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed hereinabove and/or by any other screening techniques well known for those skilled in the art.

Diagnostic and therapeutic uses of the herein disclosed molecules may also be based upon the positive functional assay hits disclosed and described below.

F. Anti-PRO Antibodies

The present invention further provides anti-PRO antibodies. Exemplary antibodies include polyclonal, monoclonal, humanized, bispecific, and heteroconjugate antibodies.

1. Polyclonal Antibodies

The anti-PRO antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, Monoclonal Antibodies: Principles and Practice, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, J. Immunol., 133:3001 (1984); Brodeur et al., Monoclonal Antibody Production Techniques and Applications, Marcel Dekker, Inc., New York, (1987) pp. 51–63].

The culture medium in which the hybridoma cells are cultured can then be assayed for the presence of monoclonal antibodies directed against PRO. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522–525 (1986); Riechmann et al., Nature, 332:323–329 (1988); and Presta, Curr. Op. Struct. Biol., 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522–525 (1986); Riechmann et al., Nature, 332:323–327 (1988); Verhoeyen et al., Science, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779–783 (1992); Lonberg et al., Nature 368 856–859 (1994); Morrison, Nature 368, 812–13 (1994); Fishwild et al., Nature Biotechnology 14, 845–51 (1996); Neuberger, Nature Biotechnology 14, 826 (1996); Lonberg and Huszar, Intern. Rev. Immunol. 13 65–93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities is for the PRO, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. $F(ab')_2$ bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from E. coli and chemically coupled to form bispecific antibodies. Shalaby et al., J. Exp. Med. 175:217 (1992) describe the production of a fully humanized bispecific antibody $F(ab')_2$ molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., J. Immunol. 148 (5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991).

Exemplary bispecific antibodies may bind to two different epitopes on a given PRO polypeptide herein. Alternatively, an anti-PRO polypeptide arm may be combined with an arm which binds to a triggering molecule on a leukocyte such as a T-cell receptor molecule (e.g. CD2, CD3, CD28, or B7), or Fc receptors for IgG (Fc γ R), such as Fc γ RI (CD64), Fc γ RII (CD32) and Fc γ RIII (CD16) so as to focus cellular defense mechanisms to the cell expressing the particular PRO polypeptide. Bispecific antibodies may also be used to localize cytotoxic agents to cells which express a particular PRO polypeptide. These antibodies possess a PRO-binding arm and an arm which binds a cytotoxic agent or a radionuclide chelator, such as EOTUBE, DPTA, DOTA, or TETA. Another bispecific antibody of interest binds the PRO polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp Med., 176: 1191–1195 (1992) and Shopes, J. Immunol., 148: 2918–2922 (1992). Homodimeric antibodies with enhanced anti-tumor activity may also be prepared using heterobifunctional cross-linkers as described in Wolff et al. Cancer Research, 53: 2560–2565 (1993). Alternatively, an antibody can be engineered that has dual Fc regions and may thereby have enhanced complement lysis and ADCC capabilities. See Stevenson et al., Anti-Cancer Drug Design, 3: 219–230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286–288 (1982) via a disulfide-interchange reaction. A chemotherapeutic agent (such as Doxorubicin) is optionally contained within the liposome. See Gabizon et al., J. National Cancer Inst., 81(19): 1484 (1989).

9. Pharmaceutical Compositions of Antibodies

Antibodies specifically binding a PRO polypeptide identified herein, as well as other molecules identified by the screening assays disclosed hereinbefore, can be administered for the treatment of various disorders in the form of pharmaceutical compositions.

If the PRO polypeptide is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA, 90: 7889–7893 (1993). The formulation herein may also contain more than one active compound as necessary for the particular indication being treated, preferably those with complementary activities that do not adversely affect each other. Alternatively, or in addition, the composition may comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles, and nanocapsules) or in macroemulsions. Such techniques are disclosed in Remington's *Pharmaceutical Sciences*, supra.

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

C. Uses for Anti-PRO Antibodies

The anti-PRO antibodies of the invention have various utilities. For example, anti-PRO antibodies may be used in diagnostic assays for PRO, e.g., detecting its expression (and in some cases, differential expression) in specific cells, tissues, or serum. Various diagnostic assay techniques known in the art may be used, such as competitive binding assays, direct or indirect sandwich assays and immunoprecipitation assays conducted in either heterogeneous or homogeneous phases [Zola, Monoclonal Antibodies: A Manual of Techniques, CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982).

Anti-PRO antibodies also are useful for the affinity purification of PRO from recombinant cell culture or natural sources. In this process, the antibodies against PRO are immobilized on a suitable support, such as SEPHADEX™ resin or filter paper, using methods well known in the art. The immobilized antibody then is contacted with a sample containing the PRO to be purified, and thereafter the support is washed with a suitable solvent that will remove substantially all the material in the sample except the PRO, which is bound to the immobilized antibody. Finally, the support is washed with another suitable solvent that will release the PRO from the antibody.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Extracellular Domain Homology Screening to Identify Novel Polypeptides and cDNA Encoding therefor The extracellular domain (ECD) sequences (including the secretion signal sequence, if any) from about 950 known secreted proteins from the Swiss-Prot public database were used to search EST databases. The EST databases included public databases (e.g., Dayhoff, GenBank), and proprietary databases (e.g. LIFESEQ™, Incyte Pharmaceuticals, Palo Alto, Calif.). The search was performed using the computer program BLAST or BLAST-2 (Altschul et al., Methods in Enzymology 266:460–480 (1996)) as a comparison of the ECD protein sequences to a 6 frame translation of the EST sequences. Those comparisons with a BLAST score of 70 (or in some cases 90) or greater that did not encode known proteins were clustered and assembled into consensus DNA sequences with the program "phrap" (Phil Green, University of Washington, Seattle, Wash.).

Using this extracellular domain homology screen, consensus DNA sequences were assembled relative to the other identified EST sequences using phrap. In addition, the consensus DNA sequences obtained were often (but not always) extended using repeated cycles of BLAST or BLAST-2 and phrap to extend the consensus sequence as far as possible using the sources of EST sequences discussed above.

Based upon the consensus sequences obtained as described above, oligonucleotides were then synthesized and used to identify by PCR a cDNA library that contained the sequence of interest and for use as probes to isolate a clone of the full-length coding sequence for a PRO polypeptide. Forward and reverse PCR primers generally range from 20 to 30 nucleotides and are often designed to give a PCR product of about 100–1000 bp in length. The probe sequences are typically 40–55 bp in length. In some cases, additional oligonucleotides are synthesized when the consensus sequence is greater than about 1–1.5 kbp. In order to screen several libraries for a full-length clone, DNA from the libraries was screened by PCR amplification, as per Ausubel et al., Current Protocols in Molecular Biology, with the PCR primer pair. A positive library was then used to isolate clones encoding the gene of interest using the probe oligonucleotide and one of the primer pairs.

The cDNA libraries used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., Science, 253:1278–1280 (1991)) in the unique XhoI and NotI sites.

Example 2

Isolation of cDNA Clones by Amylase Screening

1. Preparation of oligo dT primed cDNA library mRNA was isolated from a human tissue of interest using reagents and protocols from Invitrogen, San Diego, Calif. (Fast Track 2). This RNA was used to generate an oligo dT primed cDNA library in the vector pRK5D using reagents and protocols from Life Technologies, Gaithersburg, Md. (Super Script Plasmid System). In this procedure, the double stranded cDNA was sized to greater than 1000 bp and the SalI/NotI linkered cDNA was cloned into XhoI/NotI cleaved vector. pRK5D is a cloning vector that has an sp6 transcription initiation site followed by an SfiI restriction enzyme site preceding the XhoI/NotI cDNA cloning sites.

2. Preparation of Random Primed cDNA Library

A secondary cDNA library was generated in order to preferentially represent the 5' ends of the primary cDNA clones. Sp6 RNA was generated from the primary library (described above), and this RNA was used to generate a random primed cDNA library in the vector pSST-AMY.0 using reagents and protocols from Life Technologies (Super Script Plasmid System, referenced above). In this procedure the double stranded cDNA was sized to 500–1000 bp, linkered with blunt to NotI adaptors, cleaved with SfiI, and cloned into SfiI/NotI cleaved vector. pSST-AMY.0 is a cloning vector that has a yeast alcohol dehydrogenase promoter preceding the cDNA cloning sites and the mouse amylase sequence (the mature sequence without the secretion signal) followed by the yeast alcohol dehydrogenase terminator, after the cloning sites. Thus, cDNAs cloned into this vector that are fused in frame with amylase sequence will lead to the secretion of amylase from appropriately transfected yeast colonies.

3. Transformation and Detection

DNA from the library described in paragraph 2 above was chilled on ice to which was added electrocompetent DH10B bacteria (Life Technologies, 20 ml). The bacteria and vector mixture was then electroporated as recommended by the manufacturer. Subsequently, SOC media (Life Technologies, 1 ml) was added and the mixture was incubated at 37° C. for 30 minutes. The transformants were then plated onto 20 standard 150 mm LB plates containing ampicillin and incubated for 16 hours (37° C.). Positive colonies were scraped off the plates and the DNA was isolated from the bacterial pellet using standard protocols, e.g. CsCl-gradient. The purified DNA was then carried on to the yeast protocols below.

The yeast methods were divided into three categories: (1) Transformation of yeast with the plasmid/cDNA combined vector; (2) Detection and isolation of yeast clones secreting amylase; and (3) PCR amplification of the insert directly from the yeast colony and purification of the DNA for sequencing and further analysis.

The yeast strain used was HD56-5A (ATCC-90785). This strain has the following genotype: MAT alpha, ura3-52, leu2-3, leu2-112, his3-11, his3-15, MAL+, SUC+, GAL+. Preferably, yeast mutants can be employed that have deficient post-translational pathways. Such mutants may have translocation deficient alleles in sec 71, sec 72, sec 62, with truncated sec 71 being most preferred. Alternatively, antagonists (including antisense nucleotides and/or ligands) which interfere with the normal operation of these genes, other proteins implicated in this post translation pathway (e.g., SEC61p, SEC72p, SEC62p, SEC63p, TDJ1p or SSA1p–4p) or the complex formation of these proteins may also be preferably employed in combination with the amylase-expressing yeast.

Transformation was performed based on the protocol outlined by Gietz et al., Nucl. Acid. Res., 20:1425 (1992). Transformed cells were then inoculated from agar into YEPD complex media broth (100 ml) and grown overnight at 30° C. The YEPD broth was prepared as described in Kaiser et al., Methods in Yeast Genetics, Cold Spring Harbor Press, Cold Spring Harbor, N.Y., p. 207 (1994). The overnight culture was then diluted to about $2\times10^6$ cells/ml (approx. $OD_{600}$=0.1) into fresh YEPD broth (500 ml) and regrown to $1\times10^7$ cells/ml (approx. $OD_{600}$=0.4–0.5).

The cells were then harvested and prepared for transformation by transfer into GS3 rotor bottles in a Sorval GS3 rotor at 5,000 rpm for 5 minutes, the supernatant discarded, and then resuspended into sterile water, and centrifuged again in 50 ml falcon tubes at 3,500 rpm in a Beckman GS-6KR centrifuge. The supernatant was discarded and the cells were subsequently washed with LiAc/TE (10 ml, 10 mM Tris-HCl, 1 mM EDTA pH 7.5, 100 mM $Li_2OOCCH_3$), and resuspended into LiAc/TE (2.5 ml).

Transformation took place by mixing the prepared cells (100 µl) with freshly denatured single stranded salmon testes DNA (Lofstrand Labs, Gaithersburg, Md.) and transforming DNA (1 µg, vol.<10 µl) in microfuge tubes. The mixture was mixed briefly by vortexing, then 40% PEG/TE (600 µl, 40% polyethylene glycol-4000, 10 mM Tris-HCl, 1 mM EDTA, 100 mM $Li_2OOCCH_3$, pH 7.5) was added. This mixture was gently mixed and incubated at 30° C. while agitating for 30 minutes. The cells were then heat shocked at 42° C. for 15 minutes, and the reaction vessel centrifuged in a microfuge at 12,000 rpm for 5–10 seconds, decanted and resuspended into TE (500 µl, 10 mM Tris-HCl, 1 mM EDTA pH 7.5) followed by recentrifugation. The cells were then diluted into TE (1 ml) and aliquots (200 µl) were spread onto the selective media previously prepared in 150 mm growth plates (VWR).

Alternatively, instead of multiple small reactions, the transformation was performed using a single, large scale reaction, wherein reagent amounts were scaled up accordingly.

The selective media used was a synthetic complete dextrose agar lacking uracil (SCD-Ura) prepared as described in Kaiser et al., Methods in Yeast Genetics, Cold Spring Harbor Press, Cold Spring Harbor, N.Y., p. 208–210 (1994). Transformants were grown at 30° C. for 2–3 days.

The detection of colonies secreting amylase was performed by including red starch in the selective growth media. Starch was coupled to the red dye (Reactive Red-120, Sigma) as per the procedure described by Biely et al., Anal. Biochem., 172:176–179 (1988). The coupled starch was incorporated into the SCD-Ura agar plates at a final concentration of 0.15% (w/v), and was buffered with potassium phosphate to a pH of 7.0 (50–100 mM final concentration).

The positive colonies were picked and streaked across fresh selective media (onto 150 mm plates) in order to obtain well isolated and identifiable single colonies. Well isolated single colonies positive for amylase secretion were detected by direct incorporation of red starch into buffered SCD-Ura agar. Positive colonies were determined by their ability to break down starch resulting in a clear halo around the positive colony visualized directly.

4. Isolation of DNA by PCR Amplification

When a positive colony was isolated, a portion of it was picked by a toothpick and diluted into sterile water (30 µl) in a 96 well plate. At this time, the positive colonies were either frozen and stored for subsequent analysis or immediately amplified. An aliquot of cells (5 µl) was used as a template for the PCR reaction in a 25 µl volume containing: 0.5 µl KLENTAQ (a 5'-exo minus N-terminal deletion of Taq DNA polymerase availabe from Clontech, Palo Alto, Calif.); 4.0 µl 10 mM dNTP's (Perkin Elmer-Cetus); 2.5 µl KENTAQ buffer (Clontech); 0.25 µl forward oligo 1; 0.25 µl reverse oligo 2; 12.5 µl distilled water. The sequence of the forward oligonucleotide 1 was:

5'-TGTAAAACGACGGCCAGTTAAATAGAC-CTGCAATTATTAATCT-3' (SEQ ID NO:169)

The sequence of reverse oligonucleotide 2 was:

5'-CAGGAAACAGCTATGACCACCTGCACAC-CTGCAAATCCATT-3' (SEQ ID NO:170)

PCR was then performed as follows:

| a. | | Denature | 92° C., | 5 minutes |
|----|---|----------|---------|-----------|
| b. | 3 cycles of: | Denature | 92° C., | 30 seconds |
| | | Anneal | 59° C., | 30 seconds |
| | | Extend | 72° C., | 60 seconds |
| c. | 3 cycles of: | Denature | 92° C., | 30 seconds |
| | | Anneal | 57° C., | 30 seconds |
| | | Extend | 72° C., | 60 seconds |
| d. | 25 cycles of: | Denature | 92° C., | 30 seconds |
| | | Anneal | 55° C., | 30 seconds |
| | | Extend | 72° C., | 60 seconds |
| e. | | Hold | 4° C. | |

The underlined regions of the oligonucleotides annealed to the ADH promoter region and the amylase region, respectively, and amplified a 307 bp region from vector pSST-AMY.0 when no insert was present. Typically, the first 18 nucleotides of the 5' end of these oligonucleotides contained annealing sites for the sequencing primers. Thus, the total product of the PCR reaction from an empty vector was 343 However, signal sequence-fused cDNA resulted in considerably longer nucleotide sequences.

Following the PCR, an aliquot of the reaction (5 µl) was examined by agarose gel electrophoresis in a 1% agarose gel using a Tris-Borate-EDTA (TBE) buffering system as described by Sambrook et al., supra. Clones resulting in a single strong PCR product larger than 400 bp were further analyzed by DNA sequencing after purification with a 96 QIAQUICK PCR clean-up column (Qiagen Inc., Chatsworth, Calif.).

Example 3

Isolation of cDNA Clones Using Signal Algorithm Analysis

Various polypeptide-encoding nucleic acid sequences were identified by applying a proprietary signal sequence finding algorithm developed by Genentech, Inc. (South San Francisco, Calif.) upon ESTs as well as clustered and assembled EST fragments from public (e.g., GenBank) and/or private (LIFESEQ®, Incyte Pharmaceuticals, Inc., Palo Alto, Calif.) databases. The signal sequence algorithm computes a secretion signal score based on the character of the DNA nucleotides surrounding the first and optionally second methionine codon(s) (ATG) at the 5'-end of the sequence or sequence fragment under consideration. The nucleotides following the first ATG must code for at least 35 unambiguous amino acids without any stop codons. If the first ATG has the required amino acids, the second is not examined. If neither meets the requirement, the candidate sequence is not scored. In order to determine whether the EST sequence contains an authentic signal sequence, the DNA and corresponding amino acid sequences surrounding the ATG codon are scored using a set of seven sensors (evaluation parameters) known to be associated with secretion signals. Use of this algorithm resulted in the identification of numerous polypeptide-encoding nucleic acid sequences.

Example 4

Isolation of cDNA Clones Encoding Human PRO Polypeptides

Using the techniques described in Examples 1 to 3 above, numerous full-length cDNA clones were identified as encoding PRO polypeptides as disclosed herein. These cDNAs were then deposited under the terms of the Budapest Treaty with the American Type Culture Collection, 10801 University Blvd., Manassas, Va. 20110–2209, USA (ATCC) as shown in Table 7 below.

TABLE 7

| Material | ATCC Dep. No. | Deposit Date |
|----------|---------------|--------------|
| DNA26843-1389 | 203099 | Aug. 4,1998 |
| DNA30867-1335 | 209807 | Apr. 28, 1998 |
| DNA34431-1177 | 209399 | Oct. 17, 1997 |
| DNA38268-1188 | 209421 | Oct. 28, 1997 |
| DNA40621-1440 | 209922 | Jun. 2, 1998 |
| DNA40625-1189 | 209788 | Apr. 21, 1998 |

TABLE 7-continued

| Material | ATCC Dep. No. | Deposit Date |
| --- | --- | --- |
| DNA45409-2511 | 203579 | Jan. 12,1999 |
| DNA45495-1550 | 203156 | Aug. 25, 1998 |
| DNA49820-1427 | 209932 | Jun. 2, 1998 |
| DNA56406-1704 | 203478 | Nov. 17, 1998 |
| DNA56410-1414 | 209923 | Jun. 2, 1998 |
| DNA56436-1448 | 209902 | May 27, 1998 |
| DNA56855-1447 | 203004 | Jun. 23, 1998 |
| DNA56860-1510 | 209952 | Jun. 9, 1998 |
| DNA56862-1343 | 203174 | Sep. 1, 1998 |
| DNA56868-1478 | 203024 | Jun. 23, 1998 |
| DNA56869-1545 | 203161 | Aug. 25, 1998 |
| DNA57704-1452 | 209953 | Jun. 9, 1998 |
| DNA58723-1588 | 203133 | Aug. 18, 1998 |
| DNA57827-1493 | 203045 | Jul. 1, 1998 |
| DNA58737-1473 | 203136 | Aug. 18, 1998 |
| DNA58846-1409 | 209957 | Jun. 9, 1998 |
| DNA58850-1495 | 209956 | Jun. 9, 1998 |
| DNA58855-1422 | 203018 | Jun. 23, 1998 |
| DNA59211-1450 | 209960 | Jun. 9, 1998 |
| DNA59212-1627 | 203245 | Sep. 9, 1998 |
| DNA59213-1487 | 209959 | Jun. 9, 1998 |
| DNA59605-1418 | 203005 | Jun. 23, 1998 |
| DNA59609-1470 | 209963 | Jun. 9, 1998 |
| DNA59610-1556 | 209990 | Jun. 16, 1998 |
| DNA59837-2545 | 203658 | Feb. 9, 1999 |
| DNA59844-2542 | 203650 | Feb. 9, 1999 |
| DNA59854-1459 | 209974 | Jun. 16, 1998 |
| DNA60625-1507 | 209975 | Jun. 16, 1998 |
| DNA60629-1481 | 209979 | Jun. 16, 1998 |
| DNA61755-1554 | 203112 | Aug. 11, 1998 |
| DNA62812-1594 | 203248 | Sep. 9, 1998 |
| DNA62815-1576 | 203247 | Sep. 9, 1998 |
| DNA64881-1602 | 203240 | Sep. 9, 1998 |
| DNA64886-1601 | 203241 | Sep. 9, 1998 |
| DNA64902-1667 | 203317 | Oct. 6, 1998 |
| DNA64950-1590 | 203224 | Sep. 15, 1998 |
| DNA65403-1565 | 203230 | Sep. 15, 1998 |
| DNA66308-1537 | 203159 | Aug. 25, 1998 |
| DNA66519-1535 | 203236 | Sep. 15, 1998 |
| DNA66521-1583 | 203225 | Sep. 15, 1998 |
| DNA66658-1584 | 203229 | Sep. 15, 1998 |
| DNA66660-1585 | 203279 | Sep. 22, 1998 |
| DNA66663-1598 | 203268 | Sep. 22, 1998 |
| DNA66674-1599 | 203281 | Sep. 22, 1998 |
| DNA68862-2546 | 203652 | Feb. 9, 1999 |
| DNA68866-1644 | 203283 | Sep. 22, 1998 |
| DNA68871-1638 | 203280 | Sep. 22, 1998 |
| DNA68880-1676 | 203319 | Oct. 6, 1998 |
| DNA68883-1691 | 203535 | Dec. 15, 1998 |
| DNA68885-1678 | 203311 | Oct. 6,1998 |
| DNA71277-1636 | 203285 | Sep. 22, 1998 |
| DNA73727-1673 | 203459 | Nov. 3,1998 |
| DNA73734-1680 | 203363 | Oct. 20, 1998 |
| DNA73735-1681 | 203356 | Oct. 20, 1998 |
| DNA76393-1664 | 203323 | Oct. 6, 1998 |
| DNA77301-1708 | 203407 | Oct. 27, 1998 |
| DNA77568-1626 | 203134 | Aug. 18, 1998 |
| DNA77626-1705 | 203536 | Dec. 15, 1998 |
| DNA81754-2532 | 203542 | Dec. 15, 1998 |
| DNA81757-2512 | 203543 | Dec. 15, 1998 |
| DNA82302-2529 | 203534 | Dec. 15, 1998 |
| DNA82340-2530 | 203547 | Dec. 22, 1998 |
| DNA83500-2506 | 203391 | Oct. 29, 1998 |
| DNA84920-2614 | 203966 | Apr. 27, 1999 |
| DNA85066-2534 | 203588 | Jan. 12, 1999 |
| DNA86571-2551 | 203660 | Feb. 9, 1999 |
| DNA87991-2540 | 203656 | Feb. 9, 1999 |
| DNA92238-2539 | 203602 | Jan. 20, 1999 |
| DNA96042-2682 | PTA-382 | Jul. 20, 1999 |
| DNA96787-2534 | 203589 | Jan. 12, 1999 |
| DNA125185-2806 | PTA-1031 | Dec. 7, 1999 |
| DNA147531-2821 | PTA-1185 | Jan. 11, 2000 |
| DNA115291-2681 | PTA-202 | Jun. 8, 1999 |
| DNA164625-28890 | PTA-1535 | Mar. 21, 2000 |
| DNA131639-2874 | PTA-1784 | Apr. 25, 2000 |
| DNA79230-2525 | 203549 | Dec. 22, 1998 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposits will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Example 5

Use of PRO as a Hybridization Probe

The following method describes use of a nucleotide sequence encoding PRO as a hybridization probe.

DNA comprising the coding sequence of full-length or mature PRO as disclosed herein is employed as a probe to screen for homologous DNAs (such as those encoding naturally-occurring variants of PRO) in human tissue cDNA libraries or human tissue genomic libraries.

Hybridization and washing of filters containing either library DNAs is performed under the following high stringency conditions. Hybridization of radiolabeled PRO-derived probe to the filters is performed in a solution of 50% formamide, 5×SSC, 0.1% SDS, 0.1% sodium pyrophosphate, 50 mM sodium phosphate, pH 6.8, 2× Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO can then be identified using standard techniques known in the art.

Example 6

Expression of PRO in E. Coli

This example illustrates preparation of an unglycosylated form of PRO by recombinant expression in E. coli.

The DNA sequence encoding PRO is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO protein can then be purified using a metal chelating column under conditions that allow tight binding of the protein.

PRO may be expressed in E. coli in a poly-His tagged form, using the following procedure. The DNA encoding PRO is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an E. coli host based on strain 52 (W3110 fuhA(tonA) lon galE rpoHts (htpRts) clpP(laclq). Transformants are first grown in LB containing 50 mg/ml carbenicillin at 30° C. with shaking until an O.D.600 of 3–5 is reached. Cultures are then diluted 50–100 fold into CRAP media (prepared by mixing 3.57 g $(NH_4)_2SO_4$, 0.71 g sodium citrate-2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20–30 hours at 30° C. with shaking. Samples are removed to verify expression by SDS-page analysis, and the bulk culture is centrifuged to pellet the cells. Cell pellets are frozen until purification and refolding.

E. coli paste from 0.5 to 1 L fermentations (6–10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3–5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12–36 hours. The refolding reaction is quenched by the addition of TFA to a final concentration of 0.4% (pH of approximately 3). Before further purification of the protein, the solution is filtered through a 0.22 micron filter and acetonitrile is added to 2–10% final concentration. The refolded protein is chromatographed on a POROS™ R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of from the desired form, the reversed phase step also removes endotoxin from the samples.

Fractions containing the desired folded PRO polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Many of the PRO polypeptides disclosed herein were successfully expressed as described above.

Example 7

Expression of PRO in Mammalian Cells

This example illustrates preparation of a potentially glycosylated form of PRO by recombinant expression in mammalian cells.

The vector, pRK5 (see EP 307,247, published Mar. 15, 1989), is employed as the expression vector. Optionally, the PRO DNA is ligated into pRK5 with selected restriction enzymes to allow insertion of the PRO DNA using ligation methods such as described in Sambrook et al., supra. The resulting vector is called pRK5-PRO.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO DNA is mixed with about 1 μg DNA encoding the VA RNA gene [Thimmappaya et al., Cell, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO polypeptide. The cultures containing transfected cells may undergo further incubation (in serum free medium) and the medium is tested in selected bioassays.

In an alternative technique, PRO may be introduced into 293 cells transiently using the dextran sulfate method described by Somparyrac et al., Proc. Natl. Acad. Sci., 12:7575 (1981). 293 cells are grown to maximal density in a spinner flask and 700 µg pRK5-PRO DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed PRO can then be concentrated and purified by any selected method, such as dialysis and/or column chromatography.

In another embodiment, PRO can be expressed in CHO cells. The pRK5-PRO can be transfected into CHO cells using known reagents such as CaPO$_4$ or DEAE-dextran. As described above, the cell cultures can be incubated, and the medium replaced with culture medium (alone) or medium containing a radiolabel such as $^{35}$S-methionine. After determining the presence of PRO polypeptide, the culture medium may be replaced with serum free medium. Preferably, the cultures are incubated for about 6 days, and then the conditioned medium is harvested. The medium containing the expressed PRO can then be concentrated and purified by any selected method.

Epitope-tagged PRO may also be expressed in host CHO cells. The PRO may be subcloned out of the pRK5 vector. The subclone insert can undergo PCR to fuse in frame with a selected epitope tag such as a poly-his tag into a Baculovirus expression vector. The poly-his tagged PRO insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged PRO can then be concentrated and purified by any selected method, such as by Ni$^{2+}$-chelate affinity chromatography.

PRO may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., Current Protocols of Molecular Biology, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., Nucl. Acids Res. 24:9 (1774–1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents SUPERFECT™ (Qiagen), DOSPER™ or FUGENE™ (Boehringer Mannheim). The cells are grown as described in Lucas et al., supra. Approximately 3×10$^{-7}$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1–2 days, the cells are transferred into a 250 mL spinner filled with 150 mL selective growth medium and incubated at 37° C. After another 2–3 days, 250 mL, 500 mL and 2000 mL spinners are seeded with 3×10$^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3L production spinner is seeded at 1.2×10$^6$ cells/mL. On day 0, the cell number pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO polypeptides disclosed herein were successfully expressed as described above.

Example 8

Expression of PRO in Yeast

The following method describes recombinant expression of PRO in yeast.

First, yeast expression vectors are constructed for intracellular production or secretion of PRO from the ADH2/GAPDH promoter. DNA encoding PRO and the promoter is inserted into suitable restriction enzyme sites in the selected plasmid to direct intracellular expression of PRO. For secretion, DNA encoding PRO can be cloned into the selected plasmid, together with DNA encoding the ADH2/GAPDH promoter, a native PRO signal peptide or other mammalian signal peptide, or, for example, a yeast alpha-factor or invertase secretory signal/leader sequence, and linker sequences (if needed) for expression of PRO.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO can subsequently be isolated and purified by removing the cells from the fermentation medium by centrifugation and then concentrating the medium using selected cartridge filters. The concentrate containing PRO may further be purified using selected column chromatography resins.

Many of the PRO polypeptides disclosed herein were successfully expressed as described above.

Example 9

Expression of PRO in Baculovirus-Infected Insect Cells

The following method describes recombinant expression of PRO in Baculovirus-infected insect cells.

The sequence coding for PRO is fused upstream of an epitope tag contained a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO or the desired portion of the coding sequence of PRO such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BACULOGOLD™ virus DNA (Pharmingen) into *Spodoptera frugiperda* ("Sf9") cells (ATCC CRL 1711) using LIPOFECTIN cationic lipid (commercially available from GIBCO-BRL). After 4–5 days of incubation at 58° C., the released viruses are harvested and used for further amplifications. Viral infection and protein expression are performed as described by O'Reilley et al., Baculovirus expression vectors: A Laboratory Manual, Oxford: Oxford University Press (1994).

Expressed poly-his tagged PRO can then be purified, for example, by $Ni^{2+}$-chelate affinity chromatography as follows. Extracts are prepared from recombinant virus-infected Sf9 cells as described by Rupert et al., Nature, 362:175–179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged PRO are pooled and dialyzed against loading buffer.

Alternatively, purification of the IgG tagged (or Fc tagged) PRO can be performed using known chromatography techniques, including for instance, Protein A or protein G column chromatography.

Many of the PRO polypeptides disclosed herein were successfully expressed as described above.

Example 10

Preparation of Antibodies that Bind PRO

This example illustrates preparation of monoclonal antibodies which can specifically bind PRO.

Techniques for producing the monoclonal antibodies are known in the art and are described, for instance, in Goding, supra. Immunogens that may be employed include purified PRO, fusion proteins containing PRO, and cells expressing recombinant PRO on the cell surface. Selection of the immunogen can be made by the skilled artisan without undue experimentation.

Mice, such as Balb/c, are immunized with the PRO immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-PRO antibodies.

After a suitable antibody titer has been detected, the animals "positive" for antibodies can be injected with a final intravenous injection of PRO. Three to four days later, the mice are sacrificed and the spleen cells are harvested. The spleen cells are then fused (using 35% polyethylene glycol)

to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against PRO. Determination of "positive" hybridoma cells secreting the desired monoclonal antibodies against PRO is within the skill in the art.

The positive hybridoma cells can be injected intraperitoneally into syngeneic Balb/c mice to produce ascites containing the anti-PRO monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 11

Purification of PRO Polypeptides Using Specific Antibodies

Native or recombinant PRO polypeptides may be purified by a variety of standard techniques in the art of protein purification. For example, pro-PRO polypeptide, mature PRO polypeptide, or pre-PRO polypeptide is purified by immunoaffinity chromatography using antibodies specific for the PRO polypeptide of interest. In general, an immunoaffinity column is constructed by covalently coupling the anti-PRO polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO polypeptide by preparing a fraction from cells containing PRO polypeptide in a soluble form. This preparation is derived by solubilization of the whole cell or of a subcellular fraction obtained via differential centrifugation by the addition of detergent or by other methods well known in the art. Alternatively, soluble PRO polypeptide containing a signal sequence may be secreted in useful quantity into the medium in which the cells are grown.

A soluble PRO polypeptide-containing preparation is passed over the immunoaffinity column, and the column is washed under conditions that allow the preferential absorbance of PRO polypeptide (e.g., high ionic strength buffers in the presence of detergent). Then, the column is eluted under conditions that disrupt antibody/PRO polypeptide binding (e.g., a low pH buffer such as approximately pH 2–3, or a high concentration of a chaotrope such as urea or thiocyanate ion), and PRO polypeptide is collected.

Example 12

Drug Screening

This invention is particularly useful for screening compounds by using PRO polypeptides or binding fragment thereof in any of a variety of drug screening techniques. The PRO polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO polypeptide or fragment. Drugs are screened against such transformed cells in competitive binding assays. Such cells, either in viable or fixed form, can be used for standard binding assays. One may measure, for example, the formation of complexes between PRO polypeptide or a fragment and the agent being tested. Alternatively, one can examine the diminution in complex formation between the PRO polypeptide and its target cell or target receptors caused by the agent being tested.

Thus, the present invention provides methods of screening for drugs or any other agents which can affect a PRO polypeptide-associated disease or disorder. These methods comprise contacting such an agent with a PRO polypeptide or fragment thereof and assaying (i) for the presence of a complex between the agent and the PRO polypeptide or fragment, or (ii) for the presence of a complex between the PRO polypeptide or fragment and the cell, by methods well known in the art. In such competitive binding assays, the PRO polypeptide or fragment is typically labeled. After suitable incubation, free PRO polypeptide or fragment is separated from that present in bound form, and the amount of free or uncomplexed label is a measure of the ability of the particular agent to bind to PRO polypeptide or to interfere with the PRO polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to a PRO polypeptide, the peptide test compounds are reacted with PRO polypeptide and washed. Bound PRO polypeptide is detected by methods well known in the art. Purified PRO polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO polypeptide specifically compete with a test compound for binding to PRO polypeptide or fragments thereof. In this manner, the antibodies can be used to detect the presence of any peptide which shares one or more antigenic determinants with PRO polypeptide.

Example 13

Rational Drug Design

The goal of rational drug design is to produce structural analogs of biologically active polypeptide of interest (i.e., a PRO polypeptide) or of small molecules with which they interact, e.g., agonists, antagonists, or inhibitors. Any of these examples can be used to fashion drugs which are more active or stable forms of the PRO polypeptide or which enhance or interfere with the function of the PRO polypeptide in vivo (c.f., Hodgson, Bio/Technology, 9: 19–21(1991)).

In one approach, the three-dimensional structure of the PRO polypeptide, or of a PRO polypeptide-inhibitor complex, is determined by X-ray crystallography, by computer modeling or, most typically, by a combination of the two approaches. Both the shape and charges of the PRO polypeptide must be ascertained to elucidate the structure and to determine active site(s) of the molecule. Less often, useful information regarding the structure of the PRO polypeptide may be gained by modeling based on the structure of homologous proteins. In both cases, relevant structural information is used to design analogous PRO polypeptide-like molecules or to identify efficient inhibitors. Useful examples of rational drug design may include molecules which have improved activity or stability as shown by Braxton and Wells, Biochemistry, 31:7796–7801 (1992) or which act as inhibitors, agonists, or antagonists of native peptides as shown by Athauda et al., J. Biochem., 113: 742–746(1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO polypeptide may be made available to perform such analytical studies as X-ray crystallography. In addition, knowledge of the PRO polypeptide amino acid sequence provided herein will provide guidance to those employing computer modeling techniques in place of or in addition to X-ray crystallography.

Example 14

Pericyte c-Fos Induction (Assay 93)

This assay shows that certain polypeptides of the invention act to induce the expression of c-fos in pericyte cells and, therefore, are useful not only as diagnostic markers for particular types of pericyte-associated tumors but also for giving rise to antagonists which would be expected to be useful for the therapeutic treatment of pericyte-associated tumors. Induction of c-fos expression in pericytes is also indicative of the induction of angiogenesis and, as such, PRO polypeptides capable of inducing the expression of c-fos would be expected to be useful for the treatment of conditions where induced angiogenesis would be beneficial including, for example, wound healing, and the like. Specifically, on day 1, pericytes are received from VEC Technologies and all but 5 ml of media is removed from flask. On day 2, the pericytes are trypsinized, washed, spun and then plated onto 96 well plates. On day 7, the media is removed and the pericytes are treated with 100 µl of PRO polypeptide test samples and controls (positive control=DME+5% serum±PDGF at 500 ng/ml; negative control=protein 32). Replicates are averaged and SD/CV are determined. Fold increase over Protein 32 (buffer control) value indicated by chemiluminescence units (RLU) luminometer reading verses frequency is plotted on a histogram. Two-fold above Protein 32 value is considered positive for the assay. ASY Matrix: Growth media=low glucose DMEM=20% FBS+1× pen strep+1× fungizone. Assay Media=low glucose DMEM+5% FBS.

The following polypeptides tested positive in this assay: PRO1347 and PRO1340.

Example 15

Ability of PRO Polypeptides to Stimulate the Release of Proteoglycans from Cartilage (Assay 97)

The ability of various PRO polypeptides to stimulate the release of proteoglycans from cartilage tissue was tested as follows.

The metacarphophalangeal joint of 4–6 month old pigs was aseptically dissected, and articular cartilage was removed by free hand slicing being careful to avoid the underlying bone. The cartilage was minced and cultured in bulk for 24 hours in a humidified atmosphere of 95% air, 5% $CO_2$ in serum free (SF) media (DME/F12 1:1) with 0.1% BSA and 100 U/ml penicillin and 100 µg/ml streptomycin. After washing three times, approximately 100 mg of articular cartilage was aliquoted into micronics tubes and incubated for an additional 24 hours in the above SF media. PRO polypeptides were then added at 1% either alone or in combination with 18 ng/ml interleukin-1α, a known stimulator of proteoglycan release from cartilage tissue. The supernatant was then harvested and assayed for the amount of proteoglycans using the 1,9-dimethyl-methylene blue (DMB) colorimetric assay (Farndale and Buttle, Biochem. Biophys. Acta 883:173–177 (1985)). A positive result in this assay indicates that the test polypeptide will find use, for example, in the treatment of sports-related joint problems, articular cartilage defects, osteoarthritis or rheumatoid arthritis.

When various PRO polypeptides were tested in the above assay, the polypeptides demonstrated a marked ability to stimulate release of proteoglycans from cartilage tissue both basally and after stimulation with interleukin-1α and at 24 and 72 hours after treatment, thereby indicating that these PRO polypeptides are useful for stimulating proteoglycan release from cartilage tissue. As such, these PRO polypeptides are useful for the treatment of sports-related joint problems, articular cartilage defects, osteoarthritis or rheumatoid arthritis. The polypeptides testing positive in this assay are: PRO1565, PRO1693, PRO1801 and PRO10096.

Example 16

Detection of Polypeptides that Affect Glucose or FFA Uptake in Skeletal Muscle (Assay 106)

This assay is designed to determine whether PRO polypeptides show the ability to affect glucose or FFA uptake by skeletal muscle cells. PRO polypeptides testing positive in this assay would be expected to be useful for the therapeutic treatment of disorders where either the stimulation or inhibition of glucose uptake by skeletal muscle would be beneficial including, for example, diabetes or hyper- or hypo-insulinemia.

In a 96 well format, PRO polypeptides to be assayed are added to primary rat differentiated skeletal muscle, and allowed to incubate overnight. Then fresh media with the PRO polypeptide and +/− insulin are added to the wells. The sample media is then monitored to determine glucose and FFA uptake by the skeletal muscle cells. The insulin will stimulate glucose and FFA uptake by the skeletal muscle, and insulin in media without the PRO polypeptide is used as a positive control, and a limit for scoring. As the PRO polypeptide being tested may either stimulate or inhibit glucose and FFA uptake, results are scored as positive in the assay if greater than 1.5 times or less than 0.5 times the insulin control.

The following PRO polypeptides tested positive as either stimulators or inhibitors of glucose and/or FFA uptake in this assay: PRO4405.

Example 17

Identification of PRO Polypeptides that Stimulate TNF-α Release In Human Blood (Assay 128)

This assay shows that certain PRO polypeptides of the present invention act to stimulate the release of TNF-α in human blood. PRO polypeptides testing positive in this assay are useful for, among other things, research purposes where stimulation of the release of TNF-α would be desired and for the therapeutic treatment of conditions wherein enhanced TNF-α release would be beneficial. Specifically, 200 µl of human blood supplemented with 50 mM Hepes buffer (pH 7.2) is aliquotted per well in a 96 well test plate. To each well is then added 300 µl of either the test PRO polypeptide in 50 mM Hepes buffer (at various concentrations) or 50 mM Hepes buffer alone (negative control) and the plates are incubated at 37° C. for 6 hours. The samples are then centrifuged and 50 µl of plasma is collected from each well and tested for the presence of TNF-α by ELISA assay. A positive in the assay is a higher amount of TNF-α in the PRO polypeptide treated samples as compared to the negative control samples.

The following PRO polypeptides tested positive in this assay: PRO263, PRO295, PRO1282, PRO1063, PRO1356, PRO3543, and PRO5990.

Example 18

Tumor Versus Normal Differential Tissue Expression Distribution

Oligonucleotide probes were constructed from some of the PRO polypeptide-encoding nucleotide sequences shown in the accompanying figures for use in quantitative PCR amplification reactions. The oligonucleotide probes were chosen so as to give an approximately 200–600 base pair amplified fragment from the 3' end of its associated template in a standard PCR reaction. The oligonucleotide probes were employed in standard quantitative PCR amplification reactions with cDNA libraries isolated from different human tumor and normal human tissue samples and analyzed by agarose gel electrophoresis so as to obtain a quantitative determination of the level of expression of the PRO polypeptide-encoding nucleic acid in the various tumor and normal tissues tested. β-actin was used as a control to assure that equivalent amounts of nucleic acid was used in each reaction. Identification of the differential expression of the PRO polypeptide-encoding nucleic acid in one or more tumor tissues as compared to one or more normal tissues of the same tissue type renders the molecule useful diagnostically for the determination of the presence or absence of tumor in a subject suspected of possessing a tumor as well as therapeutically as a target for the treatment of a tumor in a subject possessing such a tumor. These assays provided the following results.

| Molecule | is more highly expressed in: | as compared to: |
|---|---|---|
| DNA26843-1389 | normal lung | lung tumor |
| | rectum tumor | normal rectum |
| DNA30867-1335 | normal kidney | kidney tumor |
| DNA40621-1440 | normal lung | lung tumor |
| DNA40625-1189 | normal lung | lung tumor |
| DNA45409-2511 | melanoma tumor | normal skin |
| DNA56406-1704 | kidney tumor | normal kidney |
| | normal skin | melanoma tumor |
| DNA56410-1414 | normal stomach | stomach tumor |
| DNA56436-1448 | normal skin | melanoma tumor |
| DNA56855-1447 | normal esophagus | esophageal tumor |
| | rectum tumor | normal rectum |
| DNA56860-1510 | normal kidney | kidney tumor |
| | rectum tumor | normal rectum |
| DNA56862-1343 | kidney tumor | normal kidney |
| | normal lung | lung tumor |
| DNA56868-1478 | normal stomach | stomach tumor |
| | normal lung | lung tumor |
| DNA56869-1545 | normal esophagus | esophageal tumor |
| | normal skin | melanoma tumor |
| DNA57704-1452 | normal stomach | stomach tumor |
| | rectum tumor | normal rectum |
| DNA58723-1588 | normal stomach | stomach tumor |
| | kidney tumor | normal kidney |
| | normal skin | melanoma tumor |
| DNA57827-1493 | normal stomach | stomach tumor |
| | normal skin | melanoma tumor |
| DNA58737-1473 | esophageal tumor | normal esophagus |
| | normal stomach | stomach tumor |
| DNA58846-1409 | lung tumor | normal lung |
| DNA58850-1495 | esophageal tumor | normal esophagus |
| | kidney tumor | normal kidney |
| DNA58855-1422 | normal stomach | stomach tumor |
| | rectum tumor | normal rectum |
| DNA59211-1450 | normal kidney | kidney tumor |
| DNA59212-1627 | normal skin | melanoma tumor |
| DNA59213-1487 | normal stomach | stomach tumor |
| | normal skin | melanoma tumor |
| DNA59605-1418 | melanoma tumor | normal skin |
| DNA59609-1470 | esophageal tumor | normal esophagus |
| DNA59610-1556 | esophageal tumor | normal esophagus |
| | lung tumor | normal lung |
| | normal skin | melanoma tumor |
| DNA59837-2545 | normal skin | melanoma tumor |
| DNA59844-2542 | normal skin | melanoma tumor |
| | esophageal tumor | normal esophagus |
| DNA59854-1459 | normal esophagus | esophageal tumor |
| | stomach tumor | normal stomach |
| | normal lung | lung tumor |
| DNA60625-1507 | normal lung | lung tumor |
| DNA60629-1481 | normal esophagus | esophageal tumor |
| | normal rectum | rectum tumor |
| DNA61755-1554 | normal stomach | stomach tumor |
| | kidney tumor | normal kidney |
| DNA62812-1594 | normal stomach | stomach tumor |
| | normal lung | lung tumor |
| | normal rectum | rectum tumor |
| | normal skin | melanoma tumor |
| DNA62815-1576 | esophageal tumor | normal esophagus |
| DNA64881-1602 | normal stomach | stomach tumor |
| | normal lung | lung tumor |
| DNA64902-1667 | esophageal tumor | normal esophagus |
| | kidney tumor | normal kidney |
| DNA65403-1565 | normal esophagus | esophageal tumor |
| DNA66308-1537 | normal lung | lung tumor |
| DNA66519-1535 | kidney tumor | normal kidney |
| DNA66521-1583 | normal esophagus | esophageal tumor |
| | normal stomach | stomach tumor |
| | normal lung | lung tumor |
| | normal rectum | rectum tumor |
| | normal skin | melanoma tumor |
| DNA66658-1584 | normal lung | lung tumor |
| | melanoma tumor | normal skin |

-continued

| Molecule | is more highly expressed in: | as compared to: |
|---|---|---|
| DNA66660-1585 | lung tumor | normal lung |
| DNA66674-1599 | kidney tumor | normal kidney |
| | normal lung | lung tumor |
| DNA68862-2546 | melanoma tumor | normal skin |
| DNA68866-1644 | normal stomach | stomach tumor |
| DNA68871-1638 | lung tumor | normal lung |
| | normal skin | melanoma tumor |
| DNA68880-1676 | normal lung | lung tumor |
| | normal skin | melanoma tumor |
| DNA68883-1691 | esophageal tumor | normal esophagus |
| DNA68885-1678 | lung tumor | normal lung |
| DNA71277-1636 | normal stomach | stomach tumor |
| DNA73734-1680 | normal lung | lung tumor |
| DNA73735-1681 | esophageal tumor | normal esophagus |
| | normal kidney | kidney tumor |
| | lung tumor | normal lung |
| | normal skin | melanoma tumor |
| DNA76393-1664 | esophageal tumor | normal esophagus |
| | stomach tumor | normal stomach |
| | lung tumor | normal lung |
| | rectum tumor | normal rectum |
| DNA77568-1626 | normal stomach | stomach tumor |
| | lung tumor | normal lung |
| DNA77626-1705 | normal rectum | rectum tumor |
| DNA81754-2532 | normal skin | melanoma tumor |
| DNA81757-2512 | esophageal tumor | normal esophagus |
| | normal stomach | stomach tumor |
| | melanoma tumor | normal skin |
| DNA82302-2529 | normal stomach | stomach tumor |
| | normal lung | lung tumor |
| DNA82340-2530 | normal esophagus | esophageal tumor |
| DNA85066-2534 | lung tumor | normal lung |
| | normal skin | melanoma tumor |
| DNA87991-2540 | esophageal tumor | normal esophagus |
| DNA92238-2539 | normal skin | melanoma tumor |
| DNA96787-2534 | normal kidney | kidney tumor |

Example 19

Identification of Receptor/Ligand Interactions

In this assay, various PRO polypeptides are tested for ability to bind to a panel of potential receptor or ligand molecules for the purpose of identifying receptor/ligand interactions. The identification of a ligand for a known receptor, a receptor for a known ligand or a novel receptor/ligand pair is useful for a variety of indications including, for example, targeting bioactive molecules (linked to the ligand or receptor) to a cell known to express the receptor or ligand, use of the receptor or ligand as a reagent to detect the presence of the ligand or receptor in a composition suspected of containing the same, wherein the composition may comprise cells suspected of expressing the ligand or receptor, modulating the growth of or another biological or immunological activity of a cell known to express or respond to the receptor or ligand, modulating the immune response of cells or toward cells that express the receptor or ligand, allowing the preparation of agonists, antagonists and/or antibodies directed against the receptor or ligand which will modulate the growth of or a biological or immunological activity of a cell expressing the receptor or ligand, and various other indications which will be readily apparent to the ordinarily skilled artisan.

The assay is performed as follows. A PRO polypeptide of the present invention suspected of being a ligand for a receptor is expressed as a fusion protein containing the Fc domain of human IgG (an immunoadhesin). Receptor-ligand binding is detected by allowing interaction of the immunoadhesin polypeptide with cells (e.g. Cos cells) expressing candidate PRO polypeptide receptors and visualization of bound immunoadhesin with fluorescent reagents directed toward the Fc fusion domain and examination by microscope. Cells expressing candidate receptors are produced by transient transfection, in parallel, of defined subsets of a library of cDNA expression vectors encoding PRO polypeptides that may function as receptor molecules. Cells are then incubated for 1 hour in the presence of the PRO polypeptide immunoadhesin being tested for possible receptor binding. The cells are then washed and fixed with paraformaldehyde. The cells are then incubated with fluorescent conjugated antibody directed against the Fc portion of the PRO polypeptide immunoadhesin (e.g. FITC conjugated goat anti-human-Fc antibody). The cells are then washed again and examined by microscope. A positive interaction is judged by the presence of fluorescent labeling of cells transfected with cDNA encoding a particular PRO polypeptide receptor or pool of receptors and an absence of similar fluorescent labeling of similarly prepared cells that have been transfected with other cDNA or pools of cDNA. If a defined pool of cDNA expression vectors is judged to be positive for interaction with a PRO polypeptide immunoadhesin, the individual cDNA species that comprise the pool are tested individually (the pool is "broken down") to determine the specific cDNA that encodes a receptor able to interact with the PRO polypeptide immunoadhesin.

In another embodiment of this assay, an epitope-tagged potential ligand PRO polypeptide (e.g. 8 histidine "His" tag) is allowed to interact with a panel of potential receptor PRO polypeptide molecules that have been expressed as fusions with the Fc domain of human IgG (immunoadhesins). Following a 1 hour co-incubation with the epitope tagged PRO polypeptide, the candidate receptors are each immunoprecipitated with protein A beads and the beads are washed. Potential ligand interaction is determined by western blot analysis of the immunoprecipitated complexes with antibody directed towards the epitope tag. An interaction is judged to occur if a band of the anticipated molecular weight of the epitope tagged protein is observed in the western blot analysis with a candidate receptor, but is not observed to occur with the other members of the panel of potential receptors.

Using these assays, the following receptor/ligand interactions have been herein identified:
(1) PRO10272 binds to PRO5801.
(2) PRO20110 binds to the human IL-17 receptor (Yao et al., *Cytokine* 9(11):794–800 (1997); also herein designated as PRO1) and to PRO20040.
(3) PRO10096 binds to PRO20233.
(4) PRO19670 binds to PRO1890.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

The invention claimed is:

1. An isolated polypeptide comprising:
   (a) the amino acid sequence of the polypeptide of SEQ ID NO: 82;
   (b) the amino acid sequence of the polypeptide of SEQ ID NO: 82, lacking its associated signal peptide; or
   (c) the amino acid sequence of the polypeptide encoded by the full-length coding sequence of the cDNA deposited under ATCC accession number 203317.

2. The isolated polypeptide of claim 1 comprising the amino acid sequence of the polypeptide of SEQ ID NO: 82.

3. The isolated polypeptide of claim 1 comprising the amino acid sequence of the polypeptide of SEQ ID NO: 82, lacking its associated signal peptide.

4. The isolated polypeptide of claim 1 comprising the amino acid sequence of the polypeptide encoded by the full-length coding sequence of the cDNA deposited under ATCC accession number 203317.

5. A chimeric polypeptide comprising a polypeptide according to claim 1 fused to a heterologous polypeptide.

6. The chimeric polypeptide of claim 5, wherein said heterologous polypeptide is a tag polypeptide or an Fc region of an immunoglobulin.

* * * * *